United States Patent

Lawrence et al.

(10) Patent No.: US 9,862,730 B2
(45) Date of Patent: Jan. 9, 2018

(54) IMIDAZOTHIADIAZOLE DERIVATIVES AS PROTEASE ACTIVATED RECEPTOR 4 (PAR4) INHIBITORS FOR TREATING PLATELET AGGREGATION

(71) Applicants: BRISTOL-MYERS SQUIBB COMPANY, Princeton, NJ (US); Universite De Montreal, Montreal (CA)

(72) Inventors: R. Michael Lawrence, Yardley, PA (US); Michael M. Miller, Pennington, NJ (US); Dietmar Alfred Seiffert, Garnet Valley, PA (US); Shoshana L. Posy, Highland Park, NJ (US); Pancras C. Wong, Plainsboro, NJ (US); Jacques Banville, Saint-Hubert (CA); Edward H. Ruediger, Greenfield Park (CA); Daniel H. Deon, Montreal (CA); Alain Martel, Delson (CA); François Tremblay, Laval (CA); Julia Guy, Montreal (CA); Jean-François Lavallée, Mille-Isles (CA); Marc Gagnon, Ville Saint-Laurent (CA)

(73) Assignees: Bristol-Myers Squibb Company, Princeton, NJ (US); Universite De Montreal, Montreal (CA)

( * ) Notice: Subject to any disclaimer, the term of this patent is extended or adjusted under 35 U.S.C. 154(b) by 273 days.

(21) Appl. No.: 14/396,807

(22) PCT Filed: Apr. 24, 2013

(86) PCT No.: PCT/US2013/037892
§ 371 (c)(1),
(2) Date: Oct. 24, 2014

(87) PCT Pub. No.: WO2013/163244
PCT Pub. Date: Oct. 31, 2013

(65) Prior Publication Data
US 2015/0133446 A1    May 14, 2015

Related U.S. Application Data

(60) Provisional application No. 61/638,591, filed on Apr. 26, 2012.

(51) Int. Cl.
*C07D 513/04*    (2006.01)
*C07D 519/00*    (2006.01)
*A61K 45/06*    (2006.01)
*A61K 31/433*    (2006.01)
*A61K 31/4355*    (2006.01)
*A61K 31/4439*    (2006.01)
*A61K 31/506*    (2006.01)
*A61K 31/5377*    (2006.01)

(52) U.S. Cl.
CPC .......... *C07D 513/04* (2013.01); *A61K 31/433* (2013.01); *A61K 31/4355* (2013.01); *A61K 31/4439* (2013.01); *A61K 31/506* (2013.01); *A61K 31/5377* (2013.01); *A61K 45/06* (2013.01); *C07D 519/00* (2013.01)

(58) Field of Classification Search
CPC .................................................. C07D 513/04
See application file for complete search history.

(56) References Cited

U.S. PATENT DOCUMENTS 6,673,815 B2    1/2004  Devasthale et al.
2007/0155779 A1  7/2007  Verhoest

FOREIGN PATENT DOCUMENTS

| CA | 2 584 745 A1 | 10/2007 |
| CN | 102372701 | 3/2012 |
| DE | 2823686 | 12/1979 |
| DE | 102006054757 | 5/2008 |
| EP | 0 005 783 A1 | 12/1979 |
| EP | 0041215 | 12/1981 |
| EP | 0 158 012 A1 | 10/1985 |
| EP | 0 185 345 A1 | 6/1986 |
| EP | 0 299 209 A2 | 1/1989 |
| EP | 0 379 979 A1 | 8/1990 |
| EP | 0497258 | 8/1992 |
| EP | 2 518 066 A1 | 10/2012 |
| IN | 903/MUM/2004 | 6/2007 |
| WO | WO 99/46232 | 9/1999 |
| WO | WO 01/27118 | 4/2001 |

(Continued)

OTHER PUBLICATIONS

Rani et al. Indian Journal of Heterocyclic Chemistry, 2008, 18, 121-124.*
STN Database Record for RN 1096958-09-6, database entry date Jan. 28, 2009.*
Rani et al. Indian Journal of Heterocyclic Chemistry 2008, 18, 121-124.*

(Continued)

*Primary Examiner* — Matthew Coughlin
(74) *Attorney, Agent, or Firm* — Hoffmann & Baron, LLP

(57) ABSTRACT

The present invention provides imidazothiadiazole compounds of Formula (I) wherein A, B, D, $R^x$, $R^1$, $R^2$, $R^3$, $X_1$, $X_2$ and s are as defined herein, or a stereoisomer, tautomer, pharmaceutically acceptable salt or solvate form thereof, wherein all of the variables are as defined herein. These compounds are inhibitors of platelet aggregation and thus can be used as medicaments.

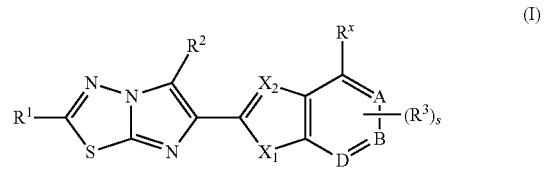

11 Claims, 5 Drawing Sheets

(56) References Cited

FOREIGN PATENT DOCUMENTS

| WO | WO 01/27119 | 4/2001 |
|---|---|---|
| WO | WO 01/81344 | 11/2001 |
| WO | WO 03/040114 | 5/2003 |
| WO | WO 03/051890 | 6/2003 |
| WO | WO 2004/063159 | 7/2004 |
| WO | WO 2004/111060 | 12/2004 |
| WO | WO 2004/111061 | 12/2004 |
| WO | WO 2005/048948 | 6/2005 |
| WO | WO 2005/048953 | 6/2005 |
| WO | WO 2005/080355 | 9/2005 |
| WO | WO 2007/002540 | 1/2007 |
| WO | WO 2007/039177 | 4/2007 |
| WO | WO 2007/106469 | 9/2007 |
| WO | WO 2007/118318 | 10/2007 |
| WO | WO 2008/083238 | 7/2008 |
| WO | WO 2008/104279 | 9/2008 |
| WO | WO 2008/141249 | 11/2008 |
| WO | WO 2009/017954 | 2/2009 |
| WO | WO 2009/023179 | 2/2009 |
| WO | WO 2009/027733 | 3/2009 |
| WO | WO 2009/040507 | 4/2009 |
| WO | WO 2009/079683 | 7/2009 |
| WO | WO 2009/123992 | 10/2009 |
| WO | 2010/006704 A1 | 1/2010 |
| WO | WO 2010/036629 | 4/2010 |
| WO | WO 2010/075376 | 7/2010 |
| WO | WO 2011/074658 | 6/2011 |
| WO | WO 2012/021696 | 2/2012 |
| WO | WO 2013/028670 | 2/2013 |
| WO | WO 2013/163241 | 10/2013 |
| WO | WO 2013/163279 | 10/2013 |
| WO | WO 2014/015167 | 1/2014 |

OTHER PUBLICATIONS

STN Database Record for RN 1096958-08-5, database entry date Jan. 28, 2009.*
STN Database Record for RN 1097016-53-9, database entry date Jan. 28, 2009.*
STN Database Record for RN 1097163-93-3, database entry date Jan. 28, 2009.*
Beresneva, Tatjana, et al., "Palladium-catalyzed synthesis of novel tetra- and penta-cyclic biologically active benzopyran- and pyridopyran-containing heterocyclic systems"; Arkivoc 2013 (ix) pp. 185-194.
Terme, Thierry, et al., "Synthesis of 2-Substituted-3-nitroimidazo[1,2-b]pyridazines as Potential Biologically Active Agents", J. Heterocyclic Chem., 39, pp. 173-177, 2002.
Barlin, Gordon B. et al., "Imidazo[1,2-b]pyridazines: Syntheses and Interaction with Central and Peripheral-Type (Mitochondrial) Benzodiazepine Receptors", J. Heterocyclic Chem., 35, pp. 1205-1217, 1998.
Barlin, Gordon B. et al., "Imidazo[1,2-b]pyridazines. XX Syntheses of Some 3-Acylaminomethyl-6-(chloro, fluoro, methoxy, methylthio, phenoxy and phenylthio)-2-(phenyl,4-t-butylphenyl, 4-cyclohexylphenyl, β-naphthyl and styryl)imidazo[1,2-b]pyridazines and Their Interaction with Central and Peripheral-Type Benzodiazepine Receptors", Aust. J. Chem, 1996, 49 pp. 451-461.
Barlin, Gordon B. et al., Imidazo[1,2-b]pyridazines. XIX Syntheses and Central Nervous System Activities of Some 6-Arylthio(aryloxy and alkylthio)-3-(acetamidomethyl, benzamidomethyl, methoxy and unsubstituted)-2-arylimidazo[1,2-b]pyridazines, Aust. J. Chem, 1996, 49 pp. 443-449.
Matyus, Peter, et al., "Ligands for the Central Benzodiazepine Receptor: Structure-Affinity Relationship Studies on Imidazo[1,2-b]pyridazines", Aust. J. Chem, 1996, 49 pp. 435-442.
Davies, Les P., et al., "New Imidazo[1,2,-b]Pyridazine Ligands for Peripheral Type Benzodiazepine Receptors on Mitochondria and Monocytes", Life Sciences, vol. 57, No. 25, pp. 381-386, 1995.
Barlin, Gordon B. et al., "Imidazo[1,2,-b]pyridazines. XVI Synthesis and Central Nervous System Activities of Some 6-(Chloro, Alkylthio, Phenylthio, Benzylthio or Pyridinylmethylthio)-3-(unsubstituted, benzamidomethyl or methoxy)-2-(styryl or benzoyl)imidazo[1,2-b]pyridazines", Aust. J. Chem, 1994, 47 pp. 1989-1999.
STN Database Record for RN 1177489-39-2, database entry date Aug. 28, 2009.
STN Database Record for RN 1177349-45-9, database entry date Aug. 28, 2009.
Abdel-Wahab, B.F. et al., "Synthesis of New 2-Naphthyl Ethers and Their Protective Activities against DNA Damage Induced by Bleomycin-Iron", Chem. Pharm. Bull., vol. 57, No. 12, pp. 1348-1351 (2009).
Barlin, G.B. et al., "Imidazo[1,2-b]pyridazines. XIII. Syntheses and Central Nervous System Activities of Some 2-Benzyl(phenethyl, biphenyl-4'-yl, 6'-methylnaphthalen-2'-yl, t-butyl and cyclohexyl)-3-methoxy(acylaminomethyl and dimethylaminomethyl)-6-(variously substituted)imidazo[1,2-b]pyridazines", Aust. J. Chem., vol. 45, pp. 1281-1300 (1992).
Bhovi, V.K. et al., "Synthesis of Some Mannich Bases and Novel Benzofuran Derivatives Containing Imidazo[2,1-b][1,3,4]thiadiazoles as Biological Agents", Current Chemical Biology, vol. 4, No. 2, pp. 145-150 (2010).
CAS Registry No. 1096958-08-5, Entered STN: Jan. 28, 2009.
CAS Registry No. 1097016-53-9, Entered STN: Jan. 28, 2009.
CAS Registry No. 1097037-01-8, Entered STN: Jan. 28, 2009.
CAS Registry No. 1097163-93-3, Entered STN: Jan. 28, 2009.
Rani, R. et al., "Microwave Assisted Facile Synthesis and Antimicrobial Activity of Some New Imidazo[2,1-b]-1,3,4-thiadiazoles", Indian Journal of Heterocyclic Chemistry, vol. 18, pp. 121-124 (2008).
Tegginamath, G. et al., "Synthesis of novel imidazo[2,1-b][1,3,4]thiadiazoles appended to sydnone as anticancer agents", Medicinal Chemistry Research, vol. 22, pp. 4367-4375 (2013).
Banville et al., U.S. Appl. No. 14/396,771, filed Oct. 24, 2014.
Martel et al., U.S. Appl. No. 14/396,831, filed Oct. 24, 2014.
Office Action for 2015-509094, dated Oct. 11, 2016.
Office Action Summary for 2015-509094, dated Oct. 11, 2016.

* cited by examiner

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Tyr Pro Gly Lys Phe
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptides
<220> FEATURE:
<221> NAME/KEY: MISC_FEATURE
<222> LOCATION: (2)..(2)
<223> OTHER INFORMATION: wherein this amino acid (the Phe amino acid in
      position 2) is fluorinated at the number 4 carbon of the side
      chain phenyl ring

<400> SEQUENCE: 2

Ala Phe Pro Gly Trp Leu Val Lys Asn Gly
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: wherein this amino acid is modified with a
      trans-cinnamoyl moiety and floronated at the number 4 carbon
```

```
<220> FEATURE:
<221> NAME/KEY: MISC_FEATURE
<222> LOCATION: (2)..(2)
<223> OTHER INFORMATION: wherein this amino acid is modified with a
      guanidino moiety at the 4 carbon

<400> SEQUENCE: 3

Phe Phe Leu Arg Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:  Synthetic
      polypeptide

<400> SEQUENCE: 4

Ser Phe Phe Leu Arg Arg
1               5
```

IMIDAZOTHIADIAZOLE DERIVATIVES AS PROTEASE ACTIVATED RECEPTOR 4 (PAR4) INHIBITORS FOR TREATING PLATELET AGGREGATION

CROSS REFERENCES TO RELATED APPLICATIONS

This application is a 371 of International Application No. PCT/US2013/037892, filed on Apr. 24, 2013, which claims the benefit of U.S. Provisional Application Ser. No. 61/638,591, filed on Apr. 26, 2012 which is incorporated herein by reference.

FIELD OF THE INVENTION

The present invention provides novel imidazothiadiazole and analogues thereof, which are inhibitors of platelet aggregation that are useful in preventing or treating thromboembolic disorders. This invention also relates to pharmaceutical compositions containing these compounds and methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., Nature, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4 Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., N. Eng. J. Med., 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", J. Med. Chem., 44(22):3746-3749 (2001) discloses in the abstract that the compound

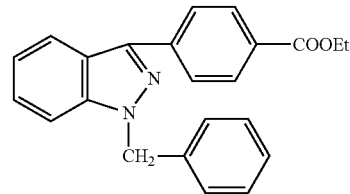

"was found to be a selective and potent inhibitor or protease-activated receptor type 4 (PAR4)-dependent platelet activation."

Compound 58 is also referred to as YD-3 in Wu, C-C. et al., "Selective Inhibition of Protease-activated Receptor 4-dependent Platelet Activation by YD-3", Thromb. Haemost., 87:1026-1033 (2002). Also, see Chen, H. S. et al., "Synthesis and platelet activity", J. Bioorg. Med. Chem., 16:1262-1278 (2008).

EP1166785 A1 and EP0667345 disclose various pyrazole derivatives which are useful as inhibitors of platelet aggregation.

SUMMARY OF THE INVENTION

It has been found that imidazothiadiazole compounds in accordance with the present invention are PAR4 antagonists which inhibit platelet aggregation in gamma-thrombin induced platelet aggregation assays. Moreover, a compound(s) of the present invention has been shown to inhibit platelet aggregation in an alpha-thrombin induced platelet aggregation assay, and to inhibit thrombus formation in an arterial thrombosis model in cynomolgus monkeys.

Accordingly, the present invention provides novel imidazothiadiazoles, and analogues thereof, which are PAR4 antagonists and are useful as selective inhibitors of platelet aggregation, including stereoisomers, tautomers, pharmaceutically acceptable salts, solvates, or prodrug esters thereof.

The present invention also provides processes and intermediates for making the compounds of the present invention or stereoisomers, tautomers, pharmaceutically acceptable salts, solvates, or prodrug esters thereof.

The present invention also provides pharmaceutical compositions comprising a pharmaceutically acceptable carrier and at least one of the compounds of the present invention or stereoisomers, tautomers, pharmaceutically acceptable salts, solvates, or prodrug esters thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug esters thereof.

The present invention also provides the compounds of the present invention or stereoisomers, tautomers, pharmaceutically acceptable salts, solvates, or prodrug esters thereof, for use in therapy.

The present invention also provides the use of the compounds of the present invention or stereoisomers, tautomers, pharmaceutically acceptable salts, solvates, or prodrug esters thereof, for the manufacture of a medicament for the treatment or prophylaxis of a thromboembolic disorder.

Other features and advantages of the invention will be apparent from the following detailed description and claims.

IMIDAZOTHIADIAZOLE COMPOUNDS OF THE INVENTION

Figure 1:
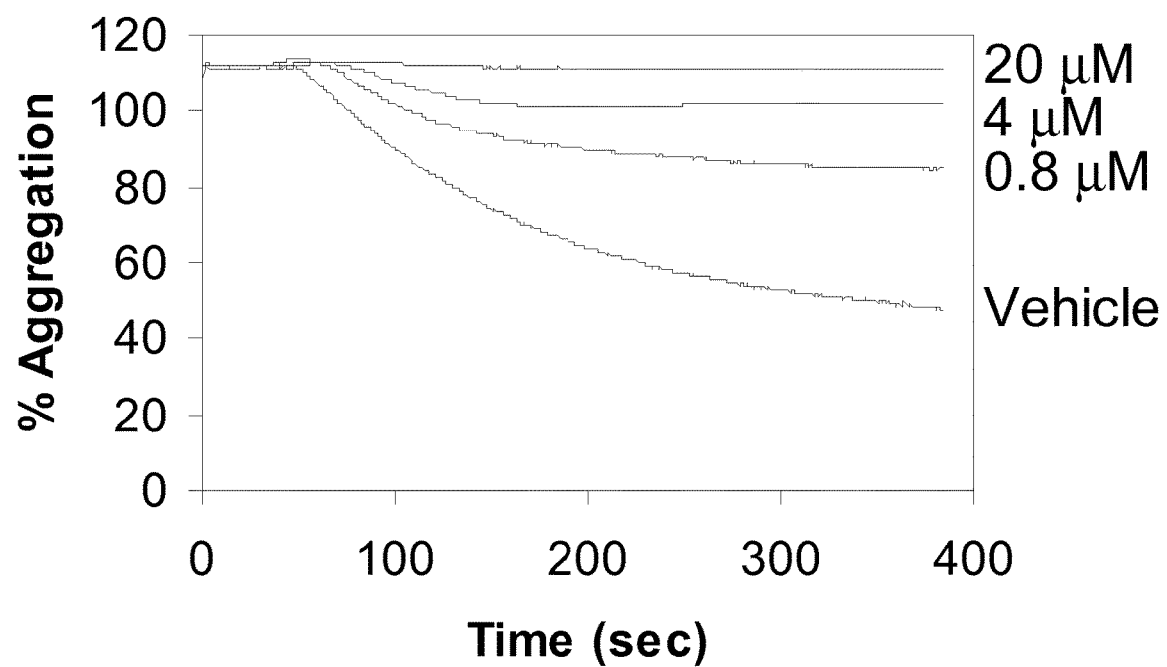
FIG. 1 shows dose-dependent inhibition of 2.5 nM alpha-thrombin-induced platelet aggregation by Example 203 (a PAR4 antagonist).

In a first aspect, the present invention provides a compound of Formula I:

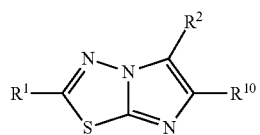

I or a stereoisomer, tautomer, pharmaceutically acceptable salt, solvate or prodrug thereof, wherein:
$R^{10}$ is

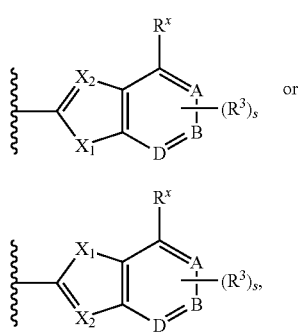

wherein A, B and D are the same or different and are independently selected from N and C, provided that A, B and D represent at least 1 carbon atom and at most 2 N atoms;
$X_1$ is selected from O, S or $NR^4$;
$X_2$ is selected from CH, $CR^5$ or N;
$R^1$ is selected from the group consisting of:
halo,
$C_1$-$C_4$ alkyl,
$C_2$-$C_3$ alkenyl,
$C_2$-$C_3$ alkynyl,
$C_1$-$C_4$ alkoxy,
$C_1$-$C_4$ alkylthio,
phenylthio,
$C_1$-$C_4$ alkylNH,
$C_1$-$C_4$-alkylOC$_1$-$C_4$-alkyl,
$(C_1$-$C_4$ alkyl)$_2$N—,
$C_3$-$C_6$ cycloalkyl,
4- to 10-membered heterocyclyl,
halo-$C_1$-$C_2$-alkyl, which contains 1 to 5 halogens, where halo is F or Cl,
halo-$C_1$-$C_2$-alkoxy, which contains 1 to 5 halogens, where halo is F or Cl,
$C_1$-$C_4$-alkoxycarbonyl-$C_1$-$C_4$-alkylthio, and
$C_1$-$C_4$-alkoxycarbonyl-$C_1$-$C_4$-alkoxy;
$R^2$ is selected from the group consisting of:
H,
halo,
$C_1$-$C_4$ alkyl,
$C_1$-$C_4$ alkoxy, and
cyano;
$R^x$, at each occurrence, is independently selected from the group consisting of:
H,
halo which is F, Cl, Br or I,
$NR^6R^7$,
$NO_2$,
cyano,
OH,
$C_1$-$C_4$ alkoxy substituted with 0 to 3 $R^{a1}$ groups,
$C_1$-$C_4$ alkylthio substituted with 0 to 3 $R^{a1}$ groups,
carboxy,
carbonyl,
$C_1$-$C_4$ alkoxycarbonyl substituted with 0 to 3 $R^{a1}$ groups,
$C_1$-$C_4$ alkylcarbonyl substituted with 0 to 3 $R^{a1}$ groups,
$C(=O)NR^6R^7$,
$C_1$-$C_4$ alkylsulfonyl substituted with 0 to 3 $R^{a1}$ groups,
$S(=O)_2NR^6R^7$,
$C_1$-$C_4$ alkyl substituted with 0 to 3 $R^{a1}$ groups,
fluoro-$C_1$-$C_4$-alkyl, which contains 1 to 5 fluorines, or
fluoro-$C_1$-$C_4$-alkoxy, which contains 1 to 5 fluorines; or
$R^x$ is selected from Y—Z—, where:
Z is a linker which is selected from the group consisting of:
a single bond,
—O—,
—S—, $$-\overset{\text{O}}{\underset{\|}{\text{C}}}-,$$

—NH—,
$C_1$-$C_4$ alkyl which is independently substituted with 0 to 3 $R^{a1}$ groups;
$C_1$-$C_4$ alkyloxy wherein the alkyl portion is independently substituted with 0 to 3 $R^{a1}$ groups;
$C_1$-$C_4$ alkylthio wherein the alkyl portion is independently substituted with 0 to 3 $R^{a1}$ groups;
$C_1$-$C_4$ alkyloxy-$C_1$-$C_4$-alkyl wherein any alkyl portion is independently substituted with 0 to 3 $R^{a1}$ groups;
$C_1$-$C_4$-alkylthio-$C_1$-$C_4$-alkyl wherein any alkyl portion is independently substituted with 0 to 3 $R^{a1}$ groups;
—S—$C_1$-$C_4$-alkyl wherein the alkyl portion is independently substituted with 0 to 3 $R^{a1}$ groups;
—O—$C_1$-$C_4$-alkyl wherein the alkyl portion is independently substituted with 0 to 3 $R^{a1}$ groups; and
$C_2$-$C_6$-alkynyl which is substituted with 0 to 3 $R^{a1}$ groups;
and Y is selected from the group consisting of:
$C_1$-$C_4$-alkyloxy-$C_1$-$C_4$-alkyl($C_1$-$C_4$-alkyl), $C_6$-$C_{10}$ aryl substituted by 0 to 3 $R^{a5}$ groups,
6- to 10-membered heteroaryl substituted by 0 to 3 $R^{a5}$ groups,
4- to 10-membered heterocyclyl substituted by 0 to 3 $R^{a5}$ groups or 0 to 1 $R^{b5}$ groups, and
$C_3$-$C_{10}$ cycloalkyl substituted by 0 to 3 $R^{a5}$ groups;
$R^3$, at each occurrence, is $R^{3a}$, $R^{3b}$ or $R^{3d}$, each of which is independently selected from the group consisting of:
H,
halo,
$NR^6R^7$,
$NO_2$,
cyano,
$CF_3$,
OH,
$C_2$-$C_4$ alkynyl substituted with 0 to 2 $R^{a1}$ groups,
$C_1$-$C_4$ alkoxy substituted with 0 to 2 $R^{a1}$ groups,
$C_1$-$C_4$ alkylthio substituted with 0 to 2 $R^{a1}$ groups,
carboxy,
—OCH=O,
$C_1$-$C_4$ alkoxycarbonyl substituted with 0 to 2 $R^{a1}$ groups,
$C_1$-$C_4$ alkylcarbonyl substituted with 0 to 2 $R^{a1}$ groups,
$C(=O)NR^6R^7$,
$C_1$-$C_4$ alkylsulfonyl substituted with 0 to 2 $R^{a1}$ groups,
$S(=O)_2NR^6R^7$,
$NR^6C(=O)R^7$,
$C_1$-$C_4$ alkyl substituted with 0 to 2 $R^{a1}$ groups,
fluoro-$C_1$-$C_4$-alkyl, which contains 1 to 5 fluorines,
fluoro-$C_1$-$C_4$-alkoxy, which contains 1 to 5 fluorines,
phenyl, where phenyl is substituted with 0 to 2 $R^{a5}$ groups,
phenyloxy, where phenyl is substituted with 0 to 2 $R^{a5}$ groups,
phenyl-$C_1$-$C_4$-alkoxy, where phenyl is substituted with 0 to 2 $R^{a5}$ groups,
5- to 10-membered heteroaryl-$C_1$-$C_4$-alkoxy, where heteroaryl is substituted with 0 to 2 $R^{a5}$ groups, and
4- to 10-membered heterocyclo-$C_1$-$C_4$-alkoxy, where heterocyclo is substituted with 0 to 2 $R^{a5}$ groups;
$R^4$ is independently selected from the group consisting of H and $C_1$-$C_4$ alkyl;
$R^5$ is independently selected from the group consisting of H, halo and $C_1$-$C_4$ alkyl;
$R^6$ and $R^7$ are, at each occurrence, independently selected from the group consisting of:
H,
$C_1$-$C_4$ alkyl substituted with 0 to 2 $R^{a1}$ groups,
$C_1$-$C_4$-alkoxy-$C_1$-$C_4$-alkyl, or
—$(CH_2)_n$-phenyl,
alternatively, $R^6$ and $R^7$, when attached to the same nitrogen, combine to form a 4- to 6-membered heterocyclic ring containing carbon atoms and 1 to 2 additional heteroatoms selected from N, $NR^c$, O, and $S(O)_p$;
$R^{a1}$ is, at each occurrence, independently selected from the group consisting of:
H,
=O,
halo,
$OCF_3$,
$CF_3$,
$OCHF_2$,
$C_1$-$C_4$ alkyl substituted with 1 to 5 fluorines,
$C_1$-$C_4$ alkyl,
$C_1$-$C_4$ alkoxy,
$C_1$-$C_4$ alkylthio,
$C_3$-$C_6$ cycloalkyl,
$C_3$-$C_6$ cycloalkyloxy,
phenyl substituted by 0 to 3 $R^{a5a}$ groups independently selected from the group consisting of halo, $C_1$-$C_3$ alkoxy, $C_1$-$C_3$ alkyl, $CF_3$, $OCF_3$, $OCHF_2$, and cyano,
OH,
CN,
$NO_2$,
$NR^{6a}R^{7a}$,
carboxy,
$C_1$-$C_4$ alkoxycarbonyl,
$C(=O)NR^{6a}R^{7a}$,
$C_1$-$C_4$ alkylsulfonyl, and
$S(=O)_2NR^{6a}R^{7a}$;
$R^{a5}$ is, at each occurrence, independently selected from the group consisting of:
H,
halo,
$OCF_3$,
$CF_3$,
$OCHF_2$,
$C_1$-$C_6$ alkyl independently substituted with 1 to 5 fluorines, hydroxyl, $C_1$-$C_4$ alkoxy, $C_3$-$C_6$ cycloalkyl, or amino,
$C_1$-$C_4$ alkyl,
$C_1$-$C_4$ alkoxy,
$C_1$-$C_4$ alkylthio,
$C_3$-$C_6$ cycloalkyloxy,
OH,
CN,
$NO_2$,
$NR^{8a}R^{9a}$,
carboxy,
$C_1$-$C_4$ alkoxycarbonyl,
$C(=O)NR^{6a}R^{7a}$,
$C_6$-$C_{10}$-arylcarbonylamino-$C_1$-$C_4$-alkyl(phenyl)carbonyl,
5- to 10-membered heteroarylcarbonylamino-$C_1$-$C_4$-alkyl(phenyl)carbonyl,
$C_6$-$C_{10}$ arylcarbonyl substituted with 0 to 5 $R^{a5a}$ groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{6a}R^{7a}$, OH, $C_1$-$C_4$-alkylcarbonyloxy-$C_1$-$C_4$-alkyl, hydroxy-$C_1$-$C_4$-alkyl, $COOR^{8a}$, $SO_2R^{8a}$, $(C=O)NR^{6a}R^{7a}$, $SO_2NR^{6a}R^{7a}$, $N(R^{8a})(C=O)NR^{6a}R^{7a}$, $N(R^{8a})(C=O)OR^{8a}$, $N(R^{8a})(C=O)R^{8a}$, $NR^{8a}S(O)R^{8a}$, $NR^{8a}SO_2R^{8a}$, $O(C=O)NR^{6a}R^{7a}$, $O(C=O)OR^{8a}$, $O(C=O)R^{8a}$, $(C=O)OR^{8a}$, and 5-6-membered heteroaryl,
$C_1$-$C_4$-alkyloxycarbonylamino-$C_1$-$C_4$-alkyl(phenyl)carbonyl,
$C_1$-$C_6$ alkylsulfonyl,
$S(=O)_2NR^{6a}R^{7a}$,
phenyloxy, wherein the phenyl is substituted by 0 to 5 $R^{a5a}$ groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{6a}R^{7a}$, OH, $C_1$-$C_4$-alkylcarbonyloxy-$C_1$-$C_4$-alkyl, hydroxy-$C_1$-$C_4$-alkyl, $COOR^{8a}$, $SO_2R^{8a}$, $(C=O)NR^{6a}R^{7a}$, $SO_2NR^{6a}R^{7a}$, $N(R^{8a})(C=O)NR^{6a}R^{7a}$, $N(R^{8a})(C=O)OR^{8a}$, $N(R^{8a})(C=O)R^{8a}$, $NR^{8a}S(O)R^{8a}$, $NR^{8a}SO_2R^{8a}$, $O(C=O)NR^{6a}R^{7a}$, $O(C=O)OR^{8a}$, $O(C=O)R^{8a}$, $(C=O)OR^{8a}$, and 5-6-membered heteroaryl,
phenylthio, wherein the phenyl is substituted by 0 to 5 $R^{a5a}$ groups independently selected from the group consisting of halo, $C_1$-$C_4$ alkoxy, halo-$C_1$-$C_4$ alkoxy, C$_1$-C$_4$ alkyl, halo-C$_1$-C$_4$ alkyl, C$_3$-C$_6$ cycloalkyl, cyano, nitro, NR$^{6a}$R$^{7a}$, OH, C$_1$-C$_4$-alkylcarbonyloxy-C$_1$-C$_4$-alkyl, hydroxy-C$_1$-C$_4$-alkyl, COOR$^{8a}$, SO$_2$R$^{8a}$, (C=O)NR$^{6a}$R$^{7a}$, SO$_2$NR$^{6a}$R$^{7a}$, N(R$^{8a}$)(C=O)NR$^{6a}$R$^{7a}$, N(R$^{8a}$)(C=O)OR$^{8a}$, N(R$^{8a}$)(C=O)R$^{8a}$, NR$^{8a}$S(O)R$^{8a}$, NR$^{8a}$SO$_2$R$^{8a}$, O(C=O)NR$^{6a}$R$^{7a}$, O(C=O)OR$^{8a}$, O(C=O)R$^{8a}$, (C=O)OR$^{8a}$, and 5-6-membered heteroaryl, C$_6$-C$_{10}$-aryl-C$_1$-C$_4$-alkoxy, wherein the aryl is substituted by 0 to 5 R$^{a5a}$ groups independently selected from the group consisting of halo, C$_1$-C$_4$ alkoxy, halo-C$_1$-C$_4$ alkoxy, C$_1$-C$_4$ alkyl, halo-C$_1$-C$_4$ alkyl, C$_3$-C$_6$ cycloalkyl, cyano, nitro, NR$^{6a}$R$^{7a}$, OH, C$_1$-C$_4$-alkylcarbonyloxy-C$_1$-C$_4$-alkyl, phenyl, phenyloxy, benzyloxy, hydroxy-C$_1$-C$_4$-alkyl, COOR$^{8a}$, SO$_2$R$^{8a}$, (C=O)NR$^{6a}$R$^{7a}$, SO$_2$NR$^{6a}$R$^{7a}$, N(R$^{8a}$)(C=O)NR$^{6a}$R$^{7a}$, N(R$^{8a}$)(C=O)OR$^{8a}$, N(R$^{8a}$)(C=O)R$^{8a}$, NR$^{8a}$S(O)R$^{8a}$, NR$^{8a}$SO$_2$R$^{8a}$, O(C=O)NR$^{6a}$R$^{7a}$, O(C=O)OR$^{8a}$, O(C=O)R$^{8a}$, (C=O)OR$^{8a}$, and 5-6-membered heteroaryl, 5- to 10-membered heteroaryl-C$_1$-C$_3$-alkoxy, wherein the heteroaryl is substituted by 0 to 5 R$^{a5a}$ groups independently selected from the group consisting of halo, C$_1$-C$_4$ alkoxy, halo-C$_1$-C$_4$ alkoxy, C$_1$-C$_4$ alkyl, halo-C$_1$-C$_4$ alkyl, C$_3$-C$_6$ cycloalkyl, cyano, nitro, NR$^{6a}$R$^{7a}$, OH, C$_1$-C$_4$-alkylcarbonyloxy-C$_1$-C$_4$-alkyl, phenyl, phenyloxy, benzyloxy, hydroxy-C$_1$-C$_4$-alkyl, COOR$^{8a}$, SO$_2$R$^{8a}$, (C=O)NR$^{6a}$R$^{7a}$, SO$_2$NR$^{6a}$R$^{7a}$, N(R$^{8a}$)(C=O)NR$^{6a}$R$^{7a}$, N(R$^{8a}$)(C=O)OR$^{8a}$, N(R$^{8a}$)(C=O)R$^{8a}$, NR$^{8a}$S(O)R$^{8a}$, NR$^{8a}$SO$_2$R$^{8a}$, O(C=O)NR$^{6a}$R$^{7a}$, O(C=O)OR$^{8a}$, O(C=O)R$^{8a}$, (C=O)OR$^{8a}$, and 5-6-membered heteroaryl, and phenyl-C$_1$-C$_3$-alkyl, wherein the phenyl is substituted by 0 to 5 R$^{a5a}$ groups independently selected from the group consisting of halo, C$_1$-C$_4$ alkoxy, halo-C$_1$-C$_4$ alkoxy, C$_1$-C$_4$ alkyl, halo-C$_1$-C$_4$ alkyl, C$_3$-C$_6$ cycloalkyl, cyano, nitro, NR$^{6a}$R$^{7a}$, OH, C$_1$-C$_4$-alkylcarbonyloxy-C$_1$-C$_4$-alkyl, hydroxy-C$_1$-C$_4$-alkyl, COOR$^{8a}$, SO$_2$R$^{8a}$, (C=O)NR$^{6a}$R$^{7a}$, SO$_2$NR$^{6a}$R$^{7a}$, N(R$^{8a}$)(C=O)NR$^{6a}$R$^{7a}$, N(R$^{8a}$)(C=O)OR$^{8a}$, N(R$^{8a}$)(C=O)R$^{8a}$, NR$^{8a}$S(O)R$^{8a}$, NR$^{8a}$SO$_2$R$^{8a}$, O(C=O)NR$^{6a}$R$^{7a}$, O(C=O)OR$^{8a}$, O(C=O)R$^{8a}$, (C=O)OR$^{8a}$, and 5-6-membered heteroaryl;

R$^{b5}$ is, at each instance, independently selected from the group consisting of:
C$_6$-C$_{10}$ aryl substituted by 0 to 3 R$^{a1}$ groups, and
6- to 10-membered heteroaryl substituted by 0 to 3 R$^{a1}$ groups, R$^{6a}$ and R$^{7a}$ are, at each occurrence, independently selected from the group consisting of:
H,
C$_1$-C$_6$ alkyl, independently substituted with 1 to 5 fluorines, hydroxyl, C$_1$-C$_4$ alkoxy, C$_3$-C$_6$ cycloalkyl, or amino, and
—(CH$_2$)$_n$-phenyl independently substituted with 1 to 3 fluorines, hydroxyl,
C$_1$-C$_4$ alkoxy, fluoro-C$_1$-C$_2$ alkoxy, C$_3$-C$_6$ cycloalkyl, or amino, alternatively, R$^{6a}$ and R$^{7a}$, when attached to the same nitrogen, combine to form a 4- to 6-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;

R$^{8a}$ and R$^{9a}$ are, at each occurrence, independently selected from the group consisting of:
H,
C$_1$-C$_6$ alkyl independently substituted with 1 to 5 fluorines, hydroxyl, C$_1$-C$_4$ alkoxy, C$_3$-C$_6$ cycloalkyl, or amino, and
—(CH$_2$)$_n$-phenyl independently substituted with 1 to 3 fluorines, hydroxyl, C$_1$-C$_4$ alkoxy, fluoro-C$_1$-C$_2$ alkoxy, C$_3$-C$_6$ cycloalkyl, or amino;

R$^c$ is independently, at each occurrence, selected from the group consisting of H, C$_1$-C$_6$ alkyl, and —(CH$_2$)$_n$-phenyl;
n, at each occurrence, is selected from 0, 1, 2, 3 and 4;
p, at each occurrence, is selected from 0, 1 and 2; and
s, at each occurrence, is selected from 0, 1, 2 and 3,
provided that when R$^1$ is Br, R$^{10}$ is other than unsubstituted

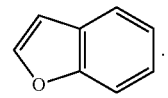

In some embodiments, the present invention provides compounds, stereoisomers, tautomers, salts, solvates or prodrugs thereof, wherein:
R$^x$ is Y—Z— which is:
C$_6$-C$_{10}$ aryl substituted with 0 to 2 R$^{a5}$ groups;
C$_6$-C$_{10}$-aryl-C$_1$-C$_4$-alkyl, wherein the aryl portion of which is independently substituted with 0 to 3 R$^{a5}$ groups, and the alkyl portion of which is independently substituted with 0 to 2 R$^{a1}$ groups;
C$_6$-C$_{10}$-aryl-C$_1$-C$_3$-alkyloxy, wherein the aryl portion of which is independently substituted with 0 to 3 R$^{a5}$ groups, and the alkyl portion of which is independently substituted with 0 to 2 R$^{a1}$ groups;
C$_6$-C$_{10}$-aryl-C$_1$-C$_3$-alkylthio, wherein the aryl portion of which is independently substituted with 0 to 3 R$^{a5}$ groups, and the alkyl portion of which is independently substituted with 0 to 2 R$^{a1}$ groups;
C$_6$-C$_{10}$ aryloxy substituted with 0 to 2 R$^{a5}$ groups;
C$_6$-C$_{10}$ arylthio substituted with 0 to 3 R$^{a5}$ groups;
C$_6$-C$_{10}$-aryl-C$_2$-C$_6$-alkynyl, wherein the aryl is substituted with 0 to 3 R$^{a5}$ groups and the alkynyl is substituted with 0 to 3 R$^{a1}$ groups;
4- to 10-membered ring heterocyclyl substituted with 0 to 3 R$^{a5}$ groups;
4- to 10-membered ring heterocyclyl-C$_1$-C$_4$-alkyl, wherein the heterocyclo portion of which is independently substituted with 0 to 3 R$^{a5}$ groups, and the alkyl portion of which is independently substituted with 0 to 2 R$^{a1}$ groups;
4- to 10-membered ring heterocyclyl-C$_1$-C$_4$-alkyloxy, wherein the heterocyclo portion of which is independently substituted with 0 to 3 R$^{a5}$ groups, and the alkyl portion of which is independently substituted with 0 to 2 R$^{a1}$ groups;
4- to 10-membered ring heterocyclyl-C$_1$-C$_4$-alkylthio, wherein the heterocyclo portion of which is independently substituted with 0 to 3 R$^{a5}$ groups, and the alkyl portion of which is independently substituted with 0 to 2 R$^{a1}$ groups;
4- to 10-membered ring heterocyclyloxy substituted with 0 to 3 R$^{a5}$ groups;
4- to 10-membered ring heterocyclylthio substituted with 0 to 3 R$^{a5}$ groups;
6- to 10-membered ring heteroaryl, wherein the heteroaryl portion of which is independently substituted with 0 to 3 R$^{a5}$ groups;

6- to 10-membered ring heteroaryl-$C_1$-$C_4$-alkyl, wherein the heteroaryl portion of which is independently substituted with 0 to 3 $R^{a5}$ groups, and the alkyl portion of which is independently substituted with 0 to 2 $R^{a1}$ groups;

6- to 10-membered ring heteroaryl-$C_1$-$C_4$-alkyloxy, wherein the heteroaryl portion of which is independently substituted with 0 to 3 $R^{a5}$ groups, and the alkyl portion of which is independently substituted with 0 to 2 $R^{a1}$ groups, 5- to 10-membered ring heteroaryloxy substituted with 0 to 3 $R^{a5}$ groups;

5- to 10-membered ring heteroarylthio substituted with 0 to 3 $R^{a5}$ groups;

5- to 10-membered heteroaryl-$C_3$-$C_6$-alkynyl, wherein the heteroaryl portion is substituted with 0 to 2 $R^{a5}$ groups, and the alkynyl is substituted with 0 to 3 $R^{a1}$ groups;

$C_1$-$C_4$-alkyloxy-$C_1$-$C_4$-alkyl($C_1$-$C_4$-alkyl)amino;

$C_3$-$C_6$ cycloalkyl substituted with 0 to 2 $R^{a5}$ groups;

$C_3$-$C_6$-cycloalkyl-$C_1$-$C_4$-alkyl, wherein the cycloalkyl portion is substituted with 0 to 2 $R^{a5}$ groups and the alkyl portion is independently substituted with 0 to 2 $R^{a1}$ groups;

$C_3$-$C_6$-cycloalkyl-$C_1$-$C_4$-alkyloxy, wherein the cycloalkyl portion is substituted with 0 to 2 $R^{a5}$ groups and the alkyl portion is independently substituted with 0 to 2 $R^{a1}$ groups;

$C_3$-$C_6$-cycloalkyl-$C_1$-$C_4$-alkylthio, wherein the cycloalkyl portion is substituted with 0 to 2 $R^{a5}$ groups and the alkyl portion is independently substituted with 0 to 2 $R^{a1}$ groups;

$C_3$-$C_6$ cycloalkyloxy substituted with 0 to 2 $R^{a5}$ groups;

$C_3$-$C_6$ cycloalkylthio substituted with 0 to 2 $R^{a5}$ groups;

$C_1$-$C_4$-alkyloxy-$C_1$-$C_4$-alkyloxy, wherein each alkyl portion of which is independently substituted with 0 to 2 $R^{a1}$ groups;

cyano-$C_1$-$C_4$-alkyloxy substituted with 0 to 2 $R^{a1}$ groups, or di-$C_1$-$C_4$-alkylamino-$C_1$-$C_4$-alkyloxy, wherein each alkyl portion of which is independently substituted with 0 to 2 $R^{a1}$ groups; or $R^x$ is any of the acyclic $R^x$ groups set out hereinbefore.

In some embodiments, the present invention provides compounds, stereoisomers, tautomers, salts, solvates or prodrugs thereof, wherein $R^1$ is halo, which is Br or Cl,
methyl,
ethyl,
$C_1$-$C_2$ alkoxy,
cyclopropyl,
$CH_3S$,

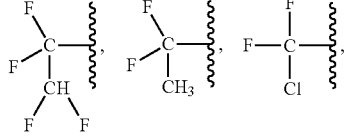

and

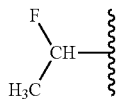

including

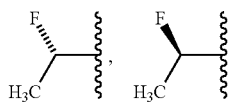

or a mixture thereof; and $R^2$ is H.

In some embodiments, the present invention provides compounds, stereoisomers, tautomers, salts, solvates or prodrugs thereof, wherein $R^{10}$ is

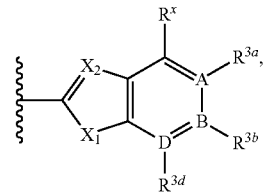

wherein:
$X_1$ is O and $X_2$ is N, or
$X_1$ is O and $X_2$ is $CR^5$, or
$X_1$ is S and $X_2$ is N, or
$X_1$ is S and $X_2$ is $CR^5$.

In some embodiments, the present invention provides compounds, stereoisomers, tautomers, salts, solvates or prodrugs thereof, wherein in $R^{10}$
$X_1$ represents O or S;
$X_2$ represents CH or N;
A, B and D are each carbon;
$R^{1a}$, $R^{3b}$ and $R^{3d}$ are independently selected from any of the $R^3$ groups.

In some embodiments, the present invention provides compounds, stereoisomers, tautomers, salts, solvates or prodrugs thereof, wherein:
$R^1$ is
$CH_3O$,

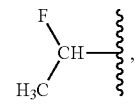

or

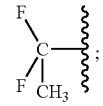

and
$R^2$ is H.

In some embodiments, the present invention provides compounds, stereoisomers, tautomers, salts, solvates or prodrugs thereof, wherein $R^{10}$ is

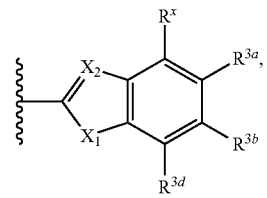

wherein:
$X_1$ is O or S,
$X_2$ is CH, $CR^5$ or N, and wherein $R^{3a}$, $R^{3b}$ and $R^{3d}$ are independently selected from any of the $R^3$ groups set out above.

In some embodiments, the present invention provides compounds, stereoisomers, tautomers, salts, solvates or prodrugs thereof, wherein $R^{10}$ is

A

[Structure with phenyl bearing $(R^{a5})_s$, O-$R^{a1}$ linker to benzofuran with $R^{3a}$, $R^{3b}$, $R^{3d}$]

or

B

[Structure with phenyl bearing $(R^{a5})_s$, O-$R^{a1}$ linker to benzoxazole with $R^{3a}$, $R^{3b}$, $R^{3d}$]

where each $R^{a5}$ group is independently selected.

In some embodiments, the present invention provides compounds, stereoisomers, tautomers, salts, solvates or prodrugs thereof, wherein:

$R^{10}$ is

C

[Structure with phenyl bearing $(R^{a5})_{1\,to\,3}$, O-$R^{a1}$ linker to benzofuran with $R^{3b}$]

$R^{3b}$ is
H,
F,
Cl,
OMe,
OEt,
OCF$_3$, or
OCHF$_2$, or

D

[Structure with phenyl bearing $(R^{a5})_{1\,to\,3}$, O-$R^{a1}$ linker to benzoxazole with $R^{3b}$]

where each $R^{a5}$ group is independently selected; and $R^{3b}$ is
H,
F,
Cl,
OMe,
OEt,
OCF$_3$, or
OCHF$_2$.

In some embodiments, the present invention provides compounds, stereoisomers, tautomers, salts, solvates or prodrugs thereof, wherein:

$R^{10}$ is the benzofuran in Formula A and C, wherein $R^{3b}$ is OMe;

$R^{a1}$ is H; and $R^{a5}$ is independently selected from:
H,
F,
Cl,
CF$_3$,
OCF$_3$,
OCHF$_2$,
OCH$_3$, or
OC$_6$H$_5$, optionally substituted with 1 to 2 $R^{a5a}$ substituents, where $R^{a5a}$ is independently selected from:
F,
Cl,
CF$_3$,
OCF$_3$,
OCHF$_2$, or
OCH$_3$, or $R^{a5}$ is OCH$_2$C$_6$H$_5$ optionally substituted with 1 to 2 $R^{a5a}$ substituents, where $R^{a5a}$ is independently selected from:
F,
Cl,
CF$_3$,
OCF$_3$,
OCHF$_2$, or
OCH$_3$.

In some embodiments, the present invention provides compounds, stereoisomers, tautomers, salts, solvates or prodrugs thereof, wherein $R^{10}$ is

[Structure with bicyclic $X_1$, $X_2$ ring fused to benzene bearing $R^x$, $R^{3a}$, $R^{3b}$, $R^{3d}$]

and
wherein
R$^x$ is selected from:
hydrogen,
halo, which is Cl, Br or F,
fluoro-C$_1$-C$_4$-alkyl, which is —CF$_3$ or —CF$_2$CF$_3$,
fluoro-C$_1$-C$_4$-alkoxy, which is —OCF$_3$, —OCF$_2$CF$_2$H, —OCF$_2$CF$_3$, or —OCF$_2$,
NH$_2$,
OH,
NO$_2$,
C$_1$-C$_6$ alkyl substituted with 0 to 2 R$^{a1}$ groups,
C$_1$-C$_6$ alkoxy substituted with 0 to 2 R$^{a1}$ groups,
phenylalkoxy, wherein the phenyl is substituted with 0 to 2 R$^{a5}$ groups,
C$_1$-C$_4$-alkoxy-C$_1$-C$_4$-alkyl(C$_1$-C$_4$-alkyl)amino;
phenylethynyl,
cyanomethoxy,
cycloalkylalkyloxy,
cycloalkyloxy,
N-pyrrolidinylalkyloxy,
N-morpholinylalkyloxy,
phenoxy,
carbonyl,
benzylaminocarbonyl, and
benzyl;
which R$^{a1}$ groups are independently selected from:
  C$_1$-C$_2$ alkyl,
  benzyl,
  phenyl,
  benzyloxy,
  C$_1$-C$_2$ alkoxy,
  C$_1$-C$_2$ alkoxycarbonyl,
  cyano,
  cyclohexyl,
  cyclohexyloxy,
  cyclobutyloxy, or
  halo, which is Cl;
R$^1$ is
CH$_3$O,

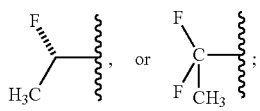

R$^2$ is H; and
R$^{3a}$, R$^{3b}$ and R$^{3d}$ are the same or different and are independently selected from:
hydrogen,
halo, which is Cl, Br or F,
fluoro-C$_1$-C$_4$-alkyl, which is —CF$_3$ or —CF$_2$CF$_3$,
fluoro-C$_1$-C$_4$-alkoxy, which is —OCF$_3$, —OCF$_2$CF$_2$H, —OCF$_2$CF$_3$ or —OCF$_2$,
NH$_2$,
OH,
NO$_2$,
C$_1$-C$_6$ alkyl substituted with 0 to 2 R$^{a1}$ groups,
C$_1$-C$_6$ alkoxy substituted with 0 to 2 R$^{a1}$ groups,
phenylalkoxy, wherein the phenyl is substituted with 0 to 2 R$^{a5}$ groups, or
4- to 10-membered heterocyclo-C$_1$-C$_4$-alkoxy, wherein the heterocyclo is substituted with 0 to 2 R$^{a5}$ groups.

In some embodiments, the present invention provides compounds, stereoisomers, tautomers, salts, solvates or prodrugs thereof, wherein R$^{10}$ is

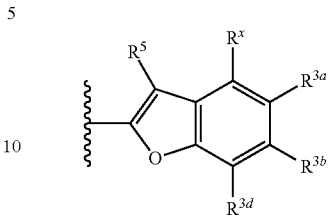

which is selected from:

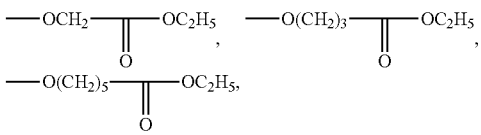
(1)

wherein R$^x$ is
H,
OCH$_3$,
OC$_2$H$_5$,
O-n-C$_3$H$_7$,
O-i-C$_3$H$_7$,
O-n-C$_4$H$_9$,
O-t-C$_4$H$_9$, —OCH$_2$—C(O)—OC$_2$H$_5$,  —O(CH$_2$)$_3$—C(O)—OC$_2$H$_5$,
—O(CH$_2$)$_5$—C(O)—OC$_2$H$_5$, —O(CH$_2$)$_3$OCH$_3$,
OCH$_2$C$_6$H$_5$,
—O(CH$_2$)$_3$—CN,
OCH$_2$CN,
—OCH$_3$,
OH,
CH$_3$,
C$_2$H$_5$,
—C$_3$H$_7$,
t-C$_4$H$_9$,
Cl,
Br,
F,
OCF$_3$,
OCH$_2$C$_6$H$_5$—F-m,
OCH$_2$C$_6$H$_5$—CH$_3$-p, or
OCH$_2$C$_6$H$_5$CN-m;

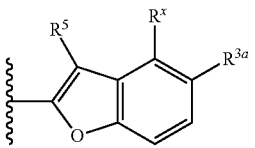
(2)

wherein $R^x$ and $R^{3a}$ are each independently —OCH$_3$ or CH$_3$ and $R^5$ is H, CH$_3$ or Br;

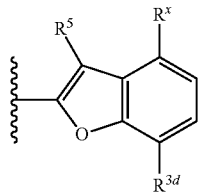  (3)

wherein $R^x$ and $R^{3d}$ are each —OCH$_3$ or $R^x$ is OCH$_3$ and $R^{3d}$ is Br;

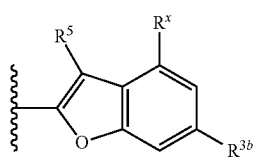  (4)

wherein:
$R^x$ is CH$_3$O and $R^{3b}$ is F, or
$R^x$ is OH and $R^{3b}$ is CH$_3$O, or
$R^x$ is Br and $R^{3b}$ is CH$_3$O, or
$R^x$ is CH$_3$O and $R^{3b}$ is Br;

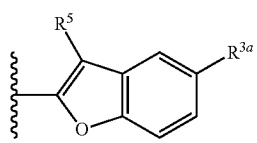  (5)

wherein $R^{3a}$ is
—CH$_3$,
—OCH$_3$,
NO$_2$,
Cl,
F, or

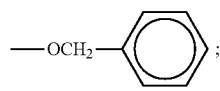;

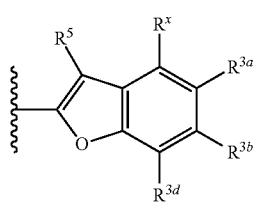  (6)

wherein $R^x$, $R^{3a}$, $R^{3b}$ and $R^{3d}$ are as follows:

| $R^x$ | $R^{3a}$ | $R^{3b}$ | $R^{3d}$ |
|---|---|---|---|
| CH$_3$O | H | H | H |
| H | CH$_3$O | H | H |
| CH$_3$O | H | CH$_3$O | H |
| H | H | CH$_3$O | H |
| H | H | Cl | H |

-continued

| $R^x$ | $R^{3a}$ | $R^{3b}$ | $R^{3d}$ |
|---|---|---|---|
| H | F | H | H |
| C$_6$H$_5$CH$_2$O— | H | CH$_3$O | H |
| Cl | H | Cl | H |
| H | Cl | CH$_3$O | H |
| H | F | CH$_3$O | H |
| C$_6$H$_5$(CH$_2$)$_2$ | H | CH$_3$O | H |
| 3-Cl-C$_6$H$_4$-CH$_2$O— | H | CH$_3$O | H |
| C$_6$H$_5$-CH$_2$-O-C$_6$H$_4$-CH$_2$O— | H | CH$_3$O | H |
| CH$_3$OCH$_2$CH$_2$N(CH$_3$)— | H | CH$_3$O | H |
| H | F | F | H |
| C$_6$H$_5$-CH$_2$-O-C$_6$H$_4$-CH$_2$O— | H | CH$_3$O | H |
| H | F | H | CH$_3$O |
| 3-CN-C$_6$H$_4$-CH$_2$O— | H | CH$_3$O | H |
| F | H | CH$_3$O | H |
| 3,5-(CH$_3$)$_2$-C$_6$H$_3$-CH$_2$O— | H | CH$_3$O | H |

(7)

wherein
$R^{3a}$ is Br, F, OCH$_3$, CH$_3$, OCH$_3$, Cl, NO$_2$, or

—OCH$_2$-C$_6$H$_5$, and
$R^5$ is H, or
$R^{3a}$ is OCH$_3$, and
$R^5$ is CH$_3$, or
$R^{3a}$ is H, and
$R^5$ is Br;

(8)

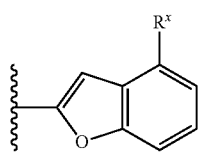

wherein R$^x$ is
OCH$_3$,
CH$_3$,
OCH$_2$CN,

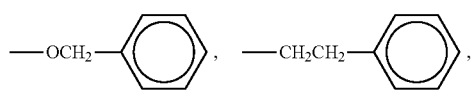

Cl,
OH, or
—OCH$_2$OCH$_3$;

(9)

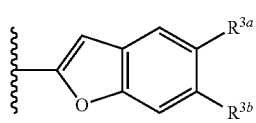

wherein R$^{3a}$ and R$^{3b}$ are as follows:

| R$^{3a}$ | R$^{3b}$ |
|---|---|
| CH$_3$O | Cl |
| CH$_3$O | C$_6$H$_5$O |
| CH$_3$ | Cl |
| CH$_3$O | Br | or (10)

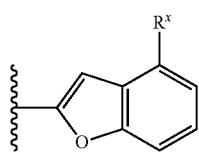

where:
R$^x$ is:

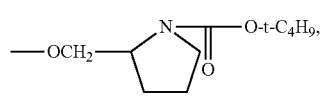

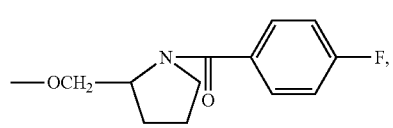

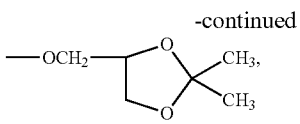

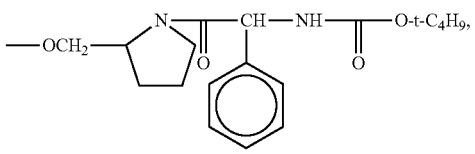

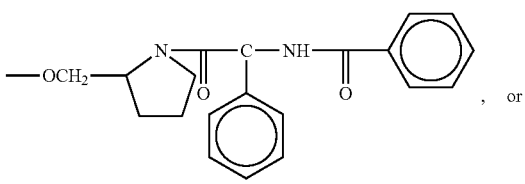

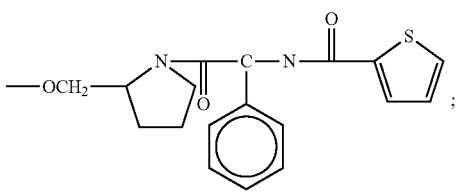

and
where R$^1$ is CH$_3$O or CH$_3$S.

In some embodiments, the present invention provides compounds, stereoisomers, tautomers, salts, solvates or prodrugs thereof, wherein R$^{10}$ is which is selected from:

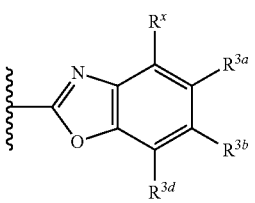

(1)

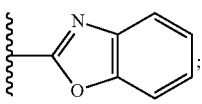

(2)

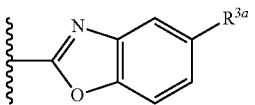

where R$^{3a}$ is
CH$_3$,
t-C$_4$H$_9$,
Br,
Cl,
F,
OCF$_3$,

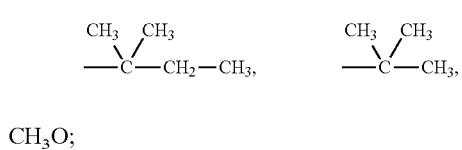
CH₃O;
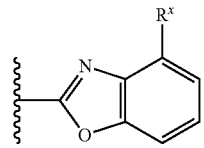
where R$^x$ is
CH₃,
OH,
OCH₃,
OC₂H₅,
O-i-C₃H₇,
OCH₂OCH₃,
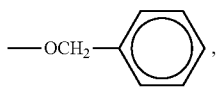
NH₂,
NO₂,

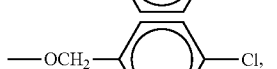, 
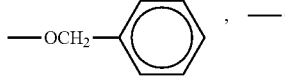

, or ;
and
R¹ is CH₃S or CH₃O;
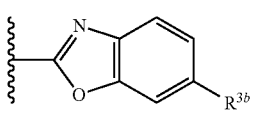
where R$^{3b}$ is
—CH₃,
—OCH₃,
—OC₂H₅—,
O-i-C₃H₇,
—O-s-C₄H₉,
—O-n-C₄H₉,
O—C₃H₇,
—O-i-C₄H₉,
(3)
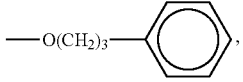
—OCH₂OCH₃,
—O(CH₂)₂F,
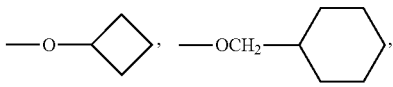
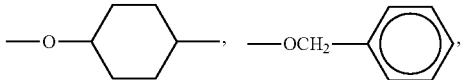
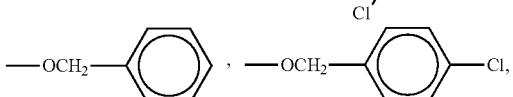
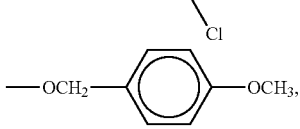
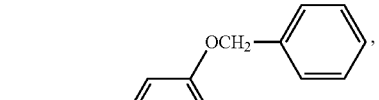
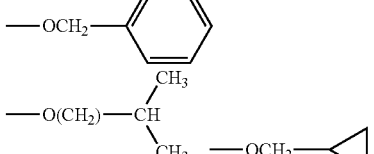
NH₂,
F,
OH,
Cl,
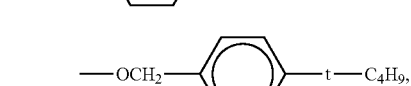
OCF₃,
(4)
, 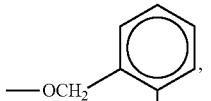

-continued

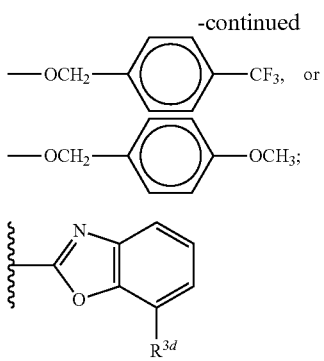

where $R^{3d}$ is
CH$_3$,
F, or

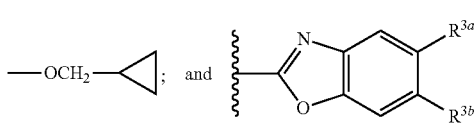

where $R^{3a}$ and $R^{3b}$ are as follows:

| $R^{3a}$ | $R^{3b}$ |
|---|---|
| CH$_3$ | CH$_3$ |
| F | F |
|  | CH$_3$ |
| phenyl |  |
| CH$_3$O | CH$_3$O |

In some embodiments, the present invention provides compounds, stereoisomers, tautomers, salts, solvates or prodrugs thereof, wherein $R^{10}$ is

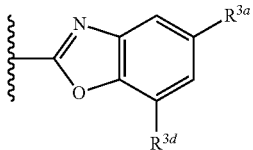

where $R^{3a}$ and $R^{3d}$ are each CH.

In some embodiments, the present invention provides compounds, stereoisomers, tautomers, salts, solvates or prodrugs thereof, wherein $R^{10}$ is

wherein:
$R^x$ is

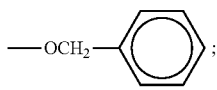

$R^{3b}$ is CH$_3$O; or
$R^x$ or $R^{3b}$ are each CH$_3$O.

In some embodiments, the present invention provides compounds, stereoisomers, tautomers, salts, solvates or prodrugs thereof, wherein $R^{10}$ is

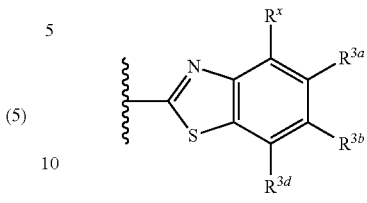

which is selected from:

(1)

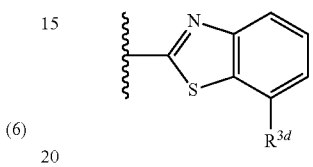

where $R^{3d}$ is OCH$_3$;

(2)

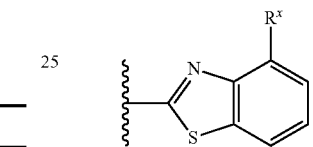

where $R^x$ is
Cl,
F,
CH$_3$O,
CH$_3$, or
OCF$_3$;

(3)

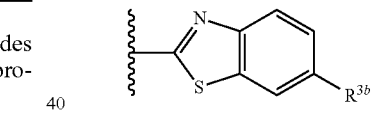

where $R^{3b}$ is
Cl,
F,
CH$_3$, or
OCF$_3$;

(4)

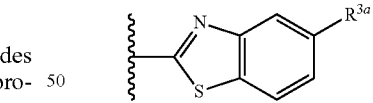

where $R^{3a}$ is F; or (5)

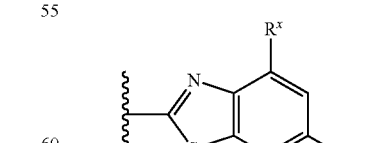

where
$R^x$ is OCH$_3$ and $R^{3c}$ is OCH$_3$ or
$R^{3b}$ is CH$_3$ and $R^{3c}$ is Cl.

In some embodiments, the present invention provides compounds, stereoisomers, tautomers, salts, solvates or prodrugs thereof, wherein $R^{10}$ is

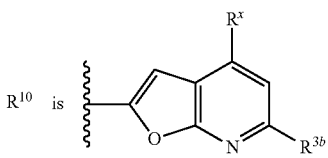

where $R^x$ and $R^{3b}$ are independently selected from $C_1$-$C_4$ alkyl such as $CH_3$ or haloalkyl such as $CF_3$; and

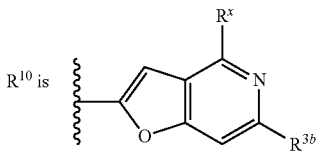

where $R^{3b}$ is halo such as Cl.

In some embodiments, the present invention provides compounds, stereoisomers, tautomers, salts, solvates or prodrugs thereof, wherein $R^{10}$ is

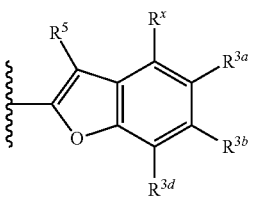

which is selected from the group consisting of (1)

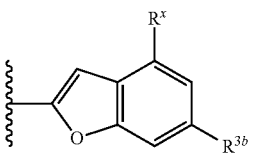

wherein:
$R^x$ is

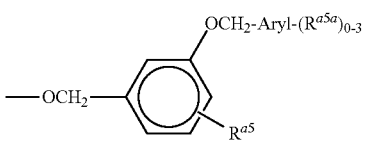

where
Aryl is phenyl or naphthyl,
$R^{a5}$ is
H,
halo, such as F or Cl,
$C_1$-$C_4$ alkyl, such as $CH_3$,
$C_1$-$C_4$ alkoxy, such as $CH_3O$, or
halo-$C_1$-$C_4$-alkyl, such as $CF_3$, and
$R^{a5a}$ is
H,
halo, such as F, Cl, Br or I,
$C_1$-$C_4$ alkyl, such as $CH_3$ or $t$-$C_4C_9$,
$C_1$-$C_4$ alkoxy, such as $CH_3O$, halo-$C_1$-$C_4$-alkoxy, such as $OCF_3$,
halo-$C_1$-$C_4$-alkyl, such as $CF_3$,
benzyloxy, or
phenoxy,
$R^{3b}$ is
halo, such as F or Cl,
$C_1$-$C_4$ alkoxy, such as $OCH_3$ or $OC_2H_5$,
H,
—OS(=O)$_2$CF$_3$,
halo-$C_1$-$C_4$-alkoxy, such as $OCF_2$,
—OCH=O,
—C≡CH, or
—NHC(=O)CH$_3$,
$R^5$ is H,
$R^2$ is H, and
$R^1$ is
$C_1$-$C_4$ alkyl, such as $CH_3$,
$C_1$-$C_4$ alkoxy, such as $CH_3O$ or $C_2H_5O$,
$C_1$-$C_4$ alkylthio, such as $CH_3S$,
halo-$C_1$-$C_4$-alkyl, such as $CF_2(CH_3)$ or $F(CH_3)CH$, or
halo, such as Cl;

(2) $R^{10}$ is

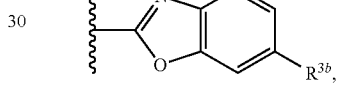

where $R^{3b}$ is 4- to 10-membered heterocyclo-$C_1$-$C_4$-alkoxy, such as (1)

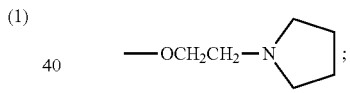

and
(3) $R^{10}$ is

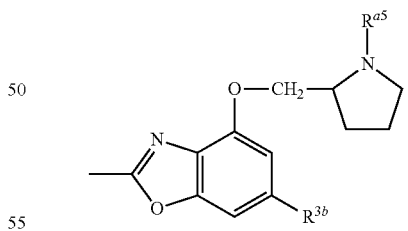

where $R^{a5}$ is:
$C_1$-$C_4$ alkoxycarbonyl, such as

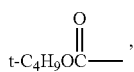

$C_1$-$C_4$-alkoxycarbonylamino-$C_1$-$C_4$-alkyl(phenyl)carbonyl, such as

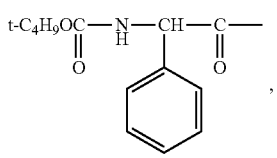, $C_6$-$C_{10}$-heteroarylcarbonylamino-$C_1$-$C_4$-alkyl(phenyl)carbonyl, such as

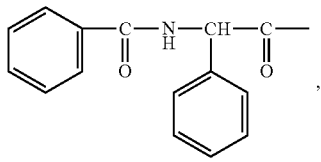 [SMILES: CC(=O)C(NC(=O)c1ccccc1)c1ccccc1], $C_5$-$C_{10}$-heteroarylcarbonylamino-$C_1$-$C_4$-alkyl(phenyl)carbonyl, such as

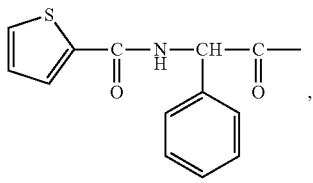 [SMILES: CC(=O)C(NC(=O)c1cccs1)c1ccccc1], or $C_6$-$C_{10}$ arylcarbonyl substituted with 0 to 3 $R^{a5a}$ groups, such as

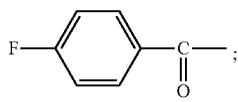;

$R^1$ is:
$C_1$-$C_4$ alkoxy, such as $CH_3O$, or
$C_1$-$C_4$ alkylthio, such as $CH_3S$, and
$R^{3b}$ is $C_1$-$C_4$ alkoxy, such as $CH_3O$; and

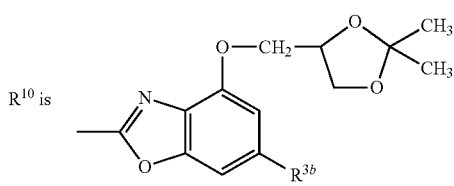 (4)

where $R^{3b}$ is $CH_3O$.

In some embodiments, the present invention provides compounds, stereoisomers, tautomers, salts, solvates or prodrugs thereof, wherein $R^1$ is $C_1$-$C_4$ alkoxy, such as $CH_3O$, or $C_1$-$C_4$ alkyl, such as $CH_3$,
$R^2$ is H; and
$R^{10}$ is

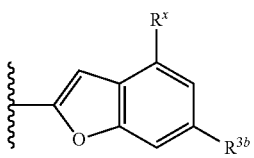

where
$R^{3b}$ is $C_1$-$C_4$ alkoxy, such as $CH_3O$, and
$R^x$ is

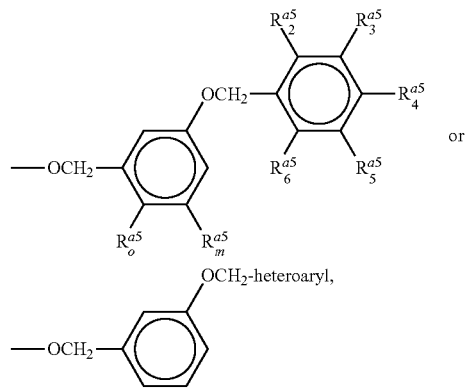 or

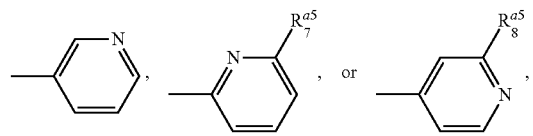

where heteroaryl is, for example

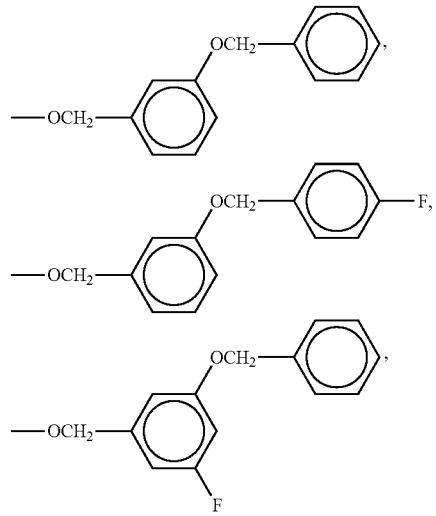

$R_m^{a5}$ is H, halo, such as F, or $C_1$-$C_4$ alkoxy, such as $CH_3O$,
$R_o^{a5}$ is H or $C_1$-$C_4$ alkoxy, such as $CH_3O$,
$R_2^{a5}$ is H, $C_1$-$C_4$ alkoxy, such as $CH_3O$, $C_1$-$C_4$ alkyl, such as $CH_3$, or halo, such as F,
$R_3^{a5}$ is H, $C_1$-$C_4$ alkoxy, such as $CH_3O$, halo-$C_1$-$C_4$-alkyl, such as $CF_3$, or halo, such as F,
$R_4^{a5}$ is H, halo, such as F, or $C_1$-$C_4$ alkoxy, such as $CH_3O$,
$R_5^{a5}$ is H, halo, such as F, or $C_1$-$C_4$ alkyl, such as $CH_3$,
$R_6^{a5}$ is H,
$R_7^{a5}$ is H or $C_1$-$C_4$ alkyl, such as $CH_3$,
$R_8^{a5}$ is H or halo, such as Cl.
Examples of the above $R^x$ groups include

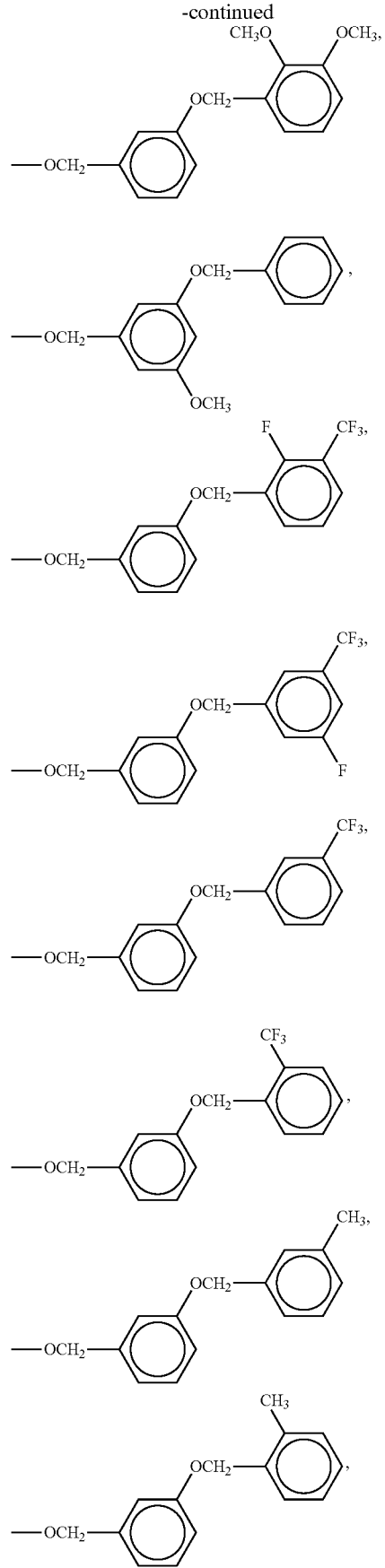
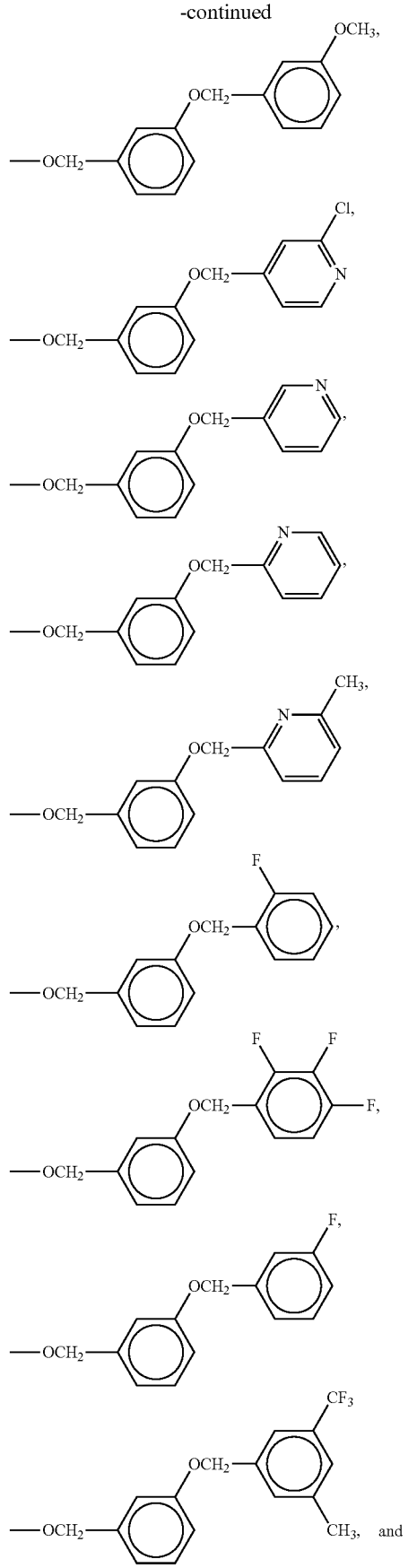

-continued

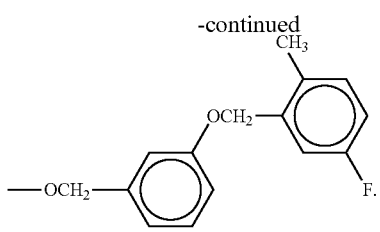

In some embodiments, the present invention provides compounds, stereoisomers, tautomers, salts, solvates or prodrugs thereof, wherein
$R^1$ is $C_1$-$C_4$ alkoxy, such as $CH_3O$;
$R^2$ is H;
$R^{10}$ is

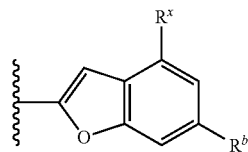

where $R^b$ is $C_1$-$C_4$ alkoxy, such as $CH_3O$;
$R^x$ is

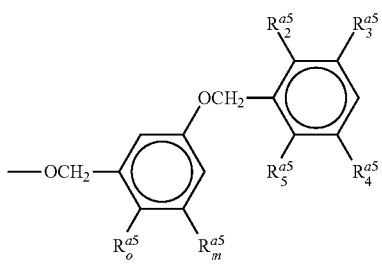

where
$R_m^{a5}$ is H or $C_1$-$C_4$ alkoxy, such as $CH_3O$,
$R_o^{a5}$ is H,
$R_2^{a5}$ is H, halo, such as F, $C_1$-$C_4$ alkoxy, such as $CH_3O$, or $C_1$-$C_4$ alkyl, such as $CH_3$,
$R_3^{a5}$ is H, halo, such as F, $C_1$-$C_4$ alkoxy, such as $CH_3O$, or $C_1$-$C_4$-alkyl, such as $CH_3$,
$R_4^{a5}$ is H,
$R_5^{a5}$ is H or halo, such as F, and
$R_6^{a5}$ is H
Examples of the above $R^x$ groups include

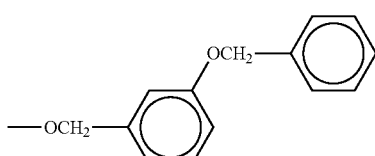

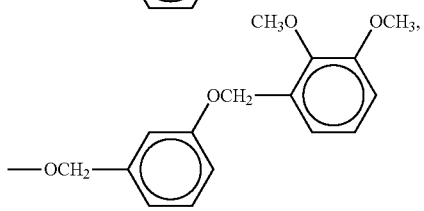

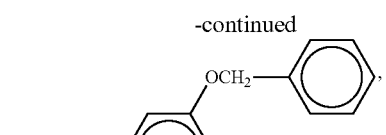

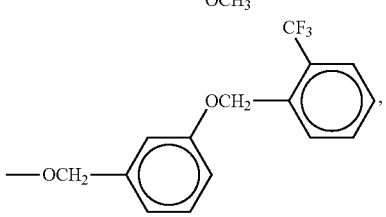

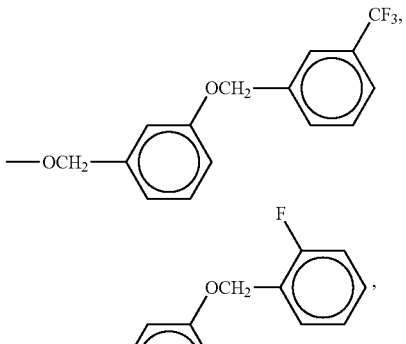

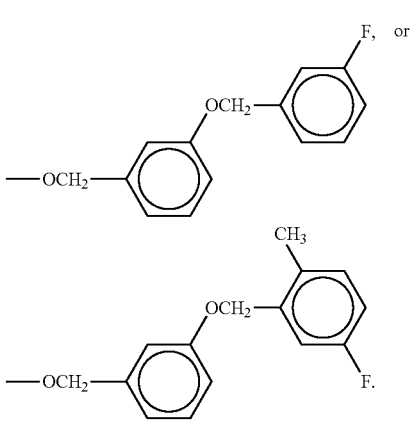

In yet another embodiment, the present invention provides compounds, stereoisomers, tautomers, salts, solvates or prodrugs thereof, wherein the compounds are selected from the examples.

It will be apparent that the Formula I compound of the invention

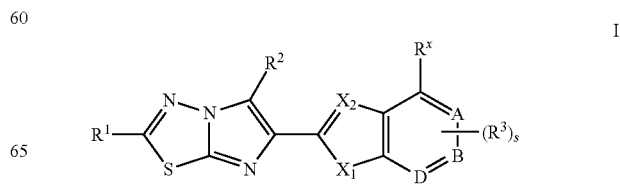

I may also be represented by the structure
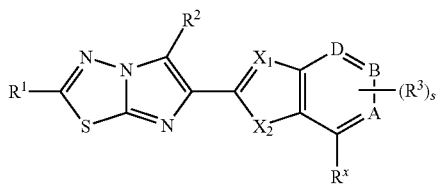
IA
and the Formula IB compound of the invention
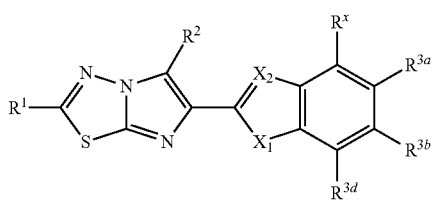
IB
may also be represented by the structure
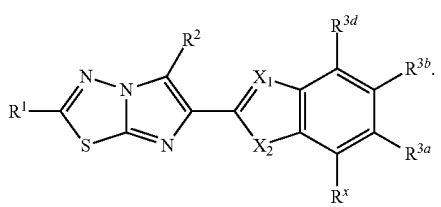
IC
In some embodiments, the present invention includes compounds of the invention having the structure:
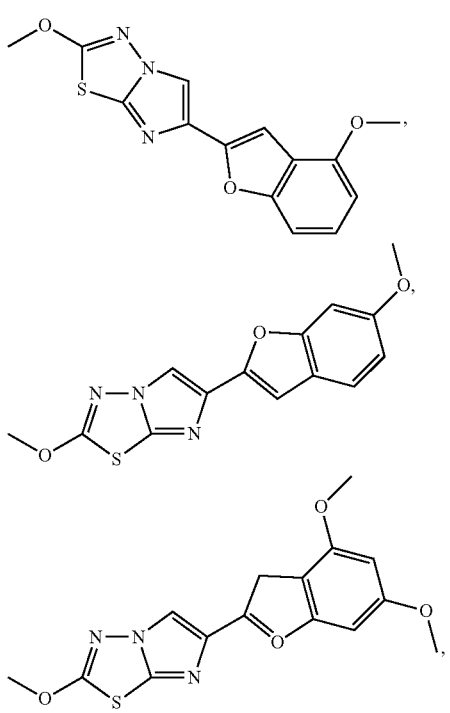
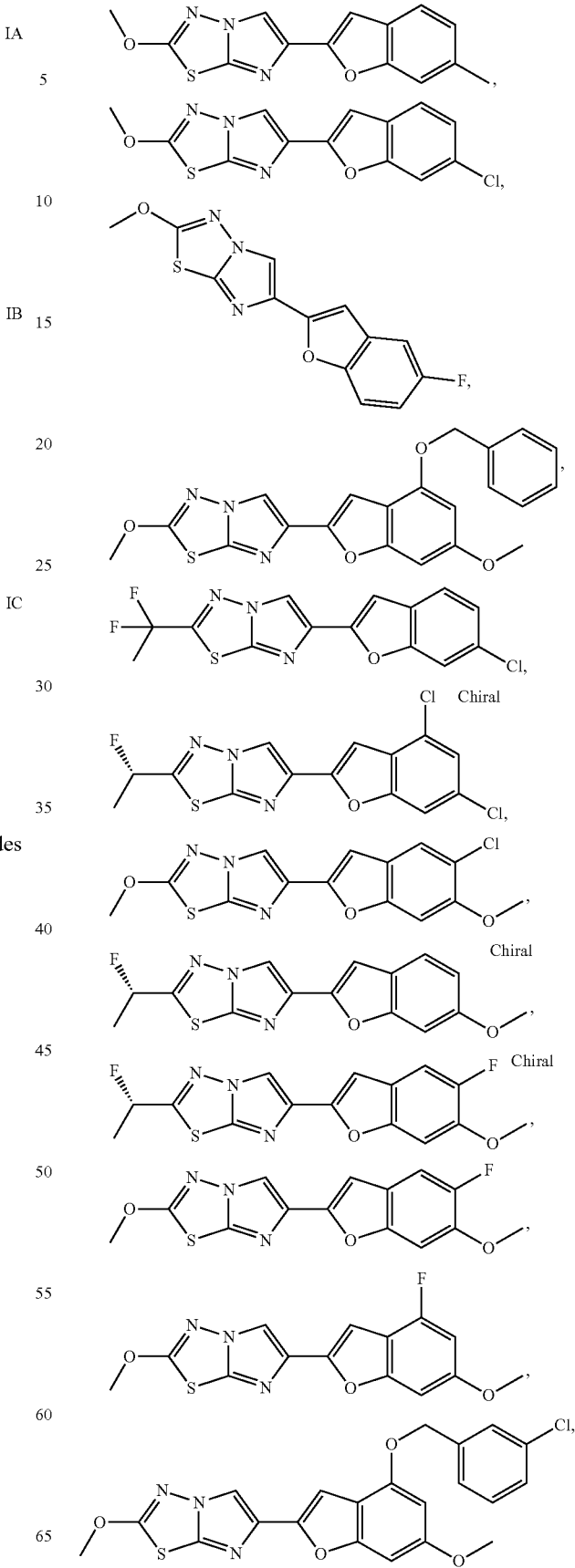

33
-continued
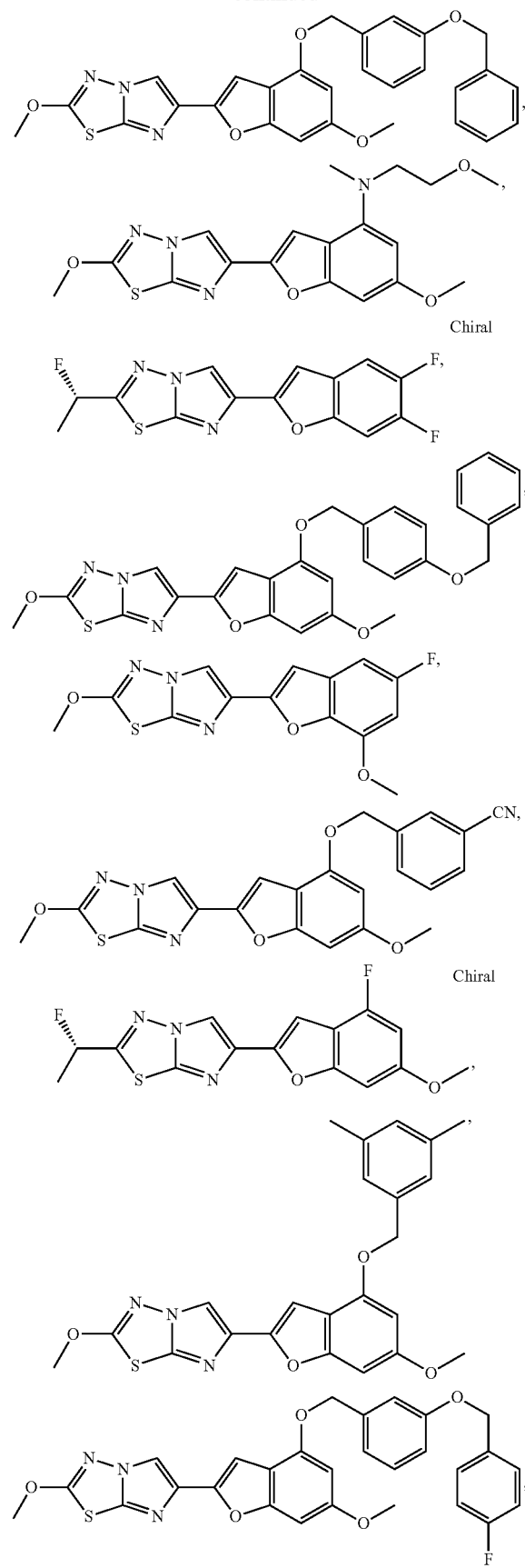
34
-continued
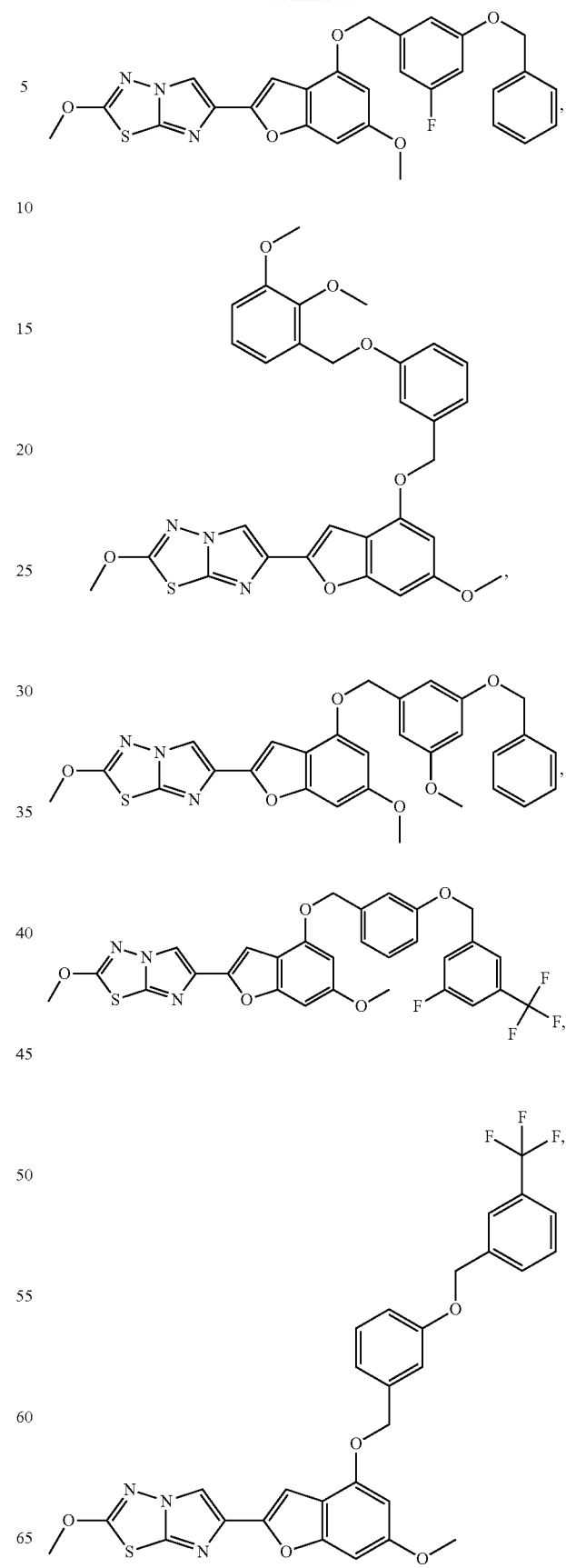

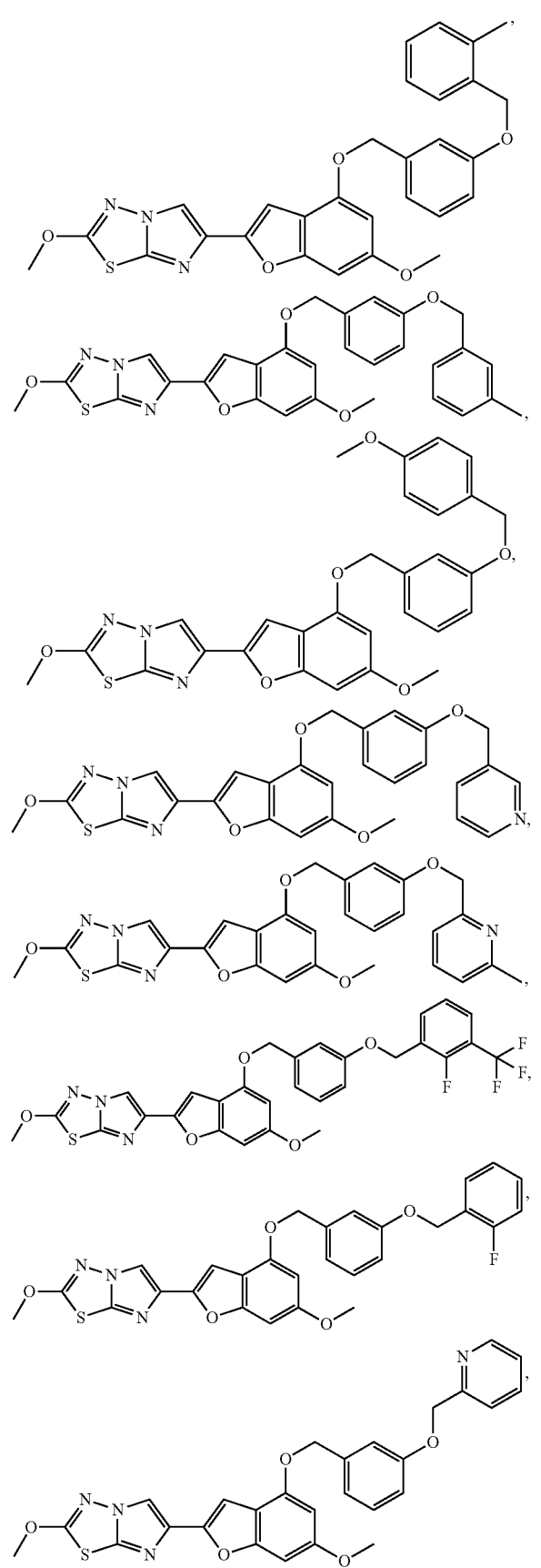
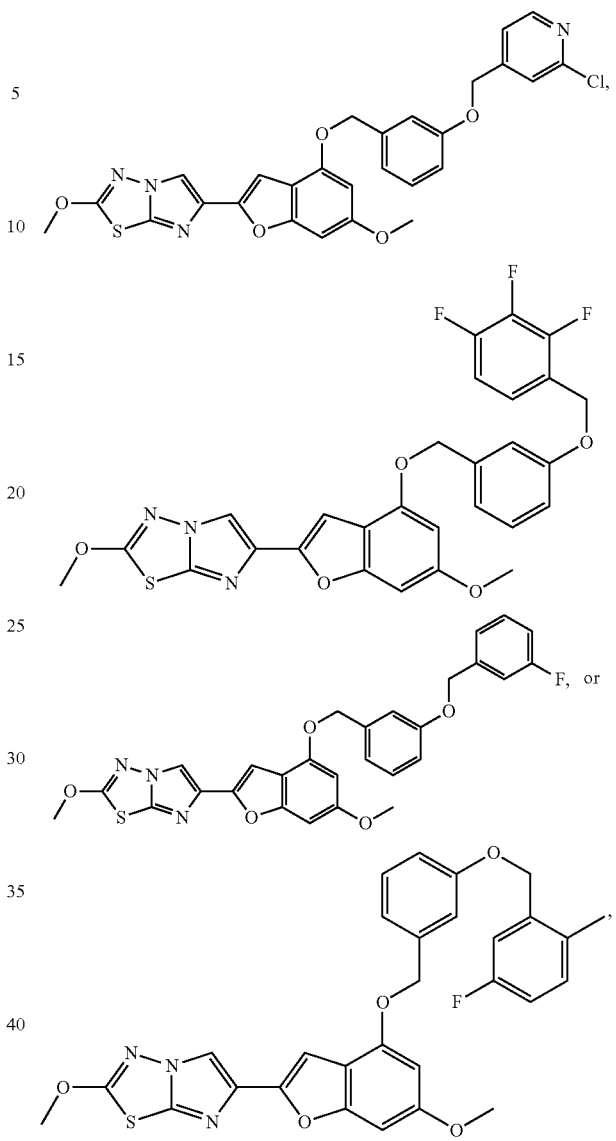
In some embodiments, the present invention includes compounds of the invention having the structure:
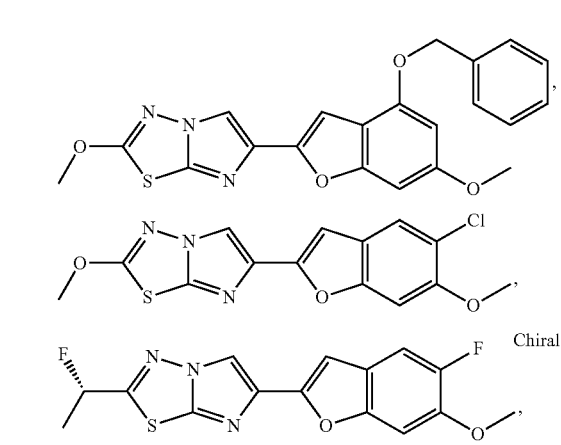

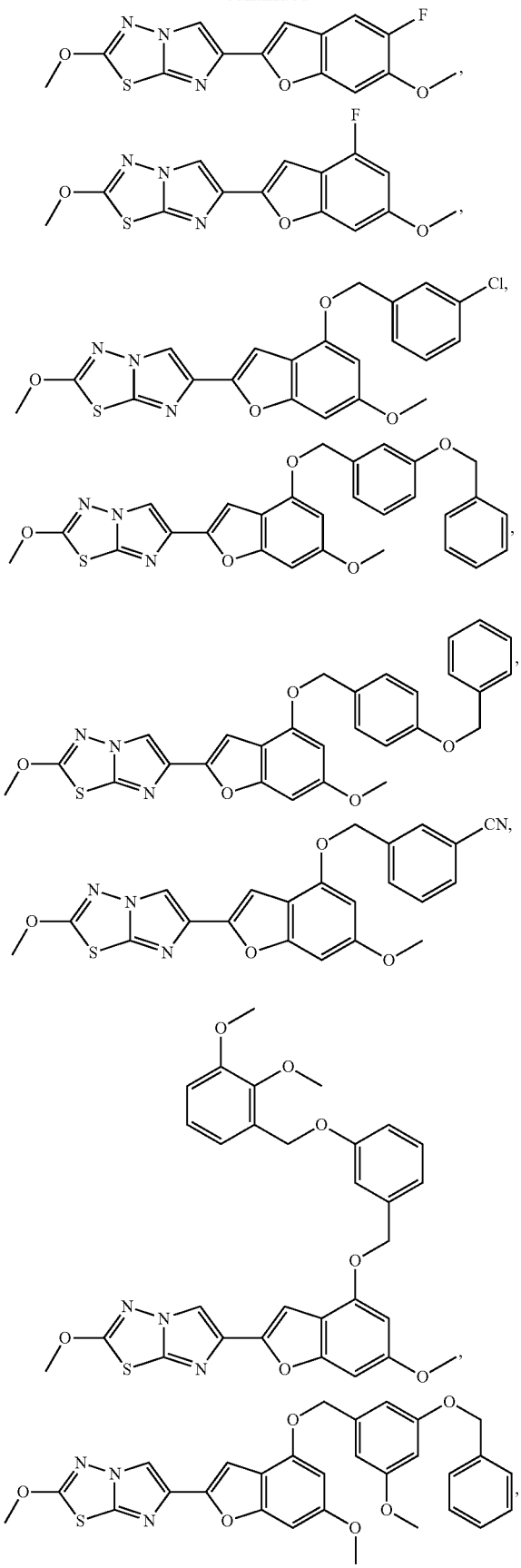

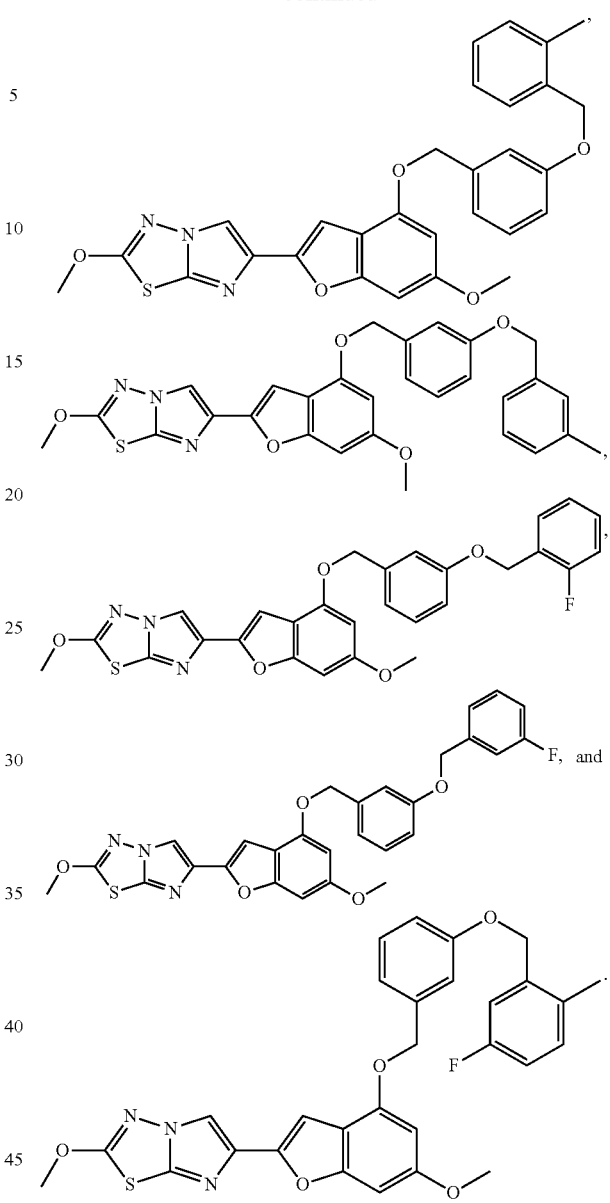

Preferably, PAR4 compounds of the invention have $IC_{50}$s in the FLIPR Assay (described hereinafter) of about 10 μM, preferably 5 μM or less, more preferably 500 nM or less, and even more preferably 10 nM or less. Activity data for compounds of the present invention is presented in the tables of Example F.

In some embodiments, the present invention provides at least one compound of the present invention or a stereoisomer, tautomer, pharmaceutically acceptable salt, solvate, or prodrug ester thereof.

In some embodiments, the present invention provides a pharmaceutical composition, which includes a pharmaceutically acceptable carrier and a therapeutically effective amount of a compound of Formula I, IA, IB or IC, preferably, a compound selected from one of the examples, or stereoisomers, tautomers, pharmaceutically acceptable salts, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors, FXIa inhibitors or thrombin inhibitors. Preferably, the FXa inhibitors are apixaban or rivaroxaban. Preferably, the thrombin inhibitor is dabigatran. For examples of FXIa inhibitors that may be useful in the present invention see International Patent Application Publication No. WO 2011/10040.

In some embodiments, the present invention provides a method for the treatment or prophylaxis of a thromboembolic disorder which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrug esters thereof.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB or IC, preferably, a compound selected from one of the examples, or stereoisomers, tautomers, pharmaceutically acceptable salts, prodrug esters, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB or IC, preferably, a compound selected from one of the examples, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB or IC, preferably, a compound selected from one of the examples, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, and non-ST-elevated myocardial infarction.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB or IC, preferably, a compound selected from one of the examples, or stereoisomers, tautomers, pharmaceutically acceptable salts, prodrug esters, or solvates thereof, wherein the thromboembolic disorder is selected from the group consisting of transient ischemic attack and stroke.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IA, IB or IC, preferably, a compound selected from one of the examples, or stereoisomers, tautomers, pharmaceutically acceptable salts, prodrug esters, or solvates thereof, wherein the thromboembolic disorder is peripheral arterial disease.

In some embodiments, the present invention includes a method as described above wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I, IA, IB or IC, preferably, a compound selected from one of the examples, of the invention.

Other Embodiments of the Invention

In some embodiments, the present invention provides a process for making a compound of the present invention or a stereoisomer, tautomer, pharmaceutically acceptable salt, solvate or prodrug ester thereof.

In some embodiments, the present invention provides an intermediate for making a compound of the present invention or a stereoisomer, tautomer, pharmaceutically acceptable salt, solvate or prodrug ester thereof.

In some embodiments, the invention provides a method of treatment or prophylaxis of a thromboembolic disorder involving administering to a subject in need thereof (e.g., a human) a therapeutically effective amount of a compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like as well as such groups which may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_1$-$C_4$ alkylene)N-$R_aR_b$, —$C(=O)NR_a(SO_2)R_b$, —$CO_2(C_1$-$C_4$ alkylene)$NR_aR_b$, —$NR_aC(=O)R_b$, —$NR_aCO_2R_b$, —$NR_a(C_1$-$C_4$ alkylene)$CO_2R_b$, =N—OH, =N—O-alkyl, wherein $R_a$ and $R_b$ are the same or different and are independently selected from hydrogen, alkyl, alkenyl, $CO_2H$, $CO_2(alkyl)$, $C_3$-$C_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of ($C_1$-$C_6$)alkyl, ($C_2$-$C_6$)alkenyl, hydroxy, halogen, cyano, nitro, $CF_3$, $O(C_1$-$C_6$ alkyl), $OCF_3$, $C(=O)H$, $C(=O)(C_1$-$C_6$ alkyl), $CO_2H$, $CO_2(C_1$-$C_6$ alkyl), $NHCO_2(C_1$-$C_6$ alkyl), —$S(C_1$-$C_6$ alkyl), —$NH_2$, $NH(C_1$-$C_6$ alkyl), $N(C_1$-$C_6$ alkyl)$_2$, $N(CH_3)_3^+$, $SO_2(C_1$-$C_6$ alkyl), $C(=O)(C_1$-$C_4$ alkylene)$NH_2$, $C(=O)(C_1$-$C_4$ alkylene)NH(alkyl), $C(=O)(C_1$-$C_4$ alkylene)N($C_1$-$C_4$ alkyl)$_2$, $C_3$-$C_7$ cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

"Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Haloalkyl" is intended to include both branched and straight-chain saturated aliphatic hydrocarbon groups having the specified number of carbon atoms, substituted with 1 to 7 halogens, preferably 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_2$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

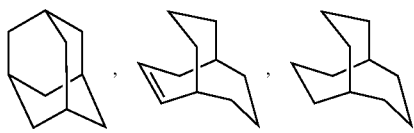

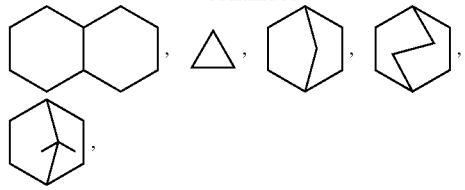

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $C_1$-$C_3$ alkyl, $CO_2H$, and $CO_2CH_3$.

As used herein, the term "heterocycle", "heterocyclo" or "heterocyclic" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, $S(=O)CH_3$, $S(=O)_2CH_3$, $C_1$-$C_3$ alkyl, $CO_2H$ and $CO_2CH_3$. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include

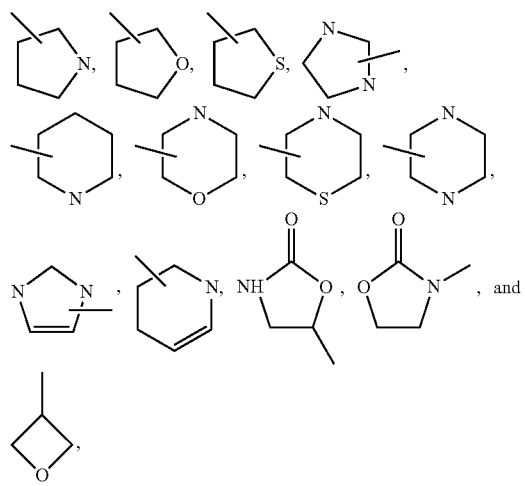

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, $S(=O)CH_3$, $S(=O)_2CH_3$, $C_1$-$C_3$ alkyl, $CO_2H$ and $CO_2CH_3$. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Preferred heteroaryl groups include

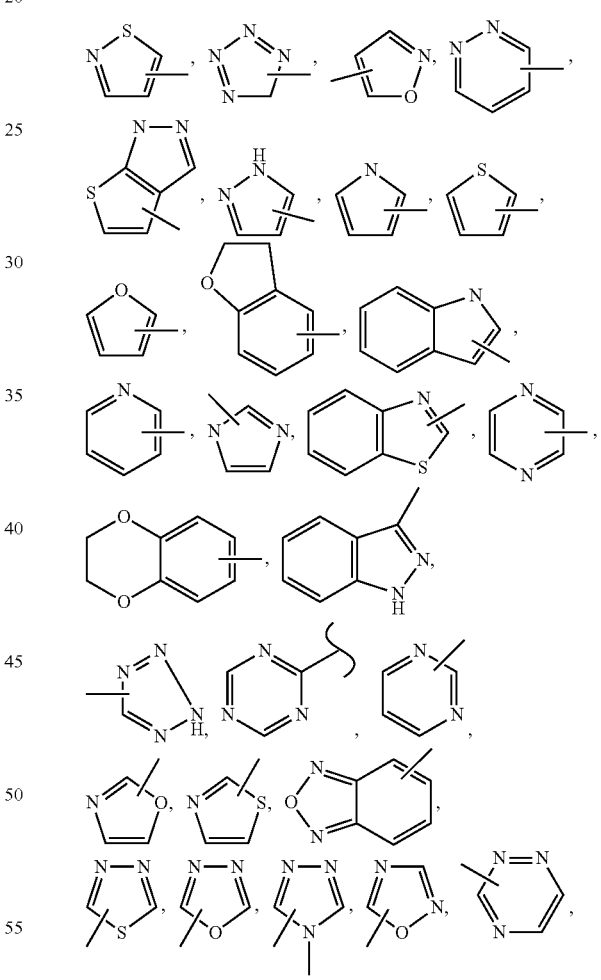

and the like.

When the term "unsaturated" is used herein to refer to a ring or group, which group may be fully unsaturated or partially unsaturated.

The term "acyl" alone or as part of another group refers to a carbonyl group linked to an organic radical, more particularly, the group $C(=O)R_e$, as well as the bivalent groups —C(=O)— or —C(=O)$R_e$—, which are linked to organic radicals. The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The designation "⌒" or

or

attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "counterion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

Isotopically labeled compounds of the present invention, i.e., wherein one or more of the atoms described are replaced by an isotope of that atom (e.g., $^{12}$C replaced by $^{13}$C or by $^{14}$C; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" for thin layer chromatography, "SM" for starting material, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| Et$_2$O | diethyl ether |
| i-PrOH or IPA | isopropanol |
| HOAc | acetic acid |
| BOP reagent | benzotriazol-1-yloxytris(dimethylamino)phosphonium hexafluorophosphate |
| BBr$_3$ | boron tribromide |
| Boc | tert-butyloxycarbonyl |
| cDNA | complimentary DNA |
| CDCl$_3$ | deuterated chloroform |
| CH$_2$Cl$_2$ | dichloromethane |
| CH$_3$CN | acetonitrile |
| CAN | acetonitrile |
| DABCO | 1,4-diazabicyclo[2.2.2]octane |
| DCE | 1,2 dichloroethane |
| DCM | dichloromethane |
| DCC | dicyclohexylcarbodiimide |
| DIEA or DIPEA | N,N,-diisopropylethylamine |
| DME | 1,2-dimethoxyethane |
| DMF | dimethyl formamide |
| DMAP | N,N-dimethylaminopyridine |
| DMSO | dimethyl sulfoxide |
| DPPA | diphenyl phosphoryl azide |
| EDC (or EDC.HCl) or EDCI (or EDCI.HCl) or EDAC | 3-ethyl-3'-(dimethylamino)propyl-carbodiimide hydrochloride or 1-(3-dimethylaminopropyl)-3-ethylcarbodiimide hydrochloride |
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperaxine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NMM | N-methylmorpholine |
| Pd/C | palladium on carbon |
| PPA | polyphosphoric acid |
| PS | polystyrene |
| PXPd2 | bis[di-tert-butl phosphinous chloride-kP]di-m-chlorodichloro dipalladium |
| PyBOP | (benzotriazol-1-yloxy)tripyrrolidino-phosphonium hexafluorophosphate |
| TEA | triethylamine |
| TFA | trifluoroacetic acid |
| THF | tetrahydrofuran |
| TRIS | tris(hydroxymethyl)aminomethane |
| KOAc | potassium acetate |
| K$_3$PO$_4$ | potassium phosphate |
| MgSO$_4$ | magnesium sulfate |
| NaCl | sodium chloride |
| NaH | sodium hydride |
| NaHCO$_3$ | sodium bicarbonate |
| NaOH | sodium hydroxide |
| Na$_2$SO$_3$ | sodium sulfite |
| Na$_2$SO$_4$ | sodium sulfate |
| NH$_3$ | ammonia |
| NH$_4$Cl | ammonium chloride |
| NH$_4$OH | ammonium hydroxide |
| OTs | tosylate, para-toluenesulfonate |
| PBr$_3$ | phosphorous tribromide |
| Pd(PPh$_3$)$_4$ | tetrakis(triphenylphosphine) palladium (0) |
| (S,S)-EtDuPhosRh(I) | (+)-1,2-bis((2S,5S)-2,5-diethylpholano)benzene(cyclooctadiene)rhodium (I) trifluoromethanesulfonate |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition, Wiley-Interscience (2006)).

Imidazothiadiazole compounds of formula I of this invention can be obtained by condensation of a substituted aminothiadiazole of formula III with a ketone of formula IV which contains a leaving group Z such as a bromide, iodide or tosylate as shown in Scheme 1. Both compounds of formula III and IV are commercially available or can be prepared by means known to one skilled in the art. This condensation is promoted by heating, either thermally or preferably by microwave irradiation.

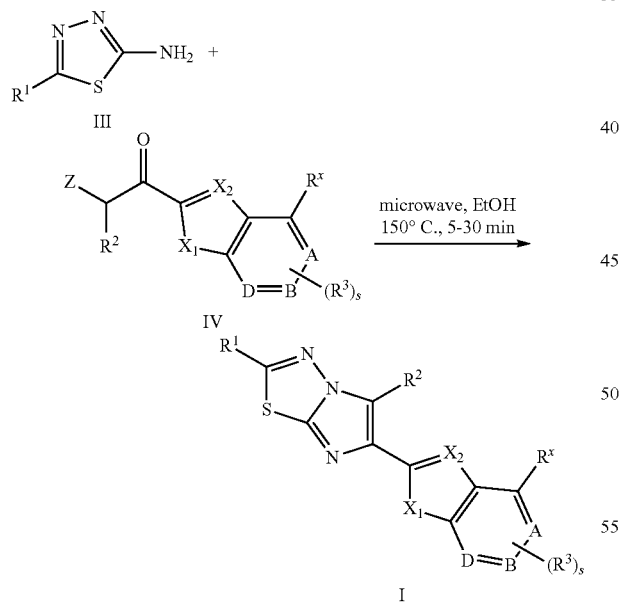

Alternatively, compounds of Formula I can be prepared from compounds of formula VI upon activation of the thiomethyl group by oxidation to a sulfone VII as shown in Scheme 2. This allows introduction of a variety of nucleophiles as groups $R^1$ such as alcohols, thiols and amines in the presence of a base such as potassium carbonate or sodium hydride either neat or in a polar, aprotic solvent such as dimethylformamide.

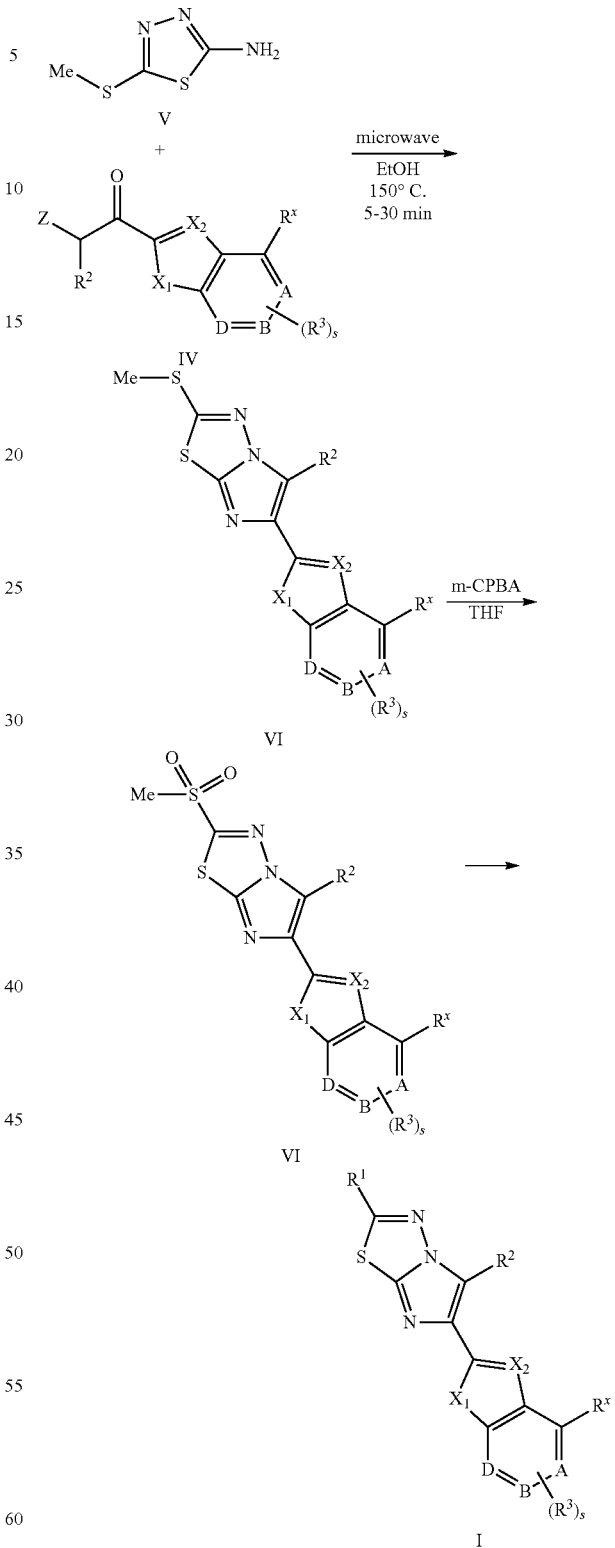

Compounds of formula Ia can be prepared by condensation of a substituted aminothiadiazole of formula III with a ketone of formula XI as shown in Scheme 3. The ketone of formula XI is available commercially or can be constructed as shown in Scheme 3 from condensation of hydroxyketones of formula VIII with ketones of formula IX bearing a leaving group Y such as chloro, bromo or tosyloxy. Both compounds of formula VIII and IX are commercially available or can be groups $R^1$ such as alcohols, thiols and amines in the presence of a base such as potassium carbonate or sodium hydride either neat or in a polar, aprotic solvent such as dimethylformamide.

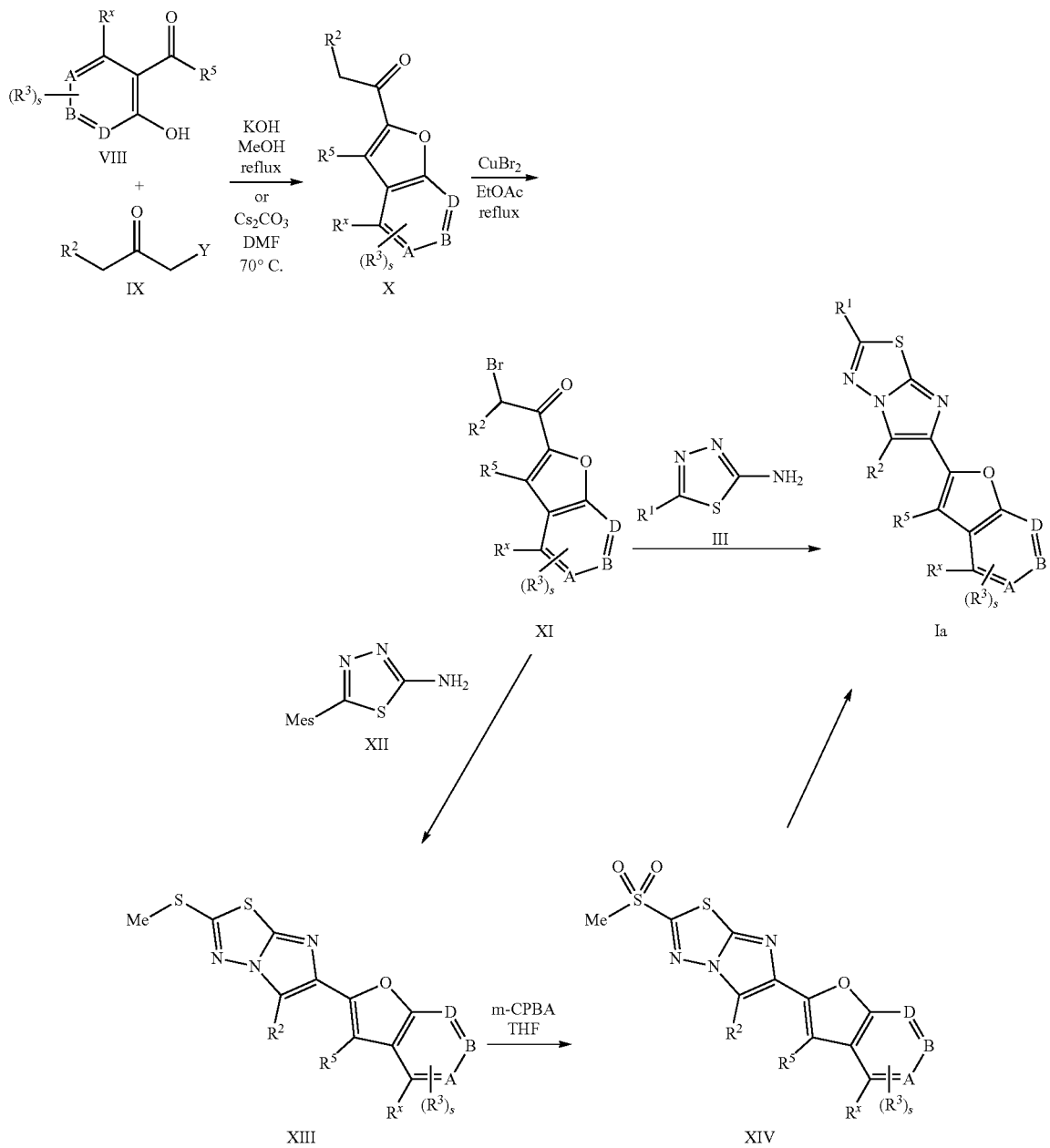

Scheme 3 prepared by means known to one skilled in the art. Conversion of compounds of formula X to bromoketones of formula XI allows for condensation of either a substituted aminothiadiazole of formula III to form compounds of formula Ia or an aminothiazole of formula XII to form compounds of formula XIII. Compounds of formula XIII can be further converted to compounds of formula Ia by oxidation and displacement of the resulting methylsulfone of compounds of formula XIV with a variety of nucleophiles as Compounds of formula Ic can be prepared from compounds of formula XV as shown in Scheme 4. Both compounds of formula XV and XVII are either commercially available or available by means known to one skilled in the art. Following the formation of bromoketones XIX formation of I can proceed directly by condensation with compounds of formula III or via the intermediacy of compounds XX and XXI as described in Scheme 2.

Scheme 4

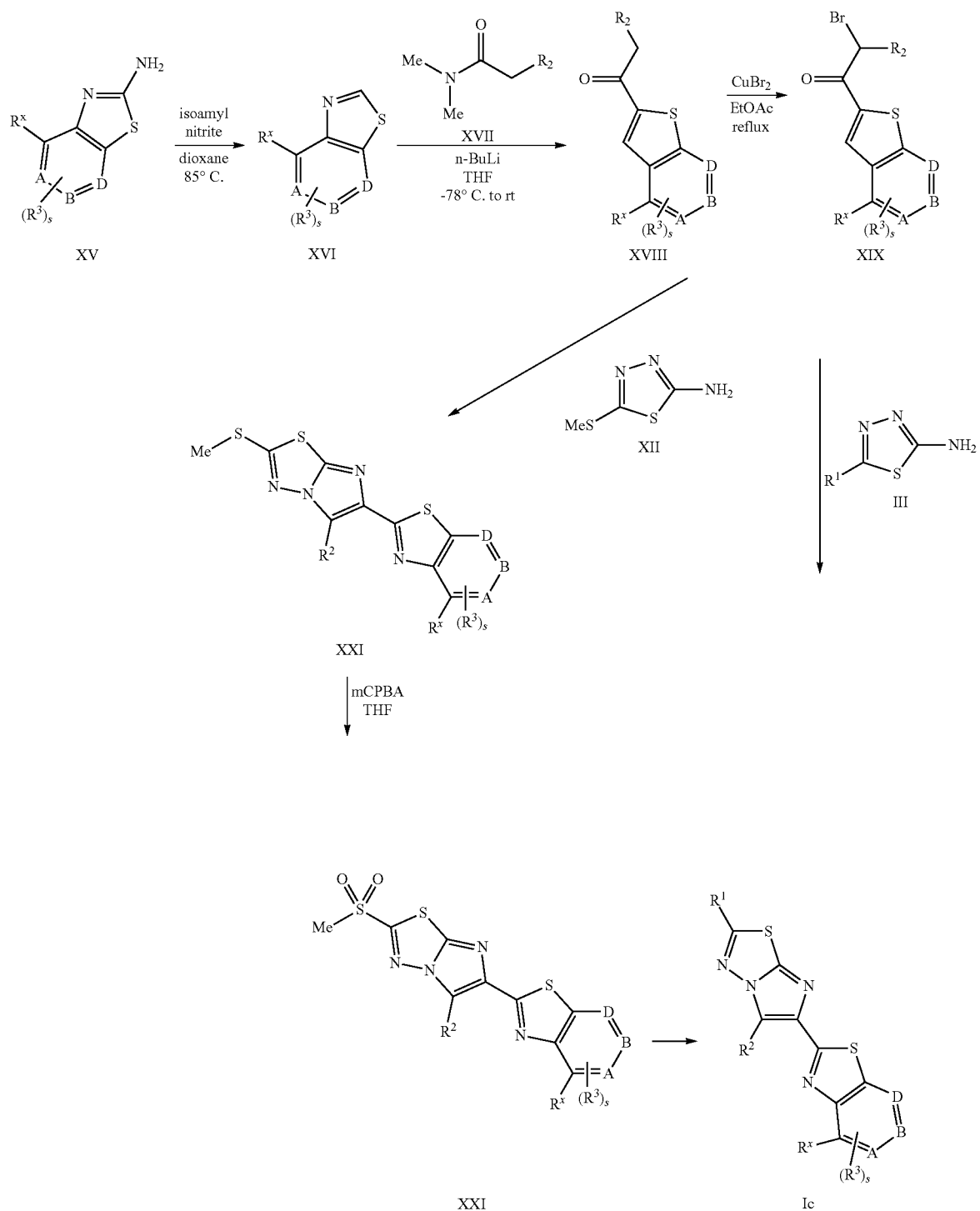

Compounds of formula Id can be prepared starting from substituted aminothiazoles III and pyruvate esters of formula XXII which contain a leaving group Z such as a bromide, iodide or tosylate as shown in Scheme 5. Both compounds of formula III and XXII are commercially available or are available by means known to one skilled in the art. Following condensation and saponification of the ester to form acid XXIV, amino phenols of formula XXV are coupled to form amides of the formula XXVI, which can be cyclized under acid catalysis to form compounds of formula Id.

Scheme 5
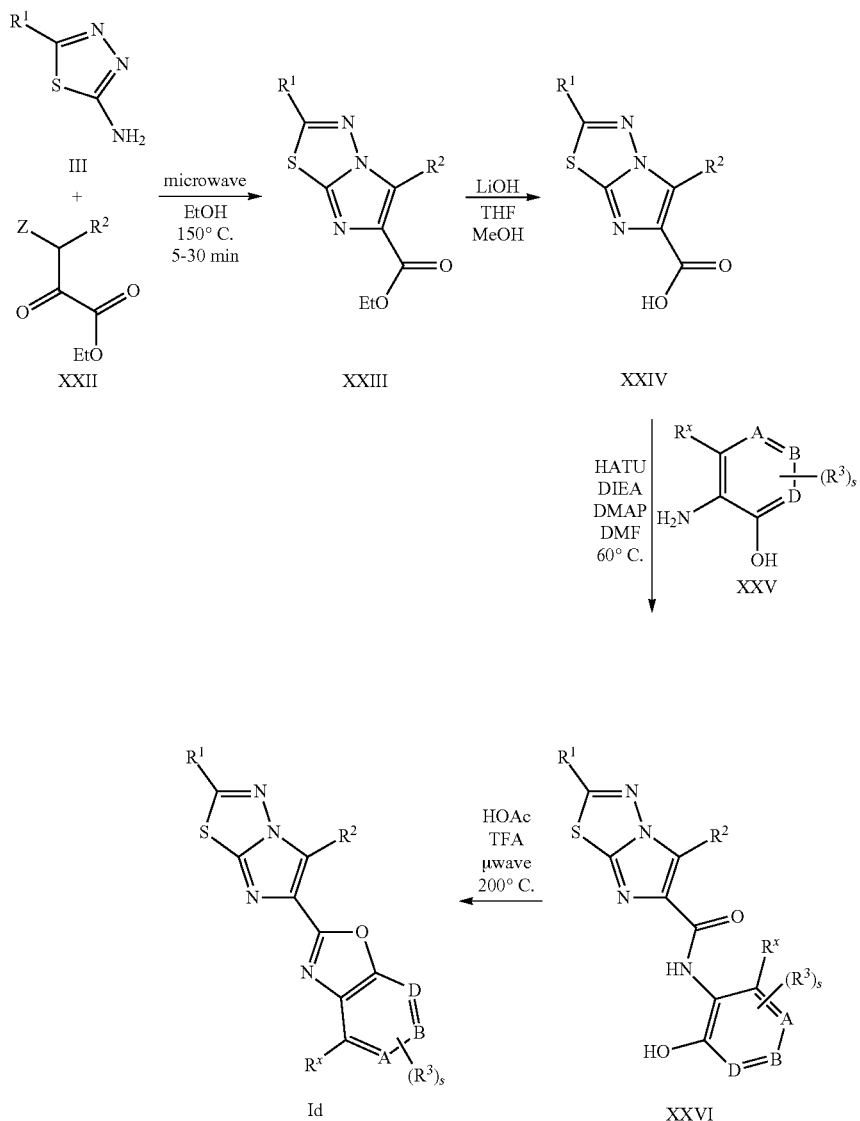
Compounds of formula Ie can be prepared from condensation of methoxyaminothiadiazole XXIX with a ketone of formula IV which contains a leaving group Z such as a bromide, iodide or tosylate as shown in Scheme 6. The methoxyaminothiadiazole XXIX can be prepared from carbon disulfide (XXVII) via the thioxanthate intermediate XVIII.
Scheme 6
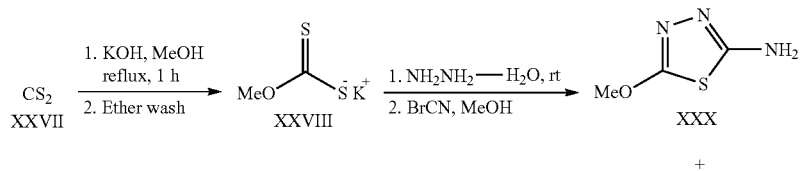

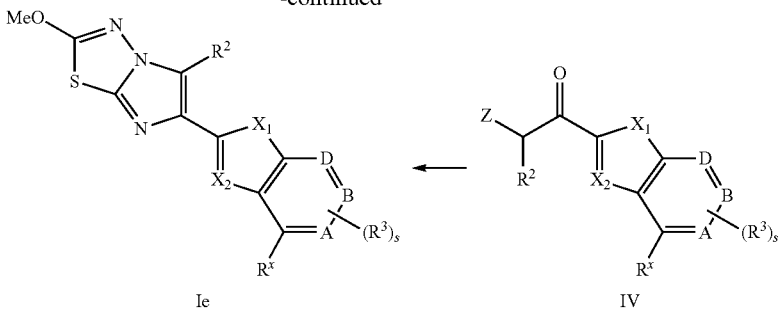

Compounds of formula If can be prepared from compounds of formula XXX by treatment with an appropriate halogenating agent as shown in Scheme 7.

Scheme 7

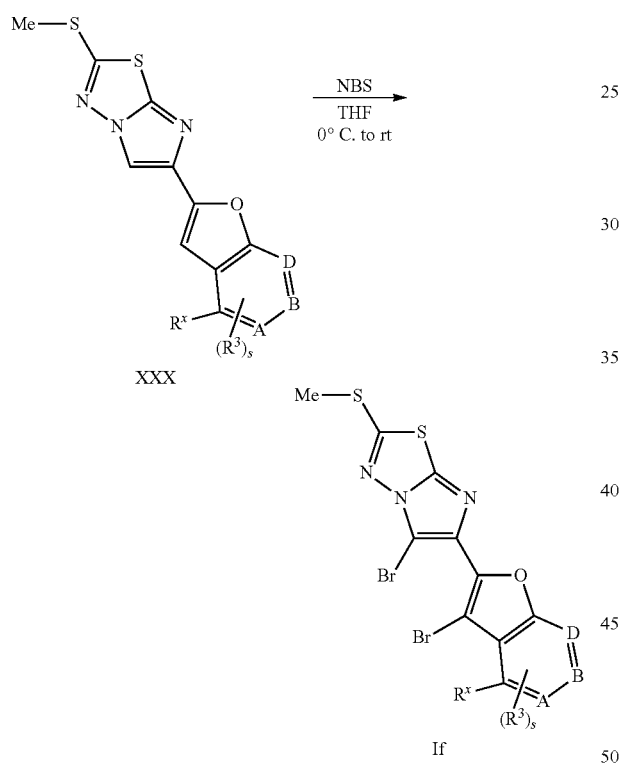

Compounds of formula Ig of this invention can be obtained by condensation of an amine of formula III with a ketone of formula XXXI which contains a leaving group Z such as a bromide, iodide or tosylate and a protecting group PG such as benzyl as shown in Scheme 8. Both compounds of formula III and XXXI are commercially available or can be prepared by means known to one skilled in the art. This condensation is promoted by heating, either thermally or preferably by microwave irradiation. The protecting group can be removed by methods known in the art, such as $BCl_3$ at −78° C. in the presence of pentamethylbenzene. Subsequent alkylation using either an alcohol XXXIII under Mitsunobu conditions or a bromide XXXIV in the presence of base such as potassium carbonate provides the compounds of Formula Ig. Alcohols and bromides XXXIII and XXXIV are commercially available or can be prepared by methods known in the art.

Scheme 8

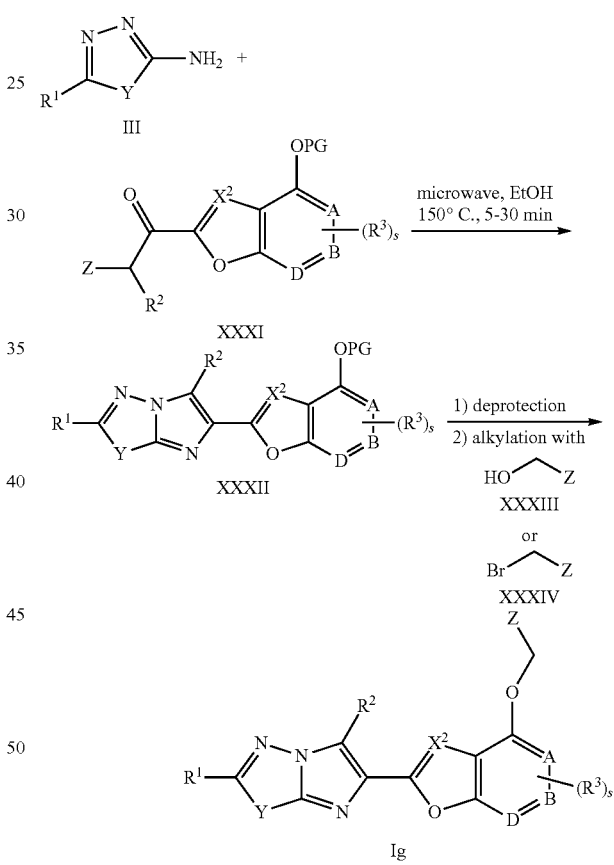

In the following experimental procedures, solution ratios express a volume relationship, unless stated otherwise. NMR chemical shifts (δ) are reported in parts per million (ppm).

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% H$_3$PO$_4$; B: 10% water, 89.9% methanol, 0.1% H$_3$PO$_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% NH$_4$OAc; B: 10% water, 89.9% methanol, 0.1% NH$_4$OAc, UV 220 nm). Purification of intermediates and final products was carried out via either normal or reverse phase chromatography. Normal phase chromatography was carried out using prepacked SiO$_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a Varian ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm). LCMS chromatograms were obtained on a Shimadzu HPLC system running Discovery VP software, coupled with a Waters ZQ mass spectrometer running MassLynx version 3.5 software using the same columns and conditions as utilized for analytical described above.

EXAMPLES

The following compounds of the invention have been prepared, isolated and characterized using the methods disclosed herein. They demonstrate a partial scope of the invention and are not meant to be limiting of the scope of the invention.

Example 1

6-(Benzofuran-2-yl)-2-(methylthio)imidazo[2,1-b][1,3,4]thiadiazole

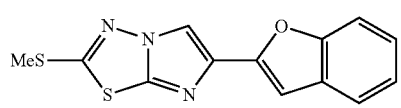

5-(Methylthio)-1,3,4-thiadiazol-2-amine (1.85 g, 12.55 mmol) and 1-(benzofuran-2-yl)-2-bromoethanone (3 g, 12.55 mmol) were dissolved in MeOH (20 mL, 0.63 M) in a microwave vial (large vessel). The reaction was heated to 100° C. in the microwave for 30 min, until formation of product was observed by HPLC analysis. The diluted reaction mixture with EtOAc was washed with H$_2$O (2×50 mL) followed by brine (sat'd NaCl, 2×50 mL). The organic layer was dried onto SiO$_2$ gel and the crude material was purified by flash chromatography (EtOAc/hexanes 0-100%). The purity of the chromatographed material was further improved by trituration using 10% EtOAc/hexane, thus providing 1.8 g of Example 1 as a tan solid. LCMS: 3.810 min, [M+1]=288.0; $^1$H NMR (500 MHz, CDCl$_3$) δ ppm 2.75-2.79 (m, 3H) 7.03-7.09 (m, 1H) 7.18-7.32 (m, 2H) 7.46-7.53 (m, 1H) 7.55-7.63 (m, 1H) 8.04-8.07 (m, 1H).

Example 2

6-(Benzofuran-2-yl)-5-bromo-2-(methylthio)imidazo[2,1-b][1,3,4]thiadiazole and

Example 3

5-Bromo-6-(3-bromobenzofuran-2-yl)-2-(methylthio)imidazo[2,1-b][1,3,4]thiadiazole

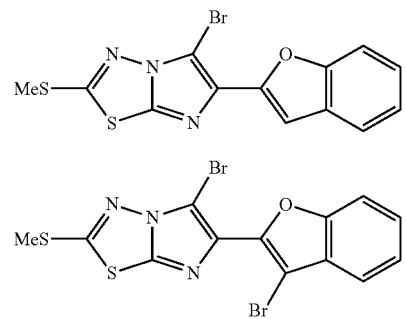

Example 1 (50 mg, 0.174 mmol) was added to a round bottom flask and dissolved in THF (281 μL). The reaction mixture was cooled to 0° C. and NBS (35 mg, 0.192 mmol) was slowly added. The reaction mixture was allowed to slowly warm up to rt overnight. Monitoring by LCMS showed that by the next morning the reaction had progressed to a ratio of 1.3:1.0 Example 2:Example 3. The mixture was quenched with Na$_2$S$_4$O$_3$ (sat'd), extracted with EtOAc, dried over Na$_2$SO$_4$, filtered, and concentrated to dryness. The crude material was purified by flash chromatography (EtOAc/hexanes 0-100%) to afford Example 2 (18 mg) and Example 3 (12.2 mg).

Example 2

LCMS: 4.106 min, [M+1]=367.8; $^1$H NMR (500 MHz, CDCl$_3$) δ ppm 7.59 (dd, J=18.42, 7.97 Hz, 2H), 7.32-7.29 (m, 2H), 7.23-7.27 (m, 2H), 2.81 (s, 3H).

Example 3

LCMS: 4.328 min, [M+1]=445.7; $^1$H NMR (500 MHz, CDCl$_3$) δ ppm 7.59 (d, J=7.70 Hz, 1H), 7.53 (d, J=7.70 Hz, 1H), 7.31-7.39 (m, 2H), 2.81 (s, 3H).

Example 4

2-(2-(Methylthio)imidazo[2,1-b][1,3,4]thiadiazol-6-yl)benzo[d]thiazole

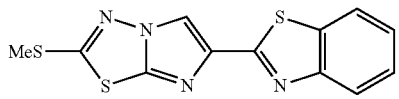

Preparation of Example 4 from 1-(benzo[d]thiazol-2-yl)-2-bromoethanone was analogous to the procedure described for Example 1. LCMS: 3.586 min, [M+1]=305.0; $^1$H NMR (500 MHz, CDCl$_3$) δ ppm 2.74-2.80 (m, 3H) 7.32-7.40 (m, 1H) 7.43-7.51 (m, 1H) 7.88-7.95 (m, 1H) 7.96-8.04 (m, 1H) 8.36-8.42 (m, 1H).

Example 5

2-(2-Methoxyimidazo[2,1-b][1,3,4]thiadiazol-6-yl)benzo[d]thiazole

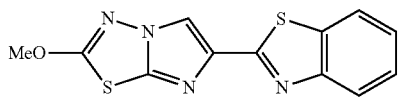

Example 4 (2 g, 6.57 mmol) was dissolved in THF (66.7 mL, 0.1 M) at 20° C. and m-CPBA (5.67 g, 32.9 mmol) was added. The reaction mixture was stirred as a slurry for a total of 12 h. THF was removed under reduced pressure and then the slurry was triturated using DCM (50 mL). The slurry in DCM was heated to near reflux, cooled, and then the solids were filtered, isolated to yield 1.66 g of 2-(2-(methylsulfonyl)imidazo[2,1-b][1,3,4]thiadiazol-6-yl)benzo[d]thiazole as a yellow solid (1:10 ratio sulfoxide:sulfone), which was used without further purification. To the suspension of 2-(2-(methylsulfonyl)imidazo[2,1-b][1,3,4]thiadiazol-6-yl)benzo[d]thiazole (2.5 g, 7.43 mmol) in MeOH (149 mL) was added sodium methoxide (1.2 g, 22.3 mmol). The reaction mixture was stirred at 20° C. for 12 h. The solvent was removed by concentrating in vacuo and the crude product was purified by trituration by adding DCM (50 mL) and heating the heterogeneous mixture to near reflux. After cooling the slurry, the solvent was removed by filtration. This trituration method was repeated three times to afford 1.52 g of Example 5 as a white solid. LCMS: 2.338 min, [M+1]=289.4; $^1$H NMR (500 MHz, CDCl$_3$) δ ppm 4.23 (s, 3H) 7.33-7.42 (m, 1H) 7.45-7.54 (m, 1H) 7.88-7.95 (m, 1H) 7.98-8.07 (m, 1H) 8.31 (s, 1H).

Example 6

4-Methoxy-2-(2-(methylthio)imidazo[2,1-b][1,3,4]thiadiazol-6-yl)benzo[d]thiazole

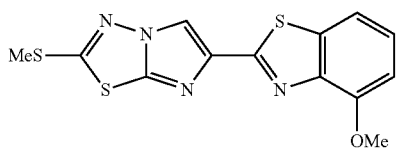

6A. 4-Methoxybenzo[d]thiazole

4-Methoxybenzo[d]thiazol-2-amine (0.5 g, 2.77 mmol) was dissolved in dioxane (27.7 mL) in a vented reaction vessel under argon. Isoamyl nitrite (0.747 mL, 5.55 mmol) was added at rt and the resulting reaction mixture was heated to 85° C. After approximately 1 h, LCMS analysis indicated consumption of the starting material and the formation of the product (LCMS: 2.270 min, [M+1]=166.0). The solvent was removed in vacuo and the residue was purified via column chromatography (EtOAc/hexanes, 0-100%) to afford 6A (286.8 mg) as a red oil. $^1$H NMR (500 MHz, CDCl$_3$) δ ppm 8.89 (s, 1H), 7.51 (d, J=8.25 Hz, 1H), 7.37 (t, J=8.25 Hz, 1H), 6.91 (d, J=7.70 Hz, 1H), 4.04 (s, 3H).

6B. 1-(4-Methoxybenzo[d]thiazol-2-yl)ethanone

In a flame dried round-bottomed flask THF (3.2 mL) was added 6A (260 mg, 1.57 mmol), followed by the dropwise addition of n-BuLi (1.6 M hexanes, 1.08 mL, 1.73 mmol). The reaction mixture was stirred at −78° C. for 15 min, then N,N-dimethylacetamide (151 mg, 1.731 mmol) was slowly added. The reaction solution was allowed to gradually warm to rt. The reaction was monitored by LCMS to show the desired product. The mixture was quenched with NH$_4$Cl (sat'd aq) and extracted with EtOAc (3×), dried over Na$_2$SO$_4$, concentrated to dryness to afford 6B (331 mg) which was directly used in the next step. LCMS: 2.716 min, [M+1]=208.0; $^1$H NMR (500 MHz, CDCl$_3$) δ ppm 7.51-7.54 (m, 1H), 7.47 (t, J=8.25 Hz, 1H), 6.94-6.97 (m, J=7.70 Hz, 1H), 4.09 (s, 3H), 2.85 (s, 3H).

6C. 2-Bromo-1-(4-methoxybenzo[d]thiazol-2-yl)ethanone 6B (331 mg, 1.597 mmol) was dissolved in ethyl acetate (6.9 mL). Copper (II) bromide (624 mg, 2.79 mmol) was added to the solution and the resulting mixture was heated under argon to reflux (60-70° C.) overnight. The green solution was filtered through SiO$_2$ gel, and the media was washed with 10% EtOAc/hexanes. The filtrate was concentrated and dried in vacuo to afford 6C as an orange solid (169.1 mg). LCMS: 3.016 min, [M+1]=288.0. This material was used directly in the next step.

Example 6

Example 6 (25.5 mg) was prepared as a solid from 5-(methylthio)-1,3,4-thiadiazol-2-amine (40 mg, 0.272 mmol) and 6C (78 mg, 0.272 mmol) as described for Example 1. LCMS: 3.606 min, [M+1]=335.0; $^1$H NMR (500 MHz, CDCl$_3$) δ ppm 8.51 (s, 1H), 7.50 (d, J=8.80 Hz, 1H), 7.31-7.35 (m, 1H), 6.92 (d, J=8.25 Hz, 1H), 4.06 (s, 3H), 2.78 (s, 3H).

Example 7

2-(2-Ethylimidazo[2,1-b][1,3,4]thiadiazol-6-yl)benzo[d]oxazole

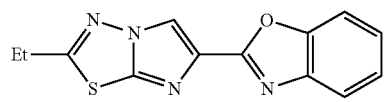

7A. Ethyl 2-ethylimidazo[2,1-b][1,3,4]thiadiazole-6-carboxylate

5-Ethyl-1,3,4-thiadiazol-2-amine (500 mg, 3.87 mmol) was placed in a microwave vial and ethyl 3-bromo-2-oxopropanoate (0.48 mL, 3.87 mmol) was added along with EtOH (18 mL). The reaction mixture was heated in microwave at 150° C. for 25 min. The solution was diluted with EtOAc and washed with NaHCO$_3$ (aq sat'd, 2×50 mL). The organic layer was dried over Na$_2$SO$_4$, filtered, and concentrated onto SiO$_2$ gel, then purified by flash chromatography (EtOAC/hexanes, 0-10%) to afford 240 mg of 7A. LCMS: 1.767 min, [M+1]=226.3; $^1$H NMR (500 MHz, CDCl$_3$) δ ppm 1.39-1.48 (m, 6H) 2.93-3.15 (m, 2H) 4.31-4.53 (m, 2H) 8.19-8.39 (s, 1H).

7B. 2-Ethylimidazo[2,1-b][1,3,4]thiadiazole-6-carboxylic acid 7A (500 mg, 2.22 mmol) was dissolved in THF (15 mL) and MeOH (15 mL) and a solution of LiOH (2.0 N, 10 mL) was slowly added at rt. The reaction mixture was stirred for 1.5 h at 20° C. The reaction mixture was diluted with EtOAc. The aqueous layer was acidified using 1N HCl to a pH of 3. The mixture was extracted using EtOAc (2×50 mL), the combined organics dried over Na$_2$SO$_4$, filtered, and concentrated to afford 420 mg of 7B (420 mg) as a white solid. $^1$H NMR (500 MHz, DMSO-d$_6$) δ ppm 1.23-1.45 (m, 3H) 2.98-3.18 (m, 2H) 8.58-8.77 (m, 1H) 12.66-12.93 (m, 1H).

7C. 2-Ethyl-N-(2-hydroxyphenyl)imidazo[2,1-b][1,3,4]thiadiazole-6-carboxamide 7B (25 mg, 0.127 mmol), 2-aminophenol (11.5 mg, 0.106 mmol), HATU (60 mg, 0.158 mmol), DIEA (54.6 mg, 0.423 mmol), and DMAP (0.065 mg, 0.005 mmol) were added to a round bottom flask containing DMF (2 mL). The reaction mixture was then heated to 60° C. for 12 h. After cooling to rt, the reaction mixture was diluted with EtOAc and washed with brine (sat'd NaCl, 3×30 mL), the organics were dried over Na$_2$SO$_4$, filtered, and concentrated onto SiO$_2$ gel. Purification by flash chromatography (EtOAc/hexanes, 0-30%) afforded 12 mg of 7C as a solid. LCMS(+): 1.973 min, [M+1]=289.4; $^1$H NMR (500 MHz, CDCl$_3$) δ ppm 1.44-1.50 (m, 3H) 3.04-3.12 (m, 2H) 6.86-6.94 (m, 1H) 7.04-7.10 (m, 1H) 7.11-7.20 (m, 2H) 8.33-8.38 (m, 1H) 9.13-9.22 (m, 1H) 9.51-9.65 (m, 1H).

Example 7

7C (30 mg, 0.104 mmol) was dissolved in acetic acid (0.5 mL) and TFA (0.5 mL) and placed in a microwave vial. The reaction mixture was heated in the microwave at 200° C. for 20 min, then was diluted with EtOAc and washed with NaHCO$_3$ (sat'd, 2×20 mL). The organic layer was dried over Na$_2$SO$_4$, filtered, and concentrated onto SiO$_2$ gel. The crude product was purified by flash chromatography (EtOAc/hexanes, 0-25%) to afford 14 mg of Example 7 as a brown solid. LCMS: 3.205 min, Mass: [M+1]=271.1; $^1$H NMR (500 MHz, CDCl$_3$) δ ppm 1.45-1.51 (m, 3H) 3.01-3.17 (m, 2H) 7.30-7.44 (m, 2H) 7.53-7.68 (m, 1H) 7.71-7.83 (m, 1H) 8.40-8.56 (m, 1H).

Example 8

6-(Benzofuran-2-yl)-2-methoxyimidazo[2,1-b][1,3,4]thiadiazole

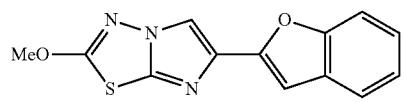 [SMILES: CSc1nn2cc(-c3cc4ccccc4o3)nc2s1]

8A. Potassium O-methyl carbonodithioate

Potassium hydroxide (45 g, 802 mmol) and MeOH (84 mL) were added into a round bottom flask and refluxed for 1 h. The reaction mixture was cooled to 20° C. and the potassium methoxide solution was decanted from the solids into another dry 500 mL round bottom flask. Carbon disulfide (61.1 g, 802 mmol) was added slowly in 15 min to the solution while stirring. The reaction mixture was then cooled to 0° C. and the precipitated solids were collected in a fritted funnel, washed with Et$_2$O (3×50 mL), and dried under reduced pressure for 24 h to afford 86 g of 8A as a pink solid, which was used in the next step without further purification.

8B. 5-Methoxy-1,3,4-thiadiazol-2-amine

To 8A (15 g, 103 mmol) in a round bottom flask was added H$_2$O (10 mL). The flask was cooled to 0° C. in an ice bath and hydrazine monohydrate (5.1 mL, 164 mmol) was then added dropwise to the reaction mixture. The mixture was warmed back to 20° C. and stirred upon completion of the addition. Solids precipitated within 15 min of stirring. The resulting slurry was allowed to continue to stir for 2 h at rt and then cooled to 0° C. The pH of the heterogeneous solution was adjusted to pH 7 using AcOH (dropwise addition) and then the solids were isolated by filtration. The light yellow solids were dried under reduced pressure for 24 h to afford 8.5 g of the product which was placed in a round bottom flask to which was added 2N NaOH solution (48 mL, 96 mmol). The reaction mixture was cooled to 0° C. and a solution of CNBr (8.48 g, 80 mmol) in MeOH (8 mL) was added dropwise. The reaction was warmed to rt over a period of 1 h, stirred for 1.5 h at 20° C. The precipitate was isolated by filtration and dried in vacuo to afford 5.92 g of 8B as a brown solid. LCMS: 0.565 min, [M+1]=131.8; $^1$H NMR (500 MHz, DMSO-d$_6$) δ ppm 3.85-3.97 (s, 3H) 6.65-6.80 (bs, 2H).

8C. 1-(Benzofuran-2-yl)-2-(2-imino-5-methoxy-1,3,4-thiadiazol-3(2H)-yl)ethanone 8B (1 g, 7.62 mmol) was dissolved in EtOH (51 mL). 1-(Benzofuran-2-yl)-2-bromoethanone (1.82 g, 7.62 mmol) was added to the vessel, which was sealed under argon and stirred overnight at rt. Upon consumption of the starting material, the slurry was filtered and the solids were collected and air dried to afford 8C (1.91 g) as an off white solid, which was used directly in the next step. LCMS: 2.698 min, [M+1]=290.1; $^1$H NMR (400 MHz, DMSO-d$_6$) δ ppm 9.92 (s, 2H), 8.13 (s, 1H), 7.92 (s, 1H), 7.79 (s, 1H), 7.61 (s, 1H), 7.43 (s, 1H), 5.83 (s, 2H), 4.06 (s, 3H).

Example 8

8C (300 mg, 1.037 mmol) was dissolved in H$_2$O (6.9 mL) and ytterbium(III) trifluoromethanesulfonate (64.3 mg, 0.104 mmol) was added. The reaction mixture was warmed to 70° C. The slurry was stirred overnight, while monitoring via LCMS. After 21 h, the analysis indicated consumption of the starting material and clean formation of Example 8 (LCMS: 3.645 min, [M+1]=272.1). The mixture was cooled. The crude solids were filtered, titurated with MeOH (15 mL) followed by filtration to afford Example 8 (174.9 mg) as a tan solid. LCMS: 3.631 min, [M+1]=272.0; $^1$H NMR (400 MHz, DMSO-$d_6$) δ ppm 8.48 (s, 1H), 7.55-7.64 (m, 2H), 7.21-7.30 (m, 2H), 7.07 (s, 1H), 4.19 (s, 3H).

Example 9

2-Methoxy-6-(7-methoxybenzofuran-2-yl)imidazo[2,1-b][1,3,4]thiadiazole

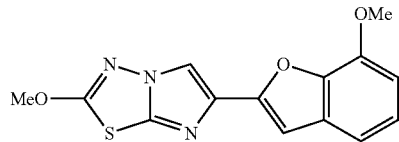

9A.
2-Bromo-1-(7-methoxybenzofuran-2-yl)ethanone 1-(7-Methoxybenzofuran-2-yl)ethanone (2 g, 10.52 mmol) was dissolved in EtOAc (46 mL) in an appropriate vial. Copper(II) bromide (4.11 g, 18.4 mmol) was added to the vessel and the resulting mixture was heated under argon to reflux (60-70° C.) overnight. The next morning LCMS indicated formation of the product (LCMS: 2.936 min, [M+1]=271.0). The dark solution was filtered through a plug of SiO$_2$ gel, and the media was washed with 10% EtOAc/hexanes. The filtrate was concentrated and dried in vacuo to afford 2.51 g of crude 9A which was used in the next step without further purification.

9B. 6-(7-Methoxybenzofuran-2-yl)-2-(methylthio)imidazo[2,1-b][1,3,4]thiadiazole 9B was prepared as described in Example 1 from 5-(methylthio)-1,3,4-thiadiazol-2-amine (219 mg, 1.486 mmol) and 8A (400 mg, 1.486 mmol) in MeOH (7.5 mL). Flash chromatography (0-30% EtOAc/hexanes) of the crude residue afforded 9B (212 mg) as a yellow solid. $^1$H NMR (500 MHz, CDCl$_3$) δ ppm 2.76-2.79 (m, 3H) 4.03-4.06 (m, 3H) 6.79-6.83 (m, 1H) 7.13-7.22 (m, 2H) 7.25-7.27 (m, 1H) 8.12-8.14 (m, 1H).

9C. 6-(7-Methoxybenzofuran-2-yl)-2-(methylsulfonyl)imidazo[2,1-b][1,3,4]thiadiazole To a round bottom flask containing THF (4 mL) was added 9B (250 mg, 0.788 mmol) and m-CPBA (544 mg, 3.15 mmol). The resulting reaction mixture was stirred for 12 h at 20° C. The crude LCMS after 12 h showed both sulfoxide and sulfone. The reaction mixture was transferred to a separatory funnel using EtOAc and water. The solids were filtered to afford 150 mg of orange solids (LCMS 1:2 ratio of sulfoxide to sulfone). Extraction of the biphasic mixture after concentration provided an additional 100 mg of the material. The two batches of material were combined to afford 250 mg of the crude 9C (2.5:1.0 sulfone:sulfoxide) which was used in the next step without further purification. LCMS: 2.995 min, [M+1]=334.1, 3.171 min. [M+1]=350.1.

Example 9

To a MeOH (2 mL) solution of 9C (150 mg, 0.429 mmol) in a round bottom flask was added sodium methoxide (69.6 mg, 1.29 mmol). The subsequent mixture was stirred at 20° C. for 2 h. The white solids were isolated from the reaction mixture by filtration, triturated using 100% MeOH, again isolated by filtration and dried to afford Example 9 (81 mg) as a white solid. LCMS: 3.436 min, [M+1]=302.1; $^1$H NMR (500 MHz, DMSO-$d_6$) δ 3.94 (s, 3H) 4.20 (s, 3H) 6.91 (dd, J=7.42, 1.37 Hz, 1H) 7.15 (t, J=7.70 Hz, 1H) 7.19 (dd, J=7.70, 1.20 Hz, 1H) 8.48 (s, 1H) 8.52 (s, 1H).

Example 10

6-(6,7-Dimethoxybenzofuran-2-yl)-2-methoxyimidazo[2,1-b][1,3,4]thiadiazole

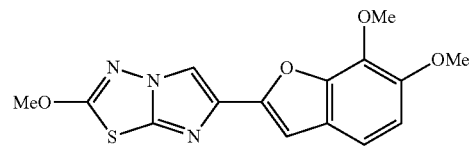 [SMILES: COc1nn2cc(-c3cc4ccc(OC)c(OC)c4o3)nc2s1]

10A. 1-(6,7-Dimethoxybenzofuran-2-yl)ethanone

2-Hydroxy-3,4-dimethoxybenzaldehyde (1.3 g, 7.14 mmol) was dissolved in MeOH (16.4 mL) in a round bottom flask. KOH (0.400 g, 7.14 mmol), previously pulverized with a mortar and pestle, was added. The reaction mixture was heated to reflux for 30 min. After which time the mixture was cooled and 1-chloropropan-2-one (8.56 g, 7.89 mmol) was added dropwise to the solution at 0-10° C. The newly prepared solution was warmed to rt and stirred over 48 h. Upon reaction completion shown by TLC analysis, the MeOH was removed, the residue was redissolved in EtOAc and H$_2$O was added. The crude product was washed with brine (sat'd NaCl), extracted 3× with EtOAc, dried over Na$_2$SO$_4$, filtered, and concentrated in vacuo to afford a dark oil. The crude material was purified by flash chromatography (EtOAc/hexanes 0-100%) to provide 1 g of 10A. LCMS: 2.398 min, [M+1]=221.1; $^1$H NMR (500 MHz, CD$_3$OD) δ ppm 2.48-2.60 (s, 3H) 3.88-3.95 (s, 3H) 4.02-4.10 (s, 3H) 7.05-7.16 (m, 1H) 7.37-7.44 (m, 1H) 7.61-7.68 (s, 1H).

10B.
2-Bromo-1-(6,7-dimethoxybenzofuran-2-yl)ethanone

To 10A (1 g, 4.54 mmol) dissolved in EtOAc (30 mL) was added copper (II) bromide (1.27 g, 5.68 mmol) and the resulting mixture was heated under argon to reflux (80° C.) overnight. The dark solution was filtered through a plug of SiO$_2$ gel. The media was rinsed with 10% EtOAc/hexanes. The filtrate was concentrated and dried in vacuo and the crude material was purified by flash chromatography (EtOAc/hexanes 0-20%) to provide 710 mg of 10B. LCMS: 2.735 min, [M+1]=301.0; $^1$H NMR (500 MHz, CD$_3$OD) δ ppm 3.93-3.95 (s, 3H) 4.07-4.09 (s, 3H) 4.53-4.57 (s, 2H) 7.12-7.16 (m, 1H) 7.41-7.45 (m, 1H) 7.78-7.81 (s, 1H).

10C. 6-(6,7-Dimethoxybenzofuran-2-yl)-2-(methyl-thio)imidazo[2,1-b][1,3,4]thiadiazole 10C was prepared as described in Example 1 from 5-(methylthio)-1,3,4-thiadiazol-2-amine (148 mg, 1.00 mmol) and 9B (300 mg, 1.00 mmol). The crude product was dried onto silica gel and purified by flash chromatography (0-15% EtOAc/hexanes) to provide 135 mg of 10C as a solid. LCMS: 3.598 min, [M+1]=348.1; $^1$H NMR (500 MHz, CD$_3$OD) δ ppm 2.78-2.85 (s, 3H) 3.86-3.93 (s, 3H) 4.06-4.12 (s, 3H) 6.95-7.03 (m, 2H) 7.18-7.24 (m, 1H) 8.24-8.32 (s, 1H).

10D. 6-(6,7-Dimethoxybenzofuran-2-yl)-2-(methyl-sulfonyl)imidazo-[2,1-b][1,3,4]thiadiazole 10C (135 mg, 0.398 mmol) and m-CPBA (335 mg, 1.94 mmol) were added to a round bottom flask containing THF (4 mL, 0.1M). The resulting mixture was stirred for 12 h at 20° C. Upon completion, the reaction mixture was diluted with EtOAc, washed with H$_2$O (2×25 mL), followed by brine (sat'd NaCl, 2×25 mL). The biphasic mixture was extracted with EtOAc (3×) and the combined organics were dried directly onto SiO$_2$ gel. The crude residue was purified by flash chromatography (0-30% EtOAc/hexanes) to provide 10D (71 mg) as a solid. LCMS: 3.100 min, [M+1]=380.1; $^1$H NMR (500 MHz, CDCl$_3$) δ ppm 3.42-3.47 (s, 3H) 3.93-3.98 (s, 3H) 4.17-4.22 (s, 3H) 6.92-6.97 (m, 1H) 7.11-7.16 (s, 1H) 7.20-7.25 (m, 1H) 8.21-8.26 (s, 1H).

Example 10

MeOH (3.7 mL, 0.05M) and sodium methoxide (30 mg, 0.531 mmol) were added to a round bottom flask containing 10D (71 mg, 0.187 mmol). The resulting mixture was stirred at 20° C. for 12 h. Upon complete consumption of the starting material, the solution was diluted with EtOAc and washed with H$_2$O (2×25 mL), followed by brine (sat'd NaCl, 2×25 mL). The biphasic mixture was extracted with EtOAc (3×) and the combined organics were concentrated directly onto SiO$_2$ gel. The crude residue was purified by flash chromatography (0-30% EtOAc/hexanes) to provide 40 mg of Example 10 as a solid. LCMS: 3.203 min, [M+1]=332.1; $^1$H NMR (500 MHz, CD$_3$OD) δ ppm 3.88-3.93 (s, 3H) 4.07-4.13 (s, 3H) 4.23-4.28 (s, 3H) 6.93-7.02 (m, 2H) 7.16-7.24 (m, 1H) 8.15-8.20 (s, 1H).

Example 11

6-(4-Methoxybenzofuran-2-yl)-2-(methylthio)imidazo[2,1-b][1,3,4]thidiazole

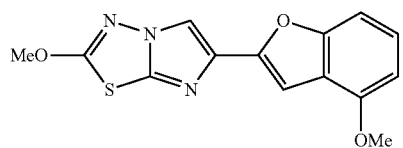 [SMILES: COc1nn2cc(-c3cc4c(OC)cccc4o3)nc2s1]

11A. 1-(4-Methoxybenzofuran-2-yl)ethanone

2-Hydroxy-6-methoxybenzaldehyde (1 g, 6.57 mmol) was dissolved in MeOH (16.4 mL) in a round bottom flask. KOH (0.369 g, 6.57 mmol), previously pulverized with a mortar and pestle, was added. The reaction mixture was heated to reflux for 30 min. After which time the mixture was cooled and 1-chloropropan-2-one (0.730 g, 7.89 mmol) was added dropwise to the solution at 0-10° C. The newly prepared solution was heated at reflux overnight. Upon reaction completion, the MeOH was removed, the residue was redissolved with CH$_2$Cl$_2$ (H$_2$O was added), extracted 3× (CH$_2$Cl$_2$), dried over Na$_2$SO$_4$, filtered, and concentrated in vacuo to afford 11A as a dark oil. The material was used in the next step without further purification. LCMS: 2.700 min, [M+1]=191.0.

11B. 2-Bromo-1-(4-methoxybenzofuran-2-yl)ethanone

To 11A (1.25 g, 6.57 mmol) in ethyl acetate (29 mL) was added copper(II) bromide (2.57 g, 11.50 mmol) and the resulting mixture was heated under argon to reflux (60-70° C.) overnight. The next morning LCMS indicated formation of the product (LCMS: 3.000 min, [M+1]=271.0). The dark solution was filtered through a plug of SiO$_2$ gel and the media was washed with 10% EtOAc/hexanes. The filtrate was concentrated and dried in vacuo affording 11B (1.51 g) which was used in the next step without further purification.

Example 11

Example 11 was prepared from 5-(methylthio)-1,3,4-thiadiazol-2-amine (100 mg, 0.679 mmol) and 11B (183 mg, 0.679 mmol) in ethanol (3.4 mL) as described for Example 1. The crude product was purified by preparative HPLC to afford Example 11 (57.8 mg) as a solid. LCMS: 3.811 min, [M+1]=318.1; $^1$H NMR (500 MHz, CDCl$_3$) δ ppm 8.02 (s, 1H), 7.30 (s, 1H), 7.21-7.24 (m, 1H), 7.12 (d, J=8.25 Hz, 1H), 6.67 (d, J=8.25 Hz, 1H), 3.95 (s, 3H), 2.79 (s, 3H).

Example 12

6-(Benzo[d]thiazol-2-yl)-N-ethylimidazo[2,1-b][1,3,4]thiadiazol-2-amine

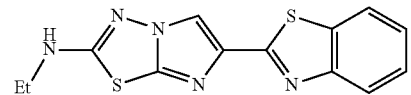 [SMILES: CCNc1nn2cc(-c3nc4ccccc4s3)nc2s1]

12A. 2-(2-(Methylsulfonyl)imidazo[2,1-b][1,3,4]thiadiazol-6-yl)benzo[d]thiazole To a solution of Example 4 (540 mg, 1.774 mmol) in THF (18 mL) in a round bottom flask was added m-CPBA (918 mg, 5.32 mmol) at rt. The mixture was stirred under nitrogen while being monitored by LCMS. After 4 h, LCMS analysis revealed a 1.0 to 1.4 ratio of sulfoxide and sulfone. Excess m-CPBA (another 3 equiv) was added. The reaction mixture was stirred continuously at rt. After approximately 16 h the reaction mixture was predominately the desired product (LCMS: 3.133 min, [M+1]=337.0). The excess oxidant was quenched with Na$_2$S$_2$O$_3$ (aq, sat'd) and the resulting mixture was diluted with EtOAc, and washed sequentially with NaHCO$_3$ and brine. The product was extracted with EtOAc (3×), and the combined organics were dried over Na$_2$SO$_4$. The resulting residue was redissolved in MeOH with warming and then cooled to form solids. The solids were isolated by filtration to afford Example 12A as an orange solid (339 mg) which was used in the next step without further purification. LCMS: 3.146 min, [M+1]=337.0; $^1$H NMR (500 MHz, CDCl$_3$) δ ppm 9.24 (s, 1H), 8.16 (d, J=7.70 Hz, 1H), 8.03 (d, J=8.25 Hz, 1H), 7.55 (t, J=7.70 Hz, 1H), 7.46 (t, J=7.42 Hz, 1H), 3.69 (s, 3H).

Example 12

Example 12A (0.02 g, 0.059 mmol) was dissolved in DMF (0.595 mL) in a microwave tube (medium size 0.2 to 2 mL). Ethylamine (0.059 mL, 0.119 mmol) was added to the solution and the vessel was sealed. The resulting slurry was subjected to microwave conditions: 70° C., 10 min. LCMS analysis of the crude mixture revealed the formation of the desired product (LCMS 3.471 min [M+1]=302.0). MeOH was added and the reaction mixture was purified by preparative HPLC (PHENOMENEX® Luna Axia, 30×100 mm; 0-100% MeCN/H$_2$O/TFA) to afford 14 mg of Example 12 as a yellow solid. LCMS: 3.481 min, [M+1]=302.0; $^1$H NMR (500 MHz, DMSO-d$_6$) δ ppm 8.51 (s, 1H), 8.18 (t, J=5.22 Hz, 1H), 8.06 (d, J=8.25 Hz, 1H), 7.92 (d, J=7.70 Hz, 1H), 7.47 (t, J=7.70 Hz, 1H), 7.37 (t, J=7.42 Hz, 1H), 3.34 (ddd, J=12.51, 7.29, 7.15 Hz, 2H), 1.20 (t, J=7.15 Hz, 3H).

Example 13

6-(7-Ethoxybenzofuran-2-yl)-2-ethylimidazo[2,1-b][1,3,4]thiadiazole

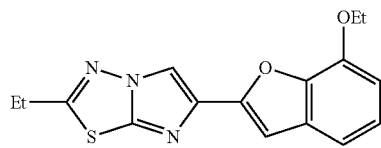

13A. 2-Ethyl-6-(7-methoxybenzofuran-2-yl)imidazo[2,1-b][1,3,4]-thiadiazole 13A was prepared as described in Example 1 from 5-ethyl-1,3,4-thiadiazol-2-amine (0.466 g, 3.60 mmol) and 2-bromo-1-(7-ethoxybenzofuran-2-yl)ethanone (0.97 g, 3.60 mmol) in EtOH (18 mL). Flash chromatography (0-100% EtOAc/hexanes) of the crude residue afforded 13A (580 mg) as a yellow solid, which was used directly in the next step. LCMS 3.615 min, [M+1]=300.1.

13B. 2-(2-Ethylimidazo[2,1-b][1,3,4]thiadiazol-6-yl)benzofuran-7-ol

To 13A (0.360 g, 1.203 mmol) in CH$_2$Cl$_2$ (6 mL) in a round bottom flask at −78° C. was added BBr$_3$ (2.77 mL, 2.77 mmol) and the resulting mixture was stirred for 30 min at −78° C. before warming to rt overnight. Upon completion (LCMS: 3.128 min, [M+1]=286.1), cold (0° C.) Et$_2$O was added, followed by MeOH. H$_2$O was added and the biphasic mixture was extracted 3× with Et$_2$O, dried over Na$_2$SO$_4$, filtered, and concentrated to afford 13B (528 mg) as a white solid which can be used directly in the next step. Alternatively, this material was purified via preparative HPLC. LCMS: 3.11 min, [M+1]=286.1; $^1$H NMR (500 MHz, DMSO-d$_6$) δ ppm 10.03 (s, 1H), 8.51 (s, 1H), 6.99-7.06 (m, 3H), 6.73 (d, J=6.05 Hz, 1H), 3.09 (q, J=7.33 Hz, 2H), 1.34 (t, J=7.42 Hz, 3H).

Example 13

13B (25 mg, 0.088 mmol) was dissolved in acetone (876 μL) and bromoethane (11.46 mg, 0.105 mmol) and K$_2$CO$_3$ (24.22 mg, 0.175 mmol) were added at rt. The resulting slurry was heated at 60° C. overnight. Upon completion (LCMS: 3.775 min, [M+l]=314.1), the reaction mixture was diluted with EtOAc, washed with brine, and extracted with EtOAc (3×). The organics were removed and the residue was redissolved in MeOH. The crude material was purified by preparative HPLC to afford Example 13 (8.4 mg) as a white solid. LCMS: 3.773 min, [M+l]=314.1; $^1$H NMR (500 MHz, CDCl$_3$) δ ppm 8.17 (s, 1H), 7.13-7.22 (m, 3H), 6.82 (d, J=7.70 Hz, 1H), 4.29 (q, J=6.78 Hz, 2H), 3.08 (q, J=7.70 Hz, 2H), 1.54 (t, J=7.15 Hz, 3H), 1.46 (t, J=7.42 Hz, 3H).

Examples 14 to 109

The following additional imidazothiadiazole Examples have been prepared, isolated and characterized using the methods disclosed above.

TABLE 1

| Example | Structure | Formula | Mol. Weight | LCMS Retention Time Min/M + 1 |
|---|---|---|---|---|
| 14 | 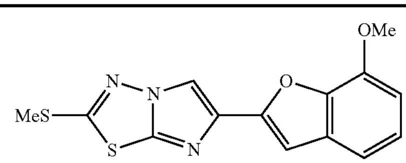 | C$_{14}$H$_{11}$N$_3$O$_2$S$_2$ | 317.386 | 3.651/318.1 |
| 15 | 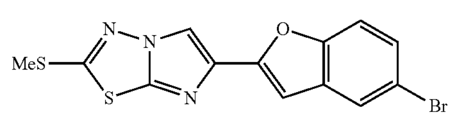 [SMILES: CSc1nn2cc(-c3cc4cc(Br)ccc4o3)nc2s1] | C$_{13}$H$_8$BrN$_3$OS$_2$ | 366.256 | 3.328/368.2 |
| 16 | 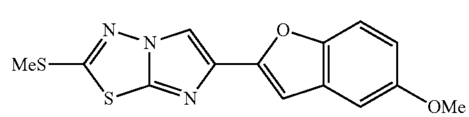 [SMILES: COc1ccc2oc(-c3cn4nc(SC)sc4n3)cc2c1] | C$_{14}$H$_{11}$N$_3$O$_2$S$_2$ | 317.386 | 2.846/318.1 |

TABLE 1-continued

| | Structure | Formula | MW | |
|---|---|---|---|---|
| 17 | MeS-[imidazo-thiadiazole]-benzothiophene | $C_{13}H_9N_3S_3$ | 303.426 | 3.876/304.0 |
| 18 | EtS-[imidazo-thiadiazole]-benzofuran | $C_{14}H_{11}N_3OS_2$ | 301.387 | 3.993/302.0 |
| 19 | (t-Bu)S-[imidazo-thiadiazole]-benzofuran | $C_{16}H_{15}N_3OS_2$ | 329.44 | 4.298/330.0 |
| 20 | MeS-[imidazo-thiadiazole]-benzofuran-OMe | $C_{14}H_{11}N_3O_2S_2$ | 317.386 | 3.756/318.1 |
| 21 | MeS-[imidazo-thiadiazole]-benzofuran-Me | $C_{14}H_{11}N_3OS_2$ | 301.387 | 3.993/302.1 |
| 22 | MeS-[imidazo-thiadiazole]-benzofuran-Me | $C_{14}H_{11}N_3OS_2$ | 301.387 | 3.990/302.1 |
| 23 | MeS-[imidazo-thiadiazole]-benzofuran-Cl | $C_{13}H_8ClN_3OS_2$ | 321.805 | 4.068/322.0 |
| 24 | MeS-[imidazo-thiadiazole]-benzofuran(Me)(OMe) | $C_{15}H_{13}N_3O_2S_2$ | 331.413 | 3.996/332.1 |
| 25 | MeS-[imidazo-thiadiazole]-benzofuran(Me)(OMe)(OMe) | $C_{16}H_{15}N_3O_3S_2$ | 361.439 | 4.083/362.1 |
| 26 | EtO-[imidazo-thiadiazole]-benzofuran | $C_{14}H_{11}N_3O_2S$ | 285.321 | 2.65/286.1 |
| 27 | EtO-[imidazo-thiadiazole]-benzothiazole | $C_{13}H_{10}N_4OS_2$ | 302.375 | 2.43/303.1 |
| 28 | PrO-[imidazo-thiadiazole]-benzofuran | $C_{15}H_{13}N_3O_2S$ | 299.348 | 2.91/300.1 |

TABLE 1-continued

| # | Structure | Formula | MW | RT/MS |
|---|---|---|---|---|
| 29 | (i-Pr)O-[thiadiazole-imidazo]-benzofuran | $C_{15}H_{13}N_3O_2S$ | 299.348 | 2.88/300.1 |
| 30 | PrO-[thiadiazole-imidazo]-benzothiazole | $C_{14}H_{12}N_4OS_2$ | 316.401 | 2.72/317.1 |
| 31 | (i-Bu)O-[thiadiazole-imidazo]-benzofuran | $C_{16}H_{15}N_3O_2S$ | 313.374 | 3.15/314.1 |
| 32 | (i-Bu)O-[thiadiazole-imidazo]-benzothiazole | $C_{15}H_{14}N_4OS_2$ | 330.428 | 2.95/331.1 |
| 33 | (i-Pr)O-[thiadiazole-imidazo]-benzothiazole | $C_{14}H_{12}N_4OS_2$ | 316.401 | 2.62/317.1 |
| 34 | MeO-[thiadiazole-imidazo]-benzofuran-OEt | $C_{15}H_{13}N_3O_3S$ | 315.347 | 2.691/316.1 |
| 35 | MeO-[thiadiazole-imidazo]-benzofuran-OMe | $C_{14}H_{11}N_3O_3S$ | 301.32 | 3.460/302.1 |
| 36 | MeO-[thiadiazole-imidazo]-benzofuran(OMe,OMe,Me) | $C_{16}H_{15}N_3O_4S$ | 345.373 | 3.516/346.1 |
| 37 | Et-[thiadiazole-imidazo]-benzofuran-OMe | $C_{15}H_{13}N_3O_2S$ | 299.348 | 2.621/300.4 |
| 38 | Et-[thiadiazole-imidazo]-benzoxazole-F,F | $C_{13}H_{8F2}N_4OS$ | 306.291 | 3.391/307.1 |
| 39 | Et-[thiadiazole-imidazo]-benzoxazole-OMe | $C_{14}H_{12}N_4O_2S$ | 300.336 | 2.02/301.1 |
| 40 | Et-[thiadiazole-imidazo]-benzoxazole-Cl | $C_{13}H_9ClN_4OS$ | 304.755 | 3.570/305.1 |

TABLE 1-continued

| | | | | |
|---|---|---|---|---|
| 41 | | $C_{13}H_9N_3OS$ | 255.295 | 3.483/256.0 |
| 42 | | $C_{14}H_{12}N_4OS$ | 284.336 | 2.24/285.1 |
| 43 | | $C_{15}H_{13}N_3O_2S$ | 299.348 | 3.740/300.1 |
| 44 | | $C_{14}H_{10}BrN_3OS$ | 348.218 | 4.033/349.9 |
| 45 | | $C_{13}H_9ClN_4OS$ | 304.755 | 3.543/305.1 |
| 46 | | $C_{15}H_{14}N_4OS$ | 298.363 | 3.655/299.2 |
| 47 | | $C_{14}H_{11}N_3OS$ | 269.322 | 3.743/270.0 |
| 48 | | $C_{14}H_{12}N_4OS$ | 284.336 | 3.466/285.1 |
| 49 | | $C_{13}H_9FN_4OS$ | 288.3 | 3.305/289.1 |
| 50 | | $C_{14}H_{12}N_4OS$ | 284.336 | 2.22/285.1 |
| 51 | | $C_{16}H_{16}N_4O_2S$ | 328.389 | 3.800/329.2 |
| 52 | | $C_{13}H_9BrN_4OS$ | 349.206 | 2.46/351.0 |

TABLE 1-continued
| | | | | |
|---|---|---|---|---|
| 53 | 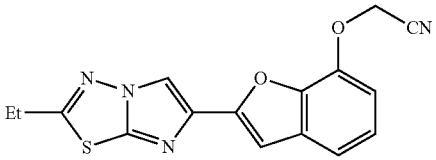 [SMILES: CCc1nn2cc(-c3cc4cccc(OCC#N)c4o3)nc2s1] | C$_{16}$H$_{12}$N$_4$O$_2$S | 324.357 | 3.238/325.1 |
| 54 | 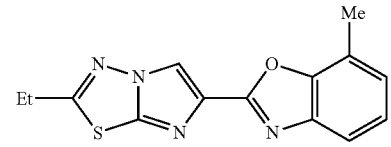 [SMILES: CCc1nn2cc(-c3nc4cccc(C)c4o3)nc2s1] | C$_{14}$H$_{12}$N$_4$OS | 284.336 | 2.22/285.1 |
| 55 | 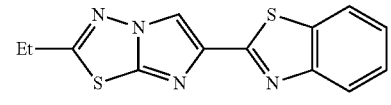 [SMILES: CCc1nn2cc(-c3nc4ccccc4s3)nc2s1] | C$_{13}$H$_{10}$N$_4$S$_2$ | 286.375 | 2.503/287.4 |
| 56 | 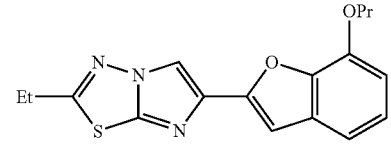 | C$_{17}$H$_{17}$N$_3$O$_2$S | 327.401 | 4.008/328.2 |
| 57 | 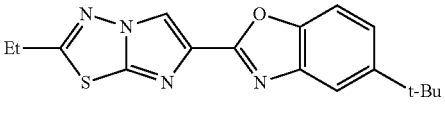 [SMILES: CCc1nn2cc(-c3nc4cc(C(C)(C)C)ccc4o3)nc2s1] | C$_{17}$H$_{18}$N$_4$OS | 326.416 | 2.80/327.1 |
| 58 | 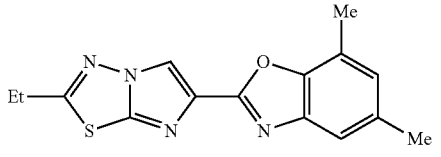 [SMILES: CCc1nn2cc(-c3nc4cc(C)cc(C)c4o3)nc2s1] | C$_{15}$H$_{14}$N$_4$OS | 298.363 | 3.721/299.2 |
| 59 | 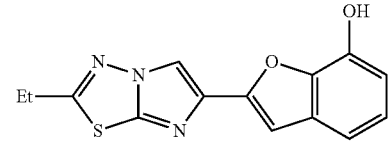 | C$_{14}$H$_{11}$N$_3$O$_2$S | 285.321 | 3.11/286.1 |
| 60 | 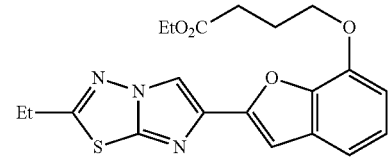 [SMILES: CCOC(=O)CCCOc1cccc2cc(-c3cn4nc(CC)sc4n3)oc12] | C$_{20}$H$_{21}$N$_3$O$_4$S | 399.463 | 3.846/400.2 |
| 61 | 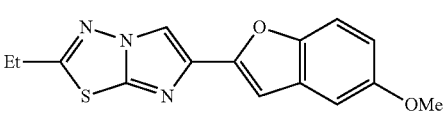 [SMILES: CCc1nn2cc(-c3cc4cc(OC)ccc4o3)nc2s1] | C$_{15}$H$_{13}$N$_3$O$_2$S | 299.348 | 2.673/300.4 |
| 62 | 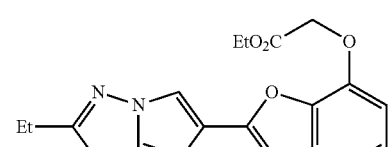 | C$_{18}$H$_{17}$N$_3$O$_4$S | 371.41 | 3.548/372.2 |
| 63 | 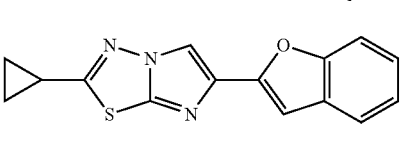 | C$_{15}$H$_{11}$N$_3$OS | 281.332 | 3.771/282.1 |

TABLE 1-continued

| Example | Structure | Formula | Mol. Weight | LCMS Retention Time Min/M + 1 | NMR |
|---|---|---|---|---|---|
| 64 | 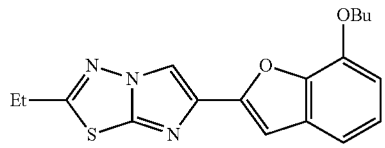 | $C_{18}H_{19}N_3O_2S$ | 341.427 | 4.193/342.2 | |
| 65 | 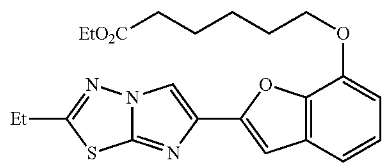 [SMILES: CCOC(=O)CCCCCOc1cccc2cc(-c3cn4nc(CC)sc4n3)oc12] | $C_{22}H_{25}N_3O_4S$ | 427.517 | 4.106/428.3 | |
| 66 | 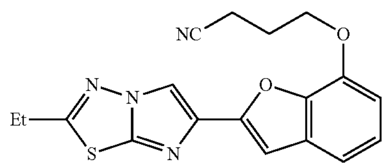 [SMILES: CCc1nn2cc(-c3cc4cccc(OCCCC#N)c4o3)nc2s1] | $C_{18}H_{16}N_4O_2S$ | 352.41 | 3.376/353.2 | |
| 67 | 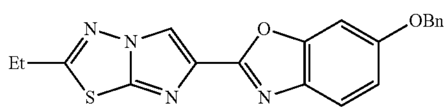 [SMILES: CCc1nn2cc(-c3nc4ccc(OCc5ccccc5)cc4o3)nc2s1] | $C_{20}H_{16}N_4O_2S$ | 376.432 | 2.763/376.9 | |
| 68 | 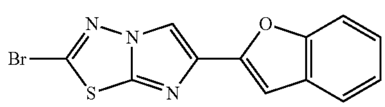 | $C_{12}H_6BrN_3OS$ | 320.165 | 3.790/321.9 | |
| 69 | 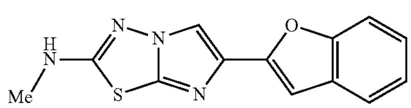 [SMILES: CNc1nn2cc(-c3cc4ccccc4o3)nc2s1] | $C_{13}H_{10}N_4OS$ | 270.31 | 3.506/271.1 | |
| 70 | 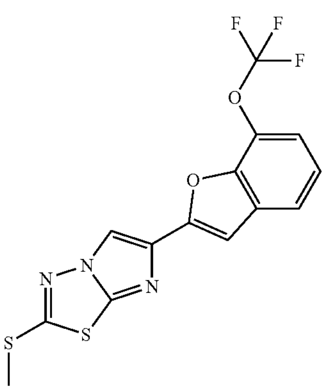 [SMILES: CSc1nn2cc(-c3cc4cccc(OC(F)(F)F)c4o3)nc2s1] | $C_{14}H_8F_3N_3O_2S_2$ | 371.36 | 4.105/372.1 | |
| 71 | 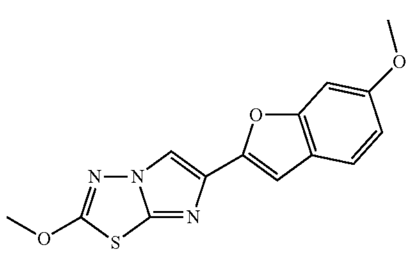 [SMILES: COc1ccc2cc(-c3cn4nc(OC)sc4n3)oc2c1] | $C_{14}H_{11}N_3O_3S$ | 301.33 | 2.498/302.1 | $^1$H NMR (500 MHz, methanol-d$_3$) d ppm 8.10 (1 H, s), 7.43 (1 H, d, J = 8.2 Hz), 7.08 (1 H, d, J = 1.6 Hz), 6.94 (1 H, s), 6.86 (1 H, dd, J = 8.8, 2.2 Hz), 4.24 (3 H, s), 3.84 (3 H, s) |

TABLE 1-continued

| # | Structure | Formula | MW | LC/MS | 1H NMR |
|---|---|---|---|---|---|
| 72 | 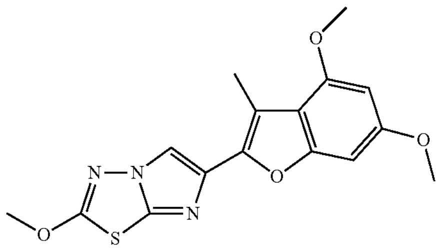 | $C_{16}H_{15}N_3O_4S$ | 345.38 | 2.883/346 | 1H NMR (500 MHz, methanol-$d_3$) d ppm 7.99 (1 H, s), 6.64 (1 H, d, J = 2.2 Hz), 6.34 (1 H, d, J = 1.6 Hz), 4.24 (3 H, s), 3.88 (3 H, s), 3.82 (3 H, s), 2.56 (3 H, s) |
| 73 | 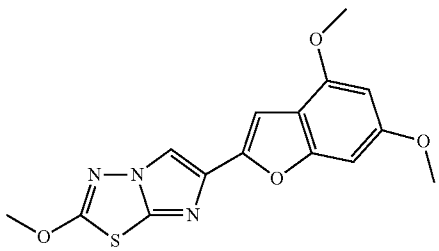 | $C_{15}H_{13}N_3O_4S$ | 331.35 | 3.515/332.1 | 1H NMR (500 MHz, methanol-$d_3$) d ppm 8.07 (1 H, s), 6.97 (1 H, s), 6.71 (1 H, d, J = 1.1 Hz), 6.38 (1 H, d, J = 1.6 Hz), 4.25 (3 H, s), 3.91 (3 H, s), 3.84 (3 H, s) |
| 74 | 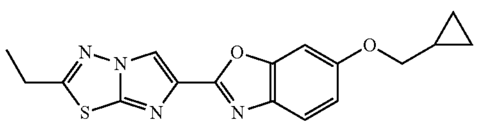 [SMILES: CCc1nn2cc(-c3nc4ccc(OCC5CC5)cc4o3)nc2s1] | $C_{17}H_{16}N_4O_2S$ | 340.41 | 2.86/340.98 | |
| 75 | 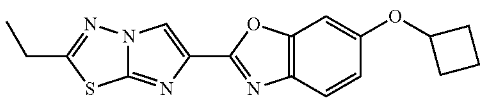 [SMILES: CCc1nn2cc(-c3nc4ccc(OC5CCC5)cc4o3)nc2s1] | $C_{17}H_{16}N_4O_2S$ | 340.41 | 2.99/340.92 | |
| 76 | 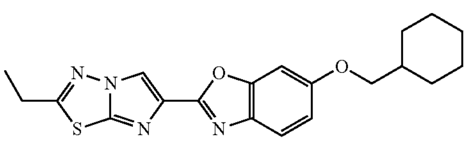 [SMILES: CCc1nn2cc(-c3nc4ccc(OCC5CCCCC5)cc4o3)nc2s1] | $C_{20}H_{22}N_4O_2S$ | 382.49 | 3.50/382.83 | |
| 77 | 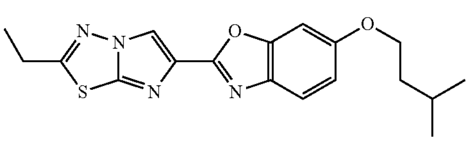 [SMILES: CCc1nn2cc(-c3nc4ccc(OCCC(C)C)cc4o3)nc2s1] | $C_{18}H_{20}N_4O_2S$ | 356.45 | 3.28/356.75 | |
| 78 | 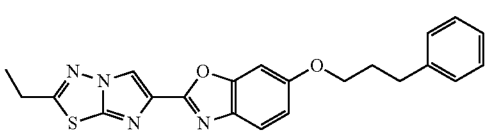 [SMILES: CCc1nn2cc(-c3nc4ccc(OCCCc5ccccc5)cc4o3)nc2s1] | $C_{22}H_{20}N_4O_2S$ | 404.49 | 3.30/404.92 | |
| 79 | 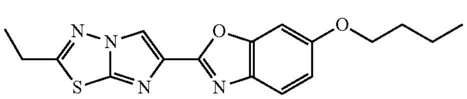 [SMILES: CCCCOc1ccc2nc(-c3cn4nc(CC)sc4n3)oc2c1] | $C_{17}H_{18}N_4O_2S$ | 342.42 | 3.13/342.85 | |
| 80 | 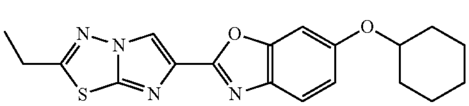 [SMILES: CCc1nn2cc(-c3nc4ccc(OC5CCCCC5)cc4o3)nc2s1] | $C_{19}H_{20}N_4O_2S$ | 368.46 | 3.26/368.89 | |
| 81 | 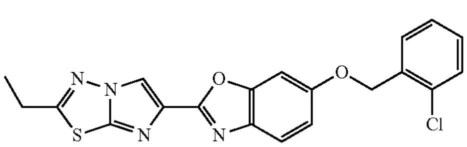 [SMILES: CCc1nn2cc(-c3nc4ccc(OCc5ccccc5Cl)cc4o3)nc2s1] | $C_{20}H_{15}ClN_4O_2S$ | 410.88 | 3.18/410.85 | |

TABLE 1-continued

| | | | | | |
|---|---|---|---|---|---|
| 82 | 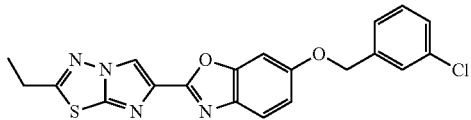 [SMILES: CCc1nn2cc(-c3nc4ccc(OCc5cccc(Cl)c5)cc4o3)nc2s1] | C₂₀H₁₅ClN₄O₂S | 410.88 | 3.21/410.83 | |
| 83 | 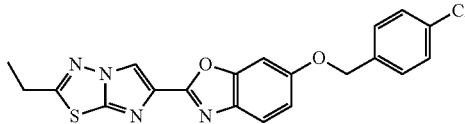 | C₂₀H₁₅ClN₄O₂S | 410.88 | 3.22/410.82 | |
| 84 | 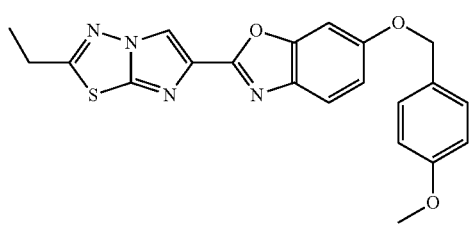 [SMILES: CCc1nn2cc(-c3nc4ccc(OCc5ccc(OC)cc5)cc4o3)nc2s1] | C₂₁H₁₈N₄O₃S | 406.46 | 3.00/406.89 | |
| 85 | 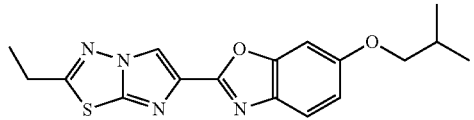 [SMILES: CCc1nn2cc(-c3nc4ccc(OCC(C)C)cc4o3)nc2s1] | C₁₇H₁₈N₄O₂S | 342.42 | 3.13/342.73 | |
| 86 | 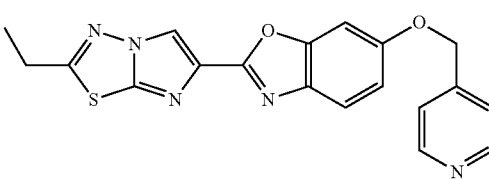 | C₁₉H₁₅N₅O₂S | 377.43 | 2.53/377.91 | |
| 87 | 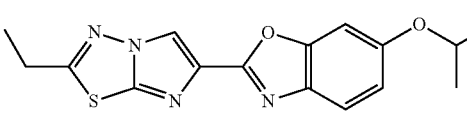 | C₁₆H₁₆N₄O₂S | 328.39 | 2.89/328.79 | |
| 89 | 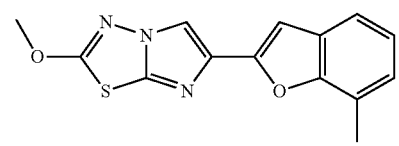 [SMILES: COc1nn2cc(-c3cc4cccc(C)c4o3)nc2s1] | C₁₄H₁₁N₃O₂S | 285.33 | 2.840/286 | ¹H NMR (500 MHz, methanol-d₃) d ppm 8.19 (1 H, s), 7.38 (1 H, d, J = 7.7 Hz), 7.05-7.14 (2 H, m), 7.01 (1 H, s), 4.25 (3 H, s), 2.54 (3 H, s) |
| 90 | 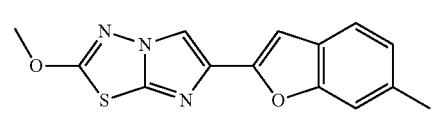 | C₁₄H₁₁N₃O₂S | 285.33 | 2.828/286 | ¹H NMR (500 MHz, methanol-d₃) d ppm 8.12 (1 H, s), 7.43 (1 H, d, J = 7.7 Hz), 7.28 (1 H, s), 7.05 (1 H, d, J = 7.7 Hz), 6.96 (1 H, d, J = 1.1 Hz), 4.23 (3 H, s), 2.45 (3 H, s) |
| 91 | 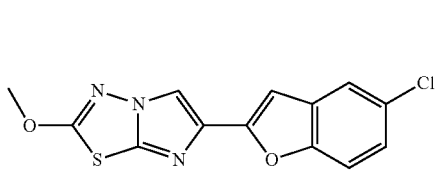 [SMILES: COc1nn2cc(-c3cc4cc(Cl)ccc4o3)nc2s1] | C₁₃H₈ClN₃O₂S | 305.74 | 2.993/306 | ¹H NMR (500 MHz, DMSO-d₆) d ppm 8.55 (1H, s), 7.71 (1 H, d, J = 2.2 Hz), 7.61 (1 H, d, J = 8.8 Hz), 7.30 (1 H, dd, J = 8.2, 2.2 Hz), 7.08 (1 H, s), 4.21 (3 H, s) |
| 92 | 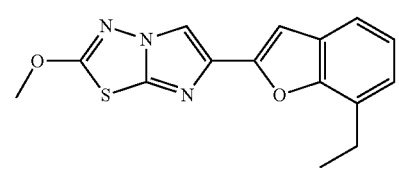 [SMILES: CCc1cccc2cc(-c3cn4nc(OC)sc4n3)oc12] | C₁₅H₁₃N₃O₂S | 299.35 | 3.8/300 | ¹H NMR (500 MHz, chloroform-d) d ppm 7.95 (1 H, s), 7.41 (1 H, d, J = 7.7 Hz), 7.13-7.18 (1 H, m), 7.08-7.11 (1 H, m), 7.01 (1 H, s), 4.21 (3 H, s), 2.99 (2 H, d, J = 7.7 Hz), 1.39 (3 H, t, J = 7.7 Hz) |

TABLE 1-continued

| | | | | | |
|---|---|---|---|---|---|
| 93 | | $C_{14}H_{11}N_3O_3S$ | 301.33 | 3.410/302.1 | $^1$H NMR (500 MHz, CDCl$_3$) d ppm 7.90 (s, 1 H), 7.36 (d, J = 8.80 Hz, 1 H), 7.03 (d, J = 2.75 Hz, 1 H), 6.99 (s, 1 H), 6.85 (dd, J = 8.80, 2.75 Hz, 1 H), 4.20 (s, 3 H), 3.84 (s, 3 H). |
| 94 | | $C_{13}H_8ClN_3O_2S$ | 305.74 | 2.953/306.1 | $^1$H NMR (500 MHz, methanol-d$_3$) d ppm 8.18 (1 H, s), 7.54 (2 H, d, J = 8.2 Hz), 7.23 (1 H, dd, J = 8.5, 1.9 Hz), 7.03 (1 H, s), 4.24 (3 H, s) |
| 95 | | $C_{14}H_{11}N_3O_2S$ | 285.33 | 2.898/286.1 | $^1$H NMR (500 MHz, methanol-d$_3$) d ppm 8.15 (1 H, s), 7.28-7.41 (2 H, m), 7.03-7.15 (1 H, m), 6.95 (1 H, s), 4.24 (3 H, s), 2.41 (3 H, s) |
| 96 | | $C_{13}H_8FN_3O_2S$ | 289.29 | 3.545/290.1 | $^1$H NMR (500 MHz, DMSO-d$_6$) d ppm 8.47 (s, 1 H), 7.63 (dd, J = 8.52, 5.77 Hz, 1 H), 7.53 (d, J = 7.15 Hz, 1 H), 7.11-7.15 (m, 1 H), 7.08 (s, 1 H), 4.20 (s, 3 H) |
| 97 | | $C_{13}H_8FN_3O_2S$ | 289.29 | 3.520/290 | $^1$H NMR (500 MHz, DMSO-d$_6$) d ppm 8.51 (s, 1 H), 7.58 (dd, J = 8.80, 3.85 Hz, 1 H), 7.43 (dd, J = 9.07, 2.47 Hz, 1 H), 7.10 (td, J = 9.07, 2.75 Hz, 1 H), 7.07 (s, 1 H), 4.20 (s, 3 H) |
| 98 | | $C_{14}H_8F_3N_3O_3S$ | 355.30 | 3.878/356.1 | $^1$H NMR (500 MHz, DMSO-d$_6$) d ppm 8.56 (s, 1 H), 7.65-7.70 (m, 2 H), 7.26 (dd, J = 8.80, 2.20 Hz, 1 H), 7.14 (s, 1 H), 4.20 (s, 3 H) |
| 99 | | $C_{13}H_8N_4O_4S$ | 316.30 | 4.55/317 | $^1$H NMR (500 MHz, DMSO-d$_6$) d 4.23 (s, 3 H) 7.31 (s, 1 H) 7.86 (d, J = 8.25 Hz, 1 H) 8.18 (dd, J = 8.52, 1.92 Hz, 1 H) 8.48 (s, 1 H) 8.69 (s, 1 H) |

TABLE 1-continued

| | | | | |
|---|---|---|---|---|
| 100 | 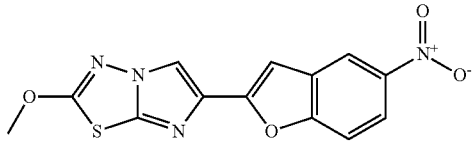 [SMILES: COc1nn2cc(-c3cc4cc([N+](=O)[O-])ccc4o3)nc2s1] | C₁₃H₈N₄O₄S | 316.30 | 4.42/317 | ¹H NMR (500 MHz, DMSO-d₆) δ 4.22 (s, 3 H) 7.30 (s, 1 H) 7.83 (d, J = 9.35 Hz, 1 H) 8.19 (dd, J = 8.80, 2.20 Hz, 1 H) 8.60 (d, J = 2.75 Hz, 1 H) 8.64 (s, 1 H) |
| 101 | 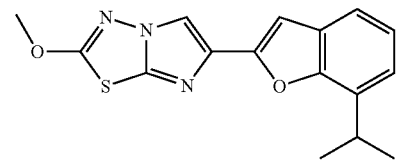 [SMILES: COc1nn2cc(-c3cc4cccc(C(C)C)c4o3)nc2s1] | C₁₆H₁₅N₃O₂S | 313.38 | 3.878/314 | ¹H NMR (500 MHz, chloroform-d) d ppm 7.95 (1 H, s), 7.41 (1 H, d, J = 7.7 Hz), 7.17 (1 H, t, J = 7.4 Hz), 7.11-7.14 (1 H, m), 7.01 (1 H, s), 4.21 (3 H, s), 3.52 (1 H, d, J = 7.1 Hz), 1.42 (6 H, d, J = 7.1 Hz) |
| 102 | 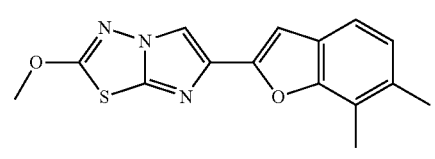 | C₁₅H₁₃N₃O₂S | 299.35 | 3.908/300.1 | ¹H NMR (500 MHz, CDCl₃) d ppm 7.92 (s, 1 H), 7.28 (d, J = 7.70 Hz, 1 H), 7.02 (d, J = 7.70 Hz, 1 H), 6.95 (s, 1 H), 4.20 (s, 3 H), 2.47 (s, 3 H), 2.38 (s, 3 H) |
| 103 | 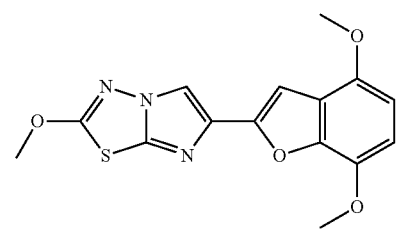 [SMILES: COc1nn2cc(-c3cc4c(OC)ccc(OC)c4o3)nc2s1] | C₁₅H₁₃N₃O₄S | 331.35 | 3.378/332.1 | ¹H NMR (500 MHz, CDCl₃) d ppm 7.97 (s, 1 H), 7.12 (s, 1 H), 6.68 (d, J = 8.25 Hz, 1 H), 6.53 (d, J = 8.80 Hz, 1 H), 4.19 (s, 3 H), 3.98 (s, 3 H), 3.90 (s, 3 H) |
| 104 | 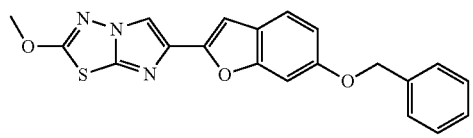 [SMILES: COc1nn2cc(-c3cc4ccc(OCc5ccccc5)cc4o3)nc2s1] | C₂₀H₁₅N₃O₃S | 377.42 | 3.878/378 | |
| 105 | 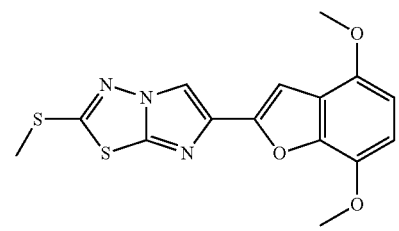 [SMILES: COc1ccc(OC)c2oc(-c3cn4nc(SC)sc4n3)cc12] | C₁₅H₁₃N₃O₃S₂ | 347.42 | 2.758/348.2 | |
| 106 | 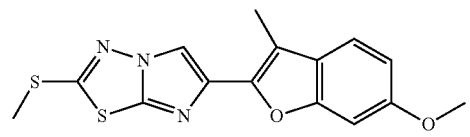 | C₁₅H₁₃N₃O₂S₂ | 331.42 | 3.961/332 | ¹H NMR (500 MHz, CDCl₃) d ppm 7.95 (s, 1 H), 7.37 (d, J = 8.80 Hz, 1 H), 7.01 (d, J = 2.20 Hz, 1 H), 6.87 (dd, J = 8.25, 2.20 Hz, 1 H), 3.85 (s, 3 H), 2.76 (s, 3 H), 2.51 (s, 3 H) |
| 107 | 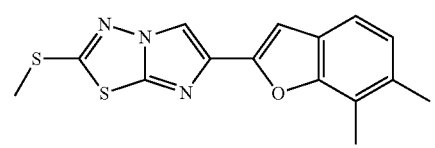 | C₁₅H₁₃N₃OS₂ | 315.42 | 4.161/316.1 | |
| 108 | 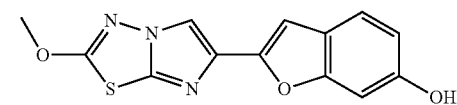 [SMILES: COc1nn2cc(-c3cc4ccc(O)cc4o3)nc2s1] | C₁₃H₉N₃O₃S | 287.30 | 3.878/287 | |

| | | | | |
|---|---|---|---|---|
| 109 | (structure) | C₁₃H₈ClN₃O₂S | 305.74 | 3.781/306 | ¹H NMR (500 MHz, CDCl₃) d ppm 7.95 (s, 1 H), 7.39 (d, J = 7.70 Hz, 1 H), 7.19-7.23 (m, 2 H), 7.16 (s, 1 H), 4.23 (s, 3 H) |

The following products (Examples 110 to 306) were analyzed by reverse phase analytical HPLC carried out on a AGILENT® Analytical HPLC system (1200 series) running Chem Station for LC system Rev. B.04.01 SP1 (647) using:

Method A: Eclipse XDB-C18 3.5 microns column (4.6× 30 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm), or Method B: Eclipse XDB-C18 3.5 microns column (4.6× 30 mm) eluted at 3 mL/min with a 2 min gradient from 100% A to 100% B (A: 5% acetonitrile, 94.95% water, 0.05% TFA; B: 5% water, 94.95% acetonitrile, 0.05% TFA, UV 220 nm) or Method C: SunfireC18 3.5 microns column (4.6×30 mm) eluted at 3 mL/min with a 2 min. gradient from 100% A to 100% B (A: 5% methanol, 94.95% water, 0.05% TFA; B: 5% water, 94.95% methanol, 0.05% TFA, UV 220 nm) or Method D: SunfireC18 3.5 microns column (4.6×30 mm) eluted at 3 mL/min with a 2 min. gradient from 100% A to 100% B (A: 5% acetonitrile, 94.95% water, 0.05% TFA; B: 5% water, 94.95% acetonitrile, 0.05% TFA, UV 220 nm) or Method E: XBridge C18 3.5 microns column (4.6×30 mm) eluted at 3 mL/min with a 2 min. gradient from 100% A to 100% B (A: 5% methanol, 94.95% water, 0.05% TFA; B: 5% water, 94.95% methanol, 0.05% TFA, UV 220 nm) or Method F: ZORBAX® SB-C18 3.5 microns column (4.6×30 mm) eluted at 3 mL/min with a 2 min. gradient from 100% A to 100% B (A: 5% methanol, 94.95% water, 0.05% TFA; B: 5% water, 94.95% methanol, 0.05% TFA, UV 220 nm).

Purification of intermediates and final products was carried out via either normal or reverse phase chromatography. Normal phase chromatography was carried out using pre-packed SiO₂ cartridges eluted with gradients of hexanes and ethyl acetate or methylene chloride and methanol. Reverse phase preparative HPLC was carried out using a AGILENT® Preparative HPLC system (1200 series) running Chem Station for LC system Rev. B.04.01 SP1 (647) using Method A: ZORBAX® 5 µm SB-C18 PrepHT 21.2×100 mm column with a 15 to 20 min gradient at 15 to 20 mL/min from 100% A to 100% B (A: 5% methanol or acetonitrile, 94.95% water, 0.05% TFA; B: 5% water, 94.95% methanol or acetonitrile, 0.05% TFA, UV 220 nm to 284 nm); Method B: Sunfire 5 µm Prep C18 OBD 19×250 mm column with a 15 to 20 min gradient at 15 to 20 mL/min from 100% A to 100% B (A: 5% methanol or acetonitrile, 94.95% water, 0.05% TFA; B: 5% water, 94.95% methanol or acetonitrile, 0.05% TFA, UV 220 nm to 284 nm).

LCMS chromatograms were obtained on a 6210 G1969A LC/MSD TOF spectrometer from AGILENT® Technologies running AGILENT® MassHunter Workstation Acquisition (Data Acquisition for TOF/Q-TOF B.02.01 (B2116)) and using the following LC conditions: ZORBAX® C18 column (3.5 microns, 2.1×30 mm) with a 2.0 min gradient at 0.3 mL/min from 0% B to 100% B (Solvent A: AcCN:H₂O:HCOOH (5:95:0.05) and Solvent B: AcCN:H₂O:HCOOH (95:5:0.05), UV 220 nm).

Example 110

2-(2-(Methylthio)imidazo[2,1-b][1,3,4]thiadiazol-6-yl)benzo[d]oxazole

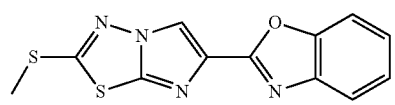 [SMILES: CSc1nn2cc(-c3nc4ccccc4o3)nc2s1]

110A. Ethyl 2-(methylthio)imidazo[2,1-b][1,3,4]thiadiazole-6-carboxylate

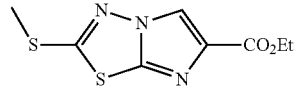

Example 110A was prepared according to the procedure described for Example 7A by using 5-thiomethyl-1,3,4-thiadiazol-2-amine (1.5 g, 310.2 mmol) instead of 5-ethyl-1,3,4-thiadiazol-2-amine. After cooling at rt the reaction mixture was partitioned between EtOAc/NaHCO₃. The organic phase was dried (MgSO₄), filtered and concentrated to dryness. The crude was purified by flash chromatography (hexanes/EtOAc 20 to 40%) followed by crystallization (EtOH) to give the title material as brown crystals (1.34 g, 5.51 mmol, 18%). The filtrate was concentrated to dryness and purified by flash chromatography (hexanes/EtOAC 10 to 55%) followed by a crystallization (EtOH) to give some additional title material (0.612 g, 2.51 mmol, 8%) as brown crystals. LC (Method B): 1.267 min. ¹H NMR (600 MHz, DMSO-d₆) δ ppm 8.76 (s, 1H), 4.27 (q, J=7.2 Hz, 2H), 2.78 (s, 3H), 1.28 (t, J=7.2 Hz, 3H).

110B. 2-(Methylthio)imidazo[2,1-b][1,3,4]thiadiazole-6-carboxylic acid

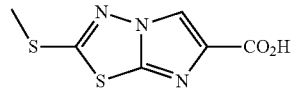

To a stirred solution of ethyl 2-(methylthio)imidazo[2,1-b][1,3,4]thiadiazole-6-carboxylate (Example 110A, 0.106 g, 0.434 mmol) in THF (4 mL) was added NaOTMS (0.608 mL, 0.608 mmol). The reaction mixture was stirred at rt for 18 hours then acidified to pH=3 with AcOH. The reaction mixture was concentrated to dryness and triturated with H$_2$O (sonicated for 1 minute). The resulting light yellow precipitate was filtered off and washed with Et$_2$O to afford the title material (58 mg, 0.27 mmol, 62%). LC (Method B): 0.912 min; LCMS: Anal. Calcd. for C$_6$H$_5$N$_3$O$_2$S$_2$: 214.98. found: 215.99 (M+1)$^+$. $^1$H NMR (600 MHz, DMSO-d$_6$) δ ppm 12.69 (b.s, 1H), 8.66 (s, 1H), 2.79 (s, 3H).

110C. N-(2-Hydroxyphenyl)-2-(methylthio)imidazo[2,1-b][1,3,4]thiadiazole-6-carboxamide

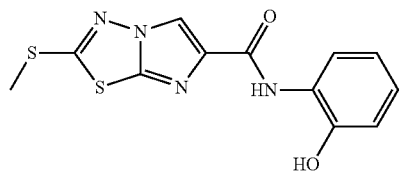 [SMILES: CSc1nn2cc(C(=O)Nc3ccccc3O)nc2s1]

To a stirred suspension of 2-(methylthio)imidazo[2,1-b][1,3,4]thiadiazole-6-carboxylic acid (Example 110B, 93.5 mg, 0.43 mmol) and HATU (173 mg, 0.46 mmol) in DMF (2.5 mL) was added DIPEA (378 µL, 2.17 mmol). After stirring for 5 minutes the resulting suspension was charged with 2-aminophenol (47.4 mg, 0.43 mmol) and the mixture was stirred at rt for 24 hours and partitioned between EtOAc/sat. NaHCO$_3$—H$_2$O (1/1). The organic phase was dried (MgSO$_4$), filtered and concentrated to dryness. The residue was purified by flash chromatography (Heptanes/EtOAc 0 to 65%) to give the title material as a tan solid (0.048 g, 0.16 mmol, 36%). The material was used as such for the next reaction. LC (Method B): 1.440 min. LCMS: Anal. Calcd. for C$_{12}$H$_{10}$N$_4$O$_2$S$_2$: 306.02. found: 307.04 (M+1)$^+$.

Example 110

2-(2-(Methylthio)imidazo[2,1-b][1,3,4]thiadiazol-6-yl)benzo[d]oxazole

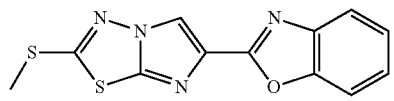 [SMILES: CSc1nn2cc(-c3nc4ccccc4o3)nc2s1]

The title material was prepared according to the procedure described for Example 7 by using N-(2-hydroxyphenyl)-2-(methylthio)imidazo[2,1-b][1,3,4]thiadiazole-6-carboxamide (1.12 g, 3.64 mmol) instead of 2-ethyl-N-(2-hydroxyphenyl)imidazo[2,1-b][1,3,4]thiadiazole-6-carboxamide and by heating the sealed vessel at 200° C. for 35 minutes and at 210° C. for 10 minutes. The desired product was obtained as a beige solid (585 mg, 2.03 mmol, 56%). LC (Method A): 2.013 min. $^1$H NMR (600 MHz, DMSO-d$_6$) δ ppm 9.00 (s, 1H), 7.73 (m, 2H), 7.38 (m, 2H), 2.80 (s, 3H).

Example 111

2-(2-Methoxyimidazo[2,1-b][1,3,4]thiadiazol-6-yl)benzo[d]oxazole

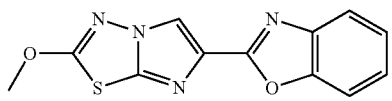 [SMILES: COc1nn2cc(-c3nc4ccccc4o3)nc2s1]

111A. 2-(2-(Methylsulfonyl)imidazo[2,1-b][1,3,4]thiadiazol-6-yl)benzo[d]oxazole

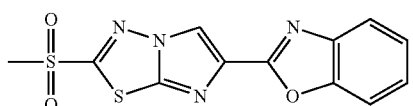

To a stirred solution of 2-(2-(methylthio)imidazo[2,1-b][1,3,4]thiadiazol-6-yl)benzo[d]oxazole (Example 110, 245 mg, 0.85 mmol) in TFA at 0° C. was added CF$_3$CO$_3$H (637 µL, 2.55 mmol) and the resulting reaction mixture was stirred for 5 minutes at 0° C. and was allowed to stir at rt for 19 hours. Then the mixture was concentrated to dryness and triturated with a mixture of DCM/MeOH. The desired product was filtered off as a beige solid (267 mg, 0.62 mmol, 72%). LC (Method A): 1.744 min.

Example 111

2-(2-Methoxyimidazo[2,1-b][1,3,4]thiadiazol-6-yl)benzo[d]oxazole

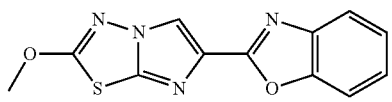

To a stirred suspension of 2-(2-(methylsulfonyl)imidazo[2,1-b][1,3,4]thiadiazol-6-yl)benzo[d]oxazole (Example 111A, 152 mg, 0.47 mmol) in MeOH (4 mL) at rt was added NaOMe (103 mg, 0.47 mmol) dropwise. The reaction mixture was stirred at rt for 10 minutes and the resulting precipitate was filtered off and rinsed with Et$_2$O to give the desired product as a beige solid (45 mg, 0.17 mmol, 35%). LC (Method A): 1.901 min; LCMS: Anal. Calcd. for C$_{12}$H$_8$N$_4$O$_2$S: 272.04. found: 273.06 (M+1)$^+$. $^1$H NMR (600 MHz, DMSO-d$_6$) δ ppm 8.93 (s, 1H), 7.75-7.74 (m, 2H), 7.40-7.39 (m, 2H), 4.23 (s, 3H).

Example 112

5-Methyl-2-(2-methylimidazo[2,1-b][1,3,4]thiadiazol-6-yl)benzo[d]oxazole

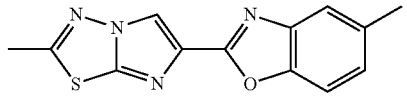

112A. Ethyl 2-methoxyimidazo[2,1-b][1,3,4]thiadiazole-6-carboxylate

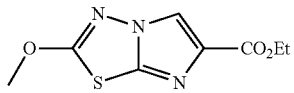

To a solution of ethyl 2-(methylthio)imidazo[2,1-b][1,3,4]thiadiazole-6-carboxylate (Example 110A, 3.50 g, 14.4 mmol) in a mixture of MeOH/H$_2$O (120 mL, 1/1) was added OXONE® (19.9 g, 64.7 mmol). The reaction mixture was stirred at rt for 20 hours and the MeOH was removed in vacuum. The crude was partitioned between H$_2$O/DCM and the organic phase was dried over MgSO$_4$ and concentrated to dryness. The resulting sulfonyl derivative was dissolved in MeOH (60 mL) and NaOMe (2.90 g, 13.4 mmol) was added. The reaction mixture was stirred at rt for 1 hour and concentrated to dryness. The crude was dissolved in hot MeOH and allowed to stand overnight at RT. The resulting crystals were filtered off and the title material was isolated as beige crystals (1.78 g, 7.82 mmol, 59%). LC (Method B): 1.106 min; LCMS: Anal. Calcd. for C$_8$H$_9$N$_3$O$_3$S: 227.04. found: 228.03 (M+1)$^+$. $^1$H NMR (600 MHz, DMSO-d$_6$) δ ppm 8.66 (s, 1H), 4.25 (q, J=7.2 Hz, 2H), 4.20 (s, 3H), 1.28 (t, J=7.2 Hz, 3H).

112B. 2-Methoxyimidazo[2,1-b][1,3,4]thiadiazole-6-carboxylic acid

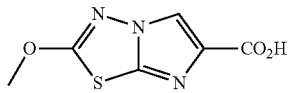

The title material was prepared according to the procedure described for Example 110B using ethyl 2-methoxyimidazo[2,1-b][1,3,4]thiadiazole-6-carboxylate (Example 112A, 0.809 g, 3.56 mmol) instead of ethyl 2-(methylthio)imidazo[2,1-b][1,3,4]thiadiazole-6-carboxylate and KOTMS instead of NaOTMS. The reaction mixture was stirred for 2.5 hours. After filtration, the resulting white solid was triturated with hot MeOH and filtered to give the title material as a white solid (224 mg, 1.12 mmol, 32%). LC (Method B): 0.769 min; LCMS: Anal. Calcd. for C$_6$H$_5$N$_3$O$_3$S: 199.01. found: 200.00 (M+1)$^+$. $^1$H NMR (600 MHz, DMSO-d$_6$) δ ppm 12.57 (s, 1H), 8.58 (s, 1H), 4.20 (s, 3H).

112C. 2-Methoxyimidazo[2,1-b][1,3,4]thiadiazole-6-carbonyl chloride

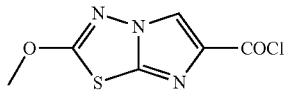

To a stirred suspension of 2-methoxyimidazo[2,1-b][1,3,4]thiadiazole-6-carboxylic acid (Example 112B, 1.50 g, 7.53 mmol) in DCM (50 mL) was added oxalyl chloride (765 μL, 9.04 mmol) and DMF (1 drop). The reaction mixture was stirred at rt for 1 hour, then concentrated to dryness to give a yellow solid (1.64 g, 7.54 mmol, 100%) which was used as such for the next reaction. LC (Method A): 1.515 min; $^1$H NMR (600 MHz, DMSO-d$_6$) δ ppm 8.58 (s, 1H), 4.20 (s, 3H).

112D. N-(2-Hydroxy-5-methylphenyl)-2-methoxyimidazo[2,1-b][1,3,4]thiadiazole-6-carboxamide

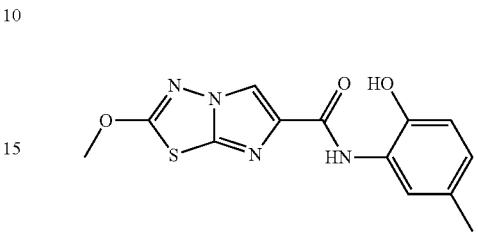

To a stirred suspension of 2-amino-4-methylphenol (214 mg, 1.74 mmol) and 2-methoxyimidazo[2,1-b][1,3,4]thiadiazole-6-carbonyl chloride (Example 112C, 151 mg, 0.69 mmol) in CH$_3$CN (6 mL) was added DIPEA (604 μL, 3.47 mmol). The reaction mixture was stirred at rt for 1.5 hours, concentrated to dryness and partitioned between DCM/sat. NaHCO$_3$. The organic phase was dried over MgSO$_4$, filtered and concentrated to dryness. The solid was triturated with MeOH and filtered off to afford the title material (79 mg, 0.26 mmol, 37%). LC (Method A): 1.902 min. (M+H)$^+$; LCMS: Anal. Calcd. for C$_{13}$H$_{12}$N$_4$O$_3$S: 304.06. found: 305.09 (M+1)$^+$, 327.06 (M+Na)$^+$. $^1$H NMR (600 MHz, DMSO-d$_6$) δ ppm 9.95 (s, 1H), 9.45 (s, 1H), 8.61 (s, 1H), 8.12 (s, 1H), 6.79 (d, J=7.8 Hz, 1H), 6.72 (d, J=7.8 Hz, 1H), 4.21 (s, 3H), 2.22 (s, 3H).

Example 112

5-Methyl-2-(2-methylimidazo[2,1-b][1,3,4]thiadiazol-6-yl)benzo[d]oxazole

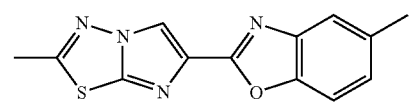

A microwave vessel was charged with N-(2-hydroxy-5-methylphenyl)-2-methoxyimidazo[2,1-b][1,3,4]thiadiazole-6-carboxamide (Example 112D, 64 mg, 0.21 mmol) and a mixture of TFA/AcOH (1.2 mL, 1/1). The reaction mixture was heated in microwave at 200° C. for 2 hours. After cooling, the reaction mixture was concentrated to dryness and partitioned between DCM/sat. NaHCO$_3$. Then the organic phase was dried over MgSO$_4$, filtered and concentrated to dryness. The crude was purified by flash chromatography (hexanes/EtOAc 0 to 80%) to give the title material as a beige solid (10 mg, 0.035 mmol, 17%). LC (Method A): 1.987 min; LCMS: Anal. Calcd. for C$_{13}$H$_{10}$N$_4$OS: 270.06. found: 271.08 (M+1)$^+$. $^1$H NMR (600 MHz, DMSO-d$_6$) δ ppm 8.99 (s, 1H), 7.62 (d, J=8.4 Hz, 1H), 7.56 (s, 1H), 7.22 (d, J=7.8 Hz, 1H), 2.78 (s, 3H), 2.44 (s, 3H).

Example 113

5-Methyl-2-(2-methylthio)imidazo[2,1-b][1,3,4]thiadiazol-6-yl)benzo[d]oxazole

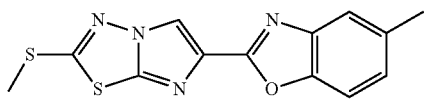

113A. 2-(Methylthio)imidazo[2,1-b][1,3,4]thiadiazole-6-carbonyl chloride

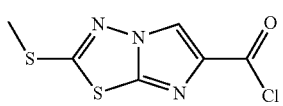

To a stirred suspension of 2-(methylthio)imidazo[2,1-b][1,3,4]thiadiazole-6-carboxylic acid (Example 110B, 15 g, 0.070 mol) in DCM (350 mL) was added oxalyl chloride (29.5 mL, 0.348 mol) followed by DMF (1 drop). Gas evolution was observed and the reaction mixture stirred at ambient temperature for 3.5 hours. The suspension was then concentrated to dryness to give a light-yellow solid and used as such by assuming a quantitative yield. LC (Method A): 1.686 min; $^1$H NMR (600 MHz, DMSO-$d_6$) δ ppm 8.68 (s, 1H) 2.78 (s, 3H).

113B. N-(2-Hydroxy-5-methylphenyl)-2-(methylthio)imidazo[2,1-b][1,3,4]thiadiazole-6-carboxamide

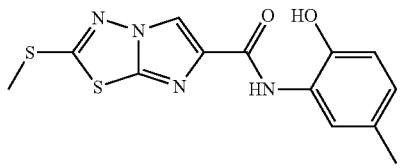

To a stirred suspension of 2-amino-4-methylphenol (214 mg, 1.74 mmol) and 2-(methylthio)imidazo[2,1-b][1,3,4]thiadiazole-6-carbonyl chloride (Example 113A, 407 mg, 1.74 mmol) in CH$_3$CN (12 mL) was added DIPEA (1.52 mL, 8.70 mmol). The reaction mixture was stirred at rt for 2 hours, concentrated to dryness and triturated with DCM to afford the title material (291 mg, 0.96 mmol, 55%). LC (Method B): 1.557 min. LCMS: Anal. Calcd. for $C_{13}H_{12}N_4O_2S_2$: 320.04. found: 321.06 (M+1)$^+$. $^1$H NMR (600 MHz, DMSO-$d_6$) δ ppm 9.93 (s, 1H), 9.44 (s, 1H), 8.66 (s, 1H), 8.09 (s, 1H), 6.76 (d, J=8.1 Hz, 1H), 6.69 (br d, J~6.4 Hz, 1H), 2.76 (s, 3H), 2.19 (s, 3H).

Example 113

5-Methyl-2-(2-methylthio)imidazo[2,1-b][1,3,4]thiadiazol-6-yl)benzo[d]oxazole

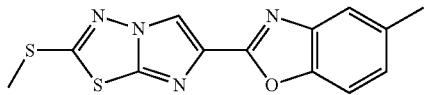

A microwave vessel was charged with N-(2-hydroxy-5-methylphenyl)-2-(methylthio)imidazo[2,1-b][1,3,4]thiadiazole-6-carboxamide (Example 113B, 190 mg, 0.62 mmol) and a mixture of TFA/AcOH (3.0 mL, 1/1). The reaction mixture was heated in microwave at 200° C. for 10 minutes. After cooling, the desired product was filtered off from the reaction mixture, rinsed with acetone and dried to give the title material as a white solid (21 mg, 0.069 mmol, 11%). LC (Method A): 2.140 min; LCMS: Anal. Calcd. for $C_{13}H_{10}N_4OS_2$: 302.03. found: 303.02 (M+1)$^+$, 325.0176 (M+Na)$^+$. $^1$H NMR (600 MHz, DMSO-$d_6$) δ ppm 8.99 (s, 1H), 7.62 (d, J=7.8 Hz, 1H), 7.55 (s, 1H), 7.21 (d, J=8.4 Hz, 1H), 2.82 (s, 3H), 2.44 (s, 3H).

Example 114

2-(2-(Methylthio)imidazo[2,1-b][1,3,4]thiadiazol-6-yl)-6-(2-(pyrrolidin-1-yl)ethoxy)benzo[d]oxazole

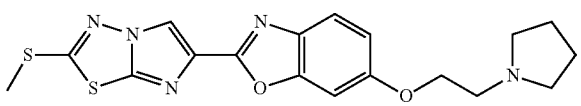 [SMILES: CSc1nn2cc(-c3nc4ccc(OCCN5CCCC5)cc4o3)nc2s1]

114A. 2-(2-(Methylthio)imidazo[2,1-b][1,3,4]thiadiazol-6-yl)benzo[d]oxazol-6-ol

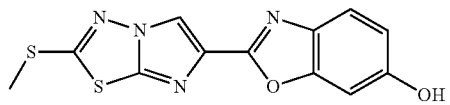 [SMILES: CSc1nn2cc(-c3nc4ccc(O)cc4o3)nc2s1]

The title material was prepared according to the procedure described for Example 113. The residue was purified by preparative HPLC to give the desired product as an amorphous beige solid (3.6 mg, 0.085 mmol). LC (Method A): 1.813 min; LCMS: Anal. Calcd. for $C_{12}H_8N_4O_2S_2$: 304.01. found: 305.01 (M+1)$^+$. $^1$H NMR (600 MHz, DMSO-$d_6$) δ ppm 9.84 (s, 1H), 8.91 (s, 1H), 7.53 (d, J=8.4 Hz, 1H), 7.06 (d, J=1.8 Hz, 1H), 7.06 (dd, $J_1$=1.8 Hz, $J_2$=8.4 Hz, 1H), 2.81 (s, 3H).

Example 114

2-(2-(Methylthio)imidazo[2,1-b][1,3,4]thiadiazol-6-yl)-6-(2-(pyrrolidin-1-yl)ethoxy)benzo[d]oxazole

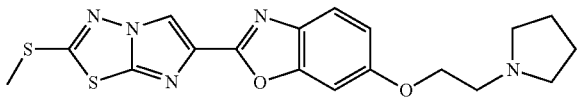 [SMILES: CSc1nn2cc(-c3nc4ccc(OCCN5CCCC5)cc4o3)nc2s1]

2-(2-(Methylthio)imidazo[2,1-b][1,3,4]thiadiazol-6-yl)benzo[d]oxazol-6-ol (Example 114A, 104 mg, 0.25 mmol), 1-(2-chloroethyl)pyrrolidine hydrochloride (51 mg, 0.30 mmol) and Cs$_2$CO$_3$ (218 mg, 0.67 mmol) were combined and heated at 100° C. for 2 hours and the resulting reaction mixture was partitioned between CHCl$_3$/H$_2$O. The organic phase was washed with brine, dried (MgSO$_4$) and concentrated to dryness to afford the desired product as a beige solid (43 mg, 0.11 mmol, 43%). LC (Method A): 1.594 min; LCMS: Anal. Calcd. for $C_{18}H_{19}N_5O_2S_2$: 401.10. found: 402.13 (M+1)$^+$. $^1$H NMR (600 MHz, DMSO-$d_6$) δ ppm 8.94 (s, 1H), 7.62 (d, J=7.8 Hz, 1H), 7.39 (s, 1H), 6.99 (d, J=7.8 Hz, 1H), 4.14 (s, 2H), 2.81 (s, 5H), 2.53 (s, 4H), 1.69 (s, 4H).

Example 115

6-(Benzyloxy)-2-(2-(methylthio)imidazo[2,1-b][1,3,4]thiadiazol-6-yl)benzo[d]oxazole

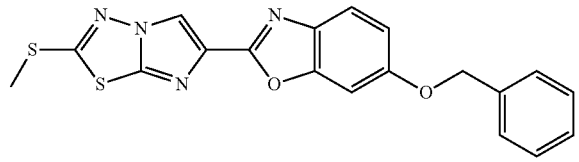 [SMILES: CSc1nn2cc(-c3nc4ccc(OCc5ccccc5)cc4o3)nc2s1]

2-(2-(Methylthio)imidazo[2,1-b][1,3,4]thiadiazol-6-yl)benzo[d]oxazol-6-ol (Example 114A, 101 mg, 0.24 mmol), benzyl bromide (28.6 µL, 0.24 mmol) and $K_2CO_3$ (50 mg, 0.36 mmol) were combined and stirred at rt for 2 hours. The reaction mixture was diluted with water and shaken vigorously. The precipitate was filtered off and rinsed with a small amount of MeOH to give the desired compound as a beige solid (104 mg, 0.26 mmol). LC (Method A): 2.309 min; LCMS: Anal. Calcd. for $C_{19}H_{14}N_4O_2S_2$: 394.06. found: 395.08 (M+1)$^+$. $^1$H NMR (600 MHz, DMSO-d$_6$) δ ppm 8.94 (s, 1H), 7.64 (d, J=8.4 Hz, 1H), 7.50-7.47 (m, 3H), 7.42-7.40 (m, 2H), 7.36-7.33 (m, 1H), 7.08-7.06 (m, 1H), 5.19 (s, 2H), 2.81 (s, 3H).

Example 116

6-Methoxy-2-(2-(methylthio)imidazo[2,1-b][1,3,4]thiadiazol-6-yl)benzo[d]oxazole

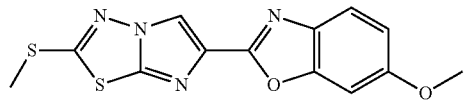

To a stirred suspension of 2-(2-(methylthio)imidazo[2,1-b][1,3,4]thiadiazol-6-yl)benzo[d]oxazol-6-ol (Example 114A, 101 mg, 0.24 mmol) and $CH_3I$ (60.0 µL, 0.96 mmol) in DMF (2.5 mL) at rt was added NaH (29 mg, 0.72 mmol). The reaction mixture was stirred at rt for 35 minutes and water was added. The mixture was vigorously shaken and the resulting precipitate was filtered off and washed with MeOH and hexanes to give the title material as a beige solid (69.5 mg, 0.22 mmol, 90%). LC (Method A): 2.055 min; LCMS: Anal. Calcd. for $C_{13}H_{10}N_4O_2S_2$: 318.02. found: 319.05 (M+1)$^+$. $^1$H NMR (600 MHz, DMSO-d$_6$) δ ppm 8.94 (s, 1H), 7.63 (d, J=8.4 Hz, 1H), 7.38 (s, 1H), 6.99 (d, J=7.2 Hz, 1H), 3.84 (s, 3H), 2.81 (s, 3H).

Example 117

2-(2-(Methylthio)imidazo[2,1-b][1,3,4]thiadiazol-6-yl)-6-(pyridin-2-ylmethoxy)benzo[d]oxazole

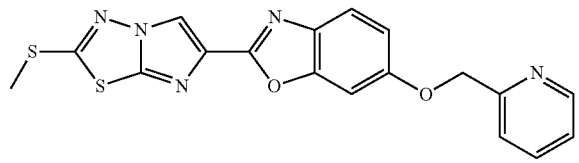 [SMILES: CSc1nn2cc(-c3nc4ccc(OCc5ccccn5)cc4o3)nc2s1]

(2-(2-(Methylthio)imidazo[2,1-b][1,3,4]thiadiazol-6-yl)benzo[d]oxazol-6-ol (Example 114A, 104 mg, 0.25 mmol), 2-(chloromethyl)pyridine hydrochloride (49 mg, 0.30 mmol) and $Cs_2CO_3$ (218 mg, 0.67 mmol) were dissolved in DMF (2 mL) and heated in a sealed vessel at 100° C. for 40 minutes. Then the reaction mixture was diluted with water and shaken vigorously. The desired product was filtered off as a beige solid and washed with MeOH (88 mg, 0.22 mmol, 90%). LC (Method A): 1.836 min; LCMS: Anal. Calcd. for $C_{18}H_{13}N_5O_2S_2$: 395.05. found: 396.05 (M+1)$^+$. $^1$H NMR (600 MHz, DMSO-d$_6$) δ ppm 8.95 (s, 1H), 8.60 (s, 1H), 7.87-7.85 (m, 1H), 7.66 (d, J=8.4 Hz, 1H), 7.58 (d, J=7.2 Hz, 1H), 7.50 (s, 1H), 7.38-7.36 (m, 1H), 7.11-7.09 (m, 1H), 5.27 (s, 2H), 2.81 (s, 3H).

Example 118

6-(2-Fluoroethoxy)-2-(2-(methylthio)imidazo[2,1-b][1,3,4]thiadiazol-6-yl)benzo[d]oxazole

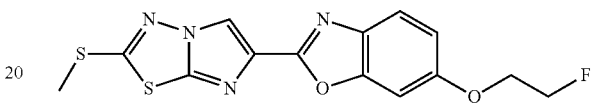

(2-(2-(Methylthio)imidazo[2,1-b][1,3,4]thiadiazol-6-yl)benzo[d]oxazol-6-ol (Example 114A, 90 mg, 0.22 mmol), 2-fluoroethanol (28 µL, 0.47 mmol) and triphenylphosphine (124 mg, 0.47 mmol) were suspended in THF (2 mL). DIAD (93 µL, 0.47 mmol) was added and the reaction mixture was heated in a sealed vessel at 70° C. for 2 hours. The resulting suspension was concentrated to dryness and triturated with MeOH (using sonication). The desired product was filtered off as a beige solid and crystallized (20 mg) from hot DMF. The title material was isolated as a light pink solid (6 mg, 0.046 mmol, 21%). LC (Method A): 1.994 min; LCMS: Anal. Calcd. for $C_{14}H_{11}FN_4O_2S_2$: 350.03. found: 351.04 (M+1)$^+$. $^1$H NMR (600 MHz, DMSO-d$_6$) δ ppm 8.96 (s, 1H), 7.65 (d, J=8.4 Hz, 1H), 7.44 (d, J=1.8 Hz, 1H), 7.03 (dd, J$_1$=2.4 Hz, J$_2$=9.0 Hz, 1H), 4.83-4.82 (m, 1H), 4.75-4.74 (m, 1H), 4.36-4.35 (m, 1H), 4.31-4.30 (m, 1H), 2.82 (s, 3H).

Example 119

4-(Benzyloxy)-6-methoxy-2-(2-(methylthio)imidazo[2,1-b][1,3,4]thiadiazol-6-yl)benzo[d]oxazole

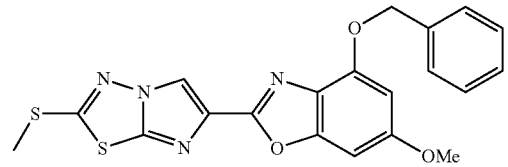 [SMILES: COc1cc(OCc2ccccc2)c2nc(-c3cn4nc(SC)sc4n3)oc2c1]

119A. 6-Methoxy-2-(2-(methylthio)imidazo[2,1-b][1,3,4]thiadiazol-6-yl)benzo[d]oxazol-4-ol

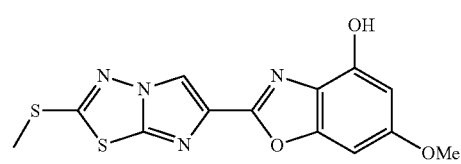 [SMILES: COc1cc(O)c2nc(-c3cn4nc(SC)sc4n3)oc2c1]

The title material was prepared according to the procedure described for Example 113. The desired product was isolated as brown crystals (44 mg, 0.098 mmol, 40%). LC (Method A): 1.961 min; LCMS: Anal. Calcd. for $C_{13}H_{10}N_4O_3S_2$: 334.02. found: 335.05 (M+1)$^+$. $^1$H NMR (600 MHz, DMSO-d$_6$) δ ppm 8.85 (s, 1H), 6.80 (d, J=2.4 Hz, 1H), 6.36 (d, J=2.4 Hz, 1H), 3.77 (s, 3H), 2.81 (s, 3H).

Example 119

4-(Benzyloxy)-6-methoxy-2-(2-(methylthio)imidazo[2,1-b][1,3,4]thiadiazol-6-yl)benzo[d]oxazole

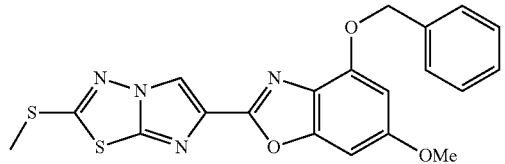 [SMILES: COc1cc(OCc2ccccc2)c2nc(-c3cn4nc(SC)sc4n3)oc2c1]

6-Methoxy-2-(2-(methylthio)imidazo[2,1-b][1,3,4]thiadiazol-6-yl)benzo[d]oxazol-4-ol (Example 119A, 203 mg, 0.61 mmol), benzyl bromide (72 µL, 0.61 mmol) and K$_2$CO$_3$ (168 mg, 1.21 mmol) were charged in a sealable vessel containing DMF (2.0 mL). The vessel was heated at 80° C. for 1 hour and at 100° C. for 3 hours. Then the reaction mixture was partitioned between DCM/H$_2$O and the organic phase was dried (MgSO$_4$), filtered and concentrated to dryness. The residue was purified by flash chromatography (DCM/EtOAc 0 to 10%) to afford the title material as a white solid (91 mg, 0.21 mmol, 35%). LC (Method A): 2.310 min; LCMS: Anal. Calcd. for $C_{20}H_{16}N_4O_3S_2$: 424.07. found: 425.09 (M+1)$^+$. $^1$H NMR (600 MHz, DMSO-d$_6$) δ ppm 8.92 (s, 1H), 7.52 (d, J=7.0 Hz, 2H), 7.43 (dd, J$_1$=2.4 Hz, J$_2$=7.2 Hz, 2H), 7.38-7.36 (m, 1H), 6.98 (d, J=2.3 Hz, 1H), 6.64 (d, J=1.8 Hz, 1H), 5.34 (s, 2H), 3.82 (s, 3H), 2.81 (s, 3H).

Example 120

2-(2-(Methylthio)imidazo[2,1-b][1,3,4]thiadiazol-6-yl)benzo[d]oxazol-4-amine

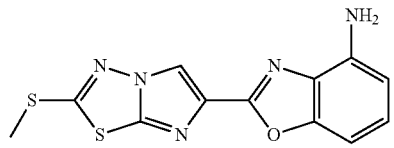

120A. 2-(2-(Methylthio)imidazo[2,1-b][1,3,4]thiadiazol-6-yl)-4-nitrobenzo[d]oxazole

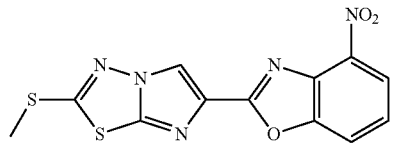 [SMILES: CSc1nn2cc(-c3nc4c([N+](=O)[O-])cccc4o3)nc2s1]

The title material was prepared according to the procedure described for Example 113 and was obtained as a beige solid (899 mg, 2.70 mmol, 95%). LC (Method A): 1.926 min; LCMS: Anal. Calcd. for $C_{12}H_7N_5O_3S_2$: 333.00. found: 334.03 (M+1)$^+$. $^1$H NMR (600 MHz, DMSO-d$_6$) δ ppm 9.21 (s, 1H), 8.25 (d, J=7.8 Hz, 1H), 8.22 (d, J=7.8 Hz, 1H), 7.63 (dd, J$_1$=7.8 Hz, J$_2$=8.4 Hz, 1H), 2.83 (s, 3H).

Example 120

2-(2-(Methylthio)imidazo[2,1-b][1,3,4]thiadiazol-6-yl)benzo[d]oxazol-4-amine

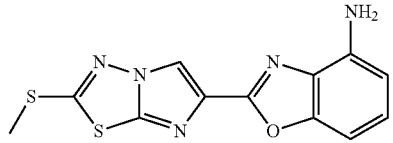 [SMILES: CSc1nn2cc(-c3nc4c(N)cccc4o3)nc2s1]

A stirred suspension 2-(2-(methylthio)imidazo[2,1-b][1,3,4]thiadiazol-6-yl)-4-nitrobenzo[d]oxazole (Example 120A, 815 mg, 2.44 mmol) in AcOH (20 mL) was charged with a suspension of 10% Pd/C (700 mg) in AcOH (10 mL). The vessel was evacuated and back-filled with H$_2$. The reaction mixture was stirred at r.t. for 17 hours then the catalyst was filtered off over CELITE® and rinsed with MeOH and DCM. The filtrate was concentrated to dryness to give the desired product (746 mg, 2.46 mmol). Assumed quantitative yield. LC (Method A): 1.825 min; LCMS: Anal. Calcd. for $C_{12}H_9N_5OS_2$: 303.02. found: 304.06 (M+1)$^+$. $^1$H NMR (600 MHz, DMSO-d$_6$) δ ppm 8.86 (s, 1H), 7.07-7.06 (m, 1H), 6.83 (d, J=8.2 Hz, 1H), 6.54 (d, J=8.2 Hz, 1H), 5.68 (br.s, 2H), 2.81 (s, 3H).

Example 121

4-(Benzyloxy)-6-methoxy-2-(2-methoxyimidazo[2,1-b][1,3,4]thiadiazol-6-yl)benzo[d]oxazole

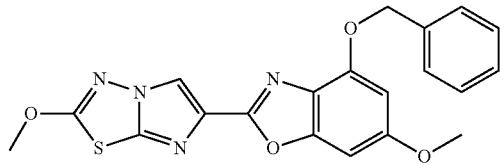 [SMILES: COc1cc(OCc2ccccc2)c2nc(-c3cn4nc(OC)sc4n3)oc2c1]

121A. 5-Bromo-2-amino-1,3,4-thiadiazole

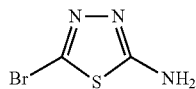

Ref: Heindl, J. et al., *Eur. J. Med. Chem.*, 10:121 (1975).

To a solution of 2-amino-1,3,4-thiadiazole (6.57 g, 0.065 mol) and sodium acetate trihydrate (8.85 g, 0.065 mol) in AcOH (35 mL) was added a solution of bromine (11.43 g, 3.67 mL, 0.0715 mol) in AcOH (15 mL) over ca. 20 min, while the internal temperature was kept below 20° C. using a cold water bath. After the addition of the bromine solution was completed, stirring was continued at room temperature for 18 h. The resulting slurry was slowly poured into ice water (200 mL), the resulting mixture was filtered and the filter-cake was washed with water and air-dried to give an off-white solid. Crystallization of this material from MeOH—H₂O afforded the product (9.52 g, 81%) as off-white needles. LCMS: Anal. Calcd. for C₂H₂BrN₃S: 180.91. found: 181.93 (M+1)⁺.

121B. Ethyl 2-bromoimidazo[2,1-b][1,3,4]thiadiazole-6-carboxylate

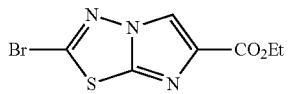 [SMILES: CCOC(=O)c1cn2nc(Br)sc2n1]

A mixture of 5-bromo-2-amino-1,3,4-thiadiazole (Example 121A, 1.98 g, 0.011 mol) and ethyl bromopyruvate (90%, 1.67 mL, 0.012 mol) in EtOH (12 mL) was heated in the microwave at 150° C. for 20 min. The resulting dark amber solution was concentrated and the residue was partitioned with DCM-saturated aqueous NaHCO₃. The organic phase was separated, dried (Na₂SO₄) and evaporated to give a dark red-brown gum. Flash chromatography (Isco/DCM, then 0-15% EtOAc-DCM) afforded a light yellow solid. Trituration of this solid with a minimum volume of MeOH afforded (after filtration and drying in vacuo) the pure product (0.526 g, 17%) as a white solid. LC (Method A): 1.605 min. LCMS: Anal. Calcd. for C₇H₆BrN₃O₂S: 276.94. found: 277.96 (M+1)⁺. ¹H NMR (600 MHz, DMSO-d₆) δ 8.85 (s, 1H), 4.24 (quart, J=7.0 Hz, 2H), 1.25 (t, J=7.0 Hz, 3H).

121C. 2-Bromoimidazo[2,1-b][1,3,4]thiadiazole-6-carboxylic acid

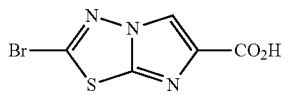

To a solution of ethyl 2-bromoimidazo[2,1-b][1,3,4]thiadiazole-6-carboxylate (Example 121B, 0.254 g, 0.92 mmol) in glacial AcOH (2.5 mL) was added 48% HBr (0.26 mL, 2.30 mmol). The resulting thick white slurry was heated at 150° C. (microwave) for 60 min, to give a white suspension; LC showed that the reaction was then essentially complete, with most of the pure product in the precipitate and only a trace of starting ester and extraneous peaks observed in the supernatant. The cooled mixture was thus filtered and the filter-cake was washed with a minimum volume of AcOH and then with DCM. Drying in vacuo gave the pure product (as HBr salt, 0.288 g, 95%) as a white solid. LC (Method A): 1.193 min. LCMS: Anal. Calcd. for C₇H₅F₂N₃O₂S: 246.91. found: 247.91 (M+1)⁺. ¹H NMR (600 MHz, DMSO-d₆) δ 8.77 (s, 1H).

121D. 2-Bromoimidazo[2,1-b][1,3,4]thiadiazole-6-carbonyl chloride

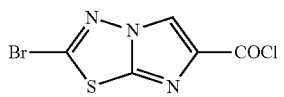 [SMILES: O=C(Cl)c1cn2nc(Br)sc2n1]

To a stirred suspension of 2-bromoimidazo[2,1-b][1,3,4]thiadiazole-6-carboxylic acid (Example 121C, 0.563 g, 2.28 mmol) in DCM (10 mL) was added oxalyl chloride (1.02 mL, 11.4 mmol) followed by DMF (1 drop). The reaction mixture was stirred at rt for 5 hours, then concentrated to dryness. The residue will be used as such in assuming a quantitative yield.

121E. 2-Bromo-N-(2,6-dihydroxy-4-methoxyphenyl)imidazo[2,1-b][1,3,4]thiadiazole-6-carboxamide

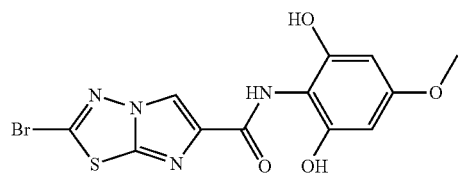 [SMILES: COc1cc(O)c(NC(=O)c2cn3nc(Br)sc3n2)c(O)c1]

To a stirred solution of 2-bromoimidazo[2,1-b][1,3,4]thiadiazole-6-carbonyl chloride (Example 121D, 0.608 g, 2.28 mmol) and 2-amino-5-methoxybenzene-1,3-diol (0.354 g, 2.28 mmol) in DMF (10 mL) at 0° C. was added triethylamine (0.953 mL, 6.84 mmol). The reaction mixture was stirred at 0° C. for 18 hours, then partitioned between DCM/sat. NaHCO₃. The organic phase was dried over anhydrous magnesium sulfate, filtered and concentrated to dryness. The residue was purified by flash chromatography (gradient of 0 to 15% EtOAc in DCM) and afforded the title material (0.107 g, 0.278 mmol, 12%) as a light pink solid. LC (Method A): 1.726 min. LCMS: Anal. Calcd. for C₁₂H₉BrN₄O₄S: 383.95. found: 284.96 (M+1)⁺, 406.94 (M+23)⁺. ¹H NMR (600 MHz, DMSO-d₆) δ 10.18 (m, 1H), 9.22 (d, J=8.8 Hz, 1H), 8.85 (br s, 1H), 5.98 (br d, 2H), 3.63 (s, 3H).

121F. 2-(2-Bromoimidazo[2,1-b][1,3,4]thiadiazol-6-yl)-6-methoxybenzo[d]oxazol-4-ol

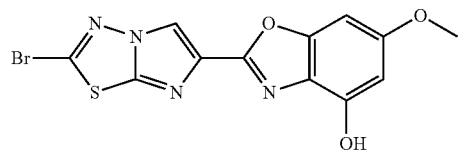 [SMILES: COc1cc(O)c2nc(-c3cn4nc(Br)sc4n3)oc2c1]

A mixture of 2-bromo-N-(2,6-dihydroxy-4-methoxyphenyl)imidazo[2,1-b][1,3,4]thiadiazole-6-carboxamide (Example 121E, 0.091 g, 0.236 mmol), TFA (1.2 mL) and AcOH (1.2 mL) was heated in a microwave oven at 150° C. for 5 minutes and then at 200° C. for 5 more minutes. The reaction was allowed to stand at rt overnight, and the solid was filtered off, rinsed with methanol and dried in vacuo to give the title material (0.024 g, 0.066 mmol, 28%) as a beige solid. LC (Method A): 1.902 min. LCMS: Anal. Calcd. for C₁₂H₇BrN₄O₃S: 365.94. found: 366.95 (M+1)', 368.95 (M+3)⁺. ¹H NMR (600 MHz, DMSO-d₆) δ 10.4 (br s, ~1H), 8.94 (s, 1H), 6.77 (br d, 1H), 6.34 (s, 1H), 3.74 (s, 3H).

121G. 4-(Benzyloxy)-2-(2-bromoimidazo[2,1-b][1,3,4]thiadiazol-6-yl)-6-methoxybenzo[d]oxazole

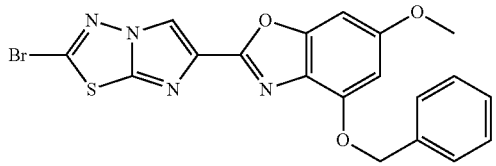 [SMILES: COc1cc(OCc2ccccc2)c2nc(-c3cn4nc(Br)sc4n3)oc2c1]

To a stirred suspension of 2-(2-bromoimidazo[2,1-b][1,3,4]thiadiazol-6-yl)-6-methoxybenzo[d]oxazol-4-ol (Example 121F, 0.024 g, 0.065 mmol) and $K_2CO_3$ (0.018 g, 0.131 mmol) in DMF (1.5 mL) was added benzyl bromide (7.5 μL, 0.065 mmol). The reaction mixture was stirred at rt for 18 hours, then water (~4 mL) was added and the mixture was sonicated for 2 min. The solid material was filtered off and dried under reduced pressure to give the title material (0.0167 g, 0.036 mmol) as a beige solid. LC (Method A): 2.259 min. LCMS: Anal. Calcd. for $C_{19}H_{13}BrN_4O_3S$: 455.99. found: 456.99 $(M+1)^+$, 458.99 $(M+3)^+$. $^1H$ NMR (600 MHz, DMSO-$d_6$) δ 9.12 (s, 1H), 7.58 (d, J=6.9 Hz, 2H), 7.49 (br t, 2H), 7.43 (br t, 1H), 7.05 (br d, 1H), 6.72 (br d, 1H), 5.41 (s, 2H), 3.88 (s, 3H).

Example 121

4-(Benzyloxy)-6-methoxy-2-(2-methoxyimidazo[2,1-b][1,3,4]thiadiazol-6-yl)benzo[d]oxazole

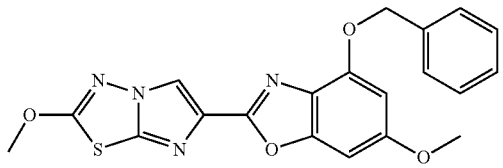 [SMILES: COc1cc(OCc2ccccc2)c2nc(-c3cn4nc(OC)sc4n3)oc2c1]

To a stirred suspension of 4-(benzyloxy)-2-(2-bromoimidazo[2,1-b][1,3,4]thiadiazol-6-yl)-6-methoxybenzo[d]oxazole (Example 121G, 0.016 g, 0.035 mmol) in methanol (2 mL) was added sodium methoxide (8 μL, 0.035 mmol). The reaction was stirred for 1.5 h, then the precipitate was filtered, rinsed with methanol and dried under reduced pressure to give the desired title material (7.8 mgs, 0.019 mmol) as a white solid. LC (Method A): 2.220 min. LCMS: Anal. Calcd. for $C_{20}H_{16}N_4O_4S$: 408.09. found: 409.09 $(M+1)^+$. $^1H$ NMR (600 MHz, DMSO-$d_6$) δ 8.79 (s, 1H), 7.48 (d, J=6.9 Hz, 2H), 7.39 (br t, 2H), 7.33 (br t, 1H), 6.93 (br d, 1H), 6.60 (d, J=2.2 Hz, 1H), 5.30 (s, 2H), 4.19 (s, 3H), 3.78 (s, 3H).

Example 122

2-(2-(1,1-Difluoro ethyl)imidazo[2,1-b][1,3,4]thiadiazol-6-yl)-4-methylbenzo[d]oxazole

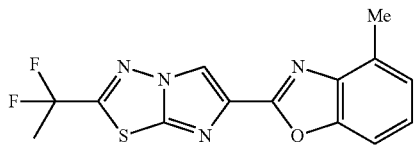 [SMILES: Cc1cccc2oc(-c3cn4nc(C(C)(F)F)sc4n3)nc12]

122A. 5-(1,1-Difluoroethyl)-1,3,4-thiadiazol-2-amine

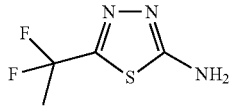

General Method: A modification of a literature procedure was used (cf. He, J. et al., *Chinese Chemical Letters*, 19:1281 (2008)). Thus, to an ice-cold suspension of thiosemicarbazide (4.97 g, 54.5 mmol) in dioxane (45 mL) was slowly added a solution of the 2,2-difluoropropanoic acid (4.50 g, 40.9 mmol) in dioxane (5 mL). To the resulting thick off-white slurry was added $POCl_3$ (4.99 mL, 54.5 mmol) dropwise and then the cooling bath was removed and the mixture was stirred at room temperature for 1 h. The vessel was then sealed and the mixture was heated at 90-95° C. (oil bath temperature) for 5 h. The resulting turbid mixture was concentrated under reduced pressure and the concentrate was poured into ice water (150 mL). This mixture was basified to ca. pH 9 using 40% aqueous NaOH and the resulting slurry was filtered and the residue was washed with water, then with ether and finally with hexanes. The residue was dried in vacuo to give the title compound (4.31 g, 64%) as a white solid which was used as such in the next step. LC (Method A): 1.045 min. LCMS: Anal. Calcd. for $C_4H_5F_2N_3S$: 165.02. found: 166.04 $(M+1)^+$. $^1H$ NMR (600 MHz, DMSO-$d_6$) δ 7.69 (s, 2H), 2.06 (t, J=19.0 Hz, 3H).

122B. Ethyl 2-(1,1-difluoroethyl)imidazo[2,1-b][1,3,4]thiadiazole-6-carboxylate

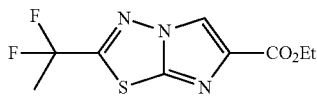 [SMILES: CCOC(=O)c1cn2nc(C(C)(F)F)sc2n1]

A mixture of 5-(1,1-difluoroethyl)-1,3,4-thiadiazol-2-amine (Example 122A, 3.000 g, 18.16 mmol) and ethyl bromopyruvate (90%, 2.79 mL, 19.98 mmol) in EtOH (17 mL) was heated at 150° C. (microwave) in a sealed vial for 45 min. The volatiles were then removed under reduced pressure and the residue was partitioned with EtOAc-sat. $NaHCO_3$. The organic phase was separated, washed (sat. $NaHCO_3$), dried ($Na_2SO_4$) and evaporated to give a dark amber gum. Flash chromatography (Isco/0-30% EtOAc-hexanes) gave the title compound (1.881 g, 40%) as an off-white solid. LC (Method A): 1.751 min. LCMS: Anal. Calcd. for $C_9H_9F_2N_3O_2S$: 261.04. found: 262.06 $(M+1)^+$. $^1H$ NMR (600 MHz, DMSO-$d_6$) δ 8.98 (s, 1H), 4.27 (q, J=7.0 Hz, 2H), 2.19 (t, J=19.3 Hz, 3H), 1.27 (t, J=7.0 Hz, 3H).

122C. 2-(1,1-Difluoroethyl)imidazo[2,1-b][1,3,4]thiadiazole-6-carboxylic acid

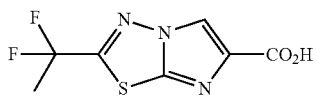

To a solution of ethyl 2-(1,1-difluoroethyl)imidazo[2,1-b][1,3,4]thiadiazole-6-carboxylate (Example 122B, 1.481 g, 5.67 mmol) in glacial AcOH (20 mL) was added 48% HBr (0.77 mL, 14.17 mmol) and the mixture was heated at 160° C. (microwave) for 4×30 min. The cooled mixture was evaporated under reduced pressure and the residue was triturated with a minimum volume of DCM to give the title compound (1.570 g, 88% as HBr salt) as a beige solid which was used as such. LC (Method A): 1.438 min. LCMS: Anal. Calcd. for $C_7H_5F_2N_3O_2S$: 233.01. found: 234.03 $(M+1)^+$. $^1H$ NMR (600 MHz, DMSO-$d_6$) δ 8.89 (s, 1H), 2.19 (t, J=19.3 Hz, 3H).

122D. 2-(1,1-Difluoroethyl)imidazo[2,1-b][1,3,4]thiadiazole-6-carbonyl chloride

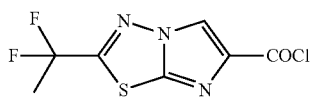

To an ice-cold mixture of 2-(1,1-difluoroethyl)imidazo[2,1-b][1,3,4]thiadiazole-6-carboxylic acid hydrobromide salt (Example 122C, 0.314 g, 1.00 mmol) and DMF (0.005 mL, 0.05 mmol) in dry DCM (10 mL) was added oxalyl chloride (0.34 mL, 4.00 mmol) dropwise. The cooling bath was then removed and the mixture was stirred at room temperature for 2 h. The resulting turbid mixture was filtered using a xx syringe filter and the volatiles were removed under reduced pressure to give the title compound (0.300 g, 90%) as a brown solid which was used as such in the next step. LC (Method B): 1.599 min (Me-ester). LCMS: Anal. Calcd. for $C_8H_7F_2N_3O_2S$ (Me-ester): 247.02. found: 248.03 $(M+1)^+$.

122E. 2-(1,1-Difluoroethyl)-N-(2-hydroxy-6-methylphenyl)imidazo[2,1-b][1,3,4]thiadiazole-6-carboxamide

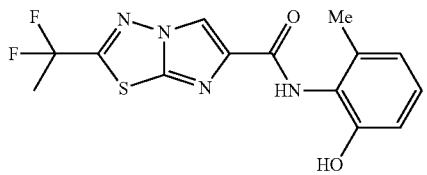 [SMILES: Cc1cccc(O)c1NC(=O)c1cn2nc(C(C)(F)F)sc2n1]

To an ice-cold solution of 2-(1,1-difluoroethyl)imidazo[2,1-b][1,3,4]thiadiazole-6-carbonyl chloride (Example 122D, 0.099 g, 0.298 mmol) in dry DCM (5 mL) under $N_2$ was added 2-amino-m-cresol (0.044 g, 0.357 mmol) and then DIEA (0.207 mL, 1.191 mmol) was added dropwise. The cooling bath was then removed and the mixture was stirred at room temperature for 2 h. The mixture was diluted with DCM, washed (saturated aqueous $NaHCO_3$), dried ($Na_2SO_4$) and evaporated to give a dark brown gum. Flash chromatography (Isco/DCM, then 0-5% EtOAc-DCM) afforded the title compound (0.048 g, 48%). as a light tan solid. LC (Method D): 1.966 min. LCMS: Anal. Calcd. for $C_{14}H_{12}F_2N_4O_2S$: 338.07. found: 339.09 $(M+1)^+$.

Example 122

2-(2-(1,1-Difluoroethyl)imidazo[2,1-b][1,3,4]thiadiazol-6-yl)-4-methylbenzo[d]oxazole

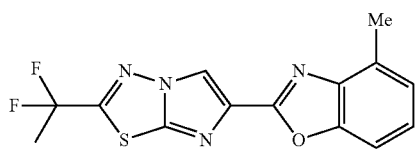

A solution of the 2-(1,1-difluoroethyl)-N-(2-hydroxy-6-methylphenyl)imidazo[2,1-b][1,3,4]thiadiazole-6-carboxamide (Example 122E, 0.048 g, 0.148 mmol) in 1:1 AcOH-TFA (2 mL) was heated at 200° C. (microwave) for 10 min. The volatiles were then removed under reduced pressure to give a solid which was purified by preparative LC to give the title compound (0.032 g, 50% as TFA salt) as the solid. LC (Method D): 2.199 min. LCMS: Anal. Calcd. for $C_{14}H_{10}F_2N_4OS$: 320.5. found: 321.08 $(M+1)^+$. $^1H$ NMR (600 MHz, DMSO-$d_6$) δ 9.24 (s, 1H), 7.55 (d, J=8.2 Hz, 1H), 7.29 (dd, J=8.2, 7.6 Hz, 1H), 7.20 (d, J=7.6 Hz, 1H), 2.55 (s, 3H), 2.22 (t, J=19.3 Hz, 3H).

Example 123

2-(2-(1,1-Difluoroethyl)imidazo[2,1-b][1,3,4]thiadiazol-6-yl)-4-nitrobenzo[d]oxazole

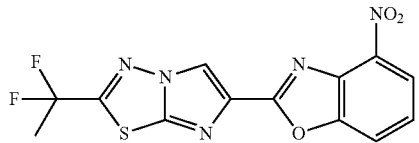 [SMILES: CC(F)(F)c1nn2cc(-c3nc4c([N+](=O)[O-])cccc4o3)nc2s1]

123A. 2-(1,1-Difluoroethyl)-N-(2-hydroxy-6-nitrophenyl)imidazo[2,1-b][1,3,4]thiadiazole-6-carboxamide

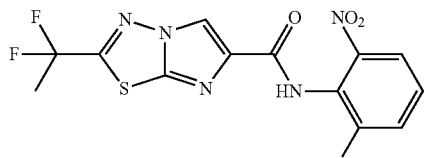

To an ice-cold solution of 2-(1,1-difluoroethyl)imidazo[2,1-b][1,3,4]thiadiazole-6-carbonyl chloride hydrobromide (Example 122C, 10.394 g, 1.185 mmol) in dry DCM (10 mL) under $N_2$ was added 2-amino-3-nitrophenol (0.219 g, 1.422 mmol) as a solid and then DIEA (0.83 mL, 4.738 mmol) was added dropwise. The cooling bath was then removed and the mixture was stirred at room temperature for 20 h. The mixture was diluted with DCM, washed ($H_2O$), dried ($Na_2SO_4$) and evaporated to give a dark red gum. Flash chromatography (Isco/DCM, then 0-10% EtOAc-DCM) afforded the pure product (0.378 g, 86%) as a yellow solid.

LC (Method A): 1.853 min. LCMS: Anal. Calcd. for $C_{13}H_9F_2N_5O_4S$: 369.03. found: 370.06 (M+1)$^+$. $^1$H NMR (600 MHz, DMSO-d$_6$) δ 10.79 (s, 1H), 9.57 (s, 1H), 8.94 (s, 1H), 7.36 (m, 1H), 7.28-7.22 (m, 2H), 2.21 (t, J=19.3 Hz, 3H).

Example 123

2-(2-(1,1-Difluoroethyl)imidazo[2,1-b][1,3,4]thiadiazol-6-yl)-4-nitrobenzo[d]oxazole

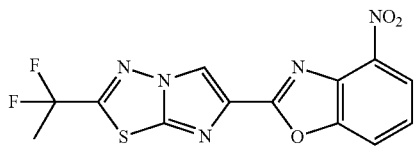 [SMILES: CC(F)(F)c1nn2cc(-c3nc4c([N+](=O)[O-])cccc4o3)nc2s1]

A solution of 2-(1,1-difluoroethyl)-N-(2-hydroxy-6-nitrophenyl)imidazo[2,1-b][1,3,4]thiadiazole-6-carboxamide (Example 123A, 0.378 g, 1.024 mmol) in AcOH-TFA (1:1, 10 mL) was heated at 200° C. (microwave) for 10 min. The volatiles were then removed under reduced pressure to give a light brown solid which was partitioned with DCM-sat. NaHCO$_3$. The organic phase was separated, dried (Na$_2$SO$_4$) and evaporated to give a beige solid. This material was triturated with a minimum volume of MeOH to give, after filtration and drying in vacuo, the title compound (0.225 g, 63%) as a light beige solid. LC (Method A): 1.952 min. LCMS: Anal. Calcd. for $C_{13}H_7F_2N_5O_3S$: 351.02. found: 352.05 (M+1)$^+$. $^1$H NMR (600 MHz, DMSO-d$_6$) δ 9.43 (s, 1H), 8.25 (d, J=8.2 Hz, 1H), 8.21 (d, J=8.2 Hz, 1H), 7.63 (t, J=8.2 Hz, 1H), 2.23 (t, J=19.3 Hz, 3H).

Example 124

2-(2-(1,1-Difluoroethyl)imidazo[2,1-b][1,3,4]thiadiazol-6-yl)-4-aminobenzo[d]oxazole

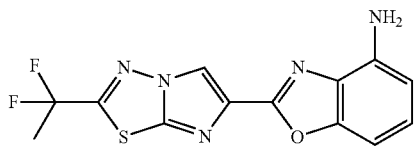 [SMILES: CC(F)(F)c1nn2cc(-c3nc4c(N)cccc4o3)nc2s1]

To a mixture of 2-(2-(1,1-difluoroethyl)imidazo[2,1-b][1,3,4]thiadiazol-6-yl)-4-nitrobenzo[d]oxazole (Example 123, 0.210 g, 0.598 mmol) in AcOH (12 mL) was added a slurry of 10% Pd/C (0.175 g) in AcOH (2 mL) and the mixture was hydrogenated under balloon pressure for 16 h. The mixture was then filtered (CELITE®) and the filter-cake was washed with AcOH and MeOH. Evaporation of the filtrate afforded a solid which was triturated with a minimum volume of MeOH to give, after filtration and drying in vacuo, the title compound (0.135 g, 70%) as a light beige solid. The filtrate was evaporated and the residue chromatographed (Isco/0-40% EtOAc-DCM) to give an additional 0.023 g of the pure product (total yield=0.158 g, 82%). LC (Method A): 1.860 min. LCMS: Anal. Calcd. for $C_{13}H_9F_2N_5OS$: 321.05. found: 322.08 (M+1)$^+$. $^1$H NMR (600 MHz, DMSO-d$_6$) δ 9.07 (s, 1H), 7.05 (t, J=8.2 Hz, 1H), 6.81 (d, J=8.2 Hz, 1H), 6.52 (d, J=8.2 Hz, 1H), 5.67 (br s, 2H), 2.21 (t, J=19.3 Hz, 3H).

Synthesis of Non-Commercial Phenols

The following phenols have been prepared and used as reagents in the preparation of Examples 125 to 179.

Synthesis of 2-amino-4-(trifluoromethoxy)phenol

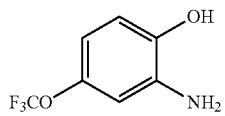

To a stirred solution of 2-nitro-4-(trifluoromethoxy)phenol (511 mg, 2.29 mmol) in EtOH (4 mL) was added 10% Pd/C (55 mg). The flask containing the stirred suspension was evacuated and back-filled with H$_2$ (2×). The reaction mixture was stirred at rt for 4 hours and the catalyst was filtered off over CELITE®. The filtrate was concentrated to dryness to give quantitatively the title material as a brown solid which was used as such. LC (Method A): 1.187 min; LCMS: Anal. Calcd. for $C_7H_6FNO_2$: 193.04. found: 194.06 (M+1)$^+$.

Synthesis of 2-amino-4-methoxyphenol

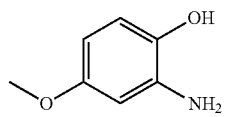

The title material was prepared according to the procedure described to prepare 2-amino-4-(trifluoromethoxy)phenol by using 4-methoxy-2-nitrophenol (1.0 g, 5.91 mmol) instead of 2-nitro-4-(trifluoromethoxy)phenol. The desired material was isolated as a brown solid (760 mg, 5.46 mmol, 92%). $^1$H NMR (600 MHz, DMSO-d$_6$) δ ppm 8.46 (s, 1H), 6.50 (d, J=8.4 Hz, 1H), 6.19 (s, 1H), 5.93 (dd, J$_j$=3.0 Hz, J$_2$=8.4 Hz, 1H), 4.54 (s, 2H), 3.58 (s, 3H).

Synthesis of 2-amino-6-fluorophenol

The title material was prepared according to the procedure described to prepare 2-amino-4-(trifluoromethoxy)phenol by using 2-amino-6-fluorophenol (1.0 g, 6.36 mmol) instead of 2-nitro-4-(trifluoromethoxy)phenol. The desired material was isolated as a brown solid (697 mg, 5.48 mmol, 86%). LC (Method A): 1.382 min. $^1$H NMR (600 MHz, DMSO-d$_6$) δ ppm 8.90 (s, 1H), 6.53-6.50 (m, 1H), 6.40-6.39 (m, 1H), 6.33-6.30 (m, 1H), 4.84 (s, 2H).

Synthesis of 2-aminobenzene-1,3-diol

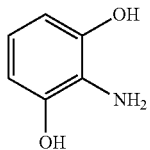

The title material was prepared according to the procedure described to prepare 2-amino-4-(trifluoromethoxy)phenol by using 2-nitrobenzene-1,3-diol (658 mg, 1.0002 mmol) instead of 2-nitro-4-(trifluoromethoxy)phenol. The filtrate was concentrated to dryness to give the title material as a brown solid (748 mg, 5.98 mmol, 91%). LC (Method A): 0.133 min. $^1$H NMR (600 MHz, DMSO-$d_6$) δ ppm 8.85 (br.s, 2H), 6.26-6.21 (m, 3H), 3.84 (br s, 2H).

Synthesis of 2-amino-5-methoxybenzene-1,3-diol

1. Synthesis of 5-methoxy-2-nitrobenzene-1,3-diol

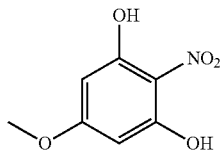

To a stirred solution of 5-methoxyresorcinol (27.4 g, 0.20 mol) in acetic acid (140 mL) and acetic anhydride (70 mL) at −4° C. was added a mixture of fuming nitric acid (10.7 mL) in acetic acid (42 mL) via addition funnel over a period of 40 minutes. The resulting dark-brown reaction mixture was stirred for 1 hour then poured over crushed ice. After the ice had melted, the product was extracted with DCM. The organic phase was washed with brine then NaHCO$_3$, dried (MgSO$_4$), filtered and concentrated to dryness. The residue was dissolved in DCM (hot), allowed to stand for 2 hours and the insoluble material was filtered off, rinsed with hexanes and Et$_2$O to afford the desired product as brown crystals (1.59 g, 8.6 mmol, 4.4%). LC (Method A): 1.626 min.

2. Synthesis of 2-amino-5-methoxybenzene-1,3-diol

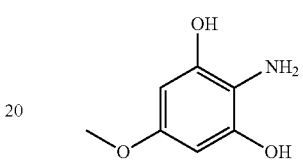

The title material was prepared according to the procedure described to prepare 2-amino-4-(trifluoromethoxy)phenol by using 5-methoxy-2-nitrobenzene-1,3-diol instead of 2-nitro-4-(trifluoromethoxy)phenol. The desired product was isolated as a brown solid. Assume quantitative yield. $^1$H NMR (600 MHz, DMSO-$d_6$) δ ppm 5.88 (s, 2H), 3.55 (s, 3H), 1.91 (s, 3H).

Examples 125 to 179

The following additional Examples have been prepared, isolated and characterized using the methods disclosed above.

| Ex. | Structure | Experimental Procedure | Formula | Exact Mass | HPLC Retention Time (Min)/Method | LCMS M + 1 | NMR |
|---|---|---|---|---|---|---|---|
| 125 | 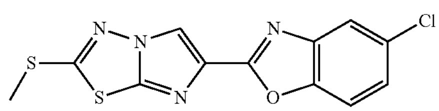 | Ex. 113 | C$_{12}$H$_7$ClN$_4$OS$_2$ | 321.98 | 1.763/B | 322.98 | $^1$H NMR (600 MHz, DMSO-$d_6$) δ ppm: 9.07 (s, 1H), 7.86 (d, J = 2.4 Hz, 1H), 7.81 (d, J = 8.4 Hz, 1H), 7.75 (dd, J$_1$ = 2.4 Hz, J$_2$ = 8.4 Hz, 1H), 2.82 (s, 3H) |
| 126 | 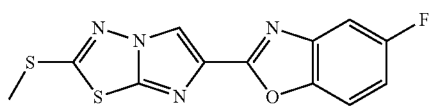 [SMILES: CSc1nn2cc(-c3nc4cc(F)ccc4o3)nc2s1] | Ex. 113 | C$_{12}$H$_7$FN$_4$OS$_2$ | 306.00 | 1.610/B | 306.00 | $^1$H NMR (600 MHz, DMSO-$d_6$) δ ppm: 9.06 (s, 1H), 7.80 (dd, J$_1$ = 4.2 Hz, J$_2$ = 8.4 Hz, 1H), 7.65 (dd, J$_1$ = 2.4 Hz, J$_2$ = 8.4 Hz, 1H), 7.29-7.25 (m, 1H), 2.82 (s, 3H) |
| 127 | 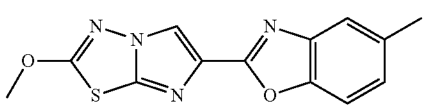 | Ex. 111 | C$_{13}$H$_{10}$N$_4$O$_2$S | 286.05 | 2.033/A | 287.08 | $^1$H NMR (600 MHz, DMSO-$d_6$) δ ppm 8.90 (s, 1H), 7.61 (d, J = 8.4 Hz, 1H), 7.54 (s, 1H), 7.20 (d, J = 8.4 Hz, 1H), 4.23 (s, 3H), 2.44 (s, 3H) |

-continued

| Ex. | Structure | Experimental Procedure | Formula | Exact Mass | HPLC Retention Time (Min)/Method | LCMS M + 1 | NMR |
|---|---|---|---|---|---|---|---|
| 128 | 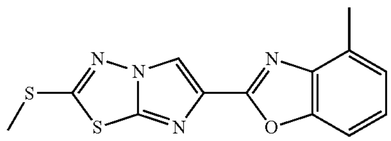 [SMILES: CSc1nn2cc(-c3nc4c(C)cccc4o3)nc2s1] | Ex. 113 | C₁₃H₁₀N₄OS₂ | 302.03 | 2.141/A | 303.05 | ¹H NMR (600 MHz, DMSO-d₆) δ ppm 9.03 (s, 1H), 7.55 (d, J = 7.8 Hz, 1H), 7.29 (dd, J₁ = J₂ = 7.8 Hz, 1H), 7.21 (d, J = 7.2 Hz, 1H), 2.82 (s, 3H), 2.57 (s, 3H) |
| 129 | 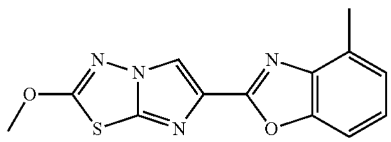 [SMILES: COc1nn2cc(-c3nc4c(C)cccc4o3)nc2s1] | Ex. 111 | C₁₃H₁₀N₄O₂S | 286.05 | 2.041/A | 287.07 | ¹H NMR (600 MHz, DMSO-d₆) δ ppm 8.93 (s, 1H), 7.54 (d, J = 8.4 Hz, 1H), 7.28 (dd, J₁ = J₂ = 7.8 Hz, 1H), 7.20 (d, J = 7.2 Hz, 1H), 4.23 (s, 3H), 2.56 (s, 3H) |
| 130 | 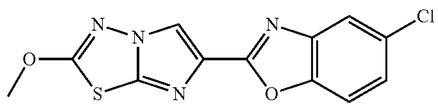 [SMILES: COc1nn2cc(-c3nc4cc(Cl)ccc4o3)nc2s1] | Ex. 111 | C₁₂H₇ClN₄O₂S | 306.00 | 2.089/A | 307.00 | ¹H NMR (600 MHz, DMSO-d₆) δ ppm 8.99 (s, 1H), 7.86 (s, 1H), 7.80 (dd, J = 9.0 Hz, 1H), 7.20 (dd, J₁ = 1.2 Hz, J₂ = 8.4 Hz, 1H), 4.23 (s, 3H) |
| 131 | 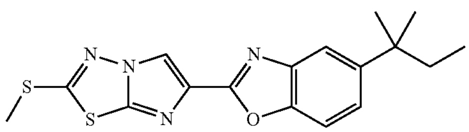 [SMILES: CCC(C)(C)c1ccc2oc(-c3cn4nc(SC)sc4n3)nc2c1] | Ex. 113 | C₁₇H₁₈N₄OS₂ | 358.09 | 2.404/A | 359.11 | ¹H NMR (600 MHz, DMSO-d₆) δ ppm 9.00 (s, 1H), 7.67-7.64 (m, 2H), 7.40 (d, J = 8.4 Hz, 1H), 2.82 (s, 3H), 1.70 (q, J = 7.2 Hz, 2H), 1.32 (s, 6H), 0.63 (t, J = 7.2 Hz, 3H) |
| 132 | 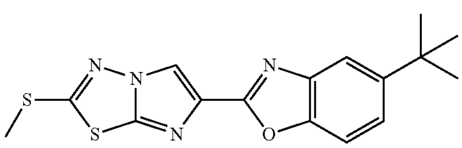 [SMILES: CSc1nn2cc(-c3nc4cc(C(C)(C)C)ccc4o3)nc2s1] | Ex. 113 | C₁₆H₁₆N₄OS₂ | 344.08 | 2.336/A | 345.10 | ¹H NMR (600 MHz, DMSO-d₆) δ ppm 9.00 (s, 1H), 7.73 (s, 1H), 7.65 (d, J = 9.0 Hz, 1H), 7.46 (dd, J₁ = 1.2 Hz, J₂ = 8.4 Hz, 1H), 2.81 (s, 3H), 1.36 (s, 9H) |
| 133 | 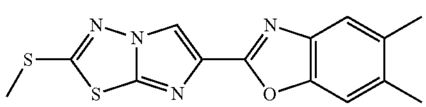 | Ex. 113 | C₁₄H₁₂N₄OS₂ | 316.05 | 2.230/A | 317.07 | ¹H NMR (600 MHz, DMSO-d₆) δ ppm 8.96 (s, 1H), 7.54 (s, 1H), 7.52 (s, 1H), 2.81 (s, 3H), 2.35 (s, 3H), 2.32 (s, 3H) |
| 134 | 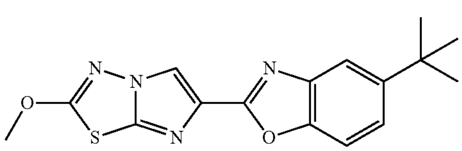 [SMILES: COc1nn2cc(-c3nc4cc(C(C)(C)C)ccc4o3)nc2s1] | Ex. 111 | C₁₆H₁₆N₄O₂S | 328.10 | 1.743/A | 329.12 | ¹H NMR (600 MHz, DMSO-d₆) δ ppm 8.95 (s, 1H), 8.00 (s, 1H), 7.87 (d, J = 9.0 Hz, 1H), 7.87 (dd, J₁ = 1.8 Hz, J₂ = 9.0 Hz, 1H), 4.33 (s, 3H), 1.39 (s, 9H) |
| 135 | 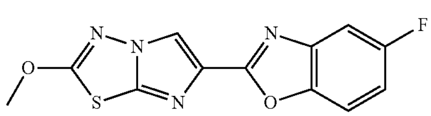 [SMILES: COc1nn2cc(-c3nc4cc(F)ccc4o3)nc2s1] | Ex. 111 | C₁₂H₇FN₄O₂S | 290.03 | 1.945/A | 291.04 | ¹H NMR (600 MHz, DMSO-d₆) δ ppm 8.97 (s, 1H), 7.79 (dd, J₁ = 4.2 Hz, J₂ = 8.4 Hz, 1H), 7.63 (dd, J₁ = 2.4 Hz, J₂ = 8.4 Hz, 1H), 7.28-7.24 (m, 1H), 4.23 (s, 3H) |
| 136 | 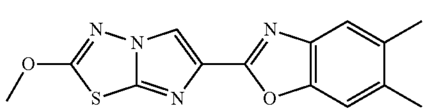 | Ex. 111 | C₁₄H₁₂N₄O₂S | 300.07 | 2.145/A | 301.09 | ¹H NMR (600 MHz, DMSO-d₆) δ ppm 8.88 (s, 1H), 7.53 (s, 1H), 7.51 (s, 1H), 4.23 (s, 3H), 2.35 (s, 3H), 2.32 (s, 3H) |

| Ex. | Structure | Experimental Procedure | Formula | Exact Mass | HPLC Retention Time (Min)/ Method | LCMS M + 1 | NMR |
|---|---|---|---|---|---|---|---|
| 137 | 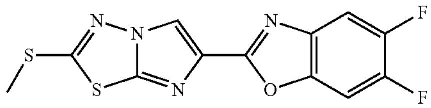 [SMILES: CSc1nn2cc(-c3nc4cc(F)c(F)cc4o3)nc2s1] | Ex. 113 | | | 2.109/A | | ¹H NMR (600 MHz, DMSO-d₆) δ ppm 9.05 (s, 1H), 8.11-8.08 (m, 1H), 7.96-7.93 (m, 1H), 2.82 (s, 3H) |
| 138 | 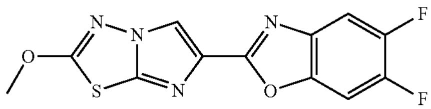 [SMILES: COc1nn2cc(-c3nc4cc(F)c(F)cc4o3)nc2s1] | Ex. 111 | $C_{12}H_6F_2N_4O_2S$ | 308.02 | 2.011/A | 309.02 | ¹H NMR (600 MHz, DMSO-d₆) δ ppm 8.96 (s, 1H), 8.09-8.06 (m, 1H), 7.94-7.91 (m, 1H), 4.23 (s, 3H) |
| 139 | 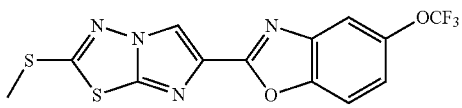 [SMILES: CSc1nn2cc(-c3nc4cc(OC(F)(F)F)ccc4o3)nc2s1] | Ex. 113 | $C_{13}H_7F_3N_4O_2S_2$ | 372.00 | 2.226/A | 373.02 | ¹H NMR (600 MHz, DMSO-d₆) δ ppm 9.09 (s, 1H), 7.90 (d, J = 8.4 Hz, 1H), 7.85 (s, 1H), 7.44 (d, J = 8.4 Hz, 1H), 2.82 (s, 3H) |
| 140 | 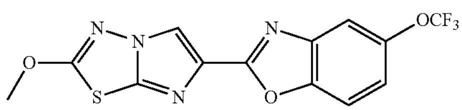 | Ex. 111 | $C_{13}H_7F_3N_4O_3S$ | 356.02 | 2.137/A | 357.05 | ¹H NMR (600 MHz, DMSO-d₆) δ ppm 9.00 (s, 1H), 7.88 (d, J = 9.0 Hz, 1H), 7.83 (s, 1H), 7.42 (d, J = 8.4 Hz, 1H), 4.24 (s, 3H) |
| 141 | 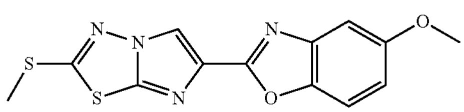 | Ex. 113 | $C_{13}H_{10}N_4O_2S_2$ | 318.02 | 2.053/A | 319.05 | ¹H NMR (600 MHz, DMSO-d₆) δ ppm 8.99 (s, 1H), 7.64 (d, J = 9.0 Hz, 1H), 7.30 (s, 1H), 6.99 (d, J = 9.0 Hz, 1H), 3.82 (s, 3H), 2.81 (s, 3H) |
| 142 | 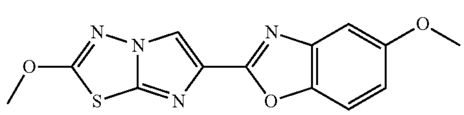 | Ex. 111 | $C_{13}H_{10}N_4O_3S$ | 302.05 | 1.948/A | 303.08 | ¹H NMR (600 MHz, DMSO-d₆) δ ppm 8.90 (s, 1H), 7.63 (d, J = 8.4 Hz, 1H), 7.29 (s, 1H), 6.98-6.96 (m, 1H), 4.23 (s, 3H), 3.82 (s, 3H) |
| 143 | 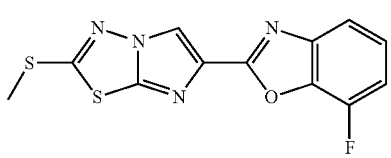 [SMILES: CSc1nn2cc(-c3nc4cccc(F)c4o3)nc2s1] | Ex. 113 | $C_{12}H_7FN_4OS_2$ | 306.00 | 2.088/A | 307.04 | ¹H NMR (600 MHz, DMSO-d₆) δ ppm 9.11 (s, 1H), 7.62-7.60 (m, 1H), 7.45-7.32 (m, 2H), 2.81 (s, 3H) |
| 144 | 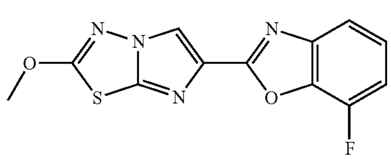 [SMILES: COc1nn2cc(-c3nc4cccc(F)c4o3)nc2s1] | Ex. 111 | $C_{12}H_7FN_4O_2S$ | 290.03 | 1.988/A | 291.04 | ¹H NMR (600 MHz, DMSO-d₆) δ ppm 9.03 (s, 1H), 7.60 (d, J = 7.2 Hz, 1H), 7.41-7.38 (m, 1H), 7.35-7.32 (m, 1H), 4.23 (s, 3H) |
| 145 | 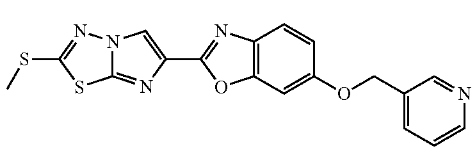 [SMILES: CSc1nn2cc(-c3nc4ccc(OCc5cccnc5)cc4o3)nc2s1] | Ex. 117 | $C_{18}H_{13}N_5O_2S_2$ | 395.05 | 1.703/A | 396.08 | ¹H NMR (600 MHz, DMSO-d₆) δ ppm 8.95 (s, 1H), 8.72 (s, 1H), 8.57 (s, 1H), 7.92 (d, J = 7.8 Hz, 1H), 7.66 (d, J = 9.0 Hz, 1H), 7.52 (s, 1H), 7.46-7.44 (m, 1H), 7.10-7.08 1H), 7.10-7.08 (m, 1H), 5.24 (s, 2H), 2.81 (s, 3H) |

| Ex. | Structure | Experimental Procedure | Formula | Exact Mass | HPLC Retention Time (Min)/ Method | LCMS M + 1 | NMR |
|---|---|---|---|---|---|---|---|
| 146 | 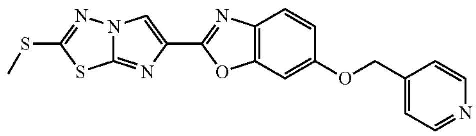 [SMILES: CSc1nn2cc(-c3nc4ccc(OCc5ccncc5)cc4o3)nc2s1] | Ex. 117 | C$_{18}$H$_{13}$N$_5$O$_2$S$_2$ | 395.05 | 1.675/A | 396.08 | $^1$H NMR (600 MHz, DMSO-d$_6$) δ ppm 8.94 (s, 1H), 8.59 (d, J = 4.2 Hz, 2H), 7.66 (d, J = 8.4 Hz, 1H), 7.48-7.47 (m, 3H), 7.10 (dd, J$_1$ = 2.4 Hz, J$_2$ = 8.4 Hz, 1H), 5.28 (s, 2H), 2.81 (s, 3H) |
| 147 | 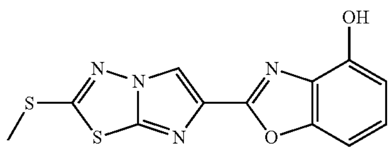 [SMILES: CSc1nn2cc(-c3nc4c(O)cccc4o3)nc2s1] | Ex. 113 | C$_{12}$H$_8$N$_4$O$_2$S$_2$ | 304.01 | 1.920/A | 305.04 | $^1$H NMR (600 MHz, DMSO-d$_6$) δ ppm 10.39 (s, 1H), 9.95 (s, 1H), 7.20-7.14 (m, 2H), 6.76 (dd, J$_1$ = 0.6 Hz, J$_2$ = 7.8 Hz, 1H), 2.81 (s, 3H) |
| 148 | 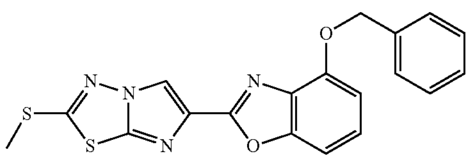 [SMILES: CSc1nn2cc(-c3nc4c(OCc5ccccc5)cccc4o3)nc2s1] | Ex. 115 Using Ex. 147 as SM | C$_{19}$H$_{14}$N$_4$O$_2$S$_2$ | 394.06 | 2.289/A | 395.05 | $^1$H NMR (600 MHz, DMSO-d$_6$) δ ppm 9.03 (s, 1H), 7.53 (d, J = 7.2 Hz, 2H), 7.44-7.42 (m, 2H), 7.38-7.31 (m, 3H), 7.05 (d, J = 7.2 Hz, 1H), 5.34 (s, 2H), 2.81 (s, 3H) |
| 149 | 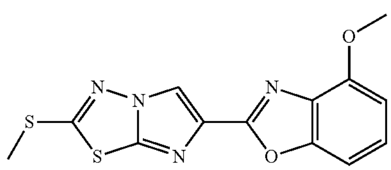 | Ex. 115 Using Ex. 147 as SM | C$_{13}$H$_{10}$N$_4$O$_2$S$_2$ | 318.02 | 2.037/A | 319.05 | $^1$H NMR (600 MHz, DMSO-d$_6$) δ ppm 9.01 (s, 1H), 7.34-7.33 (m, 2H), 6.97-6.96 (m, 1H), 3.99 (s, 3H), 2.82 (s, 3H) |
| 150 | 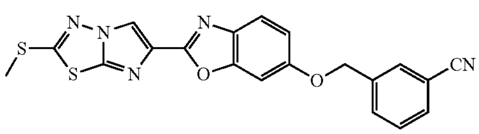 [SMILES: CSc1nn2cc(-c3nc4ccc(OCc5cccc(C#N)c5)cc4o3)nc2s1] | Ex. 115 | C$_{20}$H$_{13}$N$_5$O$_2$S$_2$ | 419.05 | 2.169/A | 420.07 | $^1$H NMR (600 MHz, DMSO-d$_6$) δ ppm 8.95 (s, 1H), 7.94 (s, 1H), 7.85-7.83 (m, 2H), 7.67-7.62 (m, 2H), 7.50 (d, J = 2.4 Hz, 1H), 7.10 (dd, J$_1$ = 2.4 Hz, J$_2$ = 9.0 Hz, 1H), 5.26 (s, 2H), 2.81 (s, 3H) |
| 151 | 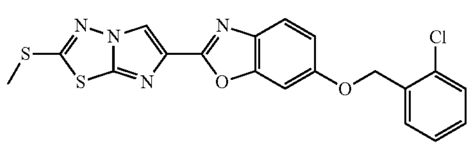 [SMILES: CSc1nn2cc(-c3nc4ccc(OCc5ccccc5Cl)cc4o3)nc2s1] | Ex. 115 | C$_{19}$H$_{13}$ClN$_4$O$_2$S$_2$ | 428.02 | 2.407/A | 429.04 | $^1$H NMR (600 MHz, DMSO-d$_6$) δ ppm 8.96 (s, 1H), 7.67-7.65 (m, 2H), 7.55-7.52 (m, 2H), 7.43-7.39 (m, 2H), 7.09 (dd, J$_1$ = 2.4 Hz, J$_2$ = 9.0 Hz, 1H), 5.24 (s, 2H), 2.81 (s, 3H) |
| 152 | 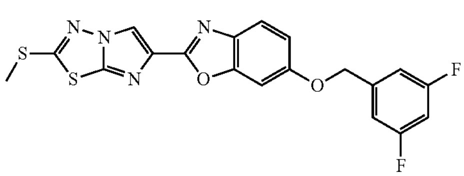 [SMILES: CSc1nn2cc(-c3nc4ccc(OCc5cc(F)cc(F)c5)cc4o3)nc2s1] | Ex. 115 | C$_{19}$H$_{12}$F$_2$N$_4$O$_2$S$_2$ | 430.04 | 2.343/A | 431.07 | $^1$H NMR (600 MHz, DMSO-d$_6$) δ ppm 9.94 (s, 1H), 7.66 (d, J = 8.4 Hz, 1H), 7.47 (d, J = 2.4 Hz, 1H), 7.24-7.21 (m, 3H), 7.09 (dd, J$_1$ = 2.4 Hz, J$_2$ = 8.4 Hz, 1H), 5.23 (s, 2H), 2.81 (s, 3H) |

-continued

| Ex. | Structure | Experimental Procedure | Formula | Exact Mass | HPLC Retention Time (Min)/ Method | LCMS M + 1 | NMR |
|---|---|---|---|---|---|---|---|
| 153 | 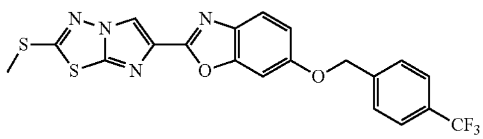 [SMILES: CSc1nn2cc(-c3nc4ccc(OCc5ccc(C(F)(F)F)cc5)cc4o3)nc2s1] | Ex. 115 | C₂₀H₁₃F₃N₄O₂S₂ | 462.04 | 2.373/A | 463.06 | ¹H NMR (600 MHz, DMSO-d₆) δ ppm 8.95 (s, 1H), 7.79 (d, J = 8.4 Hz, 2H), 7.72 (d, J = 8.4 Hz, 2H), 7.66 (d, J = 9.0 Hz, 1H), 7.49 (d, J = 1.8 Hz, 1H), 7.09 (dd, J₁ = 2.4 Hz, J₂ = 8.4 Hz, 1H), 5.32 (s, 2H), 2.81 (s, 3H) |
| 154 | 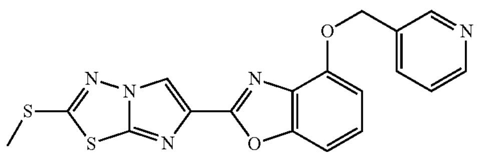 [SMILES: CSc1nn2cc(-c3nc4c(OCc5cccnc5)cccc4o3)nc2s1] | Ex. 117 Using Ex. 147 as SM | C₁₈H₁₃N₅O₂S₂ | 395.05 | 1.757/A | 396.09 | ¹H NMR (600 MHz, DMSO-d₆) δ ppm 9.01 (s, 1H), 8.73 (s, 1H), 8.56-8.55 (m, 1H), 7.93 (d, J = 7.8 Hz, 1H), 7.45-7.43 (m, 1H), 7.35-7.30 (m, 2H), 7.06-7.05 (m, 1H), 5.40 (s, 2H), 2.79 (s, 3H) |
| 155 | 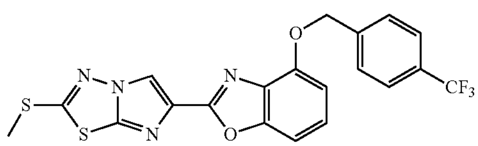 [SMILES: CSc1nn2cc(-c3nc4c(OCc5ccc(C(F)(F)F)cc5)cccc4o3)nc2s1] | Ex. 115 Using Ex. 147 as SM | C₂₀H₁₃F₃N₅O₂S₂ | 462.04 | 2.349/A | 463.06 | ¹H NMR (600 MHz, DMSO-d₆) δ ppm 9.03 (s, 1H), 7.80 (d, J = 7.8 Hz, 2H), 7.75 (d, J = 7.8 Hz, 2H), 7.37-7.31 (m, 2H), 7.04 (d, J = 7.8 Hz, 1H), 5.51 (s, 2H), 2.82 (s, 3H) |
| 156 | 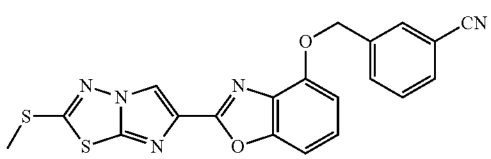 [SMILES: CSc1nn2cc(-c3nc4c(OCc5cccc(C#N)c5)cccc4o3)nc2s1] | Ex. 115 Using Ex. 147 as SM | C₂₀H₁₃N₅O₂S₂ | 419.05 | 2.182/A | 420.08 | ¹H NMR (600 MHz, DMSO-d₆) δ ppm 9.01 (s, 1H), 7.98 (s, 1H), 7.86 (d, J = 7.8 Hz, 1H), 7.83 (d, J = 7.8 Hz, 1H), 7.63 (dd, J₁ = J₂ = 7.8 Hz, 1H), 7.35-7.30 (m, 2H), 7.03 (d, J = 7.8 Hz, 1H), 5.42 (s, 2H), 2.79 (s, 3H) |
| 157 | 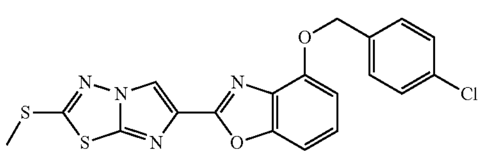 [SMILES: CSc1nn2cc(-c3nc4c(OCc5ccc(Cl)cc5)cccc4o3)nc2s1] | Ex. 115 Using Ex. 147 as SM | C₁₉H₁₃ClN₄O₂S₂ | 428.02 | 2.359/A | 429.03 | ¹H NMR (600 MHz, DMSO-d₆) δ ppm 9.00 (s, 1H), 7.53 (d, J = 8.4 Hz, 2H), 7.46 (d, J = 8.4 Hz, 2H), 7.33-7.28 (m, 2H), 7.01 (d, J = 7.8 Hz, 1H), 5.35 (s, 2H), 2.79 (s, 3H) |
| 158 | 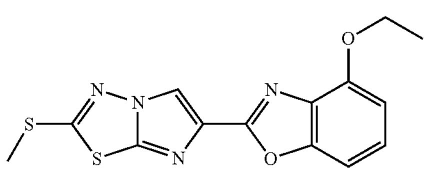 [SMILES: CCOc1cccc2oc(-c3cn4nc(SC)sc4n3)nc12] | Ex. 116 Using Ex. 147 as SM | C₁₄H₁₂N₄O₂S₂ | 332.04 | 2.192/A | 333.07 | ¹H NMR (600 MHz, DMSO-d₆) δ ppm 9.03 (s, 1H), 7.32-7.31 (m, 2H), 6.96-6.93 (m, 1H), 4.29 (q, J = 7.2 Hz, 2H), 2.82 (s, 3H), 1.42 (t, J = 7.2 Hz, 3H) |
| 159 | 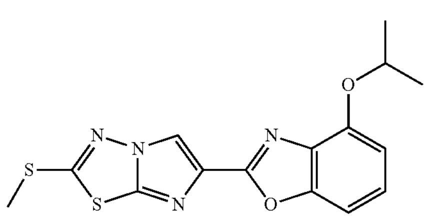 [SMILES: CSc1nn2cc(-c3nc4c(OC(C)C)cccc4o3)nc2s1] | Ex. 116 Using Ex. 147 as SM | C₁₅H₁₄N₄O₂S₂ | 346.06 | 2.250/A | 347.09 | ¹H NMR (600 MHz, DMSO-d₆) δ ppm 9.03 (s, 1H), 7.30-7.29 (m, 2H), 6.96-6.93 (m, 1H), 5.07-5.03 (m, 1H), 2.82 (s, 3H), 1.36 (s, 3H), 1.35 (s, 1H) |

-continued

| Ex. | Structure | Experimental Procedure | Formula | Exact Mass | HPLC Retention Time (Min)/ Method | LCMS M + 1 | NMR |
|---|---|---|---|---|---|---|---|
| 160 | 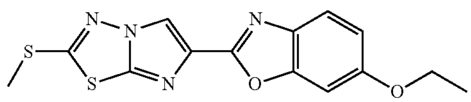 [SMILES: CCOc1ccc2nc(-c3cn4nc(SC)sc4n3)oc2c1] | Ex. 116 | C₁₄H₁₂N₄O₂S₂ | 322.04 | 2.202/A | 323.08 | ¹H NMR (600 MHz, DMSO-d₆) δ ppm 8.93 (s, 1H), 7.62 (d, J = 8.4 Hz, 1H), 7.36 (d, J = 2.4 Hz, 1H), 6.98 (dd, J₁ = 2.4 Hz, J₂ = 8.4 Hz, 1H), 4.10 (q, J = 7.2 Hz, 2H), 2.81 (s, 3H), 1.36 (t, J = 7.2 Hz, 3H) |
| 161 | 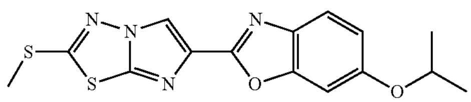 [SMILES: CSc1nn2cc(-c3nc4ccc(OC(C)C)cc4o3)nc2s1] | Ex. 116 | C₁₅H₁₄N₄O₂S₂ | 346.06 | 2.251/A | 347.09 | ¹H NMR (600 MHz, DMSO-d₆) δ ppm 8.93 (s, 1H), 7.61-7.60 (m, 1H), 7.37 (s, 1H), 6.96-6.95 (m, 1H), 4.72-4.66 (m, 1H), 2.81 (s, 3H), 1.30 (s, 6H) |
| 162 | 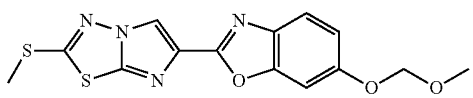 | Ex. 116 | C₁₄H₁₂N₄O₃S₂ | 348.04 | 2.117/C | 349.07 | ¹H NMR (600 MHz, DMSO-d₆) δ ppm 8.96 (s, 1H), 7.66 (d, J = 9.0 Hz, 1H), 7.44 (d, J = 2.4 Hz, 1H), 7.08 (dd, J₁ = 2.4 Hz, J₂ = 9.0 Hz, 1H), 5.27 (s, 2H), 3.41 (s, 3H), 2.81 (s, 3H) |
| 163 | 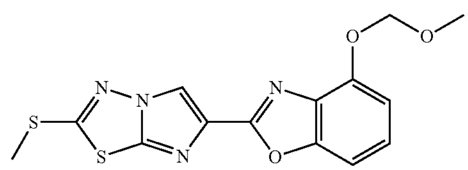 | Ex. 116 Using Ex. 147 as SM | C₁₄H₁₂N₄O₃S₂ | 348.04 | 2.103/C | 349.04 | ¹H NMR (600 MHz, DMSO-d₆) δ ppm 9.04 (s, 1H), 7.40 (d, J = 7.8 Hz, 1H), 7.32 (dd, J₁ = 7.8 Hz, J₂ = 8.4 Hz, 1H), 7.06 (d, J = 7.8 Hz, 1H), 5.47 (s, 2H), 3.45 (s, 3H), 2.82 (s, 3H) |
| 164 | 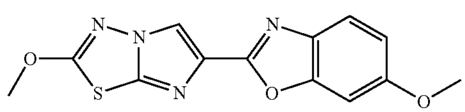 | Ex. 111 | C₁₃H₁₀N₄O₃S | 302.05 | 2.012/C | 303.07 | ¹H NMR (600 MHz, DMSO-d₆) δ ppm 8.85 (s, 1H), 7.62 (d, J = 9.0 Hz, 1H), 7.37 (d, J = 2.4 Hz, 1H), 6.99 (dd, J₁ = 2.4 Hz, J₂ = 8.4 Hz, 1H), 4.23 (s, 3H), 3.84 (s, 3H) |
| 165 | 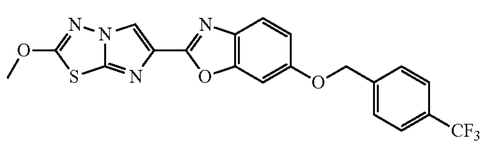 [SMILES: COc1nn2cc(-c3nc4ccc(OCc5ccc(C(F)(F)F)cc5)cc4o3)nc2s1] | Ex. 111 | C₂₀H₁₃F₃N₄O₃S | 446.07 | 2.259/A | 447.09 | ¹H NMR (600 MHz, DMSO-d₆) δ ppm 8.86 (s, 1H), 7.79 (d, J = 7.8 Hz, 2H), 7.72 (d, J = 7.8 Hz, 2H), 7.65 (d, J = 9.0 Hz, 1H), 7.48 (d, J = 2.4 Hz, 1H), 7.09 (dd, J₁ = 2.4 Hz, J₂ = 8.4 Hz, 1H), 5.32 |
| 166 | 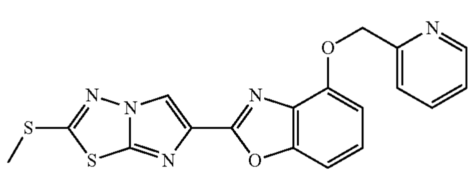 [SMILES: CSc1nn2cc(-c3nc4c(OCc5ccccn5)cccc4o3)nc2s1] | Ex. 115 Using Ex. 147 as SM | C₁₈H₁₃N₅O₂S₂ | 395.05 | 1.826/A | 396.08 | ¹H NMR (600 MHz, DMSO-d₆) δ ppm 9.03 (s, 1H), 8.61 (d, J = 4.8 Hz, 1H), 7.89-7.86 (m, 1H), 7.61 (d, J = 7.8 Hz, 1H), 7.39-7.30 (m, 3H), 7.04 (d, J = 8.4 Hz, 1H), 5.45 (s, 2H), 2.81 (s, 3H) |

-continued

| Ex. | Structure | Experimental Procedure | Formula | Exact Mass | HPLC Retention Time (Min)/Method | LCMS M + 1 | NMR |
|---|---|---|---|---|---|---|---|
| 167 | 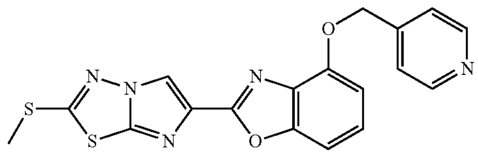 [SMILES: CSc1nn2cc(-c3nc4c(OCc5ccncc5)cccc4o3)nc2s1] | Ex. 115 Using Ex. 147 as SM | $C_{18}H_{13}N_5O_2S_2$ | 395.05 | 1.743/A | 396.08 | $^1$H NMR (600 MHz, DMSO-$d_6$) δ ppm 9.04 (s, 1H), 8.61 (d, J = 6.0 Hz, 2H), 7.51 (d, J = 5.4 Hz, 2H), 7.37 (d, J = 8.4 Hz, 1H), 7.32 (dd, $J_1$ = 7.8 Hz, $J_2$ = 8.4 Hz, 1H), 7.01 (d, J = 7.8 Hz, 1H), 5.47 (s, 2H), 2.82 (s, 3H) |
| 168 | 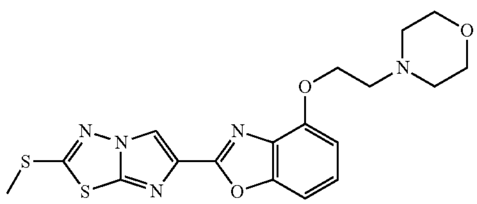 [SMILES: CSc1nn2cc(-c3nc4c(OCCN5CCOCC5)cccc4o3)nc2s1] | Ex. 115 Using Ex. 147 as SM | $C_{18}H_{19}N_5O_3S_2$ | 417.09 | 1.665/A | 418.13 | $^1$H NMR (600 MHz, DMSO-$d_6$) δ ppm 9.02 (s, 1H), 7.33-7.29 (m, 2H), 6.97 (dd, $J_1$ = 2.4 Hz, $J_2$ = 6.6 Hz, 1H), 4.37-4.35 (m, 2H), 3.60-3.58 (m, 4H), 3.34 (s, 2H), 2.81 (s, 3H), 2.79-2.77 (m, 2H), 2.45-2.40 (m, 2H) |
| 169 | 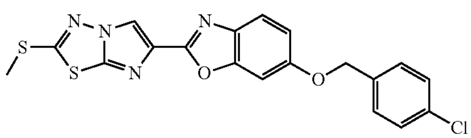 [SMILES: CSc1nn2cc(-c3nc4ccc(OCc5ccc(Cl)cc5)cc4o3)nc2s1] | Ex. 115 | $C_{19}H_{13}ClN_4O_2S_2$ | 428.02 | 2.376/A | 429.03 | $^1$H NMR (600 MHz, DMSO-$d_6$) δ ppm 8.95 (s, 1H), 7.65 (d, J = 9.0 Hz, 1H), 7.52 (d, J = 8.4 Hz, 2H), 7.48-7.47 (m, 3H), 7.07 (dd, $J_1$ = 2.4 Hz, $J_2$ = 8.4 Hz, 1H), 5.20 (s, 2H), 2.81 (s, 3H) |
| 170 | 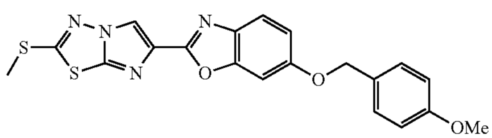 [SMILES: COc1ccc(COc2ccc3nc(-c4cn5nc(SC)sc5n4)oc3c2)cc1] | Ex. 115 | $C_{20}H_{16}N_4O_3S_2$ | 424.07 | 2.254/A | 425.09 | $^1$H NMR (600 MHz, DMSO-$d_6$) δ ppm 8.95 (s, 1H), 7.63 (d, J = 9.0 Hz, 1H), 7.46 (d, J = 2.4 Hz, 1H), 7.42 (d, J = 8.4 Hz, 2H), 7.04 (dd, $J_1$ = 2.4 Hz, $J_2$ = 9.0 Hz, 1H), 6.96 (d, J = 9.0 Hz, 2H), 5.10 (s, 2H), 3.76 (s, 3H), 2.81 (s, 3H) |
| 171 | 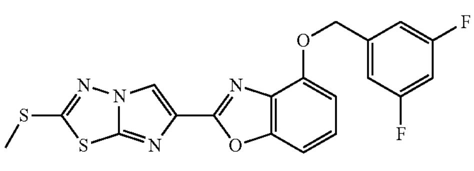 [SMILES: CSc1nn2cc(-c3nc4c(OCc5cc(F)cc(F)c5)cccc4o3)nc2s1] | Ex. 115 Using Ex. 147 as SM | $C_{19}H_{12}F_2N_4O_2S_2$ | 430.04 | 2.319/A | 431.06 | $^1$H NMR (600 MHz, DMSO-$d_6$) δ ppm 9.04 (s, 1H), 7.37 (d, J = 8.4 Hz, 1H), 7.34 (dd, $J_1$ = 7.8 Hz, $J_2$ = 8.4 Hz, 1H), 7.27-7.23 (m, 3H), 7.04 (d, J = 8.4 Hz, 1H), 5.42 (s, 2H), 2.82 (s, 3H) |
| 172 | 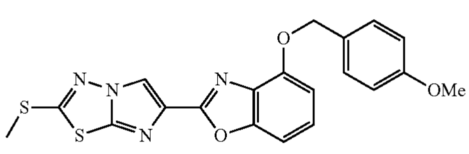 [SMILES: COc1ccc(COc2cccc3oc(-c4cn5nc(SC)sc5n4)nc23)cc1] | Ex. 115 Using Ex. 147 as SM | $C_{20}H_{16}N_4O_3S_2$ | 424.07 | 2.293/A | 425.07 | $^1$H NMR (600 MHz, DMSO-$d_6$) δ ppm 9.02 (s, 1H), 7.45 (d, J = 8.4 Hz, 2H), 7.34-7.30 (m, 2H), 7.04 (dd, $J_1$ = 1.8 Hz, $J_2$ = 7.2 Hz, 1H), 6.97 (d, J = 9.0 Hz, 2H), 5.28 (s, 2H), 3.77 (s, 3H), 2.81 (s, 3H) |

| Ex. | Structure | Experimental Procedure | Formula | Exact Mass | HPLC Retention Time (Min)/ Method | LCMS M + 1 | NMR |
|---|---|---|---|---|---|---|---|
| 173 | 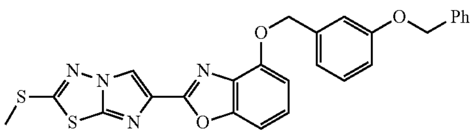 [SMILES: CSc1nn2cc(-c3nc4c(OCc5cccc(OCc6ccccc6)c5)cccc4o3)nc2s1] | Ex. 118 Using Ex. 147 as SM | $C_{26}H_{20}N_4O_3S_2$ | 500.10 | | 501.11 | $^1$H NMR (600 MHz, DMSO-d$_6$) δ ppm 9.00 (s, 1H), 7.41 (d, J = 7.5 Hz, 1H), 7.35 (t, J~7.7 Hz, 2H), 7.32-7.28 (m, 4H), 7.16 (s, 1H), 7.06 (d, J = 7.5 Hz, 1H), 7.00 (d, J = 7.6 Hz, 1H), 6.97 (dd, J$_1$ = 8.2 Hz, J$_2$ = 2.3 Hz, 1H), 5.31 (s, 2H), 5.09 (s, 2H), 2.78 (s, 3H) |
| 174 | 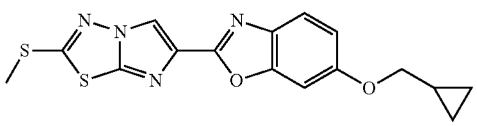 [SMILES: CSc1nn2cc(-c3nc4ccc(OCC5CC5)cc4o3)nc2s1] | Ex. 116 | $C_{16}H_{14}N_4O_2S_2$ | 358.06 | 2.214/A | 359.09 | $^1$H NMR (600 MHz, DMSO-d$_6$) δ ppm 8.94 (s, 1H), 7.62 (d, J = 9.0 Hz, 1H), 7.35 (d, J = 2.4 Hz, 1H), 6.99 (dd, J$_1$ = 2.4 Hz, J$_2$ = 8.4 Hz, 1H), 3.90 (d, J = 7.2 Hz, 2H), 2.82 (s, 3H), 1.29-1.24 (m, 1H), 0.61-0.58 (m, 2H), 0.36-0.34 (m, 2H) |
| 175 | 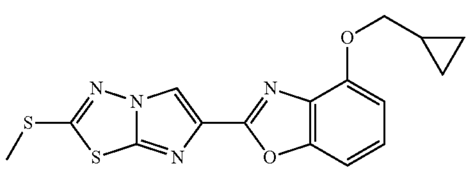 [SMILES: CSc1nn2cc(-c3nc4c(OCC5CC5)cccc4o3)nc2s1] | Ex. 116 Using Ex. 147 as SM | $C_{10}H_{14}N_4O_2S_2$ | 358.06 | 2.234/A | 359.08 | $^1$H NMR (600 MHz, DMSO-d$_6$) δ ppm 9.05 (s, 1H), 7.32-7.28 (m, 2H), 6.92 (dd, J$_1$ = 1.8 Hz, J$_2$ = 6.6 Hz, 1H), 4.08 (d, J = 7.2 Hz, 2H), 2.82 (s, 3H), 1.35-1.29 (m, 1H), 0.64-0.61 (m, 2H), 0.40-0.37 (m, 2H) |
| 176 | 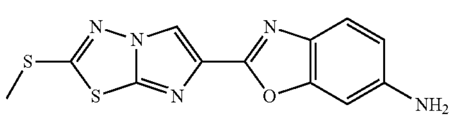 [SMILES: CSc1nn2cc(-c3nc4ccc(N)cc4o3)nc2s1] | Ex. 120 | $C_{12}H_9N_5OS_2$ | 303.02 | 1.450/A | 304.06 | $^1$H NMR (600 MHz, DMSO-d$_6$) δ ppm 8.82 (s, 1H), 7.36 (d, J = 8.2 Hz, 1H), 6.80 (s, 1H), 6.63 (dd, J$_1$ = 1.8 Hz, J$_2$ = 8.4 Hz, 1H), 5.41 (b.s, 2H), 2.81 (s, 3H) |
| 177 | 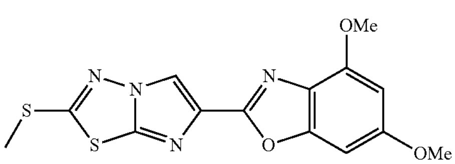 | Ex. 115 | $C_{14}H_{12}N_4O_3S_2$ | 348.04 | 2.071/A | 349.07 | $^1$H NMR (600 MHz, DMSO-d$_6$) δ ppm 8.89 (s, 1H), 6.96 (d, J = 1.8 Hz, 1H), 6.54 (d, J = 1.8 Hz, 1H), 3.96 (s, 3H), 3.83 (s, 3H), 2.81 (s, 3H) |
| 178 | 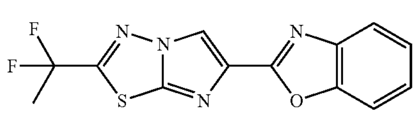 [SMILES: CC(F)(F)c1nn2cc(-c3nc4ccccc4o3)nc2s1] | Ex. 122 | $C_{13}H_8F_2N_4OS$ | 306.04 | 2.040/B | 307.07 | $^1$H NMR (600 MHz, DMSO-d$_6$) δ 9.25 (s, 1H), 7.77 (m, 2H), 7.40 (m, 2H), 2.22 (t, J = 19.3 Hz, 3H) |
| 179 | 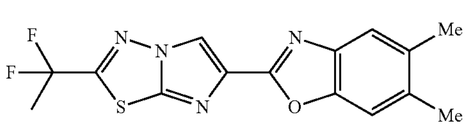 [SMILES: Cc1cc2nc(-c3cn4nc(C(C)(F)F)sc4n3)oc2cc1C] | Ex. 122 | $C_{15}H_{12}F_2N_4OS$ | 334.07 | 2.275/D | 335.09 | $^1$H NMR (600 MHz, DMSO-d$_6$) δ 9.19 (s, 1H), 7.54 (s, 1H), 7.53 (s, 1H), 2.33 (s, 3H), 2.30 (s, 3H), 2.22 (t, J = 19.3 Hz, 3H) |

Example 180

2-(2-(Methylthio)imidazo[2,1-b][1,3,4]thiadiazol-6-yl)-6-(trifluoromethoxy)benzo[d]thiazole

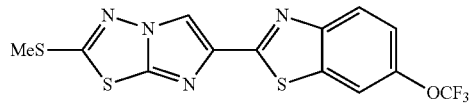

180A. 6-(Trifluoromethoxy)benzo[d]thiazol-2-amine

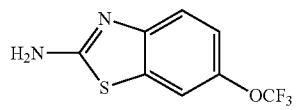

Ref.: *J. Med. Chem.*, 42:2828 (1999).

A mixture of 4-trifluoromethoxy aniline (10 g, 56.5 mmol) and potassium thiocyanate (22 g, 226 mmol) in acetic acid (90 mL) was stirred for 10 min. To this mixture was added a solution of bromine (9.03 g, 56.5 mmol) in acetic acid (20 mL) over a period of 15 min. The resulting mixture was stirred overnight, then was poured into cold water and basified with conc. ammonium hydroxide. The resulting yellow solid was collected by filtration and triturated in heptane. The product was filtered and dried under vacuum to give the title material (11.4 g, 86%) as a yellow solid. LCMS: Anal. Calcd. for $C_8H_5F_3N_2OS$: 234.01. found: 235.02 $(M+1)^+$. $^1H$ NMR (600 MHz, DMSO-$d_6$) δ 7.74 (br d, 1H), 7.62 (s, 2H), 7.32 (d, J=8.7 Hz, 1H), 7.14 (br dd, J=8.7 Hz, 1H), 1.83 (br d, J=3.7 Hz, 2H).

Example 180

2-(2-(Methylthio)imidazo[2,1-b][1,3,4]thiadiazol-6-yl)-6-(trifluoromethoxy)benzo[d]thiazole

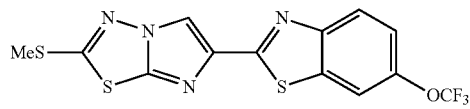

The title material was prepared from intermediate 180A according to the procedure described for Example 6. The desired product was isolated as a beige solid (55 mg, 0.14 mmol). LC (Method B): 2.120 min; LCMS: Anal. Calcd. for $C_{13}H_7F_3N_4OS_3$: 387.97. found: 388.98 $(M+1)^+$. $^1H$ NMR (600 MHz, DMSO) δ ppm 8.91 (s, 1H), 8.24 (s, 1H), 8.02 (d, J=9.0 Hz, 1H), 7.49 (d, J=9.0 Hz, 1H), 2.78 (s, 3H).

Example 181

2-(2-(Methylthio)imidazo[2,1-b][1,3,4]thiadiazol-6-yl)-4-(trifluoromethoxy)benzo[d]thiazole

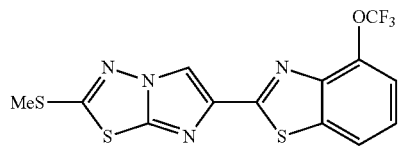 [SMILES: CSc1nn2cc(-c3nc4c(OC(F)(F)F)cccc4s3)nc2s1]

181A. 1-(2-(Trifluoromethoxy)phenyl)thiourea

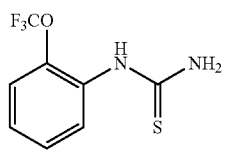 [SMILES: NC(=S)Nc1ccccc1OC(F)(F)F]

A stirred solution of 2-trifluoromethoxyaniline (7.5 g, 42.3 mmol), ammonium thiocyanate (3.4 g, 44.7 mmol), sodium hydrogen sulfide (0.3 g, 2.9 mmol) and 20% aq. HCl (8 mL) was heated at 90° C. for 14 hours. The cooled reaction mixture was filtered and the solid was washed with water. The product was then triturated in diisopropyl ether, filtered and dried under vacuum to give the title material (3.6 g, 36%) as a white solid. The product was used as such for the next reaction.

181B. 4-(Trifluoromethoxy)benzo[d]thiazol-2-amine

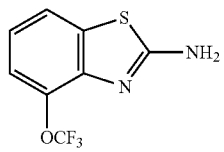 [SMILES: Nc1nc2c(OC(F)(F)F)cccc2s1]

To a stirred suspension of 1-(2-(trifluoromethoxy)phenyl)thiourea (Example 181A, 3.6 g, 15.2 mmol) in chloroform (40 mL) was added a solution of bromine (4.87 g, 30.4 mmol) in chloroform (~2 mL) dropwise. The reaction mixture was refluxed for 2.5 h and allowed to stand at rt overnight. The mixture was then concentrated under reduced pressure and the mixture was treated with diluted ammonium hydroxide. The product was extracted with dichloromethane, dried over anhydrous magnesium sulfate, filtered and concentrated to give the title material (3.18 g, 89% crude) as a green solid. $^1H$ NMR (600 MHz, DMSO) δ ppm 7.87 (s, 2H), 7.65 (d, J=7.4 Hz, 1H), 7.18 (d, J=7.5 Hz, 1H), 7.03 (t, J=8.0 Hz, 1H).

Example 181

2-(2-(Methylthio)imidazo[2,1-b][1,3,4]thiadiazol-6-yl)-4-(trifluoromethoxy)benzo[d]thiazole

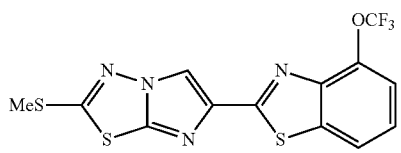

The title material was prepared according to the procedure described for Example 6, employing the Example 180B compound. The desired product was isolated as a white solid (104 mg, 0.27 mmol). LC (Method B): 2.069 min; LCMS: Anal. Calcd. for $C_{13}H_7F_3N_4OS_3$: 387.97. found: 388.99 $(M+1)^+$. $^1H$ NMR (600 MHz, DMSO) δ ppm 8.98 (s, 1H), 8.16 (d, J=7.8 Hz, 1H), 7.55-7.50 (m, 2H), 2.82 (s, 3H).

Example 182

5-Fluoro-2-(2-(methylthio)imidazo[2,1-b][1,3,4]thiadiazol-6-yl)benzo[d]thiazole

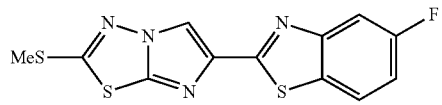 [SMILES: CSc1nn2cc(-c3nc4cc(F)ccc4s3)nc2s1]

182A. 1-(3-Fluorophenyl)thiourea

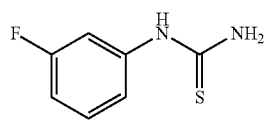

Benzoyl chloride (17 mL, 146 mmol) was added to a solution of ammonium thiocyanate (11.48 g, 151 mmol) in acetone (25 mL). The resulting suspension was heating at reflux for 20 min. and cooled in a water bath. 3-Fluoroaniline (10 mL, 104 mmol) was added portionwise to this mixture followed by acetone (20 mL). The reaction mixture was heated at reflux for 1 hour, then a solution of sodium hydroxide (16.9 g, 422.5 mmol) in water (100 mL) was added and the yellow homogeneous solution was continued to reflux for 1.5 h. After cooling down, acetone was removed in vacuo and the aqueous layer was adjusted to pH 5 with conc. HCl and then to pH 11 with ammonium hydroxide to give a pale yellow precipitate which was collected by filtration and washed with water (3×30 mL). The title material was obtained as a pale yellow solid (13.13 g, 77.2 mmol) and used as such for the next reaction.

182B. 5-Fluorobenzo[d]thiazol-2-amine

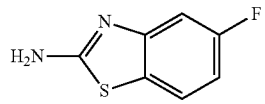

To a stirred solution of methanesulfonic acid (45.4 mL) in acetic acid (13.3 mL) was added 1-(3-fluorophenyl)thiourea (Example 182A, 7.0 g, 41.2 mmol) portionwise in keeping the temperature below 30° C. The resulting mixture was then cooled to 5-10° C. and a freshly prepared solution of N-bromosuccinimide (7.0 g, 39.14 mmol) in methanesulfonic acid (15 mL, 231 mmol) was added at 5-10° C. over 20 min. The reaction was stirred at this temperature for 30 min., then warmed to 50° C. and stirred for another 60 min. and finally cooled to RT. The mixture was added to 21% aq. NaOH (84 g in 400 mL water) prechilled at 5° C. and the temperature was kept below 30° C. during the addition. The solid was isolated by filtration and washed with water until the pH of the washings was in the range of 6 to 8 (~1 L). The title material (3.3 g, 19.6 mmol) was obtained as an off-white solid. LCMS: Anal. Calcd. for $C_7H_5FN_2S$: 168.02. found: 169.03 (M+1)$^+$. $^1$H NMR (600 MHz, DMSO) δ ppm 7.59 (s, 3H), 7.07 (d, J=10.0 Hz, 1H), 6.79 (t, J=7.5 Hz, 1H).

Example 182

5-Fluoro-2-(2-(methylthio)imidazo[2,1-b][1,3,4]thiadiazol-6-yl)benzo[d]thiazole

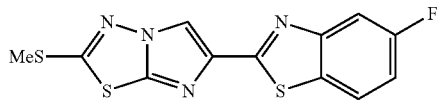 [SMILES: CSc1nn2cc(-c3nc4cc(F)ccc4s3)nc2s1]

The title material was prepared according to the procedure described for Example 6, employing the Example 182B compound. The desired product was isolated as a white solid (104 mg, 0.27 mmol). LC (Method B): 1.865 min; LCMS: Anal. Calcd. for $C_{12}H_7N_4S_3F$: 321.98. found: 3822.99 (M+1)$^+$. $^1$H NMR (600 MHz, DMSO) δ ppm 8.91 (s, 1H), 8.15 (dd, $J_1$=5.4 Hz, $J_2$=9.0 Hz, 1H), 7.99 (dd, $J_1$=2.4 Hz, $J_2$=9.6 Hz, 1H), 7.39 (ddd, $J_1$=2.4 Hz, $J_2$=9.0 Hz, 1H), 2.81 (s, 3H).

Example 183

2-(2-Bromoimidazo[2,1-b][1,3,4]thiadiazol-6-yl)-6-fluorobenzo[d]thiazole

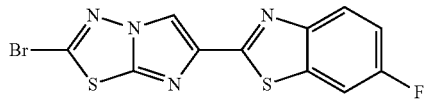

The title material was prepared by the procedure described in Example 6 by using 5-bromo-1,3,4-thiadiazol-2-amine (Example 121A, 315 mg, 1.75 mmol) instead of 5-methylthio-1,3,4-thiadiazol-2-amine and 1-(6-fluorobenzo[d]thiazol-2-yl)-2-bromo ethanone (480 mg, 1.75 mmol). The crude material was purified by flash chromatography (DCM/1% EtOAc) followed by crystallization in EtOAc. The title material was obtained as a tan solid (0.200 g, 0.563 mmol). LC (Method B): 1.845 min. LCMS: Anal. Calcd. for $C_{11}H_4N_4S_2Br$: 353.90. found: 354.92 (M+1)$^+$. $^1$H NMR (600 MHz, CDCl$_3$) δ ppm 8.48 (s, 1H), 7.96 (s, 1H), 7.62 (s, 1H), 7.24 (s, 1H).

Example 184

6-Fluoro-2-(2-methoxyimidazo[2,1-b][1,3,4]thiadiazol-6-yl)benzo[d]thiazole

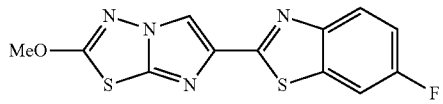

A mixture of 2-(2-bromoimidazo[2,1-b][1,3,4]thiadiazol-6-yl)-6-fluorobenzo[d]thiazole (Example 183, 0.210 g, 0.59 mmol) in dichloromethane (10 mL) and methanol (10 mL) was treated with 25% sodium methoxide in methanol (0.3 mL, ~0.075 g, ~1.48 mmol) and the mixture was stirred for 1.5 h at rt with a sonication of about 10 minutes. The mixture was neutralized to pH ~5 with HCl 1N and concentrated in vacuo. The residue was partitioned between dichloromethane (200 mL) and sat. sodium bicarbonate (~10 mL). The organic phase was dried over anhydrous magnesium sulfate and concentrated to give a yellow solid which was purified by chromatography (2 to 5% ethyl acetate/dichloromethane) to give the title material (0.109 g, 0.356 mmol) as an off-white solid. LC (Method D): 1.800 min. LCMS: Anal. Calcd. for $C_{12}H_8N_4S_2OF$: 306.00. found: 307.03 $(M+1)^+$. $^1$H NMR (600 MHz, CDCl$_3$) δ ppm 8.23 (s, 1H), 7.93 (dd, $J_1$=4.8 Hz, $J_2$=8.4 Hz, 1H), 7.59 (dd, $J_1$=2.4 Hz, $J_2$=8.4 Hz, 1H), 7.21 (ddd, $J_1$=2.4 Hz, $J_2$=$J_3$=9.0 Hz, 1H), 4.23 (s, 3H).

Example 185

2-(2-(1,1-Difluoroethyl)imidazo[2,1-b][1,3,4]thiadiazol-6-yl)benzo[d]thiazole

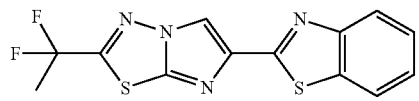

The title material was prepared by the procedure described in Example 4 by using 5-(1,1-difluoroethyl)-1,3,4-thiadiazol-2-amine (Example 122A) to give the title compound as a solid (59% yield). LC (Method A): 2.227 min. LCMS: Anal. Calcd. for $C_{13}H_8F_2N_4S_2$: 322.02. found: 323.04 $(M+1)^+$. $^1$H NMR (600 MHz, DMSO-d$_6$) δ 9.13 (s, 1H), 8.13 (d, J=8.2 Hz, 1H), 8.00 (d, J=8.2 Hz, 1H), 7.52 (t, J=7.6 Hz, 1H), 7.43 (t, J=7.6 Hz, 1H), 2.22 (t, J=19.3 Hz, 3H).

Example 186

2-(2-(1-Fluoroethyl)imidazo[2,1-b][1,3,4]thiadiazol-6-yl)benzo[d]thiazole

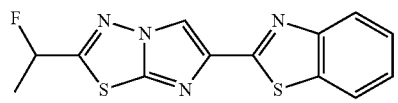

186A. 5-(1-Fluoroethyl)-1,3,4-thiadiazol-2-amine

The title material was prepared as described in Example 122A by using 2-fluoropropanoic acid. LC (Method A): 0.641 min. LCMS: Anal. Calcd. for $C_4H_6FN_3S$: 147.03. found: 148.05 $(M+1)^+$. $^1$H NMR (600 MHz, DMSO-d$_6$) δ 7.38 (s, 2H), 5.82 (d quart, J=6.4, 47.5 Hz, 1H), 1.62 (dd, J=6.4, 24.0 Hz, 3H).

Example 186

2-(2-(1-Fluoroethyl)imidazo[2,1-b][1,3,4]thiadiazol-6-yl)benzo[d]thiazole

The title material was prepared by the procedure described in Example 4 by using 5-(1-fluoroethyl)-1,3,4-thiadiazol-2-amine (Example 186A) to give the title compound as a solid as a solid (18% yield). LC (Method A): 2.121 min. LCMS: Anal. Calcd. for $C_{13}H_9FN_4S_2$: 304.03. found: 305.07 $(M+1)^+$. $^1$H NMR (600 MHz, DMSO-d$_6$) δ 8.99 (s, 1H), 8.08 (d, J=7.6 Hz, 1H), 7.94 (d, J=7.6 Hz, 1H), 7.48 (t, J=7.6 Hz, 1H), 7.38 (t, J=7.6 Hz, 1H), 6.14 (dq, J=46.9, 6.4 Hz, 1H), 1.75 (dd, J=25.2, 6.4 Hz, 3H).

Examples 187 to 199

The following additional Examples have been prepared, isolated and characterized using the methods disclosed above.

| Ex. | Structure | Experimental Procedure | Formula | Exact Mass | HPLC Retention Time (Min)/Method | LCMS M + 1 | NMR |
|---|---|---|---|---|---|---|---|
| 187 | 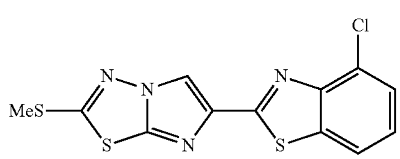 [SMILES: CSc1nn2cc(-c3nc4c(Cl)cccc4s3)nc2s1] | Ex. 6 | $C_{12}H_7N_4S_3Cl$ | 337.95 | 1.987/B | 338.96 | $^1$H NMR (600 MHz, DMSO) δ ppm 8.91 (s, 1H), 8.06 (d, J = 8.4 Hz, 1H), 7.58 (d, J = 7.8 Hz, 1H), 7.38 (dd, $J_1$ = 7.2 Hz, $J_2$ = 8.4 Hz, 1H), 2.78 (s, 3H) |
| 188 | 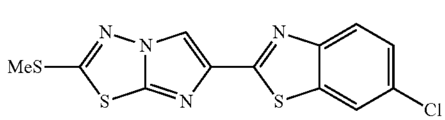 [SMILES: CSc1nn2cc(-c3nc4ccc(Cl)cc4s3)nc2s1] | Ex. 6 | $C_{12}H_7N_4S_3Cl$ | 337.95 | 2.071/B | 338.96 | $^1$H NMR (600 MHz, DMSO) δ ppm 8.89 (s, 1H), 8.25 (s, 1H), 7.93 (d, J = 8.4 Hz, 1H), 7.51 (d, J = 8.4 Hz, 1H), 2.78 (s, 3H) |

| Ex. | Structure | Experimental Procedure | Formula | Exact Mass | HPLC Retention Time (Min)/ Method | LCMS M + 1 | NMR |
|---|---|---|---|---|---|---|---|
| 189 | MeS-[imidazothiadiazole]-[benzothiazole]-OMe, OMe | Ex. 180 | C₁₄H₁₂N₄O₂S₃ | 364.01 | 1.743/B | 365.02 | ¹H NMR (600 MHz, DMSO) δ ppm 8.81 (s, 1H), 7.23 (s, 1H), 6.64 (s, 1H), 3.93 (s, 3H), 3.83 (s, 3H), 2.81 (s, 3H) |
| 190 | MeS-[imidazothiadiazole]-[benzothiazole]-Me | Ex. 6 | C₁₃H₁₀N₄S₃ | 318.01 | 1.919/B | 319.02 | ¹H NMR (600 MHz, DMSO) δ ppm 8.87 (s, 1H), 7.90 (s, 1H), 7.85 (d, J = 8.4 Hz, 1H), 7.33 (d, J = 8.4 Hz, 1H), 2.81 (s, 3H), 2.45 (s, 1H) |
| 191 | MeS-[imidazothiadiazole]-[benzothiazole]-F | Ex. 180 | C₁₂H₇N₄S₃F | 321.98 | 1.853/B | 322.98 | ¹H NMR (600 MHz, DMSO) δ ppm 8.89 (s, 1H), 8.04 (dd, J₁ = 3.0 Hz, J₂ = 8.7 Hz, 1H), 7.99 (dd, J₁ = 5.1 Hz, J₂ = 8.7 Hz, 1H), 7.39 (dd, J₁ = 3.0 Hz, J₂ = 9.0 Hz, 1H), 2.81 (s, 3H) |
| 192 | MeS-[imidazothiadiazole]-[benzothiazole]-Me, Cl | Ex. 180 | C₁₃H₉N₄S₃Cl | 351.97 | 2.276/B | 353.00 | ¹H NMR (600 MHz, CDCl₃) δ ppm 8.38 (s, 1H), 7.70 (s, 1H), 7.21 (s, 1H), 2.72 (s, 3H), 2.73 (s, 3H) |
| 193 | Br-[imidazothiadiazole]-[benzothiazole]-F | Ex. 183 | C₁₁H₄N₄S₂Br | 353.90 | 1.907/D | 354.91 | ¹H NMR (600 MHz, CDCl₃) δ ppm 8.50 (s, 1H), 7.86 (s, 1H), 7.71 (s, 1H), 7.17 (s, 1H) |
| 194 | MeO-[imidazothiadiazole]-[benzothiazole]-F | Ex. 184 | C₁₂H₇N₄S₂OF | 306.00 | 2.079/E | 307.00 | ¹H NMR (600 MHz, CDCl₃) δ ppm 8.26 (s, 1H), 7.81 (dd, J₁ = 5.1 Hz, J₂ = 8.7 Hz, 1H), 7.65 (dd, J₁ = 2.1 Hz, J₂ = 9.5 Hz, 1H), 7.11 (ddd, J₁ = 2.1 Hz, J₂ = 8.7 Hz, 1H), 4.21 (s, 3H) |
| 195 | MeO-[imidazothiadiazole]-[benzothiazole]-OCF₃ | Ex. 184 | C₁₃H₇N₅O₂S₂F₃ | 372.00 | 2.285/C | 373.03 | ¹H NMR (600 MHz, CDCl₃) δ ppm 8.38 (s, 1H), 7.83-7.82 (m, 1H), 7.35 (sb, 2H), 4.24 (s, 3H) |
| 196 | MeO-[imidazothiadiazole]-[benzothiazole]-Cl | Ex. 184 | C₁₂H₇N₄S₂OCl | 321.97 | 2.254/C | 322.98 | ¹H NMR (600 MHz, CDCl₃) δ ppm 8.38 (s, 1H), 7.78 (d, J = 7.8 Hz, 1H), 7.47 (d, J = 7.8 Hz, 1H), 7.26-7.25 (m, 1H), 4.22 (s, 3H) |
| 197 | MeO-[imidazothiadiazole]-[benzothiazole]-Me | Ex. 184 | C₁₃H₁₀N₄OS₂ | 302.03 | 2.261/C | 303.03 | LCMS: 4.533 min, [M + 1] = 303.0374, C₁₃H₁₀N₄OS₂ requires 303.0296; ¹H NMR (600 MHz, CDCl₃) δ ppm 8.27 (s, 1H), 7.88 (d, J = 8.4 Hz, 1H), 7.71 (s, 1H), 7.28 (d, J₁ = 8.4 Hz, 1H), 4.23 (s, 3H), 2.49 (s, 3H) |

| Ex. | Structure | Experimental Procedure | Formula | Exact Mass | HPLC Retention Time (Min)/ Method | LCMS M + 1 | NMR |
|---|---|---|---|---|---|---|---|
| 198 | 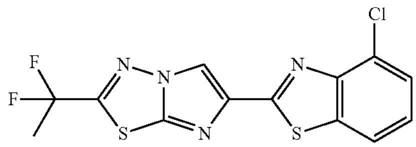 | Ex. 6 | $C_{13}H_7ClF_2N_4S_2$ | 355.98 | 2.309/A | 357.00 | $^1$H NMR (600 MHz, DMSO-$d_6$) δ 9.17 (s, 1H), 8.10 (d, J = 7.6 Hz, 1H), 7.61 (d, J = 7.6 Hz, 1H), 7.41 (t, J = 7.6 Hz, 1H), 2.22 (t, J = 19.3 Hz, 3H) |
| 199 | 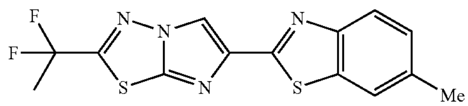 [SMILES: Cc1ccc2nc(-c3cn4nc(C(C)(F)F)sc4n3)sc2c1] | Ex. 6 | $C_{14}H_{10}F_2N_4S_2$ | 336.03 | 2.316/A | 337.06 | $^1$H NMR (600 MHz, DMSO-$d_6$) δ 9.08 (s, 1H), 7.90 (s, 1H), 7.86 (d, J = 8.2 Hz, 1H), 7.33 (d, J = 8.2 Hz, 1H), 2.42 (s, 3H), 2.21 (t, J = 19.3 Hz, 3H) |

Example 200

2-Bromo-6-(5-chloro-6-methoxybenzofuran-2-yl)imidazo[2,1-b][1,3,4]thiadiazole

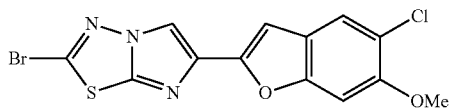

200A. 5-Chloro-2-hydroxy-4-methoxybenzaldehyde

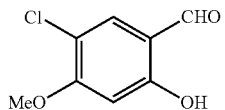

To a mixture of 2-hydroxy-4-methoxybenzaldehyde (5.33 g, 35.0 mmol) and N-chlorosuccinimide (5.38, 40.3 mmol) in chloroform (100 mL) was added concentrated HCl (2.0 mL) dropwise and then the mixture was heated to reflux under $N_2$ for 4 h. The cooled mixture was washed with water (3×100 mL) and 10% sat. $NaHCO_3$ (100 mL), and then it was dried ($Na_2SO_4$) and evaporated to give a light beige solid. Flash chromatography (Isco/0-100% DCM-hexanes) gave the title compound (4.85 g, 74%) as a white crystalline solid. LC (Method A): 1.721 min LCMS: Anal. Calcd. For $C_8H_7ClO_3$: 186.01. found: 187.02 (M+1)$^+$. $^1$H NMR (600 MHz, DMSO-$d_6$) δ 11.27 (s, 1H), 10.14 (s, 1H), 7.78 (s, 1H), 6.79 (s, 1H), 4.01 (s, 3H).

200B. 1-(5-Chloro-6-methoxybenzofuran-2-yl)ethanone

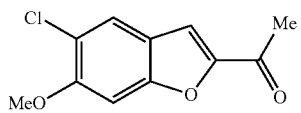

To a solution of 5-chloro-2-hydroxy-4-methoxybenzaldehyde (Example 200A, 4.73 g, 25.3 mmol) in DMF (75 mL) was added cesium carbonate (8.26 g, 25.3 mmol). The mixture was stirred under vacuum for 10 min and then the flask was back-filled with $N_2$. To this suspension was added chloroacetone (95%, 2.50 mL, 30.4 mmol) dropwise over 5 min and the resulting yellow mixture was vigorously stirred at room temperature under $N_2$ for 16 h. Another 1.65 g (0.2 equiv) of cesium carbonate was then added and the mixture was heated at 55° C. (bath temperature) for 3 h. The cooled mixture was filtered, the filter-cake was washed with DMF and the combined filtrate was evaporated. The residue was taken up in EtOAc and washed with sat. $NaHCO_3$. The aqueous phase was back-extracted with EtOAc (×2) and the combined organic phase was washed (brine), dried ($Na_2SO_4$) and evaporated to give a brown solid. This material was taken up in DCM and the solution was filtered through a short pad of $SiO_2$ (elution with DCM) to give the essentially pure title compound (4.64 g, 82%) as a tan solid. LC (Method A): 1.823 min. LCMS: Anal. Calcd. for $C_{11}H_9ClO_3$: 224.02. found: 225.05 (M+1)$^+$. $^1$H NMR (600 MHz, DMSO-$d_6$) δ 7.88 (s, 1H), 7.76 (s, 1H), 7.52 (s, 1H), 3.91 (s, 3H), 2.49 (s, 3H).

200C. 2-Bromo-1-(5-chloro-6-methoxybenzofuran-2-yl)ethanone

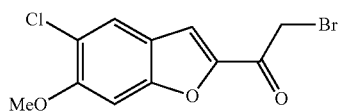

To a solution of 1-(5-chloro-6-methoxybenzofuran-2-yl)ethanone (Example 200B, 4.48 g, 19.9 mmol) in EtOAc (200 mL) was added finely ground $CuBr_2$ (9.80 g, 43.9 mmol) and the resulting mixture was heated to reflux for 4 h while being vigorously stirred. The cooled mixture was filtered, the filter-cake was washed with EtOAc and the filtrate was evaporated to give a dark brown solid. The residue was taken up in DCM and the solution was filtered through a short pad of $SiO_2$ (elution with DCM). The filtrate was evaporated to give a yellow solid which was further purified by flash chromatography (Isco/10-70% DCM-hexanes) to give the title compound (3.65 g, 60%) as a pale green solid. LC (Method A): 1.945 min. LCMS: Anal. Calcd. for $C_{11}H_8BrClO_3$: 301.93. found: 302.94 (M+1)$^+$. $^1$H NMR (600 MHz, DMSO-d$_6$) δ 7.95 (s, 1H), 7.94 (s, 1H), 7.55 (s, 1H), 4.74 (s, 2H), 3.92 (s, 3H).

Example 200

2-Bromo-6-(5-chloro-6-methoxybenzofuran-2-yl)imidazo[2,1-b][1,3,4]thiadiazole

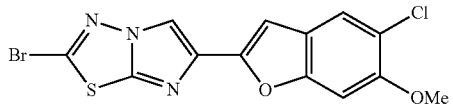

The compound was prepared using 2-bromo-1-(5-chloro-6-methoxybenzofuran-2-yl)ethanone (Example 200C) and 5-bromo-2-amino-1,3,4-thiadiazole (Example 121A) according to the general method described in Example 124B above and was then crystallized from DMF to give the title compound as a solid (19% yield). LC (Method A): 2.278 min. LCMS: Anal. Calcd. for $C_{13}H_7BrClN_3O_2S$: 384.91. found: 385.94 (M+1)$^+$. $^1$H NMR (600 MHz, DMSO-d$_6$) δ 8.67 (s, 1H), 7.73 (s, 1H), 7.46 (s, 1H), 7.08 (s, 1H), 3.92 (s, 3H).

Example 201

2-Methoxy-6-(5-chloro-6-methoxybenzofuran-2-yl)imidazo[2,1-b][1,3,4]thiadiazole

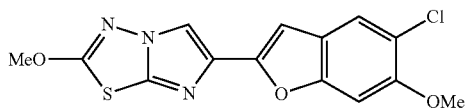 [SMILES: COc1cc2oc(-c3cn4nc(SC)sc4n3)cc2cc1Cl]

The compound was prepared using 2-bromo-6-(5-chloro-6-methoxybenzofuran-2-yl)imidazo[2,1-b][1,3,4]thiadiazole (Example 200) according to the general method described in Example 124 above to give the title compound as a solid (84% yield). LC (Method A): 2.206 min. LCMS: Anal. Calcd. for $C_{14}H_{10}ClN_3O_3S$: 335.01. found: 336.04 (M+1)$^+$. $^1$H NMR (600 MHz, DMSO-d$_6$) δ 8.43 (s, 1H), 7.70 (s, 1H), 7.45 (s, 1H), 6.98 (s, 1H), 4.21 (s, 3H), 3.91 (s, 3H).

Example 202

6-(5-Chloro-6-methoxybenzofuran-2-yl)-2-(methylthio)imidazo[2,1-b][1,3,4]thiadiazole

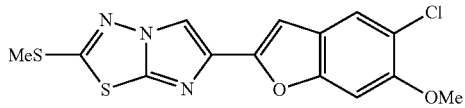

The compound was prepared using 5-(methylthio)-1,3,4-thiadiazol-2-amine and intermediate 200C according to the general method described in Example 1 above to give the title compound as a solid (39% yield). LC (Method A): 2.290 min. LCMS: Anal. Calcd. for $C_{14}H_{10}ClN_3O_2S_2$: 350.99. found: 352.02 (M+1)$^+$. $^1$H NMR (600 MHz, DMSO-d$_6$) δ 8.50 (s, 1H), 7.67 (s, 1H), 7.42 (s, 1H), 7.00 (s, 1H), 3.88 (s, 3H), 2.76 (s, 3H).

Example 203

6-(4-(Benzyloxy)-6-methoxybenzofuran-2-yl)-2-methoxyimidazo[2,1-b][1,3,4]thiadiazole

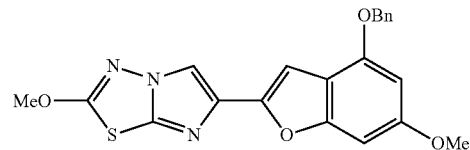 [SMILES: COc1cc(OCc2ccccc2)c2cc(-c3cn4nc(OC)sc4n3)oc2c1]

203A. 5-(Benzyloxy)-7-methoxy-2,2-dimethyl-4H-benzo[d][1,3]dioxin-4-one

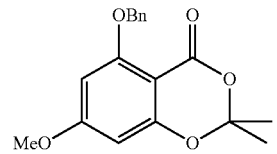 [SMILES: COc1cc(OCc2ccccc2)c2c(c1)OC(C)(C)OC2=O]

A solution of 5-hydroxy-7-methoxy-2,2-dimethyl-4H-benzo[d][1,3]dioxin-4-one (30.00 g, 0.134 mol) in N,N-dimethylformamide (400 mL) was treated with powdered anhydrous potassium carbonate (19.41 g, 0.14 mol) added all at once. The resulting mixture was stirred in vacuo for 10 min. and then flushed with nitrogen. The reaction flask was placed in a water bath (22° C.) an treated with benzyl bromide (24.03 g, 0.14 mol) added dropwise over 15 min. The resulting mixture was then stirred at 22° C. for 18 h (no starting material left by tlc). The solid was filtered and washed with N,N-dimethylformamide. The filtrate was evaporated in vacuo and the residual oil was diluted with ethyl acetate (500 mL), washed with cold 0.1 N hydrochloric acid, saturated sodium bicarbonate and brine. After drying over anhydrous magnesium sulfate, evaporation of the solvent gave a thick syrup. Crystallization form ethyl acetate (50 mL) and hexane (150 mL) gave 35.17 g of 5-(benzyloxy)-7-methoxy-2,2-dimethyl-4H-benzo[d][1,3]dioxin-4-one as large colorless prisms. Chromatography of the mother liquors on silica gel (4×13 cm, elution toluene-ethyl acetate 0-5%) gave 6.64 g of additional material to afford a total yield of 41.81 g (99%). HRMS(ESI) calcd for $C_{18}H_{19}O_5$ [M+H]$^+$ m/z 315.1227. found 315.1386. $^1$H NMR (CDCl$_3$, 600 MHz) δ 1.68 (s, 6H), 3.77 (s, 3H), 5.19 (s, 2H), 5.19 (s, 2H), 6.04 (d, J=2.03 Hz, 1H), 6.15 (d, J=2.03 Hz, 1H), 7.27 (broad t, 1H), 7.36 (broad t, 2H), 7.52 (broad d, 2H).

203B. 2-(Benzyloxy)-6-hydroxy-4-methoxybenzaldehyde

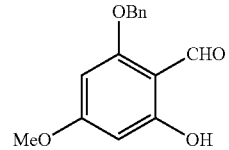

A solution of 5-(benzyloxy)-7-methoxy-2,2-dimethyl-4H-benzo[d][1,3]dioxin-4-one (Example 203A, 6.76 g, 21.5 mmol) in dichloromethane (120 mL) was cooled to −78° C. and treated with 43 mL (64.5 mmol) of a 1.5 M solution of diisobutylaluminum hydride in toluene added dropwise over 20 min. The resulting mixture was then stirred at −78° C. for 3 h. The reaction mixture was quenched by the careful addition of methanol (5 mL) added dropwise over 15 min, followed by 1N hydrochloric acid (50 mL) added dropwise over 15 min. The cooling bath was then removed and an additional 150 mL of 1N hydrochloric acid was added over 20 min. The mixture was then stirred at 22° C. for 2 h and diluted with dichloromethane (400 mL). The organic phase was collected and the aqueous phase (pH ~1) was extracted with dichloromethane (3×50 mL). The combined organic extracts were washed with brine, dried over anhydrous magnesium sulfate and concentrated in vacuo. The residual oil was diluted with tetrahydrofuran (70 mL), treated with 10 mL of 0.1N hydrochloric acid and stirred at 20° C. for 2 h. The reaction mixture was diluted with ethyl acetate (300 mL), washed with brine, dried over anhydrous magnesium sulfate, evaporated in vacuo to give a clear oil. Chromatography on silica gel (4×13 cm, elution toluene) gave 4.08 g (73% yield) of the title aldehyde as a clear oil which solidified on standing. LC (Method C): 2.237 min. HRMS (ESI) calcd for $C_{15}H_{15}O_4$ [M+H]$^+$ m/z 259.0965. found 259.1153. $^1$H NMR (CDCl$_3$, 600 MHz) δ 3.80 (s, 3H), 5.07 (s, 2H), 5.97 (d, J=2.1 Hz, 1H), 6.01 (d, J=2.1 Hz, 1H), 7.3-7.4 (m, 5H), 10.15 (s, 1H), 12.49 (s, 1H).

203C.
1-(4-(Benzyloxy)-6-methoxybenzofuran-2-yl)ethanone

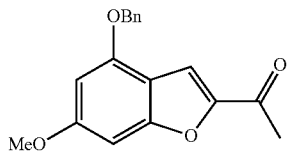 [SMILES: COc1cc(OCc2ccccc2)c2cc(C(C)=O)oc2c1]

A solution of 2-(benzyloxy)-6-hydroxy-4-methoxybenzaldehyde (Example 203B, 3.46 g, 13.4 mmol) in N,N-dimethylformamide (50 mL) was treated with powdered anhydrous cesium carbonate (4.58 g, 14.05 mmol) added all at once. The resulting mixture was stirred in vacuo for 10 min. and then flushed with nitrogen. The reaction flask was placed in a water bath (22° C.) an treated with chloroacetone (1.74 g, 18.7 mmol) added dropwise over 5 min. The resulting mixture was then stirred at 22° C. for 18 h (no starting aldehyde left by tlc and formation of the intermediate alkylated aldehyde). The solid was filtered and washed with N,N-dimethylformamide. The filtrate was evaporated in vacuo and the residual oil was diluted with ethyl acetate (300 mL), washed with cold 0.1 N hydrochloric acid, saturated sodium bicarbonate and brine. After drying over anhydrous magnesium sulfate, evaporation of the solvent gave a thick syrup. This syrup was diluted with tetrahydrofuran (50 mL) and ethyl acetate (50 mL), treated p-toluenesulfonic acid monohydrate (0.2 g) and stirred at 20° C. for 1 h (tlc indicated complete cyclization of the intermediate alkylated aldehyde to the benzofuran). The reaction mixture was diluted with ethyl acetate (300 mL), washed with saturated sodium bicarbonate and brine. After drying over anhydrous magnesium sulfate, evaporation of the solvent gave a thick syrup. Chromatography on silica gel (4×12 cm, elution toluene-ethyl acetate 2-4%) gave 3.51 g (88% yield) of the title benzofuran as a yellow solid. Recrystallization from ethyl acetate (10 mL) and hexane (20 mL) gave the title material as large yellow prisms (3.15 g). LC (Method A): 2.148 min. HRMS(ESI) calcd for $C_{18}H_{17}O_4$ [M+H]$^+$ m/z 297.1121. found 297.1092. $^1$H NMR (CDCl$_3$, 600 MHz) δ 2.51 (s, 3H), 3.82 (s, 3H), 5.13 (s, 2H), 6.37 (d, J=1.77 Hz, 1H), 6.63 (broad s, 1H), 7.34 (broad t, 1H), 7.39 (broad t, 2H), 7.44 (broad d, 2H), 7.55 (d, J=0.7 Hz, 1H).

203D. 1-(4-(Benzyloxy)-6-methoxybenzofuran-2-yl)-2-bromoethanone

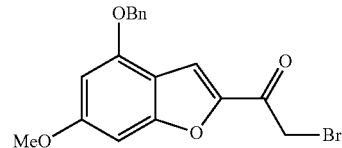 [SMILES: COc1cc(OCc2ccccc2)c2cc(C(=O)CBr)oc2c1]

A 250-mL, three-necked flask is equipped with a magnetic stirring bar and purged with a nitrogen atmosphere was charged with anhydrous tetrahydrofuran (25 mL) followed by 9.3 mL (9.3 mmol) of a 1M solution of lithium bis(trimethylsilyl)amide in tetrahydrofuran. The mixture was cooled to −78° C. and treated with a solution of 1-(4-(benzyloxy)-6-methoxybenzofuran-2-yl)ethanone (Example 203C, 2.40 g, 8.1 mmole) in tetrahydrofuran (20 mL) added dropwise over 10 min. The resulting mixture was then stirred at −78° C. for 45 min. Then chlorotrimethylsilane (1.18 mL, 9.31 mmol) was added dropwise over 5 min and the resulting solution was stirred at −78° C. for another 20 min. The cooling bath was then removed and the mixture is allowed to warm to room temperature over 30 min. The reaction mixture was then quenched by addition to a cold solution of ethyl acetate (200 mL), saturated sodium bicarbonate (30 mL) and ice. The organic phase was rapidly dried over anhydrous magnesium sulfate (magnetic stirring) and evaporated in vacuo to give the silyl enol ether as an oil which is co-evaporated with toluene (20 mL). The silyl enol ether was then dissolved in dry tetrahydrofuran (40 mL), cooled to −20° C. and treated with solid sodium bicarbonate (0.10 g) followed by N-bromosuccinimide (1.44 g, 8.1 mmol) added in small portions over 15 min. The reaction mixture was allowed to warm to 0° C. over 2 h and then quenched by addition of ethyl acetate (300 mL) and saturated sodium bicarbonate. The organic phase was washed with brine, dried over anhydrous magnesium sulfate and evaporated to give an orange oil. Chromatography on silica gel (4×12 cm, elution toluene-ethyl acetate 0-5%) gave 2.62 g (86% yield) of the title bromomethylketone as a yellow solid. Recrystallization from ethyl acetate (10 mL) and hexane (20 mL) gave yellow prisms (2.30 g). LC (Method B): 1.977 min. HRMS(ESI) calcd for $C_{18}H_{16}BrO_4$ [M+H]$^+$ m/z 375.0226. found 375.0277. $^1$H NMR (CDCl$_3$, 600 MHz) δ 3.84 (s, 3H), 4.33 (s, 2H), 5.14 (s, 2H), 6.38 (d, J=1.76 Hz, 1H), 6.64 (broad s, 1H), 7.35 (broad t, 1H), 7.40 (broad t, 2H), 7.44 (broad d, 2H), 7.70 (s, 1H).

203E. 6-(4-(Benzyloxy)-6-methoxybenzofuran-2-yl)-2-bromoimidazo[2,1-b][1,3,4]thiadiazole

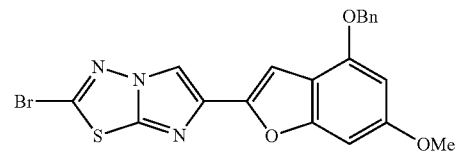

A mixture of 1-(4-(benzyloxy)-6-methoxybenzofuran-2-yl)-2-bromoethanone (Example 203D, 3.00 g, 8.0 mmol) and 5-bromo-1,3,4-thiadiazol-2-amine (1.65 g, 9.16 mmol) in isopropanol (100 mL) was heated in a pressure flask equipped with a magnetic stirring bar at 78-80° C. for 18 h (homogeneous after 20 min and then formation of a precipitate after 2 h). The cooled mixture is then transferred into five 20 mL microwave vials and then heated in a microwave apparatus to 150° C. for 30 min. Each vial was then diluted with dichloromethane (250 mL) washed with saturated sodium bicarbonate (25 mL) and brine (25 mL), dried over anhydrous magnesium sulfate. The fractions were combined and concentrated in vacuo. Chromatography of the orange-brown residual solid on silica gel (4×10 cm, slow elution with dichloromethane due to poor solubility) gave 2.96 g of the title imidazothiadiazole contaminated with some 1-(4-(benzyloxy)-6-methoxybenzofuran-2-yl)ethanone. The solid material was triturated with ethyl acetate (20 mL), filtered, washed with ethyl acetate (10 ml) and dried in vacuo to give 2.34 g (64% yield) of pure title imidazothiadiazole as an off white solid which is used as such for the next step. LC (Method B): 2.188 min. HRMS(ESI) calcd for $C_{20}H_{15}BrN_3O_3S$ [M+H]$^+$ m/z 456.00175. found 456.00397. $^1$H NMR (CDCl$_3$, 600 MHz) δ 3.82 (s, 3H), 5.16 (s, 2H), 6.38 (d, J=1.67 Hz, 1H), 6.66 (broad s, 1H), 7.15 (s, 1H), 7.31 (broad t, 1H), 7.38 (broad t, 2H), 7.45 (broad d, 2H), 8.02 (s, 1H).

Example 203

6-(4-(Benzyloxy)-6-methoxybenzofuran-2-yl)-2-methoxyimidazo[2,1-b][1,3,4]thiadiazole

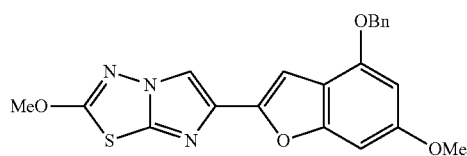 [SMILES: COc1cc(OCc2ccccc2)c2cc(-c3cn4nc(OC)sc4n3)oc2c1]

A solution of 6-(4-(benzyloxy)-6-methoxybenzofuran-2-yl)-2-bromoimidazo[2,1-b][1,3,4]thiadiazole (Example 203E, 2.30 g, 5.04 mmol) in a mixture of dichloromethane (180 mL) and methanol (45 mL) was treated at 22° C. with 4.2 mL of a 25 wt. % solution of sodium methoxide in methanol (0.2 mmol) added in one portion. More methanol (45 mL) was added and the mixture was stirred for 1 h. The reaction mixture was quenched by the addition of 25 mL of 1N hydrochloric acid followed by 20 ml of saturated sodium bicarbonate. The solvent was evaporated under reduced pressure and the residue was diluted with dichloromethane (400 mL), washed with brine, dried over anhydrous magnesium sulfate and evaporated in vacuo. Chromatography of the residue on silica gel (3×10 cm, elution with dichloromethane-ethyl acetate 0-4%) gave 1.70 g (83% yield) of the title compound as a white solid. This material was recrystallized from ethyl acetate (30 mL per gram, 80% recovery) to give white needles. LC (Method A): 2.293 min. HRMS(ESI) calcd for $C_{21}H_{18}N_3O_4S$ [M+H]$^+$ m/z 408.1013. found 408.1024. $^1$H NMR (CDCl$_3$, 600 MHz) δ 3.81 (s, 3H), 4.18 (s, 3H), 5.16 (s, 2H), 6.37 (d, J=1.75 Hz, 1H), 6.67 (broad s, 1H), 7.07 (s, 1H), 7.31 (broad t, 1H), 7.37 (broad t, 2H), 7.45 (broad d, 2H), 7.81 (s, 1H).

Example 204

6-Methoxy-2-(2-methoxyimidazo[2,1-b][1,3,4]thiadiazol-6-yl)benzofuran-4-ol

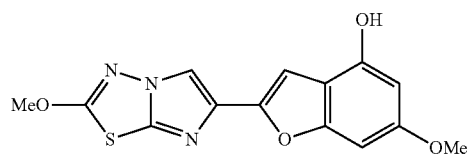 [SMILES: COc1cc(O)c2cc(-c3cn4nc(OC)sc4n3)oc2c1]

A mixture of 6-(4-(benzyloxy)-6-methoxybenzofuran-2-yl)-2-methoxyimidazo[2,1-b][1,3,4]thiadiazole (Example 203, 1.250 g, 3.06 mmol) and pentamethylbenzene (3.17 g, 21.4 mmol) in dichloromethane (200 mL) was cooled to −78° C. under a nitrogen atmosphere and then treated immediately (to avoid crystallization) with 8 mL (8 mmol) of a 1 M solution of boron trichloride in dichloromethane added dropwise over 3 min. The resulting mixture was stirred at −78° C. for 1 h. The reaction mixture was then quenched by the addition of a solution of sodium bicarbonate (6 g) in water (100 mL) added in one portion. The cooing bath was removed and the resulting mixture was stirred at room temperature for 1 h. The solid formed was filtered, washed successively with water (50 m) and dichloromethane (50 mL). The filter cake was allowed to soak with anhydrous ethanol (15 ml) and then sucked dry. The white solid obtained was then dried under vacuum for 24 h to give 0.788 g (80% yield) of pure title material (>95% by hplc). The combined filtrate and washings were diluted with dichloromethane (600 mL) and stirred in a warm water bath till the organic phase was clear with no apparent solid in suspension. The organic phase was collected, dried over anhydrous magnesium sulfate and rapidly filtered while still warm. The filtrate was evaporated and the residue (product and hexamethylbenzene) was triturated with toluene (20 mL), the solid collected and washed with toluene (20 mL) to give 0.186 g (19% yield, 99% combined yield) of title material as a tan solid (>95% by hplc). LC (Method B): 1.444 min. HRMS (ESI) calcd for $C_{14}H_{12}N_3O_4S$ [M+H]$^+$ m/z 318.0543. found 318.0578. $^1$H NMR (DMSO-d$_6$, 600 MHz) δ 3.71 (s, 3H), 4.16 (s, 3H), 6.21 (d, J=1.87 Hz, 1H), 6.61 (broad s, 1H), 6.95 (s, 1H), 8.29 (s, 1H), 9.96 (s, 1H).

Example 205

6-(4-((3-(Benzyloxy)benzyl)oxy)-6-methoxybenzofuran-2-yl)-2-methoxyimidazo[2,1-b][1,3,4]thiadiazole

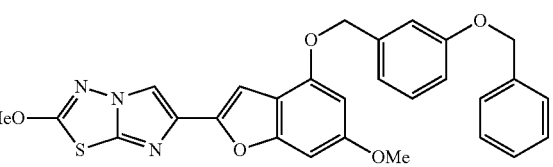

A mixture of 6-methoxy-2-(2-methoxyimidazo[2,1-b][1,3,4]thiadiazol-6-yl)benzofuran-4-ol (Example 204, 0.100 g, 0.315 mmol), triphenylphosphine (0.100 g, 0.378 mmol) and 3-benzyloxybenzyl alcohol (0.081 g, 0.378 mmol) in a 50 ml flask was maintained under vacuum for 10 min and then purged with nitrogen. Dry tetrahydrofuran (10 ml) was added and the resulting mixture was slightly warmed and maintained in an ultrasonic bath for 5 min. The cooled mixture (still heterogeneous) was treated at 22° C. with a solution of diisopropyl azodicarboxylate (0.076 g, 0.378 mmol) in tetrahydrofuran (2 ml) added dropwise over 2 min. The mixture was then stirred at 22° C. for 3 h (the mixture was placed in the ultrasonic bath for 5 min every 10 min for the first 40 min of the reaction; the solution should be clear and homogeneous at this point). The reaction mixture was quenched by the addition of dichloromethane (100 ml) and saturated sodium bicarbonate (10 ml). The organic phase was washed with brine, dried over anhydrous magnesium sulfate and concentrated in vacuo. Chromatography of the residue on silica gel (2.5×12 cm, elution toluene-ethyl acetate 5%) gave 0.113 g (70% yield) of the title material as a white solid (>95% pure by hplc). Recrystallization of this material from ethyl acetate (3 ml) gave 0.082 g of pure title material as colorless prisms. LC (Method A): 2.482 min. HRMS(ESI) calcd for $C_{28}H_{24}N_3O_5S$ [M+H]$^+$ m/z 514.1431. found 514.1406. NMR (CDCl$_3$, 600 Mz) δ 3.81 (s, 3H), 4.18 (s, 3H), 5.06 (s, 2H), 5.14 (s, 2H), 6.36 (d, J=2.82 Hz, 1H), 6.67 (broad d, 1H), 6.91 (dd, J=8.16, 2.13 Hz, 1H), 7.04 (d, J=7.57 Hz, 1H), 7.06 (s, 1H), 7.09 (broad s, 1H), 7.26-7.43 (m, 6H), 7.82 (s, 1H).

Example 206

6-(4-Ethoxy, 6-methoxybenzofuran-2-yl)-2-(methylthio)imidazo[2,1-b][1,3,4]thiadiazole

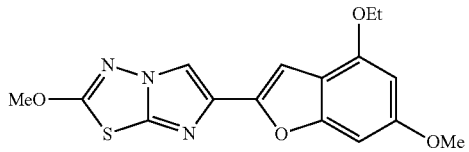

A solution of 6-methoxy-2-(2-methoxyimidazo[2,1-b][1,3,4]thiadiazol-6-yl)benzofuran-4-ol (Example 204, 122 mg, 384 mmol) in DMF (5 mL) was treated with Cs$_2$CO$_3$ (190 mg, 0.57 mmol) and ethyl iodide (0.061 mL, 0.77 mmol). The resulting reaction mixture was stirred at rt for 2 h. Then DMF was removed in vacuum and the crude dissolved in a mixture of EtOAc (200 mL) and NaHCO$_3$. The organic layer was washed with brine and dried over MgSO$_4$. The corresponding syrup residue was purified by flash chromatography (DCM/EtOAc 2-3%) and triturated with EtOAc to give the title material (132 mg, 0.38 mmol) as a solid. LC (Method A): 2.220 min. LCMS: Anal. Calcd. for $C_{16}H_{15}N_3O_4S$: 345.08. found: 346.07 (M+1)$^+$. $^1$H NMR (600 MHz, CDCl$_3$) δ ppm 7.83 (s, 1H), 7.03 (s, 1H), 6.67 (s, 1H), 6.32 (s, 1H), 4.20 (s, 3H), 4.14 (q, J=7.2 Hz, 2H), 3.84 (s, 3H), 1.47 (t, J=7.2 Hz, 3H).

Example 207

6-(Benzofuran-2-yl)-2-(1,1-difluoroethyl)imidazo[2,1-b][1,3,4]thiadiazole

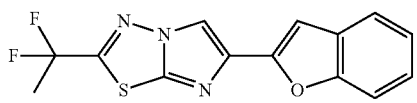

General Method: A mixture of 5-(1,1-difluoroethyl)-1,3,4-thiadiazol-2-amine (Example 122A, 0.083 g, 0.50 mmol) and 1-(benzofuran-2-yl)-2-bromoethanone (0.120 g, 0.50 mmol) in i-PrOH (2 mL) was heated at 150° C. (microwave) in a sealed vial for 45 min. The cooled mixture was partitioned with EtOAc-saturated aqueous NaHCO$_3$ and the organic phase was separated, dried (Na$_2$SO$_4$) and evaporated to give a brown solid. Flash chromatography (Isco/ 20-100% DCM-hexanes) afforded the title compound (0.094 g, 62%) as a cream solid. LC (Method A): 2.256 min. LCMS: Anal. Calcd. for $C_{14}H_9F_2N_3OS$: 305.04. found: 306.06 (M+1)$^+$. $^1$H NMR (600 MHz, DMSO-d$_6$) δ 8.82 (s, 1H), 7.66 (d, J=7.6 Hz, 1H), 7.59 (d, J=8.2 Hz, 1H), 7.31 (t, J=7.6 Hz, 1H), 7.25 (t, J=7.6 Hz, 1H), 7.21 (s, 1H), 2.22 (t, J=19.3 Hz, 3H).

Example 208

6-(Benzofuran-2-yl)-2-(1,1,2,2-tetrafluoroethyl)imidazo[2,1-b][1,3,4]thiadiazole

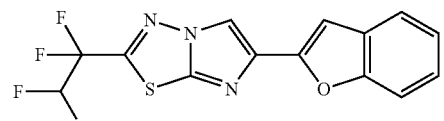

208A. 5-(1,1,2,2-Tetrafluoroethyl)-1,3,4-thiadiazol-2-amine

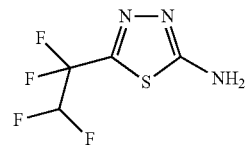

The title material was prepared as described in Example 122A by using 2,2,3,3-tetrafluoropropanoic acid. LC (Method A): 1.177 min. LCMS: Anal. Calcd. for $C_4H_3F_4N_3S$: 201.00. found: 202.03 (M+1)$^+$.

Example 208

6-(Benzofuran-2-yl)-2-(1,1,2,2-tetrafluoroethyl)imidazo[2,1-b][1,3,4]thiadiazole The title compound was prepared using 5-(1,1,2,2-tetrafluoroethyl)-1,3,4-thiadiazol-2-amine (Example 208A) and 1-(benzofuran-2-yl)-2-bromoethanone according to the general method described in Example 207 and was obtained as a solid (43% yield, as HBr salt). LC (Method A): 2.230 min. LCMS: Anal. Calcd. for $C_{14}H_7F_4N_3OS$: 341.03. found: 342.07 (M+1)$^+$. $^1$H NMR (600 MHz, DMSO-d$_6$) δ 8.91 (s, 1H), 7.67 (d, J=7.6 Hz, 1H), 7.60 (d, J=8.2 Hz, 1H), 7.32 (t, J=7.0 Hz, 1H), 7.26 (t, J=7.6 Hz, 1H), 7.23 (s, 1H), 7.14 (tt, J=51.6, 3.5 Hz, 1H).

Example 209

6-(Benzofuran-2-yl)-2-(chlorodifluoromethyl)imidazo[2,1-b][1,3,4]thiadiazole

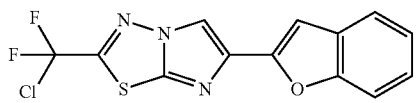 [SMILES: FC(F)(Cl)c1nn2cc(-c3cc4ccccc4o3)nc2s1]

209A. 5-(Chlorodifluoromethyl)-1,3,4-thiadiazol-2-amine

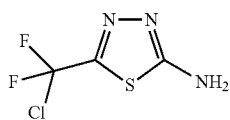

The title material was prepared as described in Example 122A by using 2,2-difluoro-2-chloroethanoic acid. LC (Method A): 1.040 min. LCMS: Anal. Calcd. for $C_3H_2ClF_2N_3S$: 184.96. found: 185.99 (M+1)$^+$.

Example 209

6-(Benzofuran-2-yl)-2-(chlorodifluoromethyl)imidazo[2,1-b][1,3,4]thiadiazole

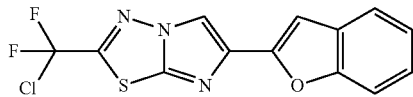 [SMILES: FC(F)(Cl)c1nn2cc(-c3cc4ccccc4o3)nc2s1]

The title compound was prepared using 5-(chlorodifluoromethyl)-1,3,4-thiadiazol-2-amine (Example 209A) and 1-(benzofuran-2-yl)-2-bromoethanone according to the general method described in Example 207 and was obtained as a solid (37% yield, as HBr salt). LC (Method A): 2.346 min. LCMS: Anal. Calcd. for $C_{13}H_6ClF_2N_3OS$: 324.99. found: 325.99 (M+1)$^+$. $^1$H NMR (600 MHz, DMSO-d$_6$) δ 8.89 (s, 1H), 7.66 (d, J=7.6 Hz, 1H), 7.59 (d, J=7.6 Hz, 1H), 7.31 (t, J=7.6 Hz, 1H), 7.25 (t, J=7.6 Hz, 1H), 7.23 (s, 1H).

Example 210

6-(4-(Benzyloxy)benzofuran-2-yl)-2-methoxyimidazo[2,1-b][1,3,4]thiadiazole

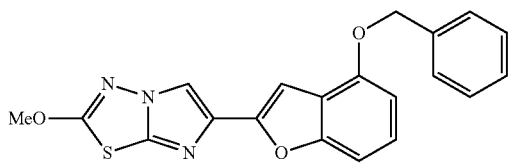 [SMILES: COc1nn2cc(-c3cc4c(OCc5ccccc5)cccc4o3)nc2s1]

210A. 6-(4-(Benzyloxy)benzofuran-2-yl)-2-bromoimidazo[2,1-b][1,3,4]thiadiazole

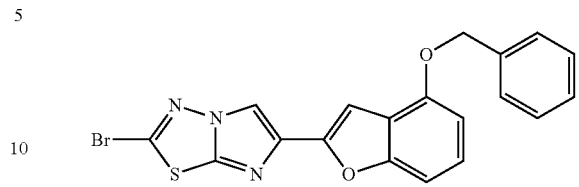

The title material was prepared from 1-(4-(benzyloxy)benzofuran-2-yl)-2-bromo ethanone according to the procedure described for Example 203E (heating time 16 h). The crude was purified by flash chromatography (DCM 100%) to give a yellowish solid. LC (Method C) 2.377 min. LCMS: Anal. Calcd. for $C_{19}H_{12}N_3O_2SBr$ S: 424.98. found: 425.99 (M+1)$^+$. $^1$H NMR (600 MHz, CDCl$_3$) δ ppm 8.11 (s, 1H), 7.49 (d, J=7.2 Hz, 2H), 7.42-7.39 (m, 2H), 7.35-7.33 (m, 1H), 7.27 (s, 1H), 7.21-7.19 (m, 1H), 7.16-7.15 (m, 1H), 6.74 (d, J=7.8 Hz, 1H), 5.23 (s, 2H).

Example 210

6-(4-(Benzyloxy)benzofuran-2-yl)-2-methoxyimidazo[2,1-b][1,3,4]thiadiazole

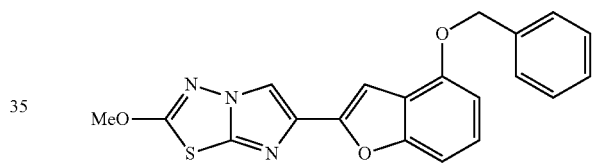

The title material was prepared from 6-(4-(benzyloxy)benzofuran-2-yl)-2-bromoimidazo[2,1-b][1,3,4]thiadiazole (Example 210A) according to the procedure described for Example 203 (LC (Method C): 2.297 min. LCMS: Anal. Calcd. for $C_{20}H_{15}N_3O_3S$: 377.08. found: 378.08 (M+1)$^+$. $^1$H NMR (600 MHz, CDCl$_3$) δ ppm 7.90 (s, 1H), 7.50-7.49 (m, 2H), 7.40-7.16 (m, 6H), 6.74-6.73 (m, 1H), 5.23 (s 2H), 4.20 (s, 3H).

Example 211

2-(2-Methoxyimidazo[2,1-b][1,3,4]thiadiazol-6-yl)benzofuran-4-ol

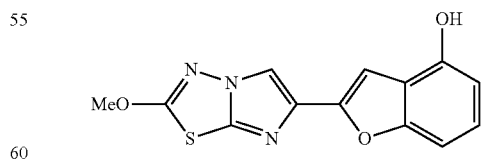

A solution of 6-(4-(benzyloxy)benzofuran-2-yl)-2-methoxyimidazo[2,1-b][1,3,4]thiadiazole (Example 210, 160 mg, 0.42 mmol) in anisole (1 mL) was treated with trifluoroacetic acid (6 mL) and the mixture was stirred at 50° C. for 6 h. After concentration in vacuum, the residue was diluted with DCM (400 mL). The resulting cloudy solution was washed with NaHCO₃ (20 mL), brine, dried over MgSO₄ and concentrated to give a yellow solid. The crude was purified by flash chromatography (CHCl₃/EtOH 0-2%) to afford 2-(2-methoxyimidazo[2,1-b][1,3,4]thiadiazol-6-yl)benzofuran-4-ol (22 mg, 0.076 mmol) as a white solid. 5-Benzyl-2-(2-methoxyimidazo[2,1-b][1,3,4]thiadiazol-6-yl)benzofuran-4-ol (2.5 mg, 0.0066 mmol) was also obtained as a yellow-green solid.

2-(2-Methoxyimidazo[2,1-b][1,3,4]thiadiazol-6-yl)benzofuran-4-ol (Example 213): LC (Method C): 2.360 min. LCMS: Anal. Calcd. for $C_{13}H_9N_3O_3S$: 287.04. found: 288.04 (M+1)⁺. ¹H NMR (600 MHz, DMSO) δ ppm 9.96 (s, 1H), 8.45 (s 1H), 7.10-7.07 (m, 1H), 7.01 (d, J=8.4 Hz, 1H), 6.61 (d, J=7.8 Hz, 1H), 4.20 (s, 3H), 3.40 (sb, 1H).

5-Benzyl-2-(2-methoxyimidazo[2,1-b][1,3,4]thiadiazol-6-yl)benzofuran-4-ol: LC (Method C): 2.024 min. LCMS: Anal. Calcd. for $C_{20}H_{15}N_3O_3S$: 377.08. found: 378.09 (M+1)⁺. ¹H NMR (600 MHz, DMSO) δ ppm 9.73 (s, 1H), 8.42 (s, 1H), 7.26-7.24 (m, 4H), 7.15-7.14 (m, 1H), 7.00 (d, J=8.4 Hz, 1H), 6.96 (d, J=8.4 Hz, 1H), 4.20 (s, 3H), 3.96 (s, 2H).

Example 212

6-(4,6-Dimethoxybenzofuran-2-yl)-2-(1-fluoroethyl)imidazo-[2,1-b][1,3,4]thiadiazole

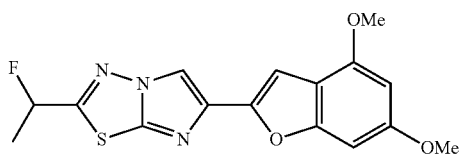 [SMILES: COc1cc(OC)c2cc(-c3cn4nc(C(C)F)sc4n3)oc2c1]

The title material was prepared according to the procedure described in Example 1 by using 5-(1-fluoroethyl)-1,3,4-thiadiazol-2-amine (Example 186A) and purified by preparative HPLC (Sunfire-C18/MeOH—H₂O-TFA) to give a solid (10% yield, as TFA salt). LC (Method A): 2.206 min. LCMS: Anal. Calcd. for $C_{16}H_{14}FN_3O_3S$: 347.07. found: 348.11 (M+1)⁺. ¹H NMR (600 MHz, DMSO-d₆) δ 8.58 (s, 1H), 6.98 (s, 1H), 6.80 (s, 1H), 6.42 (d, J=1.8 Hz, 1H), 6.14 (dq, J=46.9, 6.4 Hz, 1H), 3.86 (s, 3H), 3.79 (s, 3H), 1.77 (dd, J=24.6, 6.4 Hz, 3H).

Examples 213A and 213B (R)- and (S)-6-(4,6-Dichlorobenzofuran-2-yl)-2-(1-fluoroethyl)imidazo[2,1-b][1,3,4]thiadiazole

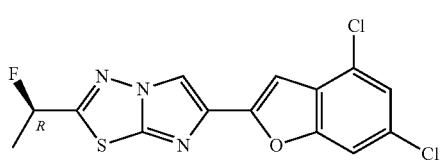
213A

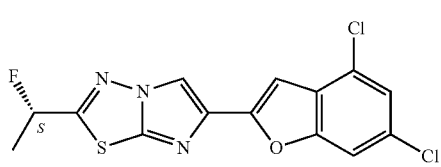 [SMILES: CC(F)c1nn2cc(-c3cc4c(Cl)cc(Cl)cc4o3)nc2s1]
213B 213-1. 6-(4,6-Dichlorobenzofuran-2-yl)-2-(1-fluoroethyl)imidazo[2,1-b][1,3,4]thiadiazole

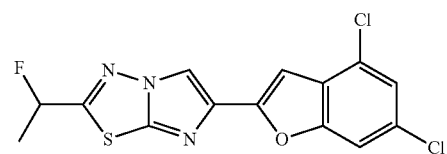

The title compound was prepared according to the general method described in Example 212 above to give a solid (25% yield). LC (Method A): 2.475 min. LCMS: Anal. Calcd. for $C_{14}H_8Cl_2FN_3OS$: 354.97. found: 355.99 (M+1)⁺. ¹H NMR (600 MHz, DMSO-d₆) δ 8.82 (s, 1H), 7.83 (s, 1H), 7.51 (s, 1H), 7.18 (s, 1H), 6.16 (dq, J=46.9, 6.4 Hz, 1H), 1.77 (dd, J=25.2, 6.4 Hz, 3H).

Examples 213A and 213B (R)- and (S)-6-(4,6-Dichlorobenzofuran-2-yl)-2-(1-fluoroethyl)imidazo[2,1-b][1,3,4]thiadiazole

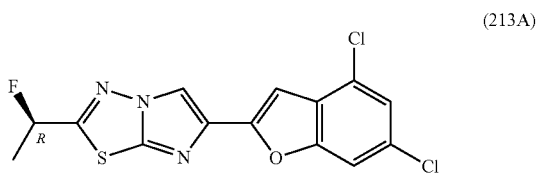
(213A)

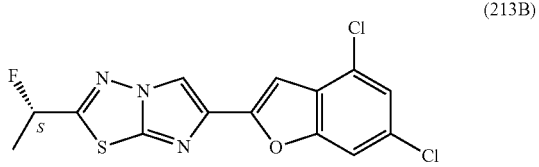
(213B)

6-(4,6-Dichlorobenzofuran-2-yl)-2-(1-fluoroethyl)imidazo[2,1-b][1,3,4]thiadiazole (Example 213-1, 0.032 g, 0.068 mmol), which was prepared as a mixture of enantiomers, was submitted to chiral SFC separation (CHIRALCEL® AS-H, 25 cm; co-solvent=10% i-PrOH; column temperature=35° C.) to give the two title compounds as white solids.

Example 213B (S)-isomer: yield=0.022 g (69%). LC (chiral SFC): 3.31 min. LCMS: Anal. Calcd. for $C_{14}H_8Cl_2FN_3OS$: 354.97. found: 355.98 (M+1)⁺. ¹HNMR (600 MHz, DMSO-d₆) δ 8.82 (s, 1H), 7.83 (s, 1H), 7.51 (s, 1H), 7.18 (s, 1H), 6.16 (dq, J=46.9, 6.4 Hz, 1H), 1.77 (dd, J=25.2, 6.4 Hz, 3H).

Example 213A (R)-isomer: yield=0.004 g (13%). LC (chiral SFC): 3.88 min. LCMS: Anal. Calcd. for $C_{14}H_8Cl_2FN_3OS$: 354.97. found: 355.98 (M+1)⁺. ¹H NMR (600 MHz, DMSO-d₆) δ 8.82 (s, 1H), 7.83 (s, 1H), 7.51 (s, 1H), 7.18 (s, 1H), 6.16 (dq, J=46.9, 6.4 Hz, 1H), 1.77 (dd, J=25.2, 6.4 Hz, 3H).

Example 214

2-(2-(Methylthio)imidazo[2,1-b][1,3,4]thiadiazol-6-yl)benzofuran-4-ol

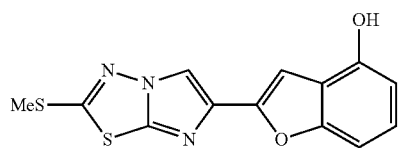

214A. 5-(Methoxymethoxy)-2,2-dimethyl-4H-benzo[d][1,3]dioxin-4-one

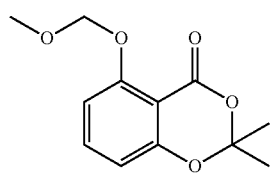

The title material was prepared according to the procedure described for Example 203A and in *Org. Synth.*, 84:102 (2007). LC (Method A): 1.667 min. $^1$H NMR (600 MHz, CDCl$_3$) δ ppm 7.43 (dd, J$_1$=J$_2$=8.4 Hz, 1H), 6.87 (d, J=8.4 Hz, 1H), 6.60 (d, J=8.4 Hz, 1H), 5.32 (s, 2H), 3.54 (s, 3H), 1.71 (s, 6H).

214B. 2-Hydroxy-6-(methoxymethoxy)benzaldehyde

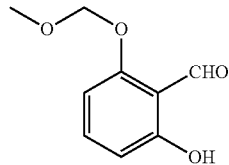

Preparation of the title material was analogous to the procedure described for Example 203B. $^1$H NMR (600 MHz, CDCl$_3$) δ ppm 11.91 (s, 1H), 10.39 (s, 1H), 7.40 (dd, J$_1$=J$_2$=8.4 Hz, 1H), 6.60 (d, J=8.4 Hz, 1H), 6.57 (d, J=8.4 Hz, 1H), 5.27 (s, 2H), 3.51 (s, 3H).

214C. 1-(4-(Methoxymethoxy)benzofuran-2-yl)ethanone

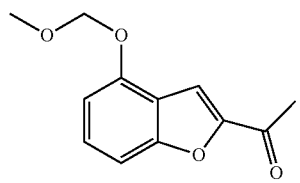 [SMILES: COCOc1cccc2oc(C(C)=O)cc12]

Preparation of the title material was analogous to the procedure described for Example 203C, using Example 214B as starting material. LC (Method C): 1.825 min. LCMS Calcd. for C$_{12}$H$_{12}$O$_4$: 220.07. found: 221.08 (M+1)$^+$ $^1$H NMR (600 MHz, CDCl$_3$) δ ppm 7.60 (s, 1H), 7.36 (dd, J$_1$=J$_2$=8.3 Hz, 1H), 7.20 (d, J=8.4 Hz, 1H), 6.90 (d, J=8.0 Hz, 1H), 5.30 (s, 2H), 3.50 (s, 3H), 2.57 (s, 3H).

214D. 2-Bromo-1-(4-(methoxymethoxy)benzofuran-2-yl)ethanone

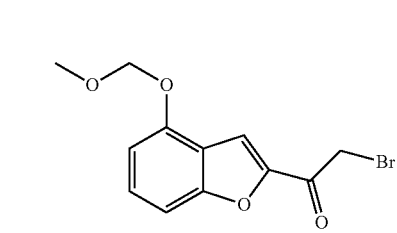 [SMILES: COCOc1cccc2oc(C(=O)CBr)cc12]

Preparation of the title material was analogous to the procedure described for Example 203D, using Example 214C as starting material. LC (Method A): 1.898 min. LCMS Calcd. for C$_{12}$H$_{11}$BrO$_4$: 297.98. found: 299.00 (M+1)$^+$ $^1$H NMR (600 MHz, CDCl$_3$) δ ppm 7.75 (s, 1H), 7.40 (dd, J$_1$=J$_2$=8.2 Hz, 1H), 7.20 (d, J=8.4 Hz, 1H), 6.92 (d, J=8.0 Hz, 1H), 5.31 (s, 2H), 4.40 (s, 2H), 3.50 (s, 3H).

Example 214

2-(2-(Methylthio)imidazo[2,1-b][1,3,4]thiadiazol-6-yl)benzofuran-4-ol

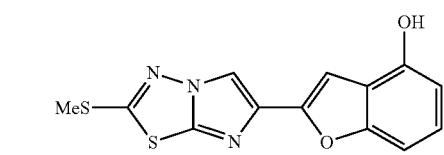

The title compound was obtained as a side-product of the reaction between 5-(methylthio)-1,3,4-thiadiazol-2-amine and 2-bromo-1-(4-(methoxymethoxy)benzofuran-2-yl)ethanone (Example 214D) as described in Example 1. The title material was obtained as a solid (25% yield). LC (Method C): 2.129 min. LCMS: Anal. Calcd. for C$_{13}$H$_9$N$_3$O$_2$S$_2$: 303.01. found: 304.03 (M+1)$^+$. $^1$H NMR (600 MHz, CDCl$_3$) δ ppm 10.1 (s, 1H), 8.68 (s, 1H), 7.22 (dd, J$_1$=7.8 Hz, J$_2$=8.4 Hz, 1H), 7.15 (d, J=8.4 Hz, 1H), 6.75 (d, J=7.8 Hz, 1H), 2.93 (s, 3H).

Example 215

6-(4-(Methoxymethoxy)benzofuran-2-yl)-2-(methylthio)imidazo[2,1-b][1,3,4]thiadiazole

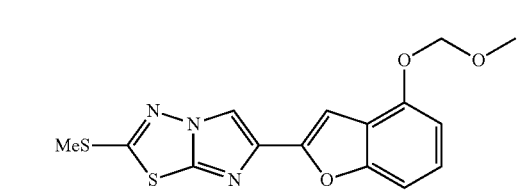 [SMILES: COCOc1cccc2oc(-c3cn4nc(SC)sc4n3)cc12]

A solution of 2-(2-(methylthio)imidazo[2,1-b][1,3,4]thiadiazol-6-yl)benzofuran-4-ol (Example 214, 0.084 g, 0.27 mmol) in DMF (1.5 mL) was treated with diisopropylethylamine (0.2 mL, 1.14 mmol) followed by a solution of MOMCl in toluene (3.5M, 0.2 mL, 0.7 mmol). The mixture was stirred at 22° C. and monitored by HPLC. After 18 h, the reaction was diluted with dichloromethane (100 mL) and washed with sat. sodium bicarbonate and brine. The organic layers were dried over anhydrous magnesium sulfate and evaporated to give a solid (0.089 g) which was found to be a mixture of the starting material and the title material. This was dissolved in DMF (2 mL) and treated with diisopropylethylamine (0.6 mL) and MOMCl (0.6 mL) and stirred at 22° C. for another 18 h. The same work-up was carried out as described before and the residue was purified by chromatography on silica gel (2.5×10 cm, AcOEt in dichloromethane 2 to 4%) to give the title material (0.041 g, 43%) as a solid. LC (Method A): 2.248 min. LCMS: Anal. Calcd. for $C_{15}H_{13}N_3O_3S_2$: 347.04. found: 348.07 (M+1)$^+$. $^1$H NMR (600 MHz, CDCl$_3$) δ ppm 8.04 (s, 1H), 7.19-7.17 (m, 3H), 6.91-6.90 (m, 1H), 5.33 (s, 2H), 3.54 (s, 3H), 2.77 (s, 3H).

Example 216

2-(Methylthio)-6-(4-(pyridin-3-ylmethoxy)benzofuran-2-yl) imidazo[2,1-b][1,3,4]thiadiazole

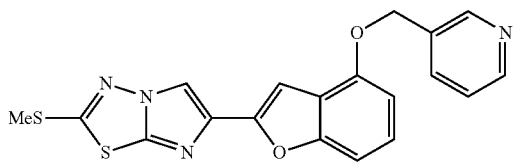 [SMILES: CSc1nn2cc(-c3cc4c(OCc5cccnc5)cccc4o3)nc2s1]

To a solution 2-(2-(methylthio)imidazo[2,1-b][1,3,4]thiadiazol-6-yl)benzofuran-4-ol (Example 214, 90 mg, 0.30 mmol) in DMF (2 mL) was added 3-(chloromethyl)pyridine hydrochloride (100 mg, 0.61 mmol) and NaH 60% in mineral oil (80 mg, 2 mmol). After stirring at rt for 25 min, the mixture was quenched with NaHCO$_3$ (10 mL) and diluted with DCM (200 mL). The organic was dried over MgSO$_4$ and the crude was purified by flash chromatography (DCM/EtOH 2-4%) to give the title material (116 mg, 0.29 mmol). LC (Method A): 1.935 min. LCMS: Anal. Calcd. for $C_{19}H_{14}N_4O_2S_2$: 394.06. found: 395.06 (M+1)$^+$. $^1$H NMR (600 MHz, CDCl$_3$) δ ppm 8.73 (s, 1H), 8.60 (d, J=4.2 Hz, 1H), 8.03 (s, 1H), 7.85 (d, J=7.8 Hz, 1H), 7.35 (dd, J$_1$=4.8 Hz, J$_2$=7.8 Hz, 1H), 7.21-7.13 (m, 3H), 7.74 (d, J=6.6 Hz, 1H), 5.25 (s, 2H), 2.77 (s, 3H).

Example 217

2-Methoxy-6-(4-(methoxymethoxy)benzofuran-2-yl) imidazo[2,1-b][1,3,4]thiadiazole

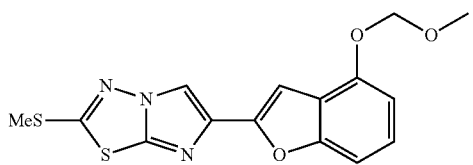 [SMILES: COCOc1cccc2oc(-c3cn4nc(SC)sc4n3)cc12]

217A. 6-(5-Bromo-4-(methoxymethoxy)benzofuran-2-yl)-2-methoxyimidazo[2,1-b][1,3,4]thiadiazole

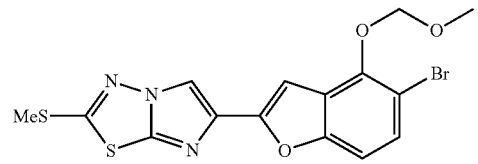

The title material was prepared by reacting 5-bromo-1,3,4-thiadiazol-2-amine (0.300 g, 1.66 mmol) and 2-bromo-1-(4-(methoxymethoxy)benzofuran-2-yl)ethanone (2×0.500 g, 1.67 mmol) as described in Example 203E. The resulting crude mixture in tetrahydrofuran (30 mL) at 0-5° C. was then treated with diisopropylethylamine (3 mL, 2.22 g, 17.2 mmol) followed by a solution of MOMCl in toluene (3.5M, 17.5 mmol) added dropwise over 10 min. The bath was removed and the mixture was stirred at 22° C. for 72 h. The reaction mixture was quenched with sat. sodium bicarbonate, diluted with dichloromethane (300 mL) and washed with brine. Evaporation of the organic layers after drying over magnesium sulfate gave an orange semi-solid which was used as such for the next reaction.

Example 217

2-Methoxy-6-(4-(methoxymethoxy)benzofuran-2-yl) imidazo[2,1-b][1,3,4]thiadiazole (217) and 6-(5-Bromo-4-(methoxymethoxy)benzofuran-2-yl)-2-methoxyimidazo[2,1-b][1,3,4]thiadiazole (217A)

(217)
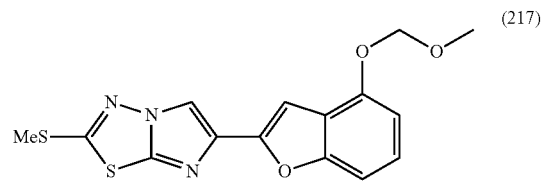

(217A)
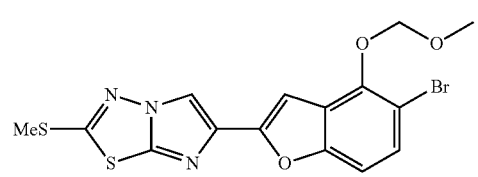 [SMILES: COCOc1c(Br)ccc2oc(-c3cn4nc(SC)sc4n3)cc12]

2-Methoxy-6-(4-(methoxymethoxy)benzofuran-2-yl)imidazo[2,1-b][1,3,4]thiadiazole (217) (0.037 g) was obtained by reacting the crude Example 218A according to the procedure described in Example 213. LC (Method C): 2.212 min. LCMS: Anal. Calcd. for $C_{15}H_{13}N_3O_4S$: 331.06. found: 332.08 (M+1)$^+$. $^1$H NMR (600 MHz, CDCl$_3$) δ ppm 7.91 (s, 1H), 7.18-7.17 (m, 2H), 7.13 (s, 1H), 6.89 (dd, J$_1$=5.4 Hz, J$_2$=3 Hz, 1H), 5.32 (s, 2H), 4.21 (s, 3H), 3.54 (s, 3H).

6-(5-Bromo-4-(methoxymethoxy)benzofuran-2-yl)-2-methoxyimidazo[2,1-b][1,3,4]thiadiazole (217A) (0.019 g) was obtained as a side-product of this reaction. LC (Method C): 2.347 min. LCMS: Anal. Calcd. for $C_{15}H_{12}BrN_3O_4S$: 408.97. found: 409.99 (M+1)$^+$. $^1$H NMR (600 MHz, CDCl$_3$) δ ppm 7.93 (s, 1H), 7.40 (d, J=9.0 Hz, 1H), 7.16-7.14 (m, 2H), 5.35 (s, 2H), 4.22 (s, 3H), 3.68 (s, 3H).

Example 218

6-Methyl, 4-trifluoromethyl-2-(2-(methylthio)imidazo[2,1-b][1,3,4]thiadiazol-6-yl)furopyridine

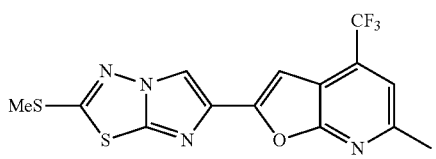 [SMILES: CSc1nn2cc(-c3cc4c(C(F)(F)F)cc(C)nc4o3)nc2s1]

218A. Methyl-5-aminofuran-2-carboxylate

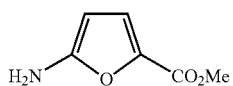

Pd/C 10% wet (2.5 g) was added to a solution of methyl-5-nitrofuran-2-carboxylate (5 g, 29.2 mmol) in EtOH (50 mL) and the reaction mixture was hydrogenated at rt for 18 h under atmospheric pressure. Then the catalyst was filtered off and the filtrate concentrated in vacuum to give a dark red solid (4.03 g, 28.6 mmol). LC (Method F): 1.059 min. LCMS: Anal. Calcd. for $C_6H_7NO_3$: 141.02. found: 142.04 (M+1)+; $^1$H NMR (600 MHz, CDCl$_3$) δ ppm 7.03 (d, J=3.6 Hz, 1H), 5.20 (d, J=3.6 Hz, 1H), 4.55 (sb, 2H), 3.75 (s, 3H).

218B. Methyl 6-methyl-4-(trifluoromethyl)furo[2,3-b]pyridine-2-carboxylate

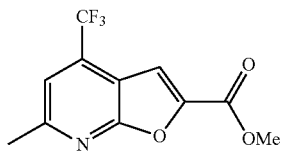 [SMILES: COC(=O)c1cc2c(C(F)(F)F)cc(C)nc2o1]

A mixture of methyl-5-aminofuran-2-carboxylate (Example 218A, 4.03 g, 28.6 mmol) and trifluoro pentandione (3.46 mL, 28.6 mmol) in AcOH (100 mL) was refluxed for 3 h 45 min. Then AcOH was removed in vacuum and the resulting gummy product was purified by flash chromatography (EtOAc/Hex: 1/9) to give an off-white solid (2.0 g, 7.72 mmol). LC (Method F): 2.002 min. LCMS: Anal. Calcd. for $C_{11}H_8NO_3F_3$: 259.05. found: 260.07 (M+1)+. $^1$H NMR (600 MHz, CDCl$_3$) δ ppm 7.62 (s, 1H), 7.43 (s, 1H), 4.00 (s, 3H), 2.76 (s, 3H).

218C. 6-Methyl-4-(trifluoromethyl)furo[2,3-b]pyridine-2-carboxylic acid

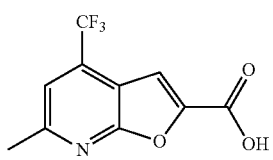 [SMILES: Cc1cc(C(F)(F)F)c2cc(C(=O)O)oc2n1]

A suspension of methyl 6-methyl-4-(trifluoromethyl)furo[2,3-b]pyridine-2-carboxylate (Example 218B, 1 g, 3.86 mmol) in aqueous NaOH 1N (50 mL) was heated at 70° C. for 3 h. The cooled solution was acidified with HCl and the resulting white precipitate was filtered and washed with water to give a white powder (946 mg, 3.86 mmol). LC (Method F): 1.816 min. LCMS: Anal. Calcd. for $C_{10}H_6NO_3F_3$: 245.03. found: 246.06 (M+1)+. $^1$H NMR (600 MHz, CDCl$_3$) δ ppm: 7.34 (s, 1H), 7.31 (s, 1H), 2.52 (s, 3H).

218D. N-Methoxy-N,6-dimethyl-4-(trifluoromethyl)furo[2,3-b]pyridine-2-carboxamide

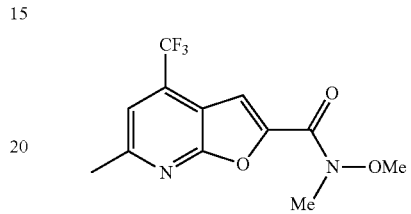

To a solution of 6-methyl-4-(trifluoromethyl)furo[2,3-b]pyridine-2-carboxylic acid (Example 218C, 716 mg, 2.92 mmol) in anhydrous THF (25 mL) was added 2-chloro-4,6-dimethoxy-1,3,5-triazine (613 mg, 3.50 mmol) and NMM (0.96 mL, 8.76 mmol). The resulting mixture was stirred at rt for 1 h and hydroxylamine hydrochloride (285 mg, 2.92 mmol) was added and the reaction mixture was stirred at rt over night under nitrogen atmosphere. The diluted reaction mixture with Et$_2$O (15 mL) was quenched with water (15 ml) and extracted with Et$_2$O (2×7 mL). The combined organic phases were washed with Na$_2$CO$_3$ (2×15 mL), HCl 10% (2×15 mL), brine (1×15 mL), dried over MgSO$_4$, filtered and concentrated to dryness to give a white solid (715 mg, 2.48 mmol). LC (Method F): 1.909 min. LCMS: Anal. Calcd. for $C_{12}H_{11}N_2O_3F_3$: 288.07. found: 289.10 (M+1)+. $^1$H NMR (600 MHz, CDCl$_3$) δ ppm 7.57 (s, 1H), 7.41 (s, 1H), 3.91 (s, 3H), 3.42 (s, 3H), 2.75 (s, 3H).

218E. 1-(6-Methyl-4-(trifluoromethyl)furo[2,3-b]pyridin-2-yl)ethanone

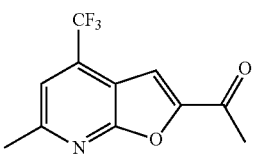 [SMILES: CC(=O)c1cc2c(C(F)(F)F)cc(C)nc2o1]

To a solution of N-methoxy-N,6-dimethyl-4-(trifluoromethyl)furo[2,3-b]pyridine-2-carboxamide (Example 218D, 223 mg, 0.77 mmol) in anhydrous THF (10 mL) was added dropwise a solution of 1M MeMgBr (3.88 mL, 3.88 mmol) in t-Bu$_2$O and the reaction mixture was stirred at rt for 4 h. Then the mixture was quenched with aqueous solution of NH$_4$Cl (15 mL) and extracted with Et$_2$O (3×15 mL). The combined organic phases were washed with Na$_2$CO$_3$ (1×15 mL), HCl 1M (2×15 mL), brine (1×15 mL), dried over MgSO$_4$, filtered and concentrated to dryness to give yellow needles (162 mg, 0.67 mmol). LC (Method F): 1.866 min. LCMS: Anal. Calcd. for $C_{11}H_8NO_2F_3$: 243.05. found: 244.08 (M+1)+. $^1$H NMR (600 MHz, CDCl$_3$) δ ppm 7.56 (s, 1H), 7.44 (s, 1H), 2.76 (s, 3H), 2.66 (s, 3H).

218F. 2-Bromo-1-(6-methyl-4-(trifluoromethyl)furo[2,3-b]pyridin-2-yl)ethanone

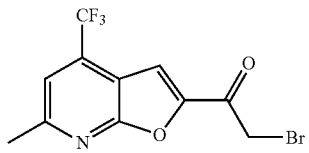 [SMILES: Cc1cc(C(F)(F)F)c2cc(C(=O)CBr)oc2n1]

To a solution of 1-(6-methyl-4-(trifluoromethyl)furo[2,3-b]pyridin-2-yl)ethanone (Example 218E, 162 mg, 0.64 mmol) in EtOAc (10 mL) was added previously grounded $CuBr_2$ (240 mg, 1.07 mmol). Then the reaction mixture was heated under reflux for 10 h. After cooling, the copper was removed by filtration and the diluted mixture with EtOAc (20 mL) was washed with $NaHCO_3$ (3×30 mL), brine (1×20 mL), dried over $MgSO_4$ and concentrated to dryness. The crude was purified by flash chromatography (Hex/5% EtOAc) to give a pale yellow oily product (134 mg, 0.42 mmol). LC (Method F): 1.990 min. LCMS: Anal. Calcd. for $C_{11}H_7NO_2F_3Br$: 320.96. found: 321.97 (M+1)$^+$. $^1$H NMR (600 MHz, $CDCl_3$) δ ppm 7.72 (s, 1H), 7.48 (s, 1H), 4.49 (s, 2H), 2.79 (s, 3H).

Example 218

6-Methyl, 4-trifluoromethyl-2-(2-(methylthio)imidazo[2,1-b][1,3,4]thiadiazol-6-yl)furopyridine

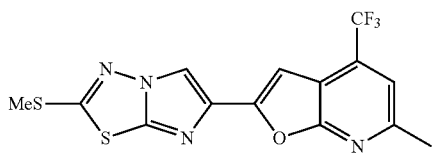 [SMILES: CSc1nn2cc(-c3cc4c(C(F)(F)F)cc(C)nc4o3)nc2s1]

5-(Methylthio)-1,3,4-thiadiazol-2-amine (55 mg, 0.37 mmol) and 2-bromo-1-(6-methyl-4-(trifluoromethyl)furo[2,3-b]pyridin-2-yl)ethanone (Example 218F, 100 mg, 0.31 mmol) were dissolved in anhydrous EtOH (5 mL) in a microwave vial. The reaction mixture was heated at 150° C. under microwave irradiation for 12 min. After evaporation of EtOH the crude was diluted in DCM (20 mL), washed with $NaHCO_3$ (1×30 mL), dried over $MgSO_4$ and filtered to give a brownish solid which was purified by trituration in $Et_2O$ to provide the desired compound as a beige solid (31 mg, 0.084 mmol). LC (Method F): 2.200 min. LCMS: Anal. Calcd. for $C_{14}H_9N_4OS_2F_3$: 370.02. found: 371.05 (M+1)$^+$. $^1$H NMR (600 MHz, $CDCl_3$) δ ppm 8.14 (s, 1H), 7.31 (s, 1H), 7.22 (s, 1H), 2.79 (s, 3H), 2.71 (s, 3H).

Example 219

2-(2-(Methylthio)imidazo[2,1-b][1,3,4]thiadiazol-6-yl)benzofuran-4-carboxylic acid

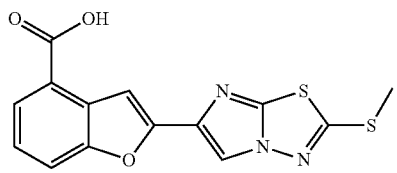 [SMILES: CSc1nn2cc(-c3cc4c(C(=O)O)cccc4o3)nc2s1]

219A. Methyl 2-(2-(methylthio)imidazo[2,1-b][1,3,4]thiadiazol-6-yl)benzofuran-4-carboxylate

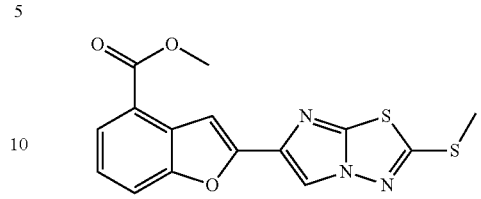

The title material was prepared as described in Example 1 by using 5-(methylthio)-1,3,4-thiadiazol-2-amine and methyl 2-(2-bromoacetyl)benzofuran-4-carboxylate. LC (Method A): 2.256 min. LCMS Calcd. for $C_{15}H_{11}N_3O_3S_2$: 345.02. found: 346.05 (M+1)$^+$. $^1$H NMR (DMSO-$d_6$) δ ppm: 8.73 (s, 1H), 7.90-7.86 (m, 2H), 7.50 (s, 1H), 7.40 (t, 1H), 3.91 (s, 3H), 2.77 (s, 3H).

Example 219

2-(2-(Methylthio)imidazo[2,1-b][1,3,4]thiadiazol-6-yl)benzofuran-4-carboxylic acid

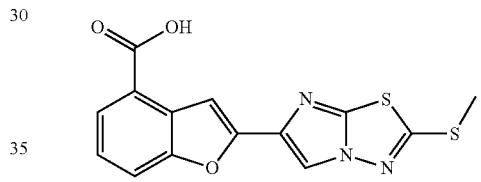

Methyl 2-(2-(methylthio)imidazo[2,1-b][1,3,4]thiadiazol-6-yl)benzofuran-4-carboxylate (Example 219A, 1.41 g, 4.1 mmol) was charged in a 20 mL microwave vessel, 15 mL acetic acid was added, followed by HBr 48% (1.16 mL, 10.2 mmol). The reaction mixture was then heated 1 hour, at 150° C. under microwave radiations. After cooling, the solid formed was collected by filtration and rinsed with ethyl acetate to give pure 2-(2-(methylthio)imidazo[2,1-b][1,3,4]thiadiazol-6-yl)benzofuran-4-carboxylic acid. LC (Method A): 2.126 min. LCMS Calcd. for $C_{14}H_9N_3O_3S_2$: 331.01. found: 332.02 (M+1)$^+$. $^1$H NMR (DMSO-$d_6$) δ ppm: 8.71 (s, 1H), 7.88-7.80 (m, 2H), 7.52 (s, 1H), 7.37 (t, 1H), 2.78 (s, 3H).

Example 220

N-Benzyl-2-(2-(methylthio)imidazo[2,1-b][1,3,4]thiadiazol-6-yl)benzofuran-6-carboxamide

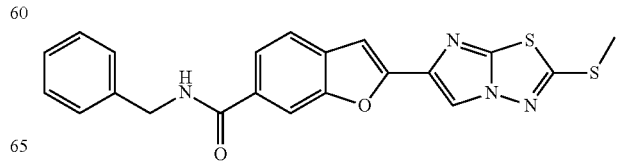

220A. Methyl 2-(2-(methylthio)imidazo[2,1-b][1,3,4]thiadiazol-6-yl)benzofuran-6-carboxylate

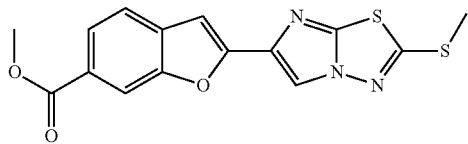 [SMILES: COC(=O)c1ccc2cc(-c3cn4nc(SC)sc4n3)oc2c1]

The title material was prepared as described in Example 1 by using 5-(methylthio)-1,3,4-thiadiazol-2-amine and methyl 2-(2-bromoacetyl)benzofuran-6-carboxylate. LC (Method A): 2.240 min. LCMS Calcd. for $C_{15}H_{11}N_3O_3S_2$: 345.02. found: 346.06 (M+1)$^+$. $^1$H NMR (DMSO-$d_6$) δ ppm: 8.69 (s, 1H), 8.08 (s, 1H), 7.85 (d, 1H), 7.73 (d, 1H), 7.22 (s, 1H), 3.87 (s, 3H), 2.88 (s, 3H).

220B. 2-(2-(Methylthio)imidazo[2,1-b][1,3,4]thiadiazol-6-yl)benzofuran-6-carboxylic acid

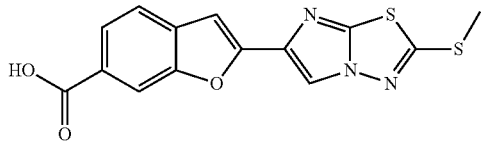 [SMILES: CSc1nn2cc(-c3cc4ccc(C(=O)O)cc4o3)nc2s1]

The title material was prepared as described in Example 219 by using methyl 2-(2-(methylthio)imidazo[2,1-b][1,3,4]thiadiazol-6-yl)benzofuran-6-carboxylate (Example 220A). LC (Method A): 2.061 min. LCMS: Calcd. for $C_{14}H_9N_3O_3S_2$: 331.01. found: 332.03 (M+1)$^+$. $^1$H NMR (DMSO-$d_6$) δ ppm: 8.62 (s, 1H), 7.99 (s, 1H), 7.79 (d, 1H), 7.67 (d, 1H), 7.17 (s, 1H) 2.73 (s, 3H).

Example 220

N-Benzyl-2-(2-(methylthio)imidazo[2,1-b][1,3,4]thiadiazol-6-yl)benzofuran-6-carboxamide

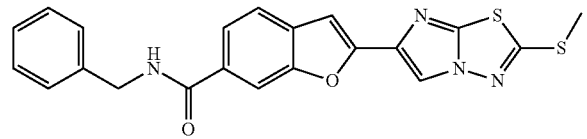 [SMILES: CSc1nn2cc(-c3cc4ccc(C(=O)NCc5ccccc5)cc4o3)nc2s1]

To a solution of 2-(2-(methylthio)imidazo[2,1-b][1,3,4]thiadiazol-6-yl)benzofuran-6-carboxylic acid (Example 220B, 15 mg, 0.043 mmol) in DMF (1 mL), benzylamine (5 µL, 0.043 mmol), di-isopropylethylamine (38 µL, 0.22 mmol) and HATU (16 mg, 0.043 mmol) were added and the reaction was stirred overnight at room temperature. The crude reaction mixture was dissolved with a 9:1 mixture of ethyl acetate and hexanes, and washed with water (2×) and brine, dried over MgSO$_4$, filtered and concentrated. The crude residue obtained was purified by preparative HPLC to give N-benzyl-2-(2-(methylthio)imidazo[2,1-b][1,3,4]thiadiazol-6-yl)benzofuran-6-carboxamide. LC (Method A): 2.135 min. LCMS: Calcd. for $C_{21}H_{16}N_4O_2S_2$: 420.07. found: 421.10 (M+1)$^+$. $^1$H NMR (DMSO-$d_6$) δ ppm: 9.08 (t, 1H), 8.68 (s, 1H), 8.09 (s, 1H), 7.81 (d, 1H), 7.69 (d, 1H), 7.32-7.29 (m, 4H), 7.24-7.20 (m, 1H), 7.18 (s, 1H), 4.48 (d, 2H), 2.78 (s, 3H).

Example 221

4-Chloro-2-(2-(methylthio)imidazo[2,1-b][1,3,4]thiadiazol-6-yl)furo[3,2-c]pyridine

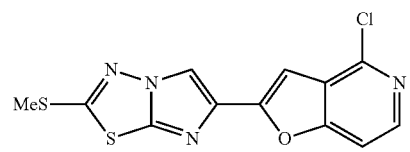 [SMILES: CSc1nn2cc(-c3cc4c(Cl)nccc4o3)nc2s1]

221A. (E)-3-(Furan-2-yl)acryloyl azide

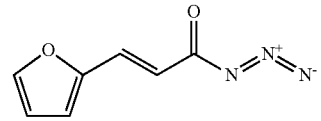 [SMILES: [N-]=[N+]=NC(=O)/C=C/c1ccco1]

To a stirred solution of furyl acrylic acid (2.028 g, 14.68 mmol) in THF (40 mL) at 0° C., was added triethylamine (2.6 mL, 18.65 mmol) and diphenylphosphorylazide (3.7 mL, 17.17 mmol) dropwise. The reaction was stirred at rt for 4 h, then the mixture was added to a mixture of ethyl acetate and sat. sodium bicarbonate. The aqueous phase was extracted with ethyl acetate (1×) and the combined organic phase was dried over anhydrous sodium sulfate and concentrated. The residue was triturated twice with methanol and filtered to give the title material (1.413 g, 59%) as a beige solid. LC (Method A): 1.765 min. $^1$H NMR (DMSO-$d_6$) δ ppm: 7.94 (s, 1H), 7.59 (d, J=15.6 Hz, 1H), 7.12 (d, J=3.6 Hz, 1H), 6.70 (m, 1H), 6.24 (d, J=15.6 Hz, 1H).

221B. Furo[3,2-c]pyridin-4(5H)-one

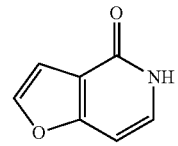

(E)-3-(Furan-2-yl)acryloyl azide (Example 221A, 0.501 g, 3.071 mmol) was dissolved in toluene (5 mL) and heated at reflux for 40 min. The mixture was then concentrated to afford a dark brown oil which was then dissolved in o-dichlorobenzene (9 mL) and iodine (8 mgs, 0.0315 mmol) was added. The reaction mixture was stirred for 2 hours at 180° C. The mixture was cooled down to rt and ethyl acetate was added. The resulting precipitate was filtered. The filtrate was evaporated and the residue was dissolved in ethyl ether (10 mL) and extracted with 0.5M aq. sodium hydroxide (2×10 mL). The aqueous phase was acidified with 1.5N aq. HCl until the pH reaches 1.0. The acidified aqueous phase was then extracted with ethyl acetate (3×) and the combined organic extracts were dried over anhydrous sodium sulfate, filtered and concentrated. The resulting red-brown solid was triturated in cold ethyl ether twice to give the title material (0.249 g, 60%) as a red-brown solid. LC (Method A): 0.883 min. $^1$H NMR (DMSO-$d_6$) δ ppm: 11.43 (br s, 1H), 7.87 (d, J=1.8 Hz, 1H), 7.29 (d, J=7.2 Hz, 1H), 6.92 (d, J=1.2 Hz, 1H), 6.65 (d, J=7.2 Hz, 1H).

221C. 4-Chlorofuro[3,2-c]pyridine

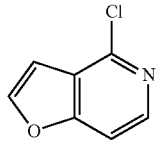

Phosphorous oxychloride (2.5 mL, 27.31 mmol) was added to furo[3,2-c]pyridin-4(5H)-one (Example 221B, 0.249 g, 1.1843 mmol) at 0° C. and the resulting mixture was stirred at reflux for 3 h. Ice was then added to the mixture and this was stirred for an additional hour at RT. The mixture was extracted with dichloromethane (3×) and the combined organic extracts were dried over anhydrous sodium sulfate, filtered and concentrated. The residue was purified by flash chromatography (Isco, ethyl acetate/dichloromethane) to give the title material (0.145 g, 51%) as white crystals. LC (Method A): 1.451 min. $^1$H NMR (DMSO-$d_6$) δ ppm: 8.30 (d, J=6.0 Hz, 1H), 8.26 (d, J=1.2 Hz, 1H), 7.78 (d, J=6.0 Hz, 1H), 7.13 (d, J=1.2 Hz, 1H).

221 D. 1-(4-Chlorofuro[3,2-c]pyridin-2-yl)ethanone

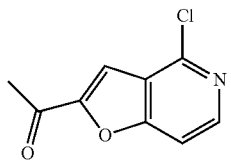

A solution of 4-chlorofuro[3,2-c]pyridine (Example 221C, 0.145 g, 0.944 mmol) in THF (5 mL) was treated with t-butyllithium (1.34M in pentane, 1.0 mL, 1.34 mmol) dropwise at −65° C. The reaction was stirred at −65° C. for 30 min. then a solution of N,N-dimethylacetamide (0.17 mL, 1.828 mmol) in ethyl ether (1 mL) was added dropwise. After stirring for 15 min. at −65° C. and 1 h at RT, water was added to the mixture. The aqueous phase was extracted with ethyl ether (3×) and the organic extracts were washed with brine, dried over anhydrous sodium sulfate, filtered and concentrated. The residue was purified by flash chromatography (Isco, ethyl acetate/dichloromethane) to give the title material (0.110 g, 59%) as a white solid. LC (Method A): 1.414 min. LCMS: Anal. Calcd. for $C_9H_6ClNO_2$: 195.01. found: 196.03 (M+1)$^+$. $^1$H NMR (DMSO-$d_6$) δ ppm: 8.47 (d, J=6.0 Hz, 1H), 8.11 (s, 1H), 7.89 (d, J=6.0 Hz, 1H), 2.62 (s, 3H).

221E. 2-Bromo-1-(4-chlorofuro[3,2-c]pyridin-2-yl)ethanone

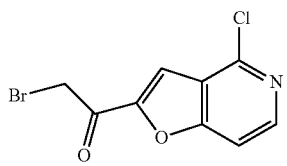

A solution of 1-(4-chlorofuro[3,2-c]pyridin-2-yl)ethanone (Example 221D, 0.170 g, 0.869 mmol) in THF (3 mL) was added dropwise for 15 min. to a stirred solution of LiHMDS (1.0M in THF, 1.0 mL, 1.00 mmol)) in THF (1 mL) at −78° C. The reaction was stirred for 45 min., then trimethylsilylchloride (0.13 mL, 1.02 mmol) was added dropwise over 2 min. at −78° C. After stirring for 15 min. at −78° C., the reaction was allowed to reach rt and was stirred for an additional hour. Cold ethyl acetate was then added, followed by ice and sat. sodium bicarbonate and the organic phase was separated and quickly washed with brine, dried over anhydrous sodium sulfate, filtered and concentrated. The residual yellow oil was then dissolved in THF (7.5 mL), cooled down to −20° C. and treated with sat. sodium bicarbonate. NBS (0.175 g, 0.983 mmol) was then added portionwise over 15 min. and the mixture was stirred for 1.5 h at −20° C. The mixture was diluted with ethyl acetated and washed with sat. sodium bicarbonate (1×) and brine, dried over anhydrous sodium sulfate, filtered and concentrated. The residue was purified by flash chromatography (Isco, 10% ethyl acetate in toluene) to give the title material (0.212 g, 89%) as a white solid. LC (Method A): 1.634 min. LCMS: Anal. Calcd. for $C_9H_5BrClNO_2$: 272.92. found: 273.94 (M+1)$^+$.)$^+$. $^1$H NMR (DMSO-$d_6$) δ ppm: 8.50 (d, J=6.0 Hz, 1H), 8.28 (s, 1H), 7.92 (d, J=6.0 Hz, 1H), 4.90 (s, 2H).

Example 221

4-Chloro-2-(2-(methylthio)imidazo[2,1-b][1,3,4]thiadiazol-6-yl)furo[3,2-c]pyridine

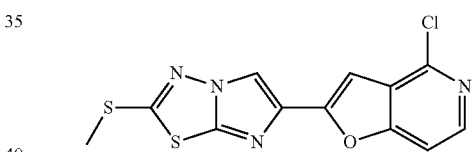

The title material was prepared as described in Example 1 by using 5-(methylthio)-1,3,4-thiadiazol-2-amine and 2-bromo-1-(4-chlorofuro[3,2-c]pyridin-2-yl)ethanone (Example 221E). LC (Method A): 2.094 min. LCMS Calcd. for $C_{12}H_{17}ClN_4OS_2$: 321.98. found: 323.00 (M+1)$^+$. $^1$H NMR (DMSO-$d_6$) δ ppm: 8.77 (s, 1H), 8.29 (d, J=5.4 Hz, 1H), 7.76 (d, J=5.4 Hz, 1H), 7.17 (s, 1H), 2.81 (s, 3H).

Example 222

2-(2-Bromoimidazo[2,1-b][1,3,4]thiadiazol-6-yl)-4-chlorofuro[3,2-c]pyridine

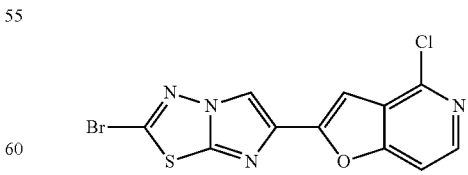

The title material was prepared as described in Example 203E by using 5-bromo-1,3,4-thiadiazol-2-amine and 2-bromo-1-(4-chlorofuro[3,2-c]pyridin-2-yl)ethanone (Example 221E). LC (Method A): 2.043 min. LCMS Calcd. for $C_{11}H_4BrClN_4OS$: 353.90. found: 354.92 (M+1)$^+$. $^1$H NMR (DMSO-d$_6$) δ ppm: 8.90 (s, 1H), 8.30 (d, J=5.4 Hz, 1H), 7.78 (d, J=5.4 Hz, 1H), 7.22 (s, 1H).

Example 223

4-Chloro-2-(2-methoxyimidazo[2,1-b][1,3,4]thiadiazol-6-yl)furo[3,2-c]pyridine

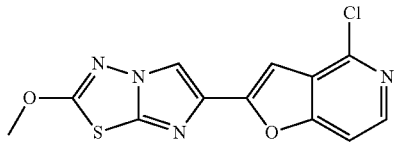 [SMILES: COc1nn2cc(-c3cc4c(Cl)nccc4o3)nc2s1]

The title material was prepared as described in Example 203 by using 2-(2-bromoimidazo[2,1-b][1,3,4]thiadiazol-6-yl)-4-chlorofuro[3,2-c]pyridine (Example 222). LC (Method A): 1.969 min. LCMS Calcd. for C$_{12}$H$_{17}$ClN$_4$O$_2$S: 306.00. found: 307.01 (M+1)$^+$. $^1$H NMR (DMSO-d$_6$) δ ppm: 8.69 (d, J=0.6 Hz, 1H), 8.28 (d, J=6.0 Hz, 1H), 7.76 (d, J=6.0 Hz, 1H), 7.13 (s, 1H), 3.90 (s, 3H).

Example 224

5-Benzyl-6-methoxy-2-(2-methoxyimidazo[2,1-b][1,3,4]thiadiazol-6-yl)benzofuran-4-ol

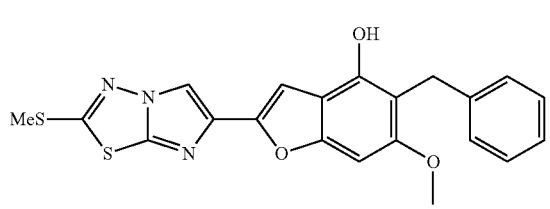 [SMILES: COc1cc2oc(-c3cn4nc(SC)sc4n3)cc2c(O)c1Cc1ccccc1]

The title material was prepared as described in Example 211 from 6-(4-(benzyloxy)-6-methoxybenzofuran-2-yl)-2-methoxyimidazo[2,1-b][1,3,4]thiadiazole (Example 203) and was obtained as a side-product. LC (Method B): 1.887 min. LCMS Calcd. for C$_{21}$H$_{17}$N$_3$O$_4$S: 407.09. found: 408.11 (M+1)$^+$. $^1$H NMR (600 MHz, DMSO-d$_6$) δ ppm 9.75 (s, 1H), 8.30 (s, 1H), 7.21-7.19 (m, 4H), 7.10 (s, 1H), 6.77 (s, 1H), 4.20 (s, 3H), 3.95 (s, 2H), 3.78 (s, 3H).

Example 225

6-(7-Bromo-4,6-dimethoxybenzofuran-2-yl)-2-(1,1-difluoroethyl)imidazo[2,1-b][1,3,4]thiadiazole

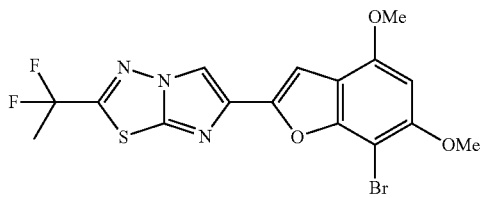 [SMILES: COc1cc(OC)c2cc(-c3cn4nc(C(C)(F)F)sc4n3)oc2c1Br]

225A. 2-Bromo-1-(7-bromo-4,6-dimethoxybenzofuran-2-yl)ethanone

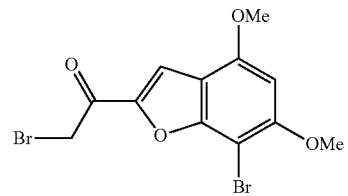 [SMILES: COc1cc(OC)c2cc(C(=O)CBr)oc2c1Br]

The title material was obtained as a side-product when reacting 1-(4,6-dimethoxybenzofuran-2-yl)ethanone with CuBr$_2$ as described in Example 200C. The compound was not separable from 2-bromo-1-(4,6-dimethoxybenzofuran-2-yl)ethanone (see Table of bromomethylketones below) and the mixture (referred to as Example 225A) was used as such for the next reaction.

Example 225

6-(7-Bromo-4,6-dimethoxybenzofuran-2-yl)-2-(1,1-difluoroethyl)imidazo[2,1-b][1,3,4]thiadiazole

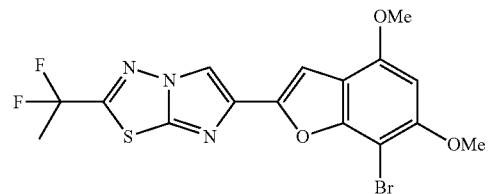 [SMILES: COc1cc(OC)c2cc(-c3cn4nc(C(C)(F)F)sc4n3)oc2c1Br]

The title material was prepared as described in Example 207 by using a mixture of 2-bromo-1-(7-bromo-4,6-dimethoxybenzofuran-2-yl)ethanone and 2-bromo-1-(4,6-dimethoxybenzofuran-2-yl)ethanone mixture (Example 225A) and was isolated as a solid side-product (5% yield, as TFA salt) by preparative HPLC. [(Sunfire-C18/MeOH—H$_2$O-TFA)] LC (Method A): 2.326 min. LCMS: Anal. Calcd. for C$_{16}$H$_{12}$BrF$_2$N$_3$O$_3$S: 444.97. found: 446.00 (M+1). $^1$H NMR (600 MHz, DMSO-d$_6$) δ 8.74 (s, 1H), 7.17 (s, 1H), 6.69 (s, 1H), 3.95 (s, 3H), 3.92 (s, 3H), 2.21 (t, J=19.3 Hz, 3H).

Example 226

6-(4-(Benzyloxy)-7-bromo-6-methoxybenzofuran-2-yl)-2-methoxyimidazo[2,1-b][1,3,4]thiadiazole

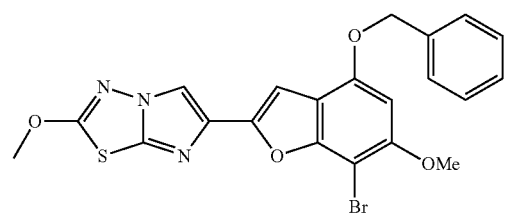 [SMILES: COc1nn2cc(-c3cc4c(OCc5ccccc5)cc(OC)c(Br)c4o3)nc2s1]

226A. 1-(4-(Benzyloxy)-7-bromo-6-methoxybenzo-furan-2-yl)-2-bromoethanone

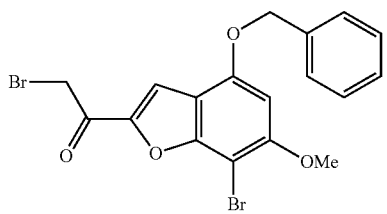 [SMILES: COc1cc(OCc2ccccc2)c2cc(C(=O)CBr)oc2c1Br]

The title material was obtained as a side-product when reacting 1-(4-(benzyloxy)-6-methoxybenzofuran-2-yl)etha-none (Example 203C) with CuBr$_2$ as described in Example 200C. The title compound was not separable from 1-(4-(benzyloxy)-6-methoxybenzofuran-2-yl)-2-bromoethanone (Example 203D) and the mixture (referred to as Example 226A) was used as such for the next reaction.

Example 226

6-(4-(Benzyloxy)-7-bromo-6-methoxybenzofuran-2-yl)-2-methoxyimidazo[2,1-b][1,3,4]thiadiazole

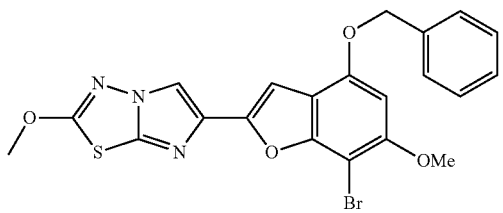 [SMILES: COc1nn2cc(-c3cc4c(OCc5ccccc5)cc(OC)c(Br)c4o3)nc2s1]

The title material was prepared as described in Example 203 by using a mixture of 1-(4-(benzyloxy)-7-bromo-6-methoxybenzofuran-yl)-2 bromoethanone and 1-(4-(benzyloxy)-6-methoxybenzofuran-2-yl)-2-bromoethanone (Example 226A). LC (Method A): 2.415 min. LCMS Calcd. for C$_{21}$H$_{16}$BrN$_3$O$_4$S: 485.00. found: 486.01 (M+1)$^+$. $^1$H NMR (600 MHz, CDCl$_3$) δ ppm: 7.93 (s, 1H), 7.45 (d, J=7.6 Hz, 2H), 7.38 (t, J~7.6 Hz, 2H), 7.32 (br t, 1H), 7.23 (s, 1H), 6.45 (s, 1H), 5.22 (s, 2H), 4.18 (s, 3H), 3.89 (s, 3H).

Synthesis of Additional Non-Commercial Benzaldehydes

The following benzaldehydes have been used as reagents to prepared Examples:

Synthesis of 5-bromo-2-hydroxy-4-methoxybenzaldehyde

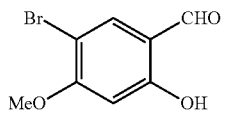

A modification of a literature procedure (cf. Meng, C. Q. et al., *J. Med. Chem.*, 50:1304-1315 (2007)) was used. Thus, to an ice-cold solution of 2-hydroxy-4-methoxybenzalde-hyde (6.00 g, 39.4 mmol) in DCM (50 mL) was added a solution of bromine (2.23 mL, 43.4 mmol) in DCM (5 mL) dropwise over ca. 30 min and then stirring was continued at 0° C. for 2 h. The cooling bath was then removed and the mixture was stirred at room temperature for 16 h. The resulting slurry was filtered and the filter-cake was washed with a minimum volume of DCM and was then dried in vacuo to give the title compound (5.19 g, 57%) as a white solid. This material was used as such in the next step without further purification. LC (Method A): 1.768 min. LCMS: Anal. Calcd. for C$_8$H$_7$BrO$_3$: 229.96. found: 230.97 (M+1)$^+$. $^1$H NMR (600 MHz, DMSO-d$_6$) δ 11.14 (s, 1H), 9.98 (s, 1H), 7.78 (s, 1H), 6.61 (s, 1H), 3.86 (s, 3H).

Synthesis of 5-fluoro-2-hydroxy-4-methoxybenzaldehyde

1. Synthesis of 4-fluoro-3-methoxyphenol

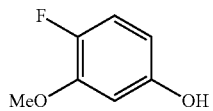

To a solution of 4-fluoro-3-methoxybenzaldehyde (10.79 g, 70.0 mmol) in DCM (250 mL) was added solid m-CPBA (20.71 g, 84.0 mmol) and the resulting solution was stirred at room temperature in a sealed flask for 18 h and then was heated to reflux under N$_2$ for 8 h. The resulting suspension was filtered, the filter-cake was washed with a little DCM and the combined filtrate was then washed (sat. NaHCO$_3$, 3×; brine), dried (Na$_2$SO$_4$) and evaporated to give an orange-yellow semi-solid. This material was taken up in 10% ethanolic KOH (100 mL) and the resulting dark brown solution which was stirred at room temperature for 2 h. The mixture was then acidified to pH 2 using 10% aqueous HCl, diluted with water (200 mL) and extracted with DCM (×3). The organic extract was dried (Na$_2$SO$_4$) and evaporated to give a brown semi-solid, which was purified by flash chromatography (Isco/DCM, then 0-5% EtOAc-DCM). The resulting material was taken up in ether, and the solution was washed (sat. NaHCO$_3$, ×4; brine), dried (Na$_2$SO$_4$) and evaporated to give the pure title compound (3.87 g, 39%) as a light yellow oil. LC (Method A): 1.238 min. LCMS: Anal. Calcd. for C$_7$H$_7$FO$_2$: 142.04. found: 143.05 (M+1)$^+$. $^1$H NMR (600 MHz, DMSO-d$_6$) δ 9.32 (s, 1H), 6.92 (dd, J=11.1, 8.8 Hz, 1H), 6.47 (dd, J=7.6, 2.9 Hz, 1H), 6.22 (dt, J=8.8, 2.9 Hz, 1H), 3.72 (s, 3H).

2. Synthesis of 5-fluoro-2-hydroxy-4-methoxybenzaldehyde

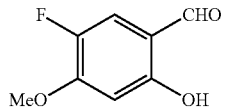

To a mixture of 4-fluoro-3-methoxyphenol (5.33 g, 35.0 mmol) and N-chlorosuccinimide (5.38, 40.3 mmol) in chloroform (100 mL) was added concentrated HCl (2.0 mL) dropwise and then the mixture was heated to reflux. To an ice-cold solution of 4-fluoro-3-methoxyphenol (1.42 g, 10.0 mmol) in MeCN (50 mL) under N$_2$ was added anhydrous magnesium chloride (1.90 g, 20.0 mmol) portionwise. To this mixture was added solid paraformaldehyde (2.10 g, 69.9 mmol) and then triethylamine (5.60 mL, 40.0 mmol) was added dropwise. The reaction flask was sealed and the mixture was heated at 75° C. (oil bath temperature) for 2 h. The cooled mixture was diluted with EtOAc, washed (1N HCl, water, brine), dried (Na$_2$SO$_4$) and evaporated to give the title compound (1.54 g, 91%) as an off-white solid. This material was used as such in the next step without further purification. LC (Method A): 1.488 min. LCMS: Anal. Calcd. for C$_8$H$_7$FO$_3$: 170.04. found: 171.05 (M+1)$^+$. $^1$H NMR (600 MHz, DMSO-d$_6$) δ 10.90 (s, 1H), 10.00 (s, 1H), 7.39 (m, 1H), 6.66 (m, 1H), 3.89 (s, 3H).

Synthesis of 3-fluoro-2-hydroxybenzaldehyde

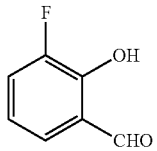

A mixture of anhydrous MgCl$_2$ (14.3 g, 0.15 mmol) in THF (25 mL) was treated with molecular sieve and stirred at RT under N$_2$ for 72 h. Then paraformaldehyde (6.75 g, 0.224 mmol) was added followed by a dropwise addition of triethylamine (21 mL, 0.15 mmol) over 5 min. The mixture was allowed to stir for 10 min and 2-fluorophenol (8.40 g, 74.9 mmol) was introduced dropwise with syringe and the reaction mixture was heated under reflux for 18 h. The cooled mixture was diluted with EtOAc (300 mL) and washed with cold 1N HCl (3×100 mL), brine and dried over MgSO$_4$. The crude was purified by flash chromatography (DCM/EtOAc 0-1%) to give the 3-fluoro-2-hydroxybenzaldehyde as an oil (10.5 g, 79.9 mmol). LC (Method C): 1.442 min. $^1$H NMR (600 MHz, CDCl$_3$) δ ppm 10.99 (s, 1H), 9.94 (s, 1H), 7.39-7.34 (m, 2H), 7.00-6.97 (m, 1H).

Synthesis of 2-hydroxy-6-(2-methoxyethoxyl)benzaldehyde

1. Preparation of 5-(2-methoxyethoxy)-2,2-dimethyl-4H-benzo[d][1,3]dioxin-4-one

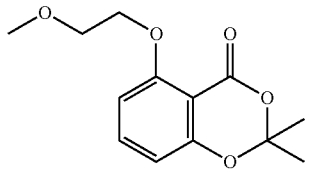

The title material was prepared according to the procedure described for Example 203A and in Org. Synth., 84:102 (2007). $^1$H NMR (600 MHz, CDCl$_3$) δ ppm 7.42 (dd, J$_1$=J$_2$=8.4 Hz, 1H), 6.63 (d, J=8.4 Hz, 1H), 6.55 (d, J=8.4 Hz, 1H), 4.23 (t, J=4.8 Hz, 2H), 3.86 (s, J=4.8 Hz, 3H), 3.50 (s, 3H), 1.70 (s, 6H).

2. Preparation of 2-hydroxy-6-(2-methoxyethoxyl)benzaldehyde

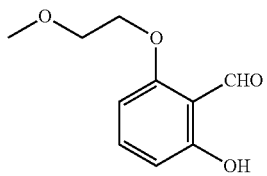

The title material was prepared from 5-(2-methoxyethoxy)-2,2-dimethyl-4H-benzo[d][1,3]dioxin-4-one according to the literature procedure (J. Org. Chem., 71:3646-3649 (2006)). $^1$H NMR (600 MHz, CDCl$_3$) δ ppm 11.97 (s, 1H), 10.39 (s, 1H), 7.41-7.38 (m, 1H), 6.54-6.53 (m, 1H), 6.38-6.37 (m, 1H), 4.21-4.19 (m, 2H), 3.80-3.78 (m, 2H), 3.45-3.44 (s, 3H).

Synthesis of methyl 2-formyl-3-hydroxybenzoate

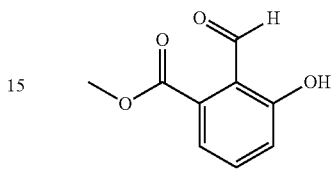

Methyl-3-hydroxybenzoate (12.3 g, 80.8 mmol) was mixed with hexamethylenetetramine (22.7 g, 161.6 mmol) in TFA (200 mL) at reflux for 4 h. After cooling, the mixture was concentrated under reduced pressure and the crude residue obtained was dissolved with water. The pH of the aqueous solution was adjusted to 8 with solid K$_2$CO$_3$ and the product was extracted with ethyl acetate (3×). The combined organic layers were washed with brine, dried over MgSO$_4$, filtered and concentrated. The crude residue obtained was purified by column chromatography eluting with a gradient of ethyl acetate (10 to 20%) in hexanes to give 6.7 g of methyl 2-formyl-3-hydroxybenzoate. $^1$H NMR (CDCl$_3$) δ ppm: 12.20 (bs, 1H), 10.62 (s, 1H), 7.55 (t, 1H), 7.46 (d, 1H), 7.18 (d, 1H), 3.95 (s, 3H).

Synthesis of methyl 4-formyl-3-hydroxybenzoate

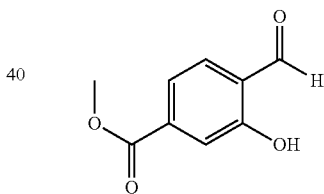

Methyl-3-hydroxybenzoate (5.0 g, 32.8 mmol) was mixed with hexamethylenetetramine (9.2 g, 65.6 mmol) in TFA (100 mL) at reflux for 4 h. After cooling, the mixture was concentrated under reduced pressure and the crude residue obtained was dissolved with water. The pH of the aqueous solution was adjusted to 8 with solid K$_2$CO$_3$ and the product was extracted with ethyl acetate (3×). The combined organic layers were washed with brine, dried over MgSO$_4$, filtered and concentrated. The crude residue obtained was purified by column chromatography eluting with a gradient of ethyl acetate (10 to 20%) in hexanes to give 1.2 g of methyl 4-formyl-3-hydroxybenzoate. $^1$H NMR (CDCl$_3$) δ ppm: 10.95 (s, 1H), 9.97 (s, 1H), 7.65-7.62 (m, 3H), 3.94 (s, 3H).

Synthesis of the Bromomethylketones

The following compounds were also prepared from various commercially or non-commercially available benzaldehydes, using the methods described in Examples 200B and 200C above. The following compounds were also used as reagents in the preparation of Examples 227-228 to 306.

| Structure | HPLC Ret. Time (Min)/ Method | LCMS | $^1$H NMR (600 MHz, DMSO-d$_6$) |
|---|---|---|---|
| 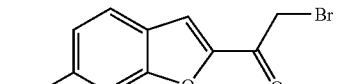 | 1.820/A | Calcd. for C$_{11}$H$_9$BrO$_3$: 267.97; found: 268.99 (M + 1)$^+$ | $^1$H NMR (600 MHz, DMSO-d$_6$) δ 8.00 (s, 1H), 7.71 (d, J = 8.8 Hz, 1H), 7.29 (d, J = 1.8 Hz, 1H), 6.98 (dd, J = 8.8, 2.3 Hz, 1H), 4.71 (s, 2H), 3.82 (s, 3H) |
| 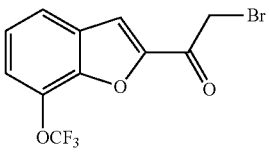 [SMILES: O=C(CBr)c1cc2cccc(OC(F)(F)F)c2o1] | | | |
| 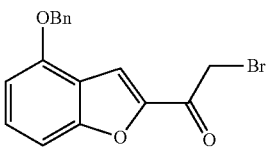 [SMILES: O=C(CBr)c1cc2c(OCc3ccccc3)cccc2o1] | 2.186/A | Calcd. for C$_{17}$H$_{13}$BrO$_3$: 344.00; found: 345.02 (M + 1)$^+$ | $^1$H NMR (600 MHz, CDCl$_3$) δ 7.79 (s, 1H), 7.47-7.18 (m, 7H), 6.76 (d, J = 6.7 Hz, 1H), 5.21 (s, 2H), 4.40 (s, 2H) |
| 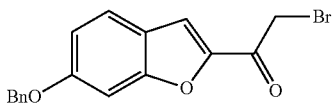 [SMILES: O=C(CBr)c1cc2ccc(OCc3ccccc3)cc2o1] | | | |
| 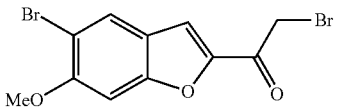 | 1.983/A | Calcd. for C$_{11}$H$_8$Br$_2$O$_3$: 345.88; found: 346.89 (M + 1)$^+$ | $^1$H NMR (600 MHz, DMSO-d$_6$) δ 8.10 (s, 1H), 7.95 (s, 1H), 7.52 (s, 1H), 4.73 (s, 2H), 3.92 (s, 3H) |
| 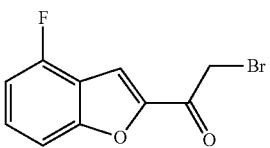 [SMILES: O=C(CBr)c1cc2c(F)cccc2o1] | 1.868/A | Calcd. for C$_{10}$H$_6$BrFO$_2$: 255.95; found: 256.96 (M + 1)$^+$ | $^1$H NMR (600 MHz, DMSO-d$_6$) δ 8.22 (s, 1H), 7.60 (m, 2H), 7.22 (m, 1H), 6.98 (dd, J = 8.8, 2.3 Hz, 1H), 4.82 (s, 2H) |
| 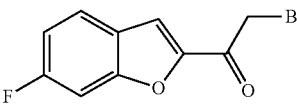 | | | |
| 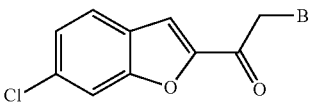 | | | |
| 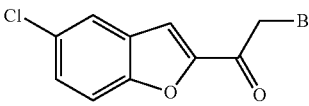 | | | |
| 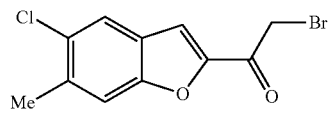 | 2.112/A | Calcd. for C$_{10}$H$_6$BrFO$_2$: 285.94; found: 286.95 (M + 1)$^+$ | $^1$H NMR (600 MHz, DMSO-d$_6$) δ 7.97 (s, 1H), 7.94 (s, 1H), 7.77 (s, 1H), 4.78 (s, 2H), 2.44 (s, 3H) |
| 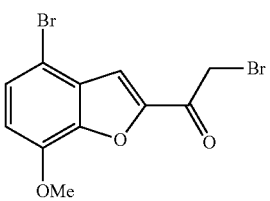 [SMILES: COc1ccc(Br)c2cc(C(=O)CBr)oc12] | 2.053/A | Calcd. for C$_{11}$H$_8$Br$_2$O$_3$: 347.88; found: 348.89 (M + 1)$^+$ | $^1$H NMR (600 MHz, DMSO-d$_6$) δ 7.78 (s, 1H), 7.47 (d, J = 8.2 Hz, 1H), 7.07 (d, J = 8.2 Hz, 1H), 4.69 (s, 2H), 3.92 (s, 3H) |

| Structure | HPLC Ret. Time (Min)/ Method | LCMS | ¹H NMR (600 MHz, DMSO-d₆) |
|---|---|---|---|
| 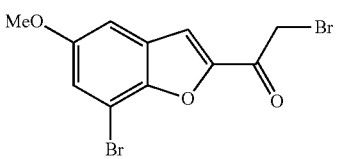 | 2.075/A | Calcd. for $C_{11}H_8Br_2O_3$: 347.88; found: 348.89 (M + 1)⁺¹ | ¹H NMR (600 MHz, DMSO-d₆) δ 8.05 (s, 1H), 7.43 (s, 1H), 7.35 (s, 1H), 4.79 (s, 2H), 3.79 (s, 3H) |
| 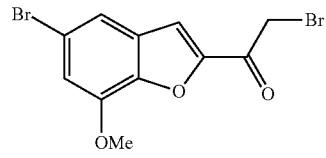 [SMILES: COc1cc(Br)cc2cc(C(=O)CBr)oc12] | 2.042/A | Calcd. for $C_{11}H_8Br_2O_3$: 347.88; found: 348.89 (M + 1)⁺ | ¹H NMR (600 MHz, DMSO-d₆) δ 7.95 (s, 1H), 7.62 (s, 1H), 7.29 (s, 1H), 4.79 (s, 2H), 3.96 (s, 3H) |
| 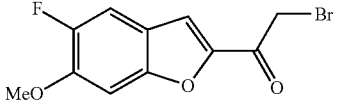 [SMILES: COc1cc2oc(C(=O)CBr)cc2cc1F] | 1.838/A | Calcd. for $C_{11}H_8BrFO_3$: 285.96; found: 286.xx (M + 1)⁺ | ¹H NMR (600 MHz, DMSO-d₆) δ 7.98 (s, 1H), 7.70 (d, J = 10.5 Hz, 1H), 7.58 (d, J = 7.0 Hz, 1H), 4.74 (s, 2H), 3.91 (s, 3H) |
| 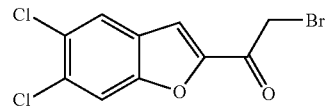 [SMILES: O=C(CBr)c1cc2cc(Cl)c(Cl)cc2o1] | 2.114/A | Calcd. for $C_{10}H_5BrCl_2O_2$: 307.88; found: 308.89 (M + 1)⁺ | ¹H NMR (600 MHz, DMSO-d₆) δ 8.22 (s, 1H), 8.20 (s, 1H), 8.02 (s, 1H), 4.81 (s, 2H) |
| 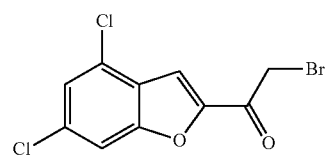 [SMILES: O=C(CBr)c1cc2c(Cl)cc(Cl)cc2o1] | 2.188/A | Calcd. for $C_{10}H_5BrCl_2O_2$: 307.88; found: 308.89 (M + 1)⁺ | ¹H NMR (600 MHz, DMSO-d₆) δ 8.19 (s, 1H), 8.00 (s, 1H), 7.65 (s, 1H), 4.84 (s, 2H) |
| 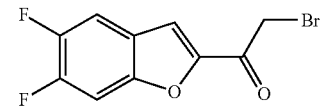 | 1.856/A | Calcd. for $C_{10}H_5BrF_2O_2$: 273.94; found: 274.95 (M + 1)⁺ | ¹H NMR (600 MHz, DMSO-d₆) δ 8.04 (s, 1H), 8.02 (dd, J = 10.5, 3.5 Hz, 1H), 7.96 (dd, J = 10.0, 8.2 Hz, 1H), 4.79 (s, 2H) |
| 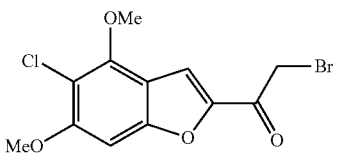 | 2.003/A | Calcd. for $C_{12}H_{10}BrClO_4$: 333.94; found: 334.95 (M + 1)⁺ | ¹H NMR (600 MHz, DMSO-d₆) δ 8.40 (s, 1H), 7.23 (s, 1H), 4.75 (s, 2H), 4.17 (s, 3H), 3.90 (s, 3H) |
| 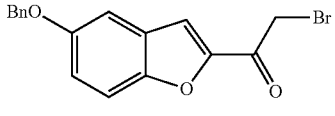 | 2.187/A | Calcd. for $C_{17}H_{13}BrO_3$: 344.00; found: 345.01 (M + 1)⁺ | ¹H NMR (600 MHz, CDCl₃) δ 7.55-7.15 (m, 9H), 5.09 (s, 2H), 4.40 (s, 2H) |
| 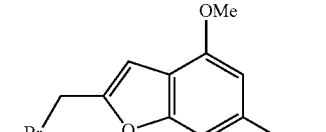 | 1.665/B | | ¹H NMR (600 MHz, CDCl₃) δ 7.66 (s, 1H), 7.23 (s, 1H), 6.62 (s, 1H), 6.30 (s, 1H), 4.33 (s, 2H), 3.89 (s, 3H), 3.85 (s, 3H) |
| 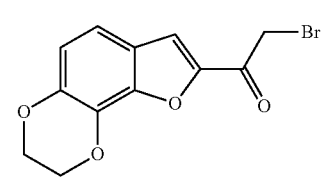 [SMILES: O=C(CBr)c1cc2ccc3c(c2o1)OCCO3] | 1.836/F | | ¹H NMR (600 MHz, CDCl₃) δ 7.57 (s, 1H), 7.14 (d, J = 8.6 Hz, 1H), 6.89 (d, J = 8.6 Hz, 1H), 4.43 (s, 2H), 4.39 (br d, 4H) |

-continued

| Structure | HPLC Ret. Time (Min)/ Method | LCMS | ¹H NMR (600 MHz, DMSO-d₆) |
|---|---|---|---|
| (structure with benzofuran, dioxole, CH₂Br ketone) | 1.838/F | Calcd. for C₁₁H₇BrO₄: 281.95; Found: 282.96 | ¹H NMR (600 MHz, CDCl₃) δ 7.60 (s, 1H), 7.22 (d, J = 8.4 Hz, 1H), 6.95 (d, J = 8.3 Hz, 1H), 6.13 (s, 2H), 4.41 (s, 2H) |
| (structure with bromoacetyl benzofuran, OMe, OBn-benzyloxy) | | Calcd for C₂₅H₂₂BrO₅ [M + H]⁺ m/z 481.0645, found 481.0635 | ¹H NMR (CDCl₃, 600 MHz) δ 3.83 (s, 3H), 4.33 (s, 2H), 5.07 (s, 2H), 5.11 (s, 2H), 6.36 (d, J = 1.8 Hz, 1H), 6.63 (broad s, 1H), 6.95 (dd, J = 2.16 Hz, and J = 8.2 Hz, 1H), 7.02 (d, J = 7.6 Hz, 1H), 7.05 (broad s, 1H), 7.31 (broad t, 2H), 7.36 (broad, t, 2H), 7.41 (broad d, 2H), 7.69 (s, 1H). |

Examples 227-228 to 306

The following additional Examples have been prepared, isolated and characterized using the methods disclosed above.

| Ex. | Structure | Experimental procedure | Formula | Exact Mass | HPLC Retention Time (Min)/ Method | LCMS M + 1 | NMR |
|---|---|---|---|---|---|---|---|
| 227-228 | (MeS-thiadiazolo-imidazo-benzofuran-OMe-OBn) | Exs. 1 and 207 | C₂₁H₁₇₃O₄S₂ | 423.07 | | 424.09 | ¹H NMR (600 MHz, CDCl₃) δ ppm 7.94 (s, 1H), 7.46 (d, J = 7.8 Hz, 2H), 7.38 (t, J = 7.8 Hz, 2H), 7.32 (t, J = 7.8 Hz, 1H), 7.12 (s, 1H), 6.68 (s, 1H), 6.39 (s, 1H), 5.17 (s, 2H), 3.82 (s, 3H), 2.75 (s, 3H) |
| 229 | (MeS-thiadiazolo-imidazo-benzofuran-diOMe) | Ex. 1 | C₁₅H₁₃N₃O₃S₂ | 347.04 | 1.876/B | 348.07 | ¹H NMR (600 MHz, CDCl₃) δ ppm 7.96 (s, 1H), 7.06 (s, 1H), 6.68 (s, 1H), 6.33 (s, 1H), 3.92 (s, 3H), 3.85 (s, 3H), 2.76 (s, 3H) |
| 230 | (MeS-thiadiazolo-imidazo-benzofuran-OBn) | Ex. 1 | C₂₀H₁₅N₃O₂S₂ | 393.06 | 2.496/C | 394.07 | ¹H NMR (600 MHz, CDCl₃) δ ppm 8.03 (s, 1H), 7.48-7.47 (m, 2H), 7.41-7.38 (m, 3H), 7.34-7.32 (m, 1H), 7.13 (s, 1H), 6.99 (s, 1H), 6.96-6.95 (m, 1H), 5.11 (s, 2H), 2.77 (s, 3H) |

-continued

| Ex. | Structure | Experimental procedure | Formula | Exact Mass | HPLC Retention Time (Min)/ Method | LCMS M + 1 | NMR |
|---|---|---|---|---|---|---|---|
| 231 | 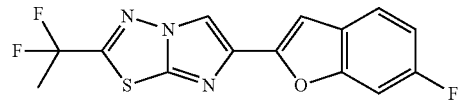 [SMILES: CC(F)(F)c1nn2cc(-c3cc4ccc(F)cc4o3)nc2s1] | Ex. 207 | $C_{14}H_8F_3N_3OS$ | 323.03 | 2.144/ A | 324.06 | $^1$H NMR (600 MHz, DMSO-d$_6$) δ 8.80 (s, 1H), 7.67 (dd, J = 8.2, 5.3 Hz, 1H), 7.56 (dd, J =9.4, 1.8 Hz, 1H), 7.21 (s, 1H), 7.15 (dt, J = 9.4, 1.8 Hz, 1H), 2.21 (t, J = 19.3 Hz, 3H) |
| 232 | 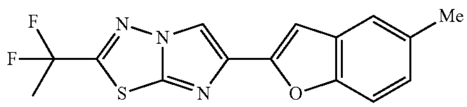 [SMILES: Cc1ccc2oc(-c3cn4nc(C(C)(F)F)sc4n3)cc2c1] | Ex. 207 | $C_{15}H_{11}F_2N_3OS$: | 319.06 | 2.233/ A | 320.09 | $^1$H NMR (600 MHz, DMSO-d$_6$) δ 8.79 (s, 1H), 7.46 (d, J = 8.2 Hz, 1H), 7.43 (s, 1H), 7.11 (m, 2H), 2.37 (s, 3H), 2.21 (t, J = 19.3 Hz, 3H) |
| 233 | 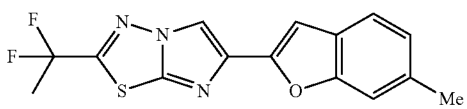 [SMILES: Cc1ccc2cc(-c3cn4nc(C(C)(F)F)sc4n3)oc2c1] | Ex. 207 | $C_{15}H_{11}F_2N_3OS$ | 319.06 | 2.229/ A | 320.09 | $^1$H NMR (600 MHz, DMSO-d$_6$) δ 8.78 (s, 1H), 7.52 (d, J = 7.6 Hz, 1H), 7.40 (s, 1H), 7.14 (s, 1H), 7.08 (d, J = 7.6 Hz, 1H), 2.47 (s, 3H), 2.21 (t, J = 19.3 Hz, 3H) |
| 234 | 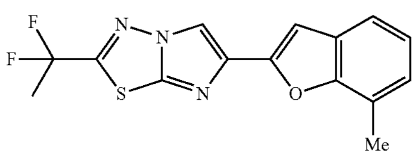 [SMILES: Cc1cccc2cc(-c3cn4nc(C(C)(F)F)sc4n3)oc12] | Ex. 207 | $C_{15}H_{11}F_2N_3OS$ | 319.06 | 2.219/ A | 320.09 | $^1$H NMR (600 MHz, DMSO-d$_6$) δ 8.82 (s, 1H), 7.46 (d, J = 6.4 Hz, 1H), 7.18 (s, 1H), 7.14 (t, J = 7.0 Hz, 1H), 7.11 (d, J = 7.0 Hz, 1H), 2.50 (s, 3H), 2.22 (t, J = 19.3 Hz, 3H) |
| 235 | 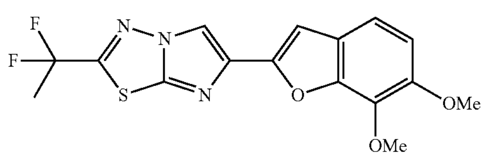 [SMILES: COc1ccc2cc(-c3cn4nc(C(C)(F)F)sc4n3)oc2c1OC] | Ex. 207 | $C_{16}H_{13}F_2N_3O_3S$ | 365.06 | 2.041/ A | 366.09 | $^1$H NMR (600 MHz, DMSO-d$_6$) δ 8.81 (s, 1H), 7.26 (d, J = 8.2 Hz, 1H), 7.12 (s, 1H), 7.02 (d, J = 8.8 Hz, 1H), 4.01 (s, 3H), 3.82 (s, 3H), 2.21 (t, J = 19.3 Hz, 3H) |
| 236 | 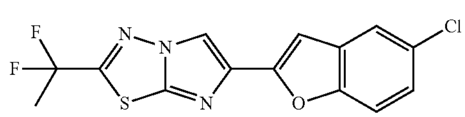 [SMILES: CC(F)(F)c1nn2cc(-c3cc4cc(Cl)ccc4o3)nc2s1] | Ex. 207 | $C_{14}H_8ClF_2N_3OS$ | 339.00 | 2.266/ A | 340.03 | $^1$H NMR (600 MHz, DMSO-d$_6$) δ 8.86 (s, 1H), 7.73 (d, J = 1.8 Hz, 1H), 7.63 (d, J = 8.8 Hz, 1H), 7.32 (dd, J = 8.8, 2.3 Hz, 1H), 7.19 (s, 1H), 2.22 (t, J = 19.3 Hz, 3H) |
| 237 | 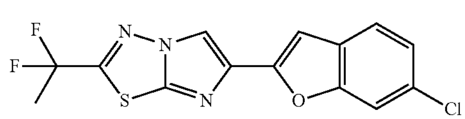 [SMILES: CC(F)(F)c1nn2cc(-c3cc4ccc(Cl)cc4o3)nc2s1] | Ex. 207 | $C_{14}H_8ClF_2N_3OS$ | 339.00 | 2.271/ A | 340.03 | $^1$H NMR (600 MHz, DMSO-d$_6$) δ 8.83 (s, 1H), 7.77 (s, 1H), 7.67 (d, J = 8.2 Hz, 1H), 7.31 (dd, J = 8.2, 1.8 Hz, 1H), 7.23 (s, 1H), 2.21 (t, J = 19.3 Hz, 3H) |

-continued

| Ex. | Structure | Experimental procedure | Formula | Exact Mass | HPLC Retention Time (Min)/ Method | LCMS M + 1 | NMR |
|---|---|---|---|---|---|---|---|
| 238 | 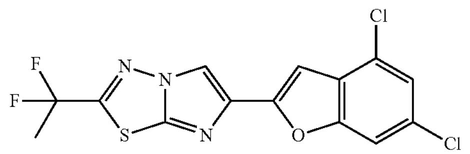 [SMILES: CC(F)(F)c1nn2cc(-c3cc4c(Cl)cc(Cl)cc4o3)nc2s1] | Ex. 207 | C$_{14}$H$_7$Cl$_2$F$_2$N$_3$OS | 372.97 | 2.468/ A | 373.98 | $^1$H NMR (600 MHz, DMSO-d$_6$) δ 8.92 (s, 1H), 7.84 (s, 1H), 7.52 (s, 1H), 7.21 (s, 1H), 2.22 (t, J = 19.3 Hz, 3H) |
| 239 | 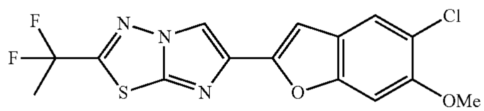 | Ex. 207 | C$_{15}$H$_{10}$ClF$_2$N$_3$O$_2$S | 369.02 | 2.193/ A | 370.04 | $^1$H NMR (600 MHz, DMSO-d$_6$) δ 8.74 (s, 1H), 7.72 (s, 1H), 7.45 (s,1H), 7.10 (s, 1H), 3.89 (s, 3H), 2.21 (t, J = 19.3 Hz, 3H) |
| 240 | 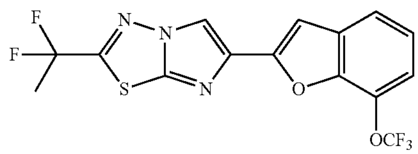 | Ex. 207 | C$_{15}$H$_8$F$_5$N$_3$O$_2$S | 389.03 | 2.270/ A | 390.05 | $^1$H NMR (600 MHz, DMSO-d$_6$) δ 8.90 (s, 1H), 7.70 (d, J = 7.6 Hz, 1H), 7.37-7.32 (m, 3H), 2.22 (t, J = 19.3 Hz, 3H) |
| 241 | 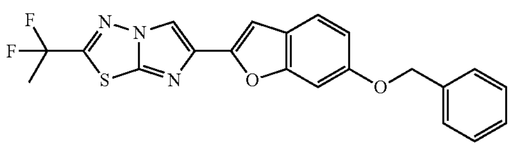 [SMILES: CC(F)(F)c1nn2cc(-c3cc4ccc(OCc5ccccc5)cc4o3)nc2s1] | Ex. 207 | C$_{21}$H$_{15}$F$_2$N$_3$O$_2$S | 411.09 | 2.440/ A | 412.12 | $^1$H NMR (600 MHz, DMSO-d$_6$) δ 8.72 (s, 1H), 7.52 (d, J = 8.2 Hz, 1H), 7.46 (d, J = 7.6 Hz, 2H), 7.38 (dd, J = 7.6, 7.0 Hz, 2H), 7.31 (t, J = 7.0 Hz, 1H), 7.27 (br s, 1H), 7.11 (s, 1H), 6.96 (dd, J = 8.8, 1.8 Hz, 1H), 5.16 (s, 2H), 2.21 (t, J = 19.3 Hz, 3H) |
| 242 | 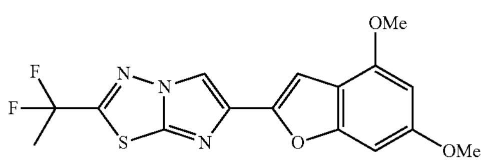 [SMILES: COc1cc(OC)c2cc(-c3cn4nc(C(C)(F)F)sc4n3)oc2c1] | Ex. 207 | C$_{16}$H$_{13}$F$_2$N$_3$O$_3$S | 365.07 | 2.278/ A | 366.09 | $^1$H NMR (600 MHz, DMSO-d$_6$) δ 8.68 (s, 1H), 7.02 (s, 1H), 6.81 (s, 1H), 6.43 (s, 1H), 3.86 (s, 3H), 3.79 (s, 3H), 2.21 (t, J = 19.3 Hz, 3H) |
| 243 | 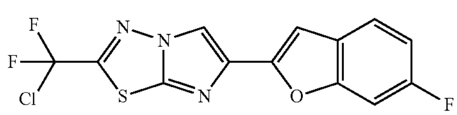 | Ex. 209 | C$_{13}$H$_5$ClF$_3$N$_3$OS | 342.98 | 2.361/ A | 343.99 | $^1$H NMR (600 MHz, DMSO-d$_6$) δ 8.87 (s, 1H), 7.67 (dd, J = 8.8, 5.9 Hz, 1H), 7.57 (dd, J = 8.8, 1.8 Hz, 1H), 7.24 (s, 1H), 7.15 (dt, J = 8.8, 1.8 Hz, 1H) |
| 244 | 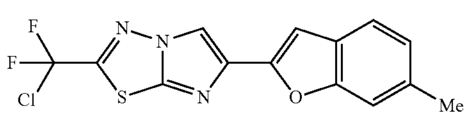 [SMILES: Cc1ccc2cc(-c3cn4nc(C(F)(F)Cl)sc4n3)oc2c1] | Ex. 209 | C$_{15}$H$_{11}$F$_2$N$_3$OS | 339.00 | 2.439/ A | 340.03 | $^1$H NMR (600 MHz, DMSO-d$_6$) δ 8.85 (s, 1H), 7.52 (d, J = 7.6 Hz, 1H), 7.40 (s, 1H), 7.16 (s, 1H), 7.08 (d, J = 7.6 Hz, 1H), 2.41 (s, 3H) |

-continued

| Ex. | Structure | Experimental procedure | Formula | Exact Mass | HPLC Retention Time (Min)/ Method | LCMS M + 1 | NMR |
|---|---|---|---|---|---|---|---|
| 245 | 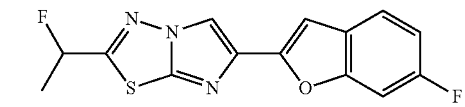 [SMILES: CC(F)c1nn2cc(-c3cc4ccc(F)cc4o3)nc2s1] | Ex. 212 | $C_{14}H_9F_2N_3OS$ | 305.04 | 2.199/ A | 306.08 | $^1$H NMR (600 MHz, DMSO-$d_6$) δ 8.70 (s, 1H), 7.65 (dd, J = 8.2, 5.3 Hz, 1H), 7.55 (dd, J = 9.4, 1.8 Hz, 1H), 7.17 (s, 1H), 7.14 (dt, J = 9.4, 2.3 Hz, 1H), 6.15 (dq, J = 46.9, 6.4 Hz, 1H), 1.77 (dd, J = 24.6, 6.4 Hz, 3H) |
| 246 | 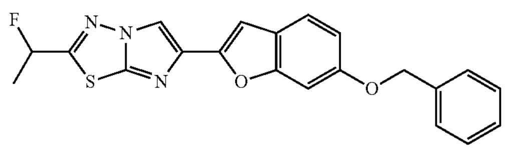 [SMILES: CC(F)c1nn2cc(-c3cc4ccc(OCc5ccccc5)cc4o3)nc2s1] | Ex. 212 | $C_{21}H_{16}FN_3O_2S$ | 393.09 | 2.386/ A | 394.13 | $^1$H NMR (600 MHz, DMSO-$d_6$) δ 8.61 (s, 1H), 7.51 (d, J = 8.2 Hz, 1H), 7.46 (d, J = 7.0 Hz, 1H), 7.38 (t, J = 7.6 Hz, 1H), 7.31 (t, J = 7.0 Hz, 1H), 7.26 (d, J = 1.8 Hz, 1H), 7.07 (s, 1H), 6.95 (dd, J = 8.8, 2.3 Hz, 1H), 6.14 (dq, J = 46.9, 6.4 Hz, 1H), 5.15 (s, 2H), 1.76 (dd, J = 24.6, 6.4 Hz, 3H) |
| 247 | 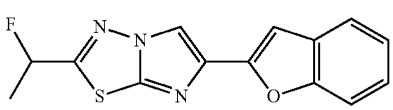 [SMILES: CC(F)c1nn2cc(-c3cc4ccccc4o3)nc2s1] | Ex. 212 | $C_{14}H_{10}FN_3OS$ | 287.05 | 2.176/ A | 288.14 | $^1$H NMR (600 MHz, DMSO-$d_6$) δ 8.71 (s, 1H), 7.63 (d, J = 7.6 Hz, 1H), 7.57 (d, J = 7.6 Hz, 1H), 7.29 (t, J = 7.6 Hz, 1H), 7.24 (t, J = 7.6 Hz, 1H), 7.16 (s, 1H), 6.15 (dq, J = 46.9, 6.4 Hz, 1H), 1.77 (dd, J = 24.6, 6.4 Hz, 3H) |
| 248 | 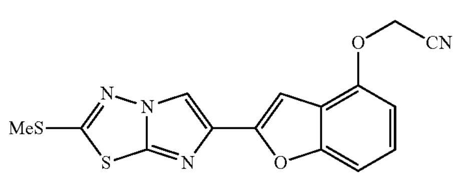 [SMILES: CSc1nn2cc(-c3cc4c(OCC#N)cccc4o3)nc2s1] | Ex. 216 | $C_{15}H_{11}N_4O_2S_2$ | 342.02 | 2.151/ C | 343.03 | $^1$H NMR (600 MHz, CDCl$_3$) δ ppm 8.05 (s, 1H), 7.28-7.23 (m, 2H), 7.13 (s, 1H), 6.78 (d, J = 7.2 Hz, 1H), 4.93 (s, 2H), 2.78 (s, 3H) |
| 249 | 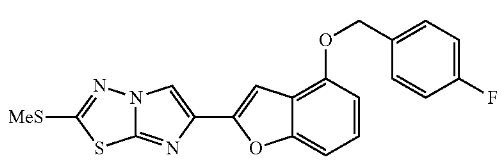 [SMILES: CSc1nn2cc(-c3cc4c(OCc5ccc(F)cc5)cccc4o3)nc2s1] | Ex. 216 | $C_{20}H_{14}N_3O_2S_2F$ | 411.05 | 2.473/ C | 412.06 | $^1$H NMR (600 MHz, CDCl$_3$) δ ppm 8.03 (s, 1H), 7.47-7.45 (m, 2H), 7.21-7.15 (m, 3H), 7.09 (dd, $J_1$ = 7.8 Hz, $J_2$ = 8.4 Hz, 2H), 6.71 (d, J = 7.2 Hz, 1H), 5.19 (s, 2H), 2.77 (s, 3H) |

-continued

| Ex. | Structure | Experimental procedure | Formula | Exact Mass | HPLC Retention Time (Min)/ Method | LCMS M + 1 | NMR |
|---|---|---|---|---|---|---|---|
| 250 | 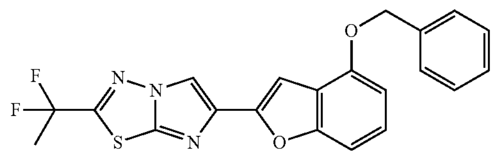 [SMILES: CC(F)(F)c1nn2cc(-c3cc4c(OCc5ccccc5)cccc4o3)nc2s1] | Ex. 207 | $C_{21}H_{15}F_2N_3O_2S$ | 411.09 | 2.422/ A | 412.11 | $^1$H NMR (600 MHz, DMSO-$d_6$) δ 8.80 (s, 1H), 7.50 (d, J = 7.0 Hz, 2H), 7.39 (t, J = 7.6 Hz, 2H), 7.32 (t, J = 7.6 Hz, 1H), 7.24-7.18 (m, 3H), 6.89 (d, J = 7.6 Hz, 1H), 5.26 (s, 2H), 2.20 (t, J = 19.3 Hz, 3H) |
| 251 | 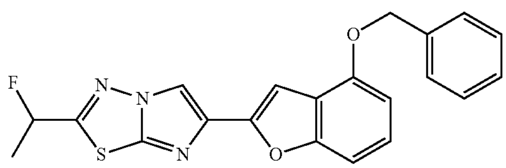 [SMILES: CC(F)c1nn2cc(-c3cc4c(OCc5ccccc5)cccc4o3)nc2s1] | Ex. 212 | $C_{21}H_{16}FN_3O_2S$ | 393.09 | 2.362/ A | 394.12 | $^1$H NMR (600 MHz, DMSO-$d_6$) δ 8.71 (s, 1H), 7.49 (d, J = 7.6 Hz, 1H), 7.39 (t, J = 7.6 Hz, 1H), 7.31 (t, J = 7.6 Hz, 1H), 7.21 (q, J = 7.6 Hz, 1H), 7.18 (d, J = 8.2 Hz, 1H), 7.15 (s, 1H), 6.88 (d, J = 7.6 Hz, 1H), 6.14 (dq, J = 46.9, 6.4 Hz, 1H), 5.26 (s, 2H), 1.76 (dd, J = 24.6, 6.4 Hz, 3H) |
| 252 | 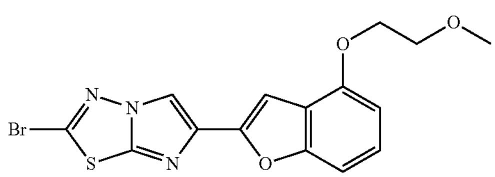 [SMILES: COCCOc1cccc2oc(-c3cn4nc(Br)sc4n3)cc12] | Ex. 203E | $C_{15}H_{13}N_3O_3SBr$ | 392.98 | 2.212/ F | 393.99 | $^1$H NMR (600 MHz, CDCl$_3$) δ ppm 8.11 (s, 1H), 7.2 (s, 1H), 7.20 (dd, J$_1$ = 7.8 Hz, J$_2$ = 8.4 Hz, 1H), 7.14 (d, J = 8.4 Hz, 1H), 6.68 (d, J = 7.8 Hz, 1H), 4.28 (t, J = 4.8 Hz, 2H), 3.84 (t, J = 4.8 Hz, 2H), 3.50 (s, 3H) |
| 253 | 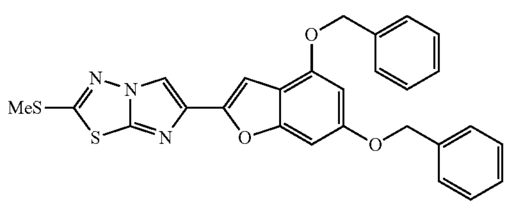 [SMILES: CSc1nn2cc(-c3cc4c(OCc5ccccc5)cc(OCc5ccccc5)cc4o3)nc2s1] | Ex. 1 | $C_{27}H_{21}N_3O_3S_2$ | 499.10 | 2.596/ A | 500.11 | $^1$H NMR (600 MHz, CDCl$_3$) δ ppm 7.95 (s, 1H), 7.47-7.45 (m, 4H), 7.41-7.38 (m, 4H), 7.35-7.32 (m, 2H), 7.13 (s, 1H), 6.76 (s, 1H), 6.49 (s, 1H), 5.17 (s, 2H), 5.09 (s, 2H), 2.76 (s, 3H) |
| 254 | 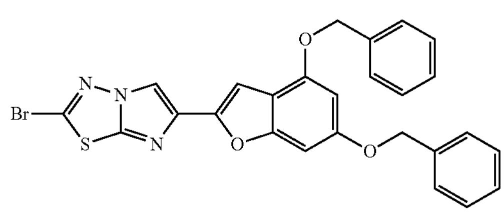 [SMILES: Brc1nn2cc(-c3cc4c(OCc5ccccc5)cc(OCc5ccccc5)cc4o3)nc2s1] | Ex. 203E | $C_{26}H_{19}N_3O_3SBr$ | 531.02 | 2.631/ C | 532.04 | $^1$H NMR (600 MHz, CDCl$_3$) δ ppm 8.04 (s, 1H), 7.48-7.45 (m, 4H), 7.41-7.39 (m, 4H), 7.35-7.33 (m, 2H), 7.17 (s, 1H), 6.75 (s, 1H), 6.50 (s, 1H), 5.17 (s, 2H), 5.09 (s, 2H) |

| Ex. | Structure | Experimental procedure | Formula | Exact Mass | HPLC Retention Time (Min)/ Method | LCMS M + 1 | NMR |
|---|---|---|---|---|---|---|---|
| 255 | 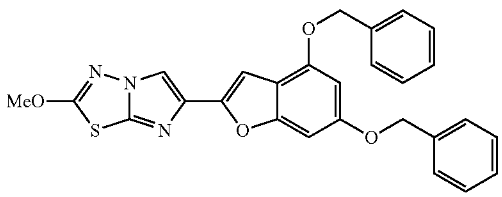 | Ex. 203 | C$_{27}$H$_{21}$N$_3$O$_4$S | 483.12 | 2.576/ C | 484.13 | $^1$H NMR (600 MHz, CDCl$_3$) δ ppm 7.83 (s, 1H), 7.48-7.45 (m, 4H), 7.41-7.38 (m, 4H), 7.35-7.32 (m, 2H), 7.09 (s, 1H), 6.76 (s, 1H), 6.50 (s, 1H), 5.18 (s, 2H), 5.09 (s, 2H), 4.20 (s, 3H) |
| 256 | 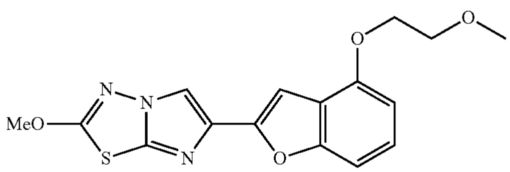 | Ex. 203 | C$_{16}$H$_{15}$N$_3$O$_4$S | 345.08 | 1.762/ F | 346.11 | $^1$H NMR (600 MHz, CDCl$_3$) δ ppm 7.90 (s, 1H), 7.18-7.13 (m, 3H), 6.67 (d, J = 7.8 Hz, 1H), 4.28 (t, J = 4.8 Hz, 2H), 4.21 (s, 3H), 3.83 (t, J = 4.8 Hz, 2H), 3.50 (s, 3H) |
| 257 | 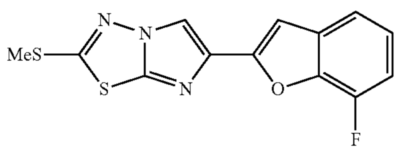 [SMILES: CSc1nn2cc(-c3cc4cccc(F)c4o3)nc2s1] | Ex. 1 | C$_{13}$H$_8$N$_3$OS$_2$F | 305.01 | 2.349/ C | 306.04 | $^1$H NMR (600 MHz, CDCl$_3$) δ ppm 8.12 (s, 1H), 7.34 (d, J = 7.2 Hz, 1H), 7.16-7.13 (m, 1H), 7.01 (d, J = 2.4 Hz, 1H), 7.03-7.00 (m, 1H), 2.78 (s, 3H) |
| 258 | 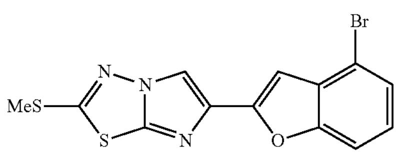 [SMILES: CSc1nn2cc(-c3cc4c(Br)cccc4o3)nc2s1] | Ex. 1 | C$_{13}$H$_8$N$_3$OS$_2$Br | 364.93 | | 365.96 | $^1$H NMR (600 MHz, CDCl$_3$) δ ppm 8.07 (s, 1H), 7.44 (d, J = 7.8 Hz, 1H), 7.38 (d, J = 7.8 Hz, 1H), 7.12 (dd, J$_1$ = 7.8 Hz, J$_2$ = 8.4 Hz, 1H), 7.11 (s, 1H), 2.78 (s, 3H) |
| 259 | 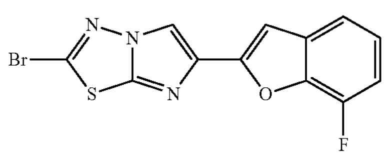 [SMILES: Fc1cccc2cc(-c3cn4nc(Br)sc4n3)oc12] | Ex. 203E | C$_{12}$H$_5$N$_3$OSFBr | 336.93 | 2.236/ A | 337.94 | $^1$H NMR (600 MHz, CDCl$_3$) δ ppm 8.21 (s, 1H), 7.36 (d, J = 7.8 Hz, 1H), 7.19-7.14 (m, 1H), 7.14 (d, J = 2.9 Hz, 1H), 7.04-7.02 (m, 1H) |
| 260 | 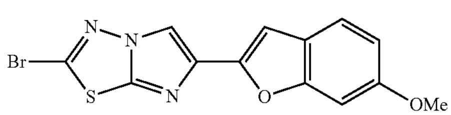 [SMILES: COc1ccc2cc(-c3cn4nc(Br)sc4n3)oc2c1] | Ex. 203E | C$_{13}$H$_8$BrN$_3$O$_2$S | 349.98 | 2.192/ A | 348.95 | $^1$H NMR (600 MHz, DMSO-d$_6$) δ 8.59 (s, 1H), 7.49 (d, J = 8.8 1H), 7.17 (d, J = 1.2 1H), 7.05 (s, 1H), 6.86 (dt, J = 8.2, 2.3 1H) |
| 261 | 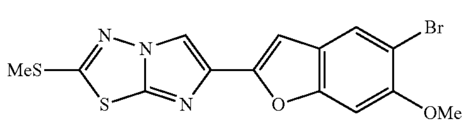 [SMILES: COc1cc2oc(-c3cn4nc(SC)sc4n3)cc2cc1Br] | Ex. 1 | C$_{14}$H$_{10}$ClN$_3$O$_2$S$_2$ | 394.94 | 2.322/ A | 395.97 | $^1$H NMR (600 MHz, DMSO-d$_6$) δ 8.54 (s, 1H), 7.86 (s, 1H), 7.43 (s, 1H), 7.03 (s, 1H), 3.90 (s, 3H), 2.80 (s, 3H) |

-continued

| Ex. | Structure | Experimental procedure | Formula | Exact Mass | HPLC Retention Time (Min)/Method | LCMS M + 1 | NMR |
|---|---|---|---|---|---|---|---|
| 262 | MeS-[imidazothiadiazole]-[benzofuran]-F | Ex. 1 | $C_{13}H_8FN_3OS_2$ | 305.01 | 2.275/A | 306.04 | $^1$H NMR (600 MHz, DMSO-d$_6$) δ 8.68 (s, 1H), 7.49 (d, J = 8.2 Hz, 1H), 7.33 (dt, J = 8.2, 5.3 Hz, 1H), 7.19 (s, 1H), 7.12 (dd, J = 9.4, 8.2 Hz, 1H), 3.92 (s, 3H) |
| 263 | MeO-[imidazothiadiazole]-[benzofuran]-F | Ex. 203 | $C_{13}H_8N_3O_2SF$ | 289.03 | 2.260/C | 290.06 | $^1$H NMR (600 MHz, CDCl$_3$) δ ppm 8.00 (s, 1H), 7.33 (dd, J$_1$ = 0.8 Hz, J$_2$ = 7.8 Hz, 1H), 7.16-7.12 (m, 1H), 7.06 (d, J = 3.0 Hz, 1H), 7.02-6.98 (m, 1H), 4.22 (s, 3H) |
| 264 | Br-[imidazothiadiazole]-[benzofuran]-F | Ex. 203E | $C_{12}H_5BrFN_3OS$ | 338.93 | 2.248/A | 339.96 | $^1$H NMR (600 MHz, DMSO-d$_6$) δ 8.67 (s, 1H), 7.63 (dd, J = 8.8, 5.9 1H), 7.52 (br d, J = 9.4 1H), 7.15 (s, 1H), 7.12 (dt, J = 9.4, 2.3 1H) |
| 265 | CF$_2$-[imidazothiadiazole]-[benzofuran]-OBn, OMe | Ex. 207 | $C_{22}H_{71}F_2N_3O_3S$ | 441.10 | 2.450/A | 442.13 | $^1$H NMR (600 MHz, DMSO-d$_6$) δ 8.68 (s, 1H), 7.48 (d, J = 7.0 Hz, 2H), 7.39 (t, J = 7.6 Hz, 2H), 7.31 (t, J = 7.6 Hz, 1H), 7.08 (s, 1H), 6.81 (s, 1H), 6.51 (s, 1H), 5.23 (s, 2H), 3.77 (s, 3H), 2.20 (t, J = 19.3 Hz, 3H) |
| 266 | MeO-[imidazothiadiazole]-[benzofuran]-OCH$_2$-C$_6$H$_4$-F | Ex. 216 from SM Ex. 211 | $C_{20}H_{15}N_3O_3SF$ | 395.07 | 2.382/F | 396.10 | $^1$H NMR (600 MHz, CDCl$_3$) δ ppm 7.90 (s, 1H), 7.47-7.45 (m, 2H), 7.19-7.16 (m, 3H), 7.10-7.07 (m, 2H), 6.72 (dd, J$_1$ = 1.2 Hz, J$_2$ = 7.2 Hz, 1H), 5.19 (s, 2H), 4.21 (s, 3H) |
| 267 | Br-[imidazothiadiazole]-[benzofuran]-OEt, OMe | Ex. 203E | $C_{15}H_{12}N_3O_3SBr$ | 392.98 | 2.335/F | 394.00 | $^1$H NMR (600 MHz, CDCl$_3$) δ ppm 8.04 (s, 1H), 7.12 (s, 1H), 6.66 (s, 1H), 6.32 (s, 1H), 4.14 (q, J = 6.6 Hz, 2H), 3.84 (s, 3H), 1.47 (t, J = 6.6 Hz, 3H) |
| 268 | MeS-[imidazothiadiazole]-[benzofuran]-OCH$_2$CH$_2$OMe | Ex. 1 | $C_{16}H_{15}N_3O_3S_2$ | 361.06 | | 362.09 | $^1$H NMR (600 MHz, CDCl$_3$) δ ppm 8.02 (s, 1H), 7.30-7.24 (m, 1H), 7.19-7.13 (m, 2H), 6.67 (d, J = 7.8 Hz, 1H), 4.28-4.24 (m, 2H), 3.85-3.82 (m, 2H), 3.50 (s, 3H), 2.77 (s, 3H) |

| Ex. | Structure | Experimental procedure | Formula | Exact Mass | HPLC Retention Time (Min)/ Method | LCMS M + 1 | NMR |
|---|---|---|---|---|---|---|---|
| 269 | 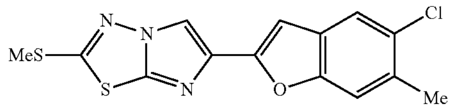 [SMILES: CSc1nn2cc(-c3cc4cc(Cl)c(C)cc4o3)nc2s1] | Ex. 1 | C$_{14}$H$_{10}$ClN$_3$OS$_2$ | 336.02 | 2.471/ A | 335.00 | $^1$H NMR (600 MHz, DMSO-d$_6$) δ ppm 8.58 (s, 1H), 7.67 (s, 1H), 7.57 (s, 1H), 7.03 (s, 1H), 2.76 (s, 3H), 2.39 (s, 3H) |
| 270 | (270-1) (270A) (270B) | Ex. 213 | C$_{15}$H$_{11}$ClFN$_3$O$_2$S | 351.02 | 2.243/ A | 352.05 | $^1$H NMR (600 MHz, DMSO-d$_6$) δ 8.63 (s, 1H), 7.69 (s, 1H), 7.43 (s, 1H), 7.05 (s, 1H), 6.14 (dq, J = 46.9, 6.4 Hz, 1H), 3.88 (s, 3H), 1.76 (dd, J = 24.6, 6.4 Hz, 3H) |
| 271 | 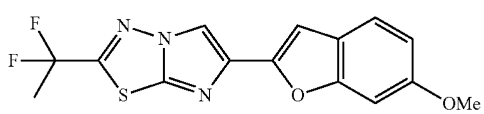 [SMILES: COc1ccc2cc(-c3cn4nc(C(C)(F)F)sc4n3)oc2c1] | Ex. 207 | C$_{15}$H$_{11}$F$_2$N$_3$O$_2$S | 335.05 | 2.258/ A | 336.08 | $^1$H NMR (600 MHz, DMSO-d$_6$) δ 8.73 (s, 1H), 7.54 (d, J = 8.8 Hz, 1H), 7.22 (br s, 1H), 7.14 (s, 1H), 6.90 (dd, J = 8.8, 2.3 Hz, 1H), 3.82 (s, 3H), 2.24 (t, J = 19.3 Hz, 3H) |
| 272 | 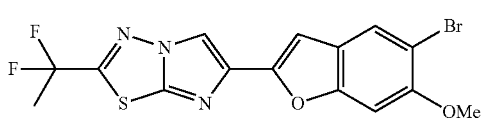 [SMILES: COc1cc2oc(-c3cn4nc(C(C)(F)F)sc4n3)cc2cc1Br] | Ex. 207 | C$_{15}$H$_{10}$BrF$_2$N$_3$O$_2$S | 414.96 | 2.344/ A | 415.99 | $^1$H NMR (600 MHz, DMSO-d$_6$) δ 8.77 (s, 1H), 7.90 (s, 1H), 7.45 (s, 1H), 7.13 (s, 1H), 3.91 (s, 3H), 2.24 (t, J = 19.3 Hz, 3H) |
| 273 | 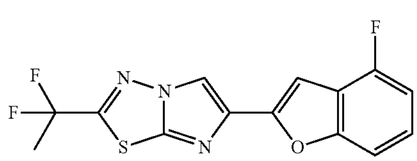 [SMILES: CC(F)(F)c1nn2cc(-c3cc4c(F)cccc4o3)nc2s1] | Ex. 207 | C$_{14}$H$_8$F$_3$N$_3$OS | 323.03 | 2.288/ A | 324.07 | $^1$H NMR (600 MHz, DMSO-d$_6$) δ 8.91 (s, 1H), 7.52 (d, J = 8.8 Hz, 1H), 7.36 (dt, J = 8.2, 5.9 Hz, 1H), 7.29 (s, 1H), 7.14 (t, J = 8.8 Hz, 1H), 2.24 (t, J = 19.3 Hz, 3H) |
| 274 | 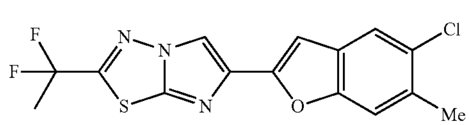 [SMILES: Cc1cc2oc(-c3cn4nc(C(C)(F)F)sc4n3)cc2cc1Cl] | Ex. 207 | C$_{15}$H$_{10}$ClF$_2$N$_3$OS | 353.02 | 2.462/ A | 354.05 | $^1$H NMR (600 MHz, DMSO-d$_6$) δ 8.86 (s, 1H), 7.74 (s, 1H), 7.65 (s, 1H), 7.17 (s, 1H), 2.44 (s, 3H), 2.24 (t, J = 19.3 Hz, 3H) |

| Ex. | Structure | Experimental procedure | Formula | Exact Mass | HPLC Retention Time (Min)/ Method | LCMS M + 1 | NMR |
|---|---|---|---|---|---|---|---|
| 275 | 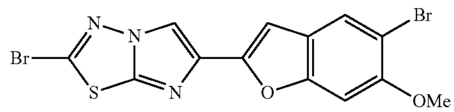 [SMILES: COc1cc2oc(-c3cn4nc(Br)sc4n3)cc2cc1Br] | Ex. 203E | $C_{13}H_7Br_2N_3O_2S$: | | 2.309/ A | | $^1$H NMR (600 MHz, DMSO-d$_6$) δ 8.67 (s, 1H), 7.88 (s, 1H), 7.44 (s, 1H), 7.08 (s, 1H), 3.91 (s, 3H) |
| 276 | 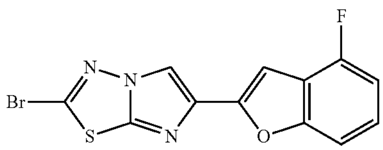 [SMILES: Fc1cccc2oc(-c3cn4nc(Br)sc4n3)cc12] | Ex. 203E | $C_{12}H_5BrFN_3OS$ | 338.93 | 2.257/ A | 339.96 | $^1$H NMR (600 MHz, DMSO-d$_6$) δ 8.81 (s, 1H), 7.50 (d, J = 8.2 Hz, 1H), 7.34 (dt, J = 8.2, 5.9 Hz, 1H), 7.23 (s, 1H), 7.13 (dd, J = 9.4, 8.8 Hz, 1H) |
| 277 | 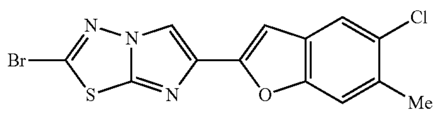 [SMILES: Cc1cc2oc(-c3cn4nc(Br)sc4n3)cc2cc1Cl] | Ex. 203E | $C_{13}H_7BrClN_3OS$ | 368.92 | 2.442/ A | 369.94 | $^1$H NMR (600 MHz, DMSO-d$_6$) δ 8.75 (s, 1H), 7.72 (s, 1H), 7.63 (s, 1H), 7.11 (s, 1H), 2.43 (s, 3H) |
| 278 | 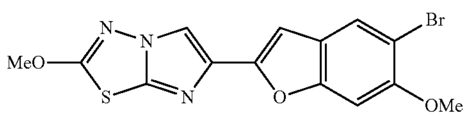 | Ex. 203 | $C_{14}H_{10}BrN_3O_3S$ | 380.96 | 2.239/ A | 381.98 | $^1$H NMR (600 MHz, DMSO-d$_6$) δ 8.43 (s, 1H), 7.85 (s, 1H), 7.42 (s, 1H), 6.98 (s, 1H), 4.21 (s, 3H), 3.90 (s, 3H) |
| 279 | 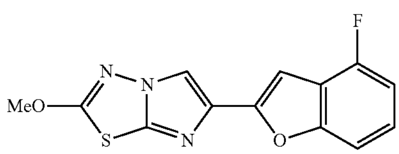 [SMILES: COc1nn2cc(-c3cc4c(F)cccc4o3)nc2s1] | Ex. 203 | $C_{13}H_8FN_3O_2S$ | 289.03 | 2.186/ A | 290.06 | $^1$H NMR (600 MHz, DMSO-d$_6$) δ 8.57 (s, 1H), 7.48 (d, J = 8.2 Hz, 1H), 7.31 (dt, J = 8.2, 5.3 Hz, 1H), 7.14 (s, 1H), 7.11 (dd, J = 9.4, 8.2 Hz, 1H), 4.21 (s, 3H) |
| 280 | 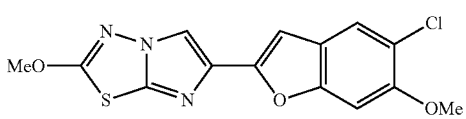 | Ex. 203 | $C_{14}H_{10}ClN_3O_2S$ | 319.02 | 2.368/ A | 320.04 | $^1$H NMR (600 MHz, DMSO-d$_6$) δ 8.52 (s, 1H), 7.69 (s, 1H), 7.60 (s, 1H), 7.02 (s, 1H), 4.21 (s, 3H), 2.42 (s, 3H) |
| 281 | 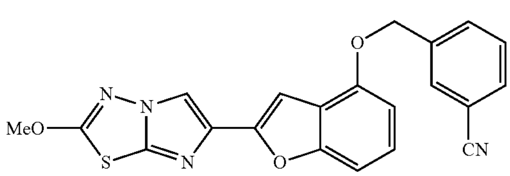 [SMILES: COc1nn2cc(-c3cc4c(OCc5cccc(C#N)c5)cccc4o3)nc2s1] | Ex. 216 from SM Ex. 211 | $C_{21}H_{14}N_4O_3S$ | 402.08 | 2.275/ F | 403.11 | $^1$H NMR (600 MHz, CDCl$_3$) δ ppm 7.92 (s, 1H), 7.79 (s, 1H), 7.74 (d, J = 7.8 Hz, 1H), 7.63 (d, J = 7.8 Hz, 1H), 7.52 (dd, J$_1$ = 7.2 Hz, J$_2$ = 7.8 Hz, 1H), 7.18-7.17 (m, 3H), 6.71-6.68 (m, 1H), 5.25 (s, 2H), 4.21 (s, 3H) |
| 282 | 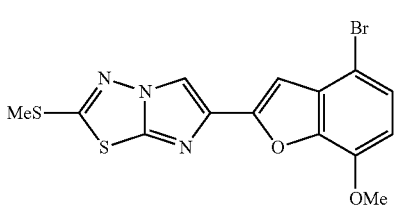 [SMILES: COc1ccc(Br)c2cc(-c3cn4nc(SC)sc4n3)oc12] | Ex. 1 | $C_{14}H_{10}BrN_3O_2S_2$ | 396.94 | 2.434/ C | 397.93 | $^1$H NMR (600 MHz, DMSO-d$_6$) δ 8.70 (s, 1H), 7.39 (d, J = 8.8 Hz, 1H), 7.01 (s, 1H), 6.93 (d, J = 8.8 Hz, 2H), 3.96 (s, 3H), 2.80 (s, 3H) |

| Ex. | Structure | Experimental procedure | Formula | Exact Mass | HPLC Retention Time (Min)/ Method | LCMS M + 1 | NMR |
|---|---|---|---|---|---|---|---|
| 283 | (MeS-thiadiazole-imidazo-benzofuran-OMe, Br) | Ex. 1 | $C_{14}H_{10}BrN_3O_2S_2$ | 396.94 | 2.482/ C | 397.97 | $^1$H NMR (600 MHz, DMSO-d$_6$) δ 8.59 (s, 1H), 7.17 (d, J = 1.8 Hz, 1H), 7.14 (s, 1H), 7.10 (d, J = 1.8 Hz, 2H), 3.77 (s, 3H), 2.77 (s, 3H) |
| 284 | (MeS-thiadiazole-imidazo-benzofuran-Br, OMe) | Ex. 1 | $C_{14}H_{10}BrN_3O_2S_2$ | 396.94 | 2.449/ C | 397.95 | $^1$H NMR (600 MHz, DMSO-d$_6$) δ 8.60 (s, 1H), 7.40 (s, 1H), 7.06 (s, 2H), 3.94 (s, 3H), 2.77 (s, 3H) |
| 285 | (Br-thiadiazole-imidazo-benzofuran-Br, OMe) | Ex. 203E | $C_{13}H_7Br_2N_3O_2S$ | 428.86 | 2.413/ A | 429.87 | $^1$H NMR (600 MHz, DMSO-d$_6$) δ 8.81 (s, 1H), 7.37 (d, J = 8.2 Hz, 2H), 7.01 (s, 1H), 6.91 (d, J = 8.2 Hz, 2H), 3.93 (s, 3H) |
| 286 | (Br-thiadiazole-imidazo-benzofuran-Br, OMe) | Ex. 203E | $C_{13}H_7Br_2N_3O_2S$ | 428.86 | 2.422/ A | 429.87 | $^1$H NMR (600 MHz, DMSO-d$_6$) δ 8.74 (s, 1H), 7.42 (d, J = 1.2 Hz, 2H), 7.10 (s, 1H), 7.07 (d, J = 1.2 Hz, 2H), 3.95 (s, 3H) |
| 287 | (MeS-thiadiazole-imidazo-benzofuran-Cl, Cl) | Ex. 1 | $C_{13}H_7Cl_2N_3OS_2$ | 354.94 | 2.545/ A | 355.96 | $^1$H NMR (600 MHz, DMSO-d$_6$) δ 8.68 (s, 1H), 7.79 (s, 1H), 7.48 (s, 1H), 7.11 (s, 1H), 2.77 (s, 3H) |
| 288 | (Br-thiadiazole-imidazo-benzofuran-Cl, Cl) | Ex. 203E | $C_{12}H_4BrCl_2N_3OS$ | 388.86 | 2.531/ A | 389.87 | $^1$H NMR (600 MHz, DMSO-d$_6$) δ 8.81 (s, 1H), 7.81 (s, 1H), 7.50 (s, 1H), 7.16 (s, 1H) |
| 289 | (MeO-thiadiazole-imidazo-benzofuran-Br, OMe) | Ex. 203 | $C_{14}H_{10}BrN_3O_3S$ | 380.96 | 2.273/ A | 381.99 | $^1$H NMR (600 MHz, DMSO-d$_6$) δ 8.56 (s, 1H), 7.35 (d, J = 8.2 Hz, 1H), 6.92 (s, 1H), 6.88 (d, J = 8.2 Hz, 1H), 4.18 (s, 3H), 3.93 (s, 3H) |
| 290 | (MeS-thiadiazole-imidazo-benzofuran-OMe, Br) | Ex. 203 | $C_{14}H_{10}BrN_3O_3S$ | 380.96 | 2.304/ A | 381.99 | $^1$H NMR (600 MHz, DMSO-d$_6$) δ 8.48 (s, 1H), 7.16 (d, J = 2.3 Hz, 1H), 7.09 (s, 1H), 7.09 (d, J = 2.3 Hz, 1H), 4.18 (s, 3H), 3.77 (s, 3H) |

-continued

| Ex. | Structure | Experimental procedure | Formula | Exact Mass | HPLC Retention Time (Min)/Method | LCMS M + 1 | NMR |
|---|---|---|---|---|---|---|---|
| 291 | 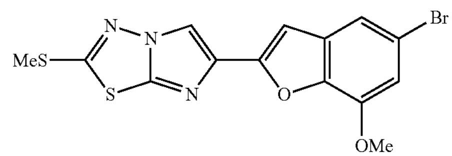 [SMILES: COc1cc(Br)cc2cc(-c3cn4nc(SC)sc4n3)oc12] | Ex. 203 | C₁₄H₁₀BrN₃O₃S | 380.96 | 2.280/A | 381.98 | ¹H NMR (600 MHz, DMSO-d₆) δ 8.50 (s, 1H), 7.39 (d, J = 1.8 Hz, 1H), 7.05 (d, J = 1.8 Hz, 1H), 7.01 (s, 1H), 4.18 (s, 3H), 3.94 (s, 3H) |
| 292 | 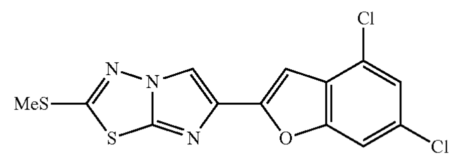 [SMILES: CSc1nn2cc(-c3cc4c(Cl)cc(Cl)cc4o3)nc2s1] | Ex. 203 | C₁₄H₇Cl₂N₃O₂S | 338.96 | 2.452/A | 339.98 | ¹H NMR (600 MHz, DMSO-d₆) δ 8.58 (s, 1H), 7.82 (s, 1H), 7.48 (s, 1H), 7.07 (s, 1H), 4.18 (s, 3H) |
| 293 | 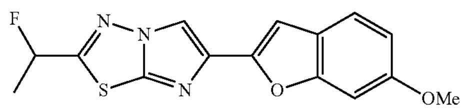 [SMILES: COc1ccc2cc(-c3cn4nc(C(C)F)sc4n3)oc2c1] | Ex. 212 | C₁₅H₁₂FN₃O₂S | 317.06 | 2.159/A | 318.09 | ¹H NMR (600 MHz, DMSO-d₆) δ 8.59 (s, 1H), 7.50 (d, J = 8.8 Hz, 1H), 7.18 (d, J = 1.8 Hz, 1H), 7.06 (s, 1H), 6.14 (dq, J = 46.9, 6.4 Hz, 1H), 3.79 (s, 3H), 1.77 (dd, J = 24.6, 6.4 Hz, 3H) |
| 294 | 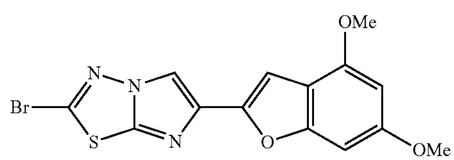 [SMILES: COc1cc(OC)c2cc(-c3cn4nc(Br)sc4n3)oc2c1] | Ex. 203E | C₁₄H₁₀BrN₃O₃S | 378.96 | 2.212/A | 379.97 | ¹H NMR (600 MHz, CDCl₃) δ 8.02 (s, 1H), 7.07 (s, 1H), 6.65 (s, H), 6.31 (d, J = 1.6 Hz, 1H), 3.90 (s, 3H), 3.83 (s, 3H) |
| 295 | 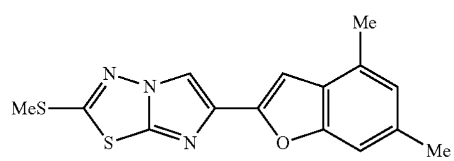 [SMILES: CSc1nn2cc(-c3cc4c(C)cc(C)cc4o3)nc2s1] | Ex. 1 | C₁₅H₁₃N₃OS₂ | 315.05 | 2.419/A | 316.08 | ¹H NMR (600 MHz, CDCl₃) δ 7.99 (s, 1H), 7.11 (s, 1H), 7.03 (s, 1H), 6.84 (s, 1H), 2.75 (s, 3H), 2.46 (s, 3H), 2.41 (s, 3H) |
| 296 | 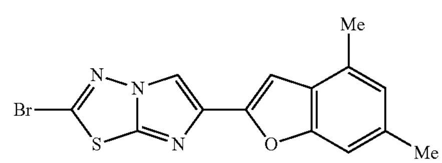 [SMILES: Cc1cc(C)c2cc(-c3cn4nc(Br)sc4n3)oc2c1] | Ex. 203E | C₁₄H₁₀BrN₃OS | 346.97 | 2.410/A | 347.99 | ¹H NMR (600 MHz, CDCl₃) δ 8.08 (s, 1H), 7.11 (s, 1H), 7.06 (s, 1H), 6.85 (s, 1H), 2.44 (s, 3H), 2.42 (s, 3H) |
| 297 | 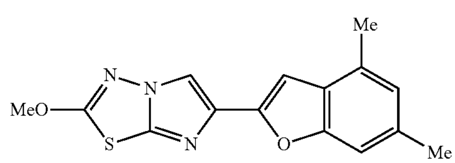 | Ex. 203 | C₁₅H₁₃N₃O₂S | 299.07 | 2.335/A | 300.08 | ¹H NMR (600 MHz, CDCl₃) δ 7.87 (s, 1H), 7.10 (s, 1H), 6.98 (s, 1H), 6.83 (s, 1H), 4.18 (s, 3H), 2.46 (s, 3H), 2.41 (s, 3H) |
| 298 | 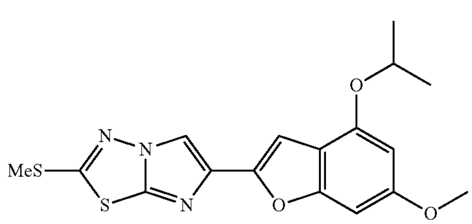 [SMILES: COc1cc(OC(C)C)c2cc(-c3cn4nc(SC)sc4n3)oc2c1] | Ex. 1 | C₁₇H₁₇N₃O₃S₂ | 375.07 | 2.348/A | 376.10 | ¹H NMR (600 MHz, CDCl₃) δ 7.93 (s, 1H), 7.03 (s, 1H), 6.64 (s, 1H), 6.32 (s, 1H), 4.62 (t, J = 6.0 Hz, 1H), 3.82 (s, 3H), 2.74 (s, 3H), 1.36 (d, J = 6.0 Hz, 6H) |

-continued

| Ex. | Structure | Experimental procedure | Formula | Exact Mass | HPLC Retention Time (Min)/ Method | LCMS M + 1 | NMR |
|---|---|---|---|---|---|---|---|
| 299 | 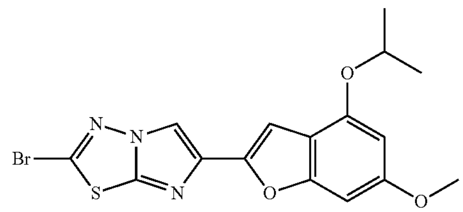 [SMILES: COc1cc(OC(C)C)c2cc(-c3cn4nc(Br)sc4n3)oc2c1] | Ex. 203E | $C_{16}H_{14}BrN_3O_3S$ | 406.99 | 2.406/ C | 408.01 | $^1$H NMR (600 MHz, CDCl$_3$) δ 8.01 (s, 1H), 7.07 (s, 1H), 6.63 (s, 1H), 6.32 (d, J = 1.6 Hz, 1H), 4.62 (t, J = 6.0 Hz, 1H), 3.82 (s, 3H), 1.36 (d, J = 6.0 Hz, 6H) |
| 300 | 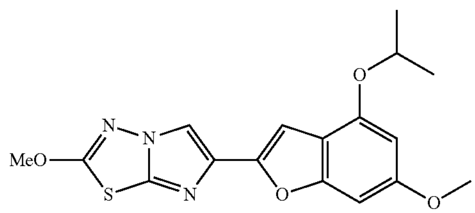 | Ex. 203 | $C_{17}H_{17}N_3O_4S$ | 359.09 | 2.344/ C | 360.11 | $^1$H NMR (600 MHz, CDCl$_3$) δ 7.80 (s, 1H), 6.98 (s, 1H), 6.64 (s, 1H), 6.31 (d, J = 1.6 Hz, 1H), 4.61 (t, J = 6.0 Hz, 1H), 4.19 (s, 3H), 3.81 (s, 3H), 1.36 (d, J = 6.0 Hz, 6H) |
| 301 | 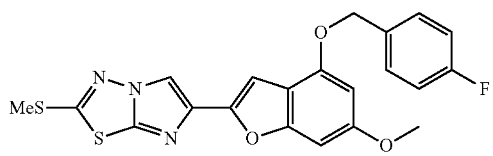 [SMILES: COc1cc(OCc2ccc(F)cc2)c2cc(-c3cn4nc(SC)sc4n3)oc2c1] | Ex. 1 | $C_{21}H_{16}FN_3O_3S_2$ | 441.06 | 2.474/ C | 442.08 | $^1$H NMR (600 MHz, CDCl$_3$) δ 7.93 (s, 1H), 7.42 (2H, m), 7.09 (d, J = 18.3 Hz, 2H), 7.06 (d, J = 15.2 Hz, 1H), 6.67 (s, 1H), 6.35 (s, 1H), 5.12 (s, 2H), 3.82 (s, 3H), 2.74 (s, 3H) |
| 302 | 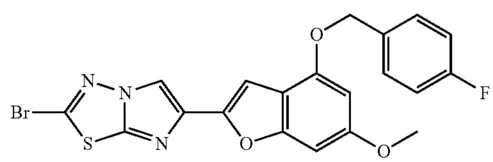 [SMILES: COc1cc(OCc2ccc(F)cc2)c2cc(-c3cn4nc(Br)sc4n3)oc2c1] | Ex. 203E | $C_{20}H_{13}BrFN_3O_3S$ | 472.98 | 2.469/ C | 473.99 | $^1$H NMR (600 MHz, CDCl$_3$) δ 8.02 (s, 1H), 7.42 (2H, m), 7.12 (s, 1H), 7.07 (s, 1H), 7.06 (d, J = 13.4 Hz, 1H), 6.67 (s, 1H), 6.36 (s, 1H), 5.11 (s, 2H), 3.82 (s, 3H) |
| 303 | 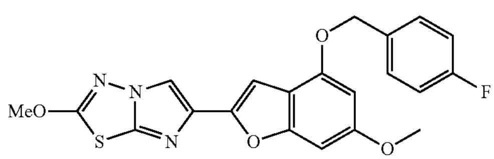 | Ex. 203 | $C_{21}H_{16}FN_3O_4S$ | 425.08 | 2.411/ C | 426.10 | $^1$H NMR (600 MHz, CDCl$_3$) δ 7.81 (s, 1H), 7.42 (m, 2H), 7.09 (d, J = 18.3 Hz, 2H), 7.06 (d, J = 15.2 Hz, 1H), 6.67 (d, J = 0.9 Hz, 1H), 6.35 (d, J = 1.8 Hz, 1H), 5.11 (s, 2H), 4.18 (s, 3H), 3.81 (s, 3H) |
| 304 | 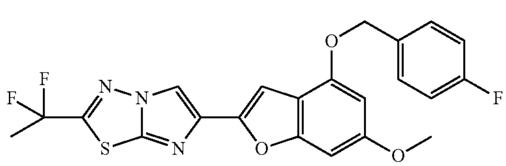 [SMILES: COc1cc(OCc2ccc(F)cc2)c2cc(-c3cn4nc(C(C)(F)F)sc4n3)oc2c1] | Ex. 207 | $C_{22}H_{16}F_3N_3O_3S$ | 459.09 | 2.437/ F | 460.09 | $^1$H NMR (600 MHz, CDCl$_3$) δ 8.04 (s, 1H), 7.42 (m, 2H), 7.16 (s, 1H), 7.06 (d, J = 8.6 Hz, 2H), 6.68 (s, 1H), 6.36 (d, J = 1.6 Hz, 1H), 5.12 (s, 2H), 3.82 (s, 3H), 2.17 (t, J = 18.4 Hz, 3H) |

| Ex. | Structure | Experimental procedure | Formula | Exact Mass | HPLC Retention Time (Min)/Method | LCMS M + 1 | NMR |
|---|---|---|---|---|---|---|---|
| 305 | (MeO-substituted imidazothiadiazole-furopyridine with CF3) | Ex. 203 | $C_{14}H_9N_4O_2S$ | 354.05 | | 355.06 | $^1$H NMR (600 MHz, CDCl$_3$) δ ppm 8.03 (s, 1H), 7.30 (s, 1H), 7.18 (s, 1H), 4.23 (s, 3H), 2.70 (s, 3H) |
| 306 | (Br-substituted imidazothiadiazole-furopyridine with CF3) | Ex. 203E | $C_{13}H_6BrF_3N_4OS$ | 401.94 | 2.271/A | 402.95 | $^1$H NMR (600 MHz, CDCl$_3$) δ ppm 8.21 (s, 1H), 7.31 (s, 1H), 7.24 (s, 1H), 2.69 (s, 3H) |

Examples 307 to 318

The following compounds were prepared employing the procedure as described below.

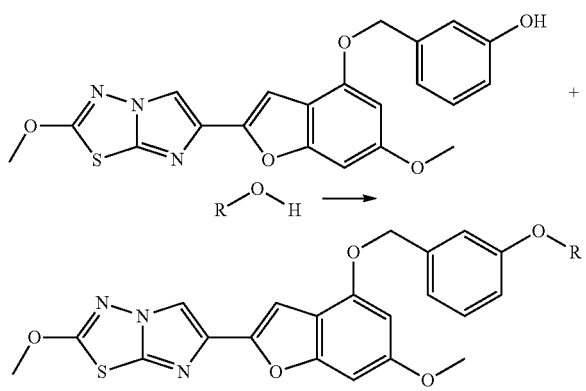

Into a 16×100 MM Wheaton tube was added 3-((6-methoxyimidazo[2,1-b][1,3,4]thiadiazol-6-yl)benzofuran-4-yloxy)methyl)phenol (1.0 eq., 0.038 mmol) in 200 µL THF (0.1M) followed with R—OH (3.0 eq., 0.113 mmol). To the reaction vial was then added PPh$_3$ (2.0 eq., 0.076 mmol) in 200 µL THF (0.1M). Reaction was sonicated for 5 minutes. To the reaction was then added DIAD (2.0 eq., 0.076 mmol) and reaction was stirred at room temperature overnight. The reaction was then blown down in a ZYMARK® tabletop dryer at 40° C. for 1 h. The crude reaction was redissolved in 2.0 mL of DMF and purified on Waters HPLC System. Purification: HPLC Waters System, Column: Waters Xbridge 19×100 mm, Sum C18, Mobile Phase: A=5:95 Acetonitrile:Water, B=95:5 Acetonitrile:Water, Modifier=0.05% TFA, Wavelength: 220 nm.

| Example No. | Structure |
|---|---|
| 307 | (structure with 6-methylpyridin-2-yl group) |
| 308 | (structure with 2-methylpyridin-3-yl group) |

309 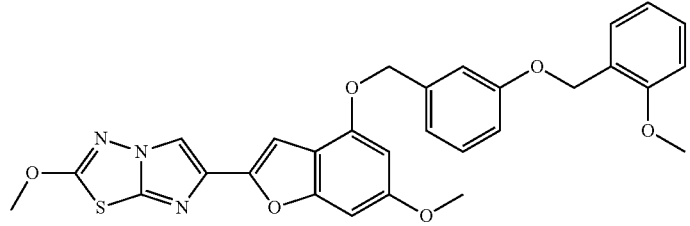
310 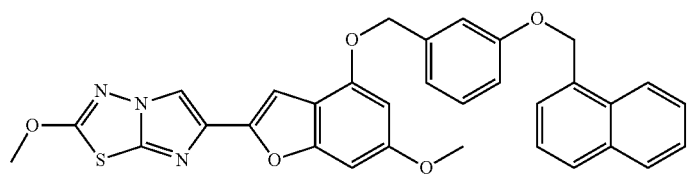 [SMILES: COc1cc(OCc2cccc(OCc3cccc4ccccc34)c2)c2cc(-c3cn4nc(OC)sc4n3)oc2c1]
311 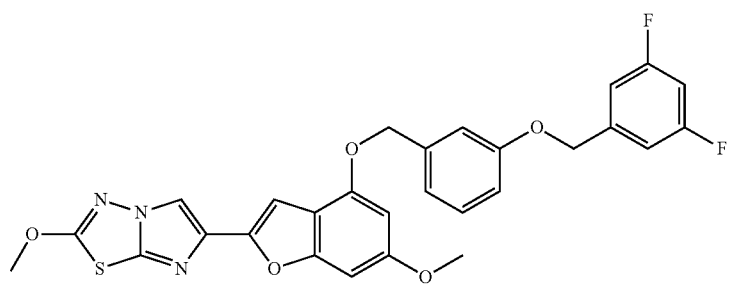 [SMILES: COc1cc(OCc2cccc(OCc3cc(F)cc(F)c3)c2)c2cc(-c3cn4nc(OC)sc4n3)oc2c1]
312 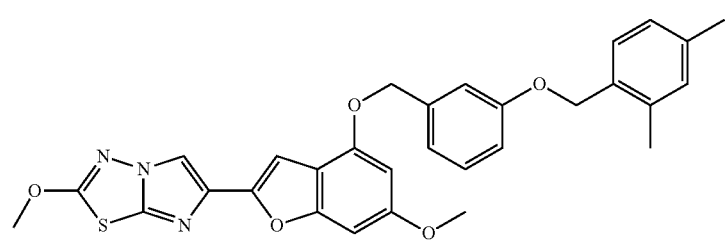
313 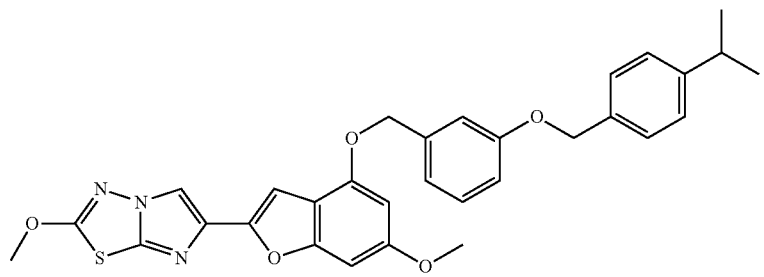 [SMILES: COc1cc(OCc2cccc(OCc3ccc(C(C)C)cc3)c2)c2cc(-c3cn4nc(OC)sc4n3)oc2c1]
314 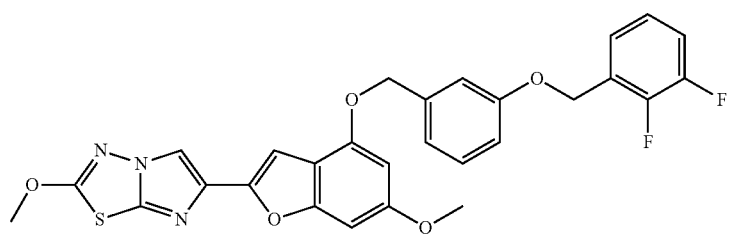 [SMILES: COc1cc(OCc2cccc(OCc3cccc(F)c3F)c2)c2cc(-c3cn4nc(OC)sc4n3)oc2c1]

315 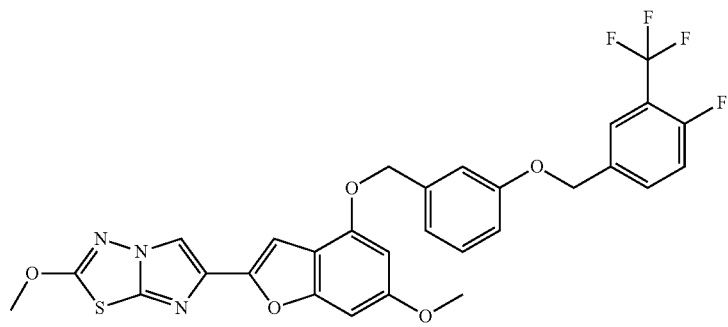 [SMILES: COc1cc(OCc2cccc(OCc3ccc(F)c(C(F)(F)F)c3)c2)c2cc(-c3cn4nc(OC)sc4n3)oc2c1]
316 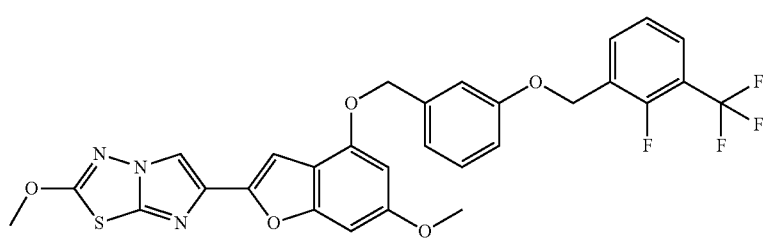 [SMILES: COc1cc(OCc2cccc(OCc3cccc(C(F)(F)F)c3F)c2)c2cc(-c3cn4nc(OC)sc4n3)oc2c1]
317 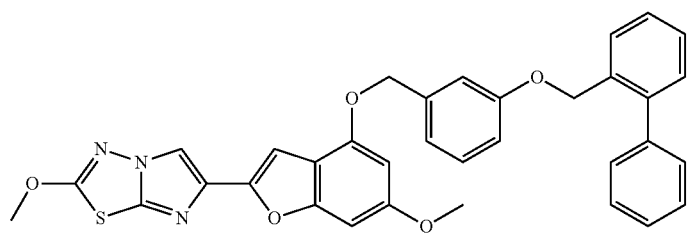 [SMILES: COc1cc(OCc2cccc(OCc3ccccc3-c3ccccc3)c2)c2cc(-c3cn4nc(OC)sc4n3)oc2c1]
318 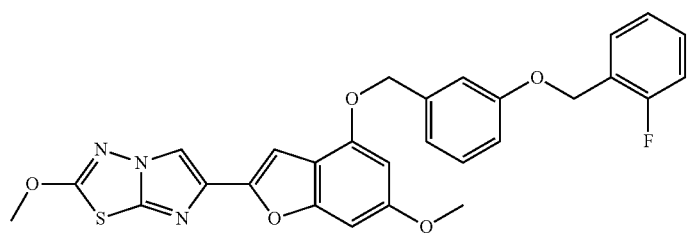 [SMILES: COc1cc(OCc2cccc(OCc3ccccc3F)c2)c2cc(-c3cn4nc(OC)sc4n3)oc2c1]
| Example No. | Formula | MW | % Purity | HPLC Rt | Obs. MS Ion |
|---|---|---|---|---|---|
| 307 | $C_{28}H_{24}N_4O_5S$ | 528.58 | 90 | 3.09 | 529.07 |
| 308 | $C_{28}H_{24}N_4O_5S$ | 528.58 | 91 | 2.97 | 529.06 |
| 309 | $C_{29}H_{25}N_3O_6S$ | 543.59 | 100 | 4.34 | 544.09 |
| 310 | $C_{32}H_{25}N_3O_5S$ | 563.62 | 100 | 4.48 | 564.11 |
| 311 | $C_{28}H_{21}F_2N_3O_5S$ | 549.55 | 100 | 4.37 | 550.09 |
| 312 | $C_{30}H_{27}N_3O_5S$ | 541.62 | 100 | 4.46 | 542.11 |
| 313 | $C_{31}H_{29}N_3O_5S$ | 555.64 | 96 | 4.50 | 556.15 |
| 314 | $C_{28}H_{21}F_2N_3O_5S$ | 549.55 | 100 | 4.34 | 550.07 |
| 315 | $C_{29}H_{21}F_4N_3O_5S$ | 599.55 | 100 | 4.37 | 600.06 |
| 316 | $C_{29}H_{21}F_4N_3O_5S$ | 599.55 | 100 | 4.37 | 600.07 |
| 317 | $C_{34}H_{27}N_3O_5S$ | 589.66 | 100 | 4.48 | 590.14 |
| 318 | $C_{28}H_{22}FN_3O_5S$ | 531.56 | 92 | 2.48 | 531.99 |

Examples 319 to 330

The following compounds were prepared employing the procedures described below.

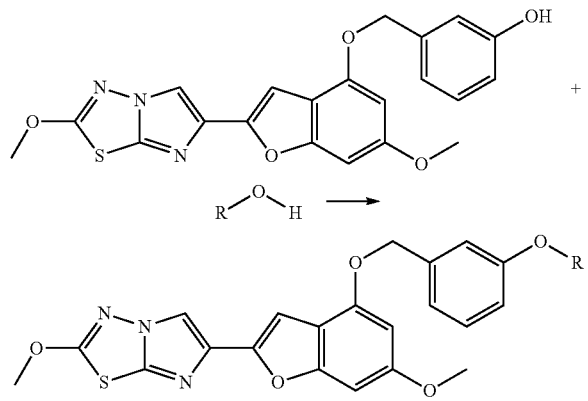

Into a 16×100 MM Wheaton tube was added 3-((6-methoxyimidazo[2,1-b][1,3,4]thiadiazol-6-yl)benzofuran-4-yloxy)methyl)phenol (1.0 eq., 0.035 mmol) followed with R—OH (3.0 eq., 0.106 mmol) and PPh$_3$ (2.0 eq., 0.071 mmol). The vial capped with septa cap, degassed and purged with N$_2$ three times. To the reaction was then added 350 μL anhydrous THF (0.1M). The reaction was degassed and purged with N$_2$ three times. The reaction was sonicated for 5 minutes. To the reaction was then added DIAD (4.0 eq., 0.142 mmol) and the reaction was stirred at room temperature overnight. The reaction was then blown down in the ZYMARK® tabletop dryer at 40° C. for 1 h. The crude reaction was redissolved in 2.0 mL of DMF and purified on Waters HPLC System. Purification: HPLC DIONEX® System, Column: Waters Xbridge 19×100 mm, 5um C18, Mobile Phase: A=5:95 Acetonitrile:Water, B=95:5 Acetonitrile:Water, Modifier=0.05% TFA, Wavelength: 220 nm.

| Example No. | Structure |
|---|---|
| 319 | 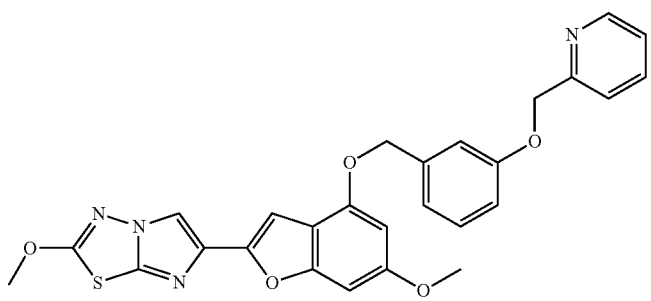 [SMILES: COc1cc(OCc2cccc(OCc3ccccn3)c2)c2cc(-c3cn4nc(OC)sc4n3)oc2c1] |
| 320 | 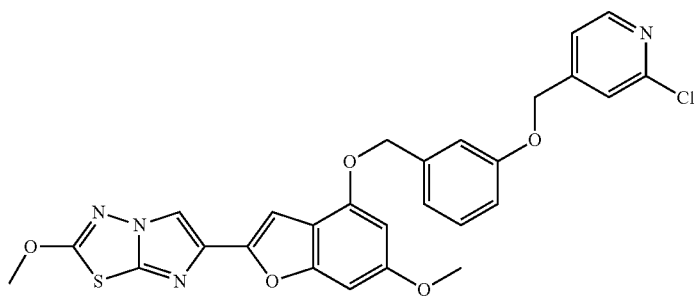 [SMILES: COc1cc(OCc2cccc(OCc3ccnc(Cl)c3)c2)c2cc(-c3cn4nc(OC)sc4n3)oc2c1] |
| 321 | 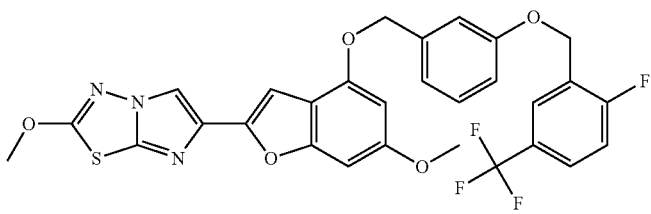 [SMILES: COc1cc(OCc2cccc(OCc3cc(C(F)(F)F)ccc3F)c2)c2cc(-c3cn4nc(OC)sc4n3)oc2c1] |

322 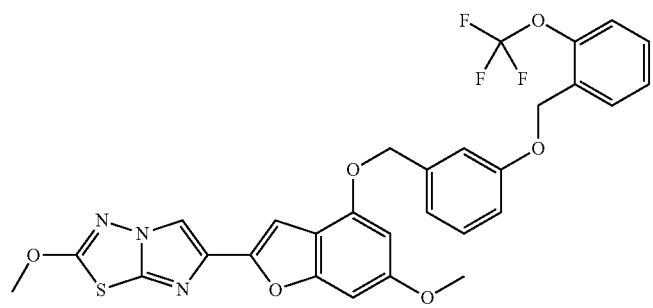 [SMILES: COc1cc(OCc2cccc(OCc3ccccc3OC(F)(F)F)c2)c2cc(-c3cn4nc(OC)sc4n3)oc2c1]
323 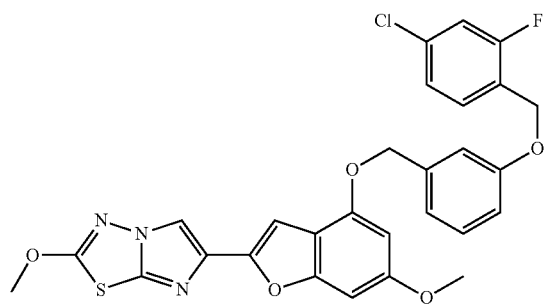 [SMILES: COc1cc(OCc2cccc(OCc3ccc(Cl)cc3F)c2)c2cc(-c3cn4nc(OC)sc4n3)oc2c1]
324 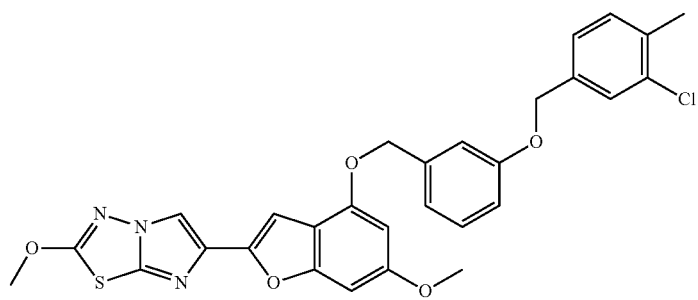 [SMILES: COc1cc(OCc2cccc(OCc3ccc(C)c(Cl)c3)c2)c2cc(-c3cn4nc(OC)sc4n3)oc2c1]
325 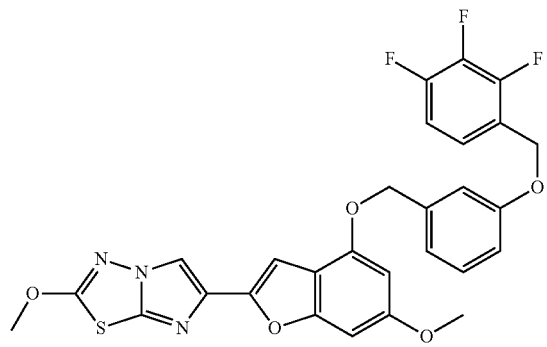 [SMILES: COc1cc(OCc2cccc(OCc3ccc(F)c(F)c3F)c2)c2cc(-c3cn4nc(OC)sc4n3)oc2c1]
326 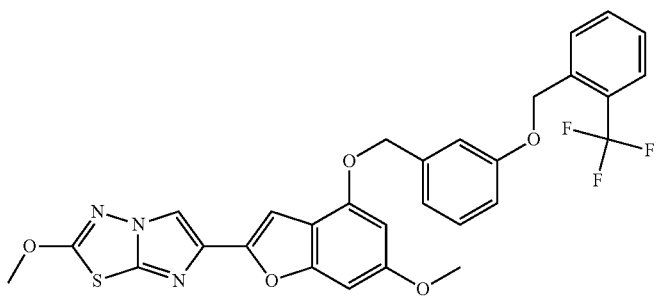 [SMILES: COc1cc(OCc2cccc(OCc3ccccc3C(F)(F)F)c2)c2cc(-c3cn4nc(OC)sc4n3)oc2c1]

327
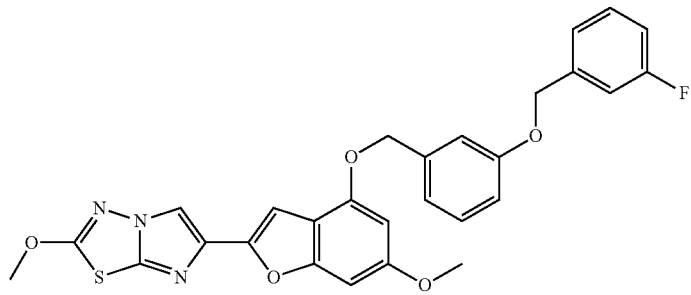 [SMILES: COc1cc(OCc2cccc(OCc3cccc(F)c3)c2)c2cc(-c3cn4nc(OC)sc4n3)oc2c1]
328
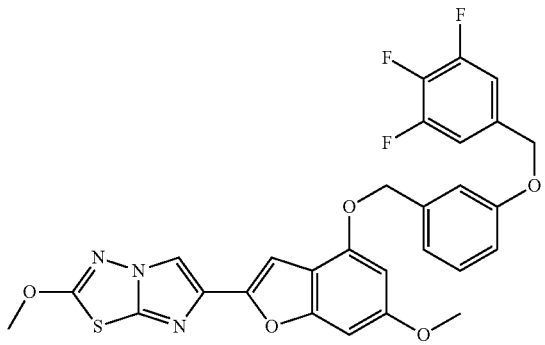 [SMILES: COc1cc(OCc2cccc(OCc3cc(F)c(F)c(F)c3)c2)c2cc(-c3cn4nc(OC)sc4n3)oc2c1]
329
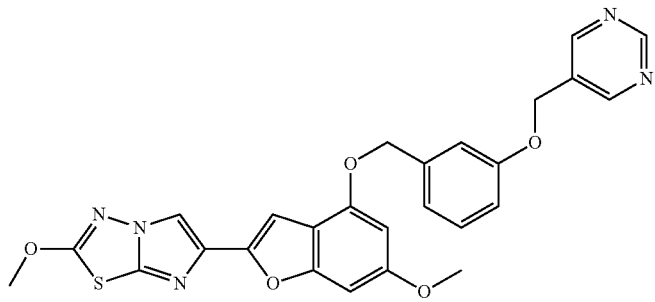 [SMILES: COc1cc(OCc2cccc(OCc3cncnc3)c2)c2cc(-c3cn4nc(OC)sc4n3)oc2c1]
330
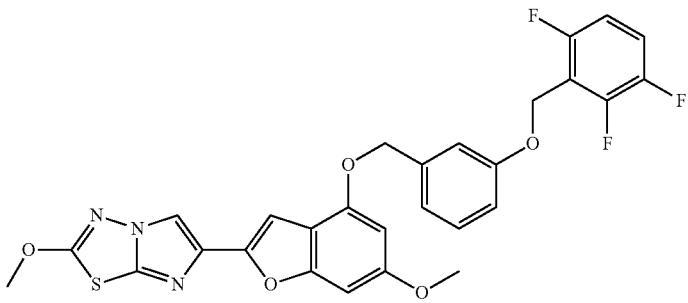 [SMILES: COc1cc(OCc2cccc(OCc3c(F)ccc(F)c3F)c2)c2cc(-c3cn4nc(OC)sc4n3)oc2c1]
| Example No. | Formula | MW | % Purity | HPLC Rt | Obs. MS Ion |
|---|---|---|---|---|---|
| 319 | $C_{27}H_{22}N_4O_5S$ | 514.56 | 92 | 1.75 | 515.15 |
| 320 | $C_{27}H_{21}ClN_4O_5S$ | 549.01 | 100 | 2.33 | 549.14 |
| 321 | $C_{29}H_{21}F_4N_3O_5S$ | 599.56 | 100 | 2.62 | 600.11 |
| 322 | $C_{29}H_{22}F_3N_3O_6S$ | 597.57 | 100 | 2.63 | 598.12 |
| 323 | $C_{28}H_{21}ClFN_3O_5S$ | 566.01 | 100 | 2.64 | 566.11 |
| 324 | $C_{29}H_{24}ClN_3O_5S$ | 562.05 | 100 | 2.71 | 562.12 |
| 325 | $C_{28}H_{20}F_3N_3O_5S$ | 567.55 | 99 | 2.55 | 568.20 |
| 326 | $C_{29}H_{22}F_3N_3O_5S$ | 581.57 | 92 | 2.61 | 582.18 |
| 327 | $C_{28}H_{22}FN_3O_5S$ | 531.56 | 89 | 2.49 | 532.19 |
| 328 | $C_{28}H_{20}F_3N_3O_5S$ | 567.55 | 99 | 2.56 | 568.14 |
| 329 | $C_{26}H_{21}N_5O_5S$ | 515.55 | 93 | 1.98 | 516.24 |
| 330 | $C_{28}H_{20}F_3N_3O_5S$ | 567.55 | 100 | 2.49 | 568.18 |

Example 331

(R)-tert-Butyl 2-(((2-(2-(methylthio)imidazo[2,1-b][1,3,4]thiadiazol-6-yl)benzo[d]oxazol-4-yl)oxy)methyl)pyrrolidine-1-carboxylate

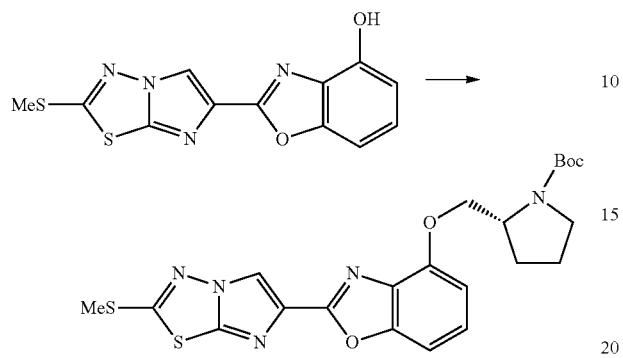

A mixture of 2-(2-(methylthio)imidazo[2,1-b][1,3,4]thiadiazol-6-yl)benzo[d]oxazol-4-ol (Example 147, 0.160 g, 0.526 mmol), BOC-D-prolinol (0.264 g, 1.31 mmol), triphenylphosphine (0.344 g, 1.914 mmol) and DIAD (0.257 mL, 1.31 mmol) in dry THF (3 mL) was stirred at 70° C. in a sealed tube for 1 h. The cooled mixture was then partitioned with EtOAc-dilute brine and the organic phase was separated, dried (MgSO$_4$) and evaporated to dryness. The residue was purified by flash chromatography (Isco/0-70% EtOAc-hexane) to give the title compound (0.161 g, 63%) as a beige solid. This material was triturated with MeOH-ether to give the analytical sample as a white solid (0.076 g, 29%). LC (Method A): 2.341 min. LCMS: Anal. Calcd. for $C_{22}H_{25}N_5O_4S_2$: 488.142. found: 488.163 (M+1)$^+$. $^1$H NMR (600 MHz, DMSO-d$_6$) δ 9.00 (s, 0.5H), 8.99 (s, 0.5H), 7.32 (m, 2H), 7.01 (m, 1H), 4.31 (s, 1H), 4.18 (m, 1H), 4.11 (s, 1H), 3.29 (m, 2H), 2.81 (s, 3H), 2.00 (m, 3H), 1.83 (br s, 1H), 1.40 (s, 4.5H), 1.37 (s, 4.5H).

Example 332

(S)-tert-Butyl 2-(((2-(2-(methylthio)imidazo[2,1-b][1,3,4]thiadiazol-6-yl)benzo[d]oxazol-4-yl)oxy)methyl)pyrrolidine-1-carboxylate

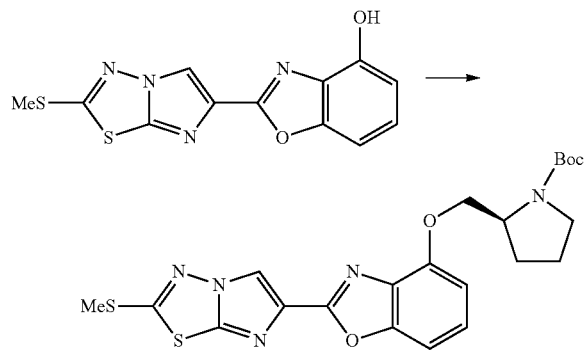

A mixture 2-(2-(methylthio)imidazo[2,1-b][1,3,4]thiadiazol-6-yl)benzo[d]oxazol-4-ol (Example 147, 0.160 g, 0.526 mmol), BOC-L-prolinol (0.264 g, 1.31 mmol), triphenylphosphine (0.344 g, 1.914 mmol) and DIAD (0.257 mL, 1.31 mmol) in dry THF (3 mL) was stirred at 70° C. in a sealed tube for 1 h. The cooled mixture was then partitioned with EtOAc-dilute brine and the organic phase was separated, dried (MgSO$_4$) and evaporated to dryness. The residue was purified by flash chromatography (Isco/0-70% EtOAc-hexane) to give the title compound (0.173 g, 67%) as a beige solid. A portion of this material was further purified by preparative HPLC (MeOH—H$_2$O-TFA) to give the analytical sample as an off-white solid. LC (Method A): 2.334 min. LCMS: Anal. Calcd. for $C_{22}H_{25}N_5O_4S_2$: 488.142. found: 488.170 (M+1)$^+$. $^1$H NMR (600 MHz, DMSO-d$_6$) δ 9.01 (s, 0.5H), 8.99 (s, 0.5H), 7.32 (m, 2H), 7.01 (m, 1H), 4.31 (s, 1H), 4.18 (m, 1H), 4.11 (s, 1H), 3.29 (m, 2H), 2.82 (s, 3H), 2.00 (m, 3H), 1.83 (br s, 1H), 1.41 (s, 4.5H), 1.37 (s, 4.5H).

Example 333 tert-Butyl ((R)-2-((R)-2-(((2-(2-(methylthio)imidazo[2,1-b][1,3,4]thiadiazol-6-yl)benzo[d]oxazol-4-yl)oxy)methyl)pyrrolidin-1-yl)-2-oxo-1-phenylethyl)carbamate

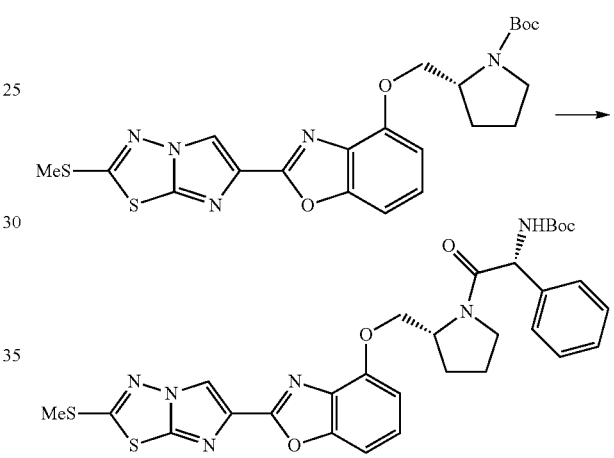

To a solution of (R)-tert-butyl 2-(((2-(2-(methylthio)imidazo[2,1-b][1,3,4]thiadiazol-6-yl)benzo[d]oxazol-4-yl)oxy)methyl)pyrrolidine-1-carboxylate (Example 331, 0.110 g, 0.226 mmol) in DCM (2 mL) was added TFA (0.5 mL) and the mixture was stirred at room temperature for 1 h. The mixture was then evaporated to dryness in vacuo and the resulting residue was used as such; LC (Method A): 1.705 min; LCMS: Anal. Calcd. for $C_{17}H_{17}N_5O_2S_2$: 387.090. found: 388.116 (M+1)$^+$. To a solution of the material obtained above in DMF (3 mL) was added BOC-D-phenylglycine (0.057 g, 0.226 mmol), followed by HATU (0.086 g, 0.226 mmol) and finally DIEA (0.197 mL, 1.13 mmol). The mixture was stirred at room temperature for 1 h and then it was partitioned with EtOAc-dilute brine. The organic phase was separated, dried (MgSO$_4$) and evaporated to dryness, and the residue was purified by flash chromatography (Isco/0-100% EtOAc-hexane) to give the title compound as a clear gum (0.140 g, 100%). A portion of this material was further purified by preparative HPLC (MeOH—H$_2$O-TFA) to give the analytical sample, which was lyophilized from MeCN-water as a white solid. LC (Method A): 2.306 min. LCMS: Anal. Calcd. for $C_{30}H_{32}N_6O_5S_2$: 620.188. found: 621.221 (M+1)$^+$. $^1$H NMR (600 MHz, DMSO-d$_6$) δ 8.95 (s, 1H), 7.32-7.24 (m, 4H), 7.15 (m, 3H), 6.94 (d, J=7.0 Hz, 1H), 5.34 (m, 1H), 4.39 (br s, 1H), 4.25 (m, 1H), 4.14 (m, 1H), 3.61 (m, 1H), 3.29 (m, 2H), 3.14 (m, 1H), 2.78 (s, 3H), 2.04-1.82 (m, 3H), 1.33 (s, 9H).

Example 334 tert-Butyl ((R)-2-((S)-2-(((2-(2-(methylthio)imidazo[2,1-b][1,3,4]thiadiazol-6-yl)benzo[d]oxazol-4-yl)oxy)methyl)pyrrolidin-1-yl)-2-oxo-1-phenylethyl)carbamate

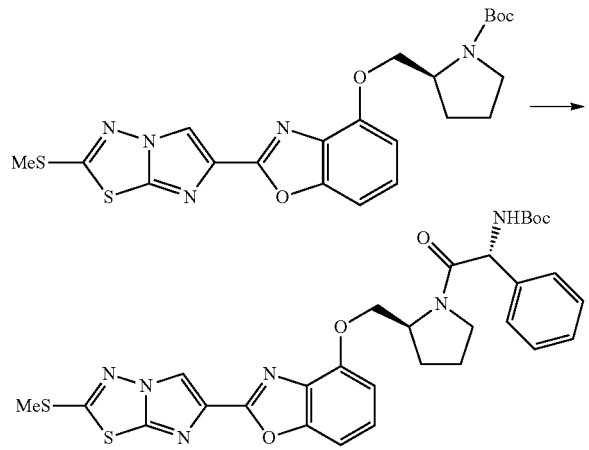

To a solution of (S)-tert-butyl 2-(((2-(2-(methylthio)imidazo[2,1-b][1,3,4]thiadiazol-6-yl)benzo[d]oxazol-4-yl)oxy)methyl)pyrrolidine-1-carboxylate (Example 332, 0.103 g, 0.211 mmol) in DCM (3 mL) was added TFA (0.5 mL) and the mixture was stirred at room temperature for 1.5 h. The mixture was then evaporated to dryness in vacuo and the resulting residue was used as such; LC (Method A): 1.723 min; LCMS: Anal. Calcd. for $C_{17}H_{17}N_5O_2S_2$: 387.090. found: 388.115 (M+1)$^+$. To a solution of the material obtained above in DMF (3 mL) was added BOC-D-phenylglycine (0.053 g, 0.211 mmol), followed by HATU (0.080 g, 0.226 mmol) and finally DIEA (0.184 mL, 1.06 mmol). The mixture was stirred at room temperature for 1 h and then it was partitioned with EtOAc-dilute brine. The organic phase was separated, dried (MgSO$_4$) and evaporated to dryness, and the residue was purified by flash chromatography (Isco/0-30% EtOAc-DCM) to give the title compound as a clear gum (0.087 g, 66%). A portion of this material was further purified by preparative HPLC (MeOH—H$_2$O-TFA) to give the analytical sample, which was lyophilized from MeCN-water as a white solid. LC (Method A): 2.321 min. LCMS: Anal. Calcd. for $C_{30}H_{32}N_6O_5S_2$: 620.188. found: 621.220 (M+1)$^+$. $^1$H NMR (600 MHz, DMSO-d$_6$) δ 8.99 (s, 1H), 7.36-7.24 (m, 9H), 7.15 (m, 1H), 7.06 (d, J=7.0 Hz, 1H), 5.34 (m, 1H), 4.37 (m, 1H), 4.30 (m, 1H), 4.15 (m, 1H), 3.69 (m, 1H), 3.03 (m, 1H), 2.78 (s, 3H), 2.11-1.93 (m, 1H), 1.87-1.75 (m, 1H), 1.32 (s, 9H).

Example 335

N—((R)-2-((R)-2-(((2-(2-(Methylthio)imidazo[2,1-b][1,3,4]thiadiazol-6-yl)benzo[d]oxazol-4-yl)oxy)methyl)pyrrolidin-1-yl)-2-oxo-1-phenylethyl)benzamide

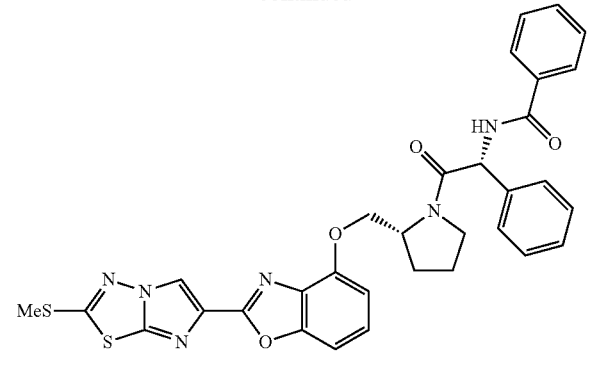

To a solution of tert-butyl ((R)-2-((R)-2-(((2-(2-(methylthio)imidazo[2,1-b][1,3,4]thiadiazol-6-yl)benzo[d]oxazol-4-yl)oxy)methyl)pyrrolidin-1-yl)-2-oxo-1-phenylethyl)carbamate (Example 333, 0.110 g, 0.177 mmol) in DCM (2 mL) was added TFA (0.5 mL) and the mixture was stirred at room temperature for 1.5 h. The mixture was then evaporated to dryness in vacuo and the resulting residue was used as such in the next step; LC (Method A): 1.938 min; LCMS: Anal. Calcd. for $C_{25}H_{24}N_6O_3S_2$: 520.135. found: 521.171 (M+1)$^+$. To a solution of half of the material obtained above (0.056 g, 0.088 mmol) in DMF (1 mL) was added benzoic acid (0.011 g, 0.088 mmol), followed by HATU (0.034 g, 0.088 mmol) and finally DIEA (0.077 mL, 0.44 mmol). The mixture was stirred at room temperature for 1 h and then it diluted with AcOH (0.2 mL) and the solution was submitted directly to preparative HPLC (MeOH—H$_2$O-TFA). The product-containing fractions were combined and evaporated and the residue was lyophilized from MeCN-water to give the title compound (0.023 g, 41%) as a white solid. LC (Method A): 2.261 min. LCMS: Anal. Calcd. for $C_{32}H_{28}N_6O_4S_2$: 624.169. found: 625.183 (M+1)$^+$. $^1$H NMR (600 MHz, DMSO-d$_6$) δ 8.96 (s, 1H), 8.85 (d, J=7.0 Hz, 1H), 7.86 (d, J=8.2 Hz, 1H), 7.50-7.26 (m, 8H), 7.19 (m, 2H), 6.99 (m, 1H), 5.87 (d, J=7.6 Hz, 1H), 4.43 (m, 1H), 4.32 (m, 1H), 4.21 (m, 1H), 3.69 (m, 1H), 3.24 (m, 1H), 2.78 (s, 3H), 2.08-1.88 (m, 4H).

Example 336

N—((R)-2-((R)-2-(((2-(2-(Methylthio)imidazo[2,1-b][1,3,4]thiadiazol-6-yl)benzo[d]oxazol-4-yl)oxy)methyl)pyrrolidin-1-yl)-2-oxo-1-phenylethyl)thiophene-2-carboxamide

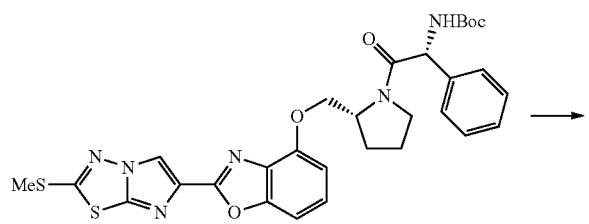

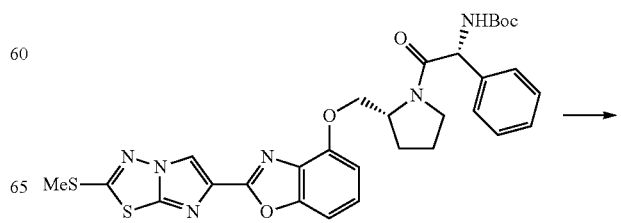

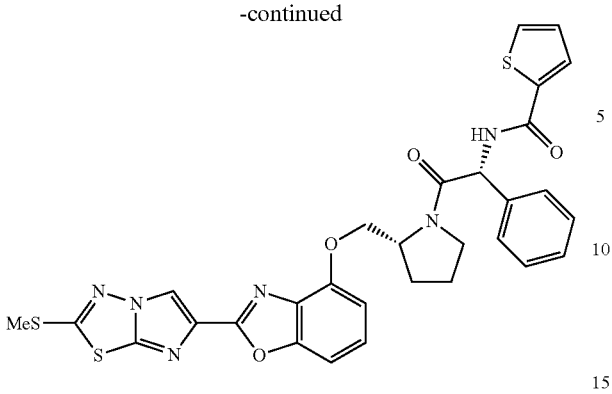

The title compound was obtained as a white solid (0.026 g, 47%) using 2-thiophene carboxylic acid in the method described in Example 335. LC (Method A): 2.241 min. LCMS: Anal. Calcd. for $C_{30}H_{26}N_6O_4S_3$: 630.125. found: 631.151 (M+1)$^+$. $^1$H NMR (600 MHz, DMSO-d$_6$) δ 8.96 (s, 1H), 8.92 (d, J=7.6 Hz, 1H), 7.95 (d, J=4.1 Hz, 1H), 7.73 (d, J=5.3 Hz, 1H), 7.36 (m, 3H), 7.30 (m, 2H), 7.20 (m, 2H), 7.09 (t, J=4.1 Hz, 1H), 7.00 (d, J=7.6 Hz, 1H), 5.83 (d, J=7.6 Hz, 1H), 4.43 (m, 1H), 4.32 (m, 1H), 4.22 (m, 1H), 3.66 (m, 1H), 3.23 (m, 1H), 2.78 (s, 3H), 2.08-1.80 (m, 4H).

Example 337

N—((R)-2-((S)-2-(((2-(2-(Methylthio)imidazo[2,1-b][1,3,4]thiadiazol-6-yl)benzo[d]oxazol-4-yl)oxy)methyl)pyrrolidin-1-yl)-2-oxo-1-phenylethyl)benzamide

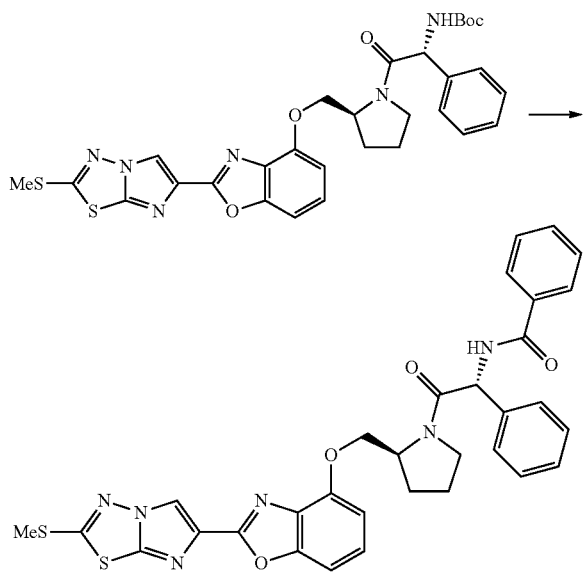

The title compound was prepared from tert-butyl ((R)-2-((S)-2-(((2-(2-(methylthio)imidazo[2,1-b][1,3,4]thiadiazol-6-yl)benzo[d]oxazol-4-yl)oxy)methyl)-pyrrolidin-1-yl)-2-oxo-1-phenylethyl)carbamate (Example 334) according to the method described in Example 335 and was isolated as a white solid (0.017 g, 39%). LC (Method A): 2.272 min. LCMS: Anal. Calcd. for $C_{32}H_{28}N_6O_4S_2$: 624.169. found: 625.184 (M+1)$^+$. $^1$H NMR (600 MHz, DMSO-d$_6$) δ 8.95 (s, 1H), 8.82 (d, J=7.6 Hz, 1H), 7.85 (d, J=7.6 Hz, 1H), 7.49-7.45 (m, 3H), 7.42-7.35 (m, 4H), 7.31-7.25 (m, 3H), 7.06 (dd, J=1.8, 7.0 Hz, 1H), 5.88 (d, J=7.6 Hz, 1H), 4.42 (dd, J=2.9, 9.4 Hz, 1H), 4.37 (m, 1H), 4.19 (t, J=8.8 Hz, 1H), 3.74 (m, 1H), 3.12 (q, J=9.4 Hz, 1H), 2.78 (s, 3H), 2.14-1.77 (m, 4H).

Example 338

N—((R)-2-((S)-2-(((2-(2-(Methylthio)imidazo[2,1-b][1,3,4]thiadiazol-6-yl)benzo[d]oxazol-4-yl)oxy)methyl)pyrrolidin-1-yl)-2-oxo-1-phenylethyl)thiophene-2-carboxamide

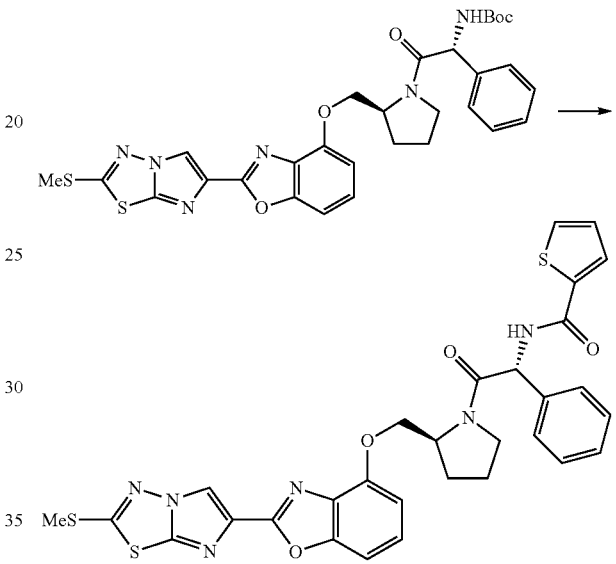

The title compound was prepared from tert-butyl ((R)-2-((S)-2-(((2-(2-(methylthio)imidazo[2,1-b][1,3,4]thiadiazol-6-yl)benzo[d]oxazol-4-yl)oxy)methyl)-pyrrolidin-1-yl)-2-oxo-1-phenylethyl)carbamate according to the method described in Example 336 and was isolated as a white solid (0.022 g, 49%). LC (Method A): 2.237 min. LCMS: Anal. Calcd. for $C_{30}H_{26}N_6O_4S_3$: 630.125. found: 631.131 (M+1)$^+$. $^1$H NMR (600 MHz, DMSO-d$_6$) δ 8.96 (s, 1H), 8.89 (d, J=7.6 Hz, 1H), 7.95 (d, J=3.5 Hz, 1H), 7.72 (d, J=5.3 Hz, 1H), 7.44 (d, J=7.0 Hz, 2H), 7.37 (t, J=7.6 Hz, 2H), 7.32-7.25 (m, 3H), 7.09-7.06 (m, 2H), 5.85 (d, J=7.6 Hz, 1H), 4.42 (dd, J=2.3, 9.4 Hz, 1H), 4.37 (m, 1H), 4.17 (t, J=8.8 Hz, 1H), 3.72 (m, 1H), 3.10 (q, J=9.4 Hz, 1H), 2.78 (s, 3H), 2.14-1.76 (m, 4H).

Example 339

(R)-6-(4-((2,2-Dimethyl-1,3-dioxolan-4-yl)methoxy)-6-methoxybenzofuran-2-yl)-2-methoxy-imidazo[2,1-b][1,3,4]thiadiazole

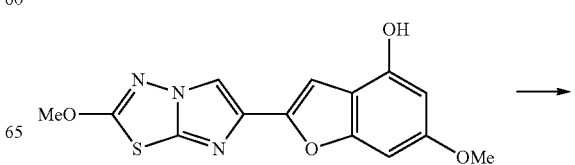

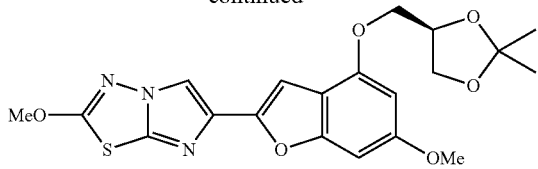

A mixture of 6-methoxy-2-(2-methoxyimidazo[2,1-b][1,3,4]thiadiazol-6-yl)benzofuran-4-ol (Example 204, 0.106 g, 0.334 mmol) and triphenylphosphine (0.263 g, 1.002 mmol) was dried under high vacuum for 30 min and then the flask was flushed with $N_2$ and dry THF (5 mL) was added. To the resulting suspension was added a mixture of (R)-(2,2-dimethyl-1,3-dioxolan-4-yl)methanol (0.132 g, 1.002 mmol) and DIAD (0.195 mL, 1.002 mmol) in dry THF (2 mL) dropwise over 1.5 h. The resulting homogeneous mixture was then stirred at room temperature under $N_2$ for 18 h, at which time LC showed that the reaction was essentially complete. The reaction mixture was subsequently evaporated to give a light amber gum which was purified by flash chromatography (Isco/DCM, then 0-20% ether-DCM) to give the product as a semi-crystalline solid. This solid was triturated with a minimum volume of ether, the resulting suspension was filtered and the filter-cake was washed with a minimum of ether and dried in vacuo to give the title compound (0.009 g, 6%) as an off-white solid. LC (Method A): 2.220 min. LCMS: Anal. Calcd. for $C_{27}H_{28}N_4O_6S$: 431.115. found: 432.127 $(M+1)^+$. $^1H$ NMR (400 MHz, DMSO-$d_6$) δ 8.32 (s, 1H), 6.85 (d, J=0.8 Hz, 1H), 6.75 (dd, J=0.8, 2.0 Hz, 1H), 6.40 (d, J=2.0 Hz, 1H), 4.40 (m, 1H), 4.14 (s, 3H), 4.12-4.04 (m, 3H), 3.77 (dd, J=6.3, 8.2 Hz, 1H), 3.73 (s, 3H), 1.32 (s, 3H), 1.26 (s, 3H).

| Ex. No. | Structure |
|---|---|
| 340 | (structure) |
| 341 | (structure) |
| 342-343 | (structure) |

| Ex. No. | Experimental procedure (Example) | Formula | Exact Mass | HPLC Retention Time (Min)/Method | LCMS M + 1 | NMR |
|---|---|---|---|---|---|---|
| 340 | Ex. 339 | $C_{24}H_{28}N_4O_6S$ | 501.1802 (M + 1) | 2.434/A | 501.1824 | $^1H$ NMR (400 MHz, acetone-$d_6$) ppm 8.10 (s, 1H) 6.97 (s, 1H) 6.69-6.80 (m, 1H) 6.39-6.61 (m, 1H) 4.23-4.31 (m, 1H) 4.27 (s, 3H) 4.06-4.23 (m, 2H) 3.86 (s, 3H) 3.32-3.50 (m, 2H) 2.07-2.18 (m, 3H) 1.85-1.96 (m, 1H) 1.45 (s, 9H) |

| | | | | | | |
|---|---|---|---|---|---|---|
| 341 | Ex. 333 | C26H23FN4O5S | 523.1446 (M + 1) | 2.316/A | 523.1461 | $^1$H NMR (400 MHz, acetone-d$_6$) δ ppm 1.81-1.97 (m, 1H) 2.07-2.34 (m, 3H) 3.53 (br. s., 1H) 3.67 (dt, J = 10.27, 7.19 Hz, 1H) 3.84 (s, 3H) 4.27 (s, 3H) 4.42 (br. s., 2H) 4.61 (br. s., 1H) 6.60 (br. s., 1H) 6.73 (dd, J = 1.76, 0.98 Hz, 1H) 7.01 (br. s., 1H) 7.10-7.28 (m, 2H) 7.47-7.74 (m, 2H) 8.10 (s, 1H). |
| 342-343 | Ex. 339 | C24H28N4O6S | 501.1821 (M + 1) | 2.435/A | 501.1802 | $^1$H NMR (400 MHz, acetone-d$_6$) δ ppm 8.11 (br. s., 1H) 6.98 (br. s., 1H) 6.67-6.82 (m, 1H) 6.41-6.64 (m, 1H) 4.22-4.32 (m, 1H) 4.26 (s, 3H) 4.06-4.22 (m, 2H) 3.86 (s, 3H) 3.31-3.49 (m, 2H) 2.07-2.17 (m, 3H) 1.82-2.00 (m, 1H) 1.45 (s, 9H). |
Examples 344 to 407
The following compounds were prepared employing the procedures indicated in the third column of the table below.
| Ex. | Structure |
|---|---|
| 344 | 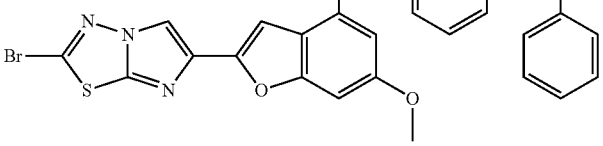 |
| 345 | 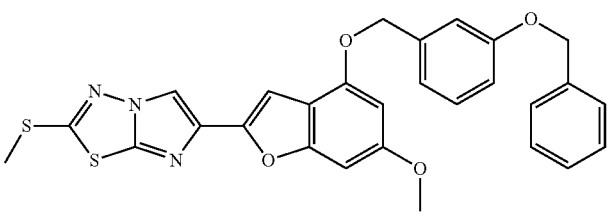 [SMILES: COc1cc(OCc2cccc(OCc3ccccc3)c2)c2cc(-c3cn4nc(SC)sc4n3)oc2c1] |
| 346 | 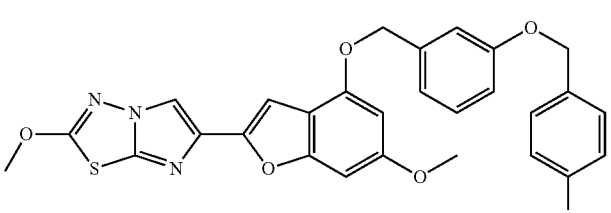 |
| 347 | 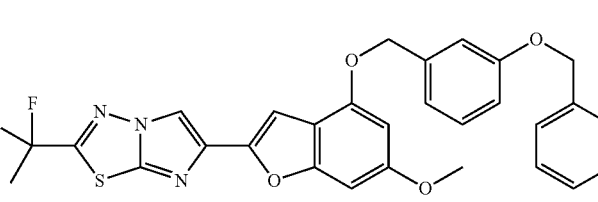 |
| 348 | 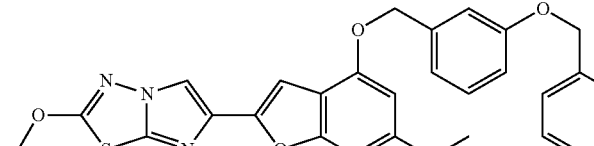 |

349 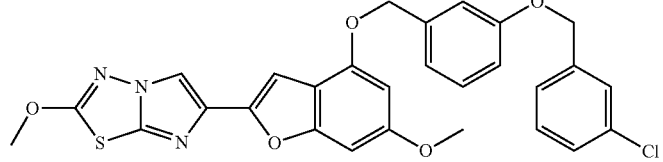
350 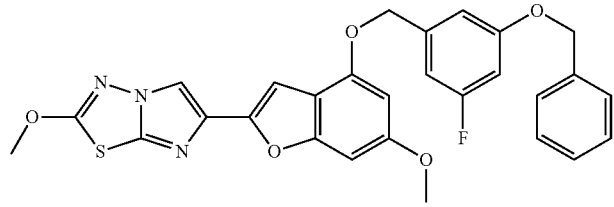 [SMILES: COc1cc(OCc2cc(F)cc(OCc3ccccc3)c2)c2cc(-c3cn4nc(OC)sc4n3)oc2c1]
351 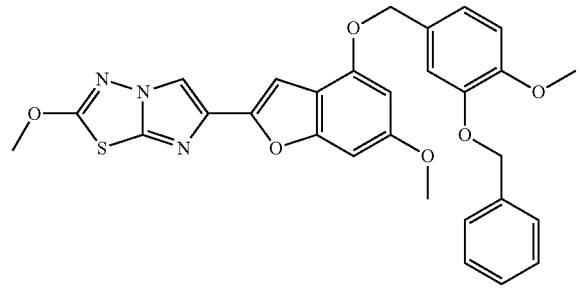
352 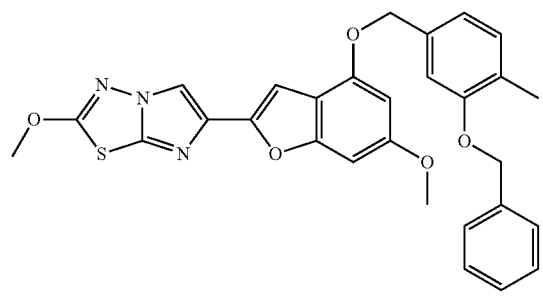 [SMILES: COc1cc(OCc2ccc(C)c(OCc3ccccc3)c2)c2cc(-c3cn4nc(OC)sc4n3)oc2c1]
353 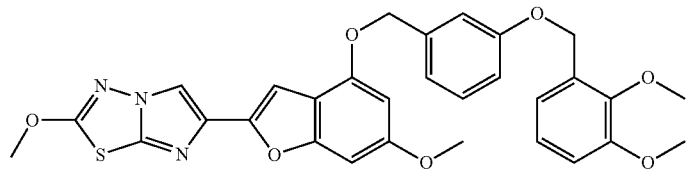
354 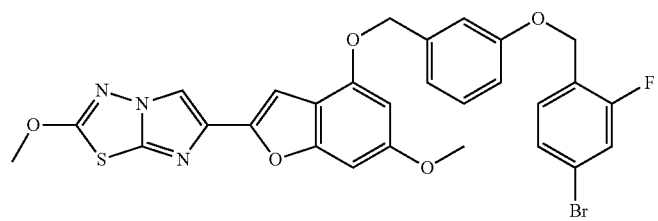 [SMILES: COc1cc(OCc2cccc(OCc3ccc(Br)cc3F)c2)c2cc(-c3cn4nc(OC)sc4n3)oc2c1]
355 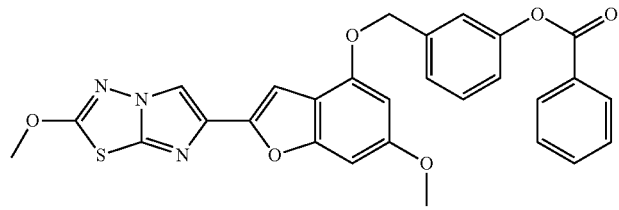 [SMILES: COc1cc(OCc2cccc(OC(=O)c3ccccc3)c2)c2cc(-c3cn4nc(OC)sc4n3)oc2c1]

356 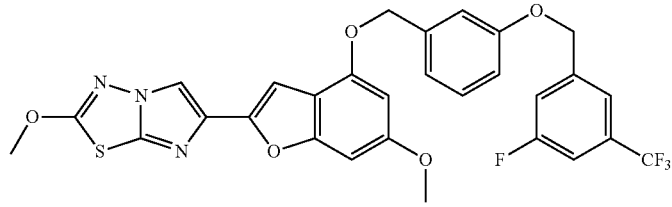 [SMILES: COc1cc(OCc2cccc(OCc3cc(F)cc(C(F)(F)F)c3)c2)c2cc(-c3cn4nc(OC)sc4n3)oc2c1]
357 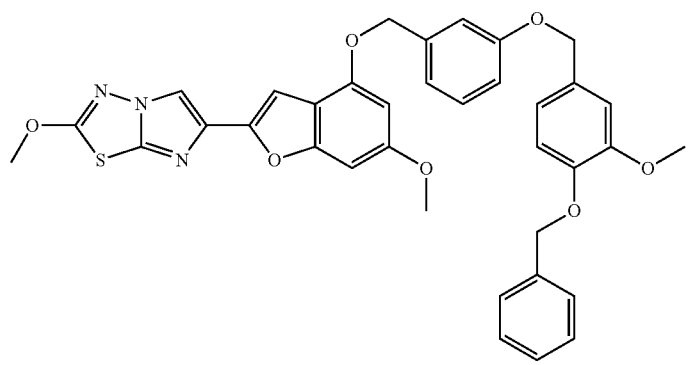
358 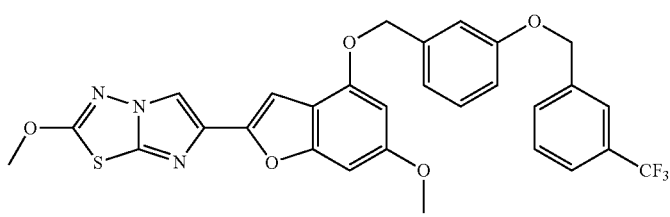 [SMILES: COc1cc(OCc2cccc(OCc3cccc(C(F)(F)F)c3)c2)c2cc(-c3cn4nc(OC)sc4n3)oc2c1]
359 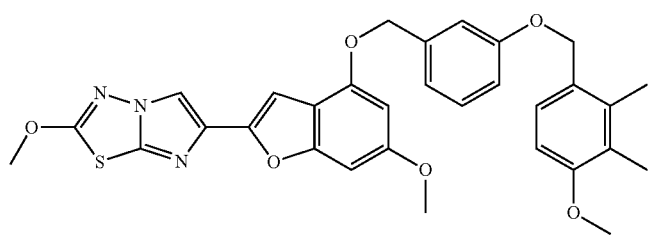
360 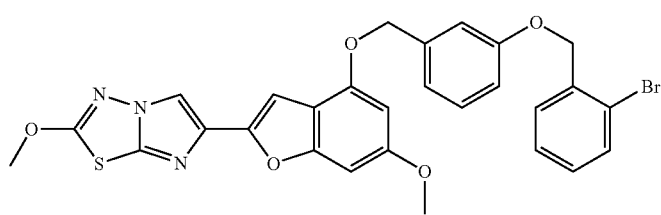 [SMILES: COc1cc(OCc2cccc(OCc3ccccc3Br)c2)c2cc(-c3cn4nc(OC)sc4n3)oc2c1]
361 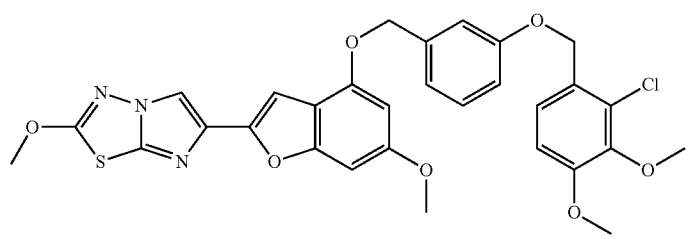

| | |
|---|---|
| 362 | 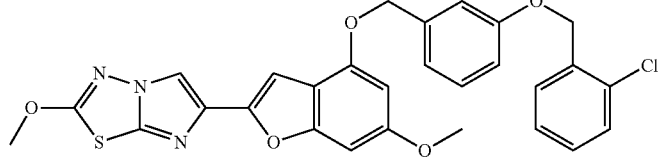 |
| 363 | 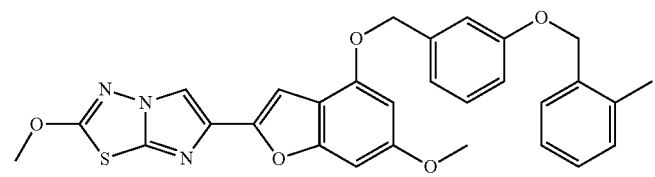 |
| 364 | 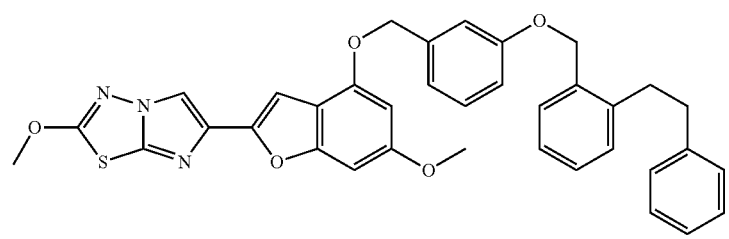 [SMILES: COc1cc(OCc2cccc(OCc3ccccc3CCc3ccccc3)c2)c2cc(-c3cn4nc(OC)sc4n3)oc2c1] |
| 365 | 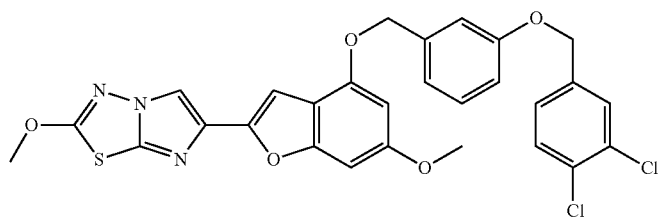 [SMILES: COc1cc(OCc2cccc(OCc3ccc(Cl)c(Cl)c3)c2)c2cc(-c3cn4nc(OC)sc4n3)oc2c1] |
| 366 | 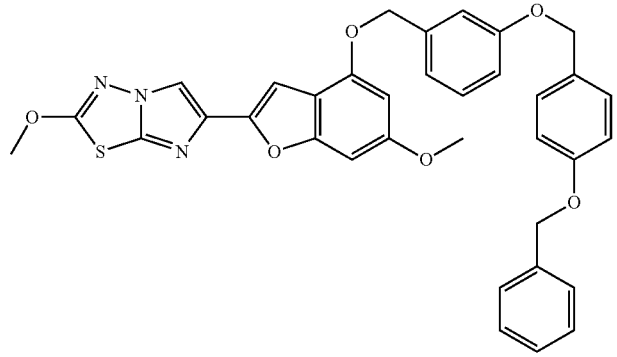 [SMILES: COc1cc(OCc2cccc(OCc3ccc(OCc4ccccc4)cc3)c2)c2cc(-c3cn4nc(OC)sc4n3)oc2c1] |
| 367 | 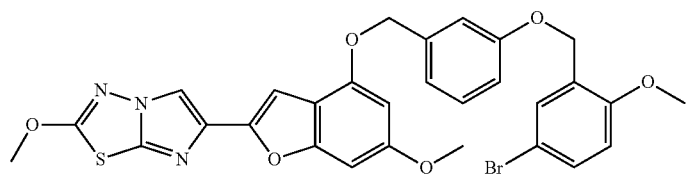 |
| 368 | 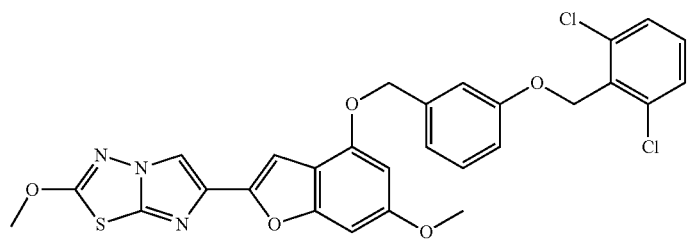 [SMILES: COc1cc(OCc2cccc(OCc3c(Cl)cccc3Cl)c2)c2cc(-c3cn4nc(OC)sc4n3)oc2c1] |

369 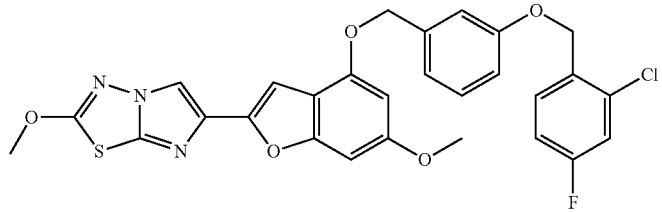 [SMILES: COc1cc(OCc2cccc(OCc3ccc(F)cc3Cl)c2)c2cc(-c3cn4nc(OC)sc4n3)oc2c1]
370 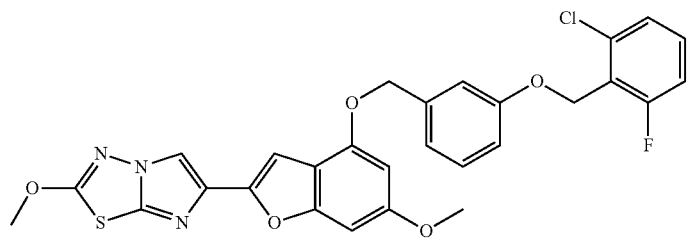 [SMILES: COc1cc(OCc2cccc(OCc3c(F)cccc3Cl)c2)c2cc(-c3cn4nc(OC)sc4n3)oc2c1]
371 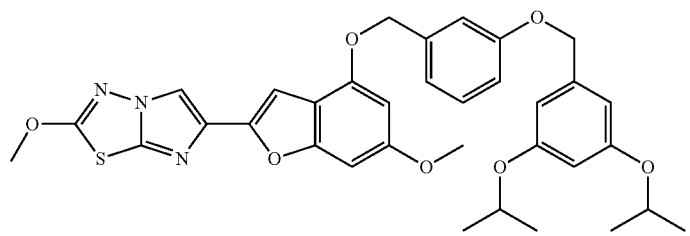 [SMILES: COc1cc(OCc2cccc(OCc3cc(OC(C)C)cc(OC(C)C)c3)c2)c2cc(-c3cn4nc(OC)sc4n3)oc2c1]
372 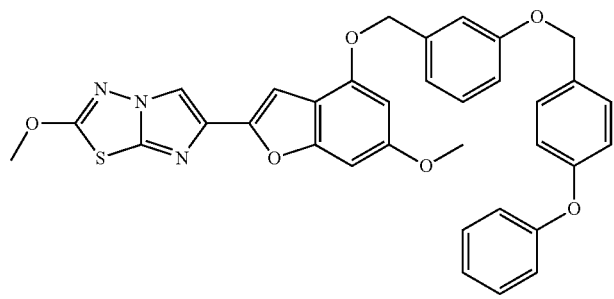 [SMILES: COc1cc(OCc2cccc(OCc3ccc(Oc4ccccc4)cc3)c2)c2cc(-c3cn4nc(OC)sc4n3)oc2c1]
373 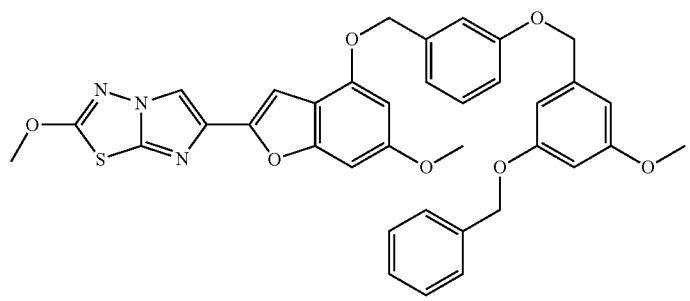
374 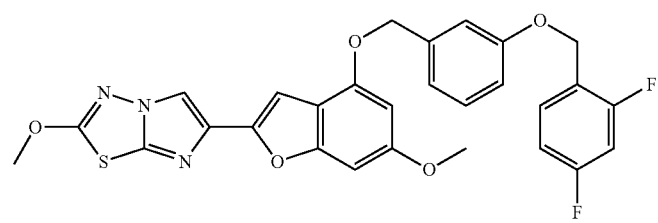 [SMILES: COc1cc(OCc2cccc(OCc3ccc(F)cc3F)c2)c2cc(-c3cn4nc(OC)sc4n3)oc2c1]

| | |
|---|---|
| 375 | 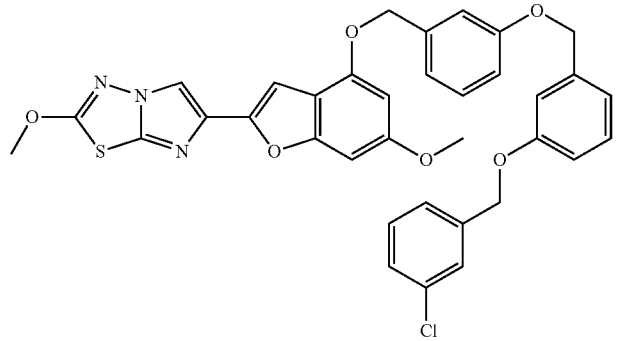 [SMILES: COc1cc(OCc2cccc(OCc3cccc(OCc4cccc(Cl)c4)c3)c2)c2cc(-c3cn4nc(OC)sc4n3)oc2c1] |
| 376 | 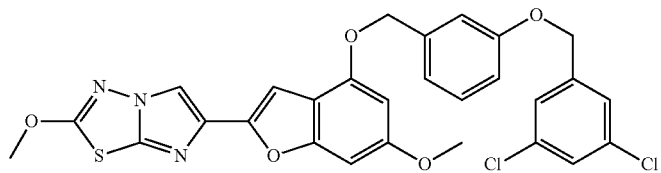 [SMILES: COc1cc(OCc2cccc(OCc3cc(Cl)cc(Cl)c3)c2)c2cc(-c3cn4nc(OC)sc4n3)oc2c1] |
| 377 | 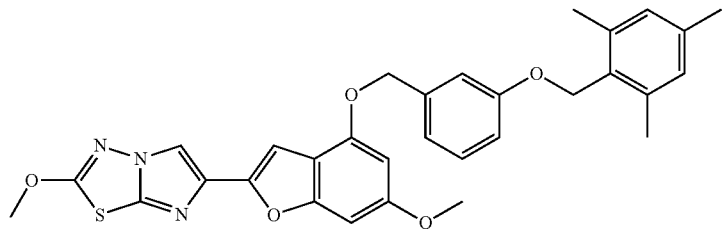 |
| 378 | 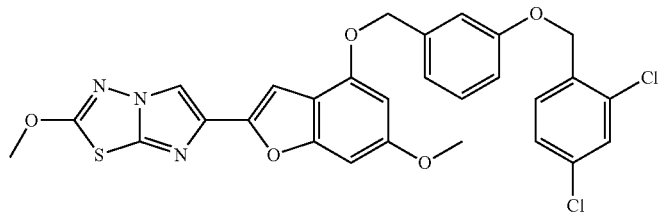 [SMILES: COc1cc(OCc2cccc(OCc3ccc(Cl)cc3Cl)c2)c2cc(-c3cn4nc(OC)sc4n3)oc2c1] |
| 379 | 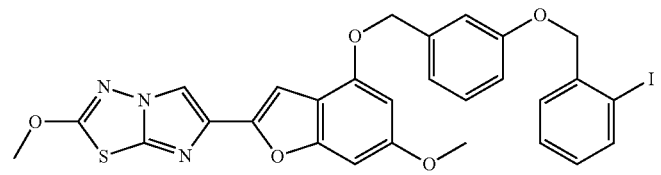 |
| 380 | 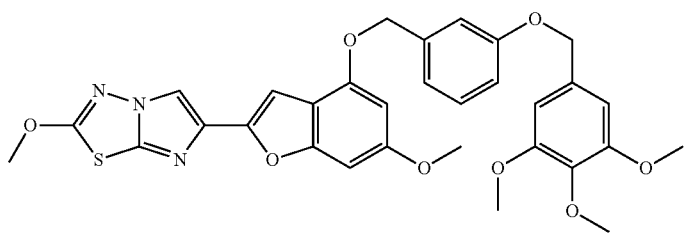 |
| 381 | 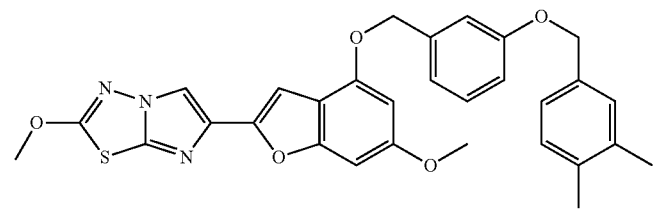 |

382 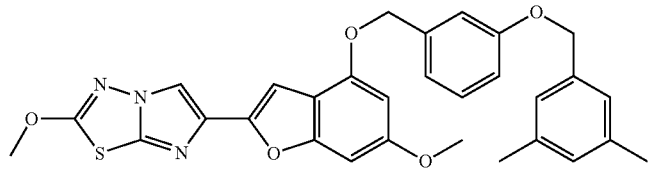
383 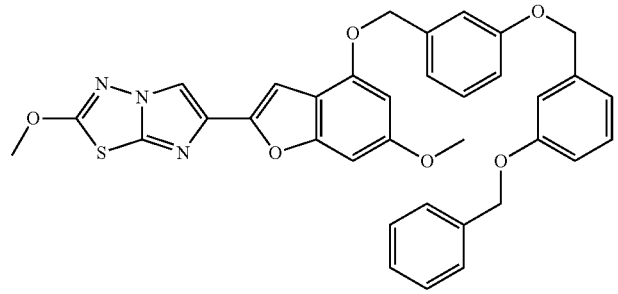 [SMILES: COc1cc(OCc2cccc(OCc3cccc(OCc4ccccc4)c3)c2)c2cc(-c3cn4nc(OC)sc4n3)oc2c1]
384 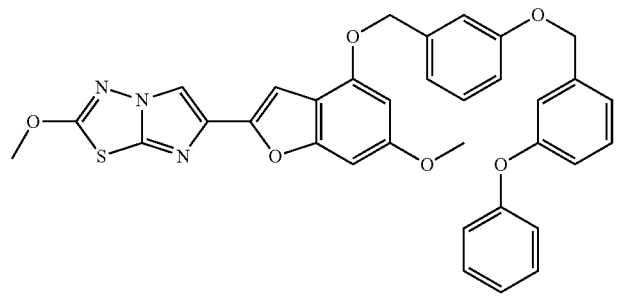 [SMILES: COc1cc(OCc2cccc(OCc3cccc(Oc4ccccc4)c3)c2)c2cc(-c3cn4nc(OC)sc4n3)oc2c1]
385 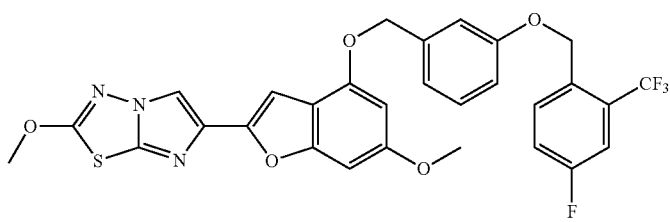 [SMILES: COc1cc(OCc2cccc(OCc3ccc(F)cc3C(F)(F)F)c2)c2cc(-c3cn4nc(OC)sc4n3)oc2c1]
386 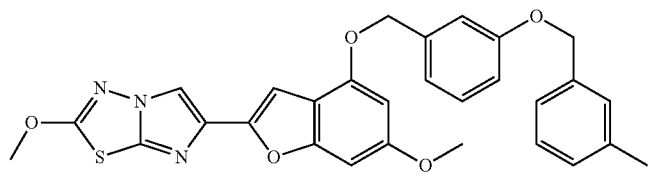
387 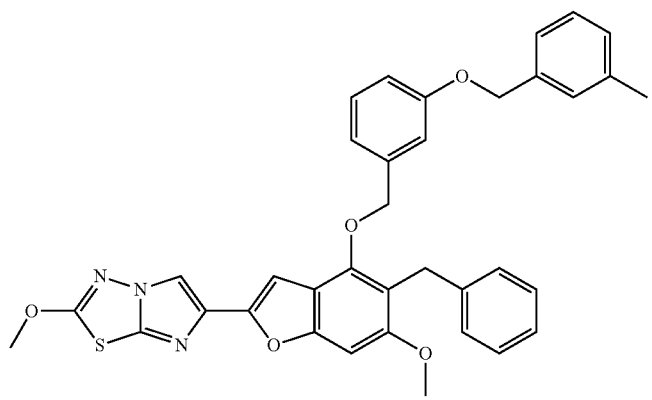

388 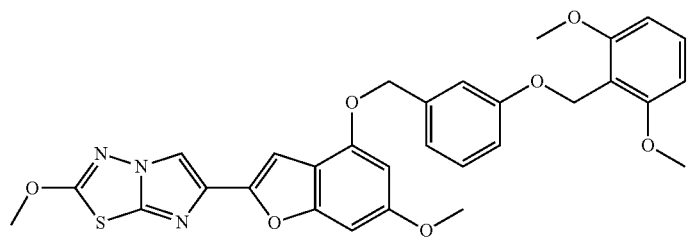
389 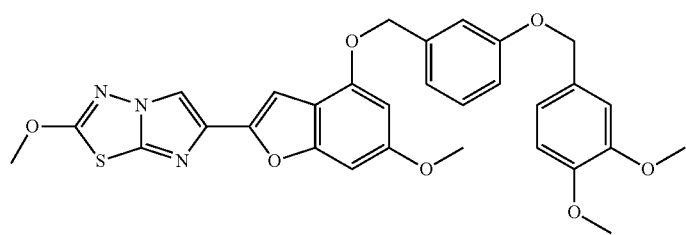
390 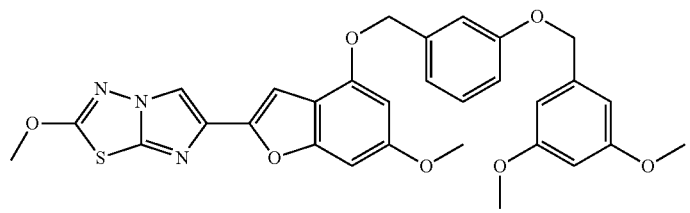
391 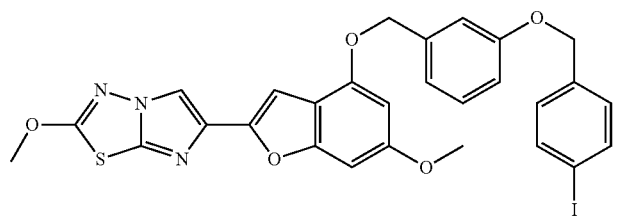
392 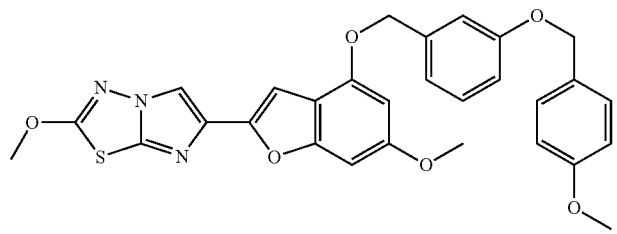
393 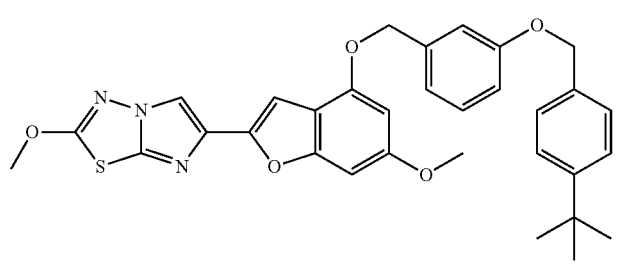 [SMILES: COc1cc(OCc2cccc(OCc3ccc(C(C)(C)C)cc3)c2)c2cc(-c3cn4nc(OC)sc4n3)oc2c1]

394
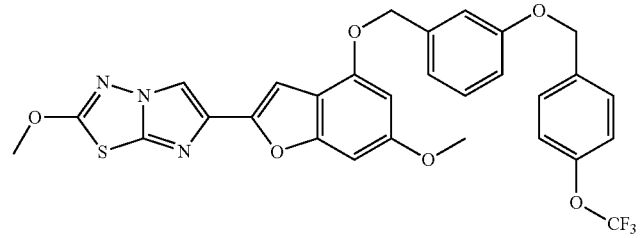 [SMILES: COc1cc(OCc2cccc(OCc3ccc(OC(F)(F)F)cc3)c2)c2cc(-c3cn4nc(OC)sc4n3)oc2c1]
395
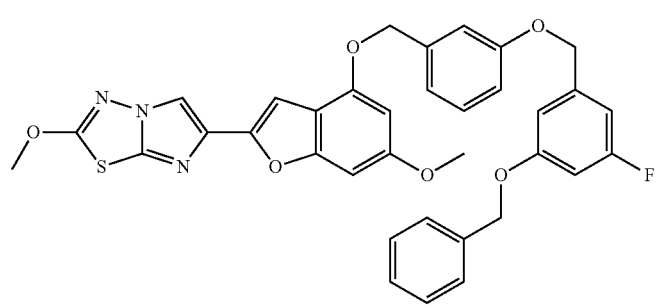 [SMILES: COc1cc(OCc2cccc(OCc3cc(F)cc(OCc4ccccc4)c3)c2)c2cc(-c3cn4nc(OC)sc4n3)oc2c1]
396
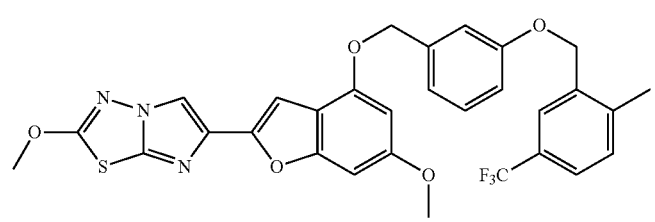
397
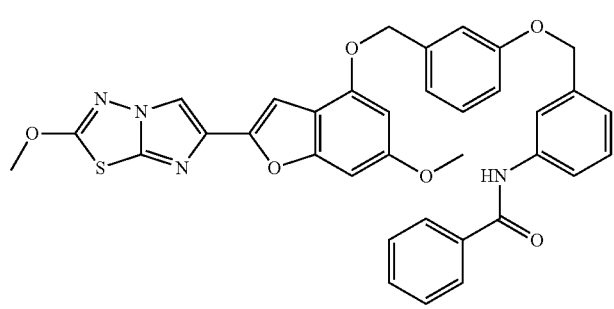 [SMILES: COc1cc(OCc2cccc(OCc3cccc(NC(=O)c4ccccc4)c3)c2)c2cc(-c3cn4nc(OC)sc4n3)oc2c1]
398
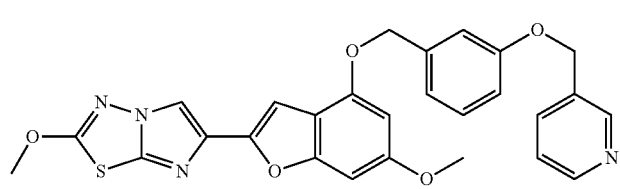 [SMILES: COc1cc(OCc2cccc(OCc3cccnc3)c2)c2cc(-c3cn4nc(OC)sc4n3)oc2c1]
399
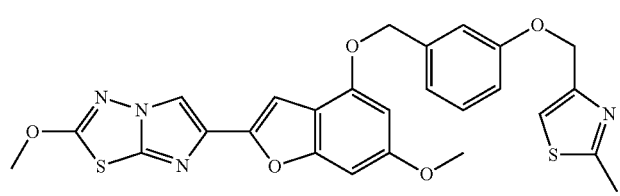

400 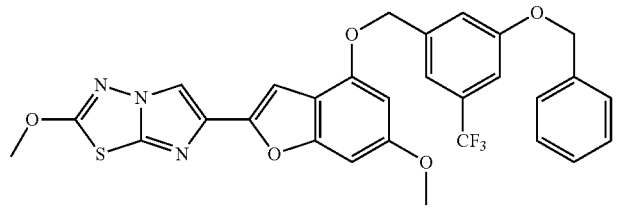 [SMILES: COc1cc(OCc2cc(OCc3ccccc3)cc(C(F)(F)F)c2)c2cc(-c3cn4nc(OC)sc4n3)oc2c1]
401 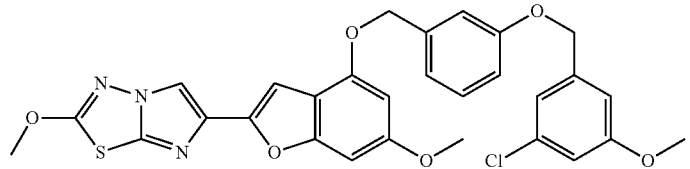
402 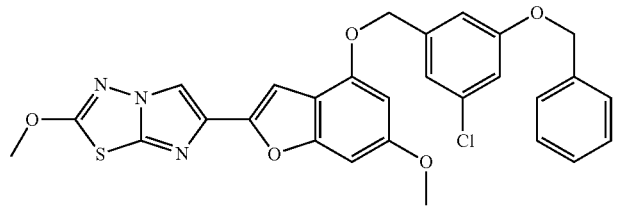 [SMILES: COc1cc(OCc2cc(Cl)cc(OCc3ccccc3)c2)c2cc(-c3cn4nc(OC)sc4n3)oc2c1]
403 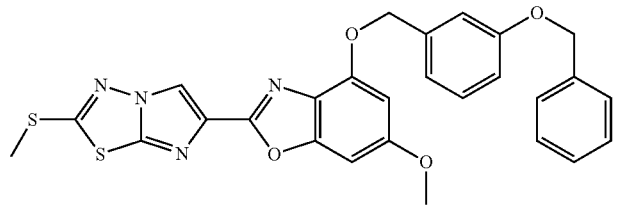 [SMILES: COc1cc(OCc2cccc(OCc3ccccc3)c2)c2nc(-c3cn4nc(SC)sc4n3)oc2c1]
404 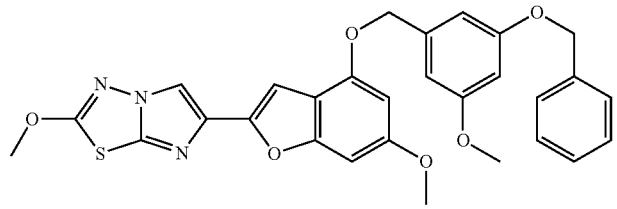 [SMILES: COc1cc(COc2cc(OC)cc3oc(-c4cn5nc(OC)sc5n4)cc23)cc(OCc2ccccc2)c1]
405 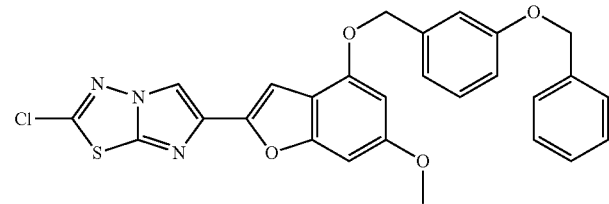 [SMILES: COc1cc(OCc2cccc(OCc3ccccc3)c2)c2cc(-c3cn4nc(Cl)sc4n3)oc2c1]
406 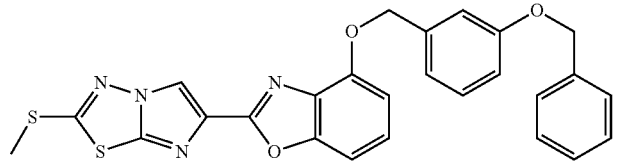 [SMILES: CSc1nn2cc(-c3nc4c(OCc5cccc(OCc6ccccc6)c5)cccc4o3)nc2s1]

407

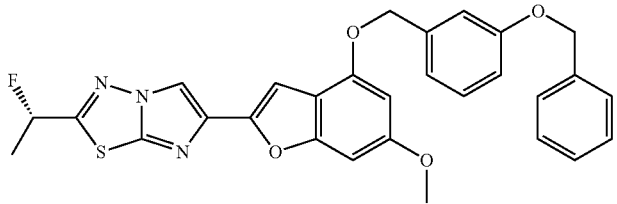 [SMILES: COc1cc(OCc2cccc(OCc3ccccc3)c2)c2cc(-c3cn4nc([C@H](C)F)sc4n3)oc2c1]

| Ex. | Experimental procedure | Formula | Exact Mass Or [M + H]+ | HPLC Retention Time (Min)/Method | LCMS [M + H]+ m/z | NMR |
|---|---|---|---|---|---|---|
| 344 | Ex. 203 | C27H20BrN3O4S | 562.0431 | 2.578/F | 562.0419 | 1H NMR (600 MHz, CDCl3) δ ppm: 8.03 (s, 1H), 7.42 (d, J = 7.7 Hz, 2H), 7.36 (t, J = 7.7 Hz, 2H), 7.29-7.32 (m, 2H), 7.14 (s, 1H), 7.09 (broad s, 1H), 7.05 (d, J = 7.5 Hz, 1H), 6.92 (dd, J = 8.2, 1.3 Hz, 1H), 6.67 (broad s, 1H), 6.36 (broad s, 1H), 5.14 (s, 2H), 5.06 (s, 2H), 3.82 (s, 3H). |
| 345 | Ex. 1 | C28H23N3O4S2 | 530.1203 | 2.592/F | 530.1195 | 1H NMR (600 MHz, CDCl3) δ ppm: 7.94 (s, 1H), 7.41 (d, J = 7.5 Hz, 2H), 7.26-7.40 (m, 4H), 7.11 (s, 1H), 7.09 (s, 1H), 7.04 (d, J = 7.5 Hz, 1H), 6.91 (d, J = 8.11, 1H), 6.67 (s, 1H), 6.36 (s, 1H), 5.13 (s, 2H), 5.06 (s, 2H), 3.81 (s, 3H), 2.74 (s, 3H). |
| 346 | Ex. 205 | C28H22FN3O5S | 532.1337 | 2.500/F | 532.1326 | 1H NMR (600 MHz, CDCl3) δ ppm: 7.82 (s, 1H), 7.38 (dd, J = 8.1, 5.64 Hz, 2H), 7.28 (t, J = 7.9 Hz, 1H), 7.02-7.07 (m, 5H), 6.89 (broad d, J = 8.2 Hz, 1H), 6.67 (broad s, 1H), 6.35 (broad s, 1H), 5.14 (s, 2H), 5.01 (s, 2H), 4.18 (s, 3H), 3.81 (s, 3H). |
| 347 | Ex. 207 | C29H23F2N3O4S | 548.1450 | 2.577/F | 548.1446 | 1H NMR (600 MHz, CDCl3) δ ppm: 8.04 (s, 1H), 7.41 (d, J = 7.25 Hz, 2H), 7.26-7.37 (m, 4H), 7.18 (s, 1H), 7.09 (s, 1H), 7.04 (d, J = 7.44 Hz, 1H), 6.91 (dd, J = 8.1, 2.1 Hz, 1H), 6.67 (broad d, 1H), 6.37 (d, J = 1.7 Hz, 1H), 5.14 (s, 2H), 5.06 (s, 2H), 3.82 (s, 3H), 2.17 (t, J = 18.36 Hz, 3H). |
| 348 | Ex. 9 | C29H25N3O5S | 528.1588 | 2.569/F | 528.1567 | 1H NMR (600 MHz, CDCl3) δ ppm: 7.80 (s, 1H), 7.42 (d, J = 7.5 Hz, 2H), 7.36 (t, J = 7.5 Hz, 2H), 7.27-7.31 (m, 2H), 7.09 (broad s, 1H), 7.06 (s, 1H), 7.04 (d, J = 7.63 Hz, 1H), 6.91 (dd, J = 8.17, 2.34 Hz, 1H), 6.67 (broad d, 1H), 6.36 (d, J = 1.84 Hz, 1H), 5.14 (s, 2H), 5.06 (s, 2H), 4.55 (q, J = 7.1 Hz, 2H), 3.81 (s, 3H), 1.49 (t, J = 7.1 Hz, 3H). |
| 349 | Ex. 205 | C28H22ClN3O5S | 548.1041 | 2.576/F | 548.1041 | 1N NMR (600 MHz, CDCl3) δ ppm: 7.82 (s, 1H), 7.43 (broad s, 1H), 7.26-7.31 (m, 4H), 7.05-7.08 (m, 3H), 6.91 (dd, J = 8.0, 2.0 Hz, 1H), 6.67 (broad d, 1H), 6.35 (d, J = 1.8 Hz, 1H), 5.14 (s, 2H), 5.03 (s, 2H), 4.19 (s, 3H), 3.81 (s, 3H). |
| 350 | Ex. 205 | C28H22FN3O5S | 532.1337 | 2.531/F | 532.1329 | 1H NMR (600 MHz, CDCl3) δ ppm: 7.83 (s, 1H), 7.41 (d, J = 7.3 Hz, 2H), 7.37 (t, J = 7.3 Hz, 2H), 7.24-7.33 (m, 1H), 7.06 (s, 1H), 6.87 (broad s, 1H), 6.78 (broad d, J = 8.8 Hz, 1H), 6.68 (broad d, 1H), 6.62 (dt, J = 10.5, 2.2 Hz, 1H), 6.32 (d, J = 1.8 Hz, 1H), 5.11 (s, 2H), 5.04 (s, 2H), 4.18 (s, 3H), 3.81 (s, 3H). |

| | | | | | | |
|---|---|---|---|---|---|---|
| 351 | Ex. 205 | C$_{29}$H$_{25}$N$_3$O$_6$S | 544.1537 | 2.434/ F | 544.1568 | $^1$H NMR (600 MHz, CDCl$_3$) δ ppm: 7.81 (s, 1H), 7.41 (d, J = 7.5 Hz, 2H), 7.33 (t, J = 7.5 Hz, 2H), 7.25-7.27 (m, 1H), 6.99-7.01 (m, 3H), 6.87 (d, J = 7.9 Hz, 1H), 6.66 (broad d, 1H), 6.33 (d, J = 1.88 Hz, 1H), 5.13 (s, 2H), 5.04 (s, 2H), 4.18 (s, 3H), 3.87 (s, 3H), 3.80 (s, 3H). |
| 352 | Ex. 205 | C$_{29}$H$_{25}$N$_3$O$_5$S | 528.1588 | 2.603/F | 528.1613 | $^1$H NMR (600 MHz, CDCl$_3$) δ ppm: 7.81 (s, 1H), 7.42 (d, J = 7.5 Hz, 2H), 7.35 (t, J = 7.5 Hz, 2H), 7.27-7.30 (m, 1H), 7.15 (d, J = 7.6 Hz, 1H), 7.04 (s, 1H), 6.99 (s, 1H), 6.95 (d, J = 7.6 Hz, 1H), 6.66 (broad d, 1H), 6.36 (d, J = 1.87 Hz, 1H), 5.11 (s, 2H), 5.07 (s, 2H), 4.18 (s, 3H), 3.80 (s, 3H), 2.27 (s, 3H). |
| 353 | Ex. 205 | C$_{30}$H$_{27}$N$_3$O$_7$S | 574.1642 | 2.471/F | 574.1672 | $^1$H NMR (600 MHz, CDCl$_3$) δ ppm: 7.82 (s, 1H), 7.29 (t, J = 7.9 Hz, 1H), 7.11 (s, 1H), 7.09 (s, 1H), 7.04-7.06 (m, 3H), 6.93 (dd, J = 8.0, 1.7 Hz, 1H), 6.88 (t, J = 4.8 Hz, 1H), 6.65 (broad s, 1H), 6.36 (d, J = 1.1 Hz, 1H), 5.15 (s, 2H), 5.11 (s, 2H), 4.20 (s, 3H), 3.85 (s, 6H), 3.81 (s, 3H). |
| 354 | Ex. 205 | C$_{29}$H$_{25}$N$_3$O$_6$S | 544.1537 | 2.518/F | 544.1639 | $^1$H NMR (600 MHz, CDCl$_3$) δ ppm: 7.82 (s, 1H), 7.41 (d, J = 7.5 Hz, 2H), 7.36 (t, J = 7.5 Hz, 2H), 7.29-7.31 (m, 1H), 7.06 (s, 1H), 6.69 (s, 1H), 6.67 (s, 1H), 6.62 (s, 1H), 6.47 (s, 1H), 6.34 (s, 1H), 5.10 (s, 2H), 5.03 (s, 2H), 4.18 (s, 3H), 3.81 (s, 3H), 3.77 (s, 3H). |
| 355 | Ex. 205 | C$_{28}$H$_{21}$N$_3$O$_6$S | 528.1224 | 2.484/F | 528.1228 | $^1$H NMR (600 MHz, CDCl$_3$) δ ppm: 8.20 (d, J = 7.3 Hz, 2H), 7.81 (s, 1H), 7.62 (t, J = 7.5 Hz, 1H), 7.50 (t, J = 7.8 Hz, 2H), 7.43 (t, J = 7.8 Hz, 1H), 7.36 (d, J = 7.8 Hz, 1H), 7.34 (s, 1H), 7.17 (d, J = 8.0 Hz, 1H), 7.07 (s, 1H), 6.68 (s, 1H), 6.37 (d, J = 1.49 Hz, 1H), 5.20 (s, 2H), 4.18 (s, 3H), 3.82 (s, 3H). |
| 356 | Ex. 205 | C$_{29}$H$_{21}$F$_4$N$_3$O$_5$S | 600.1211 | 2.570/F | 600.105 | $^1$N NMR (600 MHz, CDCl$_3$) δ ppm: 7.76 (s, 1H), 7.42 (s, 1H), 7.29 (d, J = 8.9 Hz, 1H), 7.24 (t, J = 7.8 Hz, 1H), 7.19 (d, J = 8.4 Hz, 1H), 7.01-7.03 (m, 3H), 6.83 (dd, J = 8.2, 2.0 Hz, 1H), 6.61 (s, 1H), 6.29 (d, J = 1.69 Hz, 1H), 5.09 (s, 2H), 5.03 (s, 2H), 4.12 (s, 3H), 3.75 (s, 3H). |
| 357 | Ex. 205 | C$_{36}$H$_{31}$N$_3$O$_7$S | 650.1955 | 2.614/F | 650.1969 | $^1$H NMR (600 MHz, CDCl$_3$) δ ppm: 7.86 (s, 1H), 7.42-7.46 (m, 2H), 7.34-7.40 (m, 2H), 7.28-7.34 (m, 2H), 7.16 (s, 1H), 7.11 (broad s, 1H), 7.08 (d, J = 7.6 Hz, 1H), 7.01 (d, J = 1.76 Hz, 1H), 6.95 (dd, J = 8.06, 2.2 Hz, 1H), 6.91 (dd, J = 8.2, 1.76 Hz, 1H), 6.87 (d, J = 8.2 Hz, 1H), 6.69 (broad d, 1H), 6.38 (d, J = 1.76 Hz, 1H), 5.18 (s, 2H), 5.17 (s, 2H), 5.0 (s, 2H), 4.23 (s, 3H), 3.90 (s, 3H), 3.84 (s, 3H). |
| 358 | Ex. 205 | C$_{27}$H$_{20}$ClN$_3$O$_4$S | 518.0936 | 2.633/F | 518.0934 | $^1$H NMR (400 MHz, CDCl$_3$) δ ppm: 8.0 (s, 1H), 7.26-7.43 (m, 6H), 7.14 (s, 1H), 7.09 (s, 1H), 7.04 (d, J = 7.1 Hz, 1H), 6.92 (d, J = 8.3 Hz, 1H), 6.66 (s, 1H), 6.36 (s, 1H), 5.13 (s, 2H), 5.06 (s, 2H), 3.81 (s, 3H). |

-continued

| | | | | | | |
|---|---|---|---|---|---|---|
| 359 | Ex. 205 | $C_{31}H_{29}ClN_3O_6S$ | 572.185 | 2.646/F | 572.1859 | $^1$H NMR (400 MHz, CDCl$_3$) δ ppm: 7.87 (broad s, 1H), 7.33 (t, J = 8.2 Hz, 1H), 7.21 (d, J = 8.6 Hz, 1H), 7.20 (broad s, 1H), 7.13 (broad s, 1H), 7.09 (d, J = 7.4 Hz, 1H), 6.95-6.99 (m, 1H), 6.72 (d, J = 8.2 Hz, 1H), 6.70 (broad s, 1H), 6.41 (s, 1H), 5.19 (s, 2H), 5.01 (s, 2H), 4.24 (s, 3H), 3.85 (s, 3H), 3.83 (s, 3H), 2.29 (s, 3H). 2.20 (s, 3H). |
| 360 | Ex. 205 | $C_{28}H_{22}BrN_3O_5S$ | 592.0536 | 2.649/F | 592.0543 | $^1$H NMR (400 MHz, CDCl$_3$) δ ppm: 7.85 (broad s, 1H), 7.55-7.6 (m, 2H), 7.30-7.40 (m, 2H), 7.16-7.22 (m, 1H), 7.14 (broad s, 1H), 7.11 (d, J = 7.8 Hz, 1H), 6.95 (dd, J = 8.0, 2.0 Hz, 1H), 6.73 (broad s, 1H), 6.4 (s, 1H), 5.19 (s, 2H), 5.17 (s, 2H), 4.22 (s, 3H), 3.85 (s, 3H). |
| 361 | Ex. 205 | $C_{30}H_{26}ClN_3O_7S$ | 608.1253 | 2.534/F | 608.1271 | $^1$H NMR (400 MHz, CDCl$_3$) δ ppm: 7.86 (s, 1H), 7.33 (t, J = 8.0 Hz, 1H), 7.24-7.27 (m, 1H), 7.16 (s, 1H), 7.13 (broad s, 1H), 7.10 (d, J = 7.5 Hz, 1H), 6.96 (dd, J = 7.8, 2.4 Hz, 1H), 6.86 (d, J = 8.6 Hz, 1H), 6.69 (broad d, 1H), 6.4 (d, J = 1.96 Hz, 1H), 5.19 (s, 2H), 5.13 (s, 2H), 4.23 (s, 3H), 3.90 (s, 3H), 3.89 (s, 3H), 3.85 (s, 3H). |
| 362 | Ex. 205 | $C_{28}H_{22}ClN_3O_5S$ | 548.1041 | 2.611/F | 548.1055 | $^1$H NMR (400 MHz, CDCl$_3$) δ ppm: 7.82 (s, 1H), 7.54 (dd, J = 7.2, 2.0 Hz, 1H), 7.36 (dd, J = 7.1, 2.0 Hz, 1H), 7.24-7.31 (m, 3H), 7.06-7.10 (m, 3H), 6.92 (dd, J = 8.0, 2.4 Hz, 1H), 6.67 (broad d, 1H), 6.35 (d, J = 1.75 Hz, 1H), 5.17 (s, 2H), 5.14 (s, 2H), 4.18 (s, 3H), 3.81 (s, 3H). |
| 363 | Ex. 205 | $C_{29}H_{25}N_3O_5S$ | 528.1588 | 2.573/F | 528.1599 | $^1$H NMR (400 MHz, CDCl$_3$) δ ppm: 7.81 (s, 1H), 7.39 (dd, J = 6.0, 2.0 Hz, 1H), 7.27-7.31 (m, 1H), 7.16-7.22 (m, 3H), 6.97-7.10 (m, 3H), 6.92 (d, J = 7.9 Hz, 1H), 6.67 (broad s, 1H), 6.36 (broad s, 1H), 5.14 (s, 2H), 5.03 (s, 2H), 4.17 (s, 3H), 3.80 (s, 3H), 2.35 (s, 3H). |
| 364 | Ex. 205 | $C_{36}H_{31}N_3O_5S$ | 618.2057 | 2.740/F | 618.2067 | $^1$H NMR (400 MHz, CDCl$_3$) δ ppm: 7.74 (s, 1H), 7.33 (dd, J = 8.0, 2.0 Hz, 1H), 7.0-7.3 (m, 12H), 6.82 (dd, J = 8.0, 2.0 Hz, 1H), 6.6 (broad s, 1H), 6.3 (broad s, 1H), 5.08 (s, 2H), 4.9 (s, 2H), 4.12 (s, 3H), 3.74 (s, 3H), 2.84-2.92 (m, 4H). |
| 365 | Ex. 205 | $C_{28}H_{21}Cl_2N_3O_5S$ | 582.0652 | 2.650/F | 582.0655 | $^1$H NMR (400 MHz, CDCl$_3$) δ ppm: 7.82 (s, 1H), 7.51 (d, J = 2.0 Hz, 1H), 7.4 (d, J = 8.2 Hz, 1H), 7.19-7.24 (m, 2H), 7.0-7.06 (m, 3H), 6.87 (dd, J = 7.5, 1.8 Hz, 1H), 6.66 (broad d, 1H), 6.34 (d, J = 1.7 Hz, 1H), 5.14 (s, 2H), 5.0 (s, 2H), 4.18 (s, 3H), 3.81 (s, 3H). |
| 366 | Ex. 205 | $C_{35}H_{29}N_3O_6S$ | 620.185 | 2.630/F | 620.1856 | $^1$H NMR (400 MHz, CDCl$_3$) δ ppm: 7.83 (broad s, 1H), 7.28-7.47 (m, 8H), 7.17 (broad s, 1H), 7.11 (s, 1H), 7.07 (d, J = 7.8 Hz, 1H), 6.96-7.03 (m, 2H), 6.94 (dd, J = 8.2, 2.5 Hz, 1H), 6.70 (broad s, 1H), 6.39 (s, 1H), 5.18 (s, 2H), 5.08 (s, 2H), 5.01 (s, 2H), 4.23 (s, 3H), 3.84 (s, 3H). |

| | | | | | | |
|---|---|---|---|---|---|---|
| 367 | Ex. 205 | C$_{29}$H$_{24}$BrN$_3$O$_6$S | 622.0642 | 2.616/A | 622.0647 | $^1$H NMR (400 MHz, CDCl$_3$) δ ppm: 7.82 (s, 1H), 7.56 (d, J = 2.4 Hz, 1H), 7.34 (dd, J = 8.7, 2.4 Hz, 1H), 7.26-7.31 (m, 1H), 7.1 (s, 1H), 6.96-7.07 (m, 2H), 6.92 (dd, J = 8.4, 2.4 Hz, 1H), 6.73 (d, J = 8.7 Hz, 1H), 6.66 (broad d, 1H), 6.35 (d, J = 1.75 Hz, 1H), 5.15 (s, 2H), 5.05 (s, 2H), 4.19 (s, 3H), 3.81 (s, 3H), 3.80 (s, 3H). |
| 368 | Ex. 205 | C$_{28}$H$_{21}$Cl$_2$N$_3$O$_5$S | 582.0652 | 2.582/F | 582.068 | $^1$H NMR (400 MHz, CDCl$_3$) δ ppm: 7.81 (s, 1H), 7.25-7.35 (m, 3H), 7.19-7.22 (m, 1H), 7.09-7.12 (m, 3H), 6.97 (dd, J = 8.1, 2 Hz, 1H), 6.66 (broad d, 1H), 6.37 (d, J = 1.9 Hz, 1H), 5.27 (s, 2H), 5.16 (s, 2H), 4.19 (s, 3H), 3.81 (s, 3H). |
| 369 | Ex. 205 | C$_{28}$H$_{21}$ClFN$_3$O$_5$S | 566.0947 | 2.599/F | 566.0979 | $^1$H NMR (400 MHz, CDCl$_3$) δ ppm: 7.82 (broad s, 1H), 7.50 (dd, J = 6.0, 3.0 Hz, 1H), 7.28-7.32 (m, 1H), 7.06-7.13 (m, 4H), 6.97 (dt, J = 8.2, 2.5 Hz, 1H), 6.90 (dd, J = 8.0, 2.0 Hz, 1H), 6.66 (s, 1H), 6.35 (s, 1H), 5.15 (s, 2H), 5.11 (s, 2H), 4.19 (s, 3H), 3.81 (s, 3H). |
| 370 | Ex. 205 | C$_{28}$H$_{21}$ClFN$_3$O$_5$S | 566.0947 | 2.528/F | 566.0983 | $^1$H NMR (400 MHz, CDCl$_3$) δ ppm: 7.82 (broad s, 1H), 7.25-7.33 (m, 3H), 6.95-7.15 (m, 5H), 6.66 (broad s, 1H), 6.37 (d, J = 1.4 Hz, 1H), 5.18 (s, 2H), 5.16 (s, 2H), 4.20 (s, 3H), 3.81 (s, 3H). |
| 371 | Ex. 205 | C$_{34}$H$_{35}$N$_3$O$_7$S | 630.2268 | 2.669/F | 630.2311 | $^1$H NMR (400 MHz, CDCl$_3$) δ ppm: 7.83 (broad s, 1H), 7.25-7.30 (m, 1H), 7.14 (broad s, 1H), 6.97-7.07 (m, 2H), 6.90 (dd, J = 8.0, 1.5 Hz, 1H), 6.66 (broad s, 1H), 6.53 (s, 1H), 6.52 (s, 1H), 6.35-6.36 (m, 2H), 5.14 (s, 2H), 4.97 (s, 2H), 4.47-4.53 (m, 2H), 4.20 (s, 3H), 3.81 (s, 3H), 1.29 (d, J = 6.1 Hz, 12H). |
| 372 | Ex. 205 | C$_{34}$H$_{27}$N$_3$O$_6$S | 606.1693 | 2.654/F | 606.1723 | $^1$H NMR (400 MHz, CDCl$_3$) δ ppm: 7.8 (broad s, 1H), 7.38 (d, J = 8.6 Hz, 2H), 7.29-7.31 (m, 3H), 7.14 (broad s, 1H), 7.05-7.10 (m, 3H), 6.97-7.01 (m, 4H), 6.92 (dd, J = 8.4, 1.7 Hz, 1H), 6.67 (broad s, 1H), 6.36 (s, 1H), 5.16 (s, 2H), 5.02 (s, 2H), 4.20 (s, 3H), 3.81 (s, 3H). |
| 373 | Ex. 205 | C$_{36}$H$_{31}$N$_3$O$_7$S | 650.1955 | 2.644/F | 650.1979 | $^1$H NMR (400 MHz, CDCl$_3$) δ ppm: 7.81 (s, 1H), 7.26-7.40 (m, 6H), 7.14 (s, 1H), 7.04-7.06 (m, 2H), 6.90 (dd, J = 8.6, 2.0 Hz, 1H), 6.65 (broad s, 2H), 6.58 (broad d, 1H), 6.45 (t, J = 2.2 Hz, 1H), 6.35 (d, J = 1.9 Hz, 1H), 5.15 (s, 2H), 5.01 (s, 2H), 5.0 (s, 2H), 4.20 (s, 3H), 3.80 (s, 3H), 3.75 (s, 3H). |
| 374 | Ex. 205 | C$_{28}$H$_{21}$F$_2$N$_3$O$_5$S | 550.1243 | 2.514/F | 550.1284 | $^1$H NMR (400 MHz, CDCl$_3$) δ ppm: 7.83 (s, 1H), 7.42-7.47 (m, 1H), 7.25-7.30 (m, 1H), 7.19 (s, 1H), 7.06-7.08 (m, 2H), 6.77-6.93 (m, 3H), 6.65 (broad d, 1H), 6.34 (d, J = 1.9 Hz, 1H), 5.16 (s, 2H), 5.07 (s, 2H), 4.22 (s, 3H), 3.81 (s, 3H). |
| 375 | Ex. 205 | C$_{35}$H$_{28}$ClN$_3$O$_6$S | 654.146 | 2.728/F | 654.1487 | $^1$H NMR (400 MHz, CDCl$_3$) δ ppm: 7.81 (s, 1H), 7.34 (s, 1H), 7.26-7.30 (m, 5H), 7.14 (s, 1H), 7.0-7.07 (m, 4H), 6.86-6.92 (m, 2H), 6.65 (broad s, 1H), 6.35 (d, J = 1.6 Hz, 1H), 5.15 (s, 2H), 5.04 (s, 2H), 5.0 (s, 2H), 4.20 (s, 3H), 3.80 (s, 3H). |

| | | | | | | |
|---|---|---|---|---|---|---|
| 376 | Ex. 205 | C$_{28}$H$_{21}$Cl$_2$N$_3$O$_5$S | 582.0652 | 2.713/F | 582.065 | $^1$H NMR (400 MHz, CDCl$_3$) δ ppm: 7.83 (s, 1H), 7.29-7.33 (m, 4H), 7.07-7.09 (m, 3H), 6.88-6.91 (m, 1H), 6.68 (broad d, 1H), 6.36 (d, J = 1.9 Hz, 1H), 5.16 (s, 2H), 5.01 (s, 2H), 4.20 (s, 3H), 3.82 (s, 3H). |
| 377 | Ex. 205 | C$_{31}$H$_{29}$N$_3$O$_5$S | 556.1901 | 2.676/F | 556.1908 | $^1$H NMR (400 MHz, CDCl$_3$) δ ppm: 7.83 (s, 1H), 7.32 (t, J = 8.16 Hz, 1H), 7.08-7.11 (m, 3H), 6.95-6.98 (m, 1H), 6.89 (s, 2H), 6.68 (broad d, 1H), 6.39 (d, J = 1.7 Hz, 1H), 5.17 (s, 2H), 5.01 (s, 2H), 4.20 (s, 3H), 3.83 (s, 3H), 2.35 (s, 6H), 2.28 (s, 3H). |
| 378 | Ex. 205 | C$_{28}$H$_{21}$Cl$_2$N$_3$O$_5$S | 582.0652 | 2.731/F | 582.0658 | $^1$H NMR (400 MHz, CDCl$_3$) δ ppm: 7.84 (broad s, 1H), 7.48 (d, J = 8.4 Hz, 1H), 7.38 (d, J = 2.0 Hz, 1H), 7.24-7.33 (m, 2H), 7.16 (s, 1H), 7.08-7.09 (m, 2H), 6.90-6.92 (m, 1H), 6.67 (broad d, 1H), 6.36 (d, J = 1.75 Hz, 1H), 5.17 (s, 2H), 5.13 (s, 2H), 4.22 (s, 3H), 3.82 (s, 3H). |
| 379 | Ex. 205 | C$_{28}$H$_{22}$IN$_3$O$_5$S | 640.0398 | 2.685/F | 640.0402 | $^1$H NMR (400 MHz, CDCl$_3$) δ ppm: 7.85 (s, 1H), 7.83 (s, 1H), 7.52 (d, J = 7.5 Hz, 1H), 7.30-7.37 (m, 2H), 7.13 (broad s, 2H), 6.99-7.10 (m, 2H), 6.93 (dd, J = 8.2, 2.6 Hz, 1H), 6.68 (broad s, 1H), 6.37 (broad s, 1H), 5.17 (s, 2H), 5.06 (s, 2H), 4.20 (s, 3H), 3.83 (s, 3H). |
| 380 | Ex. 205 | C$_{31}$H$_{29}$N$_3$O$_8$S | 604.1748 | 2.424/F | 604.1769 | $^1$H NMR (400 MHz, CDCl$_3$) δ ppm: 7.85 (s, 1H), 7.28-7.33 (m, 1H), 7.16 (s, 1H), 7.11 (d, J = 2.1 Hz, 1H), 7.08 (d, J = 7.7 Hz, 1H), 6.94 (dd, J = 8.3, 2.0 Hz, 1H), 6.66-6.67 (m, 3H), 6.37 (d, J = 1.9 Hz, 1H), 5.17 (s, 2H), 4.99 (s, 2H), 4.22 (s, 3H), 3.85 (s, 6H), 3.84 (s, 3H), 3.83 (s, 3H). |
| 381 | Ex. 205 | C$_{30}$H$_{27}$N$_3$O$_5$S | 542.1744 | 2.642/F | 542.1762 | $^1$H NMR (400 MHz, CDCl$_3$) δ ppm: 7.82 (s, 1H), 7.26-7.30 (m, 1H), 7.19 (s, 1H), 7.03-7.15 (m, 5H), 6.90 (dd, J = 8.1, 2.3 Hz, 1H), 6.66 (broad d, 1H), 6.35 (d, J = 1.5 Hz, 1H), 5.16 (s, 2H), 4.98 (s, 2H), 4.19 (s, 3H), 3.81 (s, 3H), 2.25 (s, 3H), 2.24 (s, 3H). |
| 382 | Ex. 205 | C$_{30}$H$_{27}$N$_3$O$_5$S | 542.1744 | 2.652/F | 542.176 | $^1$H NMR (400 MHz, CDCl$_3$) δ ppm: 7.82 (broad s, 1H), 7.26-7.30 (m, 1H), 7.03-7.15 (m, 5H), 6.91-6.95 (m, 2H), 6.68 (broad s, 1H), 6.35 (broad s, 1H), 5.15 (s, 2H), 4.99 (s, 2H), 4.20 (s, 3H), 3.82 (s, 3H), 2.31 (s, 6H). |
| 383 | Ex. 205 | C$_{35}$H$_{29}$N$_3$O$_6$S | 620.185 | 2.643/F | 620.1857 | $^1$H NMR (400 MHz, CDCl$_3$) δ ppm: 7.82 (s, 1H), 7.25-7.42 (m, 7H), 7.15 (s, 1H), 6.98-7.08 (m, 4H), 6.90-6.94 (m, 2H), 6.66 (broad s, 1H), 6.36 (d, J = 1.7 Hz, 1H), 5.16 (s, 2H), 5.05 (s, 4H), 4.21 (s, 3H), 3.82 (s, 3H). |
| 384 | Ex. 205 | C$_{34}$H$_{27}$N$_3$O$_6$S | 606.1693 | 2.654/F | 606.1694 | $^1$H NMR (400 MHz, CDCl$_3$) δ ppm: 7.82 (s, 1H), 7.26-7.32 (m, 4H), 7.04-7.16 (m, 6H), 6.97-7.0 (m, 2H), 6.87-6.93 (m, 2H), 6.65 (broad s, 1H), 6.35 (d, J = 1.1 Hz, 1H), 5.14 (s, 2H), 5.03 (s, 2H), 4.20 (s, 3H), 3.80 (s, 3H). |

| | | | | | | |
|---|---|---|---|---|---|---|
| 385 | Ex. 205 | C$_{29}$H$_{21}$F$_4$N$_3$O$_5$S | 600.1211 | 2.585/F | 600.1218 | $^1$H NMR (400 MHz, CDCl$_3$) δ ppm: 7.82 (broad s, 1H), 7.70 (dd, J = 8.5, 5.2 Hz, 1H), 7.35 (dd, J = 8.95, 2.6 Hz, 1H), 7.24-7.32 (m, 2H), 7.06-7.09 (m, 3H), 6.87 (dd, J = 7.4, 2.3 Hz, 1H), 6.67 (broad s, 1H), 6.33 (broad s, 1H), 5.21 (s, 2H), 5.14 (s, 2H), 4.19 (s, 3H), 3.81 (s, 3H). |
| 386 | Ex. 205 | C$_{29}$H$_{25}$N$_3$O$_5$S | 528.1588 | 2.592/F | 528.1595 | $^1$H NMR (400 MHz, CDCl$_3$) δ ppm: 7.83 (s, 1H), 7.21-7.31 (m, 4H), 7.10-7.13 (m, 2H), 7.08 (s, 1H), 7.06 (d, J = 7.6 Hz, 1H), 6.92 (dd, J = 8.23, 2.52 Hz, 1H), 6.68 (broad d, 1H), 6.37 (d, J = 1.8 Hz, 1H), 5.15 (s, 2H), 5.03 (s, 2H), 4.19 (s, 3H), 3.82 (s, 3H), 2.36 (s, 3H). |
| 387 | Ex. 205 | C$_{36}$H$_{31}$N$_3$O$_5$S | 618.2057 | 2.818/F | 618.2062 | $^1$H NMR (400 MHz, CDCl$_3$) δ ppm: 7.77 (s, 1H), 7.0-7.20 (m, 11H), 6.95 (broad s, 1H), 6.89 (d, J = 7.6 Hz, 1H), 6.84 (dd, J = 8.2, 2.5 Hz, 1H), 6.76 (s, 1H), 5.12 (s, 2H), 4.87 (s, 2H), 4.12 (s, 3H), 4.01 (s, 2H), 3.75 (s, 3H), 2.28 (s, 3H). |
| 388 | Ex. 205 | C$_{30}$H$_{27}$N$_3$O$_7$S | 574.1642 | 2.469/F | 574.166 | $^1$H NMR (400 MHz, CDCl$_3$) δ ppm: 7.82 (s, 1H), 7.27-7.31 (m, 2H), 7.16 (broad s, 1H), 7.07 (s, 1H), 7.04 (d, J = 7.8 Hz, 1H), 7.0 (dd, J = 8.05, 2.2 Hz, 1H), 6.68 (broad d, 1H), 6.59 (s, 1H), 6.56 (s, 1H), 6.39 (d, J = 1.8 Hz, 1H), 5.15 (s, 2H), 5.14 (s, 2H), 4.19 (s, 3H), 3.82 (s, 3H), 3.82 (s, 6H). |
| 389 | Ex. 205 | C$_{30}$H$_{27}$N$_3$O$_7$S | 574.1642 | 2.437/F | 574.165 | $^1$H NMR (400 MHz, CDCl$_3$) δ ppm: 7.83 (s, 1H), 7.27-7.31 (m, 1H), 7.11 (broad s, 1H), 7.08 (s, 1H), 7.05 (d, J = 7.7 Hz, 1H), 6.97-6.98 (m, 2H), 6.93 (dd, J = 8.3, 2.3 Hz, 1H), 6.86 (d, J = 8.7 Hz, 1H), 6.68 (broad d, 1H), 6.37 (d, J = 1.9 Hz, 1H), 5.15 (s, 2H), 5.00 (s, 2H), 4.20 (s, 3H), 3.89 (s, 3H), 3.88 (s, 3H), 3.82 (s, 3H). |
| 390 | Ex. 205 | C$_{30}$H$_{27}$N$_3$O$_7$S | 574.1642 | 2.502/F | 574.1656 | $^1$H NMR (400 MHz, CDCl$_3$) δ ppm: 7.83 (s, 1H), 7.27-7.31 (m, 1H), 6.98-7.09 (m, 3H), 6.92 (dd, J = 8.3, 2.5 Hz, 1H), 6.68 (broad d, 1H), 6.59 (s, 1H), 6.58 (s, 1H), 6.40 (t, J = 2.2 Hz, 1H), 6.37 (d, J = 1.9 Hz, 1H), 5.15 (s, 2H), 5.01 (s, 2H), 4.19 (s, 3H), 3.82 (s, 3H), 3.78 (s, 6H). |
| 391 | Ex. 205 | C$_{28}$H$_{22}$IN$_3$O$_5$S | 640.0398 | 2.645/F | 640.0407 | $^1$H NMR (400 MHz, CDCl$_3$) δ ppm: 7.82 (s, 1H), 7.66-7.69 (m, 2H), 7.25-7.29 (m, 1H), 7.14-7.16 (m, 2H), 7.09 (s, 1H), 7.03-7.06 (m, 2H), 6.87 (dd, J = 8.2, 2.3 Hz, 1H), 6.66 (broad d, 1H), 6.34 (d, J = 1.9 Hz, 1H), 5.14 (s, 2H), 5.0 (s, 2H), 4.19 (s, 3H), 3.81 (s, 3H). |
| 392 | Ex. 205 | C$_{29}$H$_{25}$N$_3$O$_6$S | 544.1537 | 2.494/A | 544.1541 | $^1$H NMR (400 MHz, CDCl$_3$) δ ppm: 7.82 (s, 1H), 7.32-7.36 (m, 2H), 7.25-7.29 (m, 1H), 7.10 (s, 1H), 7.08 (broad s, 1H), 7.03 (d, J = 7.5 Hz, 1H), 6.87-6.92 (m, 3H), 6.66 (broad d, 1H), 6.35 (d, J = 1.9 Hz, 1H), 5.14 (s, 2H), 4.98 (s, 2H), 4.19 (s, 3H), 3.81 (s, 3H), 3.79 (s, 3H). |

| | | | | | | |
|---|---|---|---|---|---|---|
| 393 | Ex. 205 | C$_{32}$H$_{31}$N$_3$O$_5$S | 570.2057 | 2.736/F | 570.2064 | $^1$H NMR (400 MHz, CDCl$_3$) δ ppm: 7.82 (s, 1H), 7.34-7.39 (m, 4H), 7.26-7.30 (m, 1H), 7.15 (s, 1H), 7.09 (broad s, 1H), 7.04 (d, J = 7.9 Hz, 1H), 6.91-6.93 (m, 1H), 6.65 (broad s, 1H), 6.36 (broad s, 1H), 5.15 (s, 2H), 5.01 (s, 2H), 4.20 (s, 3H), 3.81 (s, 3H), 1.3 (s, 9H). |
| 394 | Ex. 205 | C$_{29}$H$_{22}$F$_3$N$_3$O$_6$S | 598.1254 | 2.560/F | 598.1274 | $^1$H NMR (400 MHz, CDCl$_3$) δ ppm: 7.84 (s, 1H), 7.44-7.47 (m, 2H), 7.29-7.33 (m, 1H), 7.20-7.23 (m, 2H), 7.13 (s, 1H), 7.09 (d, J = 1.7 Hz, 1H), 7.07 (d, J = 8.0 Hz, 1H), 6.91 (dd, J = 8.2, 2.35 Hz, 1H), 6.67 (broad d, 1H), 6.36 (d, J = 1.9 Hz, 1H), 5.16 (s, 2H), 5.06 (s, 2H), 4.21 (s, 3H), 3.82 (s, 3H). |
| 395 | Ex. 205 | C$_{35}$H$_{28}$FN$_3$O$_6$S | 638.1756 | 2.653/F | 638.1771 | $^1$H NMR (400 MHz, CDCl$_3$) δ ppm: 7.82 (s, 1H), 7.25-7.49 (m, 6H), 7.14 (s, 1H), 7.05-7.07 (m, 2H), 6.88 (dd, J = 8.0, 2.0 Hz, 1H), 6.83 (s, 1H), 6.72 (d, J = 8.4 Hz, 1H), 6.65 (broad d, 1H), 6.56-6.61 (m, 1H), 6.34 (d, J = 1.7 Hz, 1H), 5.15 (s, 2H), 5.01 (s, 2H), 5.01 (s, 2H), 4.20 (s, 3H), 3.80 (s, 3H). |
| 396 | Ex. 205 | C$_{30}$H$_{24}$F$_3$N$_3$O$_5$S | 596.1462 | 2.570/F | 596.1481 | $^1$H NMR (400 MHz, CDCl$_3$) δ ppm: 7.84 (s, 1H), 7.69 (s, 1H), 7.48 (d, J = 6.7 Hz, 1H), 7.27-7.35 (m, 2H), 7.15 (s, 1H), 7.09-7.11 (m, 2H), 6.95 (dd, J = 8.2, 2.0 Hz, 1H), 6.67 (broad d, 1H), 6.37 (d, J = 1.6 Hz, 1H), 5.18 (s, 2H), 5.02 (s, 2H), 4.21 (s, 3H), 3.82 (s, 3H), 2.41 (s, 3H). |
| 397 | Ex. 205 | C$_{35}$H$_{28}$N$_4$O$_6$S | 633.1802 | 2.440/F | 633.1817 | $^1$H NMR (400 MHz, CDCl$_3$) δ ppm: 8.17 (broad s, 1H), 7.81-7.83 (m, 3H), 7.63-7.65 (m, 2H), 7.42-7.53 (m, 3H), 7.27-7.35 (m, 2H), 7.18 (d, J = 7.8 Hz, 1H), 7.13 (s, 1H), 7.05 (d, J = 1.6 Hz, 1H), 7.03 (d, J = 7.5 Hz, 1H), 6.94 (dd, J = 8.1, 2.4 Hz, 1H), 6.64 (broad d, 1H), 6.34 (d, J = 1.8 Hz, 1H), 5.15 (s, 2H), 5.12 (s, 2H), 4.22 (s, 3H), 3.81 (s, 3H). |
| 398 | Ex. 205 | C$_{27}$H$_{22}$N$_4$O$_5$S | 515.1384 | 2.166/F | 515.1432 | $^1$H NMR (400 MHz, DMSO-d6) δ ppm: 8.64 (d, J = 1.9 Hz, 1H), 8.50 (dd, J = 4.6, 1.2 Hz, 1H), 8.34 (s, 1H), 7.82-7.85 (m, 1H), 7.39 (dd, J = 7.4, 4.8 Hz, 1H), 7.30 (t, J = 8.0 Hz, 1H), 7.13 (broad s, 1H), 7.06 (d, J = 7.6 Hz, 1H), 6.97 (dd, J = 8.2, 2.5 Hz, 1H), 6.94 (s, 1H), 6.79 (broad d, 1H), 6.47 (d, J = 1.7 Hz, 1H), 5.19 (s, 2H), 5.14 (s, 2H), 4.16 (s, 3H), 3.75 (s, 3H). |
| 399 | Ex. 205 | C$_{26}$H$_{22}$N$_4$O$_5$S$_2$ | 535.1104 | 2.385/F | 535.1132 | $^1$H NMR (400 MHz, CDCl$_3$) δ ppm: 7.82 (s, 1H), 7.28 (t, J = 7.9 Hz, 1H), 7.13 (s, 1H), 7.10 (broad s, 1H), 7.04-7.06 (m, 2H), 6.92 (dd, J = 8.3, 2.5 Hz, 1H), 6.67 (broad d, 1H), 6.34 (d, J = 1.9 Hz, 1H), 5.15 (s, 2H), 5.14 (s, 2H), 4.18 (s, 3H), 3.81 (s, 3H), 2.70 (s, 3H). |
| 400 | Ex. 205 | C$_{29}$H$_{22}$F$_3$N$_3$O$_5$S | 582.1305 | 2.579/F | 582.1307 | $^1$H NMR (400 MHz, CDCl$_3$) δ ppm: 7.78 (s, 1H), 7.27-7.38 (m, 5H), 7.24 (broad s, 1H), 7.20 (broad s, 1H), 7.11 (broad s, 1H), 7.0 (s, 1H), 6.64 (broad d, 1H), 6.28 (d, J = 1.9 Hz, 1H), 5.11 (s, 2H), 5.04 (s, 2H), 4.13 (s, 3H), 3.76 (s, 3H). |

| | | | | | | |
|---|---|---|---|---|---|---|
| 401 | Ex. 205 | C$_{29}$H$_{24}$ClN$_3$O$_6$S | 578.1147 | 2.601/F | 578.115 | $^1$H NMR (400 MHz, CDCl$_3$) δ ppm: 7.76 (s, 1H), 7.22 (t, J = 8 Hz, 1H), 6.99-7.0 (m, 3H), 6.94 (m, 1H), 6.81-6.84 (m, 1H), 6.79 (m, 1H), 6.75-6.76 (m. 1H), 6.61 (broad d, 1H), 6.29 (d, J = 1.9 Hz, 1H), 5.08 (s, 2H), 4.93 (s, 2H), 4.12 (s, 3H), 3.75 (s, 3H), 3.71 (s, 3H). |
| 402 | Ex. 205 | C$_{28}$H$_{22}$ClN$_3$O$_5$S | 548.1041 | 2.634/F | 548.1068 | $^1$H NMR (400 MHz, CDCl$_3$) δ ppm: 7.83 (s, 1H), 7.31-7.41 (m, 5H), 7.05-7.06 (m, 2H), 6.96 (m, 1H), 6.91-6.92 (m, 1H), 6.68 (broad d, 1H), 6.31 (d, J = 1.9 Hz, 1H), 5.09 (s, 2H), 5.04 (s, 2H), 4.18 (s, 3H), 3.81 (s, 3H). |
| 403 | Ex. 119 | C$_{27}$H$_{22}$N$_4$O$_4$S$_2$ | 531.1155 | 2.478/F | 531.1139 | $^1$H NMR (400 MHz, DMSO-d$_6$) δ ppm: 8.94 (s, 1H), 7.45 (d, J = 7.0 Hz, 2H), 7.38 (dd, J = 7.0, 7.6 Hz, 2H), 7.34-7.31 (m, 2H), 7.18 (s, 1H), 7.08 (d, J = 7.0 Hz, 1H), 7.00 (d, J = 8.2 Hz, 1H), 6.98 (s, 1H), 6.63 (s, 1H), 5.31 (s, 2H), 5.12 (s, 2H), 3.81 (s, 3H), 2.81 (s, 3H). |
| 404 | Ex. 205 | C$_{29}$H$_{25}$N$_3$O$_6$S | 544.1537 | 2.518/F | 544.1639 | $^1$H NMR (600 MHz, CDCl$_3$) δ ppm: 7.82 (s, 1H), 7.41 (d, J = 7.5 Hz, 2H), 7.36 (t, J = 7.5 Hz, 2H), 7.29-7.31 (m, 1H), 7.06 (s, 1H), 6.69 (s, 1H), 6.67 (s, 1H), 6.62 (s, 1H), 6.47 (s, 1H), 6.34 (s, 1H), 5.10 (s, 2H), 5.03 (s, 2H), 4.18 (s, 3H), 3.81 (s, 3H), 3.77 (s, 3H). |
| 405 | Ex. 1 | C$_{27}$H$_{20}$ClN$_3$O$_4$S | 518.0936 | 2.633/F | 518.0934 | $^1$H NMR (400 MHz, CDCl$_3$) δ ppm: 8.0 (s, 1H), 7.26-7.43 (m, 6H), 7.14 (s, 1H), 7.09 (s, 1H), 7.04 (d, J = 7.1 Hz, 1H), 6.92 (d, J = 8.3 Hz, 1H), 6.66 (s, 1H), 6.36 (s, 1H), 5.13 (s, 2H), 5.06 (s, 2H), 3.81 (s, 3H). |
| 406 | Ex. 115 | C$_{26}$H$_{20}$N$_4$O$_3$S$_2$ | 501.105 | 2.456/F | 501.106 | $^1$H NMR (400 MHz, DMSO-d$_6$) δ ppm: 9.04 (s, 1H), 7.45 (d, J = 7.6 Hz, 2H), 7.38 (t, J = 7.6 Hz, 2H), 7.35-7.30 (m, 4H), 7.20 (br s, 1H), 7.10 (d, J = 7.6 Hz, 1H), 7.04 (d, J = 7.6 Hz, 1H), 7.00 (dd, J = 2.3 and 8.2 Hz, 1H), 5.35 (s, 2H), 5.12 (s, 2H), 2.82 (s, 3H). |
| 407 | Ex. 212 | C$_{29}$H$_{24}$FN$_3$O$_4$S | 529.147 | 2.529/F | 530.155 | $^1$H NMR (600 MHz, DMSO-d$_6$) δ 8.58 (s, 1H), 7.42 (d, J = 7.6 Hz, 2H), 7.35 (t, J = 7.6 Hz, 2H), 7.29 (t, J = 7.6 Hz, 2H), 7.12 (s, 1H), 7.05 (m, 2H), 7.42 (dd, J = 1.8, 8.2 Hz, 1H), 6.81 (s, 1H), 6.49 (d, J = 1.2 Hz, 1H), 6.13 (dq, J = 6.4, 46.9 Hz, 1H), 5.20 (s, 2H), 5.09 (s, 2H), 3.76 (s, 3H), 1.76 (dd, J = 6.4, 24.6 Hz, 3H). |

Example 408 (Intermediate)

6-(7-(Benzyloxy)-5-methoxybenzofuran-2-yl)-2-methoxyimidazo[2,1-b][1,3,4]thiadiazole

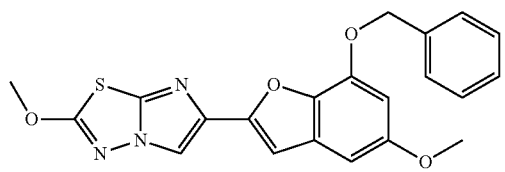 [SMILES: COc1cc(OCc2ccccc2)c2oc(-c3cn4nc(OC)sc4n3)cc2c1]

408A. 1-(7-(Benzyloxy)-5-methoxybenzofuran-2-yl)ethanone

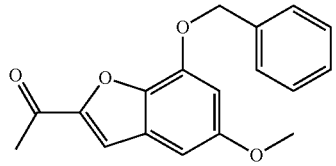 [SMILES: COc1cc(OCc2ccccc2)c2oc(C(C)=O)cc2c1]

A mixture of 1-(7-hydroxy-5-methoxybenzofuran-2-yl) ethanone (2.00 g, 9.70 mmol) and powdered potassium carbonate (1.408 g, 10.18 mmol) in N,N-dimethylformamide (40 mL) was stirred under vacuum (10 mbar) for 5 minutes and then flushed with nitrogen. Then (bromomethyl)benzene (1.991 g, 11.64 mmol) was added dropwise over 5 min and the resulting orange mixture was stirred at 25° C. for 3 h and then stored at −20° C. for 18 h. The solid formed was filtered and washed with N,N-dimethylformamide (20 mL). The combined filtrate was evaporated in vacuo to give an orange solid. The orange solid was diluted with ethyl acetate (300 mL), washed with saturated sodium bicarbonate, brine, dried over anhydrous magnesium sulfate and concentrated in vacuo. The orange solid residue was chromatographed on silica gel (4.5×10 cm, elution toluene-ethyl acetate 0-2-4%) to give the title material (2.71 g, 94%) as an orange solid. This solid was crystallized in ethyl acetate (7 mL)-hexane (14 mL) to give 2.363 g (82%) of large pale orange needles. LC (Method F): 2.292 min. HRMS(ESI) calcd for $C_{18}H_{17}O_4$ $[M+H]^+$ m/z 297.1121. found 297.1137. $^1H$ NMR (400 MHz, CDCl$_3$) δ ppm: 2.62 (s, 3H), 3.82 (s, 3H), 5.28 (s, 2H), 6.64 (d, J=2.2 Hz, 1H), 6.66 (d, J=2.2 Hz, 1H), 7.31-7.42 (m, 3H), 7.43 (s, 1H), 7.50 (broad d, J=7.0 Hz, 2H).

408B. 1-(7-(Benzyloxy)-5-methoxybenzofuran-2-yl)-2-bromoethanone

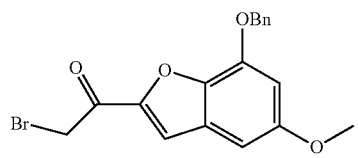 [SMILES: COc1cc(OCc2ccccc2)c2oc(C(=O)CBr)cc2c1]

To a solution of LiHMDS (6.07 mL, 6.07 mmol) in THF (20 mL) at −78° C. was added dropwise over 10 min 1-(7-(benzyloxy)-5-methoxybenzofuran-2-yl)ethanone (Example 408A, 1.5 g, 5.06 mmol) in 13 mL of THF. The resulting mixture was stirred (heterogenous) at −78° C. for 45 min at which point TMS-Cl (0.841 ml, 6.58 mmol) was added over 5 min and the solution was stirred for another 20 min at −78° C. The dry ice bath was then removed and let warm over 30 min. The reaction was quenched with cold ethyl acetate (150 mL) and sat. NaHCO$_3$ (22 mL) and ice. The organic phase was dried rapidly over MgSO$_4$, filtered and concentrated to afford a silyl enol ether oil which was co-evaporated with toluene (20 mL). This was then dissolved back in THF (32 mL), cooled to −20° C. and solid NaHCO$_3$ was added. Solid portions of NBS (0.901 g, 5.06 mmol) were then added over 15 min. and the reaction was let warm up to 0° C. over 2 h. Ethyl acetate (200 mL) was added followed by NaHCO$_3$ (30 mL). The organic phase was washed with brine and dried over MgSO$_4$, filtered and concentrated. The residue was treated with SiO$_2$ and dichloromethane and dried as a pack for chromatography (ISCO 40 g using dichloromethane/Hex 1:1, 7:3, 8:2, 9:1 then 100% dichloromethane) to provide the title material (1.647 g, 87%) as a white solid. LC (Method G)=2.356 min, LCMS(ESI) calcd for $C_{18}H_{16}BrO_4$ $[M+H]^+$ m/z 375.03. found 375.0. $^1H$ NMR (400 MHz, CDCl$_3$) δ ppm: 7.58 (s, 1H), 7.47-7.53 (m, 1H), 7.39-7.45 (m, 1H), 7.33-7.39 (m, 1H), 7.27 (s, 1H), 6.68 (s, 1H), 5.29 (s, 1H), 4.48-4.51 (m, 1H), 3.83 (s, 1H).

408C. 6-(7-(Benzyloxy)-5-methoxybenzofuran-2-yl)-2-bromoimidazo[2,1-b][1,3,4]thiadiazole

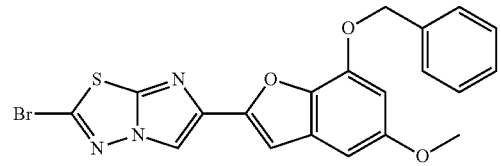 [SMILES: COc1cc(OCc2ccccc2)c2oc(-c3cn4nc(Br)sc4n3)cc2c1]

A mixture of 1-(7-(benzyloxy)-5-methoxybenzofuran-2-yl)-2-bromoethanone (Example 408B, 1.647 g, 4.39 mmol) and 5-bromo-1,3,4-thiadiazol-2-amine (0.909 g, 5.05 mmol) in propan-2-ol (60 mL) was heated at 80° C. for 16 h. The mixture was then separated in 3×20 mL micro-wave reaction vessels. All 3 reactions were heated to 150° C. for 30 min, after which LCMS was taken on each reaction and indicated that the reactions were completed. All reactions were poured in 1 L extraction flask with dichloromethane (600 mL) and sat. aqueous NaHCO$_3$ (200 mL). The organic layer was separated and the aqueous phase were extracted once more with dichloromethane. The combined organic layers were washed with brine, dried over MgSO$_4$, filtered and concentrated. The residue was co-evaporated with toluene (2×) to remove any traces of iPrOH left. The residue was then redissolved in dichloromethane/CHCl$_3$ and SiO$_2$ was added. This was purified on silica gel chromatography using 7:3 dichloromethane/hexanes, 8:2 dichloromethane/hexanes, 9:1 dichloromethane/hexanes, 100% dichloromethane to give the title material which was evaporated and suspended in ethyl acetate. After filtration, the solid was rinsed with ethyl acetate (2-3 times) to provide the title material (1.305 g, 65%) as an off-white solid. HPLC (Method F)=2.425 min. HRMS(ESI) calcd for $C_{20}H_{14}BrN_3O_3S$ $[M+H]^+$ m/z 455.9939. found 456.0003. $^1H$ NMR (400 MHz, CDCl$_3$) δ ppm 8.18 (s, 1H), 7.52 (d, J=7.43 Hz, 1H), 7.39-7.45 (m, 1H), 7.32-7.38 (m, 1H), 7.06 (s, 1H), 6.66 (d, J=2.35 Hz, 1H), 6.51 (d, J=2.35 Hz, 1H), 5.29 (s, 1H), 3.83 (s, 2H).

Example 408 (Intermediate)

6-(7-(Benzyloxy)-5-methoxybenzofuran-2-yl)-2-methoxyimidazo[2,1-b][1,3,4]thiadiazole

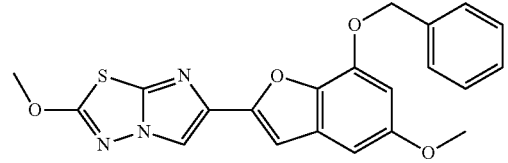 [SMILES: COc1cc(OCc2ccccc2)c2oc(-c3cn4nc(OC)sc4n3)cc2c1]

To a solution of 6-(7-(benzyloxy)-5-methoxybenzofuran-2-yl)-2-bromoimidazo[2,1-b][1,3,4]thiadiazole (Example 408C, 1.305 g, 2.86 mmol) in dichloromethane (40 mL, 622 mmol), was added methanol (25 mL, 618 mmol). Once the mixture becomes homogenous, sodium methoxide was added (2.62 mL, 11.44 mmol) and this was stirred for about 45 min. HCl 1.0 N was then added and the solution becomes yellow within 30 sec. The pH was readjusted with a sat. NaHCO$_3$ solution to close to 8. Dichloromethane and methanol were evaporated and the aqueous phase was extracted with dichloromethane (2×). The organic phase was washed with brine, dried over MgSO$_4$, filtered and concentrated to give the title material (653 mgs, 56%) as an off-white solid. LC (Method F): 2.357 min. HRMS(ESI) calcd for $C_{21}H_{17}N_3O_4S$ [M+H]$^+$ m/z 408.0940. found 408.1023. $^1$H NMR (400 MHz, CDCl$_3$) δ ppm 7.98 (s, 1H), 7.52 (d, J=7.04 Hz, 1H), 7.38-7.45 (m, 1H), 7.32-7.38 (m, 1H), 6.98 (s, 1H), 6.65 (d, J=2.35 Hz, 1H), 6.49 (d, J=1.96 Hz, 1H), 5.30 (s, 1H), 4.21 (s, 2H), 3.83 (s, 2H).

Example 409

6-(7-((3-(Benzyloxy)benzyl)oxy)-5-methoxybenzofuran-2-yl)-2-methoxyimidazo[2,1-b][1,3,4]thiadiazole

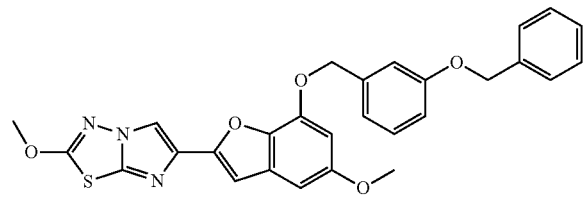 [SMILES: COc1cc(OCc2cccc(OCc3ccccc3)c2)c2oc(-c3cn4nc(OC)sc4n3)cc2c1]

409A. 5-Methoxy-2-(2-methoxyimidazo[2,1-b][1,3,4]thiadiazol-6-yl)benzofuran-7-ol

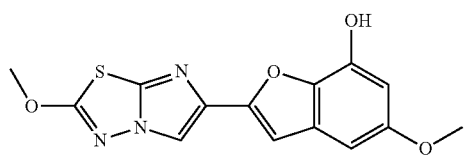

To a solution of 6-(7-(benzyloxy)-5-methoxybenzofuran-2-yl)-2-methoxyimidazo[2,1-b][1,3,4]thiadiazole (Example 408, 0.580 g, 1.424 mmol) in dichloromethane (110 mL) was added 1,2,3,4,5-pentamethylbenzene (1.477 g, 9.96 mmol). The reaction was put in a dry ice bath and, after 5 min, trichloroborane (1.0 M in dichloromethane, 4.11 mL, 4.11 mmol) was added dropwise. The reaction was stirred for approximately 45 min. and monitored by TLC and LCMS. The reaction was quenched with NaHCO$_3$ (4 g in 100 mL of water), the ice bath was removed and the reaction was stirred for 1 h. The compound precipitated out and was filtered on a buchner with a filter paper and rinsed with 4% NaHCO$_3$, then water and then EtOH (1-2 mL). The solid was dried in a dessicator over P$_2$O$_5$ over the weekend to give the title material (0.310 g, 68%) as a brownish solid. HPLC (Method F)=1.845 min. HRMS(ESI) calcd for $C_{14}H_{11}N_3O_4S$ [M+H]$^+$ m/z 318.0470. found 318.0550. $^1$H NMR (400 MHz, DMSO-d$_6$) δ ppm 10.08 (s, 1H), 8.38 (s, 1H), 6.94 (s, 1H), 6.58 (d, J=2.35 Hz, 1H), 6.33 (d, J=2.35 Hz, 1H), 4.21 (s, 3H), 3.72 (s, 3H).

Example 409

6-(7-((3-(Benzyloxy)benzyl)oxy)-5-methoxybenzofuran-2-yl)-2-methoxyimidazo[2,1-b][1,3,4]thiadiazole

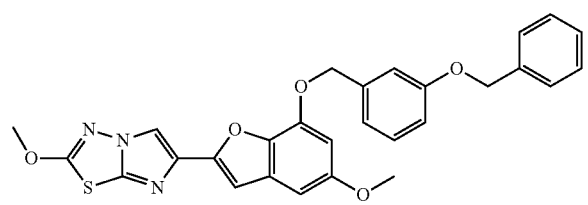 [SMILES: COc1cc(OCc2cccc(OCc3ccccc3)c2)c2oc(-c3cn4nc(OC)sc4n3)cc2c1]

To a suspension of 5-methoxy-2-(2-methoxyimidazo[2,1-b][1,3,4]thiadiazol-6-yl)benzofuran-7-ol (Example 409A, 44 mgs, 0.139 mmol) in DMF (1.5 mL) was added 1-(benzyloxy)-3-(bromomethyl)benzene (50.0 mg, 0.180 mmol) followed by K$_2$CO$_3$ (57.3 mg, 0.415 mmol). The reaction was stirred at r.t. for 1.5 h, quenched with HCl 1N (1 mL), and treated with sat. aqueous NaHCO$_3$ (3 mL). The organic phase was extracted with dichloromethane (2×) and the combined organic layers were washed with brine then dried over MgSO$_4$, filtered and concentrated. The residue was purified by silica gel chromatography (ISCO 12 g using dichloromethane and ethyl acetate (99:1 to 9:1)) to give the title material (40 mgs) with some impurities. The solid was recrystallized with dichloromethane and ethyl acetate to provide the title material (29 mgs, 40%) as colorless crystals. HPLC (Method F)=2.497. HRMS(ESI) calcd for $C_{28}H_{23}N_3O_5S$ [M+H]$^+$ m/z 514.1358. found 514.1450. $^1$H NMR (400 MHz, DMSO-d$_6$) δ ppm 8.49 (s, 1H), 7.41-7.47 (m, 2H), 7.28-7.40 (m, 4H), 7.17-7.21 (m, 1H), 7.09 (d, J=7.83 Hz, 1H), 6.96-7.03 (m, 2H), 6.73 (d, J=1.96 Hz, 1H), 6.59 (d, J=2.35 Hz, 1H), 5.28 (s, 2H), 5.11 (s, 2H), 4.20 (s, 3H), 3.76 (s, 3H).

Example 410

4-((3-(Benzyloxy)benzyl)oxy)-2-(2-methoxyimidazo[2,1-b][1,3,4]thiadiazol-6-yl)benzofuran-6-ol

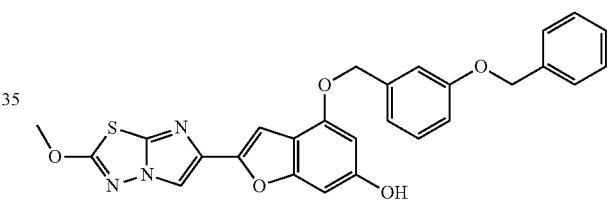

410A. 1-(4,6-Dimethoxybenzofuran-2-yl)ethanone

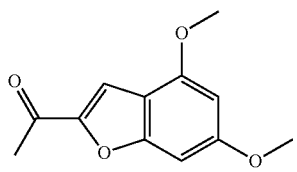 [SMILES: COc1cc(OC)c2cc(C(C)=O)oc2c1]

To a solution of 2-hydroxy-4,6-dimethoxybenzaldehyde (8.6 g, 47.2 mmol) in acetonitrile (85 mL) was added potassium iodide (1.567 g, 9.44 mmol), cesium carbonate (16.92 g, 51.9 mmol) and finally 1-chloropropan-2-one 95% (3.95 mL, 49.6 mmol). The reaction was stirred at r.t. for 3 h then cesium carbonate (1.538 g, 0.1 eq.) was added and the mixture was heated to 80° C. for 2.5 h. The reaction was filtered on silica pad of 1 inch approximately and eluted with ethyl acetate (500 mL). The crude reaction was redissolved in dichloromethane and eluted on silica pad again with 100% dichloromethane to 100% ethyl acetate to recover the title material (8.34 g, 80%) as a white solid. LC (Method G): 1.923 min. HRMS(ESI) calcd for $C_{12}H_{13}O_4$. [M+H]$^+$ m/z 221.0736. found 221.0829. $^1$H NMR (400 MHz, CDCl$_3$) δ ppm 7.54 (s, 1H), 6.63-6.67 (m, 1H), 6.31-6.35 (m, 1H), 3.92 (s, 3H), 3.87 (s, 3H), 2.55 (s, 3H).

410B. 1-(4,6-Dihydroxybenzofuran-2-yl)ethanone

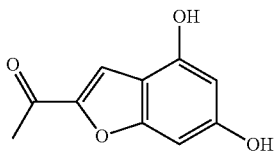

To a stirred solution of 1-(4,6-dimethoxybenzofuran-2-yl)ethanone (Example 410A, 300 mgs, 1.362 mmol) in chlorobenzene (4.2 mL) was added aluminum trichloride (599 mg, 4.50 mmol). The reaction was heated for 3 h at 90° C. and was quenched with ice and 1.0N HCl. The aqueous phase was extracted with ethyl acetate (4×) and the organic layers were dried over $MgSO_4$, filtered and concentrated. The residue was purified on silica gel chromatography (ISCO 12 g using 1:1 mixture of ethyl acetate and hexanes) to give the title material (246 mgs, 94%) as a brownish solid. LC (Method G): 1.600 min. HRMS(ESI) calcd for $C_{10}H_9O_4$ $[M+H]^+$ m/z 193.0495. found 193.0512. $^1$H NMR (400 MHz, $CD_3OD$) δ ppm 7.65-7.71 (m, 1H), 6.40-6.47 (m, 1H), 6.19-6.26 (m, 1H), 2.51 (s, 3H).

410C. 2-Acetylbenzofuran-4,6-diyl bis(trifluoromethanesulfonate)

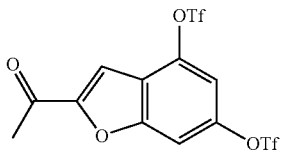

To a suspension of 1-(4,6-dihydroxybenzofuran-2-yl)ethanone (Example 410B, 1.64 g, 8.53 mmol) in dichloromethane (40 mL), was added 2,6-lutidine (2.98 mL, 25.6 mmol), and at that point the suspension became a solution (brownish). The reaction was cooled down to −40° C. (acetonitrile and dry ice) and trifluoromethanesulfonic anhydride (3.17 mL, 18.78 mmol) was added dropwise over 15 min. The reaction was stirred at −40° C. for 1.5 h and then washed with HCl 1.0N (3×30 mL portions). The organic phase was washed with brine, dried over $MgSO_4$, filtered and concentrated. The residue was triturated with diethyl ether and the filtrate was evaporated and triturated again with 1:1 hexanes/diethyl ether to maximize recovery to give the title material (3.14 g, 81%) as a brownish solid. LC (Method G): 2.299 min. HRMS(ESI) calcd for $C_{12}H_7F_6O_8S_2$ $[M+H]^+$ m/z 456.9481. found 456.9473. $^1$H NMR (400 MHz, DMSO-$d_6$) δ ppm 8.35-8.49 (m, 1H), 8.08-8.16 (m, 1H), 7.98-8.07 (m, 1H), 2.64 (s, 3H).

410D. 2-Acetyl-4-hydroxybenzofuran-6-yl trifluoromethanesulfonate

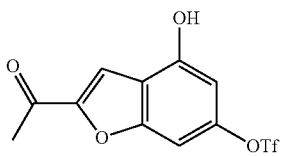 [SMILES: CC(=O)c1cc2c(O)cc(OS(=O)(=O)C(F)(F)F)cc2o1]

To a stirred solution of 2-acetylbenzofuran-4,6-diyl bis(trifluoromethanesulfonate) (Example 410C, 200 mgs, 0.438 mmol) in dimethoxyethane (9.5 mL) and water (49 µL), was added cesium carbonate (214 mgs, 0.657 mmol) and the reaction was heated to 80° C. for 2.5 h. The excess solid was filtered and the mixture was acidified to pH 5 or more. The aqueous phase was extracted with ethyl acetate (3×) and the organic layers were dried over $MgSO_4$, filtered and concentrated. The residue was purified by chromatography (BIOTAGE® 12 g column using 30% ethyl acetate in hexanes) to provide the title material (107 mgs, 75%) as a beige solid. HRMS(ESI) calcd for $C_{11}H_8F_3O_6S$ $[M+H]^+$ m/z 324.9988. found 324.9991. $^1$H NMR (400 MHz, DMSO-$d_6$) δ ppm 11.39 (s, 1H), 7.94-7.97 (m, 1H), 7.36-7.56 (m, 1H), 6.73-6.75 (m, 1H), 2.55 (s, 3H).

410E. 2-Acetyl-4-((3-(benzyloxy)benzyl)oxy)benzofuran-6-yl trifluoromethanesulfonate

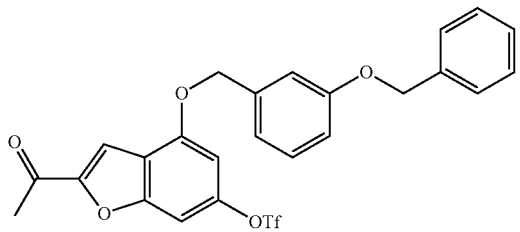 [SMILES: CC(=O)c1cc2c(OCc3cccc(OCc4ccccc4)c3)cc(OS(=O)(=O)C(F)(F)F)cc2o1]

To a solution of 2-acetyl-4-hydroxybenzofuran-6-yl trifluoromethanesulfonate (Example 410D, 2.89 g, 8.91 mmol) in a mixture of acetone (9 mL, 123 mmol) and acetonitrile (45 mL, 862 mmol) was added cesium carbonate (2.90 g, 8.91 mmol). The mixture was sonicated and 1-(benzyloxy)-3-(bromomethyl)benzene (2.59 g, 9.36 mmol) was added dropwise. The reaction was sonicated while the temperature was maintained between 25-35° C. The reaction was complete in 3.5 h and evaporated to dryness. The residue was suspended in dichloromethane and $SiO_2$ was added. The solvent was evaporated again and this was purified by column chromatography (80 g ISCO, using 10% hexanes in ethyl acetate going to 15% then 20%) and provided the title material (720 mgs, (15.5%)). HPLC (Method F): 2.460 min. HRMS(ESI) calcd for $C_{25}H_{19}F_3O_7S$ $[M+Na]^+$ m/z 543.0701. found 543.0701. $^1$H NMR (400 MHz, $CDCl_3$) δ ppm 7.60-7.65 (m, 1H), 7.31-7.47 (m, 6H), 7.14-7.19 (m, 1H), 7.03-7.11 (m, 2H), 6.96-7.03 (m, 1H), 6.66-6.70 (m, 1H), 5.19 (s, 2H), 5.11 (s, 2H), 2.61 (s, 3H).

410F. 1-(4-((3-(Benzyloxy)benzyl)oxy)-6-hydroxybenzofuran-2-yl)ethanone

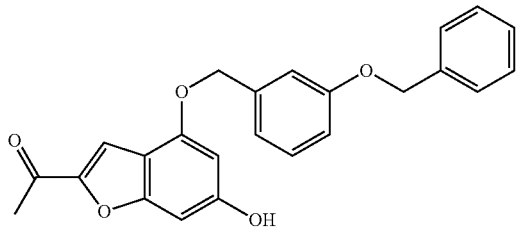 [SMILES: CC(=O)c1cc2c(OCc3cccc(OCc4ccccc4)c3)cc(O)cc2o1]

To a stirred solution of 2-acetyl-4-((3-(benzyloxy)benzyl)oxy)benzofuran-6-yl trifluoromethanesulfonate (Example 410E, 0.720 g, 1.383 mmol) in 1,4-dioxane (0.118 mL, 1.383 mmol) was added a solution of tetra-n-butylammonium hydroxide 1.0M in THF (5.74 mL, 22.13 mmol). The reaction was stirred for 2 h at r.t., quenched with HCl 1N and diluted with water. The resulting solid was dried overnight under mechanical pump to give the title material (530 mgs, 99%) as a beige solid. HPLC (Method F): 2.255 min.

HRMS(ESI) calcd for C₂₄H₂₁O₅ m/z 389.1384. found 389.1298. ¹H NMR (600 MHz, CDCl₃) δ ppm 7.57 (d, J=1.1 Hz, 1H), 7.44-7.32 (m, 6H), 7.08 (s, 1H), 7.05 (d, J=7.6 Hz, 1H), 6.98 (dd, J=2.1 and 8.2 Hz, 1H), 6.69 (d, J=0.9 Hz, 1H), 6.33 (d, J=1.8 Hz, 1H), 5.38 (s, 1H), 5.14 (s, 2H), 5.09 (s, 2H), 2.54 (s, 3H).

410G. 1-(4-((3-(Benzyloxy)benzyl)oxy)-6-((tert-butyldimethylsilyl)oxy)benzofuran-2-yl)ethanone

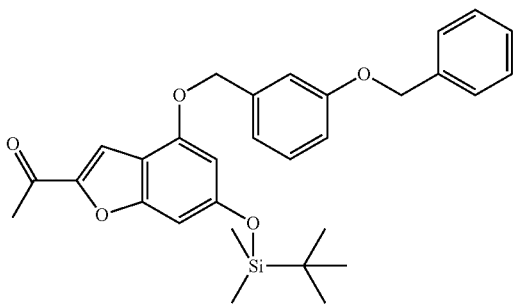 [SMILES: CC(=O)c1cc2c(OCc3cccc(OCc4ccccc4)c3)cc(O[Si](C)(C)C(C)(C)C)cc2o1]

To a solution of 1-(4-((3-(benzyloxy)benzyl)oxy)-6-hydroxybenzofuran-2-yl)ethanone (Example 410F, 537 mgs, 1.383 mmol) in dichloromethane (20 mL) was added triethylamine (0.251 mL, 1.797 mmol) followed by chlorodimethylphenylsilane (0.231 mL, 1.383 mmol). The reaction was stirred at r.t. overnight, then silica was added and the mixture was concentrated to dryness. This was purified by column chromatography (ISCO gold 40 g using steps of 5% starting with 5% ethyl acetate in hexanes going to 20% ethyl acetate) to provide the title material (526 mgs, 76%) as a light yellow oil. LC (Method G): 3.073 min. HRMS(ESI) calcd for C₃₀H₃₅O₅Si [M+H]⁺ m/z 503.2248. found 503.225. ¹H NMR (400 MHz, CDCl₃) δ ppm 7.55-7.60 (m, 1H), 7.37-7.47 (m, 4H), 7.30-7.36 (m, 2H), 7.10 (s, 1H), 7.03-7.08 (m, 1H), 6.95-7.00 (m, 1H), 6.61-6.67 (m, 1H), 6.29 (d, J=1.57 Hz, 1H), 5.14 (s, 2H), 5.10 (s, 2H), 2.55 (s, 1H), 2.16-2.21 (m, 5H), 0.95-1.01 (m, 9H), 0.18-0.24 (m, 6H).

410H. 1-(4-((3-(Benzyloxy)benzyl)oxy)-6-((tert-butyldimethylsilyl)oxy)benzofuran-2-yl)-2-bromoethanone

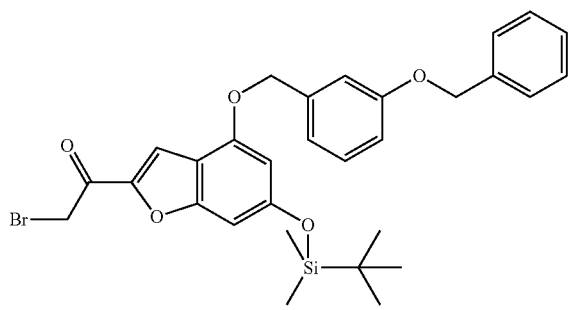 [SMILES: CC(C)(C)[Si](C)(C)Oc1cc(OCc2cccc(OCc3ccccc3)c2)c2cc(C(=O)CBr)oc2c1]

A sealed tube was charged with 1-(4-((3-(benzyloxy)benzyl)oxy)-6-((tert-butyldimethylsilyl)oxy)benzofuran-2-yl)ethanone (Example 410G, 505 mgs, 1.005 mmol) in ethyl acetate (10 mL, 1.005 mmol) and copper(II) bromide (449 mgs, 2.009 mmol) was added. The reaction was heated at 80° C. for 1 h., then evaporated to dryness with silica. This was purified by column chromatography (ISCO gold 40 g, starting 100% hexanes, then 1% ethyl acetate in hexanes and finally 2% ethyl acetate in hexanes) to give the title material (182 mgs, 31%). LC (Method G): 3.157 min. HRMS(ESI) calcd for C₃₀H₃₄BrO₅Si [M+H]⁺ m/z 581.1351. found 581.1362. ¹H NMR (400 MHz, CDCl₃) δ ppm 7.70-7.74 (m, 1H), 7.31-7.48 (m, 6H), 7.07-7.11 (m, 1H), 7.05 (d, J=7.43 Hz, 1H), 6.98 (dd, J=8.02, 2.15 Hz, 1H), 6.62-6.66 (m, 1H), 6.30 (d, J=1.57 Hz, 1H), 5.14 (s, 2H), 5.10 (s, 2H), 4.37 (s, 2H), 0.99 (s, 9H), 0.21 (s, 6H).

410I. 6-(4-((3-(Benzyloxy)benzyl)oxy)-6-((tert-butyldimethylsilyl)oxy)benzofuran-2-yl)-2-bromoimidazo[2,1-b][1,3,4]thiadiazole

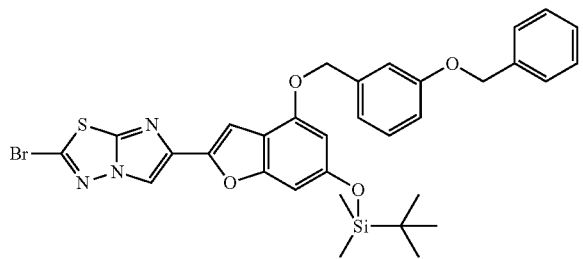 [SMILES: CC(C)(C)[Si](C)(C)Oc1cc(OCc2cccc(OCc3ccccc3)c2)c2cc(-c3cn4nc(Br)sc4n3)oc2c1]

To a solution of 1-(4-((3-(benzyloxy)benzyl)oxy)-6-((tert-butyldimethylsilyl)oxy)benzo-furan-2-yl)-2-bromoethanone (Example 410H, 40 mgs, 0.069 mmol) in propan-2-ol (1.5 ml, 0.069 mmol) was added 5-bromo-1,3,4-thiadiazol-2-amine (18.57 mgs, 0.103 mmol) and the mixture was heated at 80° C. for 16 h and then at 150° C. for 1 h. The reaction was poured in dichloromethane (5 mL) and saturated aqueous NaHCO₃ (3 mL) was added. The organic phase was extracted with dichloromethane (2×), dried over MgSO₄, filtered and concentrated. The residue was purified on silica gel chromatography (12 g BIOTAGE® column, starting 100% hexanes and going up to 9:1 hexanes/ethyl acetate) to give the title material (15 mgs, 32%). HPLC (Column F)=3.204 min. HRMS(ESI) calcd for C₃₂H₃₂BrN₃O₄SSi [M+H]⁺ m/z 662.1066. found 662.1125. ¹H NMR (400 MHz, CDCl₃) δ ppm 8.06 (s, 1H), 7.29-7.47 (m, 6H), 7.17 (s, 1H), 7.11-7.14 (m, 1H), 7.07 (d, J=7.83 Hz, 1H), 6.95 (dd, J=8.22, 2.74 Hz, 1H), 6.63-6.67 (m, 1H), 6.29 (d, J=1.96 Hz, 1H), 5.16 (s, 2H), 5.09 (s, 2H), 0.99 (s, 9H), 0.20 (s, 6H).

410J. 6-(4-((3-(Benzyloxy)benzyl)oxy)-6-((tert-butyldimethylsilyl)oxy)benzofuran-2-yl)-2-methoxyimidazo[2,1-b][1,3,4]thiadiazole

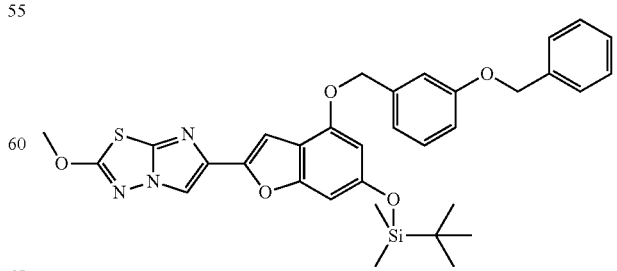

6-(4-((3-(Benzyloxy)benzyl)oxy)-6-((tert-butyldimethylsilyl)oxy)benzofuran-2-yl)-2-bromoimidazo[2,1-b][1,3,4]

thiadiazole (Example 4101, 5 mgs, 7.55 µmol) was dissolved in dichloromethane (1 mL) and methanol (1 mL) and sodium methanolate 25% (0.408 mg, 7.55 µmol) was added. The reaction was stirred at r.t. for approximately 1 h, then quenched with sat. aqueous NH$_4$Cl and concentrated to dryness. The aqueous phase was extracted with dichloromethane (2×) and the organic phase was dried over MgSO$_4$, filtered and concentrated. The residue was purified by column chromatography (ISCO 12 g column, 90:10 hexanes/ethyl acetate up to 1:1 hexanes/ethyl acetate) to give the title material (15.5 mgs, 32%). HPLC (Method F): 3.016 min. HRMS(ESI) calcd for C$_{33}$H$_{36}$N$_3$O$_5$SSi [M+H]$^+$ m/z 614.2139. found 614.2153. $^1$H NMR (400 MHz, CDCl$_3$) δ ppm 7.85 (s, 1H), 7.28-7.48 (m, 6H), 7.13 (s, 1H), 7.04-7.11 (m, 2H), 6.94 (dd, J=8.22, 2.35 Hz, 1H), 6.60-6.68 (m, 1H), 6.27-6.30 (m, 1H), 5.16 (s, 2H), 5.09 (s, 2H), 4.21 (s, 3H), 0.99 (s, 9H), 0.19 (s, 6H).

Example 410

4-((3-(Benzyloxy)benzyl)oxy)-2-(2-methoxyimidazo[2,1-b][1,3,4]thiadiazol-6-yl)benzofuran-6-ol

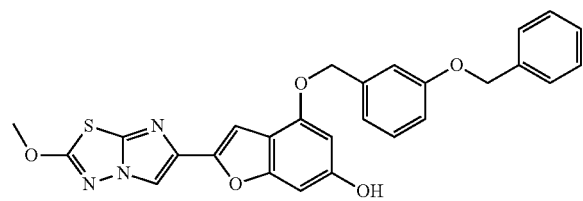 [SMILES: COc1nn2cc(-c3cc4c(OCc5cccc(OCc6ccccc6)c5)cc(O)cc4o3)nc2s1]

To a solution of 6-(4-((3-(benzyloxy)benzyl)oxy)-6-((tert-butyldimethylsilyl)oxy)benzo-furan-2-yl)-2-methoxyimidazo[2,1-b][1,3,4]thiadiazole (Example 410J, 9 mgs, 0.015 mmol) in THF (1 mL), was added acetic acid (2.098 µL, 0.037 mmol) followed by tetra-n-butylammonium fluoride 1.0M in THF (22 µL, 0.022 mmol) and the reaction was stirred at r.t. for 5 h. The reaction was then concentrated to dryness with silica and this was purified by column chromatography (ISCO 4 g column using 10% ethyl acetate/n-hexanes) to give the title material (3 mgs, 21%). HPLC (Method F): 2.355. HRMS(ESI) calcd for C$_{27}$H$_{22}$N$_3$O$_5$S [M+H]$^+$ m/z 500.1275. found 500.1289. $^1$H NMR (400 MHz, DMSO-d$_6$) δ ppm 9.60 (s, 1H), 8.36 (s, 1H), 7.43-7.49 (m, 2H), 7.36-7.42 (m, 2H), 7.28-7.36 (m, 2H), 7.15 (s, 1H), 7.07 (d, J=7.83 Hz, 1H), 6.98 (dd, J=8.02, 2.15 Hz, 1H), 6.93 (s, 1H), 6.55 (s, 1H), 6.37 (d, J=1.56 Hz, 1H), 5.17 (s, 2H), 5.12 (s, 2H), 4.20 (s, 3H).

Example 411

6-(4-((3-(Benzyloxy)benzyl)oxy)-6-ethylbenzofuran-2-yl)-2-methoxyimidazo[2,1-b][1,3,4]thiadiazole

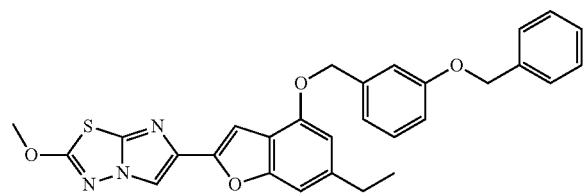 [SMILES: CCc1cc(OCc2cccc(OCc3ccccc3)c2)c2cc(-c3cn4nc(OC)sc4n3)oc2c1]

411A. 1-(4-((3-(Benzyloxy)benzyl)oxy)-6-ethylbenzofuran-2-yl)ethanone

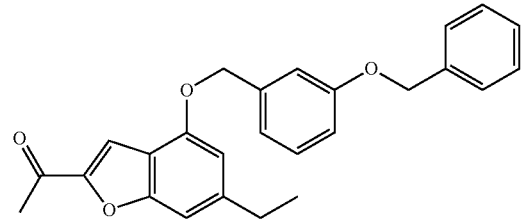 [SMILES: CCc1cc(OCc2cccc(OCc3ccccc3)c2)c2cc(C(C)=O)oc2c1]

A sealed tube charged with 2-acetyl-4-((3-(benzyloxy)benzyl)oxy)benzofuran-6-yl trifluoromethanesulfonate (Example 410E, 100 mgs, 0.192 mmol), dichloro[1,1'-bis(diphenylphosphino)-ferrocene]palladium(II) (31.4 mgs, 0.038 mmol), and anhydrous potassium phosphate (163 mgs, 0.769 mmol) was purged with argon for 10 min, then degassed THF (6.97 mL) and 1.0 M triethylborane (2.78 mL, 2.78 mmol) were added. The resulting rust-colored mixture was heated in a preheated oil bath (75° C.) for 5 h and then diluted with methylene chloride (15 mL) and washed with water and brine. The organic layers were dried over MgSO$_4$, filtered and concentrated to give a black solid which was purified by column chromatography (24 g ISCO column) to give the title material (22 mgs, 28.6%). LC (Method G): 2.408 min. HRMS(ESI) calcd for C$_{26}$H$_{24}$O$_4$ [M+H]$^+$ m/z 401.1675. found 401.1737. $^1$H NMR (400 MHz, CDCl$_3$) δ ppm 7.57 (s, 1H), 7.30-7.45 (m, 6H), 7.10 (s, 1H), 7.06 (m, 1H), 7.02 (s, 1H), 6.96 (m, 1H), 6.59 (s, 1H), 5.15 (s, 2H), 5.08 (s, 2H), 2.74 (q, J=7.42 Hz, 2H), 2.55 (s, 3H), 1.27 (t, J=7.40 Hz, 3H).

411B. 1-(4-((3-(Benzyloxy)benzyl)oxy)-6-ethylbenzofuran-2-yl)-2-bromoethanone

A sealed tube was charged with 1-(4-((3-(benzyloxy)benzyl)oxy)-6-((tert-butyldimethylsilyl)oxy)benzofuran-2-yl)ethanone (Example 411A, 15 mgs, 0.030 mmol), ethyl acetate (1.5 mL) and copper(II) bromide (13.33 mg, 0.060 mmol). The resulting mixture was then heated at 80° C. for 45 min. and concentrated to dryness with silica gel. This was purified by column chromatography (24 g ISCO gold column, 5% EtOAc in n-hexanes up to 10% EtOAc in n-hexanes) to give the title material (108 mgs, 60%). HPLC (Method F): 2.491 min. HRMS(ESI) calcd for C$_{26}$H$_{23}$BrO$_4$ [M+H]$^+$ m/z 479.0780. found 480.0815. $^1$H NMR (400 MHz, CDCl$_3$) δ ppm 7.73-7.77 (m, 1H), 7.31-7.48 (m, 6H), 7.11 (br. s, 1H), 7.05-7.09 (m, 1H), 7.04 (br. s, 1H), 6.99 (dd, J=8.22, 2.35 Hz, 1H), 6.62 (s, 1H), 5.18 (s, 2H), 5.08-5.13 (m, 2H), 4.41 (s, 2H), 2.77 (q, J=7.43 Hz, 2H), 1.29 (t, J=7.40 Hz, 4H).

411C. 6-(4-((3-(Benzyloxy)benzyl)oxy)-6-ethylbenzofuran-2-yl)-2-bromoimidazo[2,1-b][1,3,4]thiadiazole

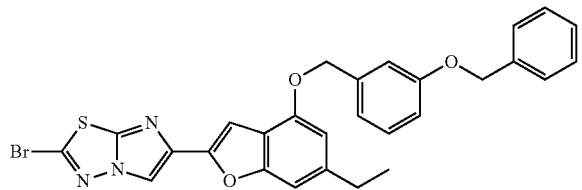 [SMILES: CCc1cc(OCc2cccc(OCc3ccccc3)c2)c2cc(-c3cn4nc(Br)sc4n3)oc2c1]

To a solution of 1-(4-((3-(benzyloxy)benzyl)oxy)-6-ethylbenzofuran-2-yl)-2-bromoethanone (Example 411B, 108 mgs, 0.225 mmol) in propan-2-ol (5 mL) was added 5-bromo-1,3,4-thiadiazol-2-amine (50.7 mgs, 0.282 mmol) and the solution was heated to 80° C. for 16 h and then 150° C. for 1 h. The reaction was poured in dichloromethane (5 mL) and saturated aqueous NaHCO$_3$ (3 mL) was added. The aqueous phase was extracted with dichloromethane (2×) and this organic layer was dried over MgSO$_4$, filtered and concentrated. The residue was purified by column chromatography (12 g column on BIOTAGE® using 100% dichloromethane) to give the title material (51 mgs, 40%). LC (Method G): 2.861 min. HRMS(ESI) calcd for C$_{28}$H$_{22}$BrN$_3$O$_3$S [M+H]$^+$ m/z 560.0565. found 560.0621. $^1$H NMR (400 MHz, CDCl$_3$) δ ppm 8.10 (s, 1H), 7.58-7.62 (m, 1H), 7.29-7.49 (m, 5H), 7.22 (br. s, 1H), 7.15 (br. s, 1H), 7.09 (d, J=7.83 Hz, 1H), 6.93-7.04 (m, 2H), 6.61 (s, 1H), 5.20 (s, 2H), 5.10 (s, 2H), 2.75 (q, J=7.43 Hz, 2H), 1.29 (t, J=7.63 Hz, 3H).

Example 411

6-(4-((3-(Benzyloxy)benzyl)oxy)-6-ethylbenzofuran-2-yl)-2-methoxyimidazo[2,1-b][1,3,4]thiadiazole

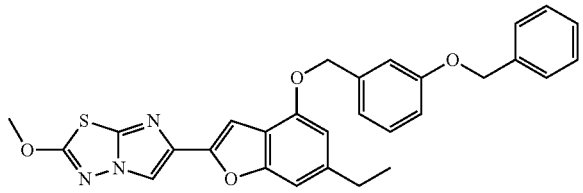 [SMILES: CCc1cc(OCc2cccc(OCc3ccccc3)c2)c2cc(-c3cn4nc(OC)sc4n3)oc2c1]

6-(4-((3-(Benzyloxy)benzyl)oxy)-6-ethylbenzofuran-2-yl)-2-bromoimidazo[2,1-b][1,3,4]thiadiazole (Example 411C, 51 mgs, 0.091 mmol) was dissolved in dichloromethane (3 mL) and in methanol (4 mL) and sodium methanolate 25% (50 µL, 0.227 mmol) was added. The mixture was stirred at r.t. for 1 h and then HCl 1.0 N was added and this was stirred for 1 min. NaHCO$_3$ was then added until pH reaches approximately 7 and the solvents were evaporated. The residue was suspended in dichloromethane (2×) and the organic layer was dried over MgSO$_4$, filtered and concentrated with silica gel. This was purified by column chromatography (ISCO 12 g, 7:3 dichloromethane/hexanes up to 100% dichloromethane and 80% dichloromethane and 20% ethyl acetate). LC (Method G)=2.999 min. HRMS(ESI) calcd for C$_{29}$H$_{25}$N$_3$O$_4$S [M+H]$^+$ m/z 512.1566. found 512.1660. $^1$H NMR (400 MHz, CDCl$_3$) δ ppm 7.88 (s, 1H), 7.44-7.49 (m, 2H), 7.37-7.43 (m, 2H), 7.29-7.36 (m, 2H), 7.13-7.17 (m, 2H), 7.10 (d, J=7.83 Hz, 1H), 7.01 (s, 1H), 6.93-6.98 (m, 1H), 6.60 (br. s, 1H), 5.21 (s, 2H), 5.10 (s, 2H), 4.20 (s, 3H), 2.74 (q, J=7.83 Hz, 2H), 1.29 (t, J=7.63 Hz, 3H).

Example 412

N-(4-((3-(Benzyloxy)benzyl)oxy)-2-(2-methoxyimidazo[2,1-b][1,3,4]thiadiazol-6-yl)benzofuran-6-yl)acetamide

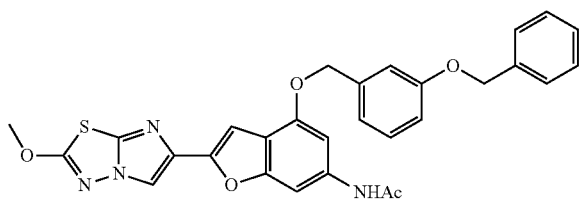 [SMILES: COc1nn2cc(-c3cc4c(OCc5cccc(OCc6ccccc6)c5)cc(NC(C)=O)cc4o3)nc2s1]

412A. N-(2-Acetyl-4-((3-(benzyloxy)benzyl)oxy)benzofuran-6-yl)acetamide

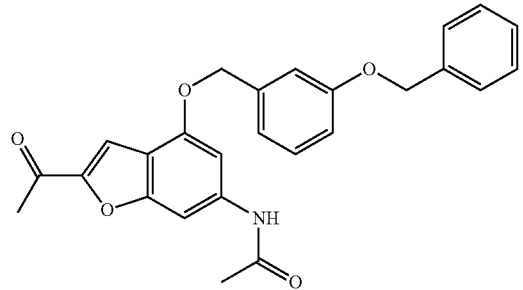 [SMILES: CC(=O)Nc1cc(OCc2cccc(OCc3ccccc3)c2)c2cc(C(C)=O)oc2c1]

A solution of 2-acetyl-4-((3-(benzyloxy)benzyl)oxy)benzofuran-6-yl trifluoromethanesulfonate (Example 410E, 100 mgs, 0.192 mmol) in nitrogen-purged isopropyl alcohol (3 mL) was added to a mixture of acetamide (45.4 mgs, 0.769 mmol), tris(dibenzylideneacetone)dipalladium(0) chloroform adduct (39.8 mgs, 0.038 mmol), potassium phosphate (122 mgs, 0.576 mmol) and di-tert-butyl(2',4',6'-triisopropyl-[1,1'-biphenyl]-2-yl)phosphine (82 mgs, 0.192 mmol) and this mixture was stirred at 90° C. for 19 h. After cooling it down to room temperature, the reaction was quenched with water, and extracted with dichloromethane. The combined organic layers were dried over MgSO$_4$ and concentrated in vacuo. The residue was purified by flash chromatography on silica gel (100% ethyl acetate to ethyl acetate/ethanol 90:10) to give the title material (16 mgs, 20%). LC (Method G): 2.229 min. HRMS(ESI) calcd for C$_{26}$H$_{23}$NO$_5$ [M+H]$^+$ m/z 430.1576. found 430.1674. $^1$H NMR (400 MHz, DMSO-d$_6$) δ ppm 10.25 (s, 1H), 7.86-7.92 (m, 1H), 7.70 (s, 1H), 7.42-7.49 (m, 2H), 7.28-7.42 (m, 4H), 7.15-7.21 (m, 1H), 7.07-7.14 (m, 2H), 7.01 (dd, J=8.22, 1.96 Hz, 1H), 5.20 (s, 2H), 5.13 (s, 2H), 2.08 (s, 3H).

412B. N-(4-((3-(Benzyloxy)benzyl)oxy)-2-(2-bromoacetyl)benzofuran-6-yl)acetamide

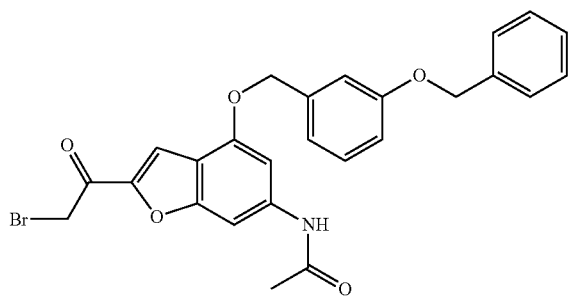 [SMILES: CC(=O)Nc1cc(OCc2cccc(OCc3ccccc3)c2)c2cc(C(=O)CBr)oc2c1]

A sealed tube was charged with N-(2-acetyl-4-((3-(benzyloxy)benzyl)oxy)benzofuran-6-yl)acetamide (Example 412A, 150 mgs, 0.349 mmol), ethyl acetate (3 mL) and copper(II) bromide (156 mgs, 0.699 mmol). The resulting mixture was heated at 80° C. for 45 min. and then evaporated to dryness with silica. This was purified by column chromatography (ISCO gold 12 g starting 100% dichloromethane, then 1% ethyl acetate in dichloromethane and finally 2% ethyl acetate in dichloromethane) to give the title material (100 mgs, 56%). HPLC (Method F): 2.315 min. LCMS (APCI) calcd for $C_{26}H_{23}BrNO_5$ [M+H]$^+$ m/z 508.08. found 508.1. $^1$H NMR (400 MHz, DMSO-d$_6$) δ ppm 9.69-9.78 (m, 1H), 8.50 (s, 1H), 8.31 (s, 1H), 8.22-8.27 (m, 1H), 7.63-7.67 (m, 1H), 7.28-7.50 (m, 5H), 7.19 (br. s., 1H), 7.08-7.16 (m, 1H), 6.97-7.06 (m, 1H), 5.23 (s, 2H), 5.13 (s, 2H), 4.81 (s, 2H), 2.09-2.17 (m, 3H).

412C. N-(4-((3-(Benzyloxy)benzyl)oxy)-2-(2-bromoimidazo[2,1-b][1,3,4]thiadiazol-6-yl)benzofuran-6-yl)acetamide

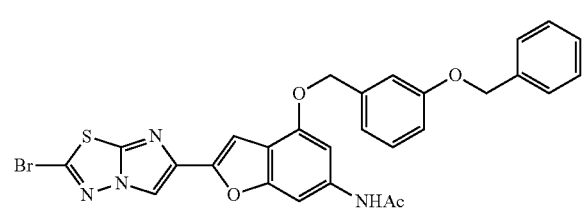 [SMILES: CC(=O)Nc1cc(OCc2cccc(OCc3ccccc3)c2)c2cc(-c3cn4nc(Br)sc4n3)oc2c1]

To a solution of N-(4-((3-(benzyloxy)benzyl)oxy)-2-(2-bromoacetyl)benzofuran-6-yl)acetamide (Example 412B, 36 mgs, 0.071 mmol) in propan-2-ol (2 mL) was added 5-bromo-1,3,4-thiadiazol-2-amine (25.5 mgs, 0.142 mmol) and the resulting solution was heated to 80° C. for 16 h and then 150° C. for 1 h. The reaction was then poured in dichloromethane (5 mL) and saturated aqueous NaHCO$_3$ (3 mL) was added. The aqueous phase was extracted with dichloromethane (2×). The organic layers were dried over MgSO$_4$, filtered and concentrated. The residue was purified by column chromatography (12 g column on BIOTAGE® using 100% dichloromethane) to give the title material (15 mgs, 32%). LC (Method G): 2.569 min. HRMS(ESI) calcd for $C_{28}H_{21}BrN_4O_4S$ [M+H]$^+$ m/z 589.0467. found 589.0551. $^1$H NMR (400 MHz, DMSO-d$_6$) δ ppm 9.59-9.78 (m, 1H), 8.08 (s, 1H), 7.25-7.49 (m, 9H), 7.15-7.22 (m, 1H), 7.06-7.14 (m, 1H), 6.93-7.04 (m, 1H), 5.18-5.27 (m, 2H), 5.09-5.16 (m, 2H), 2.03-2.18 (m, 3H).

Example 412

N-(4-((3-(Benzyloxy)benzyl)oxy)-2-(2-methoxyimidazo[2,1-b][1,3,4]thiadiazol-6-yl)benzofuran-6-yl)acetamide

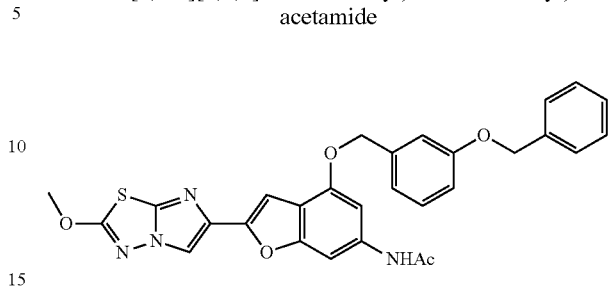

N-(4-((3-(Benzyloxy)benzyl)oxy)-2-(2-bromoimidazo[2,1-b][1,3,4]thiadiazol-6-yl)benzofuran-6-yl)acetamide (Example 412C, 17 mgs, 0.29 mmol) was dissolved in dichloromethane (1 mL) methanol (1 mL) and sodium methanolate 25% (15.98 μL, 0.072 mmol) was added. The reaction was stirred at r.t. for approximately 1 h, then quenched with saturated aqueous NH$_4$Cl and concentrated to dryness. The aqueous phase was extracted with dichloromethane (3×) and the organic phase was dried over MgSO$_4$, filtered and concentrated. The residue was purified by column chromatography (ISCO 4 g column, 100% dichloromethane up to 80% dichloromethane 20% ethyl acetate) to give the title material (14 mgs) with impurities. The solid was repurified on preparative HPLC using a ZORBAX® SB-C18 PrepHT 5 um; 21.2×100 mm to give the title material (10 mgs, 64%). HPLC (Method F): 2.399 min. LCMS (APCI) calcd for $C_{29}H_{25}N_4O_5S$ [M+H]$^+$ m/z 541.15. found 541.2. $^1$H NMR (400 MHz, DMSO-d$_6$) δ ppm 10.07 (s, 1H), 8.46 (s, 1H), 7.69 (s, 1H), 7.28-7.49 (m, 6H), 7.16 (s, 1H), 7.09 (d, J=8.22 Hz, 1H), 6.96-7.05 (m, 3H), 5.19 (s, 2H), 5.13 (s, 2H), 4.21 (s, 3H), 2.06 (s, 3H).

Example 413

6-(4-((3-(Benzyloxy)benzyl)oxy)benzofuran-2-yl)-2-methoxyimidazo[2,1-b][1,3,4]thiadiazole

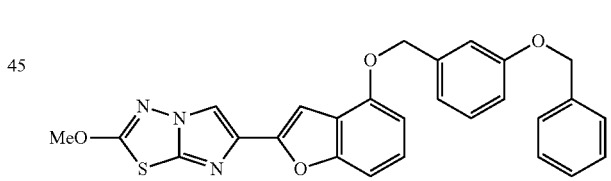

413A. 5-(Benzyloxy)-2,2-dimethyl-4H-benzo[d][1,3]dioxin-4-one

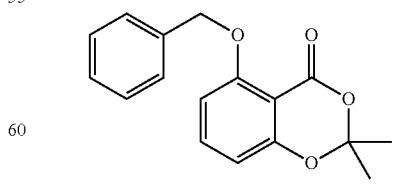

A solution of 5-hydroxy-2,2-dimethyl-4H-benzo[d][1,3]dioxin-4-one (6.00 g, 30.9 mmol) (Hadfield, A. et al., *Synthetic Communications*, 24(7):1025-1028 (1994)) in N,N-dimethylformamide (35 mL) was treated with powdered anhydrous potassium carbonate (5.15 g, 37.26 mmol) added all at once. The resulting mixture was stirred in vacuo for 10 min. and then flushed with nitrogen. The reaction flask was placed in a water bath (22° C.) an treated with benzyl bromide (5.55 g, 32.16 mmol) added dropwise over 15 min. The resulting mixture was then stirred at 22° C. for 18 h. The solid formed was filtered and washed with N,N-dimethylformamide. The filtrate was evaporated in vacuo and the residual oil was diluted with ethyl acetate (300 mL), washed with cold 0.1 N hydrochloric acid, saturated sodium bicarbonate and brine. After drying over anhydrous magnesium sulfate, evaporation of the solvent gave a thick syrup. Chromatography on silica gel (4×13 cm, elution toluene-ethyl acetate 0-5%) gave 8.78 g (100% yield) of the title material as a white solid. LC (Method F): 1.982 min. $^1$H NMR (CDCl$_3$, 600 MHz) δ ppm: 1.69 (s, 6H), 5.23 (s, 2H), 6.53 (d, J=8.2 Hz, 1H), 6.62 (d, J=8.4 Hz, 1H), 7.24-7.3 (m, 1H), 7.34-7.4 (m, 3H), 7.52 (broad d, J=7.4 Hz 2H).

413B. 2-(Benzyloxy)-6-hydroxybenzaldehyde

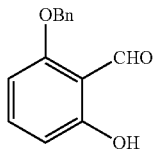

A solution of 5-(benzyloxy)-2,2-dimethyl-4H-benzo[d][1,3]dioxin-4-one (Example 413A, 4.00 g, 14.07 mmol) in dichloromethane (80 mL) was cooled to −78° C. and treated with a solution of diisobutylaluminum hydride (6.00 g, 42.2 mmol) in toluene (40 mL) added dropwise over 20 min. The resulting mixture was then stirred at −78° C. for 3 h. The reaction mixture was quenched by the careful addition of methanol (5 mL) added dropwise over 15 min, followed by 4 N hydrochloric acid (20 mL) added dropwise over 15 min. The cooling bath was then removed and an additional 80 mL of 4N hydrochloric acid was added over 10 min and the mixture was stirred vigorously at 22° C. for 4 h. The reaction mixture was diluted with ethyl acetate (200 mL), washed with brine, dried over anhydrous magnesium sulfate and evaporated in vacuo. The resulting oil was chromatographed on silica gel (4×10 cm, elution toluene) to give 2.25 g (70% yield) of the title material as a pale yellow solid. LC (Method F): 2.219 min. HRMS(ESI) calcd for C$_{14}$H$_{13}$O$_3$ [M+H]$^+$ m/z 229.0859. found 229.0859. $^1$H NMR (CDCl$_3$, 600 MHz) δ ppm: 5.12 (s, 2H), 6.43 (d, J=8.25 Hz, 1H), 6.52 (d, J=8.46 Hz, 1H), 7.34-7.4 (m, 6H), 10.39 (s, 1H), 11.95 (s, 1H).

413C. 1-(4-(Benzyloxy)benzofuran-2-yl)ethanone

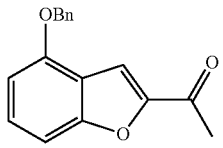

A solution of 2-(benzyloxy)-6-hydroxybenzaldehyde (Example 413B, 11.10 g, 48.63 mmole) in N,N-dimethylformamide (120 mL) was treated with powdered anhydrous cesium carbonate (15.8 g, 48.63 mmol) added all at once. The resulting mixture was stirred in vacuo for 10 min and then flushed with nitrogen. The reaction flask was placed in a water bath (22° C.) an treated with chloroacetone (4.65 mL, 58.4 mmol) added dropwise over 10 min. The resulting mixture was then stirred at 22° C. for 18 h (no starting aldehyde left by tlc and formation of the intermediate alkylated aldehyde). The reaction mixture was then maintained under vacuum (10 mbar) for 15 min to remove any un-reacted chloroacetone and then flushed with nitrogen. Then anhydrous cesium carbonate (1.0 g, 3.1 mmol) was added and the mixture was heated at 55° C. and stirred for 40 h (more cesium carbonate, 1 g, was added after 24 h and 32 h) till complete conversion of the intermediate alkylated aldehyde into the benzofuran as monitored by TLC. The solid was filtered and washed with N,N-dimethylformamide. The filtrate was evaporated in vacuo and the residual oil was diluted with ethyl acetate (400 mL), washed with cold 0.1 N hydrochloric acid, saturated sodium bicarbonate and brine. After drying over anhydrous magnesium sulfate, evaporation of the solvent gave a thick syrup. Chromatography on silica gel (4.5×12 cm, elution toluene-ethyl acetate 2-4%) gave 11.67 g (90% yield) of the title benzofuran as a light yellow solid. Recrystallization from a mixture of ethyl acetate (40 mL) and hexane (40 mL) gave colorless prisms (10.50 g). LC (Method F): 2.162 min. HRMS(ESI) calcd for C$_{17}$H$_{15}$O$_3$ [M+H]$^+$ m/z 267.1016. found 267.1022. $^1$H NMR (CDCl$_3$, 600 MHz) δ ppm: 2.56 (s, 3H), 5.20 (s, 2H), 6.73 (d, J=8.0 Hz, 1H), 7.17 (d, J=8.4 Hz, 1H), 7.3-7.5 (m, 6H), 7.63 (s, 1H).

413D. 1-(4-(Benzyloxy)benzofuran-2-yl)-2-bromoethanone

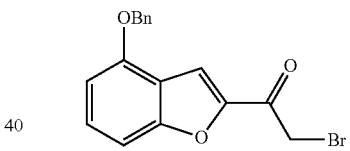

A 250-mL, three-necked flask is equipped with a magnetic stirring bar and purged with a nitrogen atmosphere, was charged with anhydrous tetrahydrofuran (40 mL) followed by 21.6 mL (21.6 mmol) of a 1M solution of lithium bis(trimethylsilyl)amide in tetrahydrofuran. The mixture was cooled to −78° C. and treated with a solution of 1-(4-(benzyloxy)benzofuran-2-yl)ethanone (Example 413C, 5.00 g, 18.77 mmole in tetrahydrofuran (20 mL) added dropwise over 10 min. The resulting mixture was then stirred at −78° C. for 45 min. Then chlorotrimethylsilane (2.74 mL, 21.6 mmol) was added dropwise over 5 min and the resulting solution was stirred at −78° C. for another 20 min. The cooling bath was then removed and the mixture is allowed to warm to room temperature over 30 min. The reaction mixture was then quenched by addition to a cold solution of ethyl acetate (300 mL), saturated sodium bicarbonate (40 mL) and ice. The organic phase was rapidly dried over anhydrous magnesium sulfate (magnetic stirring) and evaporated in vacuo to give the silyl enol ether as an oil which is co-evaporated with toluene (20 mL). The silyl enol ether was then dissolved in dry tetrahydrofuran (80 mL), cooled to −25° C. and treated with solid sodium bicarbonate (0.10 g) followed by N-bromosuccinimide (3.34 g, 18.8 mmol) added in small portions over 10 min. The reaction mixture was allowed to warm to 0° C. over 2 h and then quenched by addition of ethyl acetate (350 mL) and saturated sodium bicarbonate. The organic phase was washed with brine, dried over anhydrous magnesium sulfate and evaporated to give an orange oil. Chromatography on silica gel (4.5×12 cm, elution toluene-ethyl acetate 0-1%) gave 6.13 g of the title bromomethylketone as a yellow solid. Recrystallization from ethyl acetate (20 mL) and hexane (40 mL) gave pale yellow prisms (4.93 g, 76% yield). LC (Method F): 2.215 min. HRMS(ESI) calcd for $C_{17}H_{14}BrO$ [M+H]$^+$ m/z 345.0121. found 345.0109. $^1$H NMR (CDCl$_3$, 600 MHz) δ ppm: 4.39 (s, 2H), 5.20 (s, 2H), 6.75 (d, J=7.86 Hz, 1H), 7.17 (d, J=8.25 Hz, 1H), 7.34-7.46 (m, 6H), 7.78 (s, 1H).

413E. 6-(4-(Benzyloxy)benzofuran-2-yl)-2-bromoimidazo[2,1-b][1,3,4]thiadiazole

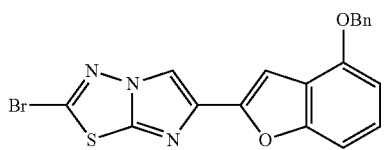 [SMILES: Brc1nn2cc(-c3cc4c(OCc5ccccc5)cccc4o3)nc2s1]

A mixture of 1-(4-(benzyloxy)benzofuran-2-yl)-2-bromoethanone (Example 413D, 3.00 g, 8.69 mmol) and 5-bromo-1,3,4-thiadiazol-2-amine (1.80 g, 10.0 mmol) in isopropanol (100 mL) was heated is a pressure flask equipped with a magnetic stirring bar at 80° C. for 20 h (homogeneous after 20 min and then formation of a precipitate after 2 h). The cooled mixture is then transferred into five 20 mL microwave vials and then heated in a microwave apparatus to 150° C. for 30 min. Each vial was then diluted with dichloromethane (250 mL) washed with saturated sodium bicarbonate (25 mL) and brine (25 mL), dried over anhydrous magnesium sulfate. The fractions were combined and concentrated in vacuo. Chromatography of the orange-brown residual solid on silica gel (4×10 cm, slow elution with dichloromethane) gave 2.82 g of the title imidazothiadiazole contaminated with some 1-(4-(benzyloxy)benzofuran-2-yl)ethanone. The solid material was triturated with ethyl acetate (15 mL), filtered, washed with ethyl acetate (10 ml) and dried in vacuo to give 2.37 g (64% yield) of pure title imidazothiadiazole as an off white solid which is used as such for the next step. LC (Method F): 2.425 min. HRMS(ESI) calcd for $C_{19}H_{13}BrN_3O_2S$ [M+H]$^+$ m/z 425.9906. found 425.9893. $^1$H NMR (CDCl$_3$, 600 MHz) δ ppm: 5.21 (s, 2H), 6.72 (d, J=8.07 Hz, 1H), 7.13 (d, J=8.26 Hz, 1H), 7.18 (broad t, 1H), 7.25 (s, 1H), 7.32 (broad t, 1H), 7.38 (broad t, 2H), 7.47 (broad d, 2H), 8.09 (s, 1H).

413F. 6-(4-(Benzyloxy)benzofuran-2-yl)-2-methoxyimidazo[2,1-b][1,3,4]thiadiazole

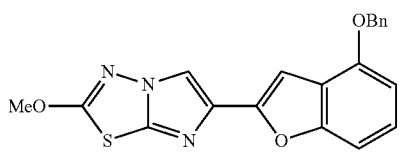

A solution of 6-(4-(benzyloxy)benzofuran-2-yl)-2-bromoimidazo[2,1-b][1,3,4]thiadiazole (Example 413E, 3.22 g, 7.55 mmol) in a mixture of dichloromethane (400 mL) and methanol (50 mL) was treated at 22° C. with 6.3 mL of a 25 wt. % solution of sodium methoxide in methanol (30.2 mmol) added in one portion. More methanol (45 mL) was added and the mixture was stirred for 40 min. The reaction mixture was quenched by the addition of 40 mL of 1 N hydrochloric acid followed by 10 ml of saturated sodium bicarbonate. The solvent was evaporated under reduced pressure and the residue was diluted with dichloromethane (400 mL), washed with brine, dried over anhydrous magnesium sulfate and evaporated in vacuo. Crystallization of the white solid residue from 1,2-dichloroethane (30 mL) gave 2.19 g of the title material as a white solid. Chromatography of the mother liquors on silica gel (3×10 cm, elution with dichloromethane-ethyl acetate 0-1%) gave another 0.46 g of product (total yield 2.65 g, 93%). LC (Method F): 2.379 min. HRMS(ESI) calcd for $C_{20}H_{16}N_3O_3S$ [M+H]$^+$ m/z 378.0907. found 378.0911. $^1$H NMR (CDCl$_3$, 600 MHz) δ ppm: 4.18 (s, 3H), 5.21 (s, 2H), 6.71 (dd, J=7.4 Hz and J=0.95 Hz, 1H), 7.12-7.17 (m, 3H), 7.32 (broad t, 1H), 7.38 (broad t, 2H), 7.47 (broad d, 2H), 7.88 (s, 1H).

413G. 2-(2-Methoxyimidazo[2,1-b][1,3,4]thiadiazol-6-yl)benzofuran-4-ol

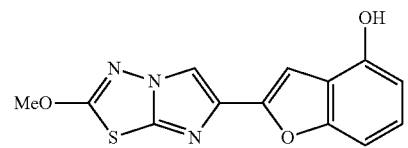 [SMILES: COc1nn2cc(-c3cc4c(O)cccc4o3)nc2s1]

A mixture of 6-(4-(benzyloxy)benzofuran-2-yl)-2-methoxyimidazo[2,1-b][1,3,4]thiadiazole (Example 413F, 2.640 g, 6.99 mmol) and pentamethylbenzene (7.25 g, 48.9 mmol) in dichloromethane (400 mL) was cooled to −78° C. under a nitrogen atmosphere and then treated immediately with 18.2 mL (8.2 mmol) of a 1 M solution of boron trichloride in dichloromethane added dropwise over 3 min. The resulting mixture was stirred at −78° C. for 1 h. The reaction mixture was then quenched by the addition of a solution of sodium bicarbonate (10.6 g) in water (50 mL) added in one portion. The cooling bath was removed and the resulting mixture was stirred at room temperature for 1 h. The solid formed was filtered, washed successively with water (50 mL) and dichloromethane (25 mL). The filter cake was allowed to soak with anhydrous ethanol (10 ml) and then sucked dry. The white solid obtained was then dried under vacuum for a few days over phosphorous pentoxide until constant weight to give 1.459 g (72% yield) of title material. The combined filtrate and washings (organic and aqueous phases from the deprotection step) were diluted with dichloromethane (500 mL) and stirred in a warm water bath till the organic phase was clear with no apparent solid in suspension. The organic phase was collected, dried over anhydrous magnesium sulfate and rapidly filtered while still warm. The filtrate was evaporated and the residue (product and pentamethylbenzene) was triturated with toluene (20 mL). The solid was collected by filtration and washed with toluene (20 mL) to give, after drying in vacuo, 0.239 g (12% yield, 84% combined yield) of title material as a tan solid. LC (Method F): 1.908 min. HRMS(ESI) calcd for $C_{13}H_{10}N_3O_3S$ [M+H]$^+$ m/z 288.0437. found 288.0446. $^1$H NMR (DMSO-d$_6$, 600 MHz) δ ppm: 4.46 (s, 3H), 6.58 (d, J=7.8 Hz, 1H), 6.97 (d, J=8.15 Hz, 1H), 7.0-7.07 (m, 3H), 8.40 (s, 1H).

Example 413

6-(4-((3-(Benzyloxy)benzyl)oxy)benzofuran-2-yl)-2-methoxyimidazo[2,1-b][1,3,4]thiadiazole

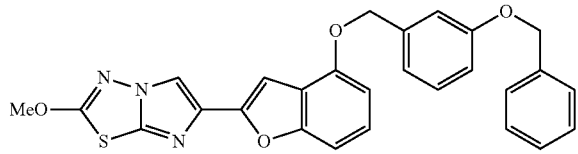 [SMILES: COc1nn2cc(-c3cc4c(OCc5cccc(OCc6ccccc6)c5)cccc4o3)nc2s1]

A mixture of 2-(2-methoxyimidazo[2,1-b][1,3,4]thiadiazol-6-yl)benzofuran-4-ol (0.110 g, 0.383 mmol), triphenylphosphine (Example 413G, 0.150 g, 0.574 mmol) and 3-benzyloxybenzyl alcohol (0.123 g, 0.574 mmol) in a 50 mL flask was maintained under vacuum for 10 min and then purged with nitrogen. Dry tetrahydrofuran (12 mL) was added and the resulting mixture was slightly warmed and maintained in an ultrasonic bath for 5 min. The cooled mixture (still heterogeneous) was treated at 22° C. with a solution of diisopropyl azodicarboxylate (0.116 g, 0.574 mmol) in tetrahydrofuran (2 mL) added dropwise over 30 min. The mixture was then stirred at 22° C. for 3 h. The clear reaction mixture was quenched by the addition of dichloromethane (100 mL) and saturated sodium bicarbonate (10 mL). The organic phase was washed with brine, dried over anhydrous magnesium sulfate and concentrated in vacuo. Chromatography of the residue on silica gel (2.5×12 cm, elution dichloromethane-ethyl acetate 0-5%) gave the title material (0.082 g, 44%) as a white solid. Recrystallization of this material from ethyl acetate (3 mL) gave 0.065 g of colorless needles. LC (Method F): 2.517 min. HRMS(ESI) calcd for $C_{27}H_{22}N_3O_4S$ [M+H]$^+$ m/z 484.1326. found 484.1315. $^1$H NMR (CDCl$_3$, 600 MHz) δ ppm: 19 (s, 3H), 5.06 (s, 2H), 5.18 (s, 2H), 6.87 (d, J=6.87 Hz, 1H), 6.91 (broad d, 1H), 7.06 (d, J=7.49 Hz, 1H), 7.10-7.17 (m, 4H), 7.27-7.31 (m, 2H), 7.36 (broad t, 2H), 7.42 (broad d, 2H), 7.89 (s, 1H).

Example 414

6-(4-((3-(Benzyloxy)benzyl)oxy)-6-chlorobenzofuran-2-yl)-2-methoxyimidazo[2,1-b][1,3,4]thiadiazole

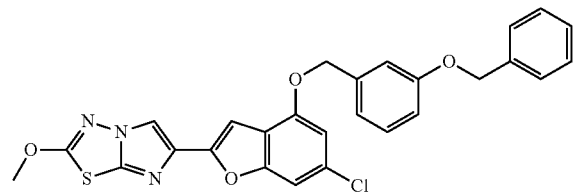 [SMILES: COc1nn2cc(-c3cc4c(OCc5cccc(OCc6ccccc6)c5)cc(Cl)cc4o3)nc2s1]

414A. 4-Chloro-2,6-dimethoxybenzaldehyde

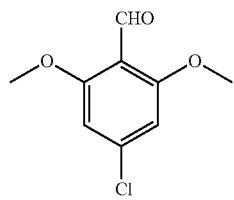

A solution of 1-chloro-3,5-dimethoxybenzene (5 g, 29.0 mmol) and TMEDA (4.37 mL, 29.0 mmol) in diethyl ether (100 mL, 962 mmol) at −78° C. under N$_2$ atmosphere was charged with BuLi (19.91 mL, 31.9 mmol) dropwise over a period of 30 minutes using a syringe pump. After stirring for 4 hours at −78° C., DMF was added and the reaction mixture continued to stir for 1.5 hours after which 1N HCl (~30 mL) was added (all at −78° C.). The reaction mixture was warmed to room temperature and extracted with ethyl acetate. The organic phase was dried (MgSO$_4$), filtered and concentrated to dryness. The residue was purified by ISCO using hexanes/EtOAc as eluent. Fractions containing the desired product were concentrated to dryness to give the title material (1.97 g, 9.82 mmol, 33.9% yield) as a light yellow solid. LC (Method B): 1.924 min. LCMS (APCI) calcd for $C_9H_{10}ClO_3$ [M+H]$^+$ m/z 201.03. found 201.0. $^1$H NMR (CDCl$_3$, 400 MHz) δ ppm: 10.28 (s, 1H), 6.87 (s, 2H), 3.86 (s, 6H).

414B. 4-Chloro-2-hydroxy-6-methoxybenzaldehyde

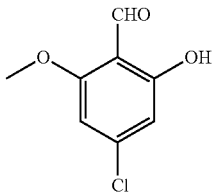

A stirred solution of 4-chloro-2,6-dimethoxybenzaldehyde (Example 414A, 1.95 g, 9.72 mmol) in DCM (20 mL, 311 mmol) at −78° C. was slowly added boron tribromide (9.72 mL, 9.72 mmol). The reaction mixture was stirred at −78° C. for 10 minutes then warmed to r.t. and stirred for 1 hour while monitoring reaction progress by LCMS. Once all s.m. had been consumed, the reaction was quenched with water and extracted with DCM. The organic phase was washed with brine, dried (MgSO$_4$), filtered and concentrated to dryness to give the title material (1.79 g, 9.59 mmol, 99% yield) as a purple solid. LC (Method B): 2.199 min. LCMS (APCI) calcd for $C_8H_8ClO_3$ [M+H]$^+$ m/z 187.02. found 187.0. $^1$H NMR (CDCl$_3$, 400 MHz) δ ppm: 11.89 (s, 1H), 10.20 (s, 1H), 6.75 (t, J=2.0 Hz, 1H), 6.66 (m, 1H), 3.91 (s, 1H).

414C. 1-(6-Chloro-4-methoxybenzofuran-2-yl)ethanone

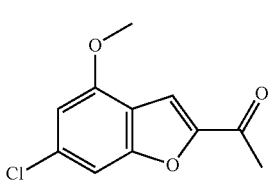

A stirred solution of 4-chloro-2-hydroxy-6-methoxybenzaldehyde (Example 414B, 1.79 g, 9.59 mmol) in N,N-dimethylformamide (15 mL, 9.59 mmol) was charged with cesium carbonate (3.75 g, 11.51 mmol) and 1-chloropropan-2-one (0.975 mL, 11.51 mmol). The reaction mixture was heated in a sealable vessel at 65° C. for 7 hours, was filtered over a Whatman filter paper to remove insolubles rinsing with DCM then washed with sat. NaHCO$_3$. The organic 414F. 1-(4-(Benzyloxy)-6-chlorobenzofuran-2-yl)-2-bromoethanone

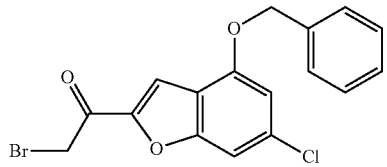

phase was dried (MgSO₄), filtered and concentrated to dryness. The residue was purified by ISCO using hexanes/EtOAc as eluent. Fractions containing the desired product were concentrated to give the title material (1.43 g, 6.37 mmol, 66% yield) as a light yellow solid. LC (Method A): 1.952 min. LCMS (APCI) calcd for $C_{11}H_{10}ClO_3$ [M+H]⁺ m/z 225.03. found 225.0. ¹H NMR (CDCl₃, 400 MHz) δ ppm: 7.94 (d, J=0.8 Hz, 1H), 7.49 (dd, J=0.8, 1.6 Hz, 1H), 6.97 (d, J=1.6 Hz, 1H), 3.97 (s, 3H).

414D. 1-(6-Chloro-4-hydroxybenzofuran-2-yl)ethanone

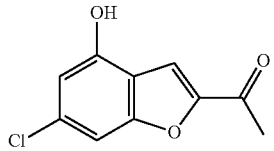

To a stirred solution of 1-(6-chloro-4-methoxybenzofuran-2-yl)ethanone (Example 414C, 1.43 g, 6.37 mmol) in chlorobenzene (15 mL, 148 mmol) was added aluminum chloride (3.40 g, 25.5 mmol) in portions over a period of 10 minutes. The reaction vessel was then sealed and heated at 100° C. for 40 minutes, then cool to r.t. and poured onto crushed ice (rinsed stirring bar with EtOAc). This was stirred for 30 minutes, then extracted with ethyl acetate. The organic phase was dried (MgSO₄), filtered and concentrated to dryness. The residue was purified by ISCO using hexanes/EtOAc as eluent. Fractions containing the desired product were concentrated to give the title material (1.18 g, 5.60 mmol, 88% yield) as a light brown solid. LC (Method A): 1.783 min. LCMS (APCI) calcd for $C_{10}H_8ClO_3$ [M+H]⁺ m/z 211.02. found 211.0. ¹H NMR (CDCl₃, 400 MHz) δ ppm: 11.01 (s, 1H), 7.89 (s, 1H), 6.72 (s, 1H), 2.52 (s, 3H).

414E. 1-(4-(Benzyloxy)-6-chlorobenzofuran-2-yl)ethanone

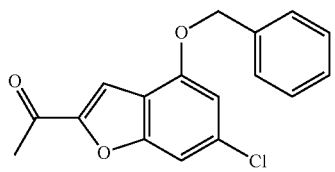 [SMILES: CC(=O)c1cc2c(OCc3ccccc3)cc(Cl)cc2o1]

A stirred solution of 1-(6-chloro-4-hydroxybenzofuran-2-yl)ethanone (Example 414D, 1.18 g, 5.60 mmol) in dry DMF (10 mL, 129 mmol) at r.t. was charged with K₂CO₃ (0.774 g, 5.60 mmol) and DMF. The reaction mixture was stirred for 1.5 hours then partitioned between ethyl acetate and water. The organic phase was washed with brine, dried (MgSO4), filtered and concentrated to dryness. The residue was purified by ISCO using hexanes/EtOAc as eluent. Fractions containing the desired product were concentrated to give the title material (1.57 g, 5.22 mmol, 93% yield) as an amber colored oil. LC (Method B): 2.420 min. LCMS (APCI) calcd for $C_{17}H_{14}ClO_3$ [M+H] m/z 301.06. found 301.0. ¹H NMR (CDCl₃, 400 MHz) δ ppm: 8.00 (d, J=0.8 Hz, 1H), 7.53 (m, 3H), 7.44 (m, 2H), 7.38 (m, 1H), 7.10 (d, J=1.6 Hz, 1H), 5.53 (s, 2H), 2.54 (s, 3H).

A flame dried 200 ml round-bottom flask equipped with a stirring bar and under nitrogen atmosphere was charged with anhydrous THF (12 mL) followed by lithium bis(trimethylsilyl)amide (6.22 mL, 6.22 mmol). The mixture was cooled to −78° C. and treated with a solution of 1-(4-(benzyloxy)-6-chlorobenzofuran-2-yl)ethanone (Example 414E, 1.56 g, 5.19 mmol) in THF (6 ml+2 ml washing) added dropwise over 10 minutes via a syringe pump. The resulting mixture was stirred at −78° C. for 45 minutes and was then charged with trimethylchlorosilane (0.769 mL, 6.02 mmol) added dropwise over 5 minutes by syringe pump then stirred for another 20 minutes. The cooling bath was removed and the mixture was allowed to warm to +10° C. for 30 minutes. The reaction mixture was quenched with a mixture of cold ethyl acetate (80 mL), sat. NaHCO₃ (12 mL) and ice. The organic phase was dried (MgSO₄), stirring for ~5 minutes to remove all traces of water), filtered and concentrated to dryness to give the silyl enol ether as a yellow oil which was co-evaporated with toluene (4 mL). The silyl enol ether was dissolved in dry THF (20 mL), cooled to −30° C. (employing a cooling bath made from 1:1 CaCl₂: water using dry ice, bath stabilizes around −30 to −45° C.) and treated with NaHCO₃ (~50 mgs) followed by N-bromosuccinimide (0.923 g, 5.19 mmol) added in small portions over 15 minutes. The reaction mixture was allowed to warm to 0° C. over 2 hours (monitored by LCMS) and then quenched by addition of ethyl acetate (100 mL) and sat. NaHCO₃. The organic phase was washed with brine, dried (MgSO₄) and evaporated to give an orange solid which was purified by ISCO using hexanes/EtOAc as eluent. Fractions containing the desired product were concentrated to give the title material 1.48 g, 3.51 mmol, 67.6% yield) as a yellow solid. LC (Method B): 2.528 min. LCMS (APCI) calcd for $C_{17}H_{13}BrClO_3$ [M+H]⁺ m/z 378.97. found 379.0.

414G. 6-(4-(Benzyloxy)-6-chlorobenzofuran-2-yl)-2-bromoimidazo[2,1-b][1,3,4]thiadiazole

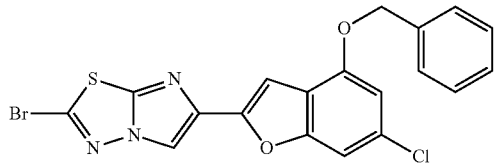 [SMILES: Clc1cc(OCc2ccccc2)c2cc(-c3cn4nc(Br)sc4n3)oc2c1]

A sealable vessel was charged with 1-(4-(benzyloxy)-6-chlorobenzofuran-2-yl)-2-bromoethanone (Example 414F, 1.48 g, 3.51 mmol), 5-bromo-1,3,4-thiadiazol-2-amine (0.632 g, 3.51 mmol) and IPA (25 mL, 324 mmol). The reaction mixture was heated in an oil bath at 80° C. for 6 hours then heated in the microwave at 150° C. for 1 hour. The reaction mixture was allowed to stand for 1 hour and the insoluble material was filtered off and rinsed with MeOH to give the desired product as a brown solid (1.19 g, 2.58 mmol, 73.6% yield). LC (Method A): 2.549 min. LCMS (APCI) calcd for $C_{19}H_{12}BrClN_3O_2S$ [M+H]$^+$ m/z 459.95. found 460.0. $^1$H NMR (CDCl$_3$, 400 MHz) δ ppm: 8.74 (s, 1H), 7.55-7.50 (m, 2H), 7.45-7.34 (m, 4H), 7.17 (d, J=0.8 Hz, 1H), 7.02 (d, J=1.6 Hz, 1H), 5.32 (s, 2H).

414H. 6-(4-(Benzyloxy)-6-chlorobenzofuran-2-yl)-2-methoxyimidazo[2,1-b][1,3,4]thiadiazole

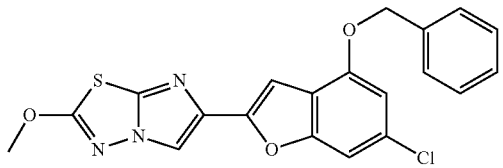 [SMILES: COc1nn2cc(-c3cc4c(OCc5ccccc5)cc(Cl)cc4o3)nc2s1]

To a stirred solution of 6-(4-(benzyloxy)-6-chlorobenzofuran-2-yl)-2-bromoimidazo[2,1-b][1,3,4]thiadiazole (Example 414G, 1.18 g, 2.56 mmol) in DCM (40 mL, 622 mmol) and methanol (10 mL, 247 mmol) was added sodium methoxide (1.164 mL, 5.12 mmol). The reaction mixture was stirred at r.t. for 1 h 15 min while monitoring by TLC (7:3 hexanes:EtOAc). The reaction mixture was quenched with 1N HCl and extracted with DCM. The organic phase was washed with brine, dried (MgSO$_4$), filtered and concentrated to dryness. The residue was triturated with MeOH (sonication) and the solid material was filtered off, rinsed with MeOH and sucked dry to give the desired compound as a brown solid (859 mg, 2.086 mmol, 81% yield). LC (Method A): 2.478 min. LCMS (APCI) calcd for $C_{20}H_{15}ClN_3O_3S$ [M+H]$^+$ m/z 412.05. found 412.0. $^1$H NMR (CDCl$_3$, 400 MHz) δ ppm: 8.50 (s, 1H), 7.52 (m, 2H), 7.43 (m, 2H), 7.36 (m, 2H), 7.09 (d, J=0.8 Hz, 1H), 7.00 (d, J=1.6 Hz, 1H), 5.31 (s, 2H), 4.21 (s, 3H).

414I. 6-Chloro-2-(2-methoxyimidazo[2,1-b][1,3,4]thiadiazol-6-yl)benzofuran-4-ol

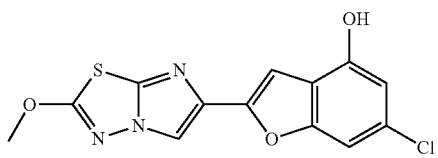 [SMILES: COc1nn2cc(-c3cc4c(O)cc(Cl)cc4o3)nc2s1]

A stirred solution of 6-(4-(benzyloxy)-6-chlorobenzofuran-2-yl)-2-methoxyimidazo[2,1-b][1,3,4]thiadiazole (Example 414H, 0.85 g, 2.064 mmol) and pentamethylbenzene (2.142 g, 14.45 mmol) in DCM under N$_2$ atmosphere was cooled to –78° C. after which boron trichloride (5.16 mL, 5.16 mmol) was added dropwise over ~4 minutes. The reaction was monitored by TLC using 1:1 hexanes:EtOAc as eluent. The reaction mixture was stirred at –78° C. for 30 minutes after which a mixture of water (40 mL) and saturated NaHCO$_3$ (5 mL) was added (at –78° C.) and the mixture was stirred until ambient temperature was obtained (removed from cooling bath). The solid precipitate was filtered off and rinsed with diethyl ether then allowed to dry overnight to give the title material (441 mgs, 1.371 mmol, 66.4% yield) as a beige solid. The filtrate was extracted with DCM. The organic phase was washed with brine, dried (MgSO$_4$) and concentrated to dryness. The residue was purified by ISCO using DCM/EtOAc as eluent. Fractions containing the desired product were concentrated to give the title material (25 mgs, 0.078 mmol, 3.77% yield) as a beige solid. LC (Method A): 2.167 min. LCMS (APCI) calcd for $C_{13}H_9ClN_3O_3S$ [M+H]$^+$ m/z 322.00. found 322.0. $^1$H NMR (CDCl$_3$, 400 MHz) δ ppm: 10.50 (br. S, 1H), 8.45 (s, 1H), 7.17 (dd, J=0.8, 1.6 Hz, 1H), 7.09 (d, J=0.8 Hz, 1H), 6.67 (d, J=2.0 Hz, 2H), 4.21 (s, 3H).

Example 414

6-(4-((3-(Benzyloxy)benzyl)oxy)-6-chlorobenzofuran-2-yl)-2-methoxyimidazo[2,1-b][1,3,4]thiadiazole

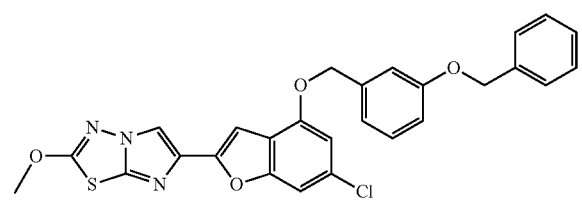 [SMILES: COc1nn2cc(-c3cc4c(OCc5cccc(OCc6ccccc6)c5)cc(Cl)cc4o3)nc2s1]

6-(4-((3-(Benzyloxy)benzyl)oxy)-6-chlorobenzofuran-2-yl)-2-methoxyimidazo[2,1-b][1,3,4]thiadiazole was prepared as described in Example 205 from 6-chloro-2-(2-methoxyimidazo[2,1-b][1,3,4]thiadiazol-6-yl)benzofuran-4-ol (Example 414I). LC (Method F): 2.660 min. HRMS (ESI) calcd for $C_{27}H_{21}ClN_3O_4S$ [M+H]$^+$ m/z 518.0936. found 518.0902. $^1$H NMR (CDCl$_3$, 400 MHz) δ ppm: 7.89 (s, 1H), 7.46-7.30 (m, 6H), 7.16-7.10 (m, 4H), 6.96 (d, J=8.3 Hz, 1H), 6.72 (s, 1H), 5.17 (s, 2H), 5.09 (s, 2H), 4.21 (s, 3H).

Example 415

6-(4-((3-(Benzyloxy)benzyl)oxy)-7-chloro-6-methoxybenzofuran-2-yl)-2 methoxyimidazo[2,1-b][1,3,4]thiadiazole

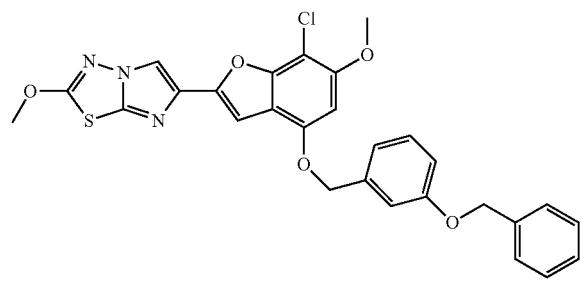 [SMILES: COc1nn2cc(-c3cc4c(OCc5cccc(OCc6ccccc6)c5)cc(OC)c(Cl)c4o3)nc2s1]

415A. 1-(4-((3-(Benzyloxy)benzyl)oxy)-7-chloro-6-hydroxybenzofuran-2-yl)ethanone

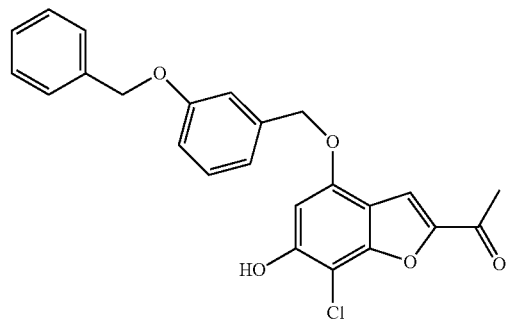 [SMILES: CC(=O)c1cc2c(OCc3cccc(OCc4ccccc4)c3)cc(O)c(Cl)c2o1]

To a stirred suspension of 1-(4-((3-(benzyloxy)benzyl)oxy)-6-hydroxybenzofuran-2-yl) ethanone (251 mgs, 0.65 mmol) in acetonitrile (5 mL) was added N-chlorosuccinimide (86 mgs, 0.65 mmol). The reaction mixture was then heated to 70° C. for 1 hour and after that period another portion of N-chlorosuccinimide (8 mgs, 0.06 mmol) was added. After 30 minutes, the mixture was cooled down and the solvent was evaporated. The residue was purified on ISCO using a REDISEP® 4 g column using CH$_2$Cl$_2$/EtOAc as eluent. The crude product was adsorbed on SiO$_2$. Fractions containing the desired product were concentrated to dryness to give the title material (190 mgs, 0.45 mmol, 69% yield) as a light yellow solid. LC (Method F): 2.291 min. HRMS(ESI) calcd for C$_{24}$H$_{20}$ClO$_5$ [M+H]$^+$ m/z 423.0994. found 423.1032. $^1$H NMR (CDCl$_3$, 600 MHz) δ ppm: 7.59 (s, 1H), 7.44-7.311 (m, 6H), 7.06-6.96 (m, 3H), 6.51 (s, 1H), 5.83 (s, 1H), 5.13 (s, 2H), 5.09 (s, 2H), 2.58 (s, 3H).

415B. 1-(4-((3-(Benzyloxy)benzyl)oxy)-7-chloro-6-methoxybenzofuran-2-yl)ethanone

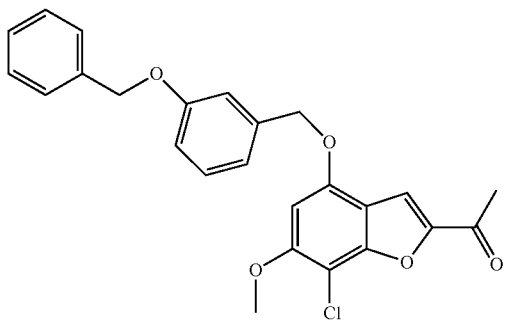 [SMILES: COc1cc(OCc2cccc(OCc3ccccc3)c2)c2cc(C(C)=O)oc2c1Cl]

To a stirred solution of 1-(4-((3-(benzyloxy)benzyl)oxy)-7-chloro-6-methoxybenzofuran-2-yl)ethanone (Example 415A, 190 mgs, 0.45 mmol) in acetone (1.8 mL) and acetonitrile (3.6 mL) were added methyl iodide (120 μL, 1.9 mmol) and Cs$_2$CO$_3$ (222 mgs, 0.68 mmol). The mixture was stirred at room temperature for 5 hours, then diluted with methylene chloride and filtered over a pad of silica gel. After evaporation of the solvents, the residue was purified on ISCO using a REDISEP® 4 g column using hexanes/EtOAc as eluent. The crude product was adsorbed on SiO$_2$. Fractions containing the desired product were concentrated to dryness to give the title material (107 mgs, 0.25 mmol, 55% yield) as a white solid. LC (Method F): 2.389 min. HRMS (ESI) calcd for C$_{25}$H$_{22}$ClO$_5$ [M+H]$^+$ m/z 437.1150. found 437.1178. $^1$H NMR (CDCl$_3$, 600 MHz) δ ppm: 7.59 (s, 1H), 7.43-7.31 (m, 6H), 7.07-6.97 (m, 3H), 6.45 (s, 1H), 5.19 (s, 2H), 5.09 (s, 2H), 3.92 (s, 3H), 2.59 (s, 3H).

415C. 1-(4-((3-(Benzyloxy)benzyl)oxy)-7-chloro-6-methoxybenzofuran-2-yl)-2-bromoethanone

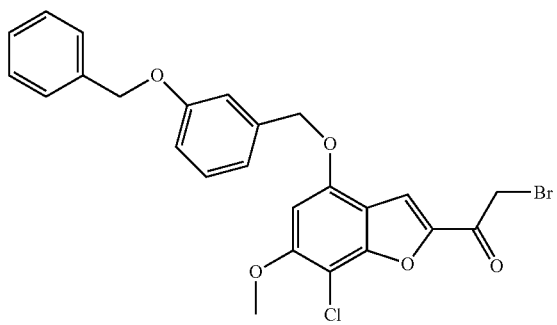 [SMILES: COc1cc(OCc2cccc(OCc3ccccc3)c2)c2cc(C(=O)CBr)oc2c1Cl]

In a 10 mL round-bottomed flask were added 1-(4-((3-(benzyloxy)benzyl)oxy)-7-chloro-6-methoxybenzofuran-2-yl)ethanone (Example 415B, 209 mgs, 0.479 mmol) and copper(II) bromide (107 mgs, 0.479 mmol) in ethyl acetate (3 ml). The mixture was heated to 80° C. for 1 hr. 45 min then diluted with ethyl acetate and filtered over silica gel. After evaporation of the solvent, the residue was purified on ISCO using a REDISEP® 4 g column (CH$_2$Cl$_2$ 100%) then with another run with hexane/ethyl acetate 10/90 to 45/55. Fractions containing the desired product were concentrated to dryness to give the title material (69 mgs, 0.134 mmol, 28%) as a yellow solid, still contains about 5-10% of starting material. LC (Method F): 2.408 min. HRMS(ESI) calcd for C$_{25}$H$_{21}$ClBrO$_5$ [M+H]$^+$ m/z 515.0255. found 515.0248. $^1$H NMR (CDCl$_3$, 600 MHz) δ ppm: 7.73 (s, 1H), 7.43-7.32 (m, 6H), 7.06-6.97 (m, 3H), 6.46 (s, 1H), 5.19 (s, 2H), 5.09 (s, 2H), 3.92 (s, 3H).

415D. 6-(4-((3-(Benzyloxy)benzyl)oxy)-7-chloro-6-methoxybenzofuran-2-yl)-2-bromoimidazo[2,1-b][1,3,4]thiadiazole

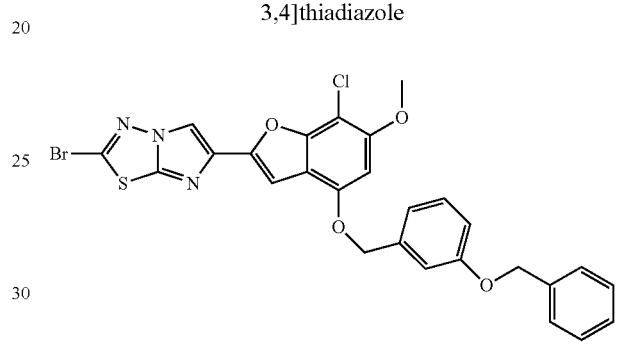

In a 0.5-2 mL microwave vial was added 1-(4-((3-(benzyloxy)benzyl)oxy)-7-chloro-6-methoxybenzofuran-2-yl)-2-bromoethanone (Example 415C, 69 mgs, 0.134 mmol) and 5-bromo-1,3,4-thiadiazol-2-amine (24 mgs, 0.133 mmol) in 2-propanol (1 mL) to give a yellow suspension. The mixture was heated to 90° C. for 5 h then the vial was placed in the microwave oven and heated to 150° C. for 25 min. After evaporation of the solvent, the residue was purified on ISCO using a REDISEP® 4 g column (hexanes/EtOAc). Fractions containing the desired product were concentrated to dryness to give the title material (30 mg, 0.134 mmol, 28%) as a yellow solid. LC (Method F): 2.607 min. HRMS(ESI) calcd for C$_{27}$H$_{20}$ClBrN$_3$O$_4$S [M+H]$^+$ m/z 596.0041. found 515.0033. $^1$H NMR (CDCl$_3$, 600 MHz) δ ppm: 8.15 (s, 1H), 7.44-7.27 (m, 6H), 7.21 (s, 1H), 7.10 (s, 1H), 7.06 (d, J=7.4 Hz, 1H), 6.95 (dd, J=1.1 and 8.2 Hz, 1H), 6.45 (s, 1H), 5.21 (s, 2H), 5.09 (s, 2H), 3.90 (s, 3H).

Example 415

6-(4-((3-(Benzyloxy)benzyl)oxy)-7-chloro-6-methoxybenzofuran-2-yl)-2-methoxyimidazo[2,1-b][1,3,4]thiadiazole

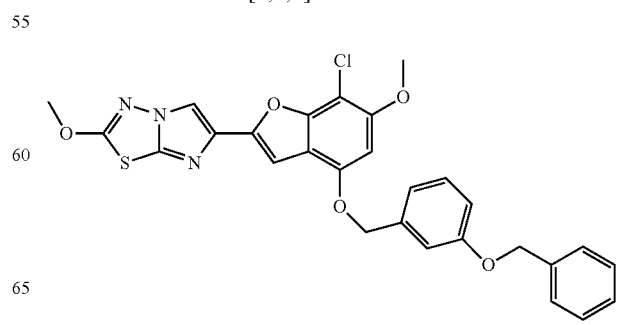

To a stirred suspension of 6-(4-((3-(benzyloxy)benzyl)oxy)-7-chloro-6-methoxybenzofuran-2-yl)-2-bromoimidazo[2,1-b][1,3,4]thiadiazole (Example 415D, 30 mgs, 0.050 mmol) in CH$_2$Cl$_2$ (1 mL) and MeOH (0.5 mL) was added a solution of sodium methoxide in methanol (4.4 M., 17 µL, 0.075 mmol). After 1 hour, TFA (4 µL) was added and the solvents were evaporated. The residue was purified on ISCO using a REDISEP® 4 g column (CH$_2$Cl$_2$/EtOAc 100/0 to 80/20). Fractions containing the desired product were concentrated to dryness to give the title material (17 mg, 0.031 mmol, 62%) as a slightly yellow solid. LC (Method F): 2.545 min. HRMS(ESI) calcd for C$_{28}$H$_{23}$ClN$_3$O$_5$S [M+H]$^+$ m/z 548.1041. found 548.1038. $^1$H NMR (CDCl$_3$, 600 MHz) δ ppm: 8.20 (s, 1H), 7.49-7.32 (m, 8H), 7.09 (dd, J=2.7 and 8.2 Hz, 1H), 6.82 (s, 1H), 5.33 (s, 2H), 5.17 (s, 2H), 4.27 (s, 3H), 3.94 (s, 3H).

Example 416

6-(4-((3-(Benzyloxy)benzyl)oxy)-6-(difluoromethoxy)benzofuran-2-yl)-2-methoxyimidazo[2,1-b][1,3,4]thiadiazole

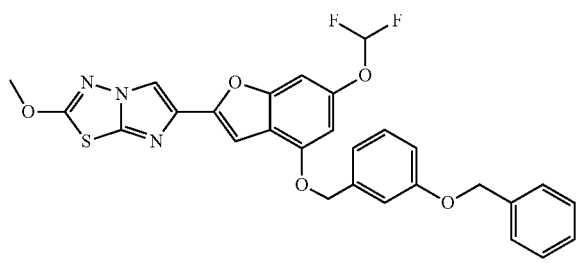 [SMILES: COc1nn2cc(-c3cc4c(OCc5cccc(OCc6ccccc6)c5)cc(OC(F)F)cc4o3)nc2s1]

416A. 1-(4-((3-(Benzyloxy)benzyl)oxy)-6-(difluoromethoxy)benzofuran-2-yl)ethanone

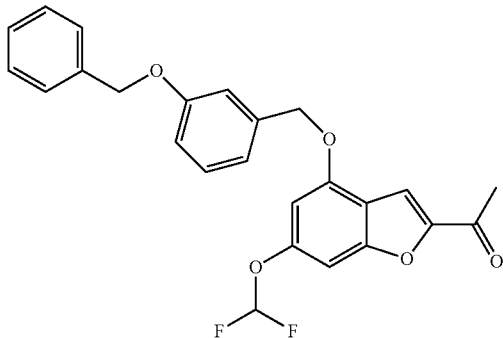 [SMILES: CC(=O)c1cc2c(OCc3cccc(OCc4ccccc4)c3)cc(OC(F)F)cc2o1]

To a degassed suspension of 1-(4-((3-(benzyloxy)benzyl)oxy)-6-hydroxybenzofuran-2-yl)ethanone (Example 410F, 132 mgs, 0.34 mmol) and K$_2$CO$_3$ (188 mgs, 1.36 mmol) in DMF (1 mL) and H$_2$O (0.25 mL) was added chlorodifluoro acetic acid (86 µL, 1.02 mmol). The reaction mixture was heated to 100° C. After 5 hours, K$_2$CO$_3$ (47 mgs, 0.34 mmol) and chlorodifluoro acetic acid (86 µL, 1.02 mmol) were added. After an additional 3 hours, another equivalent of both reagents was added. The reaction mixture was then stirred for 16 hours at same temperature then cooled down and diluted with ethyl acetate. The organic phase was washed with water, then brine and dried over Na$_2$SO$_4$. After evaporation of the solvents, the residue was purified on ISCO using a REDISEP® 4 g column using hexanes/EtOAc as eluent. Fractions containing the desired product were concentrated to dryness to give the title material (84 mgs, 0.19 mmol, 56%). LC (Method F): 2.351 min. HRMS(ESI) calcd for C$_{25}$H$_{21}$F$_2$O$_5$ [M+H]$^+$ m/z 439.1352. found 439.1381. $^1$H NMR (CDCl$_3$, 600 MHz) δ ppm: 7.60 (s, 1H), 7.44-7.32 (m, 6H), 7.08 (s, 1H), 7.05 (d, J=7.6 Hz, 1H), 6.99 (dd, J=2.0 and 8.2 Hz, 1H), 6.95 (s, 1H), 6.56 (s, 1H), 6.54 (t, J=73.0 Hz, 1H), 5.16 (s, 2H), 5.10 (s, 2H), 2.57 (s, 3H).

416B. 1-(4-((3-(Benzyloxy)benzyl)oxy)-6-(difluoromethoxy)benzofuran-2-yl)-2-bromoethanone

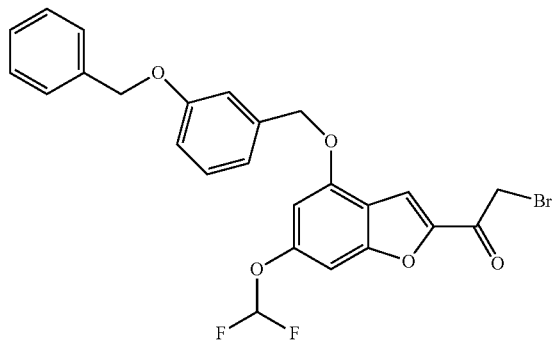 [SMILES: O=C(CBr)c1cc2c(OCc3cccc(OCc4ccccc4)c3)cc(OC(F)F)cc2o1]

In a 10 mL round-bottomed flask were added 1-(4-((3-(benzyloxy)benzyl)oxy)-6-(difluoromethoxy)benzofuran-2-yl)ethanone (Example 416A, 132 mgs, 0.30 mmol) and copper(II) bromide (134 mgs, 0.60 mmol) in ethyl acetate (2 mL). The mixture was heated to 80° C. for 1 hr. 45 min then diluted with ethyl acetate and filtered over silica gel. After evaporation of the solvent, the residue was purified on ISCO using a REDISEP® 4 g column using hexanes/EtOAc as eluent. Fractions containing the desired product were concentrated to dryness to give the title material (107 mgs, 0.21 mmol, 69%) as a white solid. LC (Method F): 2.369 min. HRMS(ESI) calcd for C$_{25}$H$_{20}$BrF$_2$O$_5$ [M+H]$^+$ m/z 517.0457. found 517.0472. $^1$H NMR (CDCl$_3$, 600 MHz) δ ppm: 7.74 (s, 1H), 7.44-7.32 (m, 6H), 7.07 (s, 1H), 7.04 (d, J=7.6 Hz, 1H), 6.99 (d, J=8.4 Hz, 1H), 6.96 (s, 1H), 6.56 (s, 1H), 6.55 (t, J=73.2 Hz, 1H), 5.16 (s, 2H), 5.10 (s, 2H), 4.38 (s, 2H).

416C. 6-(4-((3-(Benzyloxy)benzyl)oxy)-6-(difluoromethoxy)benzofuran-2-yl)-2-bromoimidazo[2,1-b][1,3,4]thiadiazole

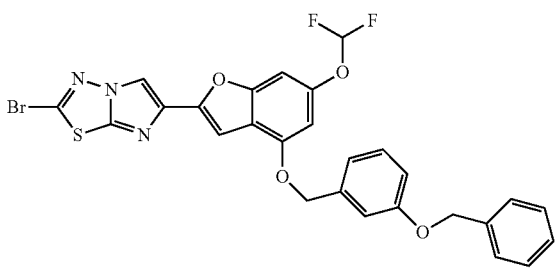 [SMILES: FC(F)Oc1cc(OCc2cccc(OCc3ccccc3)c2)c2cc(-c3cn4nc(Br)sc4n3)oc2c1]

In a 0.5-2 mL microwave vial was added 1-(4-((3-(benzyloxy)benzyl)oxy)-6-(difluoromethoxy)benzofuran-2-yl)-2-bromoethanone (Example 416B, 106 mgs, 0.20 mmol) and 5-bromo-1,3,4-thiadiazol-2-amine (41 mgs, 0.22 mmol) in 2-propanol (2 mL) to give a white suspension. The mixture was heated to 90° C. for 4 h then the vial was placed in the microwave oven and heated to 150° C. for 20 min. After evaporation of the solvent, the residue was purified on ISCO using a REDISEP® 4 g column (hexanes/EtOAc). Fractions containing the desired product were concentrated to dryness to give the title material (61 mgs, 0.11 mmol, 51%) as a slightly orange solid. LC (Method F): 2.529 min. HRMS(ESI) calcd for $C_{27}H_{18}BrF_2N_3O_4S$ [M+H]$^+$ m/z 597.0169. found 597.0175. $^1$H NMR (CDCl$_3$, 600 MHz) δ ppm: 8.09 (s, 1H), 7.45-7.30 (m, 6H), 7.21 (s, 1H), 7.10 (s, 1H), 7.06 (d, J=7.6 Hz, 1H), 6.95 (m, 2H), 6.55 (s, 1H), 6.50 (t, J=73.8 Hz, 1H) 5.17 (s, 2H), 5.09 (s, 2H).

Example 416

6-(4-((3-(Benzyloxy)benzyl)oxy)-6-(difluoromethoxy)benzofuran-2-yl)-2-methoxyimidazo[2,1-b][1,3,4]thiadiazole

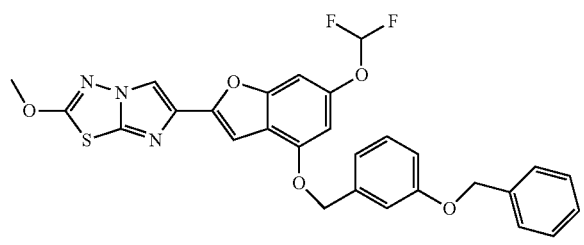 [SMILES: COc1nn2cc(-c3cc4c(OCc5cccc(OCc6ccccc6)c5)cc(OC(F)F)cc4o3)nc2s1]

To a stirred suspension of 6-(4-((3-(benzyloxy)benzyl)oxy)-6-(difluoromethoxy)benzofuran-2-yl)-2-bromoimidazo[2,1-b][1,3,4]thiadiazole. (Example 416C, 60 mgs, 0.10 mmol) in CH$_2$Cl$_2$ (1.6 mL) and MeOH (1.6 mL) was added a solution of sodium methoxide in methanol (4.4 M., 34 µL, 0.15 mmol). After 45 minutes, a solution of HCl 1N. (2 mL) was added and the reaction mixture was extracted with ethyl acetate. The organic phase was washed with brine and dried over Na$_2$SO$_4$. After evaporation of the solvents, the residue was purified on ISCO using a REDISEP® 4 g column using hexanes/EtOAc as eluent. Fractions containing the desired product were concentrated to dryness to give the title material (35 mgs 0.064 mmol, 64%). LC (Method F): 2.493 min. HRMS(ESI) calcd for $C_{28}H_{22}F_2N_3O_5S$ [M+H]$^+$ m/z 550.1243. found 550.1245. $^1$H NMR (CDCl$_3$, 600 MHz) δ ppm: 7.88 (s, 1H), 7.45-7.30 (m, 6H), 7.13-7.07 (m, 3H), 6.95 (m, 2H), 6.55 (s, 1H), 6.49 (t, J=74.1 Hz, 1H) 5.17 (s, 2H), 5.09 (s, 2H), 4.21 (s, 3H).

Examples 417 to 428

The following additional Examples have been prepared, isolated and characterized using the methods disclosed above.

| Ex. | Structure | Experimental procedure (Example) | Formula | Exact Mass Or [M + H]+ | HPLC Retention Time (Min)/ Method | LCMS [M + H]+ m/z | NMR |
|---|---|---|---|---|---|---|---|
| 417 | 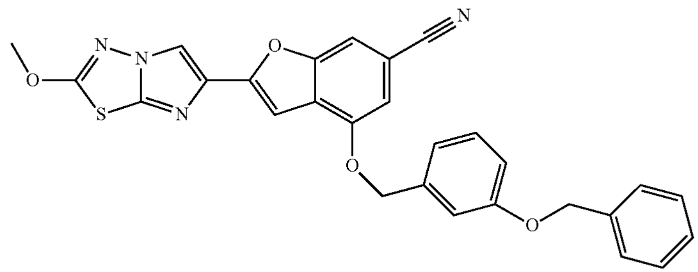 [SMILES: COc1nn2cc(-c3cc4c(OCc5cccc(OCc6ccccc6)c5)cc(C#N)cc4o3)nc2s1] | Ex. 411 | C28H20N4O4S | 509.1278 | 2.441/F | 509.1271 | 1H NMR (CDCl3, 600 MHz) δ ppm: 7.96 (s, 1H), 7.47-7.30 (m, 7H), 7.20 (s, 1H), 7.09-7.05 (m, 2H), 6.97 (d, J = 6.1 Hz, 1H), 6.91 (s, 1H), 5.20 (s, 2H), 5.09 (s, 2H), 4.22 (s, 3H). |
| 418 | 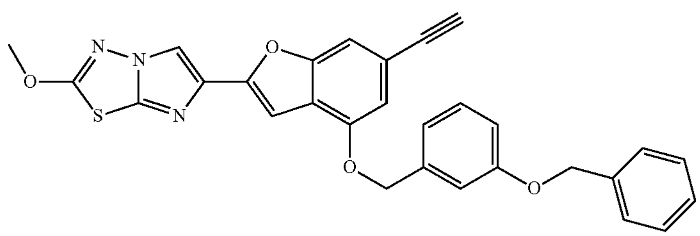 [SMILES: C#Cc1cc(OCc2cccc(OCc3ccccc3)c2)c2cc(-c3cn4nc(OC)sc4n3)oc2c1] | Ex. 411 | C29H21N3O4S | 508.1326 | 2.575/F | 508.1332 | 1H NMR (CDCl3, 600 MHz) δ ppm: 7.92 (s, 1H), 7.45-7.30 (m, 7H), 7.15 (s, 1H), 7.11 (s, 1H), 7.08 (d, J = 7.6 Hz, 1H), 6.95 (dd, J = 2.3 and 8.2 Hz, 1H), 6.85 (s, 1H), 5.18 (s, 2H), 5.09 (s, 2H), 4.21 (s, 3H), 3.09 (s, 1H). |
| 419 | 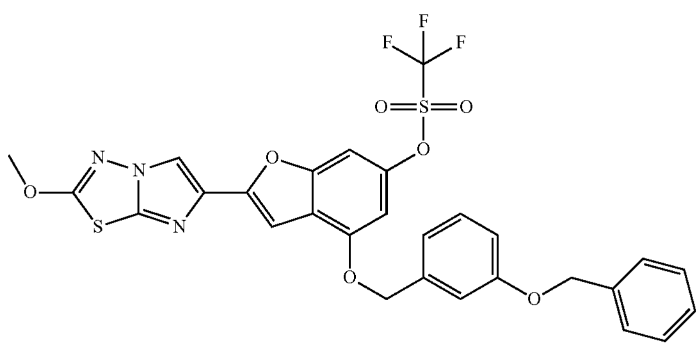 [SMILES: COc1nn2cc(-c3cc4c(OCc5cccc(OCc6ccccc6)c5)cc(OS(=O)(=O)C(F)(F)F)cc4o3)nc2s1] | Ex. 410 | C20H15N3O2S2 | 393.06 | 2.496/C | 394.07 | 1H NMR (600 MHz, CDCl3) δ ppm 8.03 (s, 1H), 7.48-7.47 (m, 2H), 7.41-7.38 (m, 3H), 7.34-7.32 (m, 1H), 7.13 (s, 1H), 6.99 (s, 1H), 6.96-6.95 (m, 1H), 5.11 (s, 2H), 2.77 (s, 3H) |

-continued

| Ex. | Structure | Experimental procedure (Example) | Formula | Exact Mass Or [M + H]+ | HPLC Retention Time (Min)/ Method | LCMS [M + H]+ m/z | NMR |
|---|---|---|---|---|---|---|---|
| 420 | 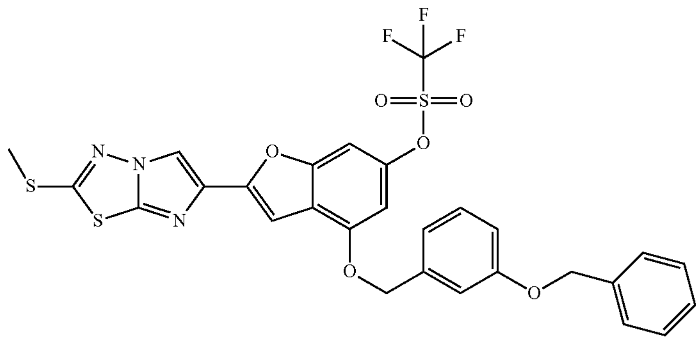 [SMILES: CSc1nn2cc(-c3cc4c(OCc5cccc(OCc6ccccc6)c5)cc(OS(=O)(=O)C(F)(F)F)cc4o3)nc2s1] | Ex. 410 | C28H20F3N3O6S3 | 648.0539 | 2.656/F | 648.0559 | 1H NMR (CDCl3, 600 MHz) δ ppm: 8.03 (s, 1H), 7.45-7.31 (m, 6H), 7.20 (s, 1H), 7.10 (d, J = 10.3 Hz, 1H), 7.06 (d, J = 7.6 Hz, 1H), 6.96 (d, J = 8.2 Hz, 1H), 6.64 (s, 1H), 5.19 (s, 2H), 5.09 (s, 2H), 2.78 (s, 3H). |
| 421 | 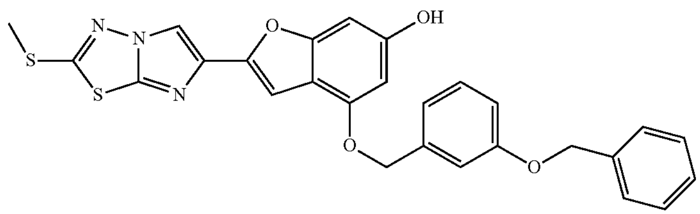 [SMILES: CSc1nn2cc(-c3cc4c(OCc5cccc(OCc6ccccc6)c5)cc(O)cc4o3)nc2s1] | Ex. 410 | C27H21N3O4S2 | 516.1046 | 2.382/F | 516.1071 | 1H NMR (CDCl3, 600 MHz) δ ppm: 7.96 (s, 1H), 7.45-7.30 (m, 6H), 7.20 (s, 1H), 7.11 (m, 2H), 7.06 (d, J = 7.7 Hz, 1H), 6.95 (dd, J = 2.4 and 8.2 Hz, 1H), 6.66 (s, 1H), 6.30 (d, J = 1.8 Hz, 1H), 5.15 (s, 2H), 5.08 (s, 2H), 4.98 (s, 1H), 2.77 (s, 3H). |
| 422 | 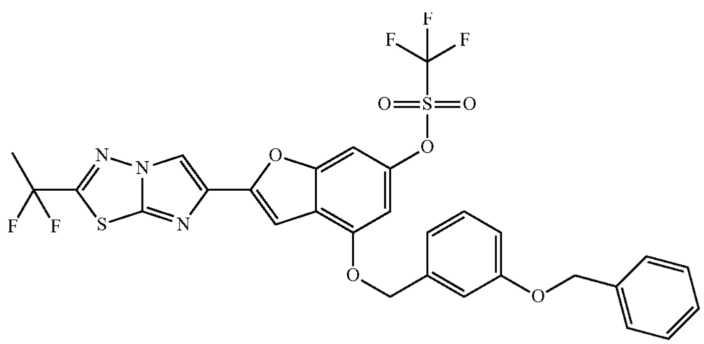 [SMILES: CC(F)(F)c1nn2cc(-c3cc4c(OCc5cccc(OCc6ccccc6)c5)cc(OS(=O)(=O)C(F)(F)F)cc4o3)nc2s1] | Ex. 410 | C29H20F5N3O6S2 | 666.0786 | 2.621/F | 666.0805 | 1H NMR (CDCl3, 600 MHz) δ ppm: 8.15 (s, 1H), 7.45-7.27 (m, 7H), 7.13-7.05 (m, 4H), 6.66 (s, 1H), 5.20 (s, 2H), 5.09 (s, 2H), 2.17 (t, J = 18.4 Hz, 3H). |

-continued

| Ex. | Structure | Experimental procedure (Example) | Formula | Exact Mass Or [M + H]+ | HPLC Retention Time (Min)/ Method | LCMS [M + H]+ m/z | NMR |
|---|---|---|---|---|---|---|---|
| 423 | 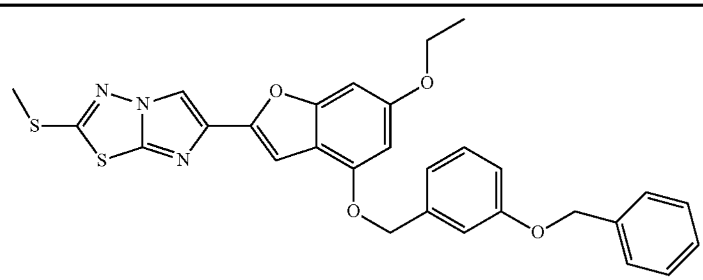 | Ex. 416 | C29H25N3O4S2 | 544.1359 | 2.635/F | 544.1369 | 1H NMR (CDCl3, 600 MHz) δ ppm: 7.96 (s, 1H), 7.45-7.30 (m, 6H), 7.12 (m, 2H), 7.06 (d, J = 7.6 Hz, 1H), 6.95 (d, J = 7.6 Hz, 1H), 6.68 (s, 1H), 6.39 (s, 1H), 5.15 (s, 2H), 5.09 (s, 2H), 4.04 (q, J = 7.0 Hz, 2H), 2.77 (s, 3H), 1.44 (t, J = 7.0 Hz, 3H). |
| 424 | 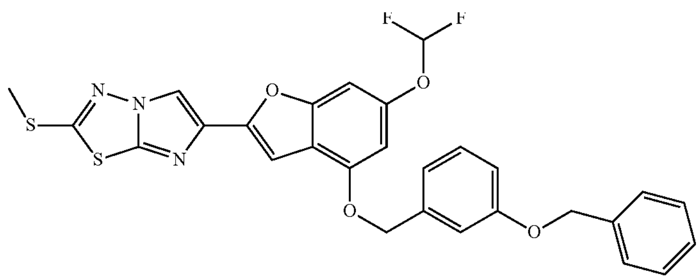 [SMILES: CSc1nn2cc(-c3cc4c(OCc5cccc(OCc6ccccc6)c5)cc(OC(F)F)cc4o3)nc2s1] | Ex. 416 | C28H21F2N3O4S2 | 566.1014 | 2.532/F | 566.1059 | 1H NMR (CDCl3, 600 MHz) δ ppm: 8.01 (s, 1H), 7.45-7.30 (m, 6H), 7.17 (s, 1H), 7.10-7.06 (m, 3H), 6.95 (m, 2H), 6.55 (s, 1H), 6.50 (t, J = 74.1 Hz, 1H), 5.17 (s, 2H), 5.09 (s, 2H), 2.77 (s, 3H). |
| 425 | 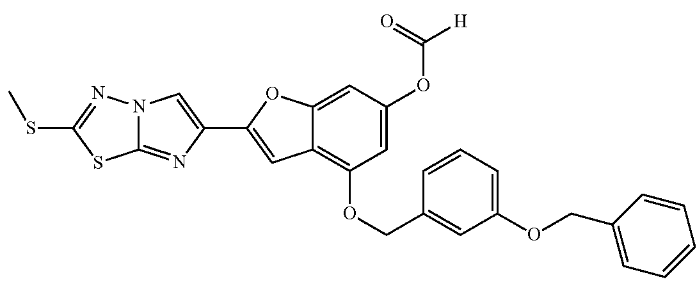 [SMILES: CSc1nn2cc(-c3cc4c(OCc5cccc(OCc6ccccc6)c5)cc(OC=O)cc4o3)nc2s1] | Ex. 416 | C28H21N3O5S2 | 544.1045 | 2.445/F | 544.1041 | 1H NMR (CDCl3, 600 MHz) δ ppm: 8.33 (s, 1H), 8.01 (s, 1H), 7.45-7.30 (m, 6H), 7.19 (s, 1H), 7.10 (s, 1H), 7.05 (d, J = 7.3 Hz, 1H), 6.98 (s, 1H), 6.95 (dd, J = 1.7 and 8.2 Hz, 1H), 6.53 (s, 1H), 5.17 (s, 2H), 5.09 (s, 2H), 2.77 (s, 3H). |

-continued

| Ex. | Structure | Experimental procedure (Example) | Formula | Exact Mass Or [M + H]+ | HPLC Retention Time (Min)/ Method | LCMS [M + H]+ m/z | NMR |
|---|---|---|---|---|---|---|---|
| 426 | 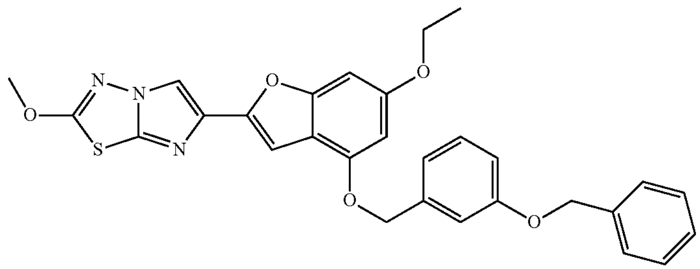 | Ex. 416 | C29H25N3O5S | 528.1588 | 2.626/F | 528.1593 | 1H NMR (CDCl3, 600 MHz) δ ppm: 7.84 (s, 1H), 7.45-7.29 (m, 6H), 7.12-7.06 (m, 3H), 6.94 (d, J = 8.2 Hz, 1H), 6.68 (s, 1H), 6.39 (s, 1H), 5.15 (s, 2H), 5.09 (s, 2H), 4.20 (s, 3H), 4.04 (q, J = 6.7 Hz, 2H), 1.44 (t, J = 6.7 Hz, 3H), |
| 427 | 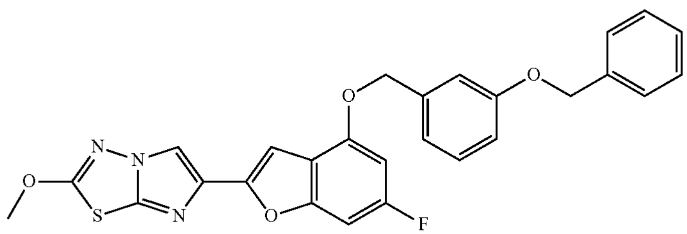 [SMILES: COc1nn2cc(-c3cc4c(OCc5cccc(OCc6ccccc6)c5)cc(F)cc4o3)nc2s1] | Ex. 414 | C27H20FN3O4S | 502.1159 | 2.620/F | 502.1240 | 1H NMR (400 MHz, CDCl3) δ ppm 7.88 (s, 1H), 7.43-7.48 (m, 2H), 7.36-7.43 (m, 2H), 7.30-7.36 (m, 2H), 7.10-7.14 (m, 2H), 7.07 (d, J = 7.43 Hz, 1H), 6.96 (dd, J = 8.02, 2.54 Hz, 1H), 6.84-6.91 (m, 1H), 6.52 (dd, J = 11.35, 1.96 Hz, 1H), 5.17 (s, 2H), 5.10 (s, 2H), 4.22 (s, 3H). |
| 428 | 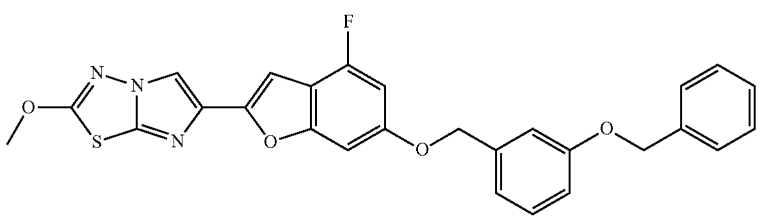 [SMILES: COc1nn2cc(-c3cc4c(F)cc(OCc5cccc(OCc6ccccc6)c5)cc4o3)nc2s1] | Ex. 414 | C27H20FN3O4S | 502.1159 | 2.631/F | 502.1239 | 1H NMR (400 MHz, CDCl3) δ ppm 7.88 (s, 1H), 7.42-7.47 (m, 2H), 7.36-7.42 (m, 2H), 7.29-7.36 (m, 2H), 7.08-7.12 (m, 1H), 7.04 (d, J = 7.83 Hz, 1H), 7.00 (br. s, 1H), 6.96 (dd, J = 8.22, 2.35 Hz, 1H), 6.88-6.92 (m, 1H), 6.67 (dd, J = 10.96, 1.96 Hz, 1H), 5.07-5.12 (m, 4H), 4.22 (s, 3H). |

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS®), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I, IA, IB, or IC, preferably, a compound selected from one of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

The activity of the PAR4 antagonists of the present invention can be measured in a variety of in vitro assays. Exemplary assays are shown in the Examples below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored. See, e.g., Example A.

AYPGKF is a known PAR4 agonist. An alternative PAR4 agonist is H-Ala-Phe(4-F)-Pro-Gly-Trp-Leu-Val-Lys-Asn-Gly-NH$_2$. As shown in Example B below, H-Ala-Phe(4-F)-Pro-Gly-Trp-Leu-Val-Lys-Asn-Gly-NH$_2$ was validated as a PAR4 agonist in the FLIPR assay. A side-by-side comparison of the IC$_{50}$ values of ~180 compounds were performed using AYPGKF versus H-Ala-Phe(4-F)-Pro-Gly-Trp-Leu-Val-Lys-Asn-Gly-NH$_2$. The results demonstrated a strong correlation between the two assays. Additionally, H-Ala-Phe(4-F)-Pro-Gly-Trp-Leu-Val-Lys-Asn-Gly-NH$_2$ has improved agonist activity as compared to AYPGKF with an EC$_{50}$ that is 10 fold lower than the EC$_{50}$ for AYPGKF in the FLIPR assay. H-Ala-Phe(4-F)-Pro-Gly-Trp-Leu-Val-Lys-Asn-Gly-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown in Example C. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

Figure 2:
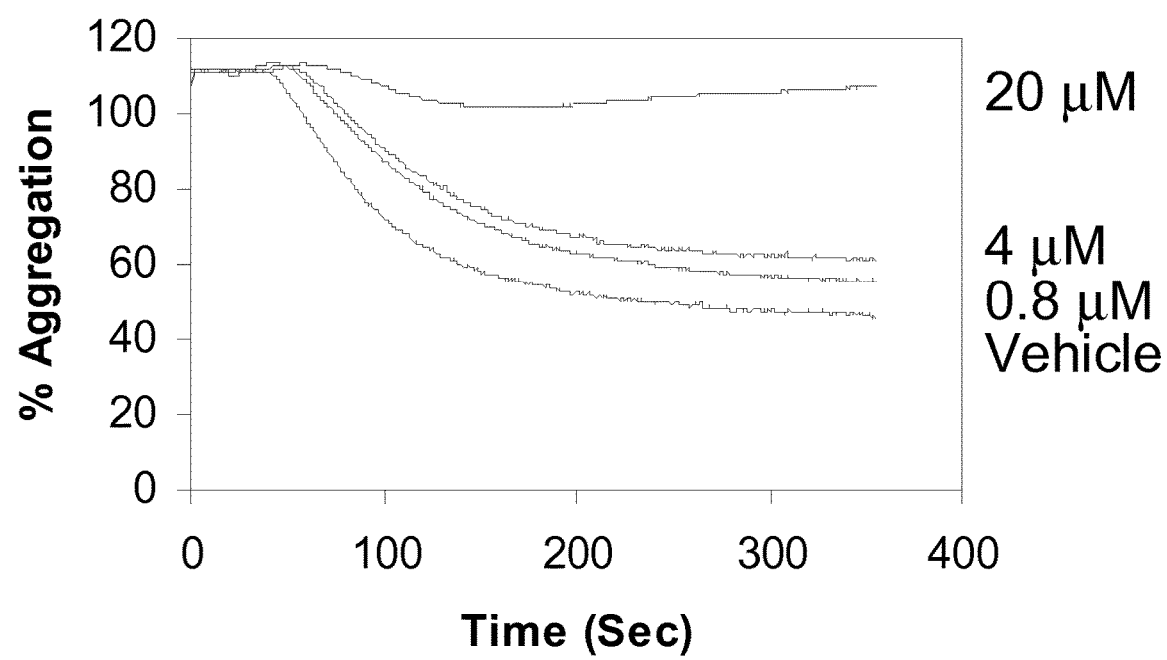
FIG. 2 shows dose-dependent inhibition of 5 nM alpha-thrombin-induced platelet aggregation by Example 203 (a PAR4 antagonist).

Example D is an alpha-thrombin-induced platelet aggregation assay. Alpha-thrombin activates both PAR1 and PAR4. The ability of a selective PAR4 antagonist of the present invention, Example 203, to inhibit platelet aggregation was measured using a standard optical aggregometer. Inhibition of alpha-thrombin induced platelet aggregation by Example 203 is shown in FIGS. 1 and 2. The data shows that a PAR4 antagonist alone can effectively inhibit platelet aggregation. The extent of platelet inhibition by the PAR4 antagonist is at least comparable to what has been previously described for PAR1 antagonists.

Example E is a tissue factor-induced platelet aggregation assay. The conditions in this assay mimic the physiological events during thrombus formation. In this assay, platelet aggregation in human PRP was initiated by the addition of tissue factor and $CaCl_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

Figure 3:
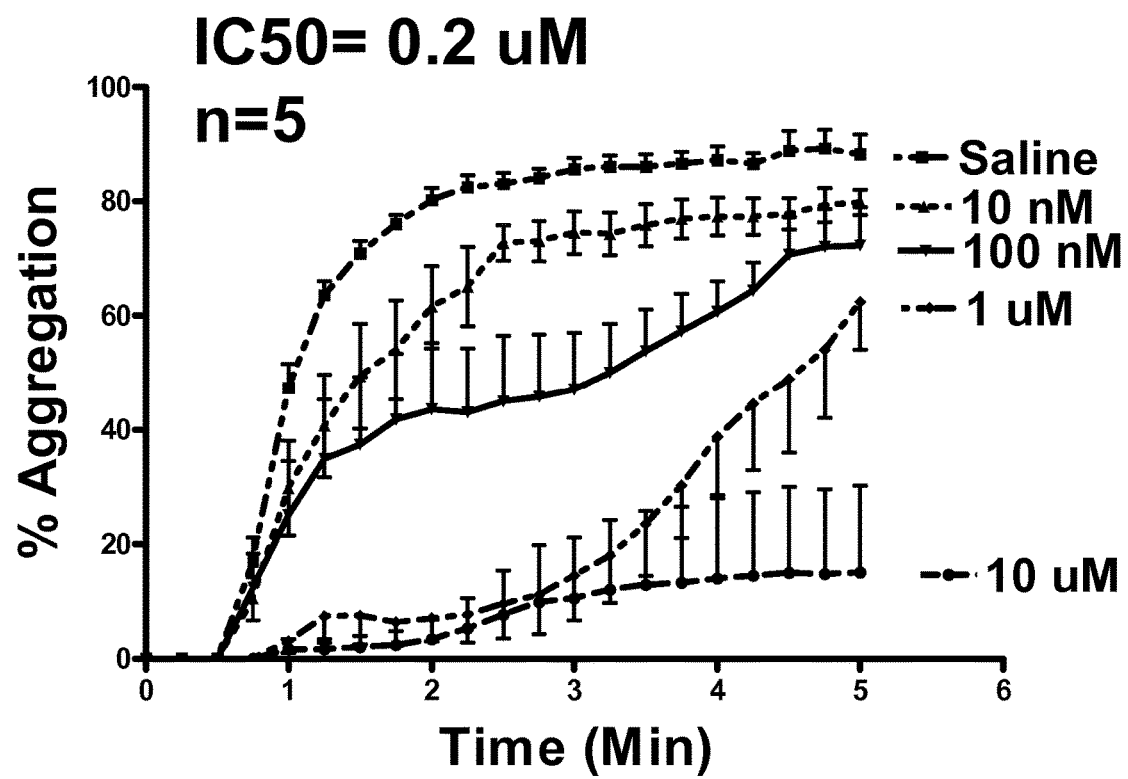
FIG. 3 shows inhibition of tissue factor-induced platelet aggregation by Example 73 (a PAR4 antagonist).
Figure 4:
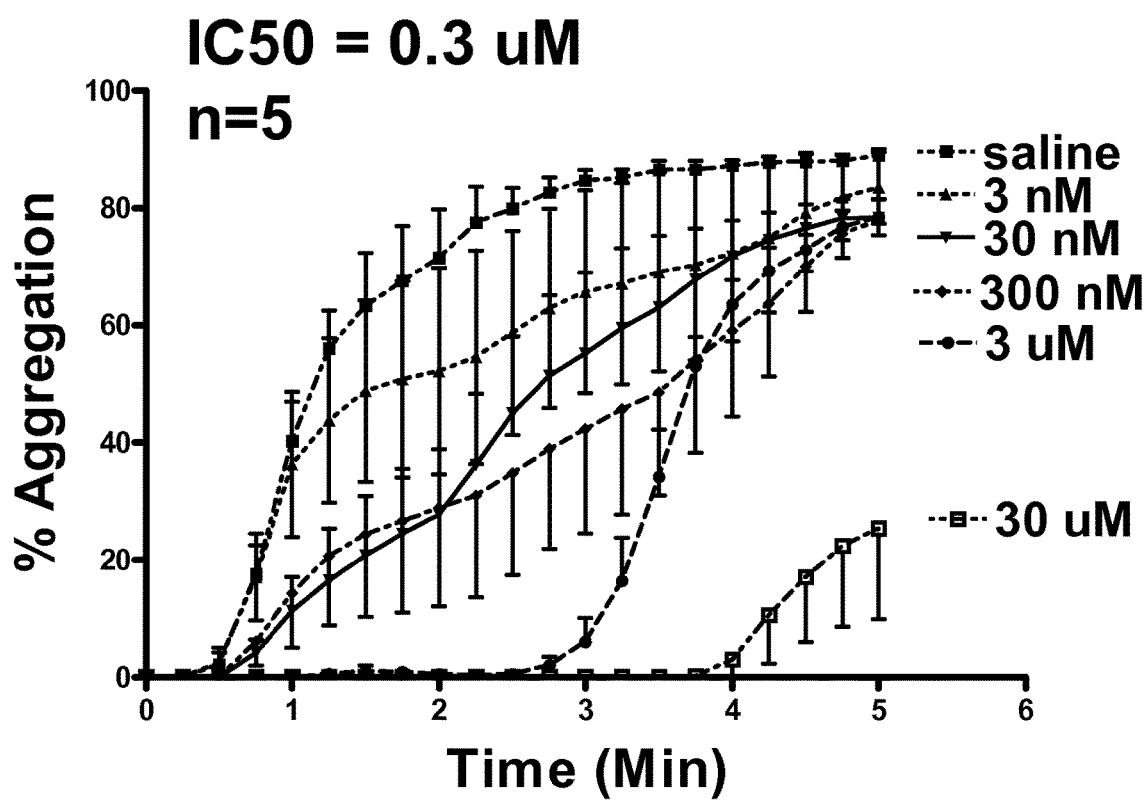
FIG. 4 shows inhibition of tissue factor-induced platelet aggregation by trans-cinnamoyl-Phe(4-F)-Phe(4-guanidino)-Leu-Arg-Arg-NH$_2$ (a PAR1 antagonist).

FIGS. 3 and 4 show effective inhibition of tissue factor-induced platelet aggregation by Example 73 (a PAR4 antagonist of the present invention), as well as by trans-cinnamoyl-Phe(4-F)-Phe(4-guanidino)-Leu-Arg-Arg-$NH_2$ (a PAR1 antagonist). The PAR4 antagonist, like the PAR1 antagonist, is shown to effectively inhibit tissue factor induced platelet aggregation in this assay. This data demonstrates that the PAR4 antagonists of the present invention can effectively inhibit thrombin mediated platelet aggregation and can serve as antithrombotic agents. Thus, PAR4 antagonists represent a novel class of antithrombotic agents that prevent robust platelet activation by thrombin during thrombotic events.

The efficacy of the PAR4 antagonists of the present invention in preventing thrombosis can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrolytic injury-induced carotid artery thrombosis, $FeCl_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention. Example G describes an in vivo model of arterial thrombosis in cynolmolgus monkeys. Compounds of the present invention can be tested in this model for their ability to inhibit thrombus formation induced by electrolytic injury of the carotid artery. Demonstration of efficacy in this model supports the utility of PAR4 antagonists of the present invention for treatment of thromboembolic diseases.

Assays

Materials
1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-$NH_2$ were synthesized. H-Ala-Phe(4-F)-Pro-Gly-Trp-Leu-Val-Lys-Asn-Gly-$NH_2$ showed improved PAR4 agonist activity over AYPGKF in the FLIPR assay ($EC_{50}$ of 8 µM for H-Ala-Phe(4-F)-Pro-Gly-Trp-Leu-Val-Lys-Gly-$NH_2$ and 60 µM for AYPGKF) and in washed platelet aggregation assay ($EC_{50}$ of 0.9 µM for H-Ala-Phe(4-F)-Pro-Gly-Trp-Leu-Val-Lys-Asn-Gly-$NH_2$ and 12 µM for AYPGKF).

2) PAR4 Expressing Cells

HEK293 cells stably expressing PAR4 were generated by a standard method of transfection of human F2R23 cDNA expression vector or by RAGE technology from Athersys Inc. (Cleveland, Ohio) and selected based on PAR4 protein expression of mRNA expression. Those cells demonstrated functional responses to PAR4 agonist peptide-induced intracellular calcium elevation using FLIPR® (Fluorometric Imaging Plate Reader; Molecular Devices Corp.). These cells express endogenous PAR1 and can elicit calcium signal upon stimulation with PAR1 agonist peptide. Cells were grown in Dulbecco's Modified Eagle's Medium (DMEM) (Invitrogen, Carlsbad, Calif.), 10% FBS, 1% PSG, 3 µg/ml puromycin and 25 nM Methotrexate) at 37° C. with 5% $CO_2$.

3) Preparation of Platelet Rich Plasma (PRP)

Human blood was collected in 3.8% sodium citrate at a ratio of 1 ml per 9 ml blood. The platelet rich plasma was isolated by centrifugation at 170 g for 14 minutes.

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~$2.5 \times 10^8$/ml in Tyrode's Buffer (137 mM NaCl, 2 mM KCl, 1.0 mM $MgCl_2$, 1 mM $CaCl_2$, 5 mM glucose, 20 mM HEPES pH 7.4).

Example A

FLIPR Assay in PAR4-Expressing HEK293 Cells

The activity of the PAR4 antagonists of the present invention were tested in PAR4 expressing cells by monitoring H-Ala-Phe(4-F)-Pro-Gly-Trp-Leu-Val-Lys-Asn-Gly-$NH_2$-induced intracellular calcium mobilization using FDSS6000 (Hamamatsu Photonics, Japan) by fluo-4. Counter screens for agonist activity and PAR1 antagonist activity were also performed. Briefly, HEK293 EBNA PAR4 clone 20664.1J cells were plated 24 hrs. prior to experiment in 384 well, Poly-D-Lysine coated, black, clear bottom plates (Greiner Bio-One, Monroe, N.C.). Cells were plated at 20,000 cells/well in 20 µl growth medium and incubated at 37° C. with 5% $CO_2$ overnight. At time of assay, media was replaced with 40 µl 1× Hank's Buffered Saline Solution (HBSS) (with 10 mM HEPES) and 20 µl test compound also diluted in 1×HBSS buffer was added at various concentrations and 0.67% DMSO final concentration on the FDSS for agonist measurement. The cells were then incubated for 30 minutes at room temperature followed by addition of 20 µl of agonist peptide for antagonist measurement on the FDSS. The agonist peptide H-Ala-Phe(4-F)-Pro-Gly-Trp-Leu-Val-Lys-Asn-Gly-$NH_2$ for PAR4 antagonist screen or SFFLRR for PAR1 counter screen were routinely tested to ensure a response at $EC_{50}$ in the assay (~2.5 µM for H-Ala-Phe(4-F)-Pro-Gly-Trp-Leu-Val-Lys-Asn-Gly-$NH_2$ and 600 nM for SFFLRR).

Example B

Validation of H-Ala-Phe(4-F)-Pro-Gly-Trp-Leu-Val-Lys-Asn-Gly-$NH_2$ as a PAR4 Agonist To validate H-Ala-Phe(4-F)-Pro-Gly-Trp-Leu-Val-Lys-Asn-Gly-$NH_2$ as a PAR4 agonist in the FLIPR assay, side-by-side comparison of the $IC_{50}$ values of ~180 compounds were performed using AYPGKF versus H-Ala-Phe(4-F)-Pro-Gly-Trp-Leu-Val-Lys-Asn-Gly-$NH_2$. The results demonstrated a strong correlation between the two assays (Spearman's rank correlation coefficient rho=0.7760, p<0.0001). The relevance of the FLIPR assay in the HEK293 cells was confirmed by a direct assay connectivity to the washed platelet assay. The $IC_{50}$ values of ~200 compounds from AYPGKF FLIPR assay was strongly correlated to that from AYPGKF washed platelet aggregation assay (Spearman's rank correlation coefficient rho=0.836, p<0.001). Similar results were obtained comparing FLIPR and washed platelet data using H-Ala-Phe(4-F)-Pro-Gly-Trp-Leu-Val-Lys-Asn-Gly-NH$_2$.

Example C

Gamma Thrombin Induced Platelet Aggregation Assays

The ability of the compounds of the current invention to inhibit platelet aggregation induced by gamma-thrombin was tested in a 96-well microplate aggregation assay format. Briefly, PRP or washed platelet suspension (100 μl) was pre-incubated for 5 minutes at room temperature with varying concentrations of compounds. Aggregation was initiated by ~10-50 nM gamma thrombin (Haematologic Technologies, Essex Junction, Vt.), which was titrated daily to achieve 80% platelet aggregation. Refludan at 1 U/mL (Berlex, Montville, N.J.) was added to the gamma thrombin sample to prevent PAR1 activation induced by residual alpha-thrombin contamination. The plate was then placed into a 37° C. Molecular Devices (Sunnyvale, Calif.) SPECTRAMAX® Plus Plate Reader. The plate was mixed for 10 seconds before the first read and 50 seconds between each read for up to 15 minutes at 405 nM. Data was collected with SOFTMAX® 4.71 software. The plate also included an untreated control sample which served as ODmax, while buffer containing no platelets was the ODmin. Platelet aggregation was determined by subtracting the ODmax from the ODmin for the 100% aggregation value. In experimental samples, the observed transmission was subtracted from the minimum value and then compared to the 100% aggregation value to determine the percentage aggregation. $IC_{50}$ values are determined using Excel Fit software.

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Example D

Alpha-Thrombin Induced Platelet Aggregation Assays

The ability of PAR4 antagonist to inhibit platelet aggregation induced by alpha-thrombin was tested using human washed platelets. Example 203 was pre-incubated with washed platelets for 5 min. Aggregation was initiated by addition of 2.5 or 5 nM alpha-thrombin (Haematologic Technologies, Essex Junction, Vt.) to 240 μl of washed platelets at stirring speed of 1200 rpm. Platelet aggregation was monitored using Optical Aggregometer (Chrono-Log, Havertown, Pa.) and the area under the curve (AUC) at 6 min was measured. $IC_{50}$ was calculated using vehicle control as 0% inhibition. The $IC_{50}$ for the inhibition of platelet aggregation by Example 203 using 2.5 nM alpha-thrombin was calculated to be 1.1±0.9 μM (n=4) (FIG. 1). The $IC_{50}$ for the inhibition of platelet aggregation by Example 203 using 5 nM alpha-thrombin was calculated to be 6.9±0.3 μM (n=3) (FIG. 2).

Example E

Tissue Factor-Induced Platelet Aggregation Assay

The ability of PAR1 or PAR4 antagonist to inhibit platelet aggregation induced by endogenous thrombin was tested in a tissue factor driven aggregation assay. The compounds were pre-incubated with PRP for 2 min (FIGS. 3 and 4). Aggregation is initiated by addition of CaCl$_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 μg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Example F

Table 2 sets out the results obtained employing various compounds of the invention tested in the FLIPR assay. As indicated above, the FLIPR assay, an in vitro assay, measures the PAR4 antagonist activity of compounds tested as described in Example A.

TABLE 2

| Example No. | PAR4 FLIPR Assay ($IC_{50}$, nM) |
|---|---|
| 1 | 13.98 |
| 4 | 12.88 |
| 5 | 351.20 |
| 6 | 618.00 |
| 9 | 223.60 |
| 10 | 1801.00 |
| 11 | 11.05 |
| 13 | 146.60 |
| 14 | 8.68 |
| 16 | 368.60 |
| 20 | 3.53 |
| 21 | 22.13 |
| 22 | 216.70 |
| 23 | 143.80 |
| 24 | 695.50 |
| 25 | 2.81 |
| 27 | 1777.00 |
| 34 | 149.10 |
| 35 | 7.65 |
| 36 | 1662.00 |
| 37 | 8.51 |
| 38 | 66.57 |
| 39 | 220.40 |
| 40 | 122.50 |
| 41 | 18.56 |
| 42 | 462.30 |
| 43 | 91.12 |
| 45 | 135.40 |
| 46 | 565.40 |
| 47 | 67.98 |
| 49 | 361.00 |
| 51 | 393.50 |
| 53 | 149.30 |
| 56 | 600.70 |
| 57 | 574.90 |
| 58 | 564.80 |
| 59 | 288.50 |
| 60 | 623.20 |
| 61 | 1653.00 |
| 62 | 587.10 |
| 63 | 200.90 |
| 64 | 1592.00 |
| 65 | 1467.00 |

TABLE 2-continued

| Example No. | PAR4 FLIPR Assay (IC$_{50}$, nM) |
|---|---|
| 66 | 2624.00 |
| 67 | 102.70 |
| 68 | 55.28 |
| 69 | 407.20 |
| 70 | 399.50 |
| 71 | 1.22 |
| 72 | 3.91 |
| 73 | 0.99 |
| 74 | 681.10 |
| 75 | 293.60 |
| 76 | 3401.00 |
| 77 | 1369.00 |
| 78 | 575.80 |
| 79 | 800.90 |
| 80 | 694.60 |
| 81 | 506.60 |
| 82 | 66.03 |
| 83 | 1006.00 |
| 84 | 101.20 |
| 85 | 392.20 |
| 86 | 1213.00 |
| 87 | 450.10 |
| 89 | 28.19 |
| 90 | 4.70 |
| 91 | 19.08 |
| 92 | 12.96 |
| 93 | 222.10 |
| 94 | 3.58 |
| 95 | 6.89 |
| 96 | 7.92 |
| 97 | 3.48 |
| 98 | 186.90 |
| 99 | 38.19 |
| 100 | 71.38 |
| 101 | 10.67 |
| 102 | 542.00 |
| 103 | 10.71 |
| 104 | 26.23 |
| 105 | 11.43 |
| 106 | 13.90 |
| 107 | 339.10 |
| 108 | 461.20 |
| 109 | 3.10 |
| 110 | 212.90 |
| 111 | 139.70 |
| 112 | 381.60 |
| 113 | 15.16 |
| 114 | 206.50 |
| 115 | 74.93 |
| 116 | 6.63 |
| 117 | 654.20 |
| 118 | 190.80 |
| 119 | 10.56 |
| 120 | 48.92 |
| 121 | 13.04 |
| 122 | 508.70 |
| 123 | 1118.00 |
| 124 | 3482.00 |
| 125 | 206.30 |
| 126 | 10.39 |
| 127 | 27.89 |
| 128 | 17.11 |
| 129 | 31.98 |
| 130 | 41.30 |
| 131 | 107.00 |
| 132 | 87.24 |
| 133 | 19.66 |
| 134 | 321.30 |
| 135 | 49.57 |
| 136 | 38.85 |
| 137 | 23.92 |
| 138 | 470.50 |
| 139 | 80.40 |
| 140 | 68.90 |
| 141 | 41.00 |
| 142 | 27.80 |
| 143 | 48.81 |
| 144 | 91.28 |
| 145 | 285.60 |
| 146 | 910.80 |
| 147 | 78.29 |
| 148 | 224.20 |
| 149 | 13.62 |
| 150 | 620.60 |
| 151 | 673.30 |
| 152 | 340.00 |
| 153 | 345.30 |
| 154 | 571.40 |
| 155 | 300.90 |
| 156 | 1018.00 |
| 157 | 1653.00 |
| 158 | 69.28 |
| 159 | 28.42 |
| 160 | 40.00 |
| 161 | 79.93 |
| 162 | 171.00 |
| 163 | 39.52 |
| 164 | 15.37 |
| 165 | 81.01 |
| 166 | 139.30 |
| 167 | 784.60 |
| 168 | 1147.00 |
| 169 | 70.47 |
| 170 | 115.80 |
| 171 | 48.11 |
| 172 | 814.40 |
| 173 | 39.38 |
| 174 | 166.80 |
| 175 | 41.30 |
| 176 | 701.30 |
| 177 | 3.78 |
| 178 | 2340.00 |
| 179 | 225.10 |
| 180 | 188.60 |
| 181 | 419.30 |
| 182 | 19.38 |
| 183 | 412.40 |
| 184 | 5.50 |
| 185 | 625.50 |
| 186 | 252.00 |
| 187 | 771.40 |
| 188 | 920.40 |
| 189 | 2195.00 |
| 190 | 203.50 |
| 191 | 30.71 |
| 192 | 989.70 |
| 193 | 1036.00 |
| 194 | 9.64 |
| 195 | 2417.00 |
| 196 | 791.40 |
| 197 | 1053.00 |
| 198 | 4715.00 |
| 199 | 2681.00 |
| 200 | 8.63 |
| 201 | 4.38 |
| 202 | 3.15 |
| 203 | 15.08 |
| 204 | 170.50 |
| 205 | 2.42 |
| 206 | 2.01 |
| 207 | 127.40 |
| 208 | 456.60 |
| 209 | 442.20 |
| 210 | 24.54 |
| 211 | 111.30 |
| 212 | 50.85 |
| 213A | 332.80 |
| 213B | 10.35 |
| 214 | 322.40 |
| 215 | 16.72 |
| 216 | 482.50 |
| 217 | 7.51 |
| 217A | 45.10 |
| 218 | 8.15 |

TABLE 2-continued

| Example No. | PAR4 FLIPR Assay (IC$_{50}$, nM) |
|---|---|
| 219 | 1285.00 |
| 220 | 307.00 |
| 221 | 12.50 |
| 222 | 463.60 |
| 223 | 21.65 |
| 224 | 97.09 |
| 225 | 300.50 |
| 226 | 590.90 |
| 227-228 | 4.05 |
| 229 | 1.22 |
| 230 | 2298.00 |
| 231 | 22.28 |
| 232 | 151.80 |
| 233 | 15.74 |
| 234 | 113.20 |
| 236 | 158.90 |
| 237 | 28.76 |
| 238 | 42.53 |
| 239 | 7.24 |
| 240 | 670.70 |
| 241 | 290.10 |
| 242 | 50.51 |
| 243 | 363.90 |
| 244 | 382.80 |
| 245 | 72.28 |
| 246 | 318.10 |
| 247 | 47.87 |
| 248 | 145.00 |
| 249 | 19.40 |
| 250 | 267.30 |
| 251 | 230.50 |
| 252 | 120.80 |
| 253 | 114.20 |
| 254 | 603.50 |
| 255 | 112.90 |
| 256 | 48.35 |
| 257 | 50.21 |
| 258 | 3.32 |
| 259 | 322.60 |
| 260 | 4.45 |
| 261 | 4.53 |
| 262 | 4.28 |
| 263 | 20.69 |
| 264 | 37.83 |
| 265 | 27.98 |
| 266 | 43.08 |
| 267 | 7.53 |
| 268 | 21.84 |
| 269 | 74.50 |
| 270A | 114.40 |
| 270B | 3.37 |
| 270-1 | 9.53 |
| 271 | 19.40 |
| 272 | 29.08 |
| 273 | 179.60 |
| 274 | 1972.00 |
| 275 | 23.14 |
| 276 | 120.40 |
| 277 | 511.50 |
| 278 | 52.60 |
| 279 | 3.46 |
| 280 | 138.30 |
| 281 | 1344.00 |
| 282 | 49.58 |
| 283 | 2706.00 |
| 284 | 138.70 |
| 285 | 317.20 |
| 286 | 275.80 |
| 287 | 8.19 |
| 288 | 94.11 |
| 289 | 29.64 |
| 290 | 2727.00 |
| 291 | 24.22 |
| 292 | 22.68 |
| 293 | 4.83 |
| 294 | 19.46 |
| 295 | 12.14 |
| 296 | 106.30 |
| 297 | 5.88 |
| 298 | 18.64 |
| 299 | 78.75 |
| 300 | 3.43 |
| 301 | 23.01 |
| 302 | 195.40 |
| 303 | 5.68 |
| 304 | 55.61 |
| 305 | 13.57 |
| 306 | 1098.00 |
| 307 | 9.23 |
| 308 | 186.80 |
| 309 | 1.22 |
| 310 | 3.45 |
| 311 | 8.82 |
| 312 | 2.13 |
| 313 | 2.11 |
| 314 | 0.72 |
| 315 | 8.88 |
| 316 | 4.17 |
| 317 | 8.36 |
| 318 | 1.92 |
| 319 | 9.20 |
| 320 | 3.93 |
| 321 | 6.73 |
| 322 | 9.97 |
| 323 | 1.48 |
| 324 | 3.52 |
| 325 | 1.64 |
| 326 | 3.36 |
| 328 | 4.50 |
| 329 | 71.60 |
| 330 | 2.62 |
| 331 | 84.33 |
| 332 | 253.20 |
| 333 | 565.60 |
| 334 | 2365.00 |
| 335 | 537.00 |
| 336 | 897.20 |
| 337 | 401.00 |
| 338 | 1165.00 |
| 339 | 0.87 |
| 340 | 2.21 |
| 341 | 22.00 |
| 342-343 | 253.2 |
| 344 | 1.12 |
| 345 | 0.97 |
| 346 | 1.68 |
| 347 | 2.74 |
| 348 | 2.26 |
| 349 | 0.32 |
| 350 | 0.76 |
| 351 | 2.23 |
| 352 | 3.61 |
| 353 | 2.25 |
| 354 | 2.06 |
| 355 | 1.65 |
| 356 | 1.66 |
| 357 | 4.92 |
| 358 | 2.54 |
| 359 | 5.49 |
| 360 | 2.47 |
| 361 | 1.35 |
| 362 | 1.24 |
| 363 | 2.42 |
| 364 | 10.51 |
| 365 | 3.27 |
| 366 | 164.30 |
| 367 | 4.09 |
| 368 | 4.69 |
| 369 | 2.98 |
| 370 | 5.30 |
| 371 | 7.56 |
| 372 | 2.27 |
| 373 | 7.63 |
| 374 | 2.30 |

TABLE 2-continued

| Example No. | PAR4 FLIPR Assay (IC$_{50}$, nM) |
|---|---|
| 375 | 259.90 |
| 376 | 7.27 |
| 377 | 6.91 |
| 378 | 7.38 |
| 379 | 7.84 |
| 380 | 1.11 |
| 381 | 2.77 |
| 382 | 1.67 |
| 383 | 8.68 |
| 384 | 5.05 |
| 385 | 3.13 |
| 386 | 1.77 |
| 387 | 41.47 |
| 388 | 3.12 |
| 389 | 0.73 |
| 390 | 1.60 |
| 391 | 3.03 |
| 392 | 1.44 |
| 393 | 35.88 |
| 394 | 3.68 |
| 395 | 38.32 |
| 396 | 4.51 |
| 397 | 2.30 |
| 398 | 2.14 |
| 399 | 0.59 |
| 400 | 7.47 |
| 401 | 1.28 |
| 402 | 6.20 |
| 403 | 0.86 |
| 404 | 2.44 |
| 405 | 4.69 |
| 406 | 39.38 |
| 407 | 1.12 |
| 409 | 3711.00 |
| 410 | 7.79 |
| 411 | 4.53 |
| 412 | 72.48 |
| 413 | 1.82 |
| 414 | 5.17 |
| 415 | 512.60 |
| 416 | 1.09 |
| 417 | 5.02 |
| 418 | 9.37 |
| 419 | 5.02 |
| 420 | 51.08 |
| 421 | 24.49 |
| 422 | 698.20 |
| 423 | 15.14 |
| 424 | 21.44 |
| 425 | 12.39 |
| 426 | 4.56 |
| 427 | 1.91 |
| 428 | 4.81 |

Table 3 sets out the results obtained employing various compounds of the invention tested in the platelet aggregation assay in PRP (PRP assay). As indicated above, the PRP assay, an in vitro assay, measures the PAR4 antagonist activity of compounds tested as described in Example C.

TABLE 3

| Example No. | PAR4 PRP Assay (Gamma Thrombin, IC$_{50}$, nM) |
|---|---|
| 5 | >30000 |
| 10 | >30000 |
| 14 | 9436.00 |
| 16 | >30000 |
| 17 | >30000 |
| 22 | 8756.00 |
| 26 | >30000 |
| 27 | >30000 |
| 34 | >30000 |
| 36 | >30000 |
| 38 | >30000 |
| 39 | >30000 |
| 57 | >30000 |
| 68 | 16700.00 |
| 72 | 2326.00 |
| 129 | >30000 |
| 131 | >30000 |
| 135 | >30000 |
| 159 | >30000 |
| 161 | >30000 |
| 164 | 9164.00 |
| 173 | 5275.00 |
| 205 | 24.74 |
| 252 | >30000 |
| 253 | >30000 |
| 255 | >30000 |
| 282 | 5630.00 |
| 301 | 2955.00 |
| 302 | >30000 |
| 303 | 3189.00 |
| 304 | >30000 |
| 307 | 101.00 |
| 316 | 93.28 |
| 318 | 36.47 |
| 319 | 124.00 |
| 320 | 75.51 |
| 325 | 86.15 |
| 327 | 37.88 |
| 337 | >30000 |
| 346 | 146.90 |
| 347 | 579.30 |
| 348 | 3083.00 |
| 350 | 85.66 |
| 353 | 10.53 |
| 355 | 33.33 |
| 356 | 108.80 |
| 358 | 95.63 |
| 363 | 38.32 |
| 364 | 5818.00 |
| 370 | 150.80 |
| 371 | 6910.00 |
| 372 | 3413.00 |
| 373 | 2495.00 |
| 376 | 677.00 |
| 383 | 594.20 |
| 384 | 568.00 |
| 386 | 54.98 |
| 387 | 2399.00 |
| 392 | 105.30 |
| 393 | 2502.00 |
| 394 | 615.90 |
| 398 | 66.22 |
| 399 | 4.95 |
| 402 | 150.80 |
| 404 | 22.50 |
| 405 | 544.30 |
| 407 | 462.50 |
| 415 | 3266.00 |
| 426 | 566.30 |
| 428 | 73.23 |

Example G

Cynomolgus Monkey Electrolytic Injury-Induced Carotid Artery Thrombosis Model

Healthy cynomolgus monkeys were used in the study. These monkeys were retired from other pharmacokinetic and pharmacodynamic studies and had at least a 4-week washout period.

On the day of the study, compounds or vehicles were administered orally at 1 to 2 hours before the experiment. Monkeys were then sedated by intramuscular administration of 0.2 mg/kg atropine, 5 mg/kg TELAZOL® (tiletamine/zolazepam) and 0.1 mg/kg hydromorphone to facilitate placement of an endotracheal tube. An intravenous catheter was placed in the left cephalic vein for fluid administration to prevent dehydration. Animals were then administered with an inhalant anesthetic, isoflurane (1-5% to effect) and oxygen, ventilated, and placed on a thermostatically controlled heating pad to maintain the body temperature at 37° C. General anesthesia was maintained at a surgical plane using inhaled isoflurane and oxygen. The left brachial artery was cannulated to record blood pressure and heart rate. Blood pressure and heart rate were monitored to maintain normal vital signs.

Figure 5:
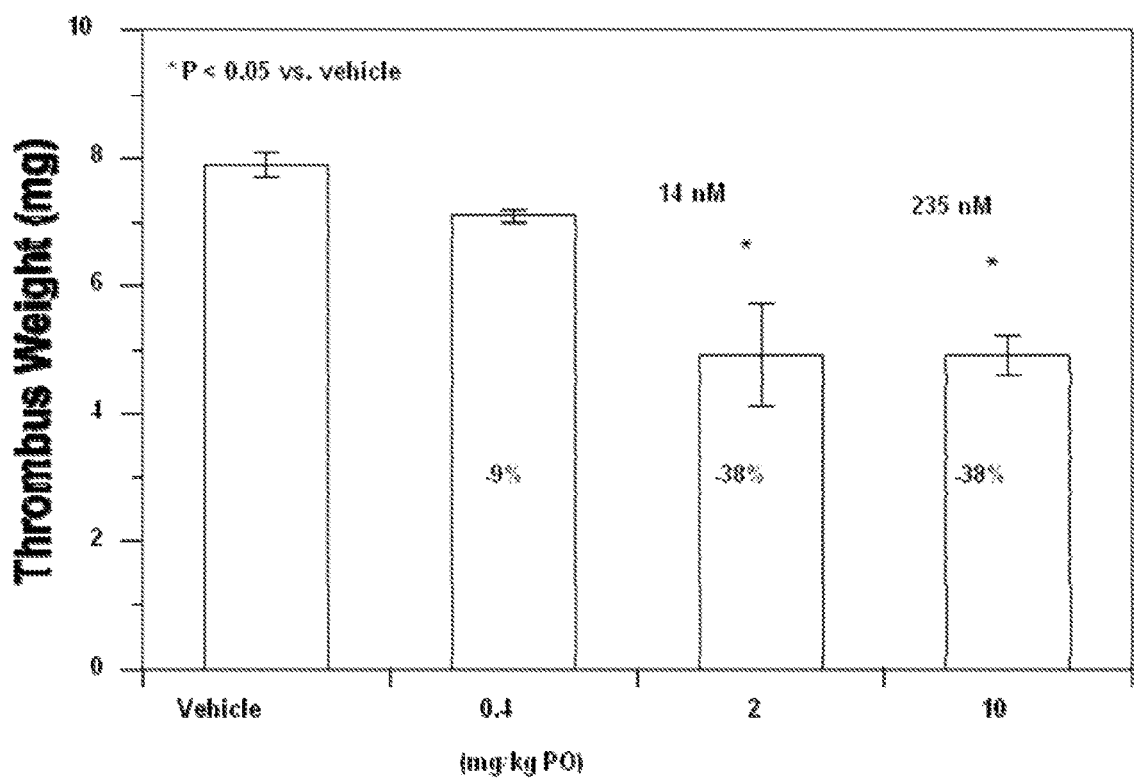
FIG. 5 is a graph which shows the antithrombotic efficacy of Example 205 in the cynomolgus monkey electrolytic injury-induced carotid artery thrombosis model.

The carotid arterial thrombosis model in monkeys was based on a rabbit arterial thrombosis model, as described by Wong et al. (Wong, P. C. et al., "Nonpeptide factor Xa inhibitors: II. Antithrombotic evaluation in a rabbit model of electrically induced carotid artery thrombosis", *J. Pharmacol. Exp. Ther.*, 295: 212-218 (2002).) Thrombosis was induced by electrical stimulation of the carotid artery for 5 min at 10 mA using an external stainless-steel bipolar electrode. Carotid blood flow was measured with an appropriately sized TRANSONIC® flow probe and a TRANSONIC® perivascular flowmeter (TS420 Model, Transonic Systems Inc., Ithaca, N.Y.). It was continuously recorded over a 90-min period to monitor thrombosis-induced occlusion. Integrated carotid blood flow was measured by the area under the flow-time curve. It was expressed as percent of total control carotid blood flow, which would result if control blood flow had been maintained continuously for 90 min. In addition, thrombus from the injured artery was removed, blotted twice on a weighing paper to remove residual fluid, and weighed. FIG. 5 shows the results of a dose response experiment with Example 205 in the cynomolgus monkey electrically-induced arterial thrombus model, demonstrating the in vivo antithrombotic efficacy of a PAR4 antagonist.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

What is claimed is:

1. A compound of Formula I:

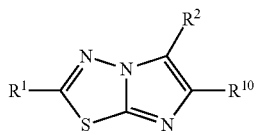

I or a stereoisomer, tautomer, pharmaceutically acceptable salt, solvate or prodrug thereof, wherein:

$R^{10}$ is

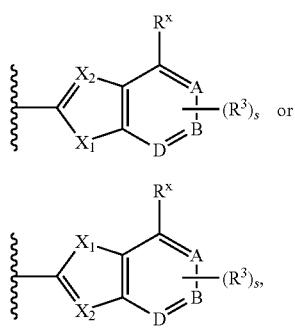

wherein A, B and D are the same or different and are independently selected from N and C, provided that A, B and D represent at least 1 carbon atom and at most 2 N atoms;

$X_1$ is selected from O, S or $NR^4$;
$X_2$ is $CR^5$;
$R^1$ is selected from the group consisting of:
  halo,
  $C_2$-$C_3$ alkenyl,
  $C_2$-$C_3$ alkynyl,
  $C_1$-$C_4$ alkoxy,
  $C_1$-$C_4$ alkylthio,
  phenylthio,
  $C_1$-$C_4$ alkylNH,
  $C_1$-$C_4$-alkylO$C_1$-$C_4$-alkyl,
  ($C_1$-$C_4$ alkyl)$_2$N—,
  $C_3$-$C_6$ cycloalkyl,
  4- to 10-membered heterocyclyl,
  halo-$C_1$-$C_2$-alkyl, which contains 1 to 5 halogens, where halo is F or Cl,
  halo-$C_1$-$C_2$-alkoxy, which contains 1 to 5 halogens, where halo is F or Cl,
  $C_1$-$C_4$-alkoxycarbonyl-$C_1$-$C_4$-alkylthio, and
  $C_1$-$C_4$-alkoxycarbonyl-$C_1$-$C_4$-alkoxy;
$R^2$ is selected from the group consisting of:
  H,
  halo,
  $C_1$-$C_4$ alkyl,
  $C_1$-$C_4$ alkoxy, and
  cyano;
$R^x$, at each occurrence, is independently selected from the group consisting of:
  H,
  halo which is F, Cl, Br or I,
  $NR^6R^7$,
  $NO_2$,
  cyano,
  OH,
  $C_1$-$C_4$ alkoxy substituted with 0 to 3 $R^{a1}$ groups,
  $C_1$-$C_4$ alkylthio substituted with 0 to 3 $R^{a1}$ groups,
  carboxy,
  carbonyl,
  $C_1$-$C_4$ alkoxycarbonyl substituted with 0 to 3 $R^{a1}$ groups,
  $C_1$-$C_4$ alkylcarbonyl substituted with 0 to 3 $R^{a1}$ groups,
  $C(=O)NR^6R^7$,
  $C_1$-$C_4$ alkylsulfonyl substituted with 0 to 3 $R^{a1}$ groups,
  $S(=O)_2NR^6R^7$,
  $C_1$-$C_4$ alkyl substituted with 0 to 3 $R^{a1}$ groups,
  fluoro-$C_1$-$C_4$-alkyl, which contains 1 to 5 fluorines, or
  fluoro-$C_1$-$C_4$-alkoxy, which contains 1 to 5 fluorines; or
$R^x$ is selected from Y-Z—, where:
Z is a linker which is selected from the group consisting of:
  a single bond,
  —O—,
  —S—,

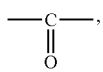

—NH—, $C_1$-$C_4$ alkyl which is independently substituted with 0 to 3 $R^{a1}$ groups;

$C_1$-$C_4$ alkyloxy wherein the alkyl portion is independently substituted with 0 to 3 $R^{a1}$ groups;

$C_1$-$C_4$ alkylthio wherein the alkyl portion is independently substituted with 0 to 3 $R^{a1}$ groups;

$C_1$-$C_4$ alkyloxy-$C_1$-$C_4$-alkyl wherein any alkyl portion is independently substituted with 0 to 3 $R^{a1}$ groups;

$C_1$-$C_4$-alkylthio-$C_1$-$C_4$-alkyl wherein any alkyl portion is independently substituted with 0 to 3 $R^{a1}$ groups;

—S—$C_1$-$C_4$-alkyl wherein the alkyl portion is independently substituted with 0 to 3 $R^{a1}$ groups;

—O—$C_1$-$C_4$-alkyl wherein the alkyl portion is independently substituted with 0 to 3 $R^{a1}$ groups; and $C_2$-$C_6$-alkynyl which is substituted with 0 to 3 $R^{a1}$ groups; and Y is selected from the group consisting of:
$C_1$-$C_4$-alkyloxy-$C_1$-$C_4$-alkyl($C_1$-$C_4$-alkyl),
$C_6$-$C_{10}$ aryl substituted by 0 to 3 $R^{a5}$ groups,
6- to 10-membered heteroaryl substituted by 0 to 3 $R^{a5}$ groups,
4- to 10-membered heterocyclyl substituted by 0 to 3 $R^{a5}$ groups or 0 to 1 $R^{b5}$ groups, and
$C_3$-$C_{10}$ cycloalkyl substituted by 0 to 3 $R^{a5}$ groups;

$R^3$, at each occurrence, is $R^{3a}$, $R^{3b}$ or $R^{3d}$, each of which is independently selected from the group consisting of:
H,
Cl, F, I,
$NR^6R^7$,
$NO_2$,
cyano,
$CF_3$,
OH,
$C_2$-$C_4$ alkynyl substituted with 0 to 2 $R^{a1}$ groups,
$C_1$-$C_4$ alkoxy substituted with 0 to 2 $R^{a1}$ groups,
$C_1$-$C_4$ alkylthio substituted with 0 to 2 $R^{a1}$ groups,
carboxy,
—OCH=O,
$C_1$-$C_4$ alkoxycarbonyl substituted with 0 to 2 $R^{a1}$ groups,
$C_1$-$C_4$ alkylcarbonyl substituted with 0 to 2 $R^{a1}$ groups,
$C(=O)NR^6R^7$,
$C_1$-$C_4$ alkylsulfonyl substituted with 0 to 2 $R^{a1}$ groups,
$S(=O)_2NR^6R^7$,
$NR^6C(=O)R^7$,
$C_1$-$C_4$ alkyl substituted with 0 to 2 $R^{a1}$ groups,
fluoro-$C_1$-$C_4$-alkyl, which contains 1 to 5 fluorines,
fluoro-$C_1$-$C_4$-alkoxy, which contains 1 to 5 fluorines,
phenyl, where phenyl is substituted with 0 to 2 $R^{a5}$ groups,
phenyloxy, where phenyl is substituted with 0 to 2 $R^{a5}$ groups,
phenyl-$C_1$-$C_4$-alkoxy, where phenyl is substituted with 0 to 2 $R^{a5}$ groups,
5- to 10-membered heteroaryl-$C_1$-$C_4$-alkoxy, where heteroaryl is substituted with 0 to 2 $R^{a5}$ groups, and
4- to 10-membered heterocyclo-$C_1$-$C_4$-alkoxy, where heterocyclo is substituted with 0 to 2 $R^{a5}$ groups;

$R^4$ is independently selected from the group consisting of H and $C_1$-$C_4$ alkyl;

$R^5$ is independently selected from the group consisting of H, halo and $C_1$, $C_3$ or $C_4$ alkyl;

$R^6$ and $R^7$ are, at each occurrence, independently selected from the group consisting of:
H,
$C_1$-$C_4$ alkyl substituted with 0 to 2 $R^{a1}$ groups,
$C_1$-$C_4$-alkoxy-$C_1$-$C_4$-alkyl, or
—$(CH_2)_n$-phenyl, alternatively, $R^6$ and $R^7$, when attached to the same nitrogen, combine to form a 4- to 6-membered heterocyclic ring containing carbon atoms and 1 to 2 additional heteroatoms selected from N, $NR^C$, O, and $S(O)_p$;

$R^{a1}$ is, at each occurrence, independently selected from the group consisting of:
H,
=O,
halo,
$OCF_3$,
$CF_3$,
$OCHF_2$,
$C_1$-$C_4$ alkyl substituted with 1 to 5 fluorines,
$C_1$-$C_4$ alkyl,
$C_1$-$C_4$ alkoxy,
$C_1$-$C_4$ alkylthio,
$C_3$-$C_6$ cycloalkyl,
$C_3$-$C_6$ cycloalkyloxy,
phenyl substituted by 0 to 3 $R^{a5a}$ groups independently selected from the group consisting of halo, $C_1$-$C_3$ alkoxy, $C_1$-$C_3$ alkyl, $CF_3$, $OCF_3$, $OCHF_2$, and cyano,
OH,
CN,
$NO_2$,
$NR^{6a}R^{7a}$,
carboxy,
$C_1$-$C_4$ alkoxycarbonyl,
$C(=O)NR^{6a}R^{7a}$,
$C_1$-$C_4$ alkylsulfonyl, and
$S(=O)_2NR^{6a}R^{7a}$;

$R^{a5}$ is, at each occurrence, independently selected from the group consisting of:
H,
halo,
$OCF_3$,
$CF_3$,
$OCHF_2$,
$C_1$-$C_6$ alkyl independently substituted with 1 to 5 fluorines, hydroxyl, $C_1$-$C_4$ alkoxy, $C_3$-$C_6$ cycloalkyl, or amino,
$C_1$-$C_4$ alkyl,
$C_1$-$C_4$ alkoxy,
$C_1$-$C_4$ alkylthio,
$C_3$-$C_6$ cycloalkyloxy,
OH,
CN,
$NO_2$,
$NR^{8a}R^{9a}$,
carboxy,
$C_1$-$C_4$ alkoxycarbonyl,
$C(=O)NR^{6a}R^{7a}$,
$C_6$-$C_{10}$-arylcarbonylamino-$C_1$-$C_4$-alkyl(phenyl)carbonyl,
5- to 10-membered heteroarylcarbonylamino-$C_1$-$C_4$-alkyl(phenyl)carbonyl,
$C_6$-$C_{10}$ arylcarbonyl substituted with 0 to 5 $R^{a5a}$ groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{6a}R^{7a}$, OH, $C_1$-$C_4$-alkylcarbonyloxy-$C_1$-$C_4$-alkyl, hydroxy-$C_1$-$C_4$-alkyl, $COOR^{8a}$, $SO_2R^{8a}$, $(C=O)NR^{6a}R^{7a}$, $SO_2NR^{6a}R^{7a}$, $N(R^{8a})(C=O)NR^{6a}R^{7a}$, $N(R^{8a})(C=O)OR^{8a}$, $N(R^{8a})(C=O)R^{8a}$, $NR^{8a}S(O)R^{8a}$, $NR^{8a}SO_2R^{8a}$, $O(C=O)NR^{6a}R^{7a}$, $O(C=O)OR^{8a}$, $O(C=O)R^{8a}$, $(C=O)OR^{8a}$, and 5-6-membered heteroaryl, $C_1$-$C_4$-alkyloxycarbonylamino-$C_1$-$C_4$-alkyl(phenyl)carbonyl, $C_1$-$C_6$ alkylsulfonyl, $S(=O)_2NR^{6a}R^{7a}$, phenyloxy, wherein the phenyl is substituted by 0 to 5 $R^{a5a}$ groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{6a}R^{7a}$, OH, $C_1$-$C_4$-alkylcarbonyloxy-$C_1$-$C_4$-alkyl, hydroxy-$C_1$-$C_4$-alkyl, $COOR^{8a}$, $SO_2R^{8a}$, $(C=O)NR^{6a}R^{7a}$, $SO_2NR^{6a}R^{7a}$, $N(R^{8a})(C=O)NR^{6a}R^{7a}$, $N(R^{8a})(C=O)OR^{8a}$, $N(R^{8a})(C=O)R^{8a}$, $NR^{8a}S(O)R^{8a}$, $NR^{8a}SO_2R^{8a}$, $O(C=O)NR^{6a}R^{7a}$, $O(C=O)OR^{8a}$, $O(C=O)R^{8a}$, $(C=O)OR^{8a}$, and 5-6-membered heteroaryl, phenylthio, wherein the phenyl is substituted by 0 to 5 $R^{a5a}$ groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{6a}R^{7a}$, OH, $C_1$-$C_4$-alkylcarbonyloxy-$C_1$-$C_4$-alkyl, hydroxy-$C_1$-$C_4$-alkyl, $COOR^{8a}$, $SO_2R^{8a}$, $(C=O)NR^{6a}R^{7a}$, $SO_2NR^{6a}R^{7a}$, $N(R^{8a})(C=O)NR^{6a}R^{7a}$, $N(R^{8a})(C=O)OR^{8a}$, $N(R^{8a})(C=O)R^{8a}$, $NR^{8a}S(O)R^{8a}$, $NR^{8a}SO_2R^{8a}$, $O(C=O)NR^{6a}R^{7a}$, $O(C=O)OR^{8a}$, $O(C=O)R^{8a}$, $(C=O)OR^{8a}$, and 5-6-membered heteroaryl, $C_6$-$C_{10}$-aryl-$C_1$-$C_4$-alkoxy, wherein the aryl is substituted by 0 to 5 $R^{a5a}$ groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{6a}R^{7a}$, OH, $C_1$-$C_4$-alkylcarbonyloxy-$C_1$-$C_4$-alkyl, phenyl, phenyloxy, benzyloxy, hydroxy-$C_1$-$C_4$-alkyl, $COOR^{8a}$, $SO_2R^{8a}$, $(C=O)NR^{6a}R^{7a}$, $SO_2NR^{6a}R^{7a}$, $N(R^{8a})(C=O)NR^{6a}R^{7a}$, $N(R^{8a})(C=O)OR^{8a}$, $N(R^{8a})(C=O)R^{8a}$, $NR^{8a}S(O)R^{8a}$, $NR^{8a}SO_2R^{8a}$, $O(C=O)NR^{6a}R^{7a}$, $O(C=O)OR^{8a}$, $O(C=O)R^{8a}$, $(C=O)OR^{8a}$, and 5-6-membered heteroaryl, 5- to 10-membered heteroaryl-$C_1$-$C_3$-alkoxy, wherein the heteroaryl is substituted by 0 to 5 $R^{a5a}$ groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{6a}R^{7a}$, OH, $C_1$-$C_4$-alkylcarbonyloxy-$C_1$-$C_4$-alkyl, phenyl, phenyloxy, benzyloxy, hydroxy-$C_1$-$C_4$-alkyl, $COOR^{8a}$, $SO_2R^{8a}$, $(C=O)NR^{6a}R^{7a}$, $SO_2NR^{6a}R^{7a}$, $N(R^{8a})(C=O)NR^{6a}R^{7a}$, $N(R^{8a})(C=O)OR^{8a}$, $NR^{8a}S(O)R^{8a}$, $NR^{8a}SO_2R^{8a}$, $O(C=O)NR^{6a}R^{7a}$, $O(C=O)OR^{8a}$, $O(C=O)R^{8a}$, $(C=O)OR^{8a}$, and 5-6-membered heteroaryl, and phenyl-$C_1$-$C_3$-alkyl, wherein the phenyl is substituted by 0 to 5 $R^{a5a}$ groups independently selected from the group consisting of halo, $C_1$-$C_4$ alkoxy, halo-$C_1$-$C_4$ alkoxy, $C_1$-$C_4$ alkyl, halo-$C_1$-$C_4$ alkyl, $C_3$-$C_6$ cycloalkyl, cyano, nitro, $NR^{6a}R^{7a}$, OH, $C_1$-$C_4$-alkylcarbonyloxy-$C_1$-$C_4$-alkyl, hydroxy-$C_1$-$C_4$-alkyl, $COOR^{8a}$, $SO_2R^{8a}$, $(C=O)NR^{6a}R^{7a}$, $SO_2NR^{6a}R^{7a}$, $N(R^{8a})(C=O)NR^{6a}R^{7a}$, $N(R^{8a})(C=O)OR^{8a}$, $N(R^{8a})(C=O)R^{8a}$, $NR^{8a}S(O)R^{8a}$, $NR^{8a}SO_2R^{8a}$, $O(C=O)NR^{6a}R^{7a}$, $O(C=O)OR^{8a}$, $O(C=O)R^{8a}$, $(C=O)OR^{8a}$, and 5-6-membered heteroaryl;

$R^{b5}$ is, at each instance, independently selected from the group consisting of:
$C_6$-$C_{10}$ aryl substituted by 0 to 3 $R^{a1}$ groups, and
6- to 10-membered heteroaryl substituted by 0 to 3 $R^{a1}$ groups, $R^{6a}$ and $R^{7a}$ are, at each occurrence, independently selected from the group consisting of:
H,
$C_1$-$C_6$ alkyl, independently substituted with 1 to 5 fluorines, hydroxyl, $C_1$-$C_4$ alkoxy, $C_3$-$C_6$ cycloalkyl, or amino, and
—$(CH_2)_n$-phenyl independently substituted with 1 to 3 fluorines, hydroxyl, $C_1$-$C_4$ alkoxy, fluoro-$C_1$-$C_2$ alkoxy, $C_3$-$C_6$ cycloalkyl, or amino, alternatively, $R^{6a}$ and $R^{7a}$, when attached to the same nitrogen, combine to form a 4- to 6-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^c$, O and $S(O)_p$;

$R^{8a}$ and $R^{9a}$ are, at each occurrence, independently selected from the group consisting of:
H,
$C_1$-$C_6$ alkyl independently substituted with 1 to 5 fluorines, hydroxyl, $C_1$-$C_4$ alkoxy, $C_3$-$C_6$ cycloalkyl, or amino, and
—$(CH_2)_n$-phenyl independently substituted with 1 to 3 fluorines, hydroxyl, $C_1$-$C_4$ alkoxy, fluoro-$C_1$-$C_2$ alkoxy, $C_3$-$C_6$ cycloalkyl, or amino;

$R^c$ is independently, at each occurrence, selected from the group consisting of H, $C_1$-$C_6$ alkyl, and —$(CH_2)_n$-phenyl;

n, at each occurrence, is selected from 0, 1, 2, 3 and 4;
p, at each occurrence, is selected from 0, 1 and 2; and
s, at each occurrence, is selected from 0, 1, 2 and 3,
provided that when $R^1$ is Br, $R^{10}$ is other than unsubstituted benzofuran.

2. The compound as defined in claim 1 wherein:
$R^1$ is selected from the group consisting of:
halo which is Br or Cl,
$C_1$-$C_2$ alkoxy,
cyclopropyl,
$CH_3S$,

[structures: $CF_3$, $CHF_2CH_3$, $CHFCl$, $CH(CH_3)F$ groups], which is

[structures: two stereoisomers of $CH(CH_3)F$], or a mixture thereof; and
$R^2$ is H.

3. The compound as defined in claim 1 wherein $R^{10}$ is

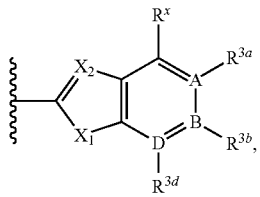

wherein:
$X_1$ is O, or
$X_1$ is S, and
wherein A, B and D are each carbon;
$R^5$ is H, and
$R^{3a}$, $R^{3b}$, and $R^{3d}$ are independently selected from any of the $R^3$ groups.

4. The compound as defined in claim 1 wherein $R^x$ is Y—Z— which is selected from the group consisting of:
$C_6$-$C_{10}$ aryl substituted with 0 to 2 $R^{a5}$ groups;
$C_6$-$C_{10}$-aryl-$C_1$-$C_4$-alkyl, wherein the aryl portion of which is independently substituted with 0 to 3 $R^{a5}$ groups, and the alkyl portion of which is independently substituted with 0 to 2 $R^{a1}$ groups;
$C_6$-$C_{10}$-aryl-$C_1$-$C_3$-alkyloxy, wherein the aryl portion of which is independently substituted with 0 to 3 $R^{a5}$ groups, and the alkyl portion of which is independently substituted with 0 to 2 $R^{a1}$ groups;
$C_6$-$C_{10}$-aryl-$C_1$-$C_3$-alkylthio, wherein the aryl portion of which is independently substituted with 0 to 3 $R^{a5}$ groups, and the alkyl portion of which is independently substituted with 0 to 2 $R^{a1}$ groups;
$C_6$-$C_{10}$ aryloxy substituted with 0 to 2 $R^{a5}$ groups;
$C_6$-$C_{10}$ arylthio substituted with 0 to 3 $R^{a5}$ groups;
$C_6$-$C_{10}$-aryl-$C_2$-$C_6$-alkynyl, wherein the aryl is substituted with 0 to 3 $R^{a5}$ groups and the alkynyl is substituted with 0 to 3 $R^{a1}$ groups;
4- to 10-membered ring heterocyclyl substituted with 0 to 3 $R^{a5}$ groups;
4- to 10-membered ring heterocyclyl-$C_1$-$C_4$-alkyl, wherein the heterocyclo portion of which is independently substituted with 0 to 3 $R^{a5}$ groups, and the alkyl portion of which is independently substituted with 0 to 2 $R^{a1}$ groups;
4- to 10-membered ring heterocyclyl-$C_1$-$C_4$-alkyloxy, wherein the heterocyclo portion of which is independently substituted with 0 to 3 $R^{a5}$ groups, and the alkyl portion of which is independently substituted with 0 to 2 $R^{a1}$ groups;
4- to 10-membered ring heterocyclyl-$C_1$-$C_4$-alkylthio, wherein the heterocyclo portion of which is independently substituted with 0 to 3 $R^{a5}$ groups, and the alkyl portion of which is independently substituted with 0 to 2 $R^{a1}$ groups;
4- to 10-membered ring heterocyclyloxy substituted with 0 to 3 $R^{a5}$ groups;
4- to 10-membered ring heterocyclylthio substituted with 0 to 3 $R^{a5}$ groups;
6- to 10-membered ring heteroaryl, wherein the heteroaryl portion of which is independently substituted with 0 to 3 $R^{a5}$ groups;
6- to 10-membered ring heteroaryl-$C_1$-$C_4$-alkyl, wherein the heteroaryl portion of which is independently substituted with 0 to 3 $R^{a5}$ groups, and the alkyl portion of which is independently substituted with 0 to 2 $R^{a1}$ groups;
6- to 10-membered ring heteroaryl-$C_1$-$C_4$-alkyloxy, wherein the heteroaryl portion of which is independently substituted with 0 to 3 $R^{a5}$ groups, and the alkyl portion of which is independently substituted with 0 to 2 $R^{a1}$ groups,
6- to 10-membered ring heteroaryloxy substituted with 0 to 3 $R^{a5}$ groups;
6- to 10-membered ring heteroarylthio substituted with 0 to 3 $R^{a5}$ groups;
6- to 10-membered heteroaryl-$C_3$-$C_6$-alkynyl, wherein the heteroaryl portion is substituted with 0 to 2 $R^{a5}$ groups, and the alkynyl is substituted with 0 to 3 $R^{a1}$ groups;
$C_1$-$C_4$-alkyloxy-$C_1$-$C_4$-alkyl($C_1$-$C_4$-alkyl)amino;
$C_3$-$C_6$ cycloalkyl substituted with 0 to 2 $R^{a5}$ groups;
$C_3$-$C_6$-cycloalkyl-$C_1$-$C_4$-alkyl, wherein the cycloalkyl portion is substituted with 0 to 2 $R^{a5}$ groups and the alkyl portion is independently substituted with 0 to 2 $R^{a1}$ groups;
$C_3$-$C_6$-cycloalkyl-$C_1$-$C_4$-alkyloxy, wherein the cycloalkyl portion is substituted with 0 to 2 $R^{a5}$ groups and the alkyl portion is independently substituted with 0 to 2 $R^{a1}$ groups;
$C_3$-$C_6$-cycloalkyl-$C_1$-$C_4$-alkylthio, wherein the cycloalkyl portion is substituted with 0 to 2 $R^{a5}$ groups and the alkyl portion is independently substituted with 0 to 2 $R^{a1}$ groups;
$C_3$-$C_6$ cycloalkyloxy substituted with 0 to 2 $R^{a5}$ groups;
$C_3$-$C_6$ cycloalkylthio substituted with 0 to 2 $R^{a5}$ groups;
$C_1$-$C_4$-alkyloxy-$C_1$-$C_4$-alkyloxy, wherein each alkyl portion of which is independently substituted with 0 to 2 $R^{a1}$ groups;
cyano-$C_1$-$C_4$-alkyloxy substituted with 0 to 2 $R^{a1}$ groups, or
di-$C_1$-$C_4$-alkylamino-$C_1$-$C_4$-alkyloxy, wherein each alkyl portion of alkyloxy is independently substituted with 0 to 2 $R^{a1}$ groups, and each alkyl portion of alkylamino can be independently substituted as defined for $R^{6a}$ and $R^{7a}$ in claim 1.

5. The compound as defined in claim 2 wherein $R^{10}$ is

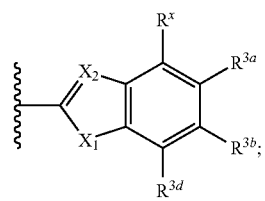

$X_1$ is O or S;
and
wherein $R^{3a}$, $R^{3b}$ and $R^{ad}$ are independently selected from any of the $R^3$ groups.

6. The compound as defined in claim 5 wherein $R^{10}$ is

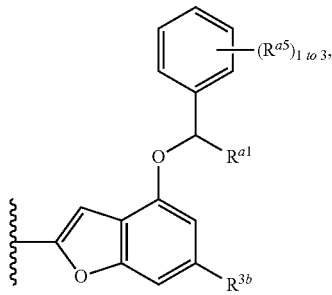

and
where $R^{3b}$ is selected from the group consisting of:
H,
F,
Cl,
OMe,
OEt,
$OCF_3$, and
$OCHF_2$.

7. The compound as defined in claim 6 wherein $R^{10}$ is the benzofuran

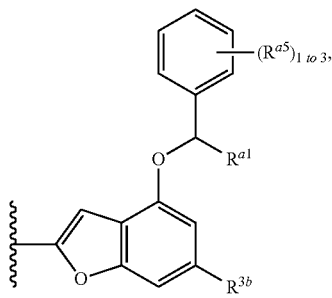

wherein:
$R^{3b}$ is OMe;
$R^{a1}$ is H; and
$R^{a5}$ is independently selected from the group consisting of H, F, Cl, $CF_3$, $OCF_3$, $OCHF_2$, $OCH_3$, and $OC_6H_5$ optionally substituted with 1 to 2 $R^{a5a}$ substituents which are independently selected from the group consisting of F, Cl, $CF_3$, $OCF_3$, $OCHF_2$ and $OCH_3$, or $R^{a5}$ is $OCH_2C_6H_5$ wherein the $C_6H_5$ of said $OCH_2C_6H_5$ can be optionally substituted with 1 to 2 $R^{a5a}$ substituents which are independently selected from the group consisting of F, Cl, $CF_3$, $OCF_3$, $OCHF_2$ and $OCH_3$.

8. The compound as defined in claim 5 wherein $R^{10}$ is

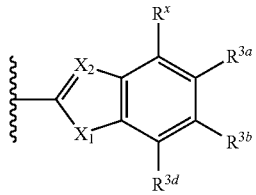

and
wherein:
$R^x$ is selected from the group consisting of:
hydrogen,
halo, which is Cl, Br or F,
fluoro-$C_1$-$C_4$-alkyl, which is —$CF_3$ or —$CF_2CF_3$,
fluoro-$C_1$-$C_4$-alkoxy, which is —$OCF_3$, —$OCF_2CF_2H$, —$OCF_2CF_3$, or —$OCHF_2$ $NH_2$,
OH,
$NO_2$,
$C_1$-$C_4$ alkyl substituted with 0 to 2 $R^{a1}$ groups,
$C_1$-$C_4$ alkoxy substituted with 0 to 2 $R^{a1}$ groups, phenyl ($C_1$-$C_4$)alkyloxy, wherein the phenyl is substituted with 0 to 2 $R^{a5}$ groups,
$C_1$-$C_4$-alkoxy-$C_1$-$C_4$-alkyl($C_1$-$C_4$-alkyl)amino,
phenylethynyl,
cyanomethoxy,
($C_3$-$C_{10}$)cycloalkyl($C_1$-$C_4$)alkyloxy,
($C_3$-$C_{10}$)cycloalkyloxy,
N-pyrrolidinyl($C_1$-$C_4$)alkyloxy,
N-morpholinyl($C_1$-$C_4$)alkyloxy,
phenoxy,
carbonyl,
benzylaminocarbonyl, and
benzyl;
which $R^{a1}$ groups are independently selected from the group consisting of:
$C_1$-$C_2$ alkyl,
phenyl,
$C_1$-$C_2$ alkoxy,
$C_1$-$C_2$ alkoxycarbonyl,
cyano,
cyclohexyl,
cyclohexyloxy,
cyclobutyloxy, and
halo, which is Cl;
wherein said $R^{a5}$ groups are independently selected from the group consisting of:
$C_1$-$C_2$ alkyl,
benzyl,
benzyloxy,
$C_1$-$C_2$ alkoxy,
$C_1$-$C_2$ alkoxycarbonyl,
cyano,
cyclohexyloxy,
cyclobutyloxy, and
halo, which is Cl;
$R^{3a}$, $R^{3b}$ and $R^{3d}$ are the same or different and are independently selected from the group consisting of:
hydrogen,
Cl, F, I,
fluoro-$C_1$-$C_4$-alkyl which contains 1 to 5 fluorines,
fluoro-$C_1$-$C_4$-alkoxy which contains 1 to 5 fluorines,
$NH_2$,
OH,
$NO_2$,
$C_1$-$C_4$ alkyl substituted with 0 to 2 $R^{a1}$ groups,
$C_1$-$C_4$ alkoxy substituted with 0 to 2 $R^{a1}$ groups,
phenyl$C_1$-$C_4$ alkoxy, wherein the phenyl is substituted with 0 to 2 $R^{a5}$ groups, and
4- to 10-membered heterocyclo-$C_1$-$C_4$-alkoxy, wherein the heterocyclo is substituted with 0 to 2 $R^{a5}$ group;
$R^1$ is
$CH_3O$,

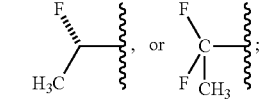

and
$R^2$ is H.

9. The compound as defined in claim 5 wherein $R^{10}$ is

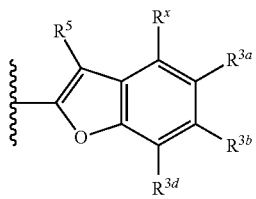

which is selected from the group consisting of:

(1)

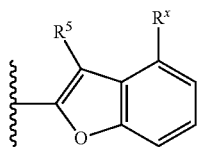

wherein $R^x$ is selected from the group consisting of:
H,
$OCH_3$,
$OC_2H_5$,
$O\text{-}n\text{-}C_3H_7$,
$O\text{-}i\text{-}C_3H_7$,
$O\text{-}n\text{-}C_4H_9$,
$O\text{-}t\text{-}C_4H_9$,

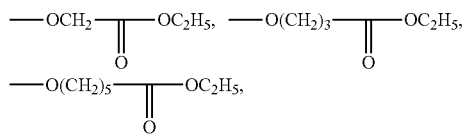

—$O(CH_2)_3OCH_3$,
$OCH_2C_6H_5$,
—$O(CH_2)_3$—CN,
$OCH_2CN$,
—$OCH_3$,
OH,
$CH_3$,
$C_2H_5$,
—$C_3H_7$,
$t\text{-}C_4H_9$,
Cl,
Br,
F,
$OCF_3$,
$OCH_2C_6H_5$—F-m,
$OCH_2C_6H_5$—$CH_{3\text{-}p}$, and
$OCH_2C_6H_5CN\text{-}m$;

(2)

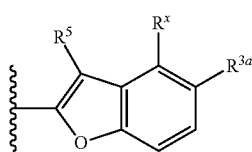

wherein $R^x$ and $R^{3a}$ are each —$OCH_3$ or $CH_3$ and $R^5$ is H, $CH_3$ or Br;

(3)

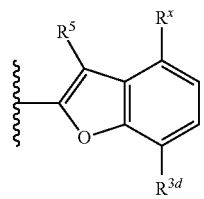

wherein $R^x$ and $R^{3d}$ are each —$OCH_3$;

(4)

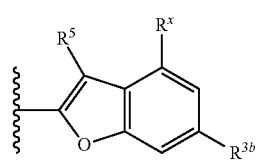

wherein $R^x$ is $CH_3O$ and $R^{3b}$ is F, or
$R^x$ is OH and $R^{3b}$ is $CH_3O$, or
$R^x$ is Br and $R^{3b}$ is $CH_3O$;

(5)

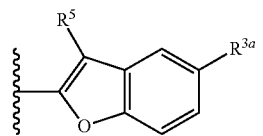

wherein $R^{3a}$ is selected from the group consisting of:
—$CH_3$,
—$OCH_3$,
$NO_2$,
Cl,
F, and

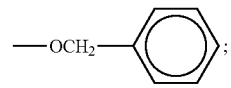

(6)

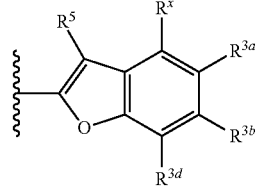

wherein $R^{3a}$, $R^{3b}$, $R^x$ and $R^{3d}$ are as follows:

| R | $R^{3a}$ | $R^{3b}$ | $R^{3d}$ |
|---|---|---|---|
| $CH_3O$ | H | H | H |
| H | $CH_3O$ | H | H |
| $CH_3O$ | H | $CH_3O$ | H |
| H | H | $CH_3O$ | H |
| H | H | Cl | H |
| H | F | H | H |
| $C_6H_5CH_2O$— | H | $CH_3O$ | H |
| Cl | H | Cl | H |
| H | Cl | $CH_3O$ | H |

-continued

| R | $R^{3a}$ | $R^{3b}$ | $R^{3d}$ |
|---|---|---|---|
| H | F | CH₃O | H |
| C₆H₅(CH₂)₂ | H | CH₃O | H |
| 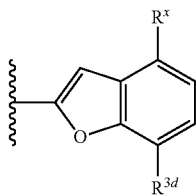 | H | CH₃O | H |
| 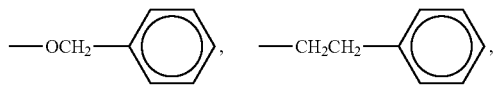 | H | CH₃O | H |
| CH₃OCH₂CH₂N(CH₃)— | H | CH₃O | H |
| H | F | F | H |
| 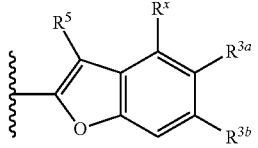 | H | CH₃O | H |
| H | F | H | CH₃O |
| 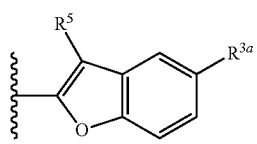 | H | CH₃O | H |
| F | H | CH₃O | H |
| 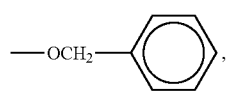 | H | CH₃O | H |

(7)

wherein
$R^{3a}$ is F, OCH₃, CH₃, OCH₃, Cl, NO₂, or

—OCH₂—⟨phenyl⟩, and
$R^5$ is H, or
$R^{3a}$ is OCH₃, and
$R^5$ is CH₃, or
$R^{3a}$ is H, and
$R^5$ is Br; or (8)

wherein $R_x$ is selected from the group consisting of:
OCH₃,
CH₃,
OCH₂CN,

—OCH₂—⟨phenyl⟩, —CH₂CH₂—⟨phenyl⟩,

Cl,
OH, or
—OCH₂OCH₃;

(9)

wherein $R^{3a}$ and $R^{3b}$ are as follows:

| $R^{3a}$ | $R^{3b}$ |
|---|---|
| CH₃O | Cl |
| CH₃O | C₆H₅O |
| CH₃ | Cl; | or (10)

where:
$R^x$ is selected from the group consisting of:

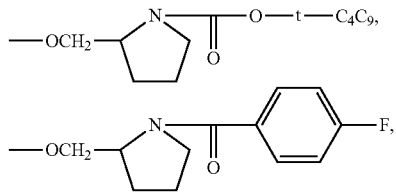

323
-continued
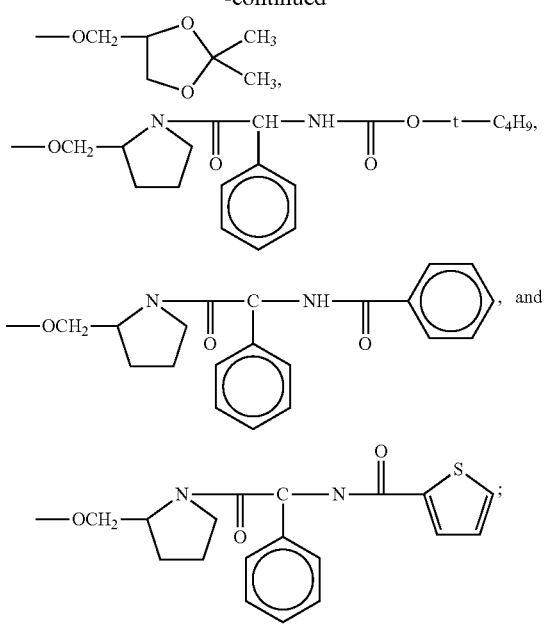
and
R¹ is CH₃O or CH₃S.
10. A compound selected from the following compounds:
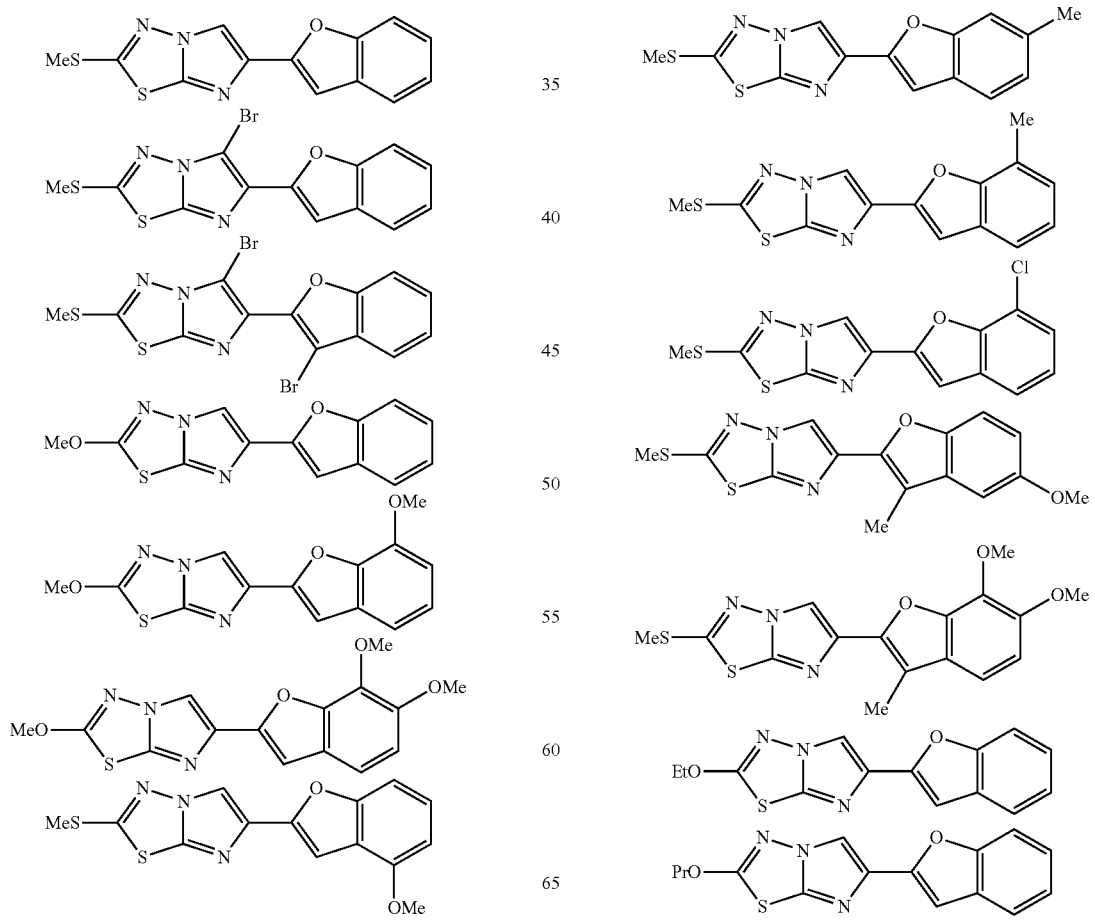
324
-continued
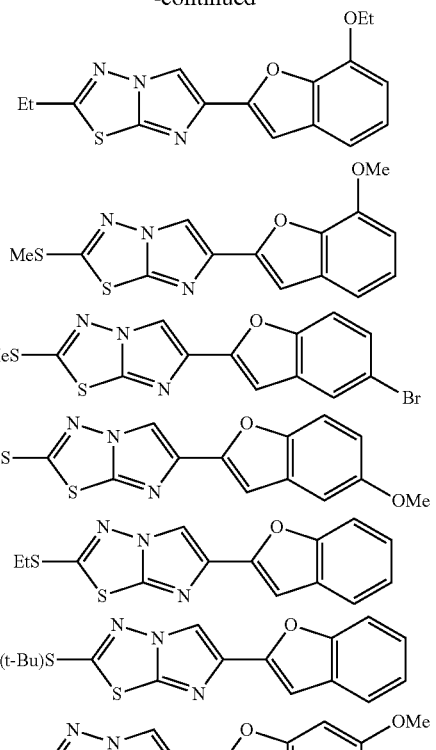

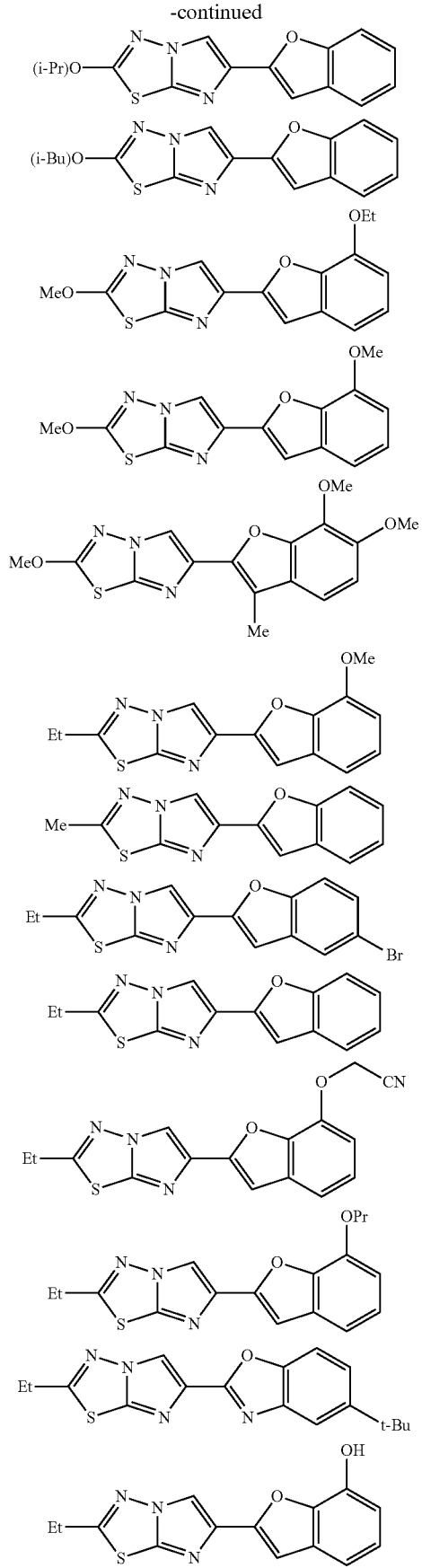
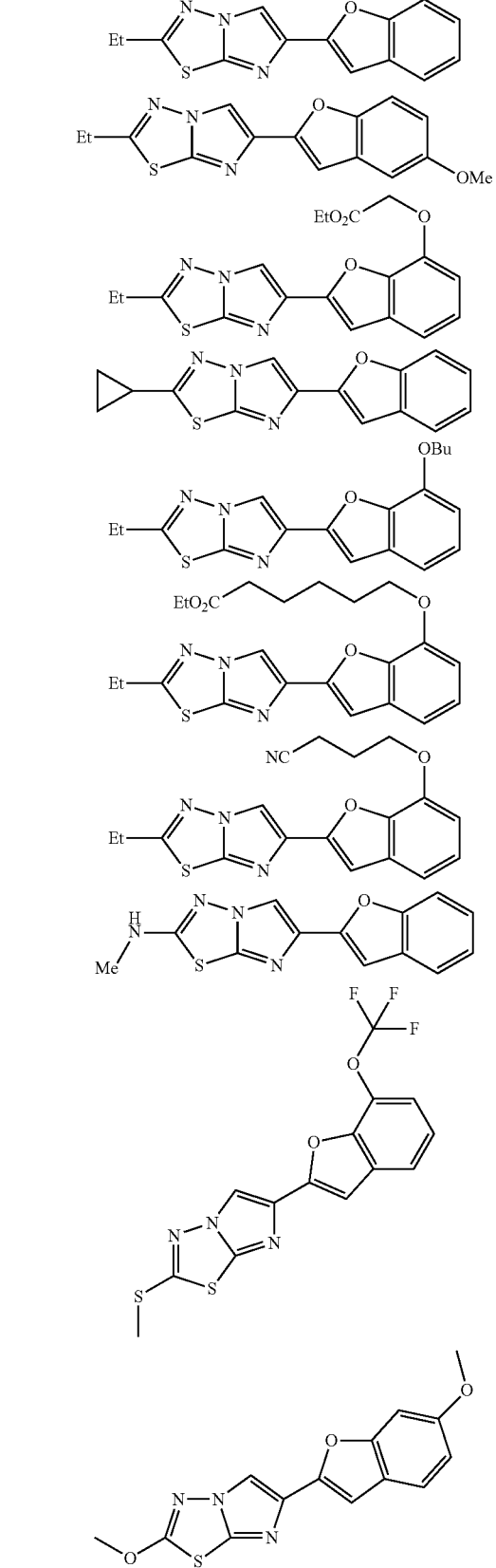

327
-continued
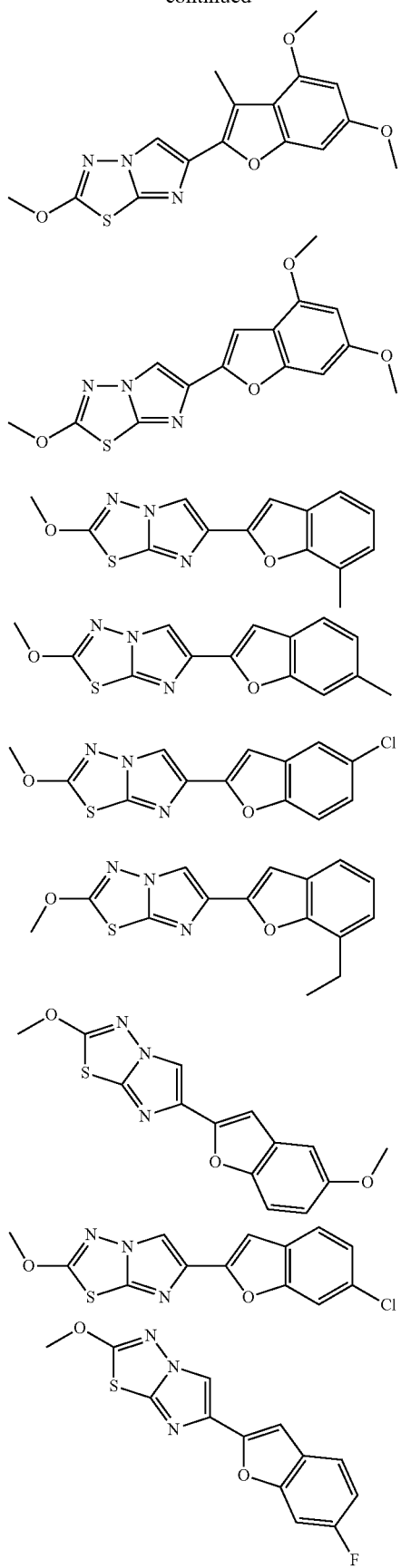
328
-continued
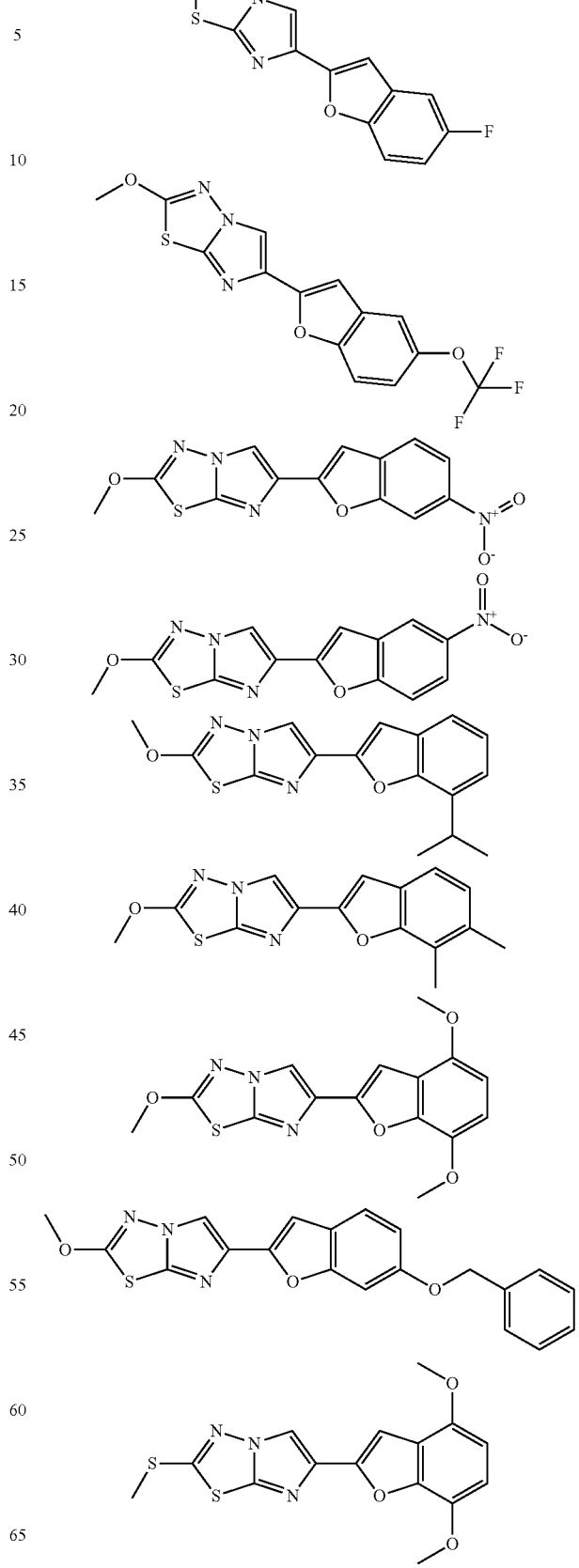

329
-continued
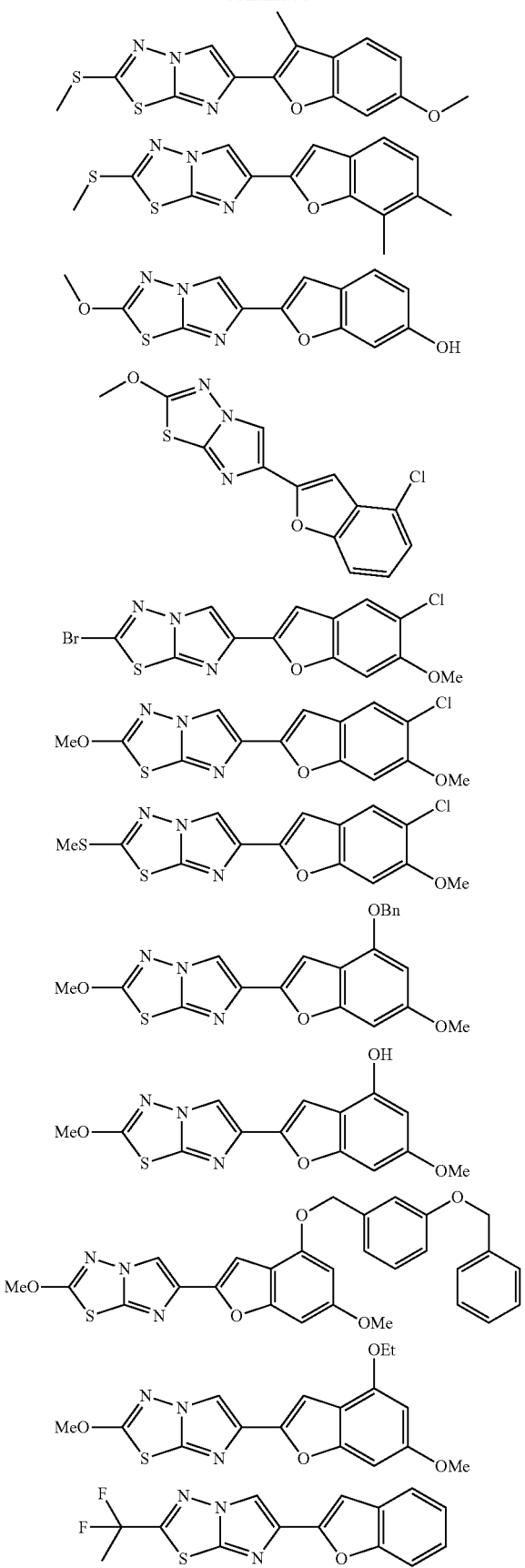
330
-continued
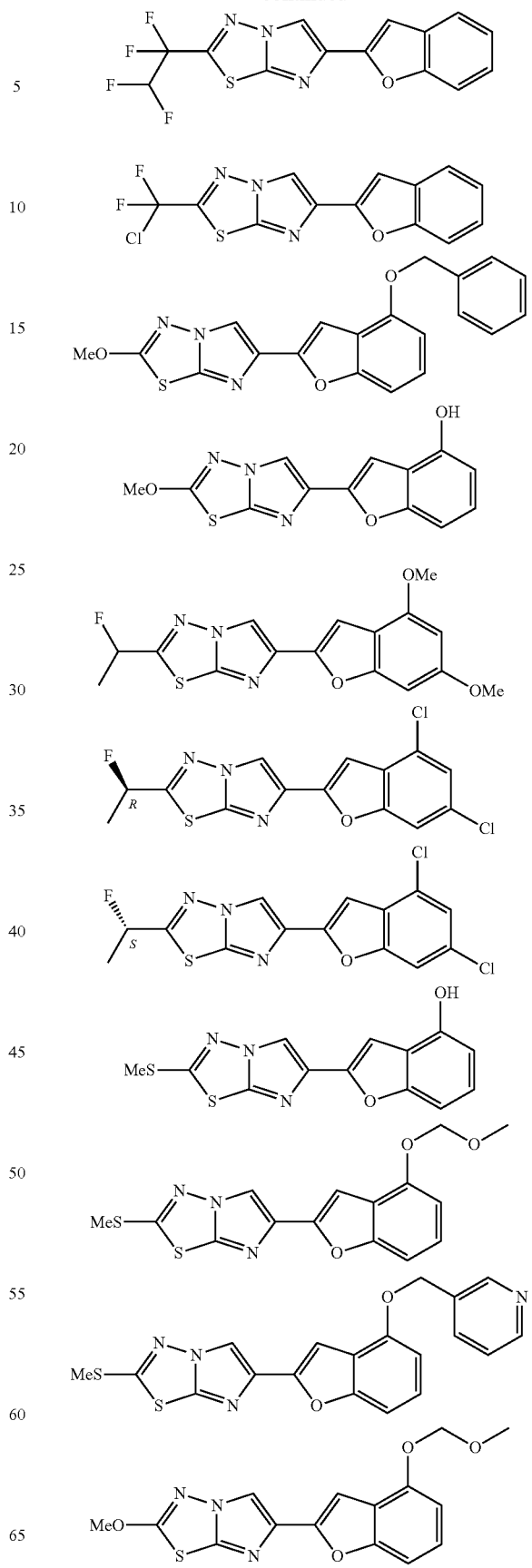

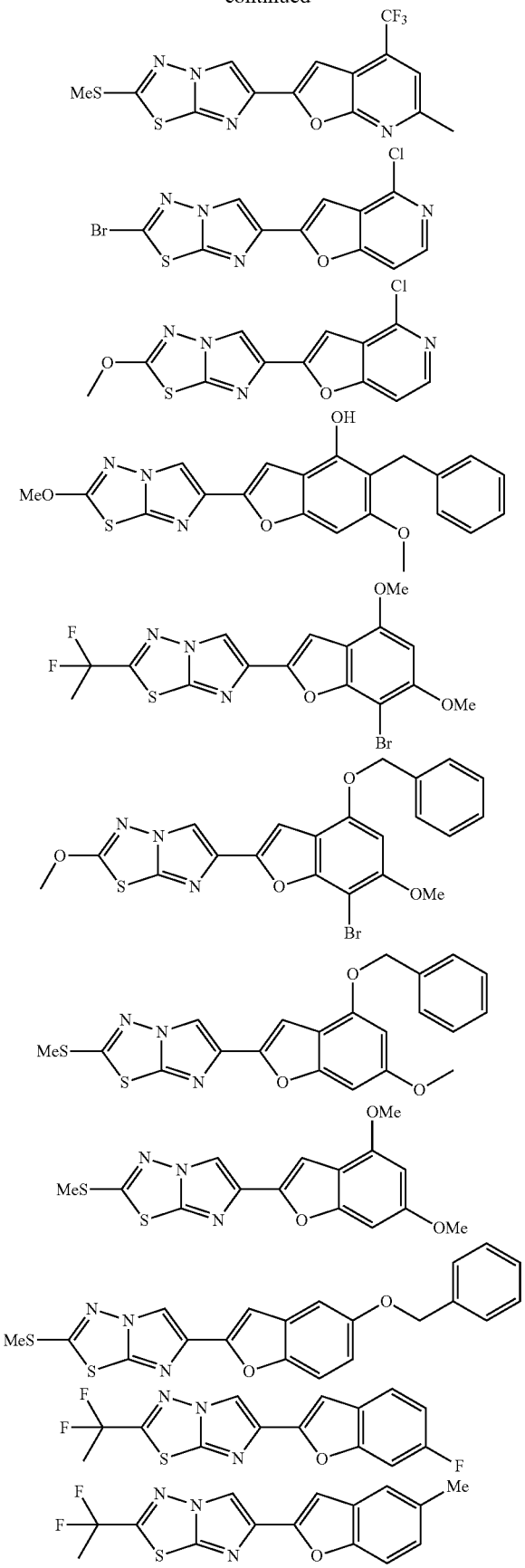
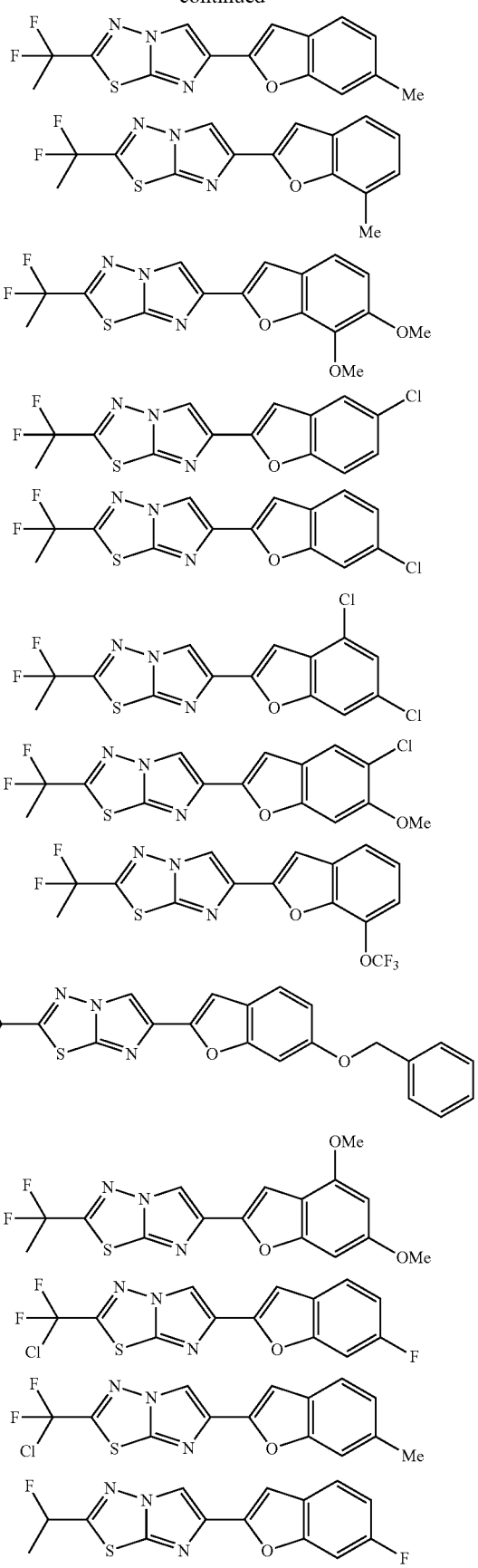

333
-continued
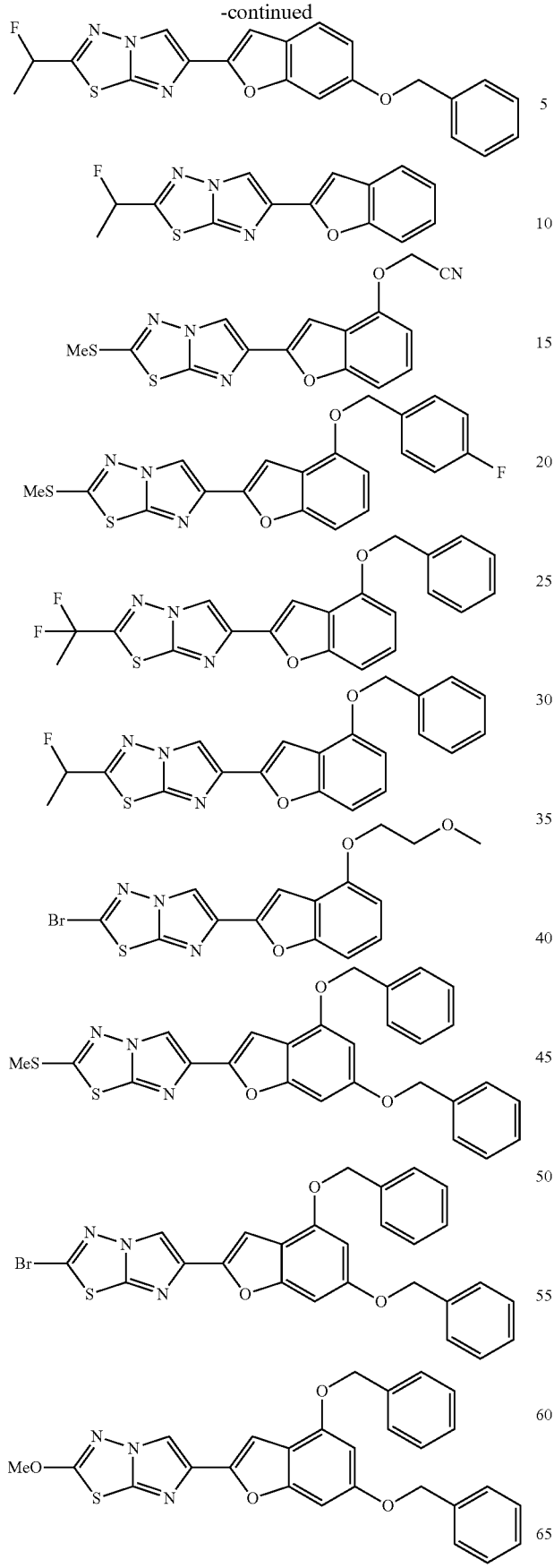
334
-continued
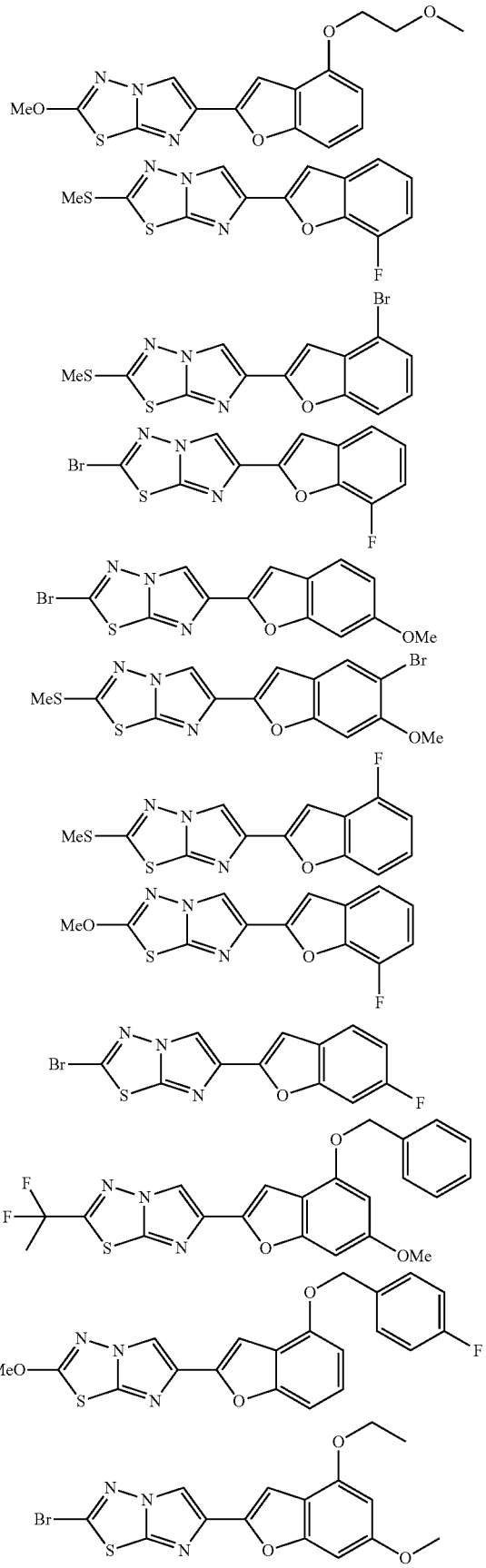

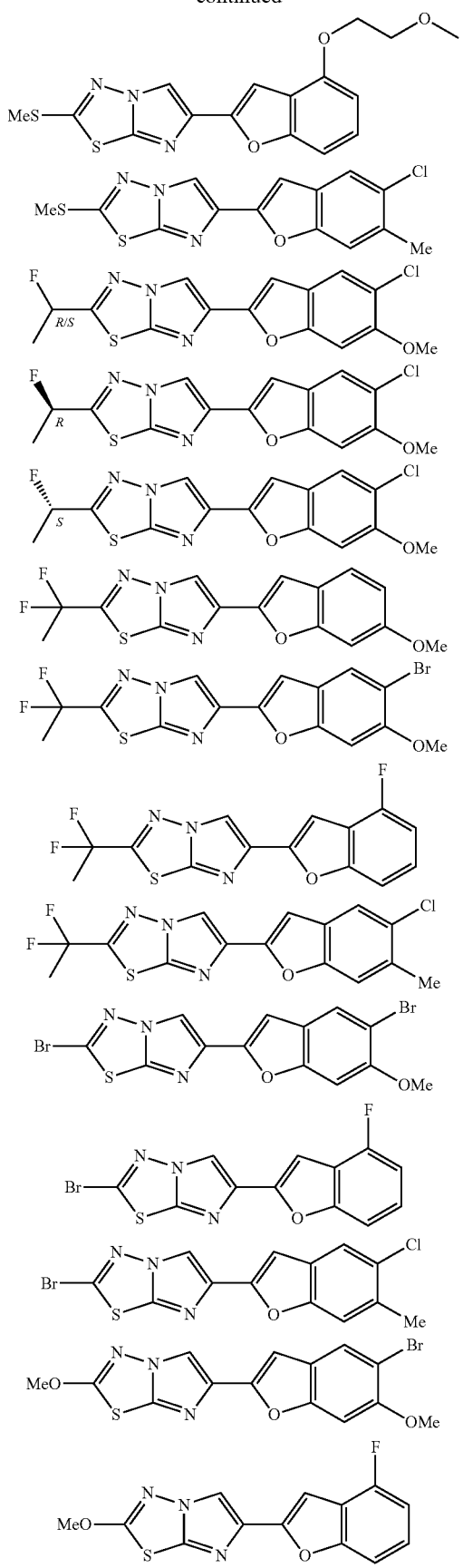
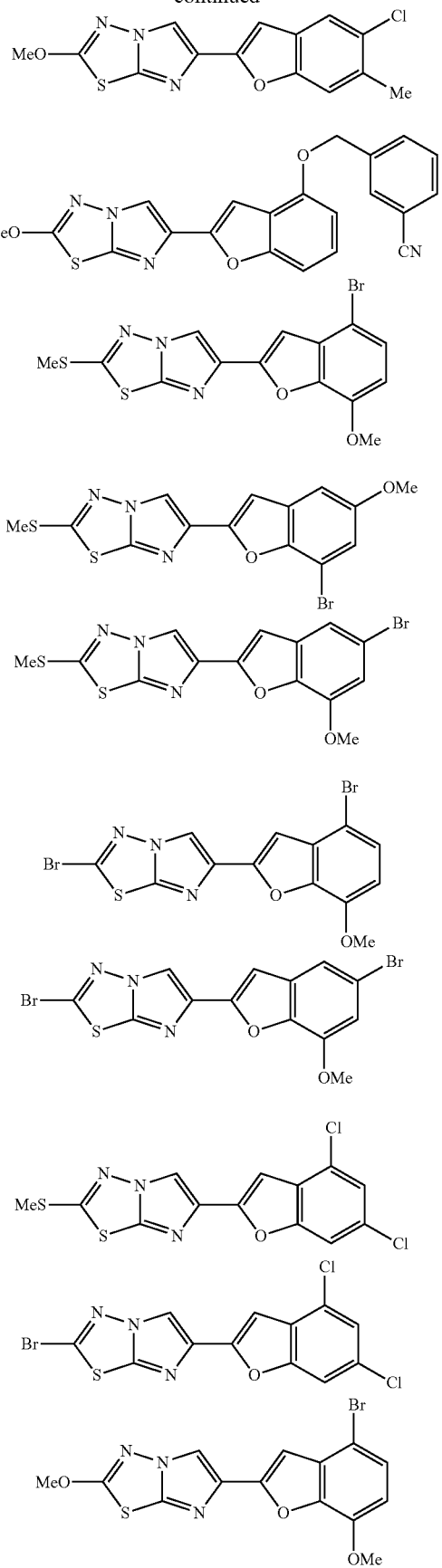

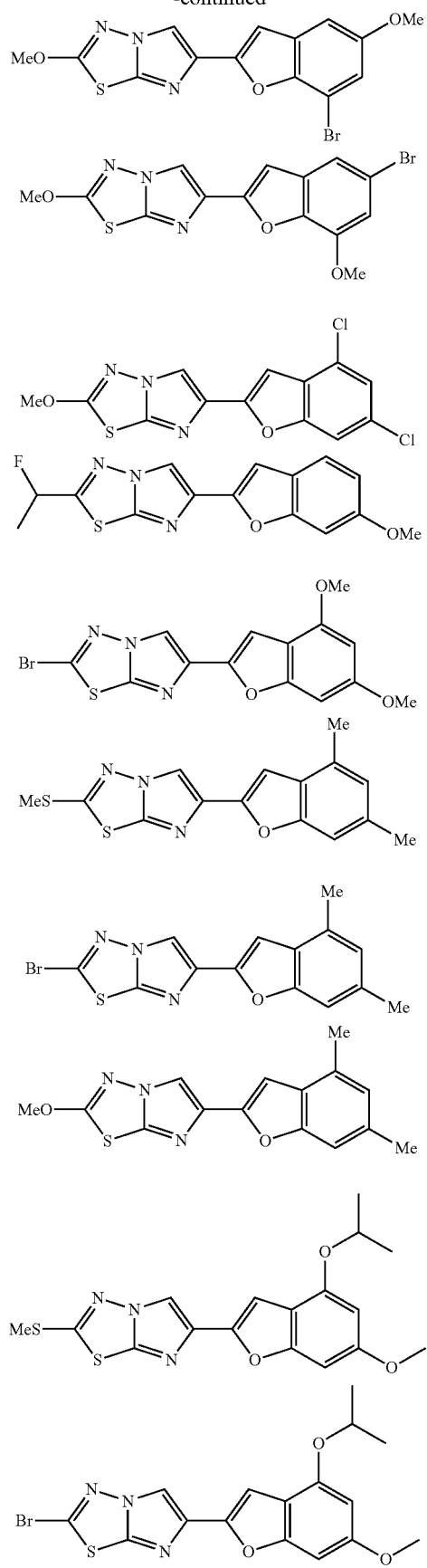
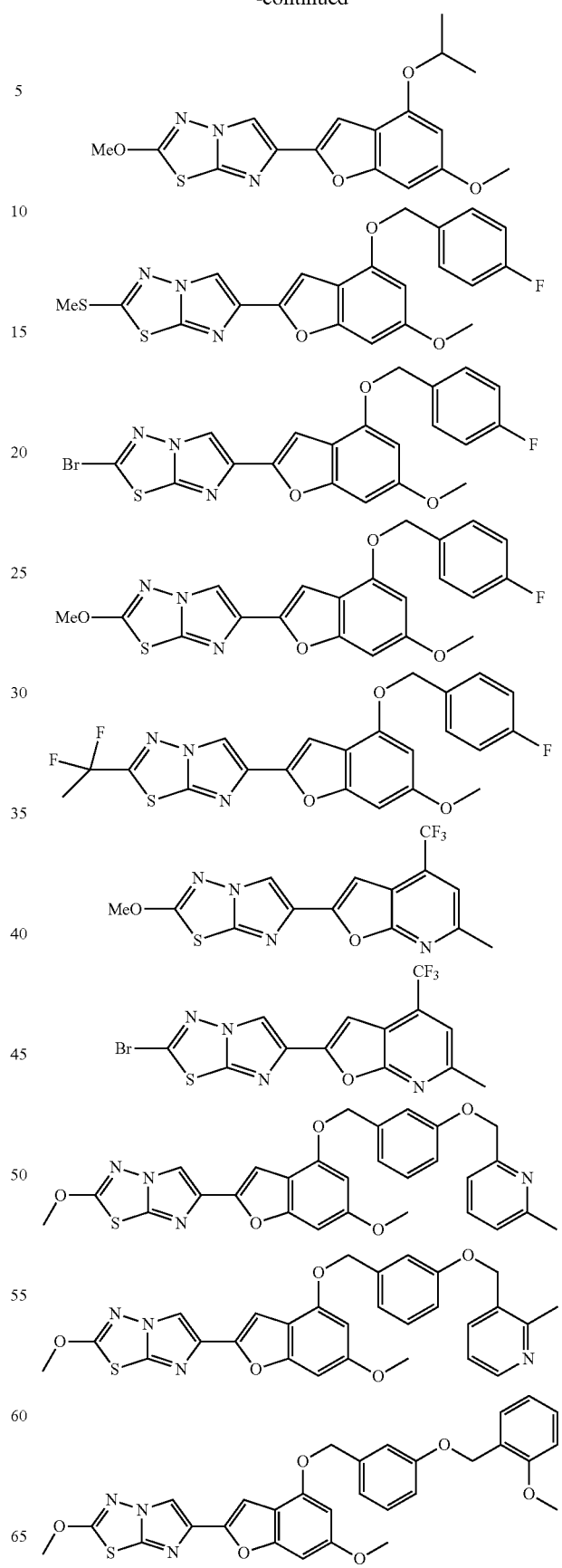

-continued
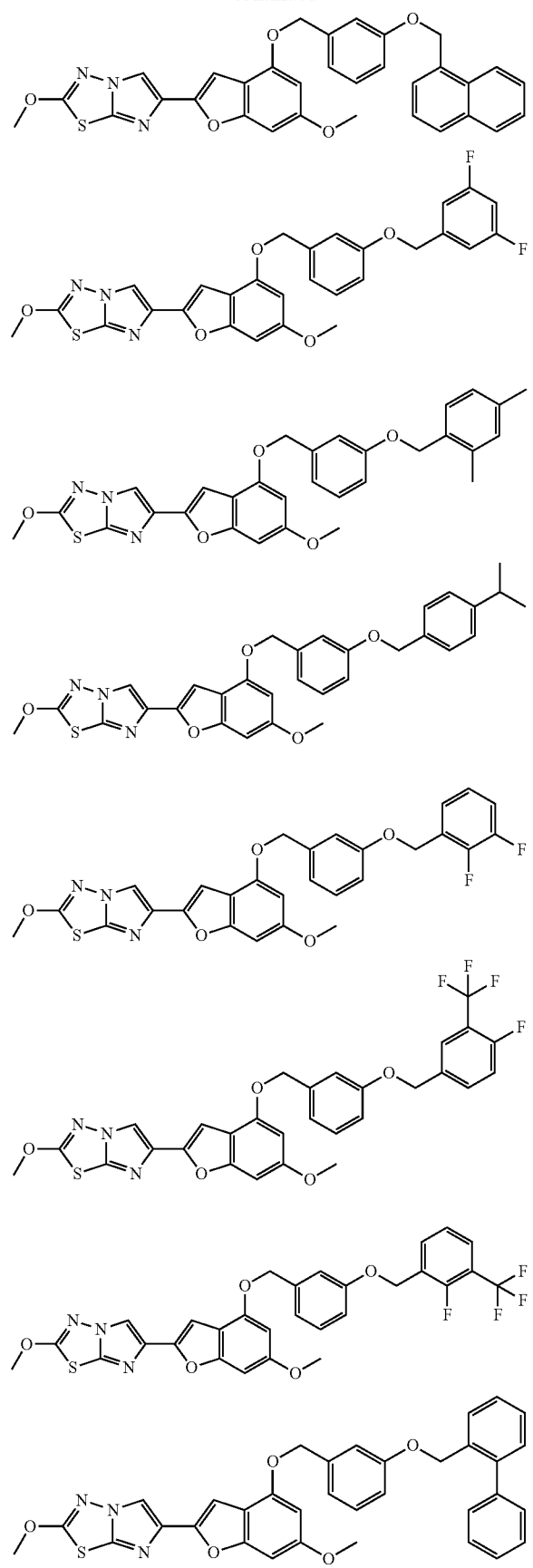
-continued
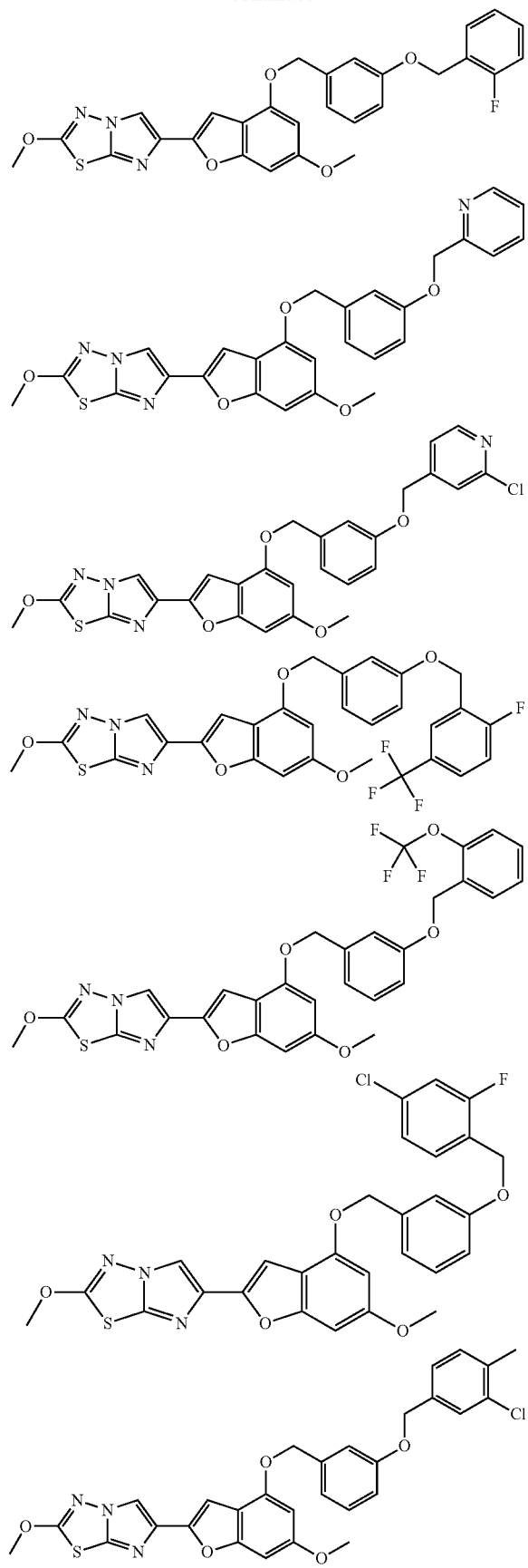

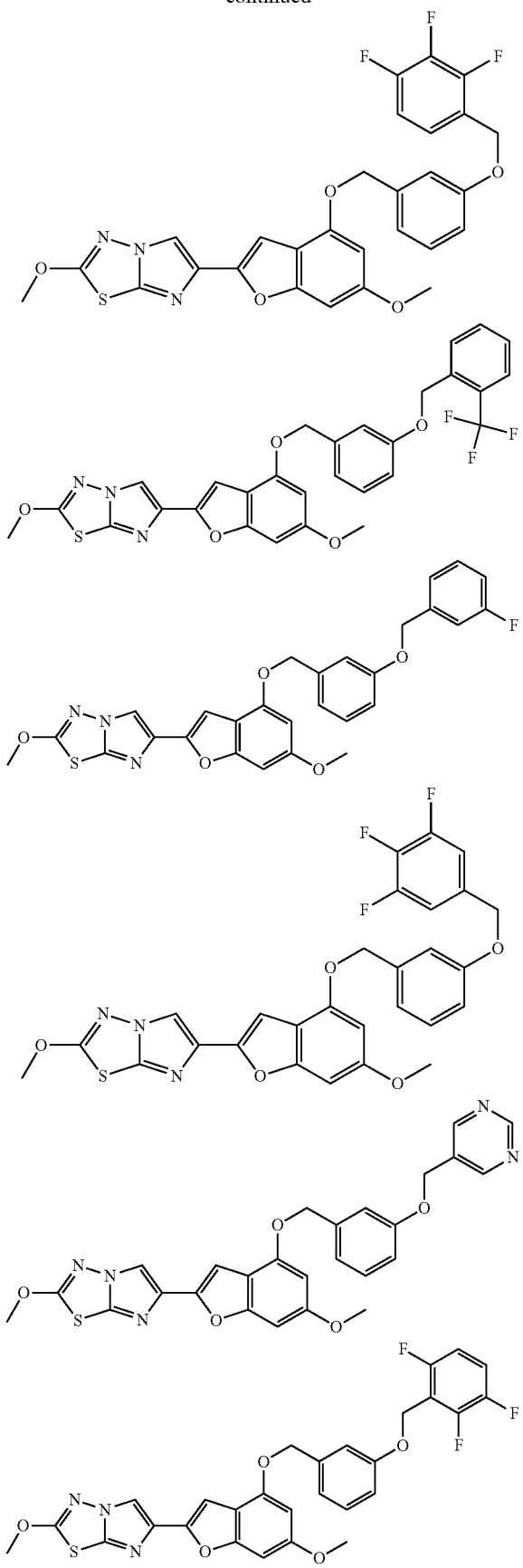
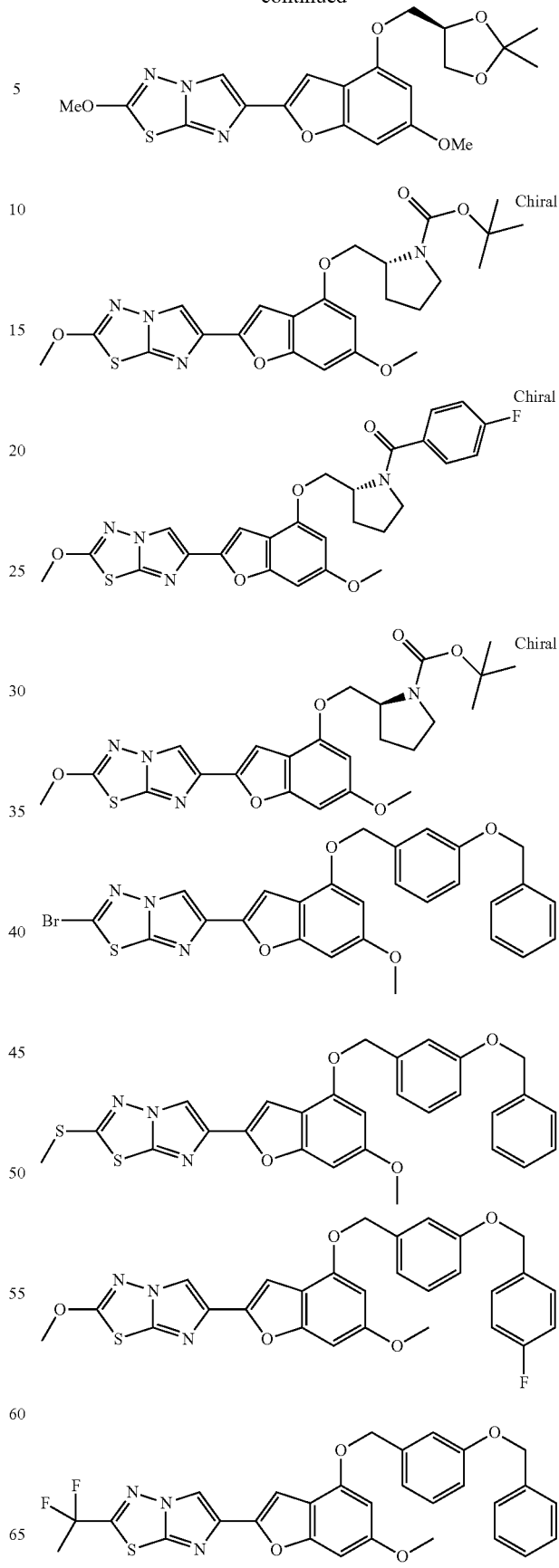

343
-continued
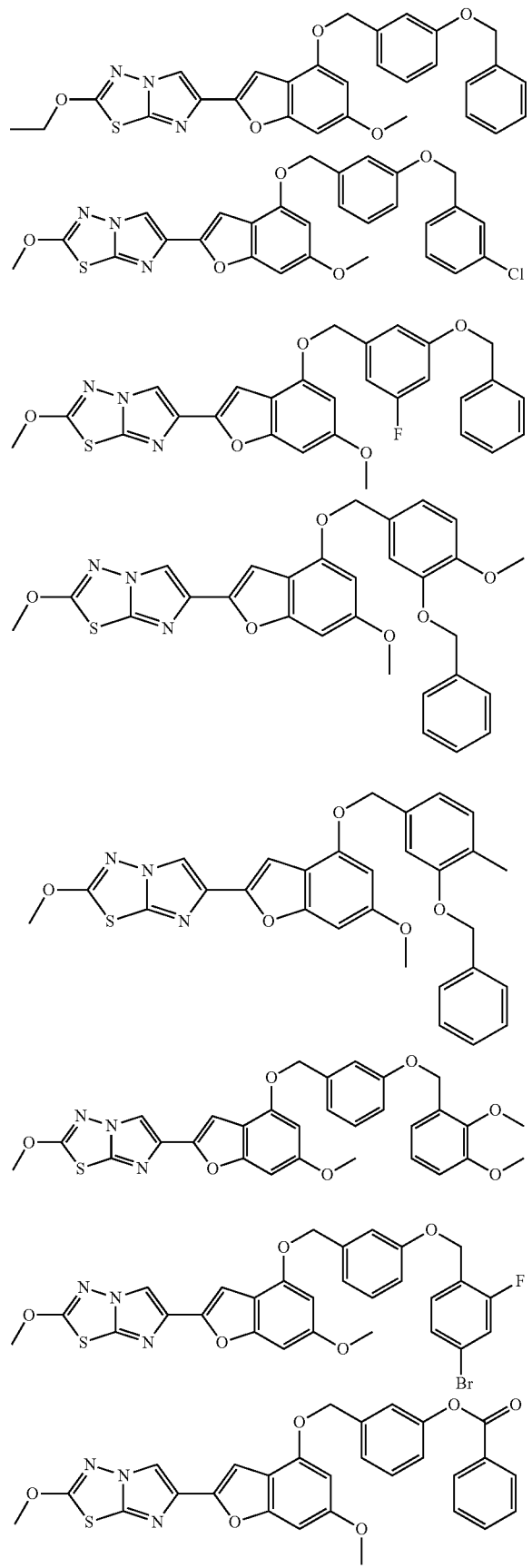
344
-continued
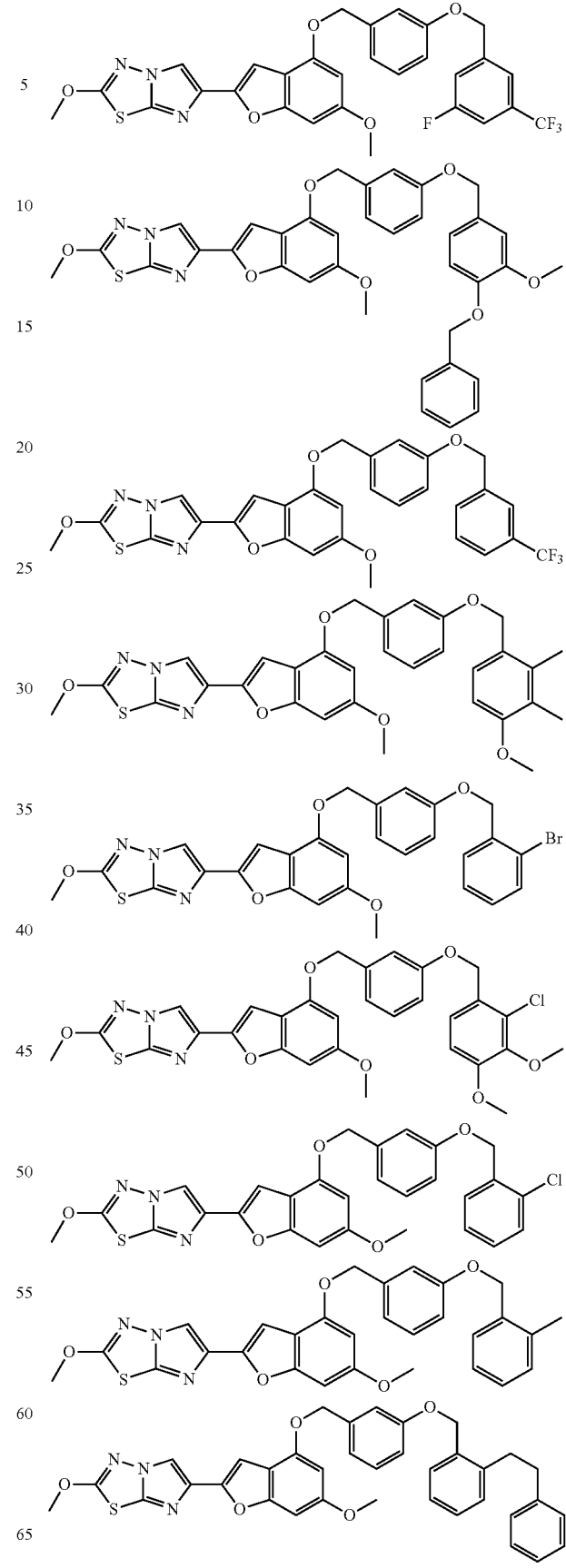

-continued
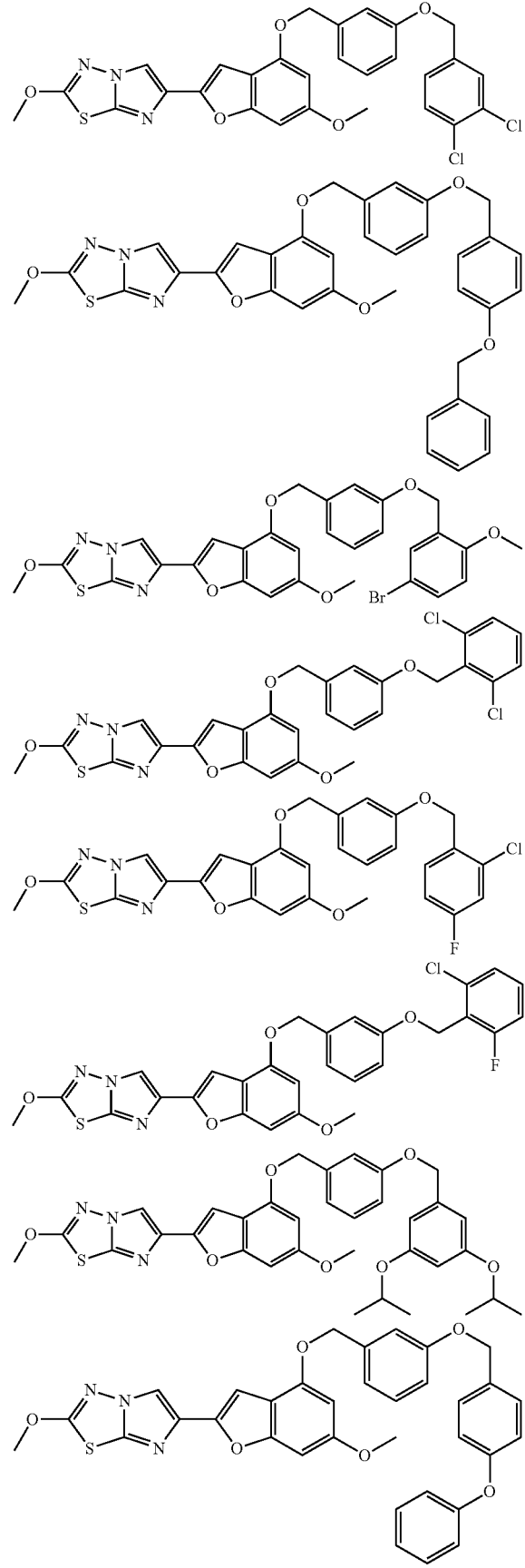
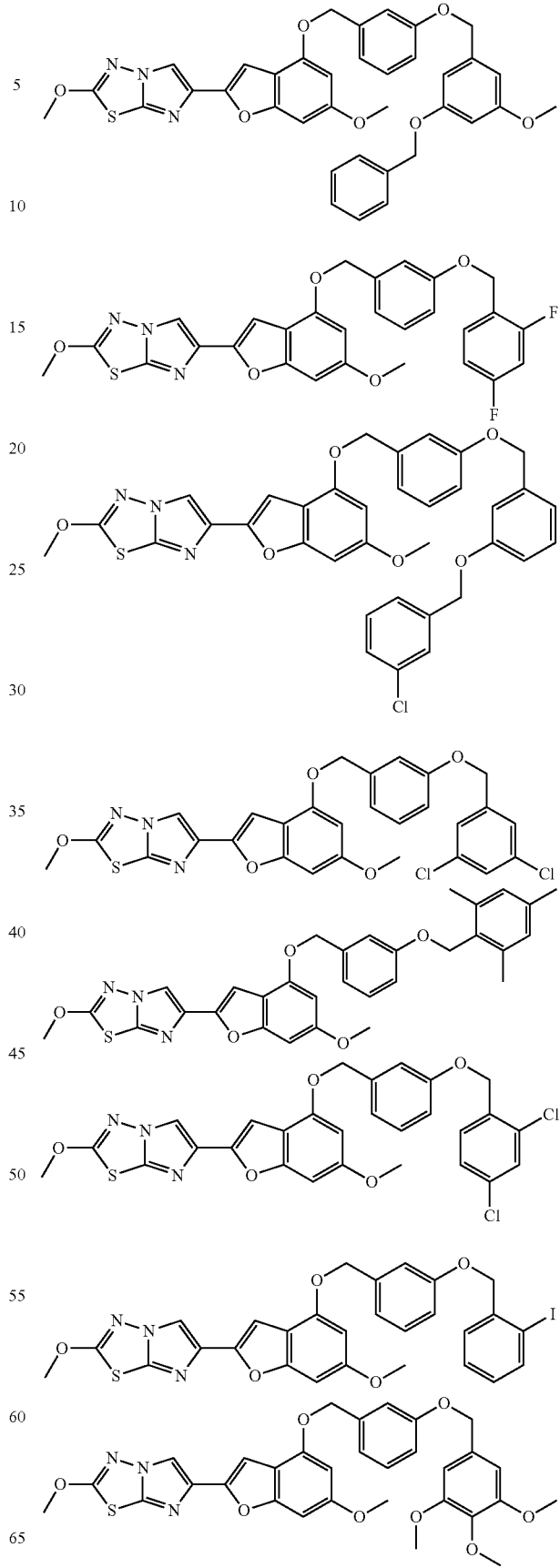

-continued
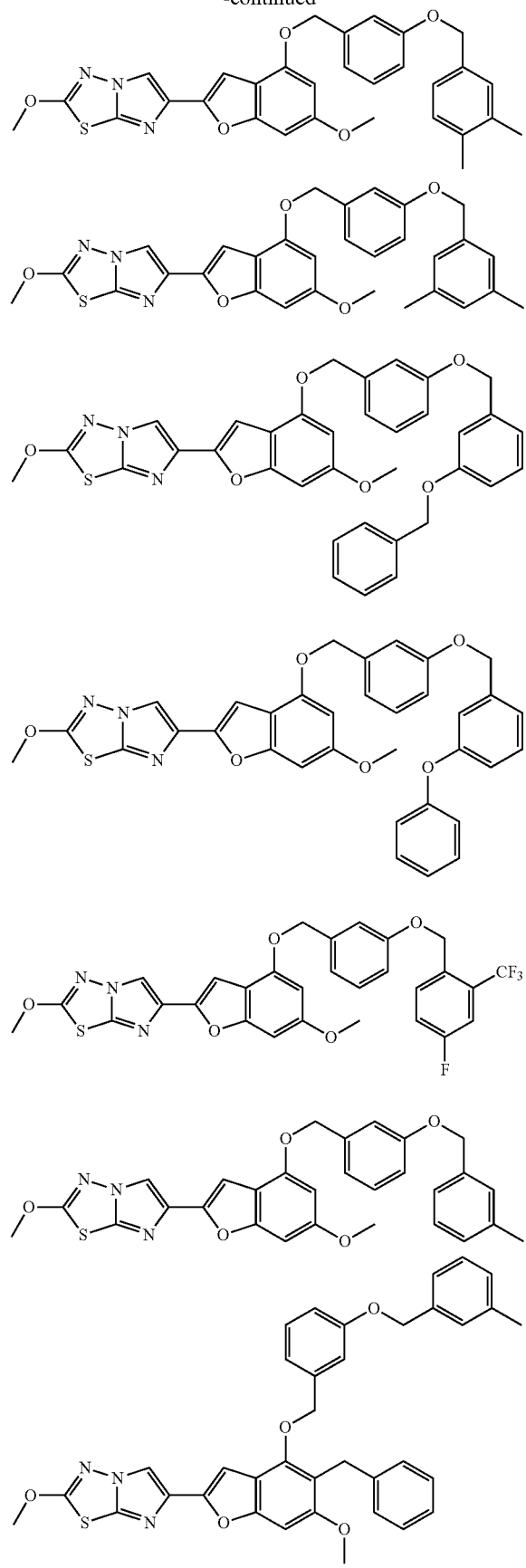
-continued
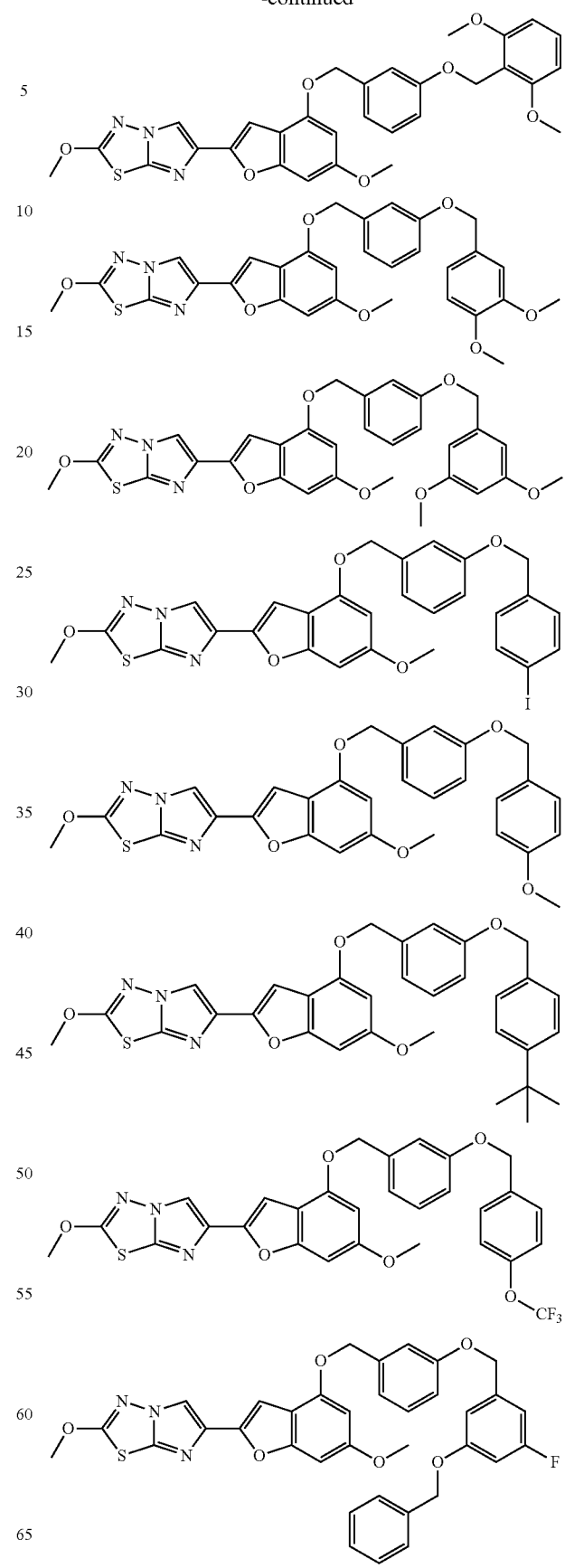

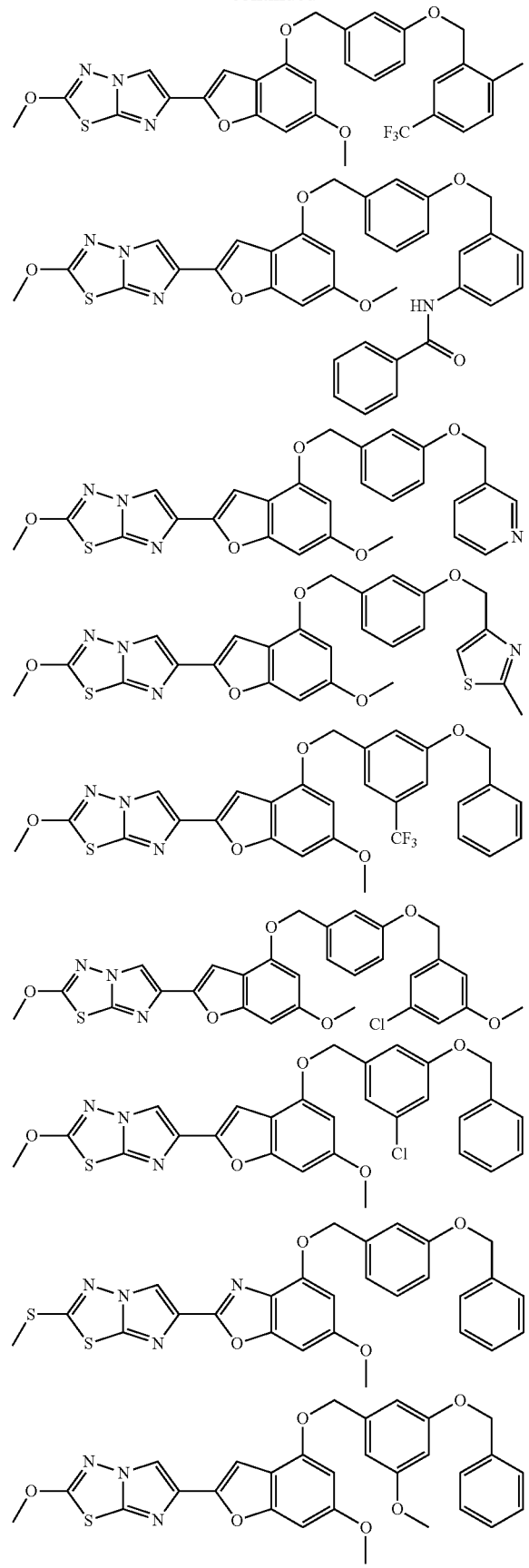
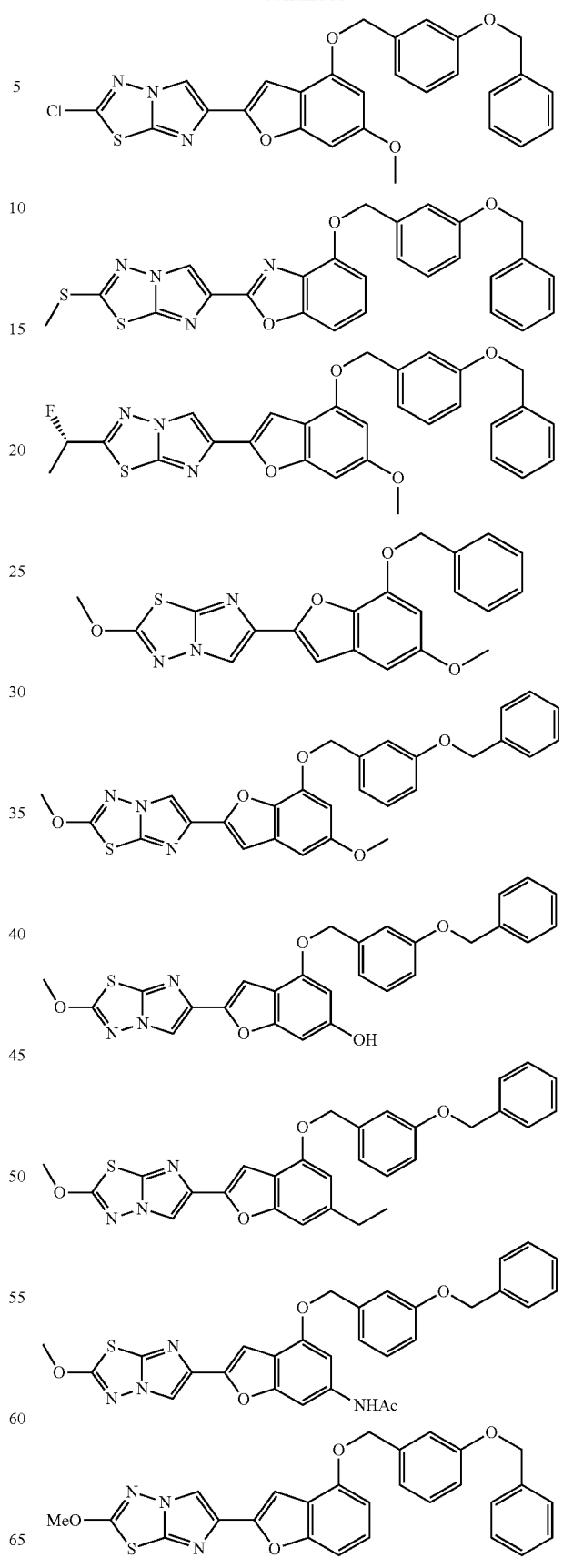

-continued
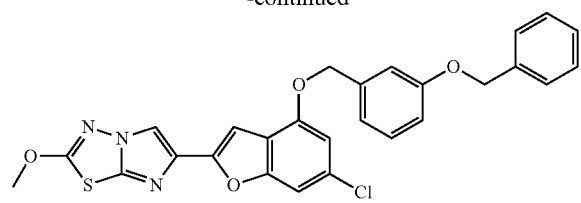
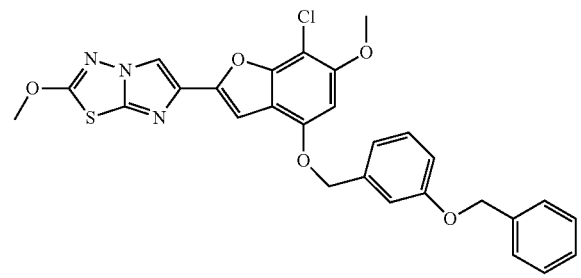
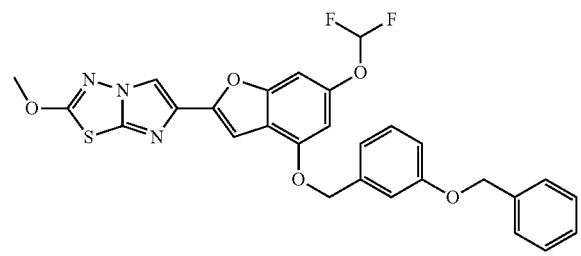
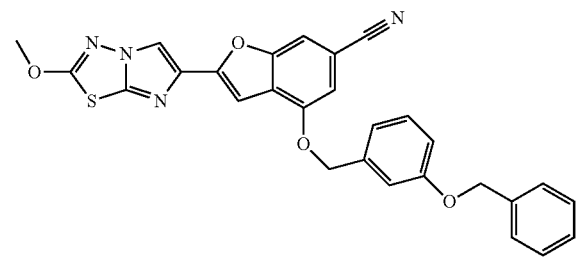
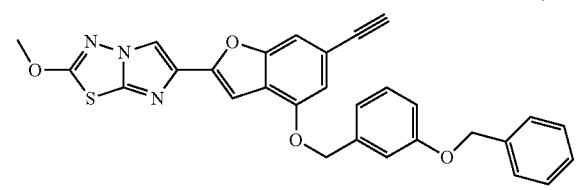
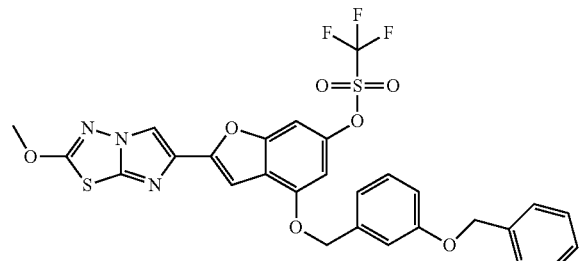
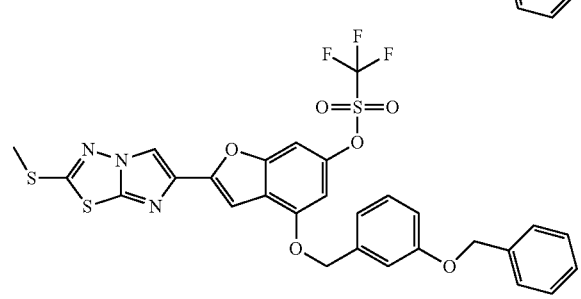
-continued
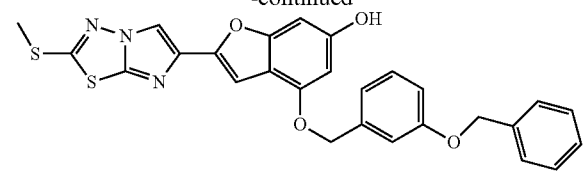
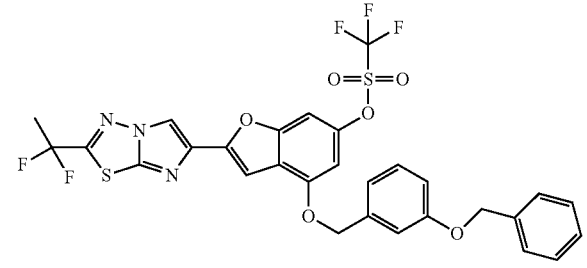
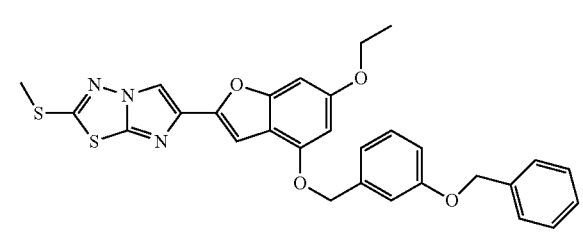
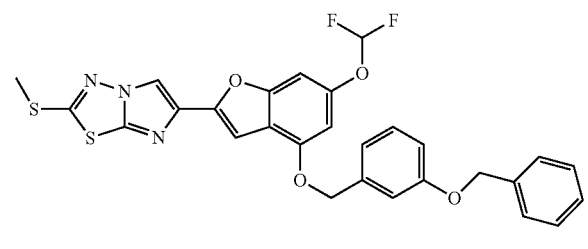
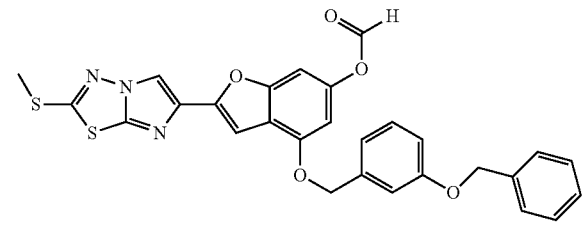
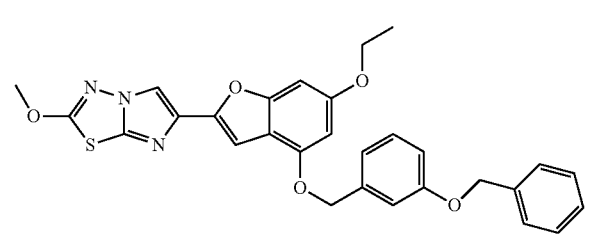
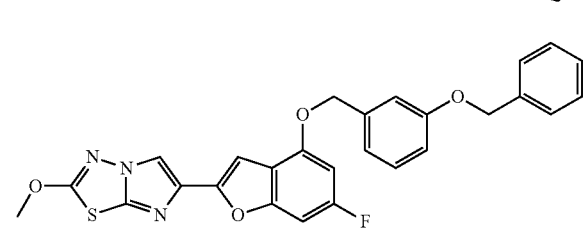
and -continued
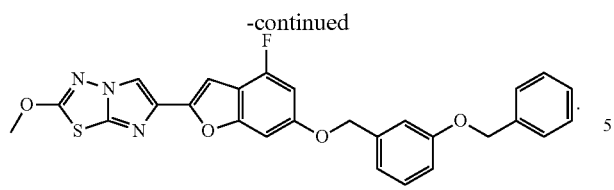 5
11. A pharmaceutical composition, which comprises a pharmaceutically acceptable carrier and a compound as defined in claim 1, or stereoisomers, tautomers, pharmaceutically acceptable salts, or solvates thereof, alone or in combination with another therapeutic agent.
* * * * *

UNITED STATES PATENT AND TRADEMARK OFFICE
CERTIFICATE OF CORRECTION

PATENT NO.         : 9,862,730 B2
APPLICATION NO.    : 14/396807
DATED              : January 9, 2018
INVENTOR(S)        : Lawrence et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 330 days.

Signed and Sealed this
Twenty-fifth Day of September, 2018

Andrei Iancu
*Director of the United States Patent and Trademark Office*